US012366575B2

(12) United States Patent
Modlin et al.

(10) Patent No.: US 12,366,575 B2
(45) Date of Patent: Jul. 22, 2025

(54) CHEMICAL COMPOSITIONS AND METHODS OF USE

(71) Applicant: Liquid Biopsy Research LLC, Charlestown (KN)

(72) Inventors: Irvin Mark Modlin, Woodbridge, CT (US); Mark Kidd, New Haven, CT (US); Ignat Drozdov, Stratford Upon Avon (GB)

(73) Assignee: Liquid Biopsy Research LLC, Charlestown (KN)

(*) Notice: Subject to any disclaimer, the term of this patent is extended or adjusted under 35 U.S.C. 154(b) by 300 days.

(21) Appl. No.: 17/501,168

(22) Filed: Oct. 14, 2021

(65) Prior Publication Data

US 2023/0022417 A1 Jan. 26, 2023

Related U.S. Application Data

(63) Continuation of application No. 16/039,041, filed on Jul. 18, 2018, now abandoned.

(60) Provisional application No. 62/535,419, filed on Jul. 21, 2017.

(51) Int. Cl.

*A61K 31/495* (2006.01)
*C12Q 1/6886* (2018.01)
*G01N 33/574* (2006.01)
*G01N 33/68* (2006.01)
*G16H 50/30* (2018.01)

(52) U.S. Cl.

CPC ..... *G01N 33/57426* (2013.01); *C12Q 1/6886* (2013.01); *G01N 33/6818* (2013.01); *G01N 33/6857* (2013.01); *G16H 50/30* (2018.01); *C12Q 2600/112* (2013.01); *C12Q 2600/118* (2013.01); *C12Q 2600/158* (2013.01); *G01N 33/57488* (2013.01); *G01N 2800/52* (2013.01); *G01N 2800/54* (2013.01); *G01N 2800/60* (2013.01); *G01N 2800/7028* (2013.01)

(58) Field of Classification Search

CPC .................................................... A61K 31/495
See application file for complete search history.

(56) References Cited

U.S. PATENT DOCUMENTS

| | | | |
|---|---|---|---|
| 7,668,659 B2 | 2/2010 | Shaughnessy et al. |
| 8,843,320 B2 | 9/2014 | Shaughnessy et al. |
| 2005/0260664 A1 | 11/2005 | Shaughnessy et al. |
| 2019/0025311 A1 | 1/2019 | Modlin et al. |

FOREIGN PATENT DOCUMENTS

| | | | |
|---|---|---|---|
| CN | 102361991 A | 2/2012 |
| JP | 2004313167 A | 11/2004 |
| JP | 2005512557 A | 5/2005 |
| JP | 2008544223 A | 12/2008 |
| WO | WO-03053215 A2 | 7/2003 |
| WO | WO-2006133420 A2 | 12/2006 |
| WO | WO-2010078531 A2 | 7/2010 |
| WO | WO-2011152884 A2 | 12/2011 |
| WO | WO-2013155048 A1 | 10/2013 |
| WO | WO-2019018540 A1 | 1/2019 |

OTHER PUBLICATIONS

Galustian et al. Drugs of Future, 2011, 36(10): 741-750.*
Herndon et al. Clinical Cancer Research, 19(17):4559-4563.*
Tohnya et al. Clinical Prostate Cancer, 2004, 2(4): 241-243.*
Morgan et al., Clinical Cancer Research, 2013, 19(21):6030-6038.*
Amin, S.B. et al. (2014) "Gene expression profile alone is inadequate in predicting complete response in multiple myeloma" Leukemia, 28:2229-2234; doi: 10.1038/leu.2014.140.
Avet-Loiseau, H. et al. (2001) "Rearrangements of the c-myc oncogene are present in 15% of primary human multiple myeloma tumors" Blood, 98:3082-3086.
Babajide Mustapha, I. and Saeed, F. (Jul. 2016) "Bioactive Molecule Prediction Using Extreme Gradient Boosting" Molecules, 21:983, doi:10.3390/molecules21080983, 11 pages.
Bodei, L. et al. (2016) "Measurement of circulating transcripts and gene cluster analysis predicts and defines therapeutic efficacy of peptide receptor radionuclide therapy (PRRT) in neuroendocrine tumors" Eur J Nucl Med Mol Imaging, 43:839-851; doi: 10.1007/s00259-015-3250-z.
Botta, C. et al. (2016) A gene expression inflammatory signature specifically predicts multiple myeloma evolution and patients survival. Blood Cancer Journal, 6:e511, doi:10.1038/bcj.2016.118, 8 pages.
Breiman, L. and Cutler, A., Random Forests™. [online]. Retrieved from: https://www.stat.berkeley.edu/ -breiman/RandomForests/cc_papers.htm; downloaded Jun. 30, 2020; 1 printed page.
Chng, W.J. et al. (2008) "The centrosome index is a powerful prognostic marker in myeloma and identifies a cohort of patients that might benefit from aurora kinase inhibition" Blood, 111:1603-1609.
Chng, W.J. et al. (2016) "Gene signature combinations improve prognostic stratification of multiple myeloma patients" Leukemia, 30:1071-1078; doi: 10.1038/leu.2015.341.
Chung, T.H. (2013) "A Novel Measure of Chromosome Instability Can Account for Prognostic Difference in Multiple Myeloma" PLoS One, 8(6):e66361; doi: 66310.61371/journal.pone.0066361, 8 pages.
Debes-Marun, C.S. et al. (2003) "Chromosome abnormalities clustering and its implications for pathogenesis and prognosis in myeloma" Leukemia, 17:427-436.

(Continued)

*Primary Examiner* — Rei Tsang Shiao
(74) *Attorney, Agent, or Firm* — Fenwick & West LLP

(57) ABSTRACT

The present invention is directed to methods for detecting a plasma cell dyscrasia like myeloma or MGUS, methods for determining whether a plasma cell dyscrasiais stable or progressive, methods for determining a risk for disease relapse, and methods for determining a response by a subject having a plasma cell dyscrasia to a therapy.

18 Claims, 11 Drawing Sheets

Specification includes a Sequence Listing.

(56) References Cited

OTHER PUBLICATIONS

Decaux, O. et al. (Oct. 2008) "Prediction of Survival in Multiple Myeloma Based on Gene Expression Profiles Reveals Cell Cycle and Chromosomal Instability Signatures in High-Risk Patients and Hyperdiploid Signatures in Low-Risk Patients: A Study of the Intergroupe Francophone du Mylome" J Clin Oncol, 26(29):4798-4805; DOI: 10.1200/JCO.2007.13.8545.
Dickens, N.J. et al. (2010) "Homozygous Deletion Mapping in Myeloma Samples Identifies Genes and an Expression Signature Relevant to Pathogenesis and Outcome" Clin Cancer Res, 16:1856-1864; doi: 10.1158/1078-0432.CCR-09-2831.
Dimopoulos, M. et al. (2011) "Consensus recommendations for standard investigative workup: report of the International Myeloma Workshop Consensus Panel 3" Blood, 117:4701-4705; doi: 10.1182/blood-2010-10-299529.
Egan, P. et al. (2016) "Towards Stratified Medicine in Plasma Cell Myeloma" Int J Mol Sci, 17(10):1760; doi: 10.3390/ijms17101760, 21 pages.
Fonseca, R. et al. (2004) "Genetics and Cytogenetics of Multiple Myeloma: A Workshop Report" Cancer Res, 64:1546-1558.
Genecards Database, Nfkbiz Gene, GC03P101827 [online]. Weizmann Institute of Science. Retrieved from: https://www.genecards.org/cgi-bin/carddisp.pl?gene=NFKBIZ&keywords=nfkbiz , downloaded Jul. 1, 2020; 24 printed pages.
Genecards Database, NR4A1 Gene, GC12P052022 [online]. Weizmann Institute of Science. Retrieved from: https://www.genecards.org/cgi-bin/carddisp.pl?gene=NR4A1&keywords=nr4a1 , downloaded Jul. 1, 2020; 30 printed pages.
Genecards Database, PRKAA1 Gene, GC05M040759 [online]. Weizmann Institute of Science. Retrieved from: https://www.genecards.org/cgi-bin/carddisp.pl?gene=PRKAA1&keywords=PRKAA1 , downloaded Jul. 1, 2020; 33 printed pages.
Genecards Database, SCYL2 Gene, GC12P100267 [online]. Weizmann Institute of Science. Retrieved from: https://www.genecards.org/cgi-bin/carddisp.pl?gene=SCYL2&keywords=scyl2 , downloaded Jul. 1, 2020; 25 printed pages.
Genecards Database, SP1 Gene; GC12P053380 [online]. Weizmann Institute of Science. Retrieved from: https://www.genecards.org/cgi-bin/carddisp.pl?gene=SP1&keywords=sp1 , downloaded Jul. 1, 2020; 31 printed pages.
GEO Series GSE7116 (Nov. 29, 2007) "Clinical, radiographic, and biomarker characterization of multiple myeloma patients with osteonecrosis of the jaw" [online]. Retrieved from: https://www.ncbi.nlm.nih.gov/geo/query/acc.cgi?acc=GSE7116 ; downloaded Jul. 2, 2020, 2 printed pages.
GITHUB (Jun. 7, 2020) "dmlc/xgboost" [online]. Retrieved from: https://github.com/dmlc/xgboost/releases ,downloaded Jun. 30, 2020, 34 printed pages.
Gonzlez, D. et al. (2007) "Immunoglobulin gene rearrangements and the pathogenesis of multiple myeloma" Blood, 110:3112-3121.
Hanahan, D and R.A. Weinberg (Mar. 4, 2011) "Hallmarks of cancer: The next generation" Cell, 144(5):646-674.
Hanahan, D. et al. (Jan. 2000). The Hallmarks of Cancer. Review. Cell, 100(1):57-70. https://doi.org/10.1007/s00262-010-0968-0.
Hermansen, N.E. et al. (2016) "Gene expression risk signatures maintain prognostic power in multiple myeloma despite microarray probe set translation" Int J Lab Hematol, 38:298-307; doi: 10.1111/ijlh. 12486.
Hose, D. et al. (2011) "Proliferation is a central independent prognostic factor and target for personalized and risk-adapted treatment in multiple myeloma" Haematologica, 96:87-95; doi: 10.3324/haematol.2010.030296.
Kidd, M. et al. (2015) "Blood and tissue neuroendocrine tumor gene cluster analysis correlate, define hallmarks and predict disease status" Endocr Relat Cancer, 22(4):561-575; doi: 10.1530/ERC-15-0092.
Kuiper, R. et al. (2012) "A gene expression signature for high-risk multiple myeloma" Leukemia, 26:2406-2413; doi: 10.1038/leu.2012.127.
Kuiper, R. et al. (2015) "Prediction of high- and low-risk multiple myeloma based on gene expression and the International Staging System" Blood, 126(17):1996-2004; DOI:10.1182/blood-2015-05-644039.
Kyle, R.A. et al. (2008) "Multiple myeloma" Blood, 111:2962-2972.
Li, S-C. et al. (2013) "Global microRNA profiling of well-differentiated small intestinal neuroendocrine tumors" Mod Pathol, 26:685-696; doi: 10.1038/modpathol.2012.216.
Liu, Y., et al. (2016) "Relationship between Bone Markers and the Progression of Multiple Myeloma", Journal of Experimental Hematology, 24(5): 1433-1436.
Melchor, L. et al. (2014) "Single-cell genetic analysis reveals the composition of initiating clones and phylogenetic patterns of branching and parallel evolution in myeloma" Leukemia, 28:1705-1715; doi: 10.1038/leu.2014.13.
Michels, T.C. et al. (2017) "Multiple Myeloma: Diagnosis and Treatment" Am Fam Physician, 95:373-383.
Modlin, I. et al. (2013) "The Identification of Gut Neuroendocrine Tumor Disease by Multiple Synchronous Transcript Analysis in Blood" Plos One, 8(5):e63364; doi: 10.1371/journal/pone/0063364, 12 pages.
Moreaux, J. et al. (2011) "A high-risk signature for patients with multiple myeloma established from the molecular classification of human myeloma cell lines" Haematologica, 96(4):574-582; doi: 10.3324/haematol.2010.033456.
Munshi, N.C. et al. (2013) "New strategies in the treatment of multiple myeloma" Clin Cancer Res, 19(13):3337-3344; DOI: 10.1158/1078-0432.CCR-12-1881.
Pawlyn, C. et al. (2015) "Coexistent hyperdiploidy does not abrogate poor prognosis in myeloma with adverse cytogenetics and may precede IGH translocations" Blood, 125(5):831-840.
Raje, N. et al. (2008) "Clinical, Radiographic, and Biochemical Characterization of Multiple Myeloma Patients with Osteonecrosis of the Jaw" Clin Cancer Res, 14(8):2387-2395; doi: 10.1158/1078-0432.CCR-07-1430.
Richardson, P.G. et al. (Jun. 16, 2005) "Bortezomib or high-dose dexamethasone for relapsed multiple myeloma" The New England Journal of Medicine, 352(24):2487-2498.
Seif, G. (May 29, 2019) "A Beginner's guide to XGBoss" [online]. Retrieved from: https://towardsdatascience.com/a-beginners-gnide-to-xgboost-87f5d4c30ed7 , on Jun. 30, 2020; 8 pages.
Shaughnessy, J.D. Jr. et al. (2007) "A validated gene expression model of high-risk multiple myeloma is defined by deregulated expression of genes mapping to chromosome 1" Blood, 109:2276-2284.
Siegel, R.L. et al. (2017) "Cancer Statistics, 2017" CA Cancer J Clin, 67:7-30.
Swerdlow, S.H. et al. (2016) "The 2016 revision of the World Health Organization classification of lymphoid neoplasms" Blood, 127:2375-2390; doi: 10.1182/blood-2016-01-643569.
Szalat, R. et al. (Nov. 15, 2016) "Gene Expression Profiles in Myeloma: Ready for the Real World?" Clin Cancer Res, 22(22):5434-5442.
Walker, B.A. et al. (2015) "APOBEC family mutational signatures are associated with poor prognosis translocations in multiple myeloma" Nat Commun, 6:6997; DOI: 10.1038/ncomms7997, 11 pages.
Walker, B.A. et al. (2015) "Mutational Spectrum, Copy Number Changes, and Outcome: Results of a Sequencing Study of Patients With Newly Diagnosed Myeloma" J Clin Oncol., 33:3911-3920; doi: 10.1200/JCO.2014.59.1503.
Wu, P. et al. (2015) "A gene expression based predictor for high risk myeloma treated with intensive therapy and autologous stem cell rescue" Leuk Lymphoma, 56(3):594-601; doi: 10.3109/10428194.10422014.10911863.
Zhan, F. et al. (Feb. 2007) Gene-expression signature of benign monoclonal gammopathy evident in multiple myeloma is linked to good prognosis. Blood, 109:1692-1700.

* cited by examiner

SEQUENCE LISTING

```
<160> NUMBER OF SEQ ID NOS: 54

<210> SEQ ID NO 1
<211> LENGTH: 1084
<212> TYPE: DNA
<213> ORGANISM: Homo sapiens

<400> SEQUENCE: 1

cacacccacg gcagacacgc acgcacccgg gcgccgaagg gaaagccgcg tctcgccctc      60

ccgccccgcc gtcggtcctg tctcagtccc tcagcagagc gggaaagcgg aggccggagc     120

cgtgacctct gaccccgtgg ttatgcggag ccgccgcatt ccttagcgat cgcggggcag     180

ccgccgctgc cgccgtgggc gactgacgca gcgcgggcgc gtggagccgc cgccgcccct     240

cccccaccgc cgctctcgcg ccagccggtc cccgcgtgcc cgccccttct ccccggccgc     300

acccgagacc tcgcgcgccg ccgctgccac gcgccccccc caccgccgcc gccgccccag     360

ccccgcgcca ccgccccagc ccgcccagcc cggaggtccc gcgtggagct gccgccgccg     420

ccggggagaa ggatgaagga caaacagaag aagaagaagg agcgcacgtg ggccgaggcc     480
```

```
gcgcgcctgg tattagaaaa ctactcggat gctccaatga caccaaaaca gattctgcag    540
gtcatagagg cagaaggact aaaggaaatg agaagtggga cttcccctct cgcatgcctc    600
aatgctatgc tacattccaa ttcaagagga ggagaggggt tgttttataa actgcctggc    660
cgaatcagcc ttttcacgct caaggtgtga gccactgcac caggcccctt catcttaatt    720
ttaatatatc tttgaataaa caccattgta tgaacctgct gtaagcttgg gagtggtctg    780
ttagtctaca gcttgtgtct gagatgtgct aattgaatat ttgctcagta cctcatctta    840
actgcctttg gctttatgtt gcttatcctt catagtatct tgttcattgg ccttttacat    900
ccataggcat cacttctctg atattcgttg tgctctttta atggattaat ggtttgcttg    960
gttggttcct ctagttagac tgtaaactcc ttgagagcag agtctgtatt ttattaatta   1020
cccacagtac taggtacata gttgccttca ataaatatat atttaatgaa aaaaaaaaaa   1080
aaaa                                                                1084
```

<210> SEQ ID NO 2
<211> LENGTH: 3061
<212> TYPE: DNA
<213> ORGANISM: Homo sapiens

<400> SEQUENCE: 2

```
cgcctccccg cccgccccac ttctcattca cttggctcgc acggcgcaga cagaccgcgc     60
agggagcaca caccgccagt ctgtgcgctg agtcggagcc agaggccgcg gggacaccgg    120
gccatgcacg cccccaactg aagctgcatc tcaaagccga agattccagc agcccagggg    180
atttcaaaga gctcagactc agaggaacat ctgcggagag acccccgaag ccctctccag    240
ggcagtcctc atccagacgc tccgctagtg cagacaggag cgcgcagtgg ccccggctcg    300
ccgcgccatg gagcggatcc ccagcgcgca accacccccc gcctgcctgc ccaaagcacc    360
gggactggag cacggagacc taccagggat gtaccctgcc cacatgtacc aagtgtacaa    420
gtcaagacgg ggaataaagc ggagcgagga cagcaaggag acctacaaat tgccgcaccg    480
gctcatcgag aaaaagagac gtgaccggat taacgagtgc atcgcccagc tgaaggatct    540
cctacccgaa catctcaaac ttacaacttt gggtcacttg gaaaaagcag tggttcttga    600
acttaccttg aagcatgtga aagcactaac aaacctaatt gatcagcagc agcagaaaat    660
cattgccctg cagagtggtt tacaagctgg tgagctgtca gggagaaatg tcgaaacagg    720
tcaagagatg ttctgctcag gtttccagac atgtgcccgg gaggtgcttc agtatctggc    780
caagcacgag aacactcggg acctgaagtc ttcgcagctt gtcacccacc tccaccgggt    840
ggtctcggag ctgctgcagg gtggtacctc caggaagcca tcagacccag ctcccaaagt    900
gatggacttc aaggaaaaac ccagctctcc ggccaaaggt tcggaaggtc ctgggaaaaa    960
ctgcgtgcca gtcatccagc ggactttcgc tcactcgagt ggggagcaga gcggcagcga   1020
cacggacaca gacagtggct atggaggaga atcggagaag ggcgacttgc gcagtgagca   1080
gccgtgcttc aaaagtgacc acggacgcag gttcacgatg ggagaaagga tcggcgcaat   1140
taagcaagag tccgaagaac cccccacaaa aaagaaccgg atgcagcttt cggatgatga   1200
aggccatttc actagcagtg acctgatcag ctccccgttc ctgggcccac acccacacca   1260
gcctcctttc tgcctgccct tctacctgat cccaccttca gcgactgcct acctgcccat   1320
gctggagaag tgctggtatc ccacctcagt gccagtgcta tacccaggcc tcaacgcctc   1380
tgccgcagcc ctctctagct tcatgaaccc agacaagatc tcggctccct tgctcatgcc   1440
ccagagactc ccttctccct tgccagctca tccgtccgtc gactcttctg tcttgctcca   1500
```

agctctgaag ccaatccccc ctttaaactt agaaaccaaa gactaaactc tctaggggat 1560
cctgctgctt tgctttcctt cctcgctact tcctaaaaag caacaaaaaa gtttttgtga 1620
atgctgcaag attgttgcat tgtgtatact gagataatct gaggcatgga gagcagattc 1680
agggtgtgtg tgtgtgtgtg tgtgtgtgta tgtgcgtgtg cgtgcacatg tgtgcctgcg 1740
tgttggtata ggactttaaa gctccttttg gcatagggaa gtcacgaagg attgcttgac 1800
atcaggagac ttggggggga ttgtagcaga cgtctgggct tttccccacc cagagaatag 1860 ccccccttcga tacacatcag ctggattttc aaaagcttca aagtcttggt ctgtgagtca 1920
ctcttcagtt tgggagctgg gtctgtggct ttgatcagaa ggtactttca aaagagggct 1980
ttccagggct cagctcccaa ccagctgtta ggaccccacc cttttgcctt tattgtcgac 2040
gtgactcacc agacgtcggg gagagagagc agtcagaccg agctttctgc taacatgggg 2100
aggtagcagg cactggcata gcacggtagt ggtttgggga ggtttccgca ggtctgctcc 2160
ccacccctgc ctcggaagaa taaagagaat gtagttccct actcaggctt tcgtagtgat 2220
tagcttacta aggaactgaa aatgggcccc ttgtacaagc tgagctgccc cggagggagg 2280
gaggagttcc ctgggcttct ggcacctgtt tctaggccta accattagta cttactgtgc 2340
agggaaccaa accaaggtct gagaaatgcg gacaccccga gcgagcaccc caaagtgcac 2400
aaagctgagt aaaaagctgc ccccttcaaa cagaactaga ctcagttttc aattccatcc 2460
taaaactcct tttaaccaag cttagcttct caaaggccta accaagcctt ggcaccgcca 2520
gatcctttct gtaggctaat tcctcttgcc caacggcata tggagtgtcc ttattgctaa 2580
aaaggattcc gtctccttca aagaagtttt atttttggtc cagagtactt gttttcccga 2640
tgtgtccagc cagctccgca gcagcttttc aaaatgcact atgcctgatt gctgatcgtg 2700
ttttaacttt ttcttttcct gtttttattt tggtattaag tcgttgcctt tatttgtaaa 2760
gctgttataa atatatatta tataaatata ttaaaaagga aaatgtttca gatgtttatt 2820
tgtataatta cttgattcac acagtgagaa aaaatgaatg tattcctgtt tttgaagaga 2880
agaataattt ttttttctc tagggagagg tacagtgttt atattttgga gccttcctga 2940
aggtgtaaaa ttgtaaatat ttttatctat gagtaaatgt taagtagttg ttttaaaata 3000
cttaataaaa taattctttt cctgtggaag agaaaaaaaa aaaaaaaaaa aaaaaaaaaa 3060
a 3061

<210> SEQ ID NO 3
<211> LENGTH: 2718
<212> TYPE: DNA
<213> ORGANISM: Homo sapiens

<400> SEQUENCE: 3
cagggtaacg ctgtcttgtg gacccgcact tcccacccga gacctctcac tgagcccgag 60
ccgcgcgcga catgagccac gggaagggaa ccgacatgct cccggagatc gccgccgccg 120
tgggcttcct ctccagcctc ctgaggaccc ggggctgcgt gagcgagcag aggcttaagg 180
tcttcagcgg ggcgctccag gaggcactca cagagcacta caaacaccac tggtttcccg 240
aaaagccgtc caagggctcc ggctaccgct gcattcgcat caaccacaag atggacccca 300
tcatcagcag ggtggccagc cagatcggac tcagccagcc ccagctgcac cagctgctgc 360
ccagcgagct gaccctgtgg gtggacccct atgaggtgtc ctaccgcatt ggggaggacg 420
gctccatctg cgtcttgtac gaggaggccc cactggccgc ctcctgtggg ctcctcacct 480

```
gcaagaacca agtgctgctg ggccggagca gcccctccaa gaactacgtg atggcagtct    540
ccagctaggc ccttccgccc ccgccctggg cgccgccgtg ctcatgctgc cgtgacaaca    600
ggccaccaca tacctcaacc tggggaactg tatttttaaa tgaagagcta tttatatata    660
ttattttttt ttaagaaagg aggaaaagaa accaaaagtt tttttaaga aaaaaaatcc     720
ttcaagggag ctgcttggaa gtggcctccc caggtgcctt tggagagaac tgttgcgtgc    780
ttgagtctgt gagccagtgt ctgcctatag gagggggagc tgttaggggg tagacctagc    840
caaggagaag tgggagacgt ttggctagca ccccaggaag atgtgagagg gagcaagcaa    900
ggttagcaac tgtgaacaga gaggtcggga tttgccctgg gggaggaaga gaggccaagt    960
tcagagctct ctgtctcccc cagccagaca cctgcatccc tggctcctct attactcagg   1020
ggcattcatg cctggactta aacaatacta tgttatcttt tcttttattt ttctaatgag   1080
gtcctgggca gagagtgaaa aggcctctcc tgattcctac tgtcctaagc tgcttttctt   1140
gaaatcatga cttgtttcta attctaccct caggggcctg tagatgttgc tttccagcca   1200
ggaatctaaa gctttgggtt ttctgagggg ggggaggagg gaactggagg ttattggggt   1260
taggatggaa gggaactctg cacaaaacct ttgctttgct agtgctgctt tgtgtgtatg   1320
tgtggcaaat aatttggggg tgatttgcaa tgaaattttg ggacccaaag agtatccact   1380
ggggatgttt tttggccaaa actcttcctt ttggaaccac atgaaagtct tgatgctgct   1440
gccatgatcc ctttgagagg tggctcaaaa gctacaggga actccaggtc ctttattact   1500
gccttctttt caaaagcaca actctcctct aaccctcccc tccccccttcc cttctggtcg  1560
ggtcatagag ctaccgtatt ttctaggaca agagttctca gtcactgtgc aaatatgcccc  1620
ctgggtccca ggagggtctg gaggaaaact ggctatcaga acctcctgat gccctggtgg   1680
gcttagggaa ccatctctcc tgctctcctt gggatgatgg ctggctagtc agccttgcat   1740
gtattccttg gctgaatggg agagtgcccc atgttctgca agactacttg gtattcttgt   1800
agggccgaca ctaaataaaa gccaaacctt gggcactgtt ttttctccct ggtgctcaga   1860
gcacctgtgg gaaaggttgc tgtctgtctc agtacaatcc aaatttgtcg tagacttgtg   1920
caatatatac tgttgtgggt tggagaaaag tggaaagcta cactgggaag aaactccctt   1980
ccttcaattt ctcagtgaca ttgatgaggg gtcctcaaaa gacctcgagt ttcccaaacc   2040
gaatcacctt aagaaggaca gggctagggc atttggccag gatggccacc ctcctgctgt   2100
tgccccttag tgaggaatct tcaccccact tcctctaccc ccaggttctc ctccccacag   2160
ccagtcccct ttcctggatt tctaaactgc tcaattttga ctcaaaggtg ctatttacca   2220
aacactctcc ctacccattc ctgccagctc tgcctccttt tcaactctcc acattttgta   2280
ttgccttccc agacctgctt ccagtcttta ttgctttaaa gttcactttg ggcccacaga   2340
cccaagagct aattttctgg tttgtgggtt gaaacaaagc tgtgaatcac tgcaggctgt   2400
gttcttgcat cttgtctgca aacaggtccc tgccttttta gaagcagcct catggtctca   2460
tgcttaatct tgtctctctt ctcttcttta tgatgttcac tttaaaaaca acaaaacccc   2520
tgagctggac tgttgagcag gcctgtctct cctattaagt aaaaataaat agtagtagta   2580
tgtttgtaag ctattctgac agaaaagaca aaggttacta attgtatgat agtgttttta   2640
tatggaagaa tgtacagctt atggacaaat gtacaccttt ttgttacttt aataaaaatg   2700
tagtaggata aaaaaaaa                                                 2718
```

<210> SEQ ID NO 4
<211> LENGTH: 5666

<212> TYPE: DNA
<213> ORGANISM: Homo sapiens

<400> SEQUENCE: 4
agaagggaga cagtggcggt cgcggcgggg ccgatccgag agttcccctt agagaacgga 60
gctcacgggc ggggaggcct cacctgctag taggacgcag aaagacagaa ggcgaaggag 120
accccgactt cccgggtcag ccccagagcc accccctgcc gtagccatct tgcctctctg 180
ctgagcggaa gcccccgttc ggctcctgtc tgttagcggc ctctctaggc taccactgac 240
accgtctctg tggcccggag cctaagagac cggaagttcg tgtttccagg cgcttccgga 300
aaccgcggga gagggtcgct gacgtggagg cgtccgaagg gcagcagggt gtgtcggggc 360
tcggattaag acatcggagt cggagacctg agagatgtta accaaattcg agaccaagag 420
cgcgcgggtc aaagggctca gctttcaccc caaaagacct tggatcctga ctagtttaca 480
taatggggtc atccagttat gggactatcg gatgtgcact ctcattgaca agtttgatga 540
acatgatggt ccagtgcgag gcattgactt ccataagcag cagccactgt tcgtctctgg 600
aggagatgac tataagatta aggtttggaa ttacaagctt cggcgctgtc ttttcacatt 660
gcttgggcac ttagattata ttcgcaccac gttttttcat catgaatatc cctggattct 720
gagtgcctcc gatgatcaga ccatccgagt gtggaactgg caatctagaa cctgtgtttg 780
tgtgttaaca gggcacaacc attatgtgat gtgtgctcag ttccacccca cagaagactt 840
ggtagtatca gccagcctgg accagactgt gcgcgtttgg gatatttctg gtctgaggaa 900
aaaaaacctg tcccctggtg cggtggaatc ggatgtgaga ggaataactg ggttgatct 960 atttggaact acagatgcag tggtgaagca tgtactagag ggtcacgatc gtggagtaaa 1020
ctgggctgcc ttccacccca ctatgcccct tattgtatct ggggcagatg atcgtcaagt 1080
gaagatctgg cgcatgaatg aatcaaaggc atgggaggtt gatacctgcc ggggccatta 1140
caacaatgta tcttgtgccg tcttccaccc tcgccaagag ttgatcctca gcaattctga 1200
ggacaagagt attcgagtct gggatatgtc taagcggact ggggttcaga ctttccgcag 1260
agaccatgat cgtttctggg tcctagctgc tcaccctaac cttaacctct ttgcagcagg 1320
ccatgatggt ggtatgattg tgtttaagct ggaacgggaa cggccagcct atgctgttca 1380
tggcaatatg ctacactatg tcaaggaccg attcttacga cagctggatt tcaacagctc 1440
caaagatgta gctgtgatgc agttgcggag tggttccaag tttccagtat tcaatatgtc 1500
atacaatcca gcagaaaatg cagtcctgct ttgtacaaga gctagcaatc tagagaatag 1560
tacctatgac ctgtacacca tccctaaaga tgctgactcc cagaatcctg atgcgcctga 1620
agggaaacga tcctcaggcc tgacagccgt ttgggtcgct cgaaatcggt ttgctgtcct 1680
agatcggatg cattcgcttc tgatcaagaa tctgaagaat gagatcacca aaaaggtaca 1740
ggtgcccaac tgtgatgaga tcttctatgc tggcacaggc aatctcctgc ttcgagatgc 1800
ggactctatc acactctttg acgtacagca gaagcggact ctggcatctg tgaagatttc 1860
taaagtgaaa tacgttatct ggtcagcaga catgtcacat gtagcactac tagccaaaca 1920
cgaacactca tgccctttgc ctcttacagc cattgtgatc tgtaaccgca aactggatgc 1980
tttatgtaac attcatgaga acattcgtgt caagagtggg gcctgggatg agagtggggt 2040
atttatctat accacaagca accacatcaa atatgctgtc accactgggg accacgggat 2100
cattcgaact ctggatttac ccatctatgt cacacgggtg aagggcaaca atgtatactg 2160
cctagacagg gagtgtcgtc cccgggtact caccattgat cccactgagt tcaaattcaa 2220

```
gctggccctg atcaacagaa aatatgatga ggtactgcac atggtgagga atgccaaact   2280
agttggccag tctattattg cttatctcca gaagaagggc tatcctgaag tggcactgca   2340
ttttgtcaag gatgagaaaa ctcgctttag tctggcactg gagtgtggaa acattgagat   2400
tgctctggaa gcagccaaag cactggatga caagaactgc tgggaaaagc tgggagaagt   2460
ggccctgctg caggggaacc accagattgt ggaaatgtgc tatcagcgta ccaaaaactt   2520
tgacaaactt tccttcctgt atcttatcac tggcaactta gaaaaacttc gcaagatgat   2580
gaagattgct gagatcagaa aggacatgag tggccactat cagaatgccc tatacctggg   2640
tgatgtgtca gagcgtgtgc ggatcctgaa gaactgtgga cagaagtccc tggcctatct   2700
cacagctgct acccatggct tagatgaaga agctgagagc ctaaaggaga catttgaccc   2760
agagaaggag acaatcccag acattgaccc taatgccaag ctgctccagc cacctgcacc   2820
tatcatgcca ttggatacca attggccttt attgactgta tccaaaggat tttttgaagg   2880
caccattgcc agcaaaggga agggaggagc actggctgct gacattgaca ttgacactgt   2940
tggtacagag ggctggggag aggatgcaga gctgcagttg gatgaagatg ggtttgtgga   3000
ggctacagaa ggtttggggg atgatgctct tggcaaggga caggaagaag gaggtggctg   3060
ggatgtagaa gaagatctgg agctccctcc tgagctggat atatcccctg ggcagctggg   3120
tggggctgaa gatggtttct ttgtgccccc aaccaaggga acaagtccaa ctcagatctg   3180
gtgtaataac tctcagcttc cagttgatca catcctggca ggctctttcg aaacagccat   3240
gcggctcctt catgaccaag taggggtaat ccagtttggc ccctacaagc aactgttcct   3300
acagacatac gcccgaggcc gcacaaccta tcaggctctg ccctgcctac cctccatgta   3360
tggctatcct aatcgcaact ggaaggatgc agggctgaag aatggtgtac cagctgtggg   3420
cctgaagctt aatgacctca tccaacggtt gcagctgtgc taccagctca ccacagttgg   3480
caaatttgag gaggctgtgg aaaaattccg ttccatcctt ctcagtgtgc cacttcttgt   3540
tgtggacaat aaacaagaga ttgcagaggc ccagcagctc atcaccattt gccgtgagta   3600
cattgtgggt ttgtccgtgg agacagaaag gaagaagctg cccaaagaga ctctagaaca   3660
gcagaagcgc atctgtgaga tggcagccta tttcacccac tcaaacctgc agcctgtgca   3720
catgatcctg gtgctgcgta cagccctcaa tctgttcttc aagctcaaga acttcaagac   3780
agctgccacc tttgctcggc gcctactaga actcgggccc aagcctgagg tggcccaaca   3840
gacccgaaaa atcctgtctg cctgtgagaa gaatcccaca gatgcctacc agctcaatta   3900
tgacatgcac aacccctttg acatttgtgc tgcatcatat cggcccatct accgtggaaa   3960
gccagtagaa aagtgtccac tcagtggggc ctgctattcc cctgagttca aaggtcaaat   4020
ctgcagggtc accacagtga cagagattgg caaagatgtg attggtttaa ggatcagtcc   4080
tctgcagttt cgctaaggcc ccctttgtgt gcatgggtca gtcaccatat gttcccccca   4140
gagaatgtgt ctatatcctc cttctaacag caccttcccc ctgcagctac tcttcagatc   4200
tggctctctg taccctaaaa cctagtatct ttttctcttc tatggaaaat ccgaaggtct   4260
aaacttgact tttttgaggt cttctcaact tgactacagt tgtgctcata attgtccttg   4320
cctttccagc ttaattattt taaggaacaa atgaaaactc tgggctgggt ggagtggctc   4380
atacctgtaa tcccagcact ttgggaggct acggtgggca gatcatctga ggccaggagt   4440
tcgagacctg cctggccaac atggcaacac cccgtctcta ataaaaatat aaaaattagc   4500
ctggcatggt agcatgcgcc tatagtccca gctgctcagg aggctgaggc atgagaatcg   4560
cttgaaccta ggaggtggag gttgcattca actgagatca taccacttca ttccagcctg   4620
```

ggtgacagag caagactctg tctcaaaaaa aaaaaaaagg aaaactctgt gatggacatt 4680
tgtttagtaa atcccttcag tatttatccc tcctttcccc acagcagctt tctttcctgt 4740
caactagaaa ggagcaggat gtaataaata catttggtg tgactaggcc acaccaactc 4800
ttaatcatct cccattttcc ttagacattt aaatttcaag gcaggtaccc tctgtgtact 4860
cagaaatttg aagaagttat ttggttttcc aaaatgcaca ctgcgggtta ttgatttgtt 4920
ctttacaact attgttctca tatttctcac actaaataaa tctctatgag agcttcttga 4980
cttggccatt tatttcttgg acactctcat gttcttgttc acccatgcag gcaccccacc 5040
aaagtacata tcttccttcc agtaataatt tttaattaca aaataaacat ccactattgg 5100
aaaaaaaaaa aaaaagctag ccgggcatgg tggtgggtgc ctgtaatccc agctactctg 5160
gaggctgagg cagaggattg cttgaacccg ggaggcggag gttgcagtaa gctgagatcg 5220
cgccaccgca ctccagcctg ggcgacagag tgagactcca tctcaaaaaa aaagaaagaa 5280
aaaaagaagc acatgttttt catagggtat atatgaggac ctaaactgct gtgaaaatga 5340
tagaaagcaa gtagctccct tattctgttt ttgattgcag ccttttatct tttgctaatt 5400
atagcaatat ttattgagca cctgccatgt gactgtcact gttctagata ttttacatgt 5460
aatatacaga taaaagaata gtactttata tatattacaa tgatacaatg attacattaa 5520
caatacaata ttttgcttgt catatgctaa gaataattgg gtagagtgac attactgtgc 5580
cttcgattaa aataagtact tttttgcgtg ttaaattcat gttttcaata aataataaat 5640
gcatatagtt gaaaaatcag taaata 5666

<210> SEQ ID NO 5
<211> LENGTH: 3570
<212> TYPE: DNA
<213> ORGANISM: Homo sapiens

<400> SEQUENCE: 5
agacaggtca ggacatttgg taggggaagg ttgaaagaca aaagcagcag gccttgggtt 60
ctcagccttt taaaaactat tattaaatat atatttttaa aatttagtgg ttagagcttt 120
tagtaatgtg cctgtattac atgtagagag tattcgtcaa ccaagaggag ttttaaaatg 180
tcaaaaccgg gaaaacctac tctaaaccat ggcttggttc ctgttgatct taaaagtgca 240
aaagagcctc taccacatca aactgtgatg aagatattta gcattagcat cattgcccaa 300
ggcctccctt tttgtcgaag acggatgaaa agaaagttgg accatggttc tgaggtccgc 360
tctttttctt tgggaaagaa accatgcaaa gtctcagaat atacaagtac cactgggctt 420
gtaccatgtt cagcaacacc aacaactttt ggggacctca gagcagccaa tggccaaggg 480
caacaacgac gccgaattac atctgtccag ccacctacag gcctccagga atggctaaaa 540
atgtttcaga gctggagtgg accagagaaa ttgcttgctt tagatgaact cattgatagt 600
tgtgaaccaa cacaagtaaa acatatgatg caagtgatag aaccccagtt tcaacgagac 660
ttcatttcat tgctccctaa agagttggca ctctatgtgc tttcattcct ggaacccaaa 720
gacctgctac aagcagctca gacatgtcgc tactggagaa ttttggctga agacaacctt 780
ctctggagag agaaatgcaa agaagagggg attgatgaac cattgcacat caagagaaga 840
aaagtaataa aaccaggttt catacacagt ccatggaaaa gtgcatacat cagacagcac 900
agaattgata ctaactggag gcgaggagaa ctcaaatctc ctaaggtgct gaaaggacat 960
gatgatcatg tgatcacatg cttacagttt tgtggtaacc gaatagttag tggttctgat 1020

```
gacaacactt taaaagtttg gtcagcagtc acaggcaaat gtctgagaac attagtggga   1080
catacaggtg gagtatggtc atcacaaatg agagacaaca tcatcattag tggatctaca   1140
gatcggacac tcaaagtgtg gaatgcagag actggagaat gtatacacac cttatatggg   1200
catacttcca ctgtgcgttg tatgcatctt catgaaaaaa gagttgttag cggttctcga   1260
gatgccactc ttagggtttg ggatattgag acaggccagt gtttacatgt tttgatgggt   1320
catgttgcag cagtccgctg tgttcaatat gatggcagga gggttgttag tggagcatat   1380
gattttatgg taaaggtgtg ggatccagag actgaaacct gtctacacac gttgcagggg   1440
catactaata gagtctattc attacagttt gatggtatcc atgtggtgag tggatctctt   1500
gatacatcaa tccgtgtttg ggatgtggag acagggaatt gcattcacac gttaacaggg   1560
caccagtcgt taacaagtgg aatggaactc aaagacaata ttcttgtctc tgggaatgca   1620
gattctacag ttaaaatctg ggatatcaaa acaggacagt gtttacaaac attgcaaggt   1680
cccaacaagc atcagagtgc tgtgacctgt ttacagttca acaagaactt tgtaattacc   1740
agctcagatg atggaactgt aaaactatgg gacttgaaaa cgggtgaatt tattcgaaac   1800
ctagtcacat tggagagtgg ggggagtggg ggagttgtgt ggcggatcag agcctcaaac   1860
acaaagctgg tgtgtgcagt tgggagtcgg aatgggactg aagaaaccaa gctgctggtg   1920
ctggactttg atgtggacat gaagtgaaga gcagaaaaga tgaatttgtc caattgtgta   1980
gacgatatac tccctgccct tccccctgca aaaagaaaaa aagaaaagaa aaagaaaaaa   2040
atcccttgtt ctcagtggtg caggatgttg gcttggggca acagattgaa aagacctaca   2100
gactaagaag gaaaagaaga agagatgaca aaccataact gacaagagag gcgtctgctg   2160
tctcatcaca taaaaggctt cacttttgac tgagggcagc tttgcaaaat gagactttct   2220
aaatcaaacc aggtgcaatt atttctttat tttcttctcc agtggtcatt gggcagtgtt   2280
aatgctgaaa catcattaca gattctgcta gcctgttctt ttaccactga cagctagaca   2340
cctagaaagg aactgcaata atatcaaaac aagtactggt tgactttcta attagagagc   2400
atctgcaaca aaaagtcatt tttctggagt ggaaaagctt aaaaaaatta ctgtgaattg   2460
tttttgtaca gttatcatga aaagcttttt tttttttttt tttgccaacc attgccaatg   2520
tcaatcaatc acagtattag cctctgttaa tctatttact gttgcttcca tatacattct   2580
tcaatgcata tgttgctcaa aggtggcaag ttgtcctggg ttctgtgagt cctgagatgg   2640
atttaattct tgatgctggt gctagaagta ggtcttcaaa tatgggattg ttgtcccaac   2700
cctgtactgt actcccagtg gccaaactta tttatgctgc taaatgaaag aaagaaaaaa   2760
gcaaattatt ttttttatt ttttttctgc tgtgacgttt tagtcccaga ctgaattcca   2820
aatttgctct agtttggtta tggaaaaaag actttttgcc actgaaactt gagccatctg   2880
tgcctctaag aggctgagaa tggaagagtt tcagataata aagagtgaag tttgcctgca   2940
agtaaagaat tgagagtgtg tgcaaagctt attttctttt atctgggcaa aaattaaaac   3000
acattccttg gaacagagct attacttgcc tgttctgtgg agaaactttt ctttttgagg   3060
gctgtggtga atggatgaac gtacatcgta aaactgacaa aatattttaa aaatatataa   3120
aacacaaaat taaaataaag ttgctggtca gtcttagtgt tttacagtat ttgggaaaac   3180
aactgttaca gttttattgc tctgagtaac tgacaaagca gaaactattc agtttttgta   3240
gtaaaggcgt cacatgcaaa caaacaaaat gaatgaaaca gtcaaatggt ttgcctcatt   3300
ctccaagagc cacaactcaa gctgaactgt gaaagtggtt taacactgta tcctaggcga   3360
tctttttcc tccttctgtt tattttttg tttgttttat ttatagtctg atttaaaaca   3420
```

```
atcagattca agttggttaa ttttagttat gtaacaacct gacatgatgg aggaaaacaa   3480

cctttaaagg gattgtgtct atggtttgat tcacttagaa attttatttt cttataactt   3540

aagtgcaata aaatgtgttt tttcatgtta                                    3570


<210> SEQ ID NO 6
<211> LENGTH: 6326
<212> TYPE: DNA
<213> ORGANISM: Homo sapiens

<400> SEQUENCE: 6

ctccttccct ccctccctcc cccgctgtcc tggcccgccc tgcccggccc gccctgcgag     60

tcagttcgct ggttccctcc ctccctgggc gcgctcgggc cgccgccgcg ctccccgccc    120

tcgagcctcg gtgccggagc cgcccgccgc cggaggagga ggtggaggga gccggagggg    180

cccgccgagg cggcggcggc ggcggcaaga tggcggactt cctgccgtcg cggtccgtgc    240

tgtccgtgtg cttccccggc tgcctgctga cgagtggcga ggccgagcag caacgcaagt    300

ccaaggagat cgacaaatgc ctgtctcggg aaaagaccta tgtgaagcgg ctggtgaaga    360

tcctgctgct gggcgcgggc gagagcggca agtccacctt cctgaagcag atgcggatca    420

tccacgggca ggacttcgac cagcgcgcgc gcgaggagtt ccgccccacc atctacagca    480

acgtgatcaa aggtatgagg gtgctggttg atgctcgaga gaagcttcat attccctggg    540

gagacaactc aaaccaacaa catggagata agatgatgtc gtttgatacc cgggcccccca   600

tggcagccca aggaatggtg gaaacaaggg ttttcttaca atatcttcct gctataagag    660

cattatgggc agacagcggc atacagaatg cctatgaccg gcgtcgagaa tttcaactgg    720

gtgaatctgt aaaatatttc ctggataact tggataaact tggagaacca gattatattc    780

catcacaaca agatattctg cttgccagaa gacccaccaa aggcatccat gaatacgact    840

ttgaaataaa aaatgttcct ttcaaaatgg ttgatgtagg tggtcagaga tcagaaagga    900

aacgttggtt tgaatgtttc gacagtgtga catcaatact tttccttgtt tcctcaagtg    960

aatttgacca ggtgcttatg gaagatcgac tgaccaatcg ccttacagag tctctgaaca   1020

tttttgaaac aatcgtcaat aaccgggttt tcagcaatgt ctccataatt ctgttcttaa   1080

acaagacaga cttgcttgag gagaaggtgc aaattgtgag catcaaagac tatttcctag   1140

aatttgaagg ggatccccac tgcttaagag acgtccaaaa attcctggtg gaatgtttcc   1200

ggaacaaacg ccgggaccag caacagaagc ccttatacca ccacttcacc actgctatca   1260

acacggagaa catccgcctt gttttccgtg acgtgaagga tactattctg catgacaacc   1320

tcaagcagct tatgctacag tgatgtacaa aagacttgct gttttaatat ctttttgtgt   1380

ttttgatgtt ttctgtttgt tttgtttttt aaaatagcag tttacaacca gaattagaac   1440

aatcttaatt ctacgtttaa cttcttgaaa atcttagtac tttttctgcg gcctttggtt   1500

tgtggctgaa agctgttgag tgactcatcg ccaagatttg ctgtaatgca ggctttgatc   1560

tgtttcacca tggcttctat tcaagtccag ttaaaacctc ccagctgacc tcagactagg   1620

catatttcag gctttaaatt attctacttt ccaaactgaa ttctcctgca gtgccaagta   1680

tcaaaggtgt ccttaaatac ttgtagggat gaggttagga atattcagtt ccaaaacaag   1740

atatcttctg tccgccttac atatagcagt gacacttgtt gcctaacttt atggtgacct   1800

cctattttgt aagggctgtt agaagttcta tctaagaaat ggcattctgt aggtttatag   1860

aaggtttagc cttcatattt taattgcttg tatacacaac agctgttttg cttttagatt   1920
```

```
tctgtgtttc tgaaggtaat gttcttcctg ttttcaagtt tacataagga tctttggtct    1980

gatgctgatg aagagttcac aggtggtatg ggagagcaaa aggcaagcta atgctgttta    2040

ccgtgttttg gtcaaacgta acgagtgaaa tagaatttgc ctttctcata tttaattatc    2100

atgtagttta atgtaccata tgtgaaacat tctggccata gcagcaacta aaaactgcaa    2160

gcaacttggt aacagaactt tctaaataaa cttaacctgt tccagaatgt catgtatttg    2220

acttttaagc cctatctcag ttggtcagta aagaccaatc cttactgtag gaaatcattg    2280

ttgtatcatc acaaacatct atcttttgct gtcctgtcca gtcccatcaa ctccacactg    2340

tgccatttgt ggcatcgttt tgtttatttg gagtttgcta agggcagtat ttttctgtca    2400

agactattca agaaggcatt atttgagatt cctgttcatt cttggtgtgt ctctaacaga    2460

tacagtatgt atacatttgt ataattgttg ttgttgaaag tccagctttt ttgaggtata    2520

ttttaaatgt tttaaggatg cttctaagga tcagtagtaa ttttttttagt tcgcacctaa    2580

agatgattac attgacctcc cccgactgct taccaaatta aaatgtgtcc acgaagtagc    2640

tttgtgatcg cagatacatt catagtgaac tcatcagaat ggctggtttg cagtactgaa    2700

atactatctt ctaggctgta tgtagtgcta caattagaga aacagaagtc caaggctggc    2760

gacagcttga aaagtctgac agcttttcta cttttcctga aaattttaag actgtgatat    2820

ctgtcatttt actgtatagc tgactgtgta ctcaggtatt ttattggtcc ttgaaagatt    2880

ggtcgttatg gatcacccag cctttccaag tcagtggctg ttgttctgtc ttgctgtctg    2940

atacgagagt ggggcttttc agtgaactaa ccagggattg ttcttgacat acctgacttt    3000

tctcacattt gaacttccac tatcattgta tccatataac ttctagcatt ttcatgccat    3060

ggtaatccat gagctacaca tacgtagccc ggcaccgtga tgcaagttca tggtatcgtg    3120

catgttcgtg gtatcatggt atcattcatg cgtgtttgaa tagttctaca tctagtgctt    3180

cttgccaaaa agaatacatt gtttaaattc acaaaattag cataattgca gtgctaatga    3240

atatcggaat atgtgcacag taacatttgg actattcatt ggagagttta cccatacatt    3300

tagcaaattg aatggccaaa acatttgact ccagtgaggg ctcaagttag atccctatag    3360

aaagaggaca cttcatctta cttaagtcat agttaagatc tgtgatacga accatagata    3420

ttgcctgaca aagcagaaat caccaagttt cccccttttg aattaccacc aagaagtgtt    3480

gaaacaccaa atagatatca tgttattttg ggcatttgca gttttcttcc ctgctgcatg    3540

taatgtctca gaatcaacat tctttaaaa tctagactat attttgaggc aatgaattac    3600

ttatattcaa cttaggcttg ttttgacatt cagtagaact ttaagttcaa tctaaaggct    3660

tcagtccaca ttttttttata cgttgtattt taaaaacgtt tgaaaggagt cttacacctg    3720

tatcatgaaa actgaatcct tttgaaatac cactatatga agagagagat gaaatttagt    3780

gaacagaatt gaaaaggtgc tcataatttc actatgcaaa cttaccccag tctctaaaaa    3840

agtaatttag atttaaagtt ctttgatgta tttgattttc taaatcttta tggttatgat    3900

ttggaataaa atgtgcctaa tcctgtgtta cattctgttc ttaaatctga atgccttctc    3960

atttaattct gaggaaatat cacacaagtg tcttcattga ccttgaagaa atgtatatac    4020

agttgcctta taaacaaca taaatttaga ccataacttt tatagagaaa gggttttgtc    4080

aaatgttttc tgaaaatctg agtaattcaa agcatgcctc tgccccttta atattttaa    4140

taacctgcat tgttgctgtc tgccaaatat taaattgaaa tcttcatttc aattttatta    4200

tctggaaagg gcactggatt gctctgcaac caaagaaagc aatatggaat gaaaaaactc    4260

attcactttt gtcttatttt cttttaaggt gtattggcat gtaatttgca tagagaaggt    4320
```

```
cctctggtta gtctctcaaa ttgaggctgt ttagggaaat ccttattcag ttggtggcag   4380

tggttggttt aaagtagaag gaaataagat cgccttaata ccagaaatga ttagaagtgc   4440

tgatttagat tcaacaaata ccatatgtcc ttatcatttt ttgtaagaag aaattggtta   4500

agtcctaact ttcaatgtgt acccaaatac ttgtatttat gcttttgata aaatgtattt   4560

tcagcattaa tacacatccg attatgcctt atttatatat gaagaataaa gttaccatgt   4620

tacactgtta tgtcctaaaa ttcaaatcac tatttgagaa accctcaaat tggtgctttc   4680

attatataat gatacattta gacaaaaccc caaactaagc catttgaaac aagattctct   4740

ccattgcagt ttgtagcaat gttatttctg tgtatgtcat gagaaggcta aatatcagtg   4800

ttaatttctt gtttgaatcc gtgaaatcat gcctgtaaag cccaaacatt tgtaacaaac   4860

tccctaataa atttagagaa agtcactctg ttaccatttc atttatttta gttttatttg   4920

agaaattaag accagaagtt ttgctcatgt ctttttcact tggaaatctg acttagtacc   4980

tagttaattt gtctctctcc catcatttta aggcgttcgc ttctgttaat cacagatgat   5040

ctgtccttgt gttgtgctgc ttgactaaaa gcactgtttt gttttgtttt gttttgtttt   5100

ttaatgatag gatacagggt ggcttttcag tctagtaaac atgaggaggg gagagattgt   5160

gggtgggtgt gggtgtgtcc gcatgtccca aatacagcac atgcccattt ttttatggta   5220

cgaggttagg gcttattaat aaatgtatac tagatcttga agtgtaagtc taagtctgaa   5280

cattttaaac aagttggact ttatggcttt ttcaagttcc atcaagtaga tactagtctt   5340

aggctggtag gtgattaaca acatcatttg gagtacagtg tttgtaccac tagcattctt   5400

atgtctgtac ttgaacgtgt agttagcatt taagttatgt tcactcttgt agcattcagg   5460

tcttaccatc tggtttcaaa tgcgagagct tatatgaaca ttgttttgaa agcatgaatg   5520

atatggcaat attttatgtc ttgataagga gagttttgtg acatatacaa atctgctgtt   5580

gatgatgaaa gtttacaggt ggatcagagt atgctggaac tcagtgtgca taaaatttca   5640

gtcagtgaat atcactgaac gtcatatact acttggtatg tgactttggt ttgtgttaag   5700

aaagcttgta tataatattt tttgccatag taagtgagaa attgtcctta atcatgcctg   5760

tttgatggta ctaggaaaga aaggggtaga gattaattct tgcacagtat aagcaacagt   5820

gcaacaaact atgccattta ccttttacct cttacttgaa ggcagaatcg caaaacgttt   5880

gaaatggctt ttctaaacta ctctactctg gtgagagctc atttaccaca agaagcctta   5940

taaaaaagta tattttgtaa taaccccgta gatactgtac ctaacaaaac atgactcgta   6000

ttagctctat aaaatatttg tggcttagga tttttttttt acatatatct ttttataact   6060

ttccaggaac taagcacatt atctgataat tgttgtaaat ttttttgtca gtgctttagt   6120

tcaggatggg caataaatta tttctaaagg aggtctaaaa gtggaaagaa tggtttgatt   6180

ttataaaatg agttgctagt tcattacagc tttttacttt tgtacatatt ttgcaaaaca   6240

tttgcctctt gctattaata tttgctttgt aaaaattact gacatttaat aaacatttgt   6300

aaacaattca aaaaaaaaaa aaaaaa                                        6326
```

<210> SEQ ID NO 7
<211> LENGTH: 1718
<212> TYPE: DNA
<213> ORGANISM: Homo sapiens

<400> SEQUENCE: 7

```
gagggtgcat aagttctcta gtagggtgat gatataaaaa gccaccggag cactccataa     60
```

-continued

```
ggcacaaact ttcagagaca gcagagcaca caagcttcta ggacaagagc caggaagaaa    120

ccaccggaag gaaccatctc actgtgtgta aacatgactt ccaagctggc cgtggctctc    180

ttggcagcct tcctgatttc tgcagctctg tgtgaaggtg cagttttgcc aaggagtgct    240

aaagaactta gatgtcagtg cataaagaca tactccaaac ctttccaccc caaatttatc    300

aaagaactga gagtgattga gagtggacca cactgcgcca acacagaaat tattgtaaag    360

ctttctgatg gaagagagct ctgtctggac cccaaggaaa actgggtgca gagggttgtg    420

gagaagtttt tgaagagggc tgagaattca taaaaaaatt cattctctgt ggtatccaag    480

aatcagtgaa gatgccagtg aaacttcaag caaatctact tcaacacttc atgtattgtg    540

tgggtctgtt gtagggttgc cagatgcaat acaagattcc tggttaaatt tgaatttcag    600

taaacaatga atagtttttc attgtaccat gaaatatcca gaacatactt atatgtaaag    660

tattatttat ttgaatctac aaaaaacaac aaataatttt taaatataag gattttccta    720

gatattgcac gggagaatat acaaatagca aaattgaggc caagggccaa gagaatatcc    780

gaactttaat ttcaggaatt gaatgggttt gctagaatgt gatatttgaa gcatcacata    840

aaaatgatgg gacaataaat tttgccataa agtcaaattt agctggaaat cctggatttt    900

tttctgttaa atctggcaac cctagtctgc tagccaggat ccacaagtcc ttgttccact    960

gtgccttggt ttctccttta tttctaagtg gaaaaagtat tagccaccat cttacctcac   1020

agtgatgttg tgaggacatg tggaagcact ttaagttttt tcatcataac ataaattatt   1080

ttcaagtgta acttattaac ctatttatta tttatgtatt tatttaagca tcaaatattt   1140

gtgcaagaat ttggaaaaat agaagatgaa tcattgattg aatagttata aagatgttat   1200

agtaaattta ttttatttta gatattaaat gatgttttat tagataaatt tcaatcaggg   1260

tttttagatt aaacaaacaa acaattgggt acccagttaa attttcattt cagataaaca   1320

acaaataatt ttttagtata agtacattat tgtttatctg aaattttaat tgaactaaca   1380

atcctagttt gatactccca gtcttgtcat tgccagctgt gttggtagtg ctgtgttgaa   1440

ttacggaata atgagttaga actattaaaa cagccaaaac tccacagtca atattagtaa   1500

tttcttgctg gttgaaactt gtttattatg tacaaataga ttcttataat attatttaaa   1560

tgactgcatt tttaaataca aggctttata tttttaactt taagatgttt ttatgtgctc   1620

tccaaatttt ttttactgtt tctgattgta tggaaatata aaagtaaata tgaaacattt   1680

aaaatataat ttgttgtcaa agtaaaaaaa aaaaaaaa                           1718
```

<210> SEQ ID NO 8
<211> LENGTH: 8675
<212> TYPE: DNA
<213> ORGANISM: Homo sapiens

<400> SEQUENCE: 8

```
ctcgttctca tttgggtgtc tgcactgttg gaagctactg cactgtgttt ccacgcagac     60

agagtacagt gggaaaggct ttctccagct gatggatggc tgttctcttt atttggagta    120

tcttactggt tatgtaagcg acctcgagag aaattatcct gacccagatc ggaggatgca    180

gtagtgcttc agctgcagga tttcttagtc gttaacacca cagtgctgat gacaaagagc    240

gagttgtaat cctcatcact gccagggctg agccagagca gacagaaaat cgtcatttgc    300

tcgttggaga cttgttaggt tacagctcct gcttcgttct gtggtcttgg cttttcttcc    360

tatacaatga cgccgctgca agtgagctca gaaatgcttg gtttgagagc catttgcctg    420

tgatttttga agactaaaga agtatttaca ctagatactc ttccagaaca aaatagaaat    480
```

-continued

```
ttcagcaaat acttactgac ctttaaagcc ttgttgtgga tttctgagat ttaaagatac    540
tttaaaattc tcaagaacaa aactttcaaa cctctggttg aaagaaatat acccagttca    600
gtcactgcag tagaattcct tgtagataag caactggatt ttttaactga agatagtgcc    660
tttcagccct accaggacga catagacagc ctaaacccag ttctcaggga caacccgcag    720
cttcatgagg aagtgaaagt ctgggtaaag gaacaaaagg ttcaggagat ttttatgcaa    780
ggtccttatt ccttaaatgg atacagagtg agagtatata gacaagactc tgccacccag    840
tggtttactg gcataattac tcatcatgat ctcttcaccc gcaccatgat cgttatgaat    900
gatcaggtac tagaaccaca gaatgtcgat ccttctatgg ttcaaatgac ctttctagat    960
gatgttgttc actctttgtt aaaaggtgaa aatattggca ttacatcacg acgcaggtct   1020
cgtgccaatc aaaacgtcaa cgctgttcac agccattata cacgtgccca agcaaatagt   1080
cccagaccag caatgaactc ccaagctgct gtaccaaaac agaatacaca ccagcaacag   1140
caacaaagaa gtatccgtcc aaataagagg aagggctcag atagcagtat accagatgaa   1200
gagaagatga aggaggaaaa atatgattat atatcacgag gagaaaatcc taaaggtaaa   1260
aacaaacact tgatgaataa aagaaggaaa cctgaggagg atgaaaagaa actaaatatg   1320
aaaagacttc gaactgacaa tgtttcagac ttttctgaga gcagtgactc agaaaattca   1380
aataagagaa taatagataa ttcctcagaa cagaagccag agaatgaatt gaaaaataaa   1440
aatacttcaa aaataaatgg agaagaagga aaaccccata ataatgagaa ggcaggagaa   1500
gagaccctaa aaaatagcca gcctccctgg gatcaaatac aggaagataa aaaacatgaa   1560
gaagcagaga agcggaagtc tgttgacact cagcttcaag aagatatgat tattcattcg   1620
tcagaacagt ccacagtttc tgatcataat tctaatgatt tacttcctca ggaatgcaat   1680
atggataaaa cacataccat ggaattgcta ccaaaggaga agtttgtatc cagaccaccc   1740
acaccaaaat gtgttattga tattacaaat gacactaatt tagaaaaggt ggctcaggaa   1800
aactcaagta cctttggcct tcagacactt cagaaaatgg atcctaatgt tagtgattca   1860
aaacactcta ttgcaaatgc aaaattcttg gaaacagcaa aaaaagattc tgaccagagc   1920
tgggtcagtg atgtagttaa agtggatcta acccaatcaa gtgttacaaa tgcttcttca   1980
ggaaatgatc acttgaacat ggaaaaagag aagtatgtct cttacatttc tcctttaagt   2040
gcagtttctg tcatggaaga taagctgcat aagcgaagtc cacctccaga gactataaaa   2100
tctaaactta atacttcagt agatactcac aagataaaat ccagcccatc acctgaagtt   2160
gttaaaccca aaataactca ttctcctgat tctgtaaagt ctaaggccac ttatgtgaac   2220
agccaagcta ctggtgaaag aagattggca aataagatag aacatgagct atcaagatgc   2280
agttttcatc caattcctac tcgaagcagt acattagaaa ctacaaagag tcctcttatc   2340
attgataaaa atgagcattt tacagtttac agagatcctg cacttattgg gtcagaaaca   2400
ggagctaatc atatttcacc tttcctaagc cagcatcctt ttcctcttca ctcctcatct   2460
catagaacct gtttaaatcc aggtacccat catcctgcct taactcctgc accccattta   2520
ctagccggat catctagtca aactccatta cctaccatta acactcatcc tctgactagt   2580
ggtccacacc atgctgttca tcaccctcat ttacttccca ctgtgttacc tggagtgcct   2640
actgcctcct tacttggtgg ccacccacga ctagagagtg ctcatgccag cagcttgagc   2700
cacttagcgc tagcacacca gcaacaacaa cagttgttac agcaccagtc acctcatctt   2760
cttggacaag cccatccttc tgcttcatat aatcagcttg gactttatcc aattatttgg   2820
```

-continued

```
cagtatccaa atggaacaca tgcatactca ggacttggtt tgccttcttc taagtgggtt   2880
cacccagaaa atgcagttaa tgctgaagct tcattaagga ggaattctcc cagtccttgg   2940
ctacatcagc ccacccctgt gacctcagca gatggtattg gattacttag tcacattcct   3000
gtcagacctt ccagtgcaga gcctcatcgg cctcttaaaa ttacagccca ttccagtcca   3060
ccattgacaa aaactttagt agatcatcat aaggaagaat tagaaagaaa agcttttatg   3120
gaaccattac ggtctgttgc atccacatca gccaaaaatg acctggatct aaataggtca   3180
cagactggaa aagattgtca cttacatagg cattttgtgg atccagtatt aaatcagtta   3240
cagaggccac cccaggagac tggagagagg ttaaacaaat acaaagagga acaccgtcga   3300
attcttcaag aaagtattga tgttgctccc tttacaacta aaatcaaggg acttgagggt   3360
gagagagaga attattccag agtggcatca tcatcttcca gtcctaaaag ccatatcatc   3420
aaacaagata tggatgtaga acgctcagta tcagatcttt ataaaatgaa gcactcagtg   3480
cctcagagtt taccccaaag taactatttc actacattgt ctaatagtgt ggtcaatgaa   3540
ccaccaagat catacccatc caaagaagtt tcaaatattt acggtgataa acagagtaat   3600
gcccttgcag cggcagcagc taatcctcaa actctgactt catttataac atctctttca   3660
aagcctccac ctttgattaa acaccaacca gaaagtgaag gtttagtagg caagatacca   3720
gaacatcttc cacatcagat tgcatctcac tcagtaacaa ccttcagaaa tgattgtagg   3780
agtcctaccc atttgacagt ttcttctaca aatacactcc gcagtatgcc tgcattacat   3840
agagcaccag tatttcaccc accaatccat cacagcctgg aaagaaagga aggcagctat   3900
agtagtcttt cccctccaac tttaactccg gtgatgccag taaatgctgg tggtaaagtt   3960
caagaatcac agaagcctcc aactctaata cccgaaccaa aagactccca ggcaaatttt   4020
aagagttctt cagaacagag tttgacggag atgtggagac ctaataataa cctcagcaaa   4080
gagaaaactg aatggcatgt ggagaaaagc agcggaaagt tacaggctgc tatggcatct   4140
gtcattgtgc gtccatcttc tagtacaaaa actgatagta tgccagcaat gcagttagct   4200
tctaaagatc gagttagtga aagatcttca gctggggcac ataaaacaga ttgcctcaaa   4260
ctagcagaag ccggagaaac tggaagaatc attttgccaa atgtgaattc agacagtgtt   4320
cacacaaaat ctgaaaaaaa ctttcaggct gtctcacagg gcagtgttcc cagttcagtc   4380
atgtctgctg taaatacgat gtgtaatacc aaaacggatg taatcacatc tgctgccgat   4440
actaccagtg tttccagctg gggtggttca gaagtaattt cctctttatc aaataccatt   4500
ttggcctcta catcatcaga atgtgtatct tcaaaaagtg tcagtcagcc agtggctcaa   4560
aaacaagaat gcaaggtcag caccacagca ccagttacat tagccagtag taagacagga   4620
agtgttgttc aacccagttc tgggttctca ggcacaactg attttatcca tttaaaaaag   4680
cacaaggcag cattggctgc agctcagtat aaaagtagta atgccagtga gactgaacct   4740
aatgctataa aaaatcagac actttcagcc tcccttcctc tggatagcac tgtaatctgt   4800
agtacaatta acaaagcaaa ctctgtagga aatgggcaag cttcccagac aagtcaacca   4860
aactaccata ctaaactgaa aaaggcctgg ctcaccagac actcagaaga agataaaaat   4920
actaataaaa tggaaaattc agggaattct gtatcagaaa ttattaagcc atgttctgtc   4980
aacttaatag cctctacatc tagtgatata caaaatagtg tagatagtaa gatcatagtt   5040
gataaatatg taaaagatga taaagtcaac aggagaaaag ccaaaagaac ttatgaatct   5100
ggctctgaaa gtggagactc agatgaaagt gaaagcaagt cagagcaaag gactaaaaga   5160
caacctaagc caacttacaa aaagaagcaa aatgatttgc aaaagagaaa aggtgaaata   5220
```

-continued

```
gaagaagatt tgaaacccaa tggagttctc agcaggagtg ccaaagaaag aagtaaactg   5280

aagttgcaaa gcaacagtaa tactggcatt cctcgttcag tattgaaaga ttggcgtaaa   5340

gtcaagaagc tgaagcaaac tggggaatcc tttttacagg atgactcctg ctgtgagata   5400

gggcctaatt tacaaaagtg tcgagaatgt agacttattc gcagtaaaaa aggagaagaa   5460

ccagctcact caccagtatt ttgtagattt tactacttta gacggttgtc atttagtaaa   5520

aacggagtag ttagaataga tggtttctct tctcctgacc aatatgatga tgaagctatg   5580

agtttgtgga cacatgaaaa ttttgaagat gatgaactag atatagagac ttctaaatat   5640

atcttggata taataggtga taagttctgt caattagtaa catctgaaaa aacagctttg   5700

tcctgggtga aaaaggatgc caaaattgcc tggaaaagag cagtgagagg agtccgggag   5760

atgtgtgatg catgtgaagc aacattgttt aacattcact gggtctgcca aaaatgtgga   5820

tttgtggtct gcttagattg ttacaaggca aaggaaagga agagttctag agataaagaa   5880

ctatatgctt ggatgaagtg tgtgaaggga cagcctcatg atcacaaaca tttaatgcca   5940

acccaaatta tacctggttc tgttttgaca gatcttctag atgccatgca cactcttagg   6000

gaaaaatatg gtattaaatc ccattgtcat tgtactaaca aacagaattt acaagttgga   6060

aattttccta caatgaatgg tgtatctcaa gttttacaga atgttcttaa tcacagtaat   6120

aaaatttctc tgtgcatgcc tgagtctcag cagcaaaata ctcctccgaa gtctgagaaa   6180

aatggtggca gcagcccaga gagtgatgta ggcacagata acaagttaac tcctccagaa   6240

tcccagtcac cactgcactg gttagcagat cttgcagagc aaaaagccag agaggaaaaa   6300

aaagaaaaca aagaacttac ccttgaaaac caaattaaag aagaaagaga acaagacaac   6360

tctgaatctc caaatggcag aacatcacct cttgtgtccc agaataatga acaaggctca   6420

accttacggg atttgctgac tacaacagct ggaaagctac gtgtggggtc tacagatgct   6480

ggcattgcct ttgccccagt atattcaatg ggagccccaa gtagcaaaag tggacggact   6540

atgcctaaca ttcttgatga cataattgct tcagttgttg aaaacaaaat tccaccaagt   6600

aaaacctcca agataaatgt aaaaccagag cttaaagaag agcctgaaga aagcataata   6660

tctgcagtgg atgaaaataa taaattatac agtgatatac cacattcttg gatctgtgag   6720

aagcatattt tatggcttaa ggattataag aatagcagta attggaagct tttcaaagaa   6780

tgttggaaac aaggacagcc tgcagtggtt tctggtgtgc ataagaaaat gaacattagc   6840

ctatggaagg cggaatcaat tagtcttgat tttggagacc accaagctga tctcctgaac   6900

tgcaaagata gcatcatttc aaatgccaat gttaaggaat tctgggatgg ttttgaagaa   6960

gtttcaaaac ggcagaaaaa caagagtgga gaaacagttg ttttaaaatt gaaagactgg   7020

ccttcaggag aagacttcaa gactatgatg ccagcaagat acgaagatct tttaaaaagt   7080

ctgccattgc cagaatattg taatccagaa ggaaaattca atttggcctc tcatttgcca   7140

ggatttttttg tacgtcctga tctaggaccc aggttgtgca gtgcctatgg tgtagttgct   7200

gctaaagatc atgatatagg aacaacaaat ctccatattg aagtttctga tgttgtaaat   7260

atactagttt atgttggcat agcaaaagga aatggcattc tctcaaaagc aggaattctc   7320

aagaaatttg aggaagaaga tttggatgac attttaagga aaagattgaa ggactcaagt   7380

gaaatacctg gtgctctgtg gcatatttat gctgggaaag atgttgacaa gataagggaa   7440

tttcttcaaa agatttcaaa agaacaaggc cttgaagttc taccagaaca tgatccaata   7500

cgtgaccaaa gttggtatgt gaacaaaaag ctccgtcaaa ggctgcttga agaatatgga   7560
```

gtcagaacct gtactcttat tcagttcctt ggtgatgcta ttgttttgcc agcgggagca 7620
cttcatcagg ttcagaattt tcacagctgt attcaggtaa ctgaagattt tgtgtctcca 7680
gaacatcttg tagagtcatt tcatttaaca caggaactga gacttttgaa ggaagaaatc 7740
aattatgatg ataaactaca ggttaaaaat attttgtatc atgcagtcaa agaaatggtg 7800
agagccttga agatacacga ggatgaagta gaggatatgg aagaaaatta agtgtgatcc 7860
agtttgatat ttttaggttg ttgaactggg attacttaac cttgaatgat gatatgtatg 7920
cacactgact ttaagcttca taaaaccatc agtgccaaga aattctcttt gtagtaatta 7980
cttgttactg acaccacagc agtatagcat atgtcacagc tcctgtgatt caatgttata 8040
aaacaagcag aattttaaaa gcagcactat atagctgttt tgtattatag tgtatatgat 8100
gtttgtgaaa atgccagatt taaaatgatg tatttatttt tggtaaaaaa taaaaaattc 8160
tatgctatat tgttgatcaa gtgtaaatgt gaccttgtac agtttactaa aattactgat 8220
atttttcact acattgagac agttactgtg agaataggac acaaacacca gctattgcct 8280
gcatctggga aattgctgaa tcgcacagca gtcatgtcat aatcagaaaa ttactgccaa 8340
ataattgtaa aatttgtaaa gtataaagta tataaagtag atactaaata cagacacttc 8400
aatattttgt tgaagctatt gactgtacaa ttaaacattt tcaaaaggtg taatttattt 8460
aaaattgtct cattttggta aaatttatgt gaacttttaa agctaaatat taaacttaat 8520
atgctatgta aatatataca tatatacatt taatgatgta ttttttttaaa acattggctt 8580 gcttttgtta aagtgcaagt gttacatatg gctttgtaca ttaaagttga aaggggtttt 8640
acattttcca ttaaaaggac tttatcaaaa attga 8675

<210> SEQ ID NO 9
<211> LENGTH: 4203
<212> TYPE: DNA
<213> ORGANISM: Homo sapiens

<400> SEQUENCE: 9
tgacaacatg gcggcgccca tggtccgtgg cccggcagtg ctcgcctaaa ggtggagaac 60
gaggagtaga ggagccgcag gccagagcct gtgagcagat ccagacctac agataaaaaa 120
cattatttaa tctatctggg atttactccg gcttatgatt tgagggcctt ctcaccttct 180
gaagaatggc ttctgtttgg cagagattgg gtttttatgc ctctcttctg aaaagacagc 240
taaatggtgg gccagatgtc atcaagtggg aaaggagagt aattcccgga tgtaccagaa 300
gcatctacag tgccacggga aagtggacaa aagagtatac attgcagaca agaaaggatg 360
ttgagaaatg gtggcatcaa cgaataaaag aacaggcctc caaaatttca gaagctgata 420
aatcgaagcc aaaatttac gtgctttcca tgttccctta tccttctggt aagctgcaca 480
tgggccatgt gcgtgtctac accatcagcg acaccatagc acggttccag aagatgagag 540
ggatgcaggt catcaacccc atgggatggg atgcttttgg attgcctgct gaaaatgccg 600
cagtcgagag gaatctacat ccacaaagtt ggacacaaag taatattaaa cacatgagga 660
aacagcttga tcgtctgggc ctgtgtttca gctgggatag ggaaataact acgtgtttgc 720
cagattacta caagtggact cagtatctct ttattaaact gtatgaggct gggctggcct 780
atcaaaagga ggccctggtt aactgggacc cagtggatca aacagtgctt gccaatgagc 840
aggtggatga acatggctgt tcatggcgtt ctggagcaaa ggtggaacag aagtacctca 900
gacaatggtt tattaagaca accgcttatg caaaggccat gcaggacgcg ttggcagacc 960
ttccagaatg gtatggaata aaaggcatgc aagcccactg gattggggac tgtgtgggct 1020

```
gccacctgga cttcacatta aaggttcatg ggcaagccac gggcgaaaag ctgactgcct   1080
atacggccac ccctgaagcc atttatggca cctcccacgt ggccatctcg cccagccaca   1140
gactcctaca tgggcacagc tctctgaagg aagccttgag gatggccctt gtccctggca   1200
aagattgcct cacgcctgta atggctgtga acatgcttac ccagcaggag gtccctgtcg   1260
ttattttggc caaagctgac ttggaaggct ctctggattc aaaaaatagga attcccagta   1320
ctagctcaga ggacaccatc ttagcccaaa ccctgggcct ggcctactct gaagtcattg   1380
aaactttgcc agatggcaca gagagactga gcagctctgc tgagttcaca ggtatgaccc   1440
ggcaggatgc ttttctagcc ctgactcaga aagcccgggg gaagagagtg ggtggagacg   1500
tgacaagtga taaactgaaa gactggctga tttcacggca gcggtactgg ggcacaccaa   1560
tccccattgt ccactgccca gtctgtggcc ccacacctgt gcccctggag gacttgcctg   1620
tgaccctgcc caacatcgcg tctttcactg gcaagggagg ccccccactg gccatggctt   1680
cagagtgggt gaactgctcc tgcccaaggt gcaagggagc agccaagaga gagacagaca   1740
cgatggatac ctttgttgat tctgcttggt actacttcag atacactgac cctcataatc   1800
cacacagccc ttttaacaca gcagtggccg attactggat gcctgtggat ttgtacattg   1860
gagggaaaga acatgccgtc atgcacttgt tctatgcaag attctttagt catttttgcc   1920
atgatcaaaa aatggttaaa catagggagc cttttcataa gctgctggcc caaggcctta   1980
tcaaggggca gacattccgc ctaccatctg gacagtatct acagagagag gaagtggatc   2040
tcacaggttc cgttcctgtt catgcaaaaa cgaaagagaa gttagaggtg acgtgggaga   2100
agatgagtaa gtccaaacac aacggggtgg acccagagga agttgtggag cagtatggga   2160
tcgacacgat tcggctctac atcctttttg ctgcccctcc tgagaaggat atcttgtggg   2220
atgtgaaaac tgatgctctc cctggggtgc tgagatggca acaacgactg tggaccttga   2280
caactcggtt tattgaggcc agggcttctg ggaagtctcc ccagcctcag ctgctgagta   2340
acaaggagaa agctgaggcc aggaagctct gggagtacaa gaactccgtc atctctcagg   2400
tgaccaccca tttcacagag gacttctcac tgaattctgc aatttctcag ctgatgggac   2460
tcagcaatgc cctctcgcaa gcctctcaga gcgtcattct ccacagcccc gagtttgagg   2520
atgctttgtg tgccctgatg gtaatggctg ctccactggc ccctcatgta acctcagaga   2580
tctgggcagg cctggcgctg gtgccgagga agctctgtgc ccactacact tgggatgcca   2640
gtgtgctgct ccaggcatgg cctgctgtgg acccggagtt cctgcagcag cctgaggttg   2700
tccagatggc agttctgatc aacaataaag cttgtggcaa aattcctgtg ccccaacaag   2760
ttgcccggga ccaggacaaa gtccacgaat ttgttcttca aagcgagctg ggtgtcaggc   2820
ttttgcaagg acgaagcatc aagaagtcct tcctttcccc gagaactgcc ctcatcaact   2880
tcctggtgca agattgacag ccaggaggct gcagctacca cgagggcctc tgaggaacct   2940
ccttccaggc ctgggatgag ggggcgatgt ctgctggccc aggggaaggg aaaagacaaa   3000
tgtcttgact gttgacctcg gtcctgtggc agactgcagt caacagtgtg cctctgtagt   3060
gtggcctggt gctggggtga aggtgagctg ggcaaaggag aaatatgagc tactgaggag   3120
ggggttggac atcctgcccc tcacccccca cccacactgc aggtagagga ggccatctga   3180
tcccatggga agccatcaga gacactgctg gtgggagcag gaaggagcag tgcccctcga   3240
gcagccagga agcctgcgga tctgggaaat ggctctgcct taggcacttc tcgggaattt   3300
gaggccagcc tgaggaactg caggactcag gtgcaatgtg ccagccactt ggaactgcta   3360
```

```
actgagcctc cagatggtag tgaatggtct ctttgccttc aggctggatg aggaagtcat   3420
ttaggaaatg ttcaaataac caatatgtgg aaatggacac agggatcttc tgaagttgct   3480
ttgaatcaaa aggcaggcag tgctggttcc tctgcctgtg tccccaccac tccccagctc   3540
tgtcatgcag gcctgtcctc cccaacccca gctggatgtg cctcccaggc ctgctgtggt   3600
tctgacacac aggatcccag gcaaggcacc acttcctcac atgaatgagg agcagcaagt   3660
cataaccact cccttgggta tacaatttgc tgtgtagtga agtggaacca ggctcaggct   3720
gctggtccca acctcagagc cccaccgcag cccagtaggg atgcagcacg ccccagaggg   3780
ctcatgtggg ccccagatgg caatgccacc attgttgatg tgactccaga gccagttatt   3840
aggaagagca agctcaccac agaggagtgg aactgaggcc ccccagatgt tgcctccggt   3900
gtccaagcca cagcggtctg gctgttggga agatggccag gaatggactc ataccattgg   3960
cacattaggc taatcctggt tttatgtgaa gtcagcaatt aagtgttccc actagaactg   4020
acctaagcca ctgattaata tttaatgagg gaaggtaggg gagaatctag ccattttata   4080
atgccagaaa tctatatatg ttatctgatg ccatttttct gaagtagcct cacatgtggt   4140
ccccctgcag ttcagcagtt aacagatgac ttttttagtg taataaaatg tttatcatct   4200
atg                                                                 4203
```

<210> SEQ ID NO 10
<211> LENGTH: 8708
<212> TYPE: DNA
<213> ORGANISM: Homo sapiens

<400> SEQUENCE: 10

```
gtaaaggact ggggccccgc aactggcctc tcctgccctc ttaagcgcag cgccatttta     60
gcaacgcaga agcccggcgc cgggaagcct cagctcgcct gaaggcaggt cccctctgac    120
gcctccggga gcccaggttt cccagagtcc ttgggacgca gcgacgagtt gtgctgctat    180
cttagctgtc cttataggct ggccattcca ggtggtggta tttagataaa accactcaaa    240
ctctgcagtt tggtcttggg gtttggagga aagcttttat ttttcttcct gctccggttc    300
agaaggtctg aagctcatac ctaaccaggc ataacacaga atctgcaaaa caaaaacccc    360
taaaaaagca gacccagagc agtgtaaaca cttctgggtg tgtccctgac tggctgccca    420
aggtctctgt gtcttcggag acaaagccat tcgcttagtt ggtctacttt aaaaggccac    480
ttgaactcgc tttccatggc gatttgcctt gtgagcactt tcaggagagc ctggaagctg    540
aaaaacggta gaaaaatttc cgtgcgggcc gtgggggct ggcggcaact gggggggcgc     600
agatcagagt gggccactgg cagccaacgg cccccggggc tcaggcgggg agcagctctg    660
tggtgtggga ttgaggcgtt ttccaagagt gggttttcac gtttctaaga tttcccaagc    720
agacagcccg tgctgctccg atttctcgaa caaaaaagca aaacgtgtgg ctgtcttggg    780
agcaagtcgc aggactgcaa gcagttgggg gagaaagtcc gccattttgc cacttctcaa    840
ccgtccctgc aaggctgggg ctcagttgcg taatggaaag taaagccctg aactatcaca    900
ctttaatctt ccttcaaaag gtggtaaact atacctactg tccctcaaga gaacacaaga    960
agtgctttaa gaggtatttt aaaagttccg gggttttgt gaggtgtttg atgacccgtt     1020
taaaatatga tttccatgtt tcttttgtct aaagtttgca gctcaaatct ttccacacgc   1080
tagtaattta agtatttctg catgtgtagt ttgcattcaa gttccataag ctgttaagaa   1140
aaatctagaa aagtaaaact agaacctatt tttaaccgaa gaactacttt ttgcctccct   1200
cacaaaggcg gcggaaggtg atcgaattcc ggtgatgcga gttgttctcc gtctataaat   1260
```

```
acgcctcgcc cgagctgtgc ggtaggcatt gaggcagcca gcgcaggggc ttctgctgag   1320
ggggcaggcg gagcttgagg aaaccgcaga taagtttttt tctctttgaa agatagagat   1380
taatacaact acttaaaaaa tatagtcaat aggttactaa gatattgctt agcgttaagt   1440
ttttaacgta attttaatag cttaagattt taagagaaaa tatgaagact tagaagagta   1500
gcatgaggaa ggaaaagata aaaggtttct aaaacatgac ggaggttgag atgaagcttc   1560
ttcatggagt aaaaaatgta tttaaaagaa aattgagaga aaggactaca gagccccgaa   1620
ttaataccaa tagaagggca atgcttttag attaaaatga aggtgactta aacagcttaa   1680
agtttagttt aaaagttgta ggtgattaaa ataatttgaa ggcgatcttt taaaaagaga   1740
ttaaaccgaa ggtgattaaa agaccttgaa atccatgacg cagggagaat tgcgtcattt   1800
aaagcctagt taacgcattt actaaacgca gacgaaaatg gaaagattaa ttgggagtgg   1860
taggatgaaa caatttggag aagatagaag tttgaagtgg aaaactggaa gacagaagta   1920
cgggaaggcg aagaaaagaa tagagaagat agggaaatta gaagataaaa acatactttt   1980
agaagaaaaa agataaattt aaacctgaaa agtaggaagc agaagaaaaa agacaagcta   2040
ggaaacaaaa agctaagggc aaaatgtaca aacttagaag aaaattggaa gatagaaaca   2100
agatagaaaa tgaaaatatt gtcaagagtt tcagatagaa aatgaaaaac aagctaagac   2160
aagtattgga gaagtataga agatagaaaa atataaagcc aaaaattgga taaaatagca   2220
ctgaaaaaat gaggaaatta ttggtaacca atttatttta aaagcccatc aatttaattt   2280
ctggtggtgc agaagttaga aggtaaagct tgagaagatg agggtgttta cgtagaccag   2340
aaccaattta gaagaatact tgaagctaga aggggaagtt ggttaaaaat cacatcaaaa   2400
agctactaaa aggactggtg taatttaaaa aaaactaagg cagaaggctt ttggaagagt   2460
tagaagaatt tggaaggcct taaatatagt agcttagttt gaaaaatgtg aaggactttc   2520
gtaacggaag taattcaaga tcaagagtaa ttaccaactt aatgtttttg cattggactt   2580
tgagttaaga ttatttttta aatcctgagg actagcatta attgacagct gacccaggtg   2640
ctacacagaa gtggattcag tgaatctagg aagacagcag cagacaggat tccaggaacc   2700
agtgtttgat gaagctagga ctgaggagca agcgagcaag cagcagttcg tggtgaagat   2760
aggaaaagag tccaggagcc agtgcgattt ggtgaaggaa gctaggaaga aggaaggagc   2820
gctaacgatt tggtggtgaa gctaggaaaa aggattccag gaaggagcga gtgcaatttg   2880
gtgatgaagg tagcaggcgg cttggcttgg caaccacacg gaggaggcga gcaggcgttg   2940
tgcgtagagg atcctagacc agcatgccag tgtgccaagg ccacagggaa agcgagtggt   3000
tggtaaaaat ccgtgaggtc ggcaatatgt tgtttttctg gaacttactt atggtaacct   3060
tttatttatt ttctaatata atgggggagt ttcgtactga ggtgtaaagg gatttatatg   3120
gggacgtagg ccgatttccg ggtgttgtag gtttctcttt ttcaggctta tactcatgaa   3180
tcttgtctga agcttttgag ggcagactgc caagtcctgg agaaatagta gatggcaagt   3240
ttgtgggttt ttttttttta cacgaatttg aggaaaacca aatgaatttg atagccaaat   3300
tgagacaatt tcagcaaatc tgtaagcagt ttgtatgttt agttggggta atgaagtatt   3360
tcagttttgt gaatagatga cctgttttta cttcctcacc ctgaattcgt tttgtaaatg   3420
tagagtttgg atgtgtaact gaggcggggg ggagttttca gtattttttt ttgtgggggt   3480
gggggcaaaa tatgttttca gttctttttc ccttaggtct gtctagaatc ctaaaggcaa   3540
atgactcaag gtgtaacaga aaacaagaaa atccaatatc aggataatca gaccaccaca   3600
```

-continued ggtttacagt ttatagaaac tagagcagtt ctcacgttga ggtctgtgga agagatgtcc 3660
attggagaaa tggctggtag ttactctttt ttccccccac cccttaatc agactttaaa 3720 agtgcttaac cccttaaact tgttattttt tacttgaagc attttgggat ggtcttaaca 3780
gggaagagag agggtggggg agaaaatgtt tttttctaag attttccaca gatgctatag 3840
tactattgac aaactgggtt agagaaggag tgtaccgctg tgctgttggc acgaacacct 3900
tcagggactg gagctgcttt tatccttgga agagtattcc cagttgaagc tgaaaagtac 3960
agcacagtgc agctttggtt catattcagt catctcagga gaacttcaga agagcttgag 4020
taggccaaat gttgaagtta agttttccaa taatgtgact tcttaaaagt tttattaaag 4080
gggaggggca aatattggca attagttggc agtggcctgt tacggttggg attggtgggg 4140
tgggtttagg taattgttta gtttatgatt gcagataaac tcatgccaga gaacttaaag 4200
tcttagaatg gaaaaagtaa agaaatatca acttccaagt tggcaagtaa ctcccaatga 4260
tttagttttt ttccccccag tttgaattgg gaagctgggg gaagttaaat atgagccact 4320
gggtgtacca gtgcattaat ttgggcaagg aaagtgtcat aatttgatac tgtatctgtt 4380
ttccttcaaa gtatagagct tttggggaag gaaagtattg aactgggggt tggtctggcc 4440
tactgggctg acattaacta caattatggg aaatgcaaaa gttgtttgga tatggtagtg 4500
tgtggttctc ttttggaatt tttttcaggt gatttaataa taatttaaaa ctactataga 4560
aactgcagag caaaggaagt ggcttaatga tcctgaaggg atttcttctg atggtagctt 4620
ttgtattatc aagtaagatt ctattttcag ttgtgtgtaa gcaagttttt ttttagtgta 4680
ggagaaatac ttttccattg tttaactgca aaacaagatg ttaaggtatg cttcaaaaat 4740
tttgtaaatt gtttatttta aacttatctg tttgtaaatt gtaactgatt aagaattgtg 4800
atagttcagc ttgaatgtct cttagagggt gggcttttgt tgatgaggga ggggaaactt 4860
tttttttttc tatagacttt tttcagataa catcttctga gtcataacca gcctggcagt 4920
atgatggcct agatgcagag aaaacagctc cttggtgaat tgataagtaa aggcagaaaa 4980
gattatatgt catacctcca ttggggaata agcataaccc tgagattctt actactgatg 5040
agaacattat ctgcatatgc caaaaaattt taagcaaatg aaagctacca atttaaagtt 5100
acggaatcta ccattttaaa gttaattgct tgtcaagcta taaccacaaa aataatgaat 5160
tgatgagaaa tacaatgaag aggcaatgtc catctcaaaa tactgctttt acaaaagcag 5220
aataaaagcg aaaagaaatg aaaatgttac actacattaa tcctggaata aaagaagccg 5280
aaataaatga gagatgagtt gggatcaagt ggattgagga ggctgtgctg tgtgccaatg 5340
tttcgtttgc ctcagacagg tatctcttcg ttatcagaag agttgcttca tttcatctgg 5400
gagcagaaaa cagcaggcag ctgttaacag ataagtttaa cttgcatctg cagtattgca 5460
tgttagggat aagtgcttat ttttaagagc tgtggagttc ttaaatatca accatggcac 5520
tttctcctga ccccttccct aggggatttc aggattgaga aatttttcca tcgagccttt 5580
ttaaaattgt aggacttgtt cctgtgggct tcagtgatgg gatagtacac ttcactcaga 5640
ggcatttgca tctttaaata atttcttaaa agcctctaaa gtgatcagtg ccttgatgcc 5700
aactaaggaa atttgtttag cattgaatct ctgaaggctc tatgaaagga atagcatgat 5760
gtgctgttag aatcagatgt tactgctaaa atttacatgt tgtgatgtaa attgtgtaga 5820
aaaccattaa atcattcaaa ataataaact atttttatta gagaatgtat acttttagaa 5880
agctgtctcc ttatttaaat aaaatagtgt ttgtctgtag ttcagtgttg gggcaatctt 5940 ggggggggatt cttctctaat ctttcagaaa ctttgtctgc gaacactctt taatggacca 6000

```
gatcaggatt tgagcggaag aacgaatgta actttaaggc aggaaagaca aattttattc   6060
ttcataaagt gatgagcata taataattcc aggcacatgg caatagaggc cctctaaata   6120
aggaataaat aacctcttag acaggtggga gattatgatc agagtaaaag gtaattacac   6180
attttatttc cagaaagtca ggggtctata aattgacagt gattagagta atactttttc   6240
acatttccaa agtttgcatg ttaactttaa atgcttacaa tcttagagtg gtaggcaatg   6300
ttttacacta ttgaccttat atagggaagg gagggggtgc ctgtggggtt ttaaagaatt   6360
ttcctttgca gaggcatttc atccttcatg aagccattca ggattttgaa ttgcatatga   6420
gtgcttggct cttccttctg ttctagtgag tgtatgagac cttgcagtga gtttatcagc   6480
atactcaaaa tttttttcct ggaatttgga gggatgggag gagggggtgg ggcttacttg   6540
ttgtagcttt tttttttttt acagacttca cagagaatgc agttgtcttg acttcaggtc   6600
tgtctgttct gttggcaagt aaatgcagta ctgttctgat cccgctgcta ttagaatgca   6660
ttgtgaaacg actggagtat gattaaaagt tgtgttcccc aatgcttgga gtagtgattg   6720
ttgaaggaaa aaatccagct gagtgataaa ggctgagtgt tgaggaaatt tctgcagttt   6780
taagcagtcg tatttgtgat tgaagctgag tacattttgc tggtgtattt ttaggtaaaa   6840
tgctttttgt tcatttctgg tggtgggagg ggactgaagc ctttagtctt ttccagatgc   6900
aaccttaaaa tcagtgacaa gaaacattcc aaacaagcaa cagtcttcaa gaaattaaac   6960
tggcaagtgg aaatgtttaa acagttcagt gatctttagt gcattgttta tgtgtgggtt   7020
tctctctccc ctcccttggt cttaattctt acatgcagga acactcagca gacacacgta   7080
tgcgaagggc cagagaagcc agacccagta agaaaaaata gcctatttac tttaaataaa   7140
ccaaacattc cattttaaat gtggggattg ggaaccacta gttctttcag atggtattct   7200
tcagactata gaaggagctt ccagttgaat tcaccagtgg acaaaatgag gaaaacaggt   7260
gaacaagctt tttctgtatt tacatacaaa gtcagatcag ttatgggaca atagtattga   7320
atagatttca gctttatgct ggagtaactg gcatgtgagc aaactgtgtt ggcgtggggg   7380
tggaggggtg aggtgggcgc taagcctttt tttaagattt ttcaggtacc cctcactaaa   7440
ggcaccgaag gcttaaagta ggacaaccat ggagccttcc tgtggcagga gagacaacaa   7500
agcgctatta tcctaaggtc aagagaagtg tcagcctcac ctgattttta ttagtaatga   7560
ggacttgcct caactccctc tttctggagt gaagcatccg aaggaatgct tgaagtaccc   7620
ctgggcttct cttaacattt aagcaagctg tttttatagc agctcttaat aataaagccc   7680
aaatctcaag cggtgcttga aggggaggga aagggggaaa gcgggcaacc acttttccct   7740
agcttttcca gaagcctgtt aaaagcaagg tctccccaca agcaacttct ctgccacatc   7800
gccaccccgt gccttttgat ctagcacaga cccttcaccc ctcacctcga tgcagccagt   7860
agcttggatc cttgtgggca tgatccataa tcggtttcaa ggtaacgatg gtgtcgaggt   7920
ctttggtggg ttgaactatg ttagaaaagg ccattaattt gcctgcaaat tgttaacaga   7980
agggtattaa aaccacagct aagtagctct attataatac ttatccagtg actaaaacca   8040
acttaaacca gtaagtggag aaataacatg ttcaagaact gtaatgctgg gtgggaacat   8100
gtaacttgta gactggagaa gataggcatt tgagtggctg agagggcttt tgggtgggaa   8160
tgcaaaaatt ctctgctaag actttttcag gtgaacataa cagacttggc caagctagca   8220
tcttagcgga agctgatctc caatgctctt cagtagggtc atgaaggttt ttcttttcct   8280
gagaaaacaa cacgtattgt tttctcaggt tttgcttttt ggcctttttc tagcttaaaa   8340
```

-continued

```
aaaaaaaaag caaaagatgc tggtggttgg cactcctggt ttccaggacg gggttcaaat   8400
ccctgcggcg tctttgcttt gactactaat ctgtcttcag gactctttct gtatttctcc   8460
ttttctctgc aggtgctagt tcttggagtt ttggggaggt gggaggtaac agcacaatat   8520
ctttgaacta tatacatcct tgatgtataa tttgtcagga gcttgacttg attgtatatt   8580
catatttaca cgagaaccta atataactgc cttgtctttt tcaggtaata gcctgcagct   8640
ggtgttttga gaagccctac tgctgaaaac ttaacaattt tgtgtaataa aaatggagaa   8700
gctctaaa                                                            8708
```

<210> SEQ ID NO 11
<211> LENGTH: 5266
<212> TYPE: DNA
<213> ORGANISM: Homo sapiens

<400> SEQUENCE: 11

```
cttgccggct tccttgcaaa gcccggtgca agggcctctt tcaaaatgaa cccactggtg     60
tgcctagcag tcggtagaag aagcgggagg gcgtccggtc tgcacgcccg ccgcgaggtt    120
acaatgctga acgcatgaga tggaagatac caacgggagg ccgaggggat ccacggcgcc    180
cgcgcgggct ccggcttcct cctgctctcg gcgccgctgg gcgaccgccc atgacccgct    240
cttgcgggct ctgtccggtt gacaggcgac cctgtggccc ggggaagcgc gggagggcgc    300
cggcggaaag ttgaagagcg tttttctcgc cgccgcgtgc attaggagct cgacgagtcc    360
gccctgggct tcctggtggg gctgggcggg cgggggaggg gccgcgcagc agcagcggaa    420
gccagacctc ggcgataaga ggctgcacag cgacatgcaa cagtcttttc actgcagctg    480
aatgagttgt ggcgcccaca atgctcccat gacaaggagc tgacaagttc cattttccgt    540
cgcgggcatc ttggaatcat gactcccaca atgccttggg cacttggtcg acagtggggc    600
cgcctctgaa aaaaaaatgt gagagcagtc actcaggaaa tgttgtttaa ggggaacctt    660
ctggatcctt ttcatggcac catggcaaga agaagctgta tcttatctat ggaagataaa    720
gcatggagtt ggctaatgga tgctgatagg accatctagt tgcaggaaaa caagctcagg    780
gctcccactg attctacatt atgggccgtt gctccaggga gaactgcaaa tatcttcatc    840
cacccccaca tttaaaaacg cagttggaga taaatggacg caataacttg attcagcaga    900
agaacatggc catgttggcc cagcaaatgc aactagccaa tgccatgatg cctggtgccc    960
cattacaacc cgtgccaatg ttttcagttg caccaagctt agccaccaat gcatcagcag   1020
ccgcctttaa tccctatctg ggacctgttt ctccaagcct ggtcccggca gagatcttgc   1080
cgactgcacc aatgttggtt acagggaatc cgggtgtccc tgtacctgca gctgctgcag   1140
ctgctgcaca gaaattaatg cgaacagaca gacttgaggt atgtcgagag taccaacgtg   1200
gcaattgcaa ccgaggagaa aatgattgtc ggtttgctca tcctgctgac agcacaatga   1260
ttgacaccaa tgacaacaca gtcactgtgt gtatggatta catcaaaggg agatgctctc   1320
gggaaaagtg caaatacttt catcccccctg cacatttgca agccaagatc aaggctgccc   1380
aataccaggt caaccaggct gcagctgcac aggctgcagc caccgcagct gccatgactc   1440
agtcggctgt caaatcactg aagcgacccc tcgaggcaac ctttgacctg ggaattcctc   1500
aagctgtact tcccccatta ccaaagaggc ctgctcttga aaaaaccaac ggtgccaccg   1560
cagtctttaa cactggtatt ttccaatacc aacaggctct agccaacatg cagttacaac   1620
agcatacagc atttctccca ccaggctcaa tattgtgcat gacacccgct acaagtgttg   1680
ttcccatggt gcacggtgct acgccagcca ctgtgtccgc agcaacaaca tctgccacaa   1740
```

-continued

```
gtgttccctt cgctgcaaca gccacagcca accagatacc cataatatct gccgaacatc   1800
tgactagcca caagtatgtt acccagatgt agaattttca tcactaaaca atcatgctaa   1860
agaggaaagg acagtgtgct tggttagagt aaaggacgag gtcattagcc atattgtata   1920
tatcgtcaag caacacacac aaaagttcct cagccacaag acatccacat attgcatgtt   1980
aaccagaaga aaagacaaca ttttccggaa atccactgca cactgttgcc tatacacttt   2040
gtacatttaa ttgatatttg tgctgaggtg atattcctgt ctaaaagaac aacattgtct   2100
ttcttttcta gcacagagtt atgcattcaa agatgcatac ctagttagtt tcctatatat   2160
tcatgccatc ttgaaaagac agactatggt gtaaccatga ttctattatg tattggtacg   2220
tctgtagacc aagatataat tttttaaaaa taagtttatt tctttcaagg tttacaaata   2280
acaaaggtgc accttgtatt taaaattgcc attatagatg agagcgtgca tgcacagtca   2340
tttttgttta agagtaatat ttttaatgta atagattgta agacgtggtg agggagggat   2400
ctgacagaga tgaatgtgcc aagcaaaacc acaactgtgt atattttaaa gcacatcatg   2460
gctttaagta ccatgttgtt aaggattctc atgaagtgcc atagactgta catcaaatta   2520
gagtattatt tcttcagtgt tattgttttc agagccacat tttgttgcat atttgctagt   2580
actaatcagt caaagggcac cattcttttt tttttttttt gaaaccaaag ctgtctcaga   2640
aatggccaat ttaactttac agtaacaata gacagcacaa cacaaactct ctcaatacag   2700
ataaactcac acatactgga gatatatata taatagatat atataaaatt attttaatgc   2760
attgtagtgt aatatttatg catactatac tgtataacat gttattcaaa agggattgcc   2820
atttctgaga cacagtaaca aaaaaatgag gaaattattt tgcttctatt tatagcctct   2880
gtcaaaagtc aaaagactat aaatgctttg caaaaatggt ttcacgtttg cttaaatgct   2940
tcatcacagt cacattcaaa atagtgactc taaacaaaga agaaagcagc actgtcatca   3000
gatgcatgat aaaccaaaat atgaaaatgg gaaatgttta attaacctag taattgggtg   3060
ggttaagtac atgggtgaat tttatatgtg atttttgttt tgttttgttt tgttcagatt   3120
aactgcttat agccttagaa agccttttac aaaattaaaa aaaaaataga tgtgcattca   3180
gtttttaaga atggaatcat ccaaaggaat tccttttttt gaggtttgga tgttgcagct   3240
agtaaaggat atttttgctc tgttcagcag ttctaaaaat tgctgaagta ggggccaggt   3300
cactggtagt tatagtatgg aatgggagaa gtgaaagttc agttatagaa ctttccatac   3360
ttccaagttt actgcaagtt tttatgcttg agagagatgc tttctaatat aagactgatg   3420
tgttgatttt actgattgta ctgtacatct attaaagcct tagattatta cattacgggt   3480
tggaacccat accaatgtaa tttcaatcgt gttaagaaag taatggtgac ttcacatgtt   3540
attgtagtta gttacattat agaatattac ttatttttct tgttaaaatg tagtttttca   3600
tttcctacat ttattagatt ttcattttct attaacaatt gaataccatt tcagtttata   3660
gacttgtttt attagatttt accaatgaat ttttcaaaat acaaaaaaaa gtagtttttc   3720
cttcataaca tactcagttt tgaattacat gtagtgtcac atgaatattc gtattgttaa   3780
ctaaatgatt tatattttac tgatttaata ttacagtgta agaatgtcag tcattgttag   3840
ttcttgtcta gttttcatta aaagaacaaa gatcttttat atggatatct tataaatata   3900
taatcattgc taagtaagaa gttaagttgt tgctatcgca acaatcctgg cagacaattg   3960
agtaatattt tgatgattta ttttgtttgt aattagttat tataagaaga tctagatcct   4020
agatattaga ataaaattta ttttctactg tatccatttc aaatgttaaa atattgttta   4080
```

atatttttga aatccctgag tatcaggcct tgttataaat aagctgcata atcaataaat 4140
agaacaaggg actttttgtt gataatccaa atactcaaag tttacgtaat gaaaattata 4200
gcgtgtgtgc aaactcttga gggttgatta tgctgcaatt tagcatgttg gaacgtctag 4260
ggagaaggtt gactttttgc acttctgtat atagtcaaaa gagagaaacc tgtataatag 4320
taagatctta ttttgaataa aaacgtctat aattacaagg agttttgtta aggctaatac 4380
aatgacagac tgagcaaaat tgcttgcaaa agtggcacag agttagcact ccatacccct 4440
tcaaacatgt tgctttgctt tcttgtggac agcttgtagt ttgccaggat tttttcagct 4500
ggaaagatac gccatccttt caaaccctca tgactgacaa aaactccatg ggccaaatc 4560 tgcctgaaga tcattaccaa aaatagcagg tacttctacc attaaggtga aatcatggat 4620
cagatattcc ttacattttt caaaactact gcatgtttaa aacttcaaca aaaaaagaga 4680
gaaagaacta tactaagaac atatattatt cagatcagtt tctgccaatt tcagtggttt 4740
attgttcaca aaaaaatctt caaaacaagt attgactttc acaaaattta aatcataaac 4800
aggcaaacca aacagcacac tgtagctata gttgttatgt gattgttttt taattgctgt 4860
aggatcctgt tctttcagca ggtgaaaaat aaaacgcagt tcaaatttca tggttttaat 4920
tttcaactca gaagcactca aaaatgcaaa atgtgataat gggcacttgt ttaaaagaat 4980
tagtgtatcc agccttcact ccagctggtt aaaaatgttg cacttatcag caaccctacc 5040
actttcatct gctgaaagga caaatgtgct tggttttact attatgtaat cacaacttac 5100
tttctgcttg tagttgctta aaattatgta ttttgtcttg ggctgcaatt tgttttatgc 5160
ttattttatt attactgcag tagttgactt tgctgtatgg aaaaataaag tgaaattgcc 5220
ctaataaaac ttctctttct taagtaaaaa aaaaaaaaaa aaaaaa 5266

<210> SEQ ID NO 12
<211> LENGTH: 3648
<212> TYPE: DNA
<213> ORGANISM: Homo sapiens

<400> SEQUENCE: 12
gcgcaaccct ccggaagctg ccgcccctttt cccctttttat gggaatactt tttttaaaaa 60
aaaagagttc gctggcgcca ccccgtagga ctggccgccc taaaaccgtg ataaaggagc 120
tgctcgccac ttctcacttc cgcttccttc cagtaaggag tcggggtctt ccccagtttt 180
ctcagccagg cggcggcggc gactggcaat gtttggcctc aaaagaaacg cggtaatcgg 240
actcaacctc tactgtgggg gggccggctt gggggccggc agcggcggcg ccacccgccc 300
gggagggcga cttttggcca ccggcgccaa ggacacaaag ccaatgggca ggtctggggc 360
caccagcagg aaggcgctgg agaccttacg acgggttggg gatggcgtgc agcgcaacca 420
cgagacggcc ttccaaggca tgcttcggaa actggacatc aaaaacgaag acgatgtgaa 480
atcgttgtct cgagtgatga tccatgtttt cagcgacggc gtaacaaact ggggcaggat 540
tgtgactctc atttcttttg gtgcctttgt ggctaaacac ttgaagacca taaaccaaga 600
aagctgcatc gaaccattag cagaaagtat cacagacgtt ctcgtaagga caaaacggga 660
ctggctagtt aaacaaagag gctgggatgg gtttgtggag ttcttccatg tagaggacct 720
agaaggtggc atcaggaatg tgctgctggc ttttgcaggt gttgctggag taggagctgg 780
tttggcatat ctaataagat agccttactg taagtgcaat agttgacttt taaccaacca 840
ccaccaccac caaaaccagt ttatgcagtt ggactccaag ctgtaacttc ctagagttgc 900
accctagcaa cctagccaga aaagcaagtg gcaagaggat tatggctaac aagaataaat 960

```
acatgggaag agtgctcccc attgattgaa gagtcactgt ctgaaagaag caaagttcag   1020
tttcagcaac aaacaaactt tgtttgggaa gctatggagg aggactttta gatttagtga   1080
agatggtagg gtggaaagac ttaatttcct tgttgagaac aggaaagtgg ccagtagcca   1140
ggcaagtcat agaattgatt acccgccgaa ttcattaatt tactgtagtg ttaagagaag   1200
cactaagaat gccagtgacc tgtgtaaaag ttacaagtaa tagaactatg actgtaagcc   1260
tcagtactgt acaagggaag cttttcctct ctctaattag ctttcccagt atacttctta   1320
gaaagtccaa gtgttcagga cttttatacc tgttatactt tggcttggtt tccatgattc   1380
ttactttatt agcctagttt atcaccaata atacttgacg gaaggctcag taattagtta   1440
tgaatatgga tatcctcaat tcttaagaca gcttgtaaat gtatttgtaa aaattgtata   1500
tatttttaca gaaagtctat ttctttgaaa cgaaggaagt atcgaattta cattagtttt   1560
tttcataccc ttttgaactt tgcaacttcc gtaattagga acctgtttct tacagctttt   1620
ctatgctaaa ctttgttctg ttcagttcta gagtgtatac agaacgaatt gatgtgtaac   1680
tgtatgcaga ctggttgtag tggaacaaat ctgataacta tgcaggttta aatttctta    1740
tctgattttg gtaagtattc cttagatagg tttttctttg aaaacctggg attgagaggt   1800
tgatgaatgg aaattctttc acttcattat atgcaagttt tcaataatta ggtctaagtg   1860
gagttttaag gttactgatg acttacaaat aatgggctct gattgggcaa tactcatttg   1920
agttccttcc atttgaccta atttaactgg tgaaatttaa agtgaattca tgggctcatc   1980
tttaaagctt ttactaaaag attttcagct gaatggaact cattagctgt gtgcatataa   2040
aaagatcaca tcaggtggat ggagagacat ttgatccctt gtttgcttaa taaattataa   2100
aatgatggct tggaaaagca ggctagtcta accatggtgc tattattagg cttgcttgtt   2160
acacacacag gtctaagcct agtatgtcaa taaagcaaat acttactgtt ttgtttctat   2220
taatgattcc caaaccttgt tgcaagtttt tgcattggca tctttggatt tcagtcttga   2280
tgtttgttct atcagactta accttttatt tcctgtcctt ccttgaaatt gctgattgtt   2340
ctgctccctc tacagatatt tatatcaatt cctacagctt tcccctgcca tccctgaact   2400
ctttctagcc cttttagatt ttggcactgt gaaacccctg ctggaaacct gagtgaccct   2460
ccctccccac caagagtcca cagacctttc atctttcacg aacttgatcc tgttagcagg   2520
tggtaatacc atgggtgctg tgacactaac agtcattgag aggtgggagg aagtcccttt   2580
tccttggact ggtatctttt caactattgt tttatcctgt ctttgggggc aatgtgtcaa   2640
aagtcccctc aggaatttc agaggaaaga acattttatg aggctttctc taaagtttcc    2700
tttgtatagg agtatgctca cttaaattta cagaaagagg tgagctgtgt taaacctcag   2760
agtttaaaag ctactgataa actgaagaaa gtgtctatat tggaactagg gtcatttgaa   2820
agcttcagtc tcggaacatg acctttagtc tgtggactcc atttaaaaat aggtatgaat   2880
aagatgacta agaatgtaat ggggaagaac tgccctgcct gcccatctca gagccataag   2940
gtcatctttg ctagagctat ttttacctat gtatttatcg ttcttgatca taagccgctt   3000
atttatatca tgtatctcta aggacctaaa agcactttat gtagttttta attaatctta   3060
agatctggtt acggtaacta aaaaagcctg tctgccaaat ccagtggaaa caagtgcata   3120
gatgtgaatt ggtttttagg ggccccactt cccaattcat taggtatgac tgtggaaata   3180
cagacaagga tcttagttga tattttgggc ttggggcagt gagggcttag gacaccccaa   3240
gtggtttggg aaaggaggag gggagtggtg ggtttatagg gggaggagga ggcaggtggt   3300
```

-continued

```
ctaagtgctg actggctacg tagttcgggc aaatcctcca aaagggaaag ggaggatttg   3360

cttagaagga tggcgctccc agtgactact ttttgacttc tgtttgtctt acgcttctct   3420

cagggaaaaa catgcagtcc tctagtgttt catgtacatt ctgtgggggg tgaacacctt   3480

ggttctggtt aaacagctgt acttttgata gctgtgccag gaagggttag gaccaactac   3540

aaattaatgt tggttgtcaa atgtagtgtg tttccctaac tttctgtttt tcctgagaaa   3600

aaaaaataaa tcttttattc aaatacaggg aaaaaaaaaa aaaaaaaa               3648
```

<210> SEQ ID NO 13
<211> LENGTH: 3801
<212> TYPE: DNA
<213> ORGANISM: Homo sapiens

<400> SEQUENCE: 13

```
ctcctcttgc cacgaggtca gacggcgagt tcttagagaa aaaggctgct tagctgctgc     60

ttatcatgta acctcaaaag gaaactgatc gtctttctca tgctgtcacg tacttgggtt    120

attatcgctg attacagctg gaaacaattg atttgctctt acgtatttgt gtgacttgac    180

tcttcaaaca caaaggttaa caggaagatc tcgagggccc tggctgaact tcaccttttg    240

gctttcttgg cctgatgctg aactctcgag gttgagcccc atatgggggt tggcaggcag    300

cagagaggcc cctttcaagg tgttcgggta aagaactcag tgaaggaact cctgttgcac    360

atccgaagtc ataaacagaa ggcttctggc caagctgtgg atgattttaa gacacaaggt    420

gtgaacatag aacagttcag agaattgaag aacacagtat catacagtgg gaaaaggaaa    480

gggcccgatt cgttgtctga tggacctgct tgcaaaaggc cagctctgtt gcattcccaa    540

tttttgacac cacctcaaac accaacgccc ggggagagca tggaagatgt tcatctcaat    600

gaacccaaac aggagagcag tgctgatctg cttcagaaca ttatcaacat taagaatgaa    660

tgcagccccg tttccctgaa cacagttcaa gttagctggc tgaaccccgt ggtggtccct    720

cagagctccc ccgcagagca gtgtcaggac ttccatggag ggcaggtctt ttctccacct    780

cagaaatgcc aaccattcca agtcaggggc tcccaacaaa tgatagacca ggcttccctg    840

taccagtatt ctccacagaa ccagcatgta gagcagcagc cacactacac ccacaaacca    900

actctggaat acagtccttt tcccatacct ccccagtccc ccgcttatga accaaacctc    960

tttgatggtc cagaatcaca gttttgccca aaccaaagct tagtttccct tcttggtgat   1020

caaagggaat ctgagaatat tgctaatccc atgcagactt cctccagtgt tcagcagcaa   1080

aatgatgctc acttgcacag cttcagcatg atgcccagca gcgcctgtga ggccatggtg   1140

gggcacgaga tggcctctga ctcttcaaac acttcactgc cattctcaaa catgggaaat   1200

ccaatgaaca ccacacagtt agggaaatca ctttttcagt ggcaggtgga gcaggaagaa   1260

agcaaattgg caaatatttc ccaagaccag tttctttcaa aggatgcaga tggtgacacg   1320

ttccttcata ttgctgttgc ccaagggaga agggcacttt cctatgttct tgcaagaaag   1380

atgaatgcac ttcacatgct ggatattaaa gagcacaatg gacagagtgc ctttcaggtg   1440

gcagtggctg ccaatcagca tctcattgtg caggatctgg tgaacatcgg ggcacaggtg   1500

aacaccacag actgctgggg aagaacacct ctgcatgtgt gtgctgagaa gggccactcc   1560

caggtgcttc aggcgattca gaagggagca gtgggaagta atcagtttgt ggatcttgag   1620

gcaactaact atgatggcct gactcccctt cactgtgcag tcatagccca caatgctgtg   1680

gtccatgaac tccagagaaa tcaacagcct cattcacctg aagttcagga gcttttactg   1740

aagaataaga gtctggttga taccattaag tgcctaattc aaatgggagc agcggtggaa   1800
```

```
gcgaaggatc gcaaaagtgg ccgcacagcc ctgcatttgg cagctgaaga agcaaatctg   1860
gaactcattc gcctcttttt ggagctgccc agttgcctgt cttttgtgaa tgcaaaggct   1920
tacaatggca acactgccct ccatgttgct gccagcttgc agtatcggtt gacacaatta   1980
gatgctgtcc gcctgttgat gaggaaggga gcagacccaa gtactcggaa cttggagaac   2040
gaacagccag tgcatttggt tcccgatggc cctgtgggag aacagatccg acgtatcctg   2100
aagggaaagt ccattcagca gagagctcca ccgtattagc tccattagct tggagcctgg   2160
ctagcaacac tcactgtcag ttaggcagtc ctgatgtatc tgtacataga ccatttgcct   2220
tatattggca aatgtaagtt gtttctatga aacaaacata tttagttcac tattatatag   2280
tgggttatat taaaagaaaa gaagaaaaat atctaatttc tcttggcaga tttgcatatt   2340
tcatacccag gtatctggga tctagacatc tgaatttgat ctcaatggta acattgcctt   2400
caattaacag tagcttttga gtaggaaagg actttgattt gtggcacaaa acattattaa   2460
tatagctatt gacagtttca aagcaggtaa attgtaaatg tttctttaag aaaaagcatg   2520
tgaaaggaaa aaggtaaata cagcattgag gcttcatttg gccttagtcc ctgggagtta   2580
ctggcgttgg acaggcttca gtcattggac tagatgaaag gtgtccatgg ttagaatttg   2640
atctttgcaa actgtatata attgttattt ttgtccttaa aaatattgta catacttggt   2700
tgttaacatg gtcatatttg aaatgtataa gtccataaaa tagaaaagaa caagtgaatt   2760
gttgctattt aaaaaaattt tacaattctt actaaggagt ttttattgtg taatcactaa   2820
gtctttgtag ataaagcaga tggggagtta cggagttgtt cctttactgg ctgaaagata   2880
tattcgaatt gtaaagatgc tttttctcat gcattgaaat tatacattat ttgtagggaa   2940
ttgcatgctt tttttttttt ttctcccgag acagggtctt gctctggcgc ccaggctgga   3000
gtacagtggc atgatcttgg ctcacttcag ccttgacttg ggctcaagtg atcctcctac   3060
ctgagccttc tgagtaactg gaactacagg tgtgcactcc tcgcctggct aatttttttat   3120
tttttgtaca ggcaggatct tgccaccttg cccaggctgg tcttgaactc ctgagctcat   3180
gccatctgcc tgccttagtc tcccaaaatg ctgggattac aggagtgagc caccatgccc   3240
ggctggcagt tgcatggaag agaacacctc tttatggctt accctctaga atttctaatt   3300
tatgtgttct gttgaaattt ttgttttttt acctttattg aaacaacaaa aagtcagtat   3360
tgaaacatat cttcctgttt tctgttgtca aatgatgata atgtgccatg atgttttata   3420
tatatcattc agaaaaagtt ttattttttta ataacattct attaacatta ttttgcttgc   3480
cgctggcatg cctgaggaat gtatttggct ttgattacac actaagtttt tgtaataaat   3540
ttgactcatt aaaaaccttt tttttttaaa aaaaaaaaaa aagaaaatct cattagtgaa   3600
cttatctttg cagctgagta cttaaattct ttttaaaaag ataccctttg gattgatcac   3660
attgtttgac ccagtatgtc ttgtagacac gttagttata atcaccttgt atctctaaat   3720
atggtgtgat atgaaccagt ccattcacat tggaaaaact gatggtttta aataaactaa   3780
ttcactaata ttaaaaaaaa a                                             3801
```

<210> SEQ ID NO 14
<211> LENGTH: 2603
<212> TYPE: DNA
<213> ORGANISM: Homo sapiens

<400> SEQUENCE: 14

```
ttcctggtgt aagctttggt atggatggtg gccgtctccc tacagactgg gagctgttag     60
```

-continued

```
agggcaggga tcctagctga cacatctatg tcctcgcctt ggttggaggc ctccaccatg    120
gacagaggcc aggccctgcc cctcccaggc agcctggctc cttctgctgg gccctgaagg    180
cagacgggat aatgtggttg gccaaggcct gttggtccat ccagagtgag atgccctgta    240
tccaagccca atatgggaca ccagcaccga gtccgggacc ccgtgaccac ctggcaagcg    300
acccccctgac ccctgagttc atcaagccca ccatggacct ggccagcccc gaggcagccc    360
ccgctgcccc cactgccctg cccagcttca gcaccttcat ggacggctac acaggagagt    420
ttgacacctt cctctaccag ctgccaggaa cagtccagcc atgctcctca gcctcctcct    480
cggcctcctc cacatcctcg tcctcagcca cctcccctgc ctctgcctcc ttcaagttcg    540
aggacttcca ggtgtacggc tgctaccccg gccccctgag cggcccagtg gatgaggccc    600
tgtcctccag tggctctgac tactatggca gcccctgctc ggccccgtcg ccctccacgc    660
ccagcttcca gccgccccag ctctctccct gggatggctc cttcggccac ttctcgccca    720
gccagactta cgaaggcctg cgggcatgga cagagcagct gcccaaagcc tctgggcccc    780
cacagcctcc agccttcttt tccttcagtc ctcccaccgg ccccagcccc agcctggccc    840
agagccccct gaagttgttc ccctcacagg ccacccacca gctgggggag ggagagagct    900
attccatgcc tacggccttc ccaggtttgg cacccacttc tccacacctt gagggctcgg    960
ggatactgga tacacccgtg acctcaacca aggcccggag cggggcccca ggtggaagtg   1020
aaggccgctg tgctgtgtgt ggggacaacg cttcatgcca gcattatggt gtccgcacat   1080
gtgagggctg caagggcttc ttcaagcgca cagtgcagaa aaacgccaag tacatctgcc   1140
tggctaacaa ggactgccct gtggacaaga ggcggcgaaa ccgctgccag ttctgccgct   1200
tccagaagtg cctggcggtg ggcatggtga aggaagttgt ccgaacagac agcctgaagg   1260
ggcggcgggg ccggctacct tcaaaaccca agcagccccc agatgcctcc cctgccaatc   1320
tcctcacttc cctggtccgt gcacacctgg actcagggcc cagcactgcc aaactggact   1380
actccaagtt ccaggagctg gtgctgcccc actttgggaa ggaagatgct ggggatgtac   1440
agcagttcta cgacctgctc tccggttctc tggaggtcat ccgcaagtgg gcggagaaga   1500
tccctggctt tgctgagctg tcaccggctg accaggacct gttgctggag tcggccttcc   1560
tggagctctt catcctccgc ctggcgtaca ggtctaagcc aggcgagggc aagctcatct   1620
tctgctcagg cctggtgcta caccggctgc agtgtgcccg tggcttcggg gactggattg   1680
acagtatcct ggccttctca aggtccctgc acagcttgct tgtcgatgtc cctgccttcg   1740
cctgcctctc tgcccttgtc ctcatcaccg accggcatgg gctgcaggag ccgcggcggg   1800
tggaggagct gcagaaccgc atcgccagct gcctgaagga gcacgtggca gctgtggcgg   1860
gcgagcccca gccagccagc tgcctgtcac gtctgttggg caaactgccc gagctgcgga   1920
ccctgtgcac ccagggcctg cagcgcatct tctacctcaa gctggaggac ttggtgcccc   1980
ctccacccat cattgacaag atcttcatgg acacgctgcc cttctgaccc ctgcctggga   2040
acacgtgtgc acatgcgcac tctcatatgc cacccccatgt gcctttagtc cacggacccc   2100
cagagcaccc ccaagcctgg gcttgagctg cagaatgact ccaccttctc acctgctcca   2160
ggaggtttgc agggagctca agcccttggg gagggggatg ccttcatggg ggtgacccca   2220
cgatttgtct tatcccccccc agcctggccc cggcctttat gtttttttgta agataaaccg   2280
tttttaacac atagcgccgt gctgtaaata agcccagtgc tgctgtaaat acaggaagaa   2340
agagcttgag gtgggagcgg ggctgggagg aagggatggg ccccgccttc ctgggcagcc   2400
tttccagcct cctgctggct ctctcttcct accctccttc cacatgtaca taaactgtca   2460
```

ctctaggaag aagacaaatg acagattctg acatttatat ttgtgtattt tcctggattt 2520
atagtatgtg acttttctga ttaatatatt taatatattg aataaaaaat agacatgtag 2580
ttggaactga aaaaaaaaaa aaa 2603

<210> SEQ ID NO 15
<211> LENGTH: 3884
<212> TYPE: DNA
<213> ORGANISM: Homo sapiens

<400> SEQUENCE: 15
atcacatacc ctaaagaacc ctgggatgac taaggcagag agagtctgag aaaactcttt 60
ggtgcttctg cctttagttt taggacacat ttatgcagat gagcttataa gagaccgttc 120
cctccgcctt cttcctcaga ggaagtttct tggtagatca ccgacacctc atccaggcgg 180
ggggttgggg ggaaacttgg caccagccat cccaggcaga gcaccactgt gatttgttct 240
cctggtggag agagctggaa ggaaggagcc agcgtgcaaa taatgaagga gcacgggggc 300
accttcagta gcaccggaat cagcggtggt agcggtgact ctgctatgga cagcctgcag 360
ccgctccagc ctaactacat gcctgtgtgt ttgtttgcag aagaatctta tcaaaaatta 420
gcaatggaaa cgctggagga attagactgg tgtttagacc agctagagac catacagacc 480
taccggtctg tcagtgagat ggcttctaac aagttcaaaa gaatgctgaa ccgggagctg 540
acacacctct cagagatgag ccgatcaggg aaccaggtgt ctgaatacat ttcaaatact 600
ttcttagaca agcagaatga tgtggagatc ccatctccta cccagaaaga cagggagaaa 660
aagaaaaagc agcagctcat gacccagata agtggagtga agaaattaat gcatagttca 720
agcctaaaca atacaagcat ctcacgcttt ggagtcaaca ctgaaaatga agatcacctg 780
gccaaggagc tggaagacct gaacaaatgg ggtcttaaca tctttaatgt ggctggatat 840
tctcacaata gacccctaac atgcatcatg tatgctatat tccaggaaag agacctccta 900
aagacattca gaatctcatc tgacacattt ataacctaca tgatgacttt agaagaccat 960
taccattctg acgtggcata tcacaacagc ctgcacgctg ctgatgtagc ccagtcgacc 1020
catgttctcc tttctacacc agcattagac gctgtcttca cagatttgga gatcctggct 1080
gccatttttg cagctgccat ccatgacgtt gatcatcctg gagtctccaa tcagtttctc 1140
atcaacacaa attcagaact tgctttgatg tataatgatg aatctgtgtt ggaaaatcat 1200
caccttgctg tgggtttcaa actgctgcaa gaagaacact gtgacatctt catgaatctc 1260
accaagaagc agcgtcagac actcaggaag atggttattg acatggtgtt agcaactgat 1320
atgtctaaac atatgagcct gctggcagac ctgaagacaa tggtagaaac gaagaaagtt 1380
acaagttcag gcgttcttct cctagacaac tataccgatc gcattcaggt ccttcgcaac 1440
atggtacact gtgcagacct gagcaacccc accaagtcct tggaattgta tcggcaatgg 1500
acagaccgca tcatggagga atttttccag cagggagaca aagagcggga gaggggaatg 1560
gaaattagcc caatgtgtga taaacacaca gcttctgtgg aaaaatccca ggttggtttc 1620
atcgactaca ttgtccatcc attgtgggag acatgggcag atttggtaca gcctgatgct 1680
caggacattc tcgatacctt agaagataac aggaactggt atcagagcat gatacctcaa 1740
agtccctcac caccactgga cgagcagaac agggactgcc agggtctgat ggagaagttt 1800
cagtttgaac tgactctcga tgaggaagat tctgaaggac ctgagaagga gggagaggga 1860
cacagctatt tcagcagcac aaagacgctt tgtgtgattg atccagaaaa cagagattcc 1920

```
ctgggagaga ctgacataga cattgcaaca gaagacaagt cccccgtgga tacataatcc   1980
ccctctccct gtggagatga acattctatc cttgatgagc atgccagcta tgtggtaggg   2040
ccagcccacc atgggggcca agacctgcac aggacaaggg ccacctggcc tttcagttac   2100
ttgagtttgg agtcagaaag caagaccagg aagcaaatag cagctcagga aatcccacgg   2160
ttgacttgcc ttgatggcaa gcttggtgga gagggctgaa gctgttgctg gggccgatt    2220
ctgatcaaga cacatggctt gaaaatggaa gacacaaaac tgagagatca ttctgcacta   2280
agtttcggga acttatcccc gacagtgact gaactcactg actaataact tcatttatga   2340
atcttctcac ttgtcccttt gtctgccaac ctgtgtgcct tttttgtaaa acattttcat   2400
gtctttaaaa tgcctgttga atacctggag tttagtatca acttctacac agataagctt   2460
tcaaagttga caaacttttt tgactctttc tggaaaaggg aaagaaaata gtcttccttc   2520
tttcttgggc aatatccttc actttactac agttactttt gcaaacagac agaaaggata   2580
cacttctaac cacattttac ttccttcccc tgttgtccag tccaactcca cagtcactct   2640
taaaacttct ctctgtttgc ctgcctccaa cagtactttt aactttttgc tgtaaacaga   2700
ataaaattga acaaattagg gggtagaaag gagcagtggt gtcgttcacc gtgagagtct   2760
gcatagaact cagcagtgtg ccctgctgtg tcttggaccc tgccccccac aggagttgta   2820
cagtccctgg ccctgttccc tacctcctct cttcaccccg ttaggctgtt ttcaatgtaa   2880
tgctgccgtc cttctcttgc actgccttct gcgctaacac ctccattcct gtttataacc   2940
gtgtatttat tacttaatgt atataatgta atgttttgta agttattaat ttatatatct   3000
aacattgcct gccaatggtg gtgttaaatt tgtgtagaaa actctgccta agagttacga   3060
ctttttcttg taatgttttg tattgtgtat tatataaccc aaacgtcact tagtagagac   3120
atatggcccc cttggcagag aggacagggg tgggcttttg ttcaaagggt ctgccctttc   3180
cctgcctgag ttgctacttc tgcacaaccc ctttatgaac cagttttgga aacaatattc   3240
tcacattaga tactaaatgg tttatactga gcttttactt ttgtatagct tgataggggc   3300
agggggcaat gggatgtagt ttttacccag gttctatcca aatctatgtg ggcatgagtt   3360
gggttataac tggatcctac tatcattgtg gctttggttc aaaaggaaac actacatttg   3420
ctcacagatg attcttctga atgctcccga actactgact ttgaagaggt agcctcctgc   3480
ctgccattaa gcaggaatgt catgttccag ttcattacaa aagaaaacaa taaaacaatg   3540
tgaattttta taataaaatg tgaactgatg tagcaaatta cgcaaatgtg aagcctcttc   3600
tgataacact tgttaggcct cttactgatg tcagtttcag tttgtaaaat atgtttcatg   3660
ctttcagttc agcattgtga ctcagtaatt acagaaaatg gcacaaatgt gcatgaccaa   3720
tgtatgtcta tgaacactgc attgtttcag gtggacattt tatcattttc aaatgtttct   3780
cacaatgtat gttatagtat tattattata tattgtgttc aaatgcattc taaagagact   3840
tttatatgag gtgaataaag aaaagcatga ttagattaaa aaaa                    3884
```

<210> SEQ ID NO 16
<211> LENGTH: 11434
<212> TYPE: DNA
<213> ORGANISM: Homo sapiens

<400> SEQUENCE: 16

```
cggaggcgga gctcccgcgc cgttcacgtg acgggcccgg ctgtagcggc ggcggccgcg     60
gcgtcttaag cggcgcccag tgcaggatgg tgctggaggc ggcggcggcc gtggtggcgg    120
cagcgtcgtt ggcggcagcg ggagtgggtg cggcggcagc ggcggcggcg cccgcgggtg    180
```

gtataaaatg gcggatttcg aagagttgag ggatctccag tacaatgttg aatagaagct 240
gtgatggggg catcctgatc ttgttcctga ttttaaaggg aatgctttca aagtttcaca 300
agtggctgta ccattttaca tccctaccag caatgtatgg agtgatccag tttctcagca 360
tcctcgccag catttggtgt tatcagtgtt tttcatttta gccattctga atatggtttc 420
tagttttagg gtttctgaac tacaagtatt actaggcttt gctggacgga ataaaagtgg 480
acgcaagcat gacctcctga tgagggcgct gcatttattg aagagcggct gcagccctgc 540
ggttcagatt aaaatccgag aattgtatag acgccgatat ccacgaactc ttgaaggact 600
ttctgattta tccacaatca aatcatcggt tttcagtttg gatggtggct catcacctgt 660
agaacctgac ttggccgtgg ctggaatcca ctcgttgcct tccacttcag ttacacctca 720
ctcaccatcc tctcctgttg gttctgtgct gcttcaagat actaagccca catttgagat 780
gcagcagcca tctcccccaa ttcctcctgt ccatcctgat gtgcagttaa aaaatctgcc 840
cttttatgat gtccttgatg ttctcatcaa gcccacgagt ttagttcaaa gcagtattca 900
gcgatttcaa gagaagtttt ttatttttgc tttgacacct caacaagtta gagagatatg 960
catatccagg gattttttgc caggtggtag gagagattat acagtccaag ttcagttgag 1020
actttgcctg gcagagacaa gttgccctca agaagataac tatccaaata gtctatgtat 1080
aaaagtaaat gggaagctat ttcctttgcc tggctatgca ccaccgccta aaaatgggat 1140
tgaacagaag cgccctggac gcccccttga tattacatct ttagttaggt tatcttcagc 1200
tgtgccaaac caaatttcca tttcttgggc atcagaaatt gggaagaatt actctatgtc 1260
tgtatatctt gtacggcagc ttacatcagc catgttatta cagagattaa aaatgaaagg 1320
tattagaaac cctgatcatt ccagagcact aattaaagaa aaacttactg cagatcctga 1380
tagtgaaatt gctacaacta gccttcgggt atccttgatg tgccctttag gaaaaatgag 1440
gctgacaatc ccatgccgtg cagtgacttg tacacatctg cagtgttttg atgctgccct 1500
ctatctacaa atgaatgaga aaaagcccac ctggatttgt cctgtgtgtg acaaaaaagc 1560
tgcctatgaa agtctaatat tagatgggct ttttatggaa attctcaatg actgttctga 1620
tgtagatgag atcaaattcc aagaagatgg ttcttggtgt ccaatgagac cgaagaaaga 1680
agctatgaaa gtatccagcc aaccgtgtac aaaaatagaa agttcaagcg tcctcagtaa 1740
gccttgttca gtgactgtag ccagtgaggc aagcaagaag aaagtagatg ttattgatct 1800
tacaatagaa agctcttctg acgaagagga agaccctcct gccaaaagga aatgcatctt 1860
tatgtcagaa acacaaagca gcccaaccaa aggggttctc atgtatcagc catcttctgt 1920
aagggtgccc agtgtgactt cggttgatcc tgctgctatt ccgccttcat taacagacta 1980
ctcagtacca ttccaccata cgccaatatc aagcatgtca tcagatttgc caggtttgga 2040
ttttctttcc cttattccag ttgatcccca gtctcacctc acccttaaca gcaagcagta 2100
cgtctgtcac caccaccagc tcccatgaaa gcagtactca tgttagttca tccagcagca 2160
ggagtgagac aggggtcata accagcagtg gaagtaacat tcctgacatc atctcattgg 2220
actaaaggag gactcacttg attctgggaa tcattcatca gaactgcttt ttcttggatc 2280
tctagtctgt ggaaacgttc tttttttttt tttttaata atttggtatt tattgaaagt 2340
cagatggatt cttttgcttt ctgaggggtg aacacagaag actgcaacaa gaaccaaatg 2400
acatgcaagg atttttctta attatgctgt actctcagca tcagatacat tcaaccataa 2460
ctgtatcttc ctgagagatg gatttcactt tcatacgtta atggatggag tctacaaatc 2520
agtgaaaaaa gtttttgtta aaataaagag caataaaatt atgtaaatat tcaagtaacc 2580
ttttttctaa ttaaaaaaaa aattgtaatc actgattcta gaatgacagc aacttctgtt 2640
taaccttacg tgaaggaaaa aaaatatatg gaaagaactt aatgtttgct gaatgagtcc 2700
tttccatgga gatttgctct gtttcattga agtaatgaag tttcagtacg tggccaaagc 2760
ttggattcca cttttcgtcc tgcatttcca cttttcttcg tgattgcatc aaagaaaaat 2820
ggcattcgtg ttacttggtt tttttcctgc ttatcattta cactttgacg ttgtttgcta 2880
atgagtgctg tgtgaagttc tgggatttgg ctactcttca ttggtgatta tgtttaaaag 2940
cactatgcag attctgccct gacataaagt gtgttattat gtttttagta attgtacatt 3000
tttcattcta gagttttcta taaatttgag gcttgccttc tcaaaaaaga aactatgcag 3060
ccattgaatg aaatgtcttt ggggtacggt gtgactggaa tgtttgttag aaatttgttc 3120
acactatcaa atattgatat cttggagcca gcagaagagc agattttggg aggtggtaat 3180
aacaaaattt aatttcttcc caacaactta attttctcat ttattttaca gaatagtagt 3240
gaaatatttg atgaaacttt gtattttggt agcactacat agaaaatgtg ttttagattt 3300
atgatgatca tatttctcac caatgtaatt tcagtctcag cagtgatttt caaacttagg 3360
gaaagggaca gcattagatt tttttttttt ttcatttttt taaaatgata tcttacctga 3420
aactacaaac gacaaaagag aattagaaat gtttgaatta aagtgaagaa gggttggggg 3480
agatgggcct gaacccactt cctgtctcaa tccatgctac cccaaacact ccagggaacc 3540
tctgaggttt tattgggtgc actttgaaaa tttctcttct atagtgtgtt tgtttgattt 3600
taaatcacag agaaaactgg gttttactct tagagaaaca ttttcatcca gtttttttagt 3660
ttgcttcatt tgacttccta aatcattttt gagttcacaa ggatttggta cttttctgtt 3720
tagctttctc tctctaagct ttatctacct taaaaacaaa gtcctttttt taatggccag 3780
tccaaccaat tgatttctca aactgaagtg cccaggtgtg gactcatcaa tttccgttag 3840
aatagggaca tcctacttaa gagttggtgc agctccaagg agctgacttg tccttgcttg 3900
gggttttttt tttttttctt tcaccttctc aagtttccat ggcctttgtg tgttcttttt 3960
atgttgattt aaattcatat ggttttccac aaatcccttc tttggctaca ttgtctcctt 4020
attcaatgga ttatcccttt gtgggggctg cttattttaa agatgttggg ggggaaacaa 4080
acccaaatct acgagcagta gttgcacata gttgccagtt ttaccttctt agtcattaga 4140
tttccaaacc atgttgcagt tttttggtcc agatatagta tttctttcta ataaagtttt 4200
atgttgctgc tctaaataca gatgcaatat ttattgactc tgtaatcaga tagaaaaaac 4260
ttaacttggt ttgtgtggta tgacttataa agaaatgatg tatatttgtt attttgttac 4320
cctttagatt gtcagagact cccccaattt aatcaacaaa gttttataaa gtaaatgaaa 4380
atattaatag aaattagttt atttacttgg ttcttataac tgatatctct gtgcttttat 4440
aattgtgatt tgtttttttg tttttttttc tattttctgt gaacagtttt aatgttcggt 4500
tttggtgttt tacactgaaa ttacatataa atttttaatt tatttcatac aggcaacttg 4560
cattttaaaa aatacacttt gaagtttatc atcttgaaat tggggcttac gttgtttatc 4620
tgtcttgagc attagtactt tatgactttg gccttatggc aacatcatga ttattaatcc 4680
gtcagccttt aatgtggtca ctgtttctta tccagaccct gactttctag tagtttattt 4740
tgctagccca gatttctgct taaccaaata taagggagtt tcagaggggt gatcttagct 4800
gtcacctaga ttctgtcagc caaccagtga ttgtctggaa tatcttagga aatgaactgt 4860
aattgtcagc ctcctaaaat caattttttt tttttttttt ttgaggctga gtcttgctct 4920
tgttgcccgg gatggagtgc aatggtgcga tcttggctca ccgcaacctc cacctacagg 4980
gttcaagcga ttctcctgcc tcagcctccc gagtagctgg gattacaggc atgtatcacc 5040
acgcccagct aattttgtat ttttagtaga tacggggttt ctccattttg gtcaggctgg 5100
tctcgaactc ccgacctcag gtgatccgcc tgccttggcc tcccaaagtg ctgggattta 5160
caggcgtgag ccaccgcgcc tggccaaaat aaaatgtttt tatctttctt cacttagaac 5220
tatgaaggcc ttttcttgtt ctggtaaccc cccacagtgt aattggtgct gaaaatagtt 5280
tcgtgcctga ggtctgttgt cactcactca ctttctgaca attaggtgag ccacttgagg 5340
attttctggc ctgaagttat aaaaacttgg catctgtcct aaggtaattg taaaggcaaa 5400
atgaaagcat tgaggtgaat ttaggttata tggcatttat ctggtaatgt gtttcagaaa 5460
agctagaatg aaaatgtgat gtaagggata gcaagtgtag gttgattcat aattcttggt 5520
ataaaaccaa gttttcctta gtcttgagga atttgaagaa aggtaaaatg ttggatttta 5580
agcaaagtag gattgaccag agactgttct gactttgaca ttcagacctt tcagatgttc 5640
ttccttcaga ccagtccaag acactcagca tttccagcca agttgtcttt tttttctgcc 5700
aataaagtat tcattagttg acgtttgttt gtattttaag taaagtcaat ttttttttaaa 5760
gcattaattt aattcacggg tatgcctttc atttctctgg ccttcagttg gtttaaaaaa 5820
aaaaaaaaaa aaaaaagcac ttagccggac cattctttct ttagtaaaca tttttatttt 5880
cttaattttt cctgaaagat tttcttcatt ttcatggaat gtcataatga cactaccatt 5940
attttctagc tctttgcata atagaaaaat gtagagcagt gcaccattta aacacgtctg 6000
acattggatt tagtggtcct aggttcatgt gatttgggag ccttaagttg ttatttagat 6060
tgattcagcc tgattcacca tcttttttac tacagttcta catgaatgtg gtgaaacagg 6120
tagaagaaaa ttaagcattt ctctgctttt ggagtctaat gttcctgcct agtgactggt 6180
ttgtaacacc cccctcaccc ctactttgtt aggaacctgc aattcctaaa agaaataaat 6240
aaagctgtac ccaatgtcca ttctttaatg cttgcctggt tgaataatgt ttgttttttc 6300
tgtttatgtc agtagtacat gcttattgtg gaaaatttag acaatacaga aaagtataac 6360
aattaattgc ctatgattct gtcaccagaa aaaatcactt gatatttttg catcttcctt 6420
gccattgtct ttgctacttc tgcatatttt tacttagttt catcattctc agtgtaattt 6480
atatcttggg gtttttcccc gcaacctaca ggcattattc catgtcatta aaactgtgtc 6540
aactattatt aattttatgg tactccattg ttatggatgt gccatgtttc atataacctt 6600
tacttatttt gaacagttta gattatatct cataatgcca caatgaatgt ctttgtgtat 6660
aaattatttt cttaggataa aatactggag gtggaatttc tagtcaaggg tatatgaaca 6720
cttttgtagt tcttgattca taccactttt ccacatgggt atgttaattt atactgcagc 6780
tagatggtat gggaagggtg gtctagccat attttccaag aacatgcaac gttttatctt 6840
tatgcaggca tctgcactaa gaccctctgc ctttctgact ctatggaacg gggttaactg 6900
atatggagat cattggcaga gattttccca agctttctta gttttaaata tatctgacat 6960
gggccgggta tggaggctca cgcctgtaat cccagcactt tgggaggcca aggcgggcag 7020
ataatctgaa gtcaggagtt ggagaccagc ctggctaaca tggaacatgg tgaaacccca 7080
tctctagcaa aaacataaat taggtgggtg tgatggcagg cgcctgtagt cccagctact 7140
tgggagaccg aggcaggaga atcgcttgaa cccaggaggc ggaggatttg cagtgatccg 7200
agattgtgcc actgcactcc agcctgggta acaaagcaag actctctaaa aaaaaaaaaa 7260

```
aaaaaaaaaa aaaatatata tatatatata tatatatata taaaatctga catgtttcag   7320
aaacacctac gtatggctat ccaagctttt cccatgattt tactggcact gtaaagttgc   7380
acaaatattc tttgtcagac tacgttttcc atctttagtt caaaagtttt gtcacttttt   7440
aaaaaaagcc tcttgtacct aaggcctgcc cttaagaggt cagctctctt tttcctcttc   7500
ctgtaggccc cattatggcc tttctgagct ccccaaagcc agtagaatct actgagccaa   7560
aggcattcca tccccaaact gaaaagtggt aaggctaaaa gctataaaaa caggcaaaca   7620
ttgcctgttt tcactttata ttcccttatg tttccaataa gggtagctgc agggaaagaa   7680
aaaaacagat tgctaccttc agatgtttga ggtacaacat tttcttgatt ggcgtagcac   7740
aatcatttcc caaactgctt cctatttctg aatggctttt ttaaaaagct ttattttgtg   7800
ttctcaaagc ttaattattt taagtgacga agagtgttac cgtgttgtag aatagcatat   7860
gcctcttatt ttggccttca tcaaactgtt taataaatgt ttagagtgtt ttgtaagtac   7920
acgtggaata gagtgttaca gaagttttgg ttccagacat caggcagctt ataatcaagg   7980
ttccaaaaat caagaattct taagctgggc atggtggctc atgcctgtaa tcccagcact   8040
ttgggaagcc aaggcaggca aatcacttga ggccaggagt ttgagaccag cctggccaac   8100
ttggtaaaac cccatctcta ctaaaaatac aaaaaattag ggcatgatgg ctcatgtctg   8160
taatcccagc tacttgggag gctgagggat gagaattgct tgaacctgag aggcggaggt   8220
tgcagtgact caggatcatg accctgtact ccagcctggg tgacagagtg agaccaaaaa   8280
aaaaaaaaaa aaaaaaaaaa aaaagtaaca ggcattgtgc aaagaatttt ccaagaatgt   8340
ctcattcttg caatggcttc tcagaggaaa gtggtgttat tccccatttt acaaatgaaa   8400
caggtttagg taagtttccc aaggtcacag tgaatgagta gtggacttgg gagtctgacc   8460
tagacttacc ccaaaagctc tctgcgtaaa ctgaagtgac gttaattagc tgtgctatct   8520
aggagactga tatgggaatc tagacttaaa attatgagaa ctggtttcag atgatggcca   8580
gagtaataag gaaggagtgg atgctgaagc catttcaaag gaagactcaa gattcagtga   8640
ctgaatatag gagtaagggt tgagtgcatt tttcatccat ttttcaagcc tgggtaactt   8700
ggatgttaat ggcactatct acagagacag gaggcagttt agagtgaaga cgaatcatgt   8760
atgggagaca gtgatgaatg ttaagcatgg gatttcagaa atgaagcatc catgaggctc   8820
attcctggtt tttctgcagt cttttaaata aaagtacaaa cctcccttgt catccatttt   8880
tgccttcact tatctccatt ctgtattatg ttctagtcac gccccagtca ctgatccctt   8940
cctaggccat acttggctac atcttagcct tttcttttga tttttctctt cactgccttg   9000
cccattacaa atttggctgc cacctgaggc cctgccatac cctacagctc acaccagcgt   9060
gggctgtgtt cacattctac atatctcaag atacagtggt tgctgtcctt ccccccctact  9120
gcatcgttac acgtctctaa aaaatctctg cctctgaagc tcatgccaag aggttatact   9180
atcagctacc tctagtctta taactgcctg atcattccct ttgatttgct ggaagctttg   9240
actcacagtg ttccttgcct tccttgattc tggtcattat tattaatatc ttgaacattc   9300
tatagatgat ttatccaagt tggtctgtga ggtattggtt actttacctc cagcattttc   9360
gtctactgaa ccacgctttc tgttttcctc tttgctactt gtccagactg ttctttcatt   9420
attgcagcct tgaagaaatc ctcagtaacc tatccatcct ccgacatgac gtagcatagt   9480
tcctttgccc attctcatca gttataacaa atgttattgc cctcttttca ggccacttcc   9540
ttctcagaag atgactttgc tgcttaattc aaacagaagg gacagtccga aagcatgatt   9600
tcttccccac ctatgaccac ctccatcctt ttttgtttcc agtttcagag aatgaggtag   9660
```

```
gcctttaagg ccaactgact ctggtctcct cctgtcatct tcaggacctt cctctgtcag   9720
acttcccctc tcttatctcc atgtctctca cctctctact gctgcttttc ttggcttaca   9780
aatggtctca gtcatccagt atttgagatt atattaggtg ccaggcattg tatcaggcac   9840
ttggaacaca aggcaggatc ctgcccccac caaagttgtg ctccaatagc gtcaacagag   9900
gtgtgaaata gggagattac aatgttaatg gtaaaagaca aagtataggg tgctacaaga   9960
gcatgtaaat gaggcacctc aatgatttaa tagaagtaat gtggagaaat gtgaggattg  10020
atgaaaagct tgtccaaaaa gggccagaaa tgtttagaat tgctggaagt ttgctaagga  10080
atattgagaa atatgcatag atagatcgtg aagggccttg taaaacagtg atgagacatt  10140
gaagagtttt catgatcatt agtagtaatg agaatttgtt gagtttggca tgattatctc  10200
catattacaa atgtggaaac agattctgac aggataagcg acttacttgc ccagggtcat  10260
gcagcttgta attgaggagt caggtttcaa atccagtttt aactactttc tcagaggcct  10320
ttcttgatca ttctatctaa aaagcaagtg ttccctaact attatcccag taccctggtt  10380
tatatactct taatacataa aataatccct gcatattgtg tgtttcccct actagattgt  10440
aagctccatg agggcagagg tgataacttt tttcacttgc atcccagagc ctaacatgat  10500
atgggctaca tagaaggtgc ccagtaaata ttggtggatg aagaaatggt ggataaccat  10560
ttgcatttga cttatgctga ctggaaattc aatacctttg gaatatataa tacctcagca  10620
gtaagcattc accaagagag gaaaacagaa ggaggtgcat gtttagggta ggtggtacgg  10680
gagatggatg ctgaggtgtt gaaaggcagc atactcacct tctgaactcc aaaacttaca  10740
ggggcaaggg ccattaatga ggggtgggta gagcagtgca cagtggggat aatatgggag  10800
taggtgtatt aaacctggaa gtgtaagcaa ctccttgtag acccacccta ctgtgtataa  10860
aaggctggag aaattcttca tatgatctac tctaggttat gtactgagga ccaccttatc  10920
tgggtcaggt acactacaca gagtgctaca atataattgt aaacataatt tatcctcact  10980
gtgatggcta gccacctgac ccaaatcatt attagactca atactttgga actggaacaa  11040
aaatcagttg acctgatgtc tgaaagacat gcccacctgc tatttgacaa gctatagaca  11100
tatcctacca attgatgggt agtagcactg aaactatgaa agtggatgaa ctcatccaga  11160
ggagttgatg agtgagaaaa gaagactgga aaaggaacac aaggaaatca agaagcagca  11220
gctgagactg aaggaaaata acgtggtatt acagaggcca aaaaatagag tatttcaaga  11280
agcaagtggt tagtggagtt aaaagctgct gatacaacct aaaaaagtaa gtatccattt  11340
tttaaaaaac tttcatttaa aataccacca tattttattg aatctaagta cctgattgta  11400
agacattaaa gaaaaattaa acctgctaat taaa                              11434
```

<210> SEQ ID NO 17
<211> LENGTH: 5085
<212> TYPE: DNA
<213> ORGANISM: Homo sapiens

<400> SEQUENCE: 17

```
agcgccatgc gcagactcag ttcctggaga aagatggcga cagccgagaa gcagaaacac     60
gacgggcggg tgaagatcgg ccactacatt ctgggtgaca cgctgggggt cggcaccttc    120
ggcaaagtga aggttggcaa acatgaattg actgggcata aagtagctgt gaagatactc    180
aatcgacaga agattcggag ccttgatgtg gtaggaaaaa tccgcagaga aattcagaac    240
ctcaagcttt tcaggcatcc tcatataatt aaactgtacc aggtcatcag tacaccatct    300
```

```
gatattttca tggtgatgga atatgtctca ggaggagagc tatttgatta tatctgtaag    360
aatggaaggc tggatgaaaa agaaagtcgg cgtctgttcc aacagatcct ttctggtgtg    420
gattattgtc acaggcatat ggtggtccat agagatttga aacctgaaaa tgtcctgctt    480
gatgcacaca tgaatgcaaa gatagctgat tttggtcttt caaacatgat gtcagatggt    540
gaatttttaa gaacaagttg tggctcaccc aactatgctg caccagaagt aatttcagga    600
agattgtatg caggcccaga ggtagatata tggagcagtg gggttattct ctatgcttta    660
ttatgtggaa cccttccatt tgatgatgac catgtgccaa ctctttttaa gaagatatgt    720
gatgggatct tctatacccc tcaatattta aatccttctg tgattagcct tttgaaacat    780
atgctgcagg tggatcccat gaagagggcc acaatcaaag atatcaggga acatgaatgg    840
tttaaacagg accttccaaa atatctcttt cctgaggatc catcatatag ttcaaccatg    900
attgatgatg aagccttaaa agaagtatgt gaaaagtttg agtgctcaga agaggaagtt    960
ctcagctgtc tttacaacag aaatcaccag gatcctttgg cagttgccta ccatctcata   1020
atagataaca ggagaataat gaatgaagcc aaagatttct atttggcgac aagcccacct   1080
gattcttttc ttgatgatca tcacctgact cggccccatc ctgaaagagt accattcttg   1140
gttgctgaaa caccaagggc acgccatacc cttgatgaat taaatccaca gaaatccaaa   1200
caccaaggtg taaggaaagc aaaatggcat ttaggaatta gaagtcaaag tcgaccaaat   1260
gatattatgg cagaagtatg tagagcaatc aaacaattgg attatgaatg gaaggttgta   1320
aacccatatt atttgcgtgt acgaaggaag aatcctgtga caagcactta ctccaaaatg   1380
agtctacagt tataccaagt ggatagtaga acttatctac tggatttccg tagtattgat   1440
gatgaaatta cagaagccaa atcagggact gctactccac agagatcggg atcagttagc   1500
aactatcgat cttgccaaag gagtgattca gatgctgagg ctcaaggaaa atcctcagaa   1560
gtttctctta cctcatctgt gacctcactt gactcttctc ctgttgacct aactccaaga   1620
cctggaagtc acacaataga atttttttgag atgtgtgcaa atctaattaa aattcttgca   1680
caataaacag aaaactttgc ttatttcttt tgcagcaata agcatgcata ataagtcaca   1740
gccaaatgct tccatttgta atcaagttat acataattat aaccgagggc tggcgttttg   1800
gaatgcaatt tgcacaggga ttggaacatg atttatagtt aaaagcctaa tatgcagaaa   1860
tgaattaaga tcattttgtt gttcattgtg cagtatgtat atagcataat atacacagtg   1920
aattataggt ctcaggctta cttgattttt ggctatttta tatttagtgt acacagggct   1980
ttgaaatatt aatttacata aaggccttca tatattatta cgtgttatat attacgtgtt   2040
ataaatttat tcaataaata tttgcctaga attcccaaga cctttatagg tgattttgtt   2100
ttctgggctc cttaacttca taaatagcta gtatcttcca gcagtagtaa cagtctggat   2160
aacttcttcc atatccctcc ctctttgttt ttttgagaca gtgtcacttt gtcacccagg   2220
ctggagtgca atggtgtggt ctcggctcac tgcaacctcc acctcccggg ttcaagtgat   2280
tctcccgcct cagcttcctg agtagctgga actacaggcg tgtgccacca cacccggcta   2340
atttttcgta tttttagtgt agacggggtt tcactatgtt gcccaggctg gtctcgaact   2400
cctgaccgcg tgatccacca cctcagcttc ccaaagtggt gggattacag gcgtgagcca   2460
ccgcacccgg cctccatatc cccctttttaa aattctgtag tgtatggtaa gtcatatcag   2520
atatcagacc taatttaaat ttcattttag ctttacaagt ccaaaaacac agaatttata   2580
tattcagata ctctagcact aattttagtc ttaaaatatt cccacgatat tctgtacaca   2640
aaatgttctt tttgttacaa gagctgagtt gcatatactg tagataaatc atattatttt   2700
```

tgccaatttc acaaattcct ctggcccatc atgtcagtca ttattgagta tatgcacaca 2760
ttgctactta tttgattatg tatcttttaa attgattcag tgcatagaaa actatctctt 2820
acaaacttta agtgctctga tatgacttcc cccccaaatt ttattatgaa catttttaaa 2880
aacagaaaaa ttgaaaaact gtttggtaag cacatgtata tctaccattt agattcagca 2940
gttgttaatg ttttgtcatt tgttttctct atacctatat atgtatagat acagctagtt 3000
atgcatatat atgcatatat gtgtttgttt gtgtatgtat atatgctttt ttccccctga 3060
accatttgga tgttacagac atacttatca ccgtgaaaat acttcaagta tctcctacag 3120
ataatgacat tctcctaaaa atccgtaata ccattgtaaa agtaataatt ccccaatatc 3180
atctaatcaa gccatattta aatttctgaa gttaactcca aatttcttta tagctgatta 3240
tttcaaacta ggatccaatt aaagtttaca tatgacactt ggttataact ctttagttgg 3300
atataacatt attattattt tgataaaata tggaacaaat caattctatt aataagtggt 3360
cacatttgtt ttgggcttaa attacttttt aaagatactg gattttccta agatttctga 3420
tttacactga tatttttttt tgtcattctt aattgcatca cacaatagat gtaaatgaag 3480
atgtagtcac ctcagataaa attggtatcg tgtatgataa tattgtatca tttatatttg 3540
ccttatgtta actttaagaa attgattttt ttgtattaat cattttccca ttgcaacaga 3600
gctatatttt ttctatttta agaatcatat tttaggatta tttttggcaa atacagtgag 3660
cacttatgta accagatgat aatgaactca aatgtcatga tagcttgcat aaatggtgac 3720
tctagtagat ttgactcaag cacttctaga atcatgcact gaattcaaaa gaaaaatctt 3780
gctgcttttt gtccagggct tgttctattc aacttctaat ttgaaagctg tacaaagtaa 3840
tagaagttcc atttaaatat gagttcaaaa ctgtatttac tttttatgtg gccctctctt 3900
taggggattc taattttact tagggtctct aagtgcagca taatgttcct gatgttaaca 3960
gaagactgta tttttaaagt tacaaatttg tatatggaat taagtaatgg cgctatatac 4020
gctgttgtgg ggagggggga agaaaaggag gaaccaatta aataggacct tttaaaaatt 4080
gttaattttg taaactttgc ttctcttata agttattgtg attcatttta gttactgtgt 4140
tttattttga aaatatttaa atattgcact tctataaata gtatgataaa tgcacagaca 4200
attgcagtaa attctttttt aagctaggat atttgaaatg acaacctttg gttaagtgtg 4260
tcaaggttgc aacagaattt tcacaatttt tttgttgttt gcaaattgtt actaatattg 4320
aagaggtaag ggaggcaatg caaatgattt ttaatctttt tttattatct tttcagcagt 4380
ttatattttt tgtgacttta tgcaaccata tttttacttt gtcttgacaa ctgaaagatg 4440
tataaggttt tttgccagaa atgtactgta tacatagttt taagtataac agattttact 4500
gatatgtaaa aattttgcca ttaaaataaa tgatttctca ctgagaggaa cttttctacc 4560
aggttggggc atatgggagc ttaatatatc atatctaatt taaaataatt tcactgaaat 4620
aaactccatt gcttttacct aattttttttc ttgagatgct tttgtagttt ttcagagttt 4680
tagatgattt tatacaaaat cctctgccta gcactgctct ttttgatgtt gtagtgacac 4740
catttacatt gaattaatgc ttggtagcct ggggctagat gtggaactcc atggatctgt 4800
gttctgactg gcacctttgg aatgaaagaa aagtgtgtgc tgtccaaatt ttttcccctt 4860
aattctttcc ctcatcttct cacccataat agaaatttta tttccattgt gagttctgac 4920
aagaatgaaa ttccacatac aacataactg taaattgttg gtaggtagaa gttaatattt 4980
gtggttcatg tatattttga ccagagtata tttaagtata taatttcagc ttccttgatt 5040

-continued tagaaatatg atataataaa gaaaaactcc atttatcatc tgtta 5085

<210> SEQ ID NO 18
<211> LENGTH: 5636
<212> TYPE: DNA
<213> ORGANISM: Homo sapiens

<400> SEQUENCE: 18
aggaagtgac gtcatgcccc cggccggcag gtcttttagt ctttttcccc ctcccttact 60
cttcgtcccc ggtccctccc ctccccaccc ctttccttct agctccgacg tttgcggccg 120
cgggggcggc ggaggatatg gagtaaagcc agagtcagtg gccaggcacg aaggcagagc 180
aggaacagcc aggaggcgtt tattaggggg gcggggggaa agagccccag caccgcccct 240
cctggaagaa ggaagaggta actataacta cccaatattg cagccatgga gtccatgctt 300
aataaattga agagtactgt tacaaaagta acagctgatg tcactagtgc tgtaatggga 360
aatcctgtca ctagagaatt tgatgttggt cgacacattg ccagtggtgg caatgggcta 420
gcttggaaga tttttaatgg cacaaaaaag tcaacaaagc aggaagtggc agtttttgtc 480
tttgataaaa aactgattga caagtatcaa aaatttgaaa aggatcaaat cattgattct 540
ctaaaacgag gagtccaaca gttaactcgg cttcgacacc ctcgacttct tactgtccag 600
catcctttag aagaatccag ggattgcttg gcattttgta cagaaccagt tttgccagt 660 ttagccaatg ttcttggtaa ctgggaaaat ctaccttccc ctatatctcc agacattaag 720
gattataaac tttatgatgt agaaaccaaa tatggtttgc ttcaggtttc tgaaggattg 780
tcattcttgc atagcagtgt gaaaatggtg catggaaata tcactcctga aaatataatt 840
ttgaataaaa gtggagcctg gaaaataatg ggttttgatt tttgtgtatc atcaaccaat 900
ccttctgaac aagagcctaa atttccttgt aaagaatggg acccaaattt accttcattg 960
tgtcttccaa atcctgaata tttggctcct gaatacatac tttctgtgag ctgtgaaaca 1020
gccagtgata tgtattcttt aggaactgtt atgtatgctg tatttaataa agggaaacct 1080
atatttgaag tcaacaagca agatatttac aagagtttca gtaggcagtt ggatcagttg 1140
agtcgtttag gatctagttc acttacaaat atacctgagg aagttcgtga acatgtaaag 1200
ctactgttaa atgtaactcc gactgtaaga ccagatgcag atcaaatgac aaagattccc 1260
ttctttgatg atgttggtgc agtaacactg caatattttg ataccttatt ccaaagagat 1320
aatcttcaga aatcacagtt tttcaaagga ctgccaaagg ttctaccaaa actgcccaag 1380
cgtgtcattg tgcagagaat tttgccttgt ttgacttcag aatttgtaaa ccctgacatg 1440
gtaccttttg ttttgcccaa tgttctactt attgctgagg aatgcaccaa agaagaatat 1500
gtcaaattaa ttcttcctga acttggccct gtgtttaagc agcaggagcc aatccagatt 1560
ttgttaattt tcctacaaaa aatggatttg ctactaacca aaacccctcc tgatgagata 1620
aagaacagtg ttctacccat ggtttacaga gcactagaag ctccttccat tcagatccag 1680
gagctctgtc taaacatcat tccaaccttt gcaaatctta tagactaccc atccatgaaa 1740
aacgctttga taccaagaat taaaaatgct tgtctacaaa catcttccct tgcggttcgt 1800
gtaaattcat tagtgtgctt aggaaagatt ttggaatact tggataagtg gtttgtactt 1860
gatgatatcc taccettctt acaacaaatt ccatccaagg aacctgcggt cctcatggga 1920
attttaggta tttacaaatg tacttttact cataagaagt tgggaatcac caaagagcag 1980
ctggccggaa aagtgttgcc tcatcttatt cccctgagta ttgaaaacaa tcttaatctt 2040
aatcagttca attctttcat ttccgtcata aaagaaatgc ttaatagatt ggagtctgaa 2100

```
cataagacta aactggagca acttcatata atgcaagaac agcagaaatc tttggatata   2160
ggaaatcaaa tgaatgtttc tgaggagatg aaagttacaa atattgggaa tcagcaaatt   2220
gacaaagttt ttaacaacat tggagcagac cttctgactg gcagtgagtc cgaaaataaa   2280
gaggacgggt tacagaataa acataaaaga gcatcactta cacttgaaga aaaacaaaaa   2340
ttagcaaaag aacaagagca ggcacagaag ctgaaaagcc agcagcctct taaaccccaa   2400
gtgcacacac ctgttgctac tgttaaacag actaaggact tgacagacac actgatggat   2460
aatatgtcat ccttgaccag cctttctgtt agtaccccta aatcttctgc ttcaagtact   2520
ttcacttctg ttccttccat gggcattggt atgatgtttt ctacaccaac tgataataca   2580
aagagaaatt tgacaaatgg cctaaatgcc aatatgggct ttcagacttc aggattcaac   2640
atgcccgtta atacaaacca gaacttctac agtagtccaa gcacagttgg agtgaccaag   2700
atgactctgg gaacacctcc cactttgcca aacttcaatg ctttgagtgt tcctcctgct   2760
ggtgcaaagc agacccaaca aagacccaca gatatgtctg cccttaataa tctctttggc   2820
cctcagaaac ccaaagttag catgaaccag ttatcacaac agaaaccaaa tcagtggctt   2880
aatcagtttg tacctcctca aggttctcca actatgggca gttcagtaat ggggacacag   2940
atgaacgtga taggacaatc tgcttttggt atgcagggta atcctttctt taacccacag   3000
aactttgcac agccaccaac tactatgacc aatagcagtt cagctagcaa tgatttaaaa   3060
gatcttttg ggtgaggtgt cttacttcta ttttgaagga ttatttcagt ttcaatcatg   3120
ggtgagctga tttacatctt tatatagttg gcttggagga agtacttcta tgggaaagtg   3180
aacagttctg tgacaggaaa catctctgtc catgccagca tagtagttgt atggacttct   3240
aaccagttga gtttttaaa gcattgagga tttttcctc ttaccaactc ctcttcaggt   3300
ttttaaagac ccagcccttc ccaatctcaa agagaaaaag gaaactgagt tatcttgaat   3360
aacataactt tttaatcaaa tgtttatttt ggcttgtgga tcttggtgtt atttaaaaaa   3420
ttgaggtgat ggtcattgca agctcatcta ttaagtacta tatggtacac agtctatgag   3480
tcattagtct tcattttaat atgtaaaaaa tcttgatgct gtattgattt gtttgcattt   3540
aagatgacag tgagaaaatg ataagcataa agagaagtat caggttattt gctttttcca   3600
aacttttcag atgaactatt gtttagtaca gagactgagc aaatactaca aaattcaact   3660
taaccttcat ttcattggtt taaatgcgtt attaaccatc ttaagtgcaa actaatcatt   3720
gtaaattata ttttagcatg gtctgcctca aatagtaatg tatttttctg cattcacttg   3780
gatatattta gaatcacttt tttcctcctg tatcaaggaa gaggtatgtg ctgatttgtt   3840
tggatatttg acaaggcact ctgatgtgac ttccctgact actaccttca tatttcattt   3900
caaattcaaa cttctgaggt tgcagcatat atgaattgca ttttcaaaag aagatttgta   3960
agaattaaac tatatttatg agtaaacttt tgaggtttct gctgtattgt ttcaaatgta   4020
ataaacttta cttctgtaaa aattgagcag ttgtatcttc tgaccaccaa cagattttca   4080
gcttgccatg atagtctgac ctcattaatt actgctactg aagttcaatt tttttctagg   4140
aattttagga accttttgtt taaatatttt aatttctatt agccattttt aggaaggaaa   4200
gaatcaattc tcttaacagg aaacatgctt tatttttcaa aacctttctc tgatattttt   4260
ctttaatttg ctgattattc aaccacagag ccttatgcta taaatgtcat ttgtatttta   4320
aaaaataata ttccactcat aaaactttaa aaccatcttt caacgaacta tatatgtatt   4380
atagttgctg ccatagagtt gatggttttt aattatctgg aaccagcaat catttaaaat   4440
```

-continued

```
aaaccatatt aagtttagta tgctggtatt gtttattcat tttatatgaa tattcattga   4500
aaatatatac acaatatatg taatacacag cacttgatta caaaatgtaa tttaattata   4560
ttattgctgg cagcattcag ttaagagggt actttaaaaa atagaagtca gctttcacat   4620
ctgatttctg tatgggctgt acttggttaa cttgatttta gaaaaaggac taacagaatt   4680
gctaaagaaa tgcatccaat aaatgaaaaa cagtaggaag atcaaatgtt tttgtcaaat   4740
atattcacaa cttgaccaga ttagctgtcc tgtttgtaat gcaatattaa tatgtctttt   4800
gggaaaaagc ctacatatgg aataaaataa gtattgaaga atttttcttt gtaacaattt   4860
agtagtcact gtttattgag aaattgtttt ttattttgta aaataacatg atgttagtgt   4920
tgaactctta aacagaaaga aagcttaata taacagctta tagaacttga actactaaat   4980
atgaaaataa gtcatttgaa aaaaatacag tatgtaaaat ttgttcattc gttgaggtaa   5040
tggtgctatg tttttacaaa attgttccta cacctttttt ctacttcagg tattttattt   5100
caaccatttc catcaattga actgttacca ttgccttttt ctgttgagaa attgcctctg   5160
aaaaatagtg ctatttttca gcttaagtgt tcttaagtga atgaaatttt caaagtacta   5220
gatcacctta aaattatttc acgtactgaa gacaattaag tccgttatgt ttagagtaga   5280
aaatgtttag gttaaagagc atctgtcaac agaatctaca aaaaagattc ccttgcattt   5340
gaattagttc tctattctcc tattgctaaa tgtgtgatat atagagagga tgtataaaag   5400
gaaatggaaa tagactatgt acttgtctgg tttttgtttg tttttatttt ggaatgctta   5460
taagcctcct ttacactgaa taaggaagta gtttttgttt tcttttgacc tgtaaaatac   5520
ctcacatggt tgtttttaca catgaaagaa aaaggtatat gcgaacatac ctgatatcaa   5580
gaggagtatg caccaaataa attttagctt tgataaaact ttccataaaa aaaaaa       5636
```

<210> SEQ ID NO 19
<211> LENGTH: 2770
<212> TYPE: DNA
<213> ORGANISM: Homo sapiens

<400> SEQUENCE: 19

```
gttgggcggg gcagggagtt cgtagccgcc tctgggtaac tcgactcggg cggccaaacc     60
tccggaggcc ggggacggaa ggcgggcccg cagcagatcc tggatccgga atctcccggg    120
caggagcgga atctgtcccg aaccgggtct gtgaggaact cgcgaacttg gattaggaaa    180
tcccggagcc cggatcgaca aatcccggaa cccggaatta agatcgccaa gtcccggatc    240
gcggagcaca gagcacggag tggactcgac gcggagcccg gagtccggat cgcggcaccg    300
cgggacggga cggagcgatg tcgggccgag gcgcgggcgg gttcccgctg cccccgctaa    360
gccctggcgg cggcgccgtg gctgcggccc tgggagcgcc gcctcccccc gcgggacccg    420
gcatgctgcc cggaccggcg ctccggggac cgggtccggc aggaggcgtg gggggccccg    480
gggccgccgc cttccgcccc atgggccccg cgggccccgc ggcgcagtac cagcgacctg    540
gcatgtcacc agggaaccgg atgcccatgg ctggcttgca ggtgggaccc cctgctggct    600
ccccatttgg tgcagcagct ccgcttcgac ctggcatgcc acccaccatg atggatccat    660
tccgaaaacg cctgcttgtg ccccaggcgc agcctcccat gcctgcccag cgccgggggt    720
taaagaggag gaagatggca gataaggttc tacctcagcg aatccgggag cttgttccag    780
agtctcaggc gtacatggat ctcttggctt ttgagcggaa gctggaccag accattgctc    840
gcaagcggat ggagatccag gaggccatca aaaagcctct gacacaaaag cgaaagcttc    900
ggatctacat ttccaatacg ttcagtccca gcaaggcgga aggcgatagt gcaggaactg    960
```

```
cagggacccc tgggggaacc ccagcagggg acaaggtggc ttcctgggaa ctccgagtgg   1020
aaggaaaact gctggatgat cctagcaaac agaagaggaa gttttcttca ttctttaaga   1080
gcctcgtcat tgagctggac aaggagctgt acgggcctga caatcacctg gtggagtggc   1140
accggatgcc caccacccag gagacagatg gcttccaagt aaaacggcct ggagacctca   1200
acgtcaagtg caccctcctg ctcatgctgg atcatcagcc tccccagtac aaattggacc   1260
cccgattggc aaggctgctg ggagtgcaca cgcagacgag ggccgccatc atgcaggccc   1320
tgtggcttta catcaagcac aaccagctgc aggatgggca cgagcgggag tacatcaact   1380
gcaaccgtta cttccgccag atcttcagtt gtggccgact ccgtttctcc gagattccca   1440
tgaagctggc agggttgctg cagcatccag accccattgt catcaaccat gtcattagtg   1500
tcgaccctaa cgaccagaag aagacagcct gttacgacat cgatgtggag gtggacgacc   1560
cactgaaggc ccaaatgagc aattttctgg cctctaccac caatcagcag gagatcgcct   1620
cccttgatgt caagatccat gagaccattg agtccatcaa ccagctgaag acccagagag   1680
atttcatgct cagttttagc accgaccccc aggacttcat ccaggaatgg ctccgttccc   1740
agcgccgaga cctcaagatc atcactgatg tgattggaaa tcctgaggag gagagacgag   1800
ctgctttcta ccaccagccc tgggcccagg aagcagtagg caggcacatc tttgccaagg   1860
tgcagcagcg aaggcaggaa ctggaacagg tgctgggaat tcgcctgacc taactgctca   1920
gggatctttc ttcccagccc tggagcctgg agggagacca ccctctgggt ccttgctggg   1980
gccgcagaca cgtaggctgg ggtgaggagt gtctgctgtc accctctact ctccagcttt   2040
agtcttataa atgtagtgat aggattcctt gttgcttggt ccccaaagcc ttatactttt   2100
tgcattggct ttaattgggt tcagcagatg cctcctctgc ccccctgcag gcaggcccaa   2160
gtaggactgc tggaggctgt gctttgacat tgtaagacat ttccgaacca aaggctgctg   2220
ggtttgcatg tttacagact ccccctgggg cgagggtcag agctggctct ggggagctgg   2280
gctaggaaga ggaggtgcag cccagactct tcctagcctt tctaaaccaa agttctttgc   2340
cattcctaca agcccagcct tgctgctggt tttttccttt cctttgggta tttgcactat   2400
tttgggagca agttttctat gtgggagcca cttttttttgt acaggggtaa gttgggggtt   2460
ttcagggagc ctgttaggtg cctccttctt ttctttcctc aatctatgca agcggctctg   2520
gccgccatca tctcctggga tgccagaggg ctgcctctcc agcggcttgg gccggggagg   2580
ggacactcca gttctctagc atggcctgag gtatggggta tgtgcatgtg gaggccaggg   2640
taaggtgaat ggggaggctg ggaggactgg tgttgccctt tggagcttgg tgaggagggt   2700
gggcctaggg cttggcgagt gccacatctg gcaggtttgg aaatttccaa ataaatcctt   2760
ttgtctattg                                                          2770
```

<210> SEQ ID NO 20
<211> LENGTH: 7523
<212> TYPE: DNA
<213> ORGANISM: Homo sapiens

<400> SEQUENCE: 20

```
gtccgggttc gcttgcctcg tcagcgtccg cgtttttccc ggcccccccc aacccccccg     60
gacaggaccc ccttgagctt gtccctcagc tgccaccatg agcgaccaag atcactccat    120
ggatgaaatg acagctgtgg tgaaaattga aaaaggagtt ggtggcaata atgggggcaa    180
tggtaatggt ggtggtgcct tttcacaggc tcgaagtagc agcacaggca gtagcagcag    240
```

-continued

```
cactggagga ggagggcagg gtgccaatgg ctggcagatc atctcttcct cctctggggc    300
tacccctacc tcaaaggaac agagtggcag cagtaccaat ggcagcaatg gcagtgagtc    360
ttccaagaat cgcacagtct ctggtgggca gtatgttgtg gctgccgctc ccaacttaca    420
gaaccagcaa gttctgacag gactacctgg agtgatgcct aatattcagt atcaagtaat    480
cccacagttc cagaccgttg atgggcaaca gctgcagttt gctgccactg gggcccaagt    540
gcagcaggat ggttctggtc aaatacagat cataccaggt gcaaaccaac agattatcac    600
aaatcgagga agtggaggca acatcattgc tgctatgcca aacctactcc agcaggctgt    660
ccccctccaa ggcctggcta ataatgtact ctcaggacag actcagtatg tgaccaatgt    720
accagtggcc ctgaatggga acatcacctt gctacctgtc aacagcgttt ctgcagctac    780
cttgactccc agctctcagg cagtcacgat cagcagctct gggtcccagg agagtggctc    840
acagcctgtc acctcaggga ctaccatcag ttctgccagc ttggtatcat cacaagccag    900
ttccagctcc tttttcacca atgccaatag ctactcaact actactacca ccagcaacat    960
gggaattatg aactttacta ccagtggatc atcagggacc aactctcaag gccagacacc   1020
ccagagggtc agtgggctac aggggtctga tgctctgaac atccagcaaa accagacatc   1080
tggaggctca ttgcaagcag gccagcaaaa agaaggagag caaaaccagc agacacagca   1140
gcaacaaatt cttatccagc ctcagctagt tcaaggggga caggccctcc aggccctcca   1200
agcagcacca ttgtcagggc agacctttac aactcaagcc atctcccagg aaaccctcca   1260
gaacctccag cttcaggctg ttccaaactc tggtcccatc atcatccgga caccaacagt   1320
ggggcccaat ggacaggtca gttggcagac tctacagctg cagaacctcc aagttcagaa   1380
cccacaagcc caaacaatca ccttagcccc aatgcagggt gtttccttgg ggcagaccag   1440
cagcagcaac accactctca cacccattgc ctcagctgct tccattcctg ctggcacagt   1500
cactgtgaat gctgctcaac tctcctccat gccaggcctc cagaccatta acctcagtgc   1560
attgggtact tcaggaatcc aggtgcaccc aattcaaggc ctgccgttgg ctatagcaaa   1620
tgccccaggt gatcatggag ctcagcttgg tctccatggg gctggtggtg atggaataca   1680
tgatgacaca gcaggtggag aggaaggaga aaacagccca gatgcccaac cccaagccgg   1740
tcggaggacc cggcgggaag catgcacctg cccctactgt aaagacagtg aaggaagggg   1800
ctcgggggat cctggcaaaa agaaacagca tatttgccac atccaaggct gtgggaaagt   1860
gtatggcaag acctctcacc tgcgggcaca cttgcgctgg catacaggcg agaggccatt   1920
tatgtgtacc tggtcatact gtgggaaacg cttcacacgt tcggatgagc tacagaggca   1980
caaacgtaca cacacaggtg agaagaaatt tgcctgccct gagtgtccta agcgcttcat   2040
gaggagtgac cacctgtcaa aacatatcaa gacccaccag aataagaagg gaggcccagg   2100
tgtagctctg agtgtgggca ctttgcccct ggacagtggg gcaggttcag aaggcagtgg   2160
cactgccact ccttcagccc ttattaccac caatatggta gccatggagg ccatctgtcc   2220
agagggcatt gcccgtcttg ccaacagtgg catcaacgtc atgcaggtgg cagatctgca   2280
gtccattaat atcagtggca atggcttctg agatcaggca cccggggcca gagacatatg   2340
ggccataccc cttaaccccg ggatgcaagg tagcatgggt ccaagagaca tggaagagag   2400
agccatgaag cattaaaatg catggtgttg agaagaatca ggagagggat acaagagagg   2460
agatggggtc ccggcaccca tctgtatcat cagtgcctct ttgaaggtgg gaaacattag   2520
tgaaaattct gttggtgcca cgctttgatg agcatttgtt tgaccccagt ttcttcttac   2580
acttcttacc ccagcctacc cttcctgcat ttctcttctc agctcttcca tgatggattc   2640
```

-continued

```
ccccccctttt cctaaagcca tcatgccttg ataaatatat atgatcattg aaatactttt   2700
taacaaaaaa cagattctat attattatat atatatatat atatataaag atatatagag   2760
atgcattcac aggggttggc tgggaggagg aagaccattc tgtgaccaaa ataccttggt   2820
cattttttt atattgcctt atttccctat ggctgagcct tgttgtgaca catcaagctt   2880
ttctgtagat gttgtcttgg cttcccacca gcttaagcgt tcatatgctc tgcttttagt   2940
tcatatatac atacataatg tttttccttt cttaatttg tctttttgtt tgggatcagc   3000
ttcttgcact ccttccctaa ctcaactgtt gccgtctcat cttctctcat ctgatcactt   3060
catgttttgt ttttgttact gcctggatga ggcacttctg tcaatttttt caggacctta   3120
gttccagcag cagaatggaa aaatccttga agcccaggct gatgcttgaa gtaactgtgg   3180
agggagtgtt caaaatacta ctgacgcagg caccttcttg gcgctggaga gtcaaaggca   3240
tctcccttca ttagctgctc tgagcatcaa gaattagaag tctttcagtg gaattgtaca   3300
agagtccctt tgaagataat aatcttggct cagtttgtat aaactgtcaa attttcaaat   3360
aataggtagg gggctttcac taggaaaatc atgtgctcag aagaggaaat gactcgtagt   3420
caggttcagg agttagtgga gtatttggac tttggtactg ctgtcttcca aggtagctct   3480
aagttttgat gtgtgggctt ctgagtttat attctgaaag gaaatacact tcttttgaac   3540
atccccacta ggttcttttc cattgtcaat aaggagcatc agccagtgaa tctgtttcag   3600
gtttccattc tgcagaactc ctccaaagca tgtgctagtg gcaagacagt ggttcttatg   3660
atgttttccc ttaacttttc cttgtatgtt cttgggtggt tcctaaggga aagggaagca   3720
catgatcatg ggaatgatag cccagaacaa aaagaaatct tgtcttacca cagtgtttta   3780
taggagagat tgggagaaat catcctgttt tctctgtgac ctgatttcag aagagactga   3840
tccaaaaatt ataacggcag ggaacctagt gcatttggca ctgagattta aatgcaacca   3900
gaattgtcct caaggcccag ccataaaagc attgtctctc tcgaccttct ggtatcttgt   3960
tagagagctt ttcactgtga ggaagtgtgg aaaaatagct ctgtgtgtgt gtgtgtgtgt   4020
gtgtgtgtgt gtgtgtgtaa tctgttaggt tggggatagg ttttctgcta gccaatatta   4080
aaagagacct gcaataaaaa aattaccctg atctgataga aagcaagtgt ttttgtatgt   4140
gtgggtgaat gtgtgttcat gcccgtatat gtctacacac agatgacaaa ttatatttga   4200
aatcgttgga aaataaattc agatcaaaat gcctttcagg cccattacct agaaatctat   4260
cttaaaacct gggtatgttc ctaaggtcat ttctttgctt atgctaaatt aattacaatt   4320
atgaatggag gatattctac tgtacttttt taaaaagaaa ctatttttgt gtttgaaagt   4380
gaaaccaaca tccagatcta tagcagagtc cttattcttc tcataaatct ttttactttg   4440
gctacaaata gatgatggta tgattctatt atatatttta tataaaatcc atccaaatta   4500
agttttgggt aagtgtgttg tttaatctga actatagtaa cttaatactc taaacaatag   4560
ttcactccat ttggtccttt ctccacagat gtaattatgt tttcaactca ggaactatgg   4620
caaggaactt tccccagatc aaattctatt aacgctgaga tacaagtcat ccatgcacag   4680
ccactatcat accctttatt ctcactgaaa ggcagaactc agaacctgtt attttatgtc   4740
tgtaatcatg tactttggca tcttttggag gaaaggggca ggataactca ctggaatgta   4800
cagtattttg ctagtgcatt tcaaggaatg gaatcttctc cagtatgaaa ttaccagata   4860
taaaataatg taatgatgct gaggatataa gcttttagaa ggtaatttga tggtatttct   4920
ttctcgaatg aaaagctgct ggtttaccct caaccctatt cattagcatt accatgagtg   4980
```

```
aatttatatc taattatttc cacttgccct gttctcttca caccaaggaa gctccagatc   5040
cagtatcttg tttggcctca aaacagaagc agcttctttt gtctcccagc agtagtgagc   5100
cactcagtct cttccacagg aagtttggag cctacattcc ttgagtcagg agcttattac   5160
agaaaaaccc cgtttccctg aacttttggc taacagaaat taatttaact gacatgcata   5220
ttgattctga aattttttc ctaagttttt ttcatttttt tgaatgagtt ttttaaattt   5280
tttagatgac caaaacttgc agggcagggg atgcccagaa gagtggtgag atagtaaaac   5340
acttattccc tcatcctttc aggttttcag gttgcccatt tatattcatt tacatgtcat   5400
ttgactgtct cactttttac ccagaacagt aacaacccac accgtcttcc ttcagggatt   5460
tccaactggc actctgtggg tgctacacag aatgcaattt aatggatatt tctcagcctg   5520
gttcagaata aattgatcct ttgatcccag aaagtatata ctgaagtgtg ggataaagat   5580
tatgattagg ggagggttgg agacaaaagc tgtaaattac tatggctgat ttatttctac   5640
tatatacata tatatttttt gcttttgtat atcctatata ggaaactaag cattgtattt   5700
tttttaacaa atctaaaaaa gcactatgaa ctacaggtgt ttgactttca aaatatattt   5760
tgtattgtta atatcttcac attgtgtgaa tactggaagc tgcagatctt tgctaggacg   5820
caataaattt atatactttt tgaggggttc ttctggggtg ctaatcaggc ccctgttatg   5880
cttaggggga gccctggtgc tacttgcttg aagttttcag tgtaagtacc ctgatgcctt   5940
ttggaccttg ggatcagatc aagagttttg gagatcaggt accaaggaaa taaggacagt   6000
ctagctgcct caagtgaggg gccctttgca tagctctcct tccccctcac tgaagctggg   6060
tagcctattg gggttgagag ggaaaatgtg aaatctcaga atttatctcc cttagaagag   6120
agccagtaac ttatgtacaa ggatgaaaga aaggtcgcag cagtagcttt ggggaaaggg   6180
aggaagatat ggcacttctc caaccccgga aaacattgct tttgaaaact gctgataaaa   6240
tatgagccgg ttattacttc tgtttgggag actgtgctct ctgtggtgcc tctcttggct   6300
ctactccaca gataccagac ctcttctaag aggatgagca gaccagcttt gaggttgacc   6360
tgtttctctt tgtctgcctt cccaaaacac cagcccccag gaagacatta agcagcctta   6420
agcttaaatt cctactccct cttccaaatt tggctcactt gccttagatc caaggcaggg   6480
aaaggaaaag aagggggtc tctggcttta ttactcccct aagtctttac tctgacttcc   6540
ccaaacccag aaagatttc tccacagtgt tcatttgaaa gaggagtatt ttgtcccatt   6600
ttccccttcc tcattatcaa acagccccag tcttccttgt ctctgctaag aaagtagagg   6660
catgatgatc tgcctctcaa ctgccctaag tcctagctaa gtatcagggg aaaaaaaaaa   6720
aaaaaaagcc taacaaatgg gattagacta gggctgcaag tagtgaggat tttgttgata   6780
cctctgctgg gatgtgtgct ttcccatatc ttgccttcag gaattacact gtgccttttc   6840
cccagggata tgggctctgt ctacccagtg ctccagtttc ccggtaactg ctcttgaaca   6900
ttgtggacaa gggcaggtct tcatattttt gatcatccct ttctcccagt gaaatcccat   6960
agcccttacc tagagtctag ggcacaaaga cttcggggaa gatacactga gattgacctg   7020
aggagacatc tacacacacc agtggcagct gccccagggc ctgcttcccc ttcctaagtc   7080
tgtcatcctc tggaagggat gggtggtgct ccaatctctg gtgcctaaaa acccaagttt   7140
atttctctct taacactggc aataaccagt ccacaccact gttgcctttt aaaacctctt   7200
aataatctca tgctgtgttt gttttgattc caatccaatt atcaccaggg ctgtgtgggt   7260
aaatgctttt aaatgctctc tcatcttgtt cttccccctc accccccact cttaggtatg   7320
tatgatgcta atcttgtccc taagtaagtt tcttcctgct ccttttgtat cttcctttct   7380
```

```
tgtctttcct cctacctttt gtctcttggt gttttgggac tttttttttt tttttttttgg   7440

ccttttgtac aaagattagt ttcaatgtag tctgtagcct cctttgtaaa ccaattaaaa   7500

agttttttaa taaaaaaaaa aaa                                          7523


<210> SEQ ID NO 21
<211> LENGTH: 1651
<212> TYPE: DNA
<213> ORGANISM: Homo sapiens

<400> SEQUENCE: 21

attttgtgga gcgccagagc tgctaagtgc gtcagttgtg gagtggcgta gacgagttaa     60

gtcctggtct gcgtggaggt cgacgactcc gtcgcagact acggacctgt ctgggtctca    120

gccgccaaag accccgtccg gtaggtgagt ggctcacttt gagggcaagc cttctcggat    180

cgaggcttct tcatggccgc tcagatcgtg agcggccggg gctgctctct ttgcggagga    240

tggcgtctaa tgagcgcagt tgattcgagg aagtactagc cggacatcat gagtggctgt    300

cgggtattca tcgggagact aaatccagcg gccagggaga aggacgtgga aagattcttc    360

aagggatatg gacggataag agatattgat ctgaaaagag gctttggttt tgtggaattt    420

gaggatccaa gggatgcaga tgatgctgtg tatgagcttg atggaaaaga actctgtagt    480

gaaagggtta ctattgaaca tgctagggct cggtcacgag gtggaagagg tagaggacga    540

tactctgacc gttttagtag tcgcagacct cgaaatgata gacgaaatgc tccacctgta    600

agaacagaaa atcgtcttat agttgagaat ttatcctcaa gagtcagctg gcaggatctc    660

aaagatttca tgagacaagc tggggaagta acgtttgcgg atgcacaccg acctaaatta    720

aatgaagggg tggttgagtt tgcctcttat ggtgacttaa agaatgctat tgaaaaactt    780

tctggaaagg aaataaatgg gagaaaaata aaattaattg aaggcagcaa aaggcacagt    840

aggtcaagaa gcaggtctcg atcccggacc agaagttcct ctaggtctcg tagccgatcc    900

cgttcccgta gtcgcaaatc ttacagccgg tcaagaagca ggagcaggag ccggagccgg    960

agcaagtccc gttctgttag taggtctccc gtgcctgaga agagccagaa acgtggttct   1020

tcaagtagat ctaagtctcc agcatctgtg gatcgccaga ggtcccggtc ccgatcaagg   1080

tccagatcag ttgacagtgg caattaaact gtaaataact tgccctgggg gccttttttt   1140

aaaaaacaaa aaccacaaaa attcccaaac catacttgct aaaaattctg gtaagtatgt   1200

gcttttctgt gggggtggga tttggaaggg gggttgggtt gggctggata tctttgtaga   1260

tgtggaccac caaggggttg ttgaaaacta attgtattaa atgtcttttg ataagccttc   1320

tgctcacatt tttgtgaatg tctgaagtat atagtttgtg tatattgaca gagctctttt   1380

ataactaaag caaatttaat ttttttgtac tagaaaaaaa tttgaacatt ttagttcttg   1440

gttataaaaa tgttaattca gaattagttt aatgccttaa ttaaactaat taatagcttt   1500

ggacacttaa aagagctcta aatttgcttg tacataaagg cttaatttgt tttccttgtt   1560

agggtcaagg gtgtcctcca ctctttaaca gctgctggac agacacatta gagcagctgt   1620

ttgttattga taataaaata ttataaaact a                                1651


<210> SEQ ID NO 22
<211> LENGTH: 3516
<212> TYPE: DNA
<213> ORGANISM: Homo sapiens

<400> SEQUENCE: 22
```

-continued

```
atactattga ccacattatg cggccaacga tacccatttt cttacctgga tctttgcttc     60
ttaacactgt agtctaattt ttctcgttgc cttgttttct tggctgtaga agttaagaag    120
agaaagaagg tgctgtcctg gccctttctc atgagaaggc tctcccctgc atcagatttt    180
tctggggctt tggagacaga cttgaaagca tcgctatttg atcagccctt gtcaattatc    240
tgcggtgaca gtgacacact ccccagaccc atccaggaca ttctcactat tctatgcctt    300
aaaggccctt caacggaagg gatattcagg agagcagcca acgagaaagc ccgtaaggag    360
ctgaaggagg agctcaactc tggggatgcg gtggatctgg agaggctccc cgtgcacctc    420
ctcgctgtgg tctttaagga cttcctcaga agtatccccc ggaagctact ttcaagcgac    480
ctctttgagg agtggatggg tgctctggag atgcaggacg aggaggacag aatcgaggcc    540
ctgaaacagg ttgcagataa gctcccccgg cccaacctcc tgctactcaa gcacttggtc    600
tatgtgctgc acctcatcag caagaactct gaggtgaaca ggatggactc cagcaatctg    660
gccatctgca ttggacccaa catgctcacc ctggagaatg accagagcct gtcatttgaa    720
gcccagaagg acctgaacaa caaggtgaag acactggtgg aattcctcat tgataactgc    780
tttgaaatat ttggggagaa cattccagtg cattccagta tcacttctga tgactccctg    840
gagcacactg acagttcaga tgtgtcgacc ctgcagaatg actcagccta cgacagcaac    900
gaccctgatg tggaatccaa cagcagcagt ggcatcagct ctcccagcag gcagccccag    960
gtgcccatgg ccacagctgc tggcttggat agcgcgggcc cacaggatgc ccgagaggtc   1020
agcccagagc ccattgtgag caccgtggcc aggctgaaaa gctccctcgc acagcccgat   1080
aggagatact cagagcccag catgccatcc tcccaggagt gcctcgagag ccgggtgaca   1140
aaccaaacac taacaaagag tgaaggggac ttccccgtgc cccgggtagg ctctcgtttg   1200
gaaagtgagg aggctgaaga cccatttcca gaggaggtct tccctgcagt gcaaggcaaa   1260
accaagaggc cggtggacct gaagatcaag aacttggccc cgggttcggt gctcccgcgg   1320
gcactggttc tcaaagcctt ctccagcagc tcgctggacg cgtcctctga cagctcgccc   1380
gtggcttctc cttccagtcc caaaagaaat ttcttcagca gacatcagtc tttcaccaca   1440
aagacagaga aaggcaagcc cagccgagaa attaaaaagc actccatgtc tttcaccttt   1500
gcccctcaca aaaaagtgct gaccaaaaac ctcagcgcgg gctctgggaa atcgcaagac   1560
tttaccaggg accacgtccc gaggggtgtc agaaaggaaa gccagcttgc cggccgaatc   1620
gtgcaggaaa atgggtgtga aacccacaac caaacagccc gcggcttctg cctgagaccc   1680
cacgccctct cggtggatga tgtgttccag ggagctgact gggagaggcc tggaagccca   1740
ccctcttatg aagaggccat gcagggcccg gcagccagac tagtggcctc cgagagccag   1800
accgtgggga gcatgacggt ggggagcatg agggcgagga tgctggaggc gcactgcctc   1860
ctaccccctc ttccacctgc tcaccacgta gaggactcaa gacacagggg cagcaaagag   1920
ccactccctg gccacggact ctctcccctg cctgagcgat ggaaacagag cagaactgtc   1980
catgcttctg ggactctct ggggcacgtg tctggcccag ggagacctga gctcctcccg   2040
ctgaggaccg tctccgagtc cgtgcagagg aataagcggg actgtctcgt gcgacgatgt   2100
agccagccgg tctttgaggc tgaccaattc caatatgcca aagaatcgta tatttaggag   2160
ggaggccata cgccatgcca tagcttgtgc tatctgtaaa tatgagactt gtaaagaact   2220
gcctgtagat tgtttttaaa aggtcttgaa taagctcctt gagaaagttg tggaaagccc   2280
tcctcagtga ggatagctac accatggcca tggcgcatca gatagtctct gtgtacctgg   2340
atttgtgcaa tatgtaaaaa tgtatcaaat gtattataga taaggtgtta ggtgcaaagg   2400
```

atgtctaata atccctgcac acgttttgaa cttgcagtga agtacactgc tgttccttgc 2460
ttcctggggc acttttctct tggttagtgt ttaaaaatta tcttcgcttt tttaatgtgg 2520
cctcaaatgt catgccaatt ttcacatctt ccacaaactc catttaggga gaaatgttta 2580
aatctctggt ataagtttac tccataccag agtaaactat atattactct atataagcag 2640
tcttgcaata actaatcacc accatagaag aaagaaacag actgcaagga acagagttga 2700
gtgtctggag tcatcaaagg cattaaaaac tccagtaaaa gctggggccg tagcaaaaat 2760
catgaaaaac acttcaacgt gtcctttcaa tcatccaatt aaatgtgggt agattaatga 2820
aaatgtatta catcaatatt aactcatcta tagcactttg agtatctttg tagttcatga 2880
tatcctatcc tataatgtgg aggtaaatga ttttatatgc attgggggtc atatataaaa 2940
cttcaatgta atttcactac aataaattgc cttccttatt tgaaagtaaa aatgttcttt 3000
ttttattgac atgttaactc ctttccctca attaatagaa atccactaag aaaatcattc 3060
acatattggt tcactcaaca agcatttatt aaatatatat tcactattct agactaatag 3120
caagaccggg gatcttgttt aggaagaagc agtccctgtt ctccagaatt tgcaaaacca 3180
ttaaaaaagc acctacttta agccattttt tttcagcaag gagtcattct gccagaaaaa 3240
tgtagtacac aaatacagga taatataaca aatgtaaaat ttctcatttc tagtgaatta 3300
aactttccag taattttaca tctcacctca ttcttatgat gctcagtttg cttaattatt 3360
ggcaaacata atggtaaaat gtttgtactg tattagagct ttactgttcg attattaaga 3420
tatttatcca gtatcttaga gatgctggac ttcaattttc cttattttat ctttttaaaa 3480
taaaatatca tgcatgcttc tgatttgtta tagaaa 3516

<210> SEQ ID NO 23
<211> LENGTH: 2060
<212> TYPE: DNA
<213> ORGANISM: Homo sapiens

<400> SEQUENCE: 23
actcggccag gcgccggcga cctgagggga gagggaacgc agctgaaagc gtgaactgta 60
cctgtcattt actccatcct ttatagtgat gctacaggac gaagaggaat ggataaaaac 120
attggcgagc aactcaataa agcgtatgaa gccttccggc aggcatgcat ggatagagat 180
tctgcagtaa aagaattaca gcaaaagact gagaactatg agcagagaat acgtgaacaa 240
caggaacagc tgtcacttca acagactatt attgacaagc taaaatctca gttacttctt 300
gtgaattcca ctcaagataa caattatggc tgtgttcctc tgcttgaaga cagtgaaaca 360
agaaagaata atttgactct tgatcagcca caagataaag tgatttcagg aatagcaaga 420
gaaaaactac caaaggtaag aagacaagag gtttcttctc ctagaaaaga aacttcagca 480
aggagtcttg gcagtccttt gctccatgaa aggggtaata tagagaagac tttctgggat 540
ctgaaagaag aatttcataa aatatgcatg ctagcaaaag cacagaaaga ccacttaagc 600
aaacttaata taccagacac tgcaactgaa acacagtgct ctgtgcctat acagtgtacg 660
gataaaacag ataaacaaga agcgctgttt aagcctcagg ctaaagatga tataaataga 720
ggtgcaccat ccatcacatc tgtcacacca agaggactgt gcagagatga ggaagacacc 780
tcttttgaat cactttctaa attcaatgtc aagtttccac ctatggacaa tgactcaact 840
ttcttacata gcactccaga gagacccggc atccttagtc ctgccacgtc tgaggcagtg 900
tgccaagaga aatttaatat ggagttcaga gacaacccag ggaactttgt taaaacagaa 960

```
gaaactttat ttgaaattca gggaattgac cccatagctt cagctataca aaaccttaaa   1020
acaactgaca aaacaaagcc ctcaaatctc gtaaacactt gtatcaggac aactctggat   1080
agagctgcgt gtttgccacc tggagaccat aatgcattat atgtaaatag cttcccactt   1140
ctggacccat ctgatgcacc ttttccctca ctcgattccc cgggaaaagc aatccgagga   1200
ccacagcagc ccatttggaa gccctttcct aatcaagaca gtgactcggt ggtactaagt   1260
ggcacagact cagaactgca tatacctcga gtatgtgaat tctgtcaagc agttttccca   1320
ccatccatta catccagggg ggatttcctt cggcatctta attcacactt caatggagag   1380
acttaagaca catttgaaaa cagacatatc aagttctatg tgatgatttt gggtttttaa   1440
tactataaat acttgattgt aaactaaatt caagatcatt tataggaaaa tctagtttca   1500
cagctatttg aatttttttc tggatttact atataactct tattttttaa aagatcattc   1560
tgttctttca aggagaaata agcctaaaag aagaaaaaca aaaaaaattc tgtataaaac   1620
tgtaatcctt tgtattcatg tttacagtgc tattactata attcaaaatt atgtatgtga   1680
cttagagtta tataatcata atttatgttt atttcaaata tctaagttta ttgcttggat   1740
ttctagtgag agctgttgaa tttggtgatg tcaaatgttt ctagggtttt tttagtttgt   1800
ttttattgaa aaatttaatt atttatgcta taggtgatat tctctttgaa taaacctata   1860
atagaaaata gcagacaaca taaacatctt tgtaaatatc aaacctaata catttcttgt   1920
ccagtgataa aacaactggt agaattattt aaacacttta gatttttaaa taatatacat   1980
ggctttaatt tttactgtgt gtatagctac atgatgaaat taattaaata ttaagaggta   2040
aaaataaaaa aaaaaaaaaa                                               2060
```

<210> SEQ ID NO 24
<211> LENGTH: 5174
<212> TYPE: DNA
<213> ORGANISM: Homo sapiens

<400> SEQUENCE: 24

```
ggagagctcg ccagagcgct cgcatggcgg gccggtgatt gtagtcaatc tggccgtatt     60
ctcaggcagg gtcgcccggg gcggactaca tctcccggga tgctgcgcgg ccgcccccgcg   120
gaagattgtg aatatgtatc agaatgttaa tgattagctg ctgctaaatt tggtcaaaga    180
agtcacctac acagagcgtg ttgttagagc tgtgctgagc gggtgtttgg gttgttggct    240
gctttcttcc ccctttctca cacacttgta tattattttg aggtggtgtt cgcagagttt    300
gaaaggagag agaattaaaa aaaaaagccg caagcgtttc actcttttat ttttataatc    360
cccttcaatt tggggttaaa aaaaagacaa gaaaacagga aggaagagaa ataaggaaat    420
gagatgtggt aaaagaagct aaaaggtgcc ttttaaaaga tcgttgctgt gaagtgaaaa    480
aaatctccag agaaaccaaa aagcaccgcc gagacctctt ccgaaccaaa ggagtttgtg    540
tttgctttta gggaagaaga aagatcattc attcggagga ataacaacca attaaaagac    600
aaataaaaaa agtttggagt gggacgcaga gcgagcgaga ggagctgccg gcgggcggtg    660
gggcgcggag cccgcacttt cccggccggg tgagcggcgg ccgcggcgcc gggctcggcg    720
ggtgcgcctc ggcggagcga acgtcggagc gttgccttgg gagacgcgcg ccggacaatg    780
cccgcggcgg gccagtgacg cccgcgggga atgcggagcg gcccggcagc cggcacccag    840
ccgccgccgc gcgttcctgc cgcccgtgtc acgcgagacc cggcgggggc cgggaccgcc    900
cgagccgccc ctcagaccga gccggccgcc tccgctgccg cggccgcctc ctcttcgggg    960
tcattaaagc caatgagccg cgcgcctctg ccgagcgcag ccaactaaat cggcttggat   1020
```

```
gattcgcgac ctgagcaaga tgtacccgca gaccagacac ccggcaccgc atcagcctgc   1080
tcaacccttt aaatttacaa tttccgaatc ctgtgatcgg attaaggaag agtttcagtt   1140
tttacaggct caataccaca gtctgaagct ggaatgtgag aaactcgcca gtgagaagac   1200
agagatgcag cggcattatg tcatgtatta tgaaatgtcc tatgggttga atatagaaat   1260
gcacaagcag gcagagattg tcaagaggct gaatgctatc tgtgcacaag tcattccttt   1320
cctgtcccaa gagcaccagc aacaagtggt gcaggctgtg gaacgggcca agcaggtgac   1380
catggcagaa ctgaacgcca tcattgggca acaactccag gcccagcatt tatcacatgg   1440
acatggtctc cccgtacctc tgactccaca cccttcaggg ctccagcccc ctgccattcc   1500
acccatcggt agcagtgccg ggcttctggc cctctccagt gctctaggag gtcagtccca   1560
tcttccaatt aaagatgaga agaagcacca tgacaatgat caccaaagag acagagactc   1620
catcaagagc tcttcagtat ccccatcagc cagtttccga ggtgctgaga agcacagaaa   1680
ctccgcagac tactcctcag agagcaaaaa gcagaaaact gaagaaaagg aaattgcagc   1740
tcgttatgac agcgatggtg agaaaagtga tgacaacttg gtggttgacg tttccaatga   1800
ggatccatct tcccctcgag ggagcccagc acattccccc agagagaatg gcctagacaa   1860
gacacgcctg ctcaagaaag atgccccgat tagtccagcc tctattgcat cttccagcag   1920
tactccctcc tccaaatcca aagaacttag ccttaagagg gatatgggga aattgagtga   1980
aacacgtctt agcgaagatg aacaatgcac attggggtta cagagatggt tttgtcgcct   2040
gtggtttatg aatgaaaaat ctactactcc cgtctcaaag tccaataccc ctactccacg   2100
aactgatgcg cccaccccag gcagtaactc tactcccgga ttgaggcctg tacctggaaa   2160
accaccagga gttgaccctt tggcctcaag cctaaggacc ccaatggcag taccttgtcc   2220
atatccaact ccatttggga ttgtgcccca tgctggaatg aacggagagc tgaccagccc   2280
cggagcggcc tacgctgggc tccacaacat ctcccctcag atgagcgcag ctgctgccgc   2340
cgccgctgct gctgctgcct atgggagatc accagtggtg ggatttgatc cacaccatca   2400
catgcgtgtg ccagcaatac ctccaaacct gacaggcatt ccaggaggaa aaccagcata   2460
ctccttccat gttagcgcag atggtcagat gcagcctgtc ccttttccac ccgacgccct   2520
catcggacct ggaatccccc ggcatgctcg ccagatcaac accctcaacc acggggaggt   2580
ggtgtgcgcg gtgaccatca gcaaccccac gagacacgtg tacacgggtg ggaagggctg   2640
cgtcaaggtc tgggacatca gccacccagg caataagagt cctgtctccc agctcgactg   2700
tctgaacagg gataactaca tccgttcctg cagattgctc cctgatggtc gcaccctaat   2760
tgttggaggg gaagccagta ctttgtccat ttgggacctg gcggctccaa ccccacgcat   2820
caaggcagag ctgacatcct cggcccccgc ctgctatgcc ctggccatca gccccgattc   2880
caaggtctgc ttctcatgct gcagcgacgg caacatcgct gtgtgggatc tgcacaacca   2940
gaccttggtg aggcaattcc agggccacac agatggagcc agctgtattg acatttctaa   3000
tgatggcacc aagctctgga caggtggttt ggacaacacg gtcaggtcct gggacctgcg   3060
cgaggggcgg cagctgcagc agcacgactt cacctcccag atcttttctc tgggctactg   3120
cccaactgga gagtggcttg cagtggggat ggagaacagc aatgtggaag ttttgcatgt   3180
caccaagcca gacaaatacc aactacatct tcatgagagc tgtgtgctgt cgctcaagtt   3240
tgcccattgt ggcaaatggt ttgtaagcac tggaaaggac aaccttctga atgcctggag   3300
aacaccttat ggggccagta tattccagtc caaagaatcc tcatcggtgc ttagctgtga   3360
```

catctccgtg gacgacaaat acattgtcac tggctctggg gataagaagg ccacagttta 3420
tgaagttatt tattaaagac aaatcttcat gcagactgga cttctcctcc tggtagcact 3480
ttgctctgtc atcctttttg ttcacccccca tccccgcatc taaaaccaag gatttcagat 3540
actcattgca gttgtggagt ttaatcccct ttcttaacct cacttcccac ttgctattga 3600
attgtgaata gtcattaaaa acctgtgata ccaaatcttc agctgtctac ttggaagaac 3660
atggaataag catacttaac agtgaaaaga atctttaatt atgtattata tctgtaatat 3720
atttattttg tttaaagaag gctttctaac aatgactgac taaataaagc tgtctgctcc 3780
tgcattgata atgaaggtgc gttgtatttg atacccctcc ccccttttt ttggcaaagg 3840 aggggaaagg aaggtttaaa ataattgatt taaaatgtca ctaagtgtag actgatgact 3900
gtatagagat gtgaaatgta taattacaca tggaagcaat atgttgctgt gttgttatta 3960 ggttttttt gtttttgttt tctacatctt ttaaagactt ttggaaattt ggctgaacaa 4020
ttagaacaca acaggccaac tcatactcat ttggatctat ttagacaacg ttaaccaata 4080
tatctatagc tttagattat attcgataaa agtaattgga ctttttttct ttttttgact 4140
cgttgacaag tgtctttgta atatgttttt agttcccttt ttttgttgta ttataggcag 4200
atgaacaaat taaatttggc ctcaaagaga gaacttactc ccttctggat atttttgcca 4260
catttctttg caaaaggaga tatatatatc tttagtcagt tttgttgtta tgagaaatta 4320
tgggttattt tgtggcatgc tctttgggag ctgcacagtt atggggagga ctcccactgc 4380
tgtgcaagtt aagtctttta caaaacaagg acagcagagg agggtttgca gagacctccc 4440
tctgaaaaac acaaagaatg gactctctcc tgggatgagg acttgctttc tttacctccg 4500
gttctttcca tgtcttagtt ggatgtccct gaaatggaca caggctgtgc cattgtgcca 4560
gaaacattgt gttatctttt atgttgttgt tgttgctgtt aaactataat atgtgacttc 4620
ttttttattt attttttgtt tgaatgcttt aaaaatcttt taagtctgtg gatctgctga 4680
tgtacagtgc ctttgctgct atggatcaaa atcaaaagaa ccgtgtagat atactttatt 4740
gtataagtag aaaattactt aatttcatac tagaaatgga tggatgctgc aagttgaaat 4800
ggactgtcca ttgacgttcc taatgtggta gcagaaaaaa aaaaatggtg tcttaagtgc 4860
ttagtgtttg atgtcattaa cagtttcgta aaactctaca gtgtagaaag attttgatac 4920
taaactgtgc gttgtacata gttctaatgc attgtattga ccaccagtac ttctataatg 4980
gtagattgtt tgtgaattca gacttttaag cattaaacat aaataacttc tagtatgctt 5040
atttttctaa ttctttgtct tgatgacatt agtttatttt ttatctttgg ctgtgccact 5100
cctatatatt aaaaatgcct agttttttca agggagattg ttgttaaagt aaagtggttt 5160
tttttgttgt taaa 5174

<210> SEQ ID NO 25
<211> LENGTH: 4814
<212> TYPE: DNA
<213> ORGANISM: Homo sapiens

<400> SEQUENCE: 25
cttcgtgcca cgtcaccgcc tgcgtcgctt ccggaggcgc agcgggcgat gacgtagagg 60
gacgtgccct ctatatgagg ttggggagcg gctgagtcgg ccttttccgc ccgctccccc 120
ctccccccga gcgccgctcc ggctgcaccg cgctcgctcc gagtttcagg ctcgtgctaa 180
gctagcgccg tcgtcgtctc ccttcagtcg ccatcatgat tatctaccgg gacctcatca 240
gccacgatga gatgttctcc gacatctaca agatccggga gatcgcggac gggttgtgcc 300

```
tggaggtgga ggggaagatg gtcagtagga cagaaggtaa cattgatgac tcgctcattg    360
gtggaaatgc ctccgctgaa ggccccgagg gcgaaggtac cgaaagcaca gtaatcactg    420
gtgtcgatat tgtcatgaac catcacctgc aggaaacaag tttcacaaaa gaagcctaca    480
agaagtacat caaagattac atgaaatcaa tcaaagggaa acttgaagaa cagagaccag    540
aaagagtaaa accttttatg acaggggctg cagaacaaat caagcacatc cttgctaatt    600
tcaaaaacta ccagttcttt attggtgaaa acatgaatcc agatggcatg gttgctctat    660
tggactaccg tgaggatggt gtgaccccat atatgatttt ctttaaggat ggtttagaaa    720
tggaaaaatg tgatgcaaaa gaaagaaatc cctgcgcttt ctgtctgtct ttgtggcggc    780
ccagattgaa ttggggaata catctttagc ctggaaatgt aggctgcatg ttaatggtaa    840
tgtaactttt gcagtgtaat gtttgaaaaa tattaatgta gtttttgctt ttacagtaac    900
aaatgtggca attattttgg atctatcacc tgtcatcata actggcttct gcttgtcatc    960
cacacaacac caggacttaa gacaaatggg actgatgtca tcttgagctc ttcatttatt   1020
ttgactgtga tttatttgga gtggaggcat tgtttttaag aaaaacatgt catgtaggtt   1080
gtctaaaaat aaaatgcatt taaactcatt tgagagaatg ccttttagtt taatgcatat   1140
ttaaactaaa ttgatcctgt agtgttcctg gagaagctag agcctgattg taggctacta   1200
ctcatcaatt aacttctaca gtggagacta cttctgggac tggaatataa aaaagaatca   1260
aaggttctga ttttgagttg caataaaggg aaagaccatg ctcatagcag tgccaacatc   1320
tgaagtgtgg agccttaccc atttcatcac ctacaacgga agtagttaac tggaagagat   1380
taccaagaga ataaaaagag actcattcag tggaagcaac tttgtctcag cttatttcac   1440
ataaagagag cgaagtcttt tgggatgaat gttaattaaa ctccctggta actagaacag   1500
ggactggcaa actagcctat ctgaccacct gttttgtaca ctttaaggtg gttggttgcc   1560
tttttaaatg gttgagggga aaagaatacc ttgtgggata tggaatttaa gttcgagtcc   1620
agttttattg gaacgtggct atgcttattc atttatggat tgactgtggc tgttgtcagt   1680
gcatgagcag agttgtgtct aacagactag agcctgcaag tttgccagcc cctgatttaa   1740
aagatgaagg tacacagaat gtgggctggc tggtgggcaa aggggtaaaa atgttctcta   1800
tattgtatct gaaaagatgg ggtgtctgaa taagaaaatg catctatttg acagacctgg   1860
agcagttgct atctgctgct atggtttcca ccacagatgc aagaagaaca tgtccttgcg   1920
ctttccgtct gtctaattgt ggcagctgag attgaataga ggaatacagg aggaaaaaaa   1980
gcgggaagag tttttgaggc aggtcggtca cccaggcttg tagtgcagtg gcacaagcaa   2040
ctcactgcat tctctgcatc ctgtgctcaa gccattttcc cacctcagtc tcactagttg   2100
ctgggactgc aggcatgcac ccctatgccc agctaatttt tgtagagacc gagtatcgct   2160
tagttgccca gggtggtctc aactcctggg ctcaaggaga tctgcccacc tcagcctccc   2220
aaagtgcagg cctagcctgg gaggggaatt ttcaaaacgt gagttttggg aaatagtcta   2280
tcagccttac ctggttgatt acacttgtaa aagaaagatt aaaagcaggc cagtgactct   2340
ggtctgcttg aacatgtgaa tgtagtggtt tgagcaatct ggagtttgcc ctagtgtcaa   2400
attccagact gtccatagtg tccaaaacct gaggcagata ctaatgttaa cccccagcac   2460
cccgtgattg gaaacaaacc taaatacgta ttgggaactt aatagcaatt ttaagcattc   2520
tgatagattt tttgtaggga tggggtcatg ccatgtggcc caggctggtc tgaaaactct   2580
ggcctcaagt gatctcaagc tttggccttc taaagtgttg ggattacagg tgtgaggcat   2640
```

-continued

```
tgcacctggc ttagcgttct gatttgacat tgtaatgaaa agtgtgagtc tcatctacag   2700
ggccttttgt cctctgaaat gatagcagga agggaatttt caggcagtgg tcaaagctgg   2760
ggaaaccagg atagtgaaga aggccttgag gtgagagatg gaagctaatt ggtgaactag   2820
ccttggaagc ctgaaacaga caagtagcaa ttcagagact ttgtgggctc cactgctcca   2880
acttgttttg aagattttca gttctgcaga agaggtattt ccccagttgt cctttcagtg   2940
ctcttagctg ttttcccaac atccagatcc aatcaaggct gggacatagc attttatcat   3000
gtctatttaa gtcagaagtg atgaacccca gctgtttacc tcatggtaaa cctttgaaga   3060
ttccaggtag aatcttctca gactttgaag actgtctcat tttatatctt tttctcgtta   3120
ttcctagggt caagacgttt tgggcaagaa taaggatgtg aacatcagaa agctcataac   3180
attttgtttt tgatgctaag tttaacaaag gcatgcttta gtagcctgtg ggccctaggg   3240
tttgttaaag tgtggagaac aactgagtgg agcaagagga cttttctagg aaggtccttg   3300
taatgtgaca tttgaaaaca aatgaaggtg tggaagtagg ccatgtggat atcaggacaa   3360
accattccag gccaagacaa cagcagttag tctggagtgt gatgtgttct gggaaaaaag   3420
tggccacttt gctaacccaa gaagacagga agggttgtaa agcagtggga gtgtgcaagg   3480
aaggaagacc agacctcaag gaaaccacag gcgctctgag cagaagagtt acatgatatg   3540
actcaaattt ttaaaggatc actttggctg ccaggtggca gggtaaaagc atagaataat   3600
tgtgtataat gtgtttttaa ggcaaagata gtggcttagt ctagggtagt agactgaggt   3660
ggtaggaaat gaagatagag acaacaggat atgctggtgg gtgaggatgg atttaatgtt   3720
gatacaagta ttttggtctg agcgtttgga agaaagttgg cactgaggtg ggaagtcgag   3780
tttagttttg ttagttttgg atgtgttaag tttgagatgc tgattcttca gagaagtcta   3840
agctggagaa ctatatagag agtggaaaga taacaataga cattgaaagc catgatacag   3900
gataaggtca tttggagaga ggatagactg cattccaaca tgagattggt tgacaaagag   3960
aaaccaacaa aggtaattaa gaggtgctcc cactgcactt gtactcagaa ggctgaggta   4020
ggattgttag aggccagcct gggcaccaca gggagacccc atctctaaaa tttagccagg   4080
aaccatggct catgcctgta gccccaggaa tttgggaggc tgagtgggga ggatcgcttg   4140
aggtcaggag tttgagacca gcctgggcaa catagggaga cctaaaaaaa ttaattgggc   4200
atctgtagtc ccagctactc aggcggctga gctgagagga tggcttgagt ccgagagatt   4260
gagggtgcag tgagctgtga tcataccact gcactccagc ctgggcggca gtgagacact   4320
atctgaaaaa agtttaaaaa ttttaaaaaa gaaggaactg cccctgaggt aagaaccaag   4380
ggagggcctc ccagaggtca ggtggaaaaa gttttaggaa ggaggaagta gtcaacaggg   4440
ttacctgttg caaagtactt aagtaatatg aggcctgata gtggtaaact tgactaccgt   4500
tggatttcac tagtgggaaa ggaagtctaa ttaaaatgca ctcaagagac taacagtcgc   4560
aggcatgaaa tacaatacag gtacatggtt ttttattatg tgtgcatctg cttcagtaat   4620
aggtgtgaat tactcatttg gatcattagg agtttcaaaa tctagttaaa tgactagatt   4680
tttgttgatg taaattctgt cattctgaac tgcagggatt gtcagtaact taactgcaaa   4740
ctaaactggt gataattatg gtaaaattgc aagacgagca ataaatctca accaacttga   4800
gagaacactg ataa                                                     4814
```

<210> SEQ ID NO 26
<211> LENGTH: 1781
<212> TYPE: DNA
<213> ORGANISM: Homo sapiens

<400> SEQUENCE: 26

```
cgccgtgaaa accagctgct gcagccgcag aggcagccgg aggcagaggg gcggcgggca     60
ggaccagaca gggctgggca gggggctggc cgagcgccgt gcgccgcttg ggagaaggcc    120
ggaagcttac cagccgagaa ggaattccta gctagcttca gagccggtgc ctccggagcc    180
agcgtggtgg ccatagacaa caagatcgaa caggccatgg atctggtgaa gaatcatctg    240
atgtatgctg tgagagagga ggtggagatc ctgaaggagc agatccgaga gctggtggag    300
aagaactccc agctagagcg tgagaacacc ctgttgaaga ccctggcaag cccagagcag    360
ctggagaagt tccagtcctg tctgagccct gaagagccag ctcccgaatc cccacaagtg    420
cccgaggccc ctggtggttc tgcggtgtaa gtggctctgt cctcagggtg ggcagagcca    480
ctaaacttgt tttacctagt tctttccagt ttgtttttgg ctccccaagc atcatctcac    540
gaggagaact ttacacctag cacagctggt gccaagagat gtcctaagga catggccacc    600
tgggtccact ccagcgacag accccctgaca agagcaggtc tctggaggct gagttgcatg    660
gggcctagta acaccaagcc agtgagcctc taatgctact gcgccctggg ggctcccagg    720
gcctgggcaa cttagctgca actggcaaag gagaagggta gtttgaggtg tgacaccagt    780
ttgctccaga aagtttaagg ggtctgtttc tcatctccat ggacatcttc aacagcttca    840
cctgacaacg actgttccta tgaagaagcc acttgtgttt taagcagagg caacctctct    900
cttctcctct gtttcgtgaa ggcaggggac acagatggga gagattgagc caagtcagcc    960
ttctgttggt taatatggta taatgcatgg ctttgtgcac agcccagtgt gggattacag   1020
ctttgggatg accgcttaca aagttctgtt tggttagtat tggcatagtt tttctatata   1080
gccataaatg cgtatatata cccatagggc tagatctgta tcttagtgta gcgatgtata   1140
catatacaca tccacctaca tgttgaaggg cctaaccagc cttgggagta ttgactggtc   1200
ccttacctct tatggctaag tctttgactg tgttcattta ccaagttgac ccagtttgtc   1260
ttttaggtta agtaagactc gagagtaaag gcaaggaggg gggccagcct ctgaatgcgg   1320
ccacggatgc cttgctgctg caaccctttc cccagctgtc cactgaaacg tgaagtcctg   1380
ttttgaatgc caaacccacc attcactggt gctgactaca tagaatgggg ttgagagaag   1440
atcagtttgg gcttcacagt gtcatttgaa aacgtttttt gttttgtttt gtaattattg   1500
tggaaaactt tcaagtgaac agaaggatgg tgtcctactg tggatgaggg atgaacaagg   1560
ggatggcttt gatccaatgg agcctgggag gtgtgcccag aaagcttgtc tgtagcgggt   1620
tttgtgagag tgaacacttt ccactttttg acaccttatc ctgatgtatg gttccaggat   1680
ttggattttg attttccaaa tgtagcttga aatttcaata aactttgctc tgtttttcta   1740
aaaataaaaa aaaaaaaaaa aaaaaaaaaa aaaaaaaaaa a                       1781
```

<210> SEQ ID NO 27
<211> LENGTH: 4360
<212> TYPE: DNA
<213> ORGANISM: Homo sapiens

<400> SEQUENCE: 27

```
gcggccgcgg cagggctggg cctgcgacta cccgaggagg ctgacctcca gcccgggcgc     60
ccggttcagc gccgccccgg ccggcgccgg tgcctgccag gcactcaggg aggcgggggc    120
gcagtggagg aggcggcgcc atcgcgaagc gagcgcctcg cccgcactca gccttgccac    180
cccgcccgca gtccaggctg gactgggcgg catttgccga ggctcctcgg ccaggccccg    240
```

-continued

```
tccgcccgag ccgcgctgag acccgggcag cggccgcgtg gagaggaggt ggcagcggcc    300
cgggaggccg gagccaagcc agcgacccac catggagacc cgctacaacc tgaagagtcc    360
ggctgttaaa cgtttaatga aagaagcggc agaattgaaa gatccaacag atcattacca    420
tgcgcagcct ttagaggata acctttttga atggcacttc acggttagag ggcccccaga    480
ctccgatttt gatggaggag tttatcacgg gcggatagta ctgccaccag agtatcccat    540
gaaaccacca agcattattc tcctaacggc taatggtcga tttgaagtgg gcaagaaaat    600
ctgtttgagc atctcaggcc atcatcctga aacttggcag ccttcgtgga gtataaggac    660
agcattatta gccatcattg ggtttatgcc aacaaaagga gagggagcca taggttctct    720
agattacact cctgaggaaa gaagagcact tgccaaaaaa tcacaagatt tctgttgtga    780
aggatgtggc tctgccatga aggatgtcct gttgccttta aaatctggaa gcgattcaag    840
ccaagctgac caagaagcca aagaactggc taggcaaata agctttaagg cagaagtcaa    900
ttcatctgga aagactatct ctgagtcaga cttaaaccac tctttttcac taactgattt    960
acaagatgat atacctacaa cattccaggg tgctacggcc agtacatcgt acggactcca   1020
gaattcctca gcagcatcct ttcatcaacc tacccaacct gtagctaaga atacctccat   1080
gagccctcga cagcgccggg cccagcagca gagtcagaga aggttgtcta cttcaccaga   1140
tgtaatccag ggccaccagc caagagacaa ccacactgat catggtgggt cagctgtact   1200
gattgtcatc ctgactttgg cattggcagc tcttatattc cgacgaatat atctggcaaa   1260
cgaatacata tttgactttg agttataata tggttttgtg acttatgagc tgtgactcaa   1320
ctgcttcatt aaacattctg cattgggtat aatctaagaa ttgtttacaa aaagattatt   1380
ttgtatttac ccttcattcc ttttttgat ccttgtaagt ttagtataaa tatatctaga   1440
cattcagact gtgtctagca gttacgtcct gcttaaaggg actagaagtc aaagttcctt   1500
gtctcactat ttgatctgct ttgcagggaa ataacttgtt ttttctcatg tttcatcttc   1560
tttttatgta aatttgtaat actttcctat attgcccttt gaaatttttg gataaaagat   1620
gatgttttaa gttccaatga gtattactag ttactcaata ccacttattg agtactctgt   1680
ttctacgtat gtagaatgta tagggataga agagttgaaa agggaaagca aaactcctca   1740
agtagcttcc ttaaaatgtc attcatagga gatgtactgg aattgctcat tctgtgactt   1800
tatttgtgtc ctaaacattc ttcagtgaaa ataattttat ttcagtcaaa catttatgag   1860
gaaatgagat cacatctttg tcactggatg ctacttgaag agggagtact ttgtaaccac   1920
tttgatatgc tgttatcacc accccctgcc ctctgctgcc ataatcacac aaatttaaaa   1980
agaaagaaaa cagtcttcca tagattttta aggaagaaag ggcccaagcc aggagatcgc   2040
ttggttttct tccagaagtt aaatgggggg atctgaagat ttgaatgttt ggtctgcttt   2100
gaaatgtatg tcttttggga tgtattatat gcctagcttt ataatcagta taaattttaa   2160
ttattccagg aatatgcata atattgaaat atttcatgtc ctattttaat agaaaacctc   2220
agggcccaag taacagtgat agaagttaga aaaaccttta cttagaattg tccacctagt   2280
cagagcccaa gaaagaattt tcagtggaaa aatcaatata taacttagtg ctagctagcg   2340
ccacagactc tagtagataa tattatcatc ataatggctg gtgaaaccat ataatcacag   2400
aaaaacattg ccttcagcat gttcagttcg cagcactgag ggcactcttg agggtgttgt   2460
taatgaagat ttaattttta aatacaggtg gttccaagct ttcaaatagg ttatgctcca   2520
aaagtgttat ttgtaagtta attttttac aagtcaaaca atgttggaag tggtatttag   2580
gttctagatc ggtccacgaa agttagccca tatgtatatc ttgaatagta taggggaggg   2640
```

tattcataaa gtccttatgt ggttttaact aagtgaaatt atggacaaga gaaataattg 2700
taaaatcgtc ttaaaggaaa atttaatttt tactcctgtt tatgggacat tcgttctatt 2760
aactgtcaga cacaatttct gttttcatct gagagccagt tttcctttat ttctacatct 2820
aaaataagaa catattgtac actattatat aatacagaat tgtcttaaac tttaataaat 2880
tcgcatttta aaggtgttta cagattattt tttatatctg tagctgaatt tgttaaagtc 2940
taaaaagctc aaggacttta tgaagatctc attatatgag gaaaatcata ggttaccatt 3000
ttataactct attgccataa gaaaatacac tctaaaatct tgatttgaaa catattagaa 3060
accttgattc agtgctcagt ggtctcctag taagaagtca ccgacggtag cgtcatatga 3120
gaagaaagaa atccccacca cctcaacctc tgctgagatt gtgtgctagg aacagccttc 3180
cctccgtttc ccctcagtca aacttgagcc agcctctgga tcgatgtgat cttattgcat 3240
gtttccatgg ggtgtaccta tactttaagc caatcctgct gcattcactg ctaagttaaa 3300
taaaaagcca agaagatttt gcactgtgca gatcctttgc tatctgactt gcatctcttc 3360
ccccacctgt cagctagcca cctgcttgtt tgtgttggga tattttttag cacctgaagc 3420
accatctgaa aggggcacca ttttcttctt ccctttgatc tcacatatgc tccctaaaaa 3480
tccttaagtt gtcaatctga tccccagtgt gaggttaatg agcaaaattg gtctttgggg 3540 cccttttttgt ccaagcccca ctgaaaggcc tcttcagaaa actattatct ttaaagccct 3600
actttaactc cttaattcca gcatacagct aaaactggat gtatattctg gcaagtaaag 3660
gctgaggact cctctttaat cctcagatct agataactca tgacatttta tttgaccaac 3720
atagcacatg atgagatatc aaggtaatta aaatagcatg cttgaaaaaa aaatacgtaa 3780
tctgtttcac ctgtaactgt ttaagccaat aaacttttca aaatttatgt aatgtggggc 3840
ttttatgtag cactttacgt tttcatgctg cttattgttt tattctactg aaaaaaatga 3900
atttcaagat tctcaacttt tttaatttca aaaattgttt attgttttga ctataggaat 3960
acaaaatttc ctattttggg agaataagaa ctctttttgt catttttggc tatgaataaa 4020
ctttctggtc ttttgagacc acccattttt atagatcaga atcagaaaac aggtaaacct 4080
cactcacaca tttggactca tttgaacaaa aatctaggcc aaaatactga aaagcctatg 4140
tgttttttta attggaagta tatgtaaggt taatgcattt agtgaacgtg actaacaaag 4200
actaatgtgc acattaacag atgtactttt taaggtttta tgggaggctg tgcattgctc 4260
aaaagctgtt gggaacgcct tctgaacagt tgccttcaga actagtttga gctgctcaat 4320
aaaaccagtg actttactca taaaaaaaaa aaaaaaaaaa 4360

<210> SEQ ID NO 28
<211> LENGTH: 6137
<212> TYPE: DNA
<213> ORGANISM: Homo sapiens

<400> SEQUENCE: 28
gtcttttgtc cctcggcgga caccgtttgc cagccaaagc tatgtctgcg cgctcaccga 60
cttcataggg tgccgaattc ttttttcccc aggcttgcca tggctagtcg aggggctcgg 120
cagcgcctga agggcagcgg ggccagcagt ggggatacgg ccccggctgc ggacaagctg 180
cgggagctgc tgggcagccg agaggcgggc ggcgcggagc accggaccga gttatctggg 240
aacaaagcag gacaagtctg ggcacctgaa ggatctactg ctttcaagtg tctgctttca 300
gcaaggttat gtgctgctct cctgagcaac atctctgact gtgatgaaac attcaactac 360

-continued

```
tgggagccaa cacactacct catctatggg gaagggtttc agacttggga atattcccca    420
gcatatgcca ttcgctccta tgcttacctg ttgcttcatg cctggccagc tgcatttcat    480
gcaagaattc tacaaactaa taagattctt gtgttttact ttttgcgatg tcttctggct    540
tttgtgagct gtatttgtga actttacttt tacaaggctg tgtgcaagaa gtttgggttg    600
cacgtgagtc gaatgatgct agccttcttg gttctcagca ctggcatgtt ttgctcatca    660
tcagcattcc ttcctagtag cttctgtatg tacactacgt tgatagccat gactggatgg    720
tatatggaca agacttccat tgctgtgctg ggagtagcag ctggggctat cttaggctgg    780
ccattcagtg cagctcttgg tttacccatt gcctttgatt tgctggtcat gaaacacagg    840
tggaagagtt tctttcattg gtcgctgatg gccctcatac tatttctggt gcctgtggtg    900
gtcattgaca gctactatta tgggaagttg gtgattgcac cactcaacat tgttttgtat    960
aatgtcttta ctcctcatgg acctgatctt tatggtacag aaccctggta tttctattta   1020
attaatggat ttctgaattt caatgtagcc tttgctttgg ctctcctagt cctaccactg   1080
acttctctta tggaatacct gctgcagaga tttcatgttc agaatttagg ccacccgtat   1140
tggcttacct tggctccaat gtatatttgg tttataattt tcttcatcca gcctcacaaa   1200
gaggagagat ttcttttccc tgtgtatcca cttatatgtc tctgtggcgc tgtggctctc   1260
tctgcacttc agaaatgtta ccactttgtg tttcaacgat atcgcctgga gcactatact   1320
gtgacatcga attggctggc attaggaact gtcttcctgt ttgggctctt gtcattttct   1380
cgctctgtgg cactgttcag aggatatcac gggccccttg atttgtatcc agaattttac   1440
cgaattgcta cagacccaac catccacact gtcccagaag gcagacctgt gaatgtctgt   1500
gtgggaaaag agtggtatcg atttcccagc agcttccttc ttcctgacaa ttggcagctt   1560
cagttcattc catcagagtt cagaggtcag ttaccaaaac cttttgcaga aggacctctg   1620
gccacccgga ttgttcctac tgacatgaat gaccagaatc tagaagagcc atccagatat   1680
attgatatca gtaaatgcca ttatttagtg gatttggaca ccatgagaga aacaccccgg   1740
gagccaaaat attcatccaa taaagaagaa tggatcagct tggcctatag accattcctt   1800
gatgcttcta gatcttcaaa gctgctgcgg gcattctatg tccccttcct gtcagatcag   1860
tatacagtgt acgtaaacta caccatcctc aaaccccgga aagcaaagca aatcaggaag   1920
aaaagtggag gttagcaaca cacctgtggc cccaaaggac aaccatcttg ttaactattg   1980
attccagtga cctgactccc tgcaagtcat cgcctgtaac atttgtaata aaggtcttct   2040
gacatgaata ctggaatctg ggtgctctgg gctagtcaaa gtctatttca aagtctaatc   2100
aaagtcacat ttgctccctg tgtgtgtctc tgttctgcat gtaaactttt tgcagctagg   2160
cagagaaagg ccctaaagca cagatagata tattgctcca catctcattg tttttcctct   2220
gttcaattat ttactagacc ggagaagagc agaaccaact tacaggaaga attgaaaatc   2280
ctggtactgg atggctgtga taagctgttc tccacactct ggcctggcat ctgagaacta   2340
gcaagcctct cttaggccat atgggcttct ccaccaaagc tgtttggcag ctcctagcag   2400
accttcttat tgaaatcctc atgctgaaaa tgaacacagc ctagttgcca acccacatgt   2460
ccttttcacc tccagcaaga ctaagcttct ttaaagcact tcacaggact aggaccctgt   2520
cctggagcta tctcaggaaa aaggtgacca tttgaggaac tgtgacctaa ttttattata   2580
atgatgcctc taattttcat ttcctttaca accaactgta actataaggt tgtattgctt   2640
ttttgttcag ttttagcatg ctattttttg aattctagac tcctccatgt gaagatatca   2700
acagacaaaa ctacaactgt ataggacata tttggagaaa attctatcaa ttgatacatt   2760
```

```
tggatgacat cacattttta agtaatgtaa tctgaggcca ttgctgagga aattaagaat   2820
tttccttttt ttttaaccac ccccagtgaa aaggatcagt gtatatttat agcacctatt   2880
ttttagttct gtctgttgtg aggcacatcc tgcatggggc acttctagtc aaataggcaa   2940
tgataaggac ctaattaaaa tgtgataagt gtatactatt actttaaaag cctttacagt   3000
cagtacttca gtttacaagg cactttcaca gcatctcgtt tgatcctcac agtcacaaca   3060
tgtggtagac aaggcaggtg atttttatcc ccattttaca gataaggaaa caggctgcgg   3120
gtggggagtg aggggaggta aagatagtta gttgcctaag gtcacacagc cagtaagtaa   3180
tagagctggg actggaaccc aggtttcctt actctcatct attgctcctc catattcctc   3240
actcaaccat gaaaacatta cttgaaagga ctgatgaggt taaccagaga cctaactgat   3300
attgtaactt tctattttaa ggaagaattg tgtctgtatt tgagttcttt ggagcctcca   3360
gtctgcctgt gtgttagacc agcacagcag tgctgtgtga tgcagcctga cctgtggcag   3420
gaaagtagtg cttctgtttg gaagtcatgt tcttttgcag ccacacagga tccaaatatc   3480
agtactattc ctgtagtcaa tctggggtca cattataggt gccttatttc cctaagggta   3540
actgatctga atatctgcaa ataggatgaa tctatttttc agaagttcca tctttcattt   3600
ttcttttttt ttttgagaca gagtctcatt ctgtcgccca tgctggagtg cagtggcgcg   3660
atctcggctc gctgcaacct ctgcctccca ggttgaagca attctcatgc ctcagccacc   3720
cgagtagctg ggattacagg catgcgccat catgcccagc taatttatgt atttttagta   3780
gagttggagt ttcaccatgt tggccaggct ggtcttggac tcctgacctc aggtcatcca   3840
cccgcctcag cctcccaaag tgctggtatt acaggcgtga gccaccgcac ccagccccat   3900
ctttcatttt caaagagaag ggcattctaa taggaactgg tgccaagaga gaagaaaaga   3960
agtgataaca gaagaaatgg ctagttacaa tattaaaaag ctcctctttg agatctcctc   4020
tgcaggaata tcagagacgg agttgaagcg ctggagaggt aataggtcta gacagtacag   4080
aacaataact ggggagtgtg tgaggataga ctgggctccc ccttgcttga aagatctctg   4140
gcatttaatt ctcaattctt gattactatt ttccagtgta aaactagcac atatgatctg   4200
actacaggac agagaatttt aagtgaaaca tttgccttac ttgcagtaat aatgtgctgt   4260
tcttcacagt agctaaggcc ctctatgttt cccagaggta aataagaatc caggaatgga   4320
ggtccatctg tgatgaatgg ctttttttcta atcaaagtag tataatgctg ttttatctgt   4380
tttgtcatct tgtttttttt ttttttaaa aaaacaaaac cttaattata atatagcgca   4440
aagaaaggcc aggactgatg cagggattcc ttggaaatat cagttcctat cacttttaaa   4500
acctgatttt ggatctctct gttctatgta tgtctttagt gagagcacaa tacatggcag   4560
aacgctgtgc caaatgttat aggtaaggaa tatagaaatg aatgtttttt gttgtgaagg   4620
tgttttcatg tgatatttta taaacacatt ttaaaaaatc tccatcactt tttagtatag   4680
gaaggatagc tttgcctggg aaaaacagtt tcaacacacc tgctcagagt agcagttctc   4740
cctcaaaaaa gcagtgttca gcctgcactg actgttctgc ttgccaaaag gaggaagcat   4800
gcaagatact tatttctcca tagattgtgg agtatagagg gatgtgggac tacagattat   4860
tatttttttt ccccgagaca gagtcttgct ctgtcgccca ggttggaaca caatggcacg   4920
acctcagctc actgcaacct ctgtctcccg ggttcaagca attctcctgc ttcagcctcc   4980
tgagtagctg ggattacagg cacacaccac caccgcactc agctaatttt tgtattttta   5040
gtagaggtgg ggttttacca tgttggccag gctggtctta aactcctgac cttgtaatca   5100
```

tcccgcctcg gcctcctaaa gtgctaggat tacaggcatg agccaccgca cccggcccag 5160
ataattttta atagcctttg atcatggggt gagtgaggga gtaggtatac ttggcaaatg 5220
catggttctc tgatttctag ctctaaagca gccttatctg aatccccaaa tcttgtgatg 5280
ctgagtacca ttactgaacc agtctgcacg gtaggcatct gctaccaaaa tttacctcct 5340
acctggtagg tgtcatctga taagaaagaa gacaggttat tttaattttt tgagataatc 5400
acagaaaatt gcagcccata ctctttatta ccgaattcaa gtttggaaat agaccctttg 5460
ttttaaatca tgatgggtct ttatcccaat catttatctg ggtcattttt ccaactttgg 5520
agttctagga aagaaccttg aaaacctgat atgattctgc agcatgaggt ctacggtgac 5580
catttgggca aagctccagt ggcaatcatt tattgtgttt tgcatttcct gggatttatt 5640
gaaataagaa ttcactgtga ttatgtagtc ttctggctag tatcaggcag ctctgctttt 5700
aatttggtta attttatttt ctctgaagag ggagaagagg tacaatttaa tcttggcctc 5760
cacaagcata ttaaagctca cgtgttaatc agtgcattct tatgctccta cattaaatgc 5820
cttgggtaaa tggataaatg gacatgtgcc cagctttaat ttttttgca acagaaagat 5880 cagacttccg tatggcatcg ttggatttca gaggctttct ggtgtatctg taaatctgaa 5940
tgttgccttc tgccagtctg tataaccagg tgattcatgc tgcaaatgaa atcaggaagc 6000
agtaaagtgt taaagcaaga gtattgtcca attcacttgt cttcctgatc cttgtacttt 6060
atttcacgtg tcggtgttta cattacatac ttatatttcc tgtgaaagaa agagttaaat 6120
aaattgtagc agtttga 6137

<210> SEQ ID NO 29
<211> LENGTH: 3531
<212> TYPE: DNA
<213> ORGANISM: Homo sapiens

<400> SEQUENCE: 29
agcggagcgc caggcagcgc ggagcggagg ccaggcccac agccgctccg cctcccggcc 60
cgcagatccc cgacggccgc accgcgggct cctctggccc gcaagaacac gtgcatggcg 120
tcctggggaa ggcgctgagt gcggagtcgc ggcgccgcac gcggcaccat ggccctggag 180
caggcgctgc aggcggcgcg gcagggcgag ctggacgtgc tgaggtcgct gcacgccgca 240
ggcctcctgg ggccctcgct gcgcgacccg ctggacgcgc tgcccgtgca ccacgcggcc 300
cgcgctggga agctgcactg tctgcgcttc ctggtggagg aagccgccct ccccgccgcg 360
gcccgcgccc gcaacggcgc cacaccggcc cacgacgcct ccgccaccgg ccacctcgcc 420
tgcctgcagt ggctgctgtc gcagggcggc tgcagagtgc aggacaaaga caattctggt 480
gccacagtct tgcatctggc tgcccgcttc ggccaccccg aggtggtgaa ctggctcttg 540
catcatggcg gtggggaccc caccgcggcc acagacatgg gcgccctgcc tatccactac 600
gctgccgcca aggagactt cccctccctg aggcttctcg tcgagcacta ccctgaggga 660
gtgaatgccc aaaccaagaa cggtgccacg cccctgtacc tggcgtgcca ggagggccac 720
ctggaggtga cccagtacct ggtgcaggaa tgcggcgcag acccgcacgc gcgcgcccac 780
gacggcatga ccccgctgca cgccgcggcg cagatgggcc acagcccagt catcgtgtgg 840
ttggtgagct gcaccgacgt gagcctgtcc gagcaggaca aagacggcgc caccgccatg 900
cacttcgcgg cgagccgcgg ccacaccaag gtgctcagct ggctgctgct gcacggcggg 960
gagatctcgg ctgacctgtg ggcgggaccc ccgctgcacg acgccgccga gaacggggag 1020
ctagagtgct gccagatcct ggtagtgaac ggcgcggagc tggacgtccg cgaccgcgac 1080

-continued gggtacacgg ccgccgacct gtcggacttc aacggccaca gccactgcac ccgctacctg 1140
cgcacggtgg agaacctgag cgtggagcac cgcgtgcttt cccgggatcc atccgcagag 1200
ctggaggcta agcagccgga ttcaggcatg tcctcaccca ataccacggt gtcggtccag 1260
ccgctgaact ttgacctcag ctcgcctacc agcaccctct ccaactacga ctcctgctcc 1320
tccagccact ccagcatcaa gggccagcac cctccatgtg ggctttccag cgctagagct 1380
gcagacatac agagctacat ggacatgctg aacccggagc tgggcctgcc tcggggcacg 1440
attgggaagc ccacaccccc accaccccca cccagcttcc ccccgccacc cccgccccca 1500
ggcacccaac tgcccccacc cccacctggc tacccagctc ccaagcctcc tgtaggacca 1560
caggcagctg acatctacat gcagaccaag aacaaactcc gccacgtgga gacagaggcc 1620
ctcaagaagg agctgagctc ctgtgacggc cacgacgggc tgcggaggca ggactccagc 1680
cgcaagcccc gcgccttcag caagcagccc agcacggggg actactaccg gcagctgggc 1740
cgctgccccg gcgagacgct ggccgcacgc ccgggcatgg cgcacagcga ggaggtgcgt 1800
gcccgccagc ccgcgcgcgc cggctgcccg cgcctcggcc ctgccgcccg cggctcactc 1860
gaaggcccct ccgctccccc gcaggcggcg ctgcttcctg ggaaccatgt tcctaacggc 1920
tgcgccgcgg accccaaggc gtccagggag ctgccaccgc cgcccccacc gccgccgccg 1980
cccctgccgg aggccgcgag ttcgccaccg ccggccccgc ctctgcccct cgagagcgct 2040
ggccctggct gcgggcagcg ccgctcctcc tcgtccaccg gcagcaccaa gtctttcaac 2100
atgatgtccc cgacgggcga caactcggag ctactggctg agattaaggc aggcaagagc 2160
ctgaagccga cgccccagag caaggggctg accacagtgt tctcaggcat cgggcagccg 2220
gccttccagc ccgattcgcc gctgccttct gtgtcacctg cactgtcacc agtccggagc 2280
cccacaccgc cagctgcggg gtttcagccg ctgctcaatg gaagcttggt tcccgtgccg 2340
cccactactc ctgcgccggg agtgcagctg gacgtggagg ctctcatccc cacgcacgat 2400
gagcagggcc ggcccatccc cgagtggaag cgccaggtga tggtgcgcaa gatgcagctg 2460
aagatgcagg aggaggagga gcagaggcgg aaggaggagg aggaggaggc ccggctggcc 2520
agcatgcccg cctggaggcg ggacctcctg cggaagaagc tggaagaaga gagggagcag 2580
aagcggaaag aggaggagcg acagaagcag gaggagctgc ggcgggagaa ggaacagtca 2640
gagaagctgc ggacgctggg ctacgatgag agcaagctgg cgccctggca gcgacaggtc 2700
atcctgaaga agggggacat cgctaagtac tagaggccgc agactcctgt ccgcagcctc 2760
gcagctccgt ggggccctcc gccccagccc cagccagcca ggccctggtg gaaaggctgg 2820
gagccgcaca gccctcccct cctgcgctgg aaaccctccc tgacccccac cctggccccc 2880
cgtatcccca gcccttggca acactggagt gcacacgccg ccacggttgc ccagaaaaag 2940
tgcccaagct gctgacgcaa acaacaacaa atgctgctta tttgcatgcc gacttacata 3000
tatttgcatg ttcgttgact atcaaagagt gcagagctct ccccagcccc gtgggtggtg 3060
actttgtttt cctgcggggc tcagcccct ccaggatgca gccccctccc ccgcaccccg 3120
gaaccggcgt cgctggcgca tcctgggtgg aggcaggccc cgagctcggg gaaggggttt 3180
tcccttcctc tctgacccag atctgcgcgc ggcctagccc gggcctcatt tcttatcccc 3240
gccaagggtt tcctctcagt catttgttta ccagaaacat gaaaactgcc tgtctggccg 3300
ggccgcactt gtggcccccg ggaccccacc tctggcccca cctccctcaa gtctgcgccc 3360
cgtccccagc cagacccact cgctgccggg accctttcac tgccccggtg gagtgaatag 3420

-continued

```
aggatgaggg gccctgaccc tgtgtctcca actgctgcac cccatcccga ccctgtctcc   3480

gccacctcgc agccccatta aagcgctctc atctgggctc cggttcactc a            3531


<210> SEQ ID NO 30
<211> LENGTH: 2272
<212> TYPE: DNA
<213> ORGANISM: Homo sapiens

<400> SEQUENCE: 30

ttgggcggtg gaccgcccct cggccccggg gtaggctgac acgggagggt cctcagctaa     60

agccaaaagc agatcaaagt ggtgggactc gcgtcgcggc cgcggagacg tgaagctctc    120

gaggctcctc ccgctgcggg tcggcgctcg ccctcgctct cctcgccctc cgccccggcc    180

ccggccccgc gcccgccatg gagaagactg agctgatcca gaaggccaag ctggccgagc    240

aggccgagcg ctacgacgac atggccacct gcatgaaggc agtgaccgag cagggcgccg    300

agctgtccaa cgaggagcgc aacctgctct ccgtggccta caagaacgtg gtcgggggcc    360

gcaggtccgc ctggagggtc atctctagca tcgagcagaa gaccgacacc tccgacaaga    420

agttgcagct gattaaggac tatcgggaga aagtggagtc cgagctgaga tccatctgca    480

ccacggtgct ggaattgttg gataaatatt taatagccaa tgcaactaat ccagagagta    540

aggtcttcta tctgaaaatg aagggtgatt acttccggta ccttgctgaa gttgcgtgtg    600

gtgatgatcg aaaacaaacg atagataatt cccaaggagc ttaccaagag gcatttgata    660

taagcaagaa agagatgcaa cccacacacc caatccgcct ggggcttgct cttaactttt    720

ctgtatttta ctatgagatt cttaataacc cagagcttgc ctgcacgctg gctaaaacgg    780

cttttgatga ggccattgct gaacttgata cactgaatga agactcatac aaagacagca    840

ccctcatcat gcagttgctt agagacaacc taacactttg gacatcagac agtgcaggag    900

aagaatgtga tgcggcagaa ggggctgaaa actaaatcca tacagggtgt catccttctt    960

tccttcaaga aacctttta cacatctcca ttccttattc cacttggatt tcctatagca    1020

aagaaaccca ttcatgtgta tggaatcaac tgtttatagt cttttcacac tgcagctttg   1080

ggaaaacttc attccttgat ttgtgtttgt cttggccttc ctggtgtgca gtactgctgt   1140

agaaaagtat taatagcttc atttcatata aacataagta actcccaaac acttatgtag   1200

aggactaaaa atgtatctgg tatttaagta atctgaacca gttctgcaag tgactgtgtt   1260

ttgtattact gtgaaaataa gaaaatgtag ttaattacaa tttaaagagt attccacata   1320

acttcttaat ttctacattc cctcccttac tcttcggggg tttcctttca gtaagcaact   1380

tttccatgct cttaatgtat tcctttttag taggaatccg gaagtattag attgaatgga   1440

aaagcacttg ccatctctgt ctaggggtca caaattgaaa tggctcctgt atcacatacg   1500

gaggtcttgt gtatctgtgg caacagggag tttccttatt cactctttat ttgctgctgt   1560

ttaagttgcc aacctcccct cccaataaaa attcacttac acctcctgcc tttgtagttc   1620

tggtattcac tttactatgt gatagaagta gcatgttgct gccagaatac aagcattgct   1680

tttggcaaat taaagtgcat gtcatttctt aatacactag aaaggggaaa taaattaaag   1740

tacacaagtc caagtctaaa actttagtac ttttccatgc agatttgtgc acatgtgaga   1800

gggtgtccag tttgtctagt gattgttatt tagagagttg gaccactatt gtgtgttgct   1860

aatcattgac tgtagtccca aaaaagcctt gtgaaaatgt tatgccctat gtaacagcag   1920

agtaacataa aataaaagta cattttataa accatttact atggctttgt aacaattgca   1980

tacccatatt ttaaggacaa ggtgaattta ctactttcta aagtttattg atacttccct   2040
```

tttatgtaaa atgtagtagt gatacctata tttccacatt gtgcattgtg acacacttgt 2100
ctagggatgc ctggaagtgt ataaaattgg actgcatttc ttagagtgtt ttactataga 2160
tcagtctcat gggccatctc ttcctcagat gtaaatgata tctggttaag tgttatatgg 2220
aataaagtgg acattttaaa actagcaaag ttaaaaaaaa aaaaaaaaaa aa 2272

<210> SEQ ID NO 31
<211> LENGTH: 4510
<212> TYPE: DNA
<213> ORGANISM: Homo sapiens

<400> SEQUENCE: 31
gcagaggggg cggagagcgc ccccgggggc ggggcacgca agtgacggcg gcgcgggtgg 60
tggagcgctg ggcggccagg ctccctggct ggccggtttg ggcgtctggg ccgtgaaggt 120
gggacctcct gttccgggcc gcaagtttcc ctctccagcc gcccgccgtt cgtagcatgt 180
cccccagaac tcggggagcg caggcaggac aggcttagag aagacgcggt ccccagcgct 240
tgggccacgg acgtcccacc ccgctcctct gtcgctggag aaccgccggg ccgagccact 300
gggagaagca ggccagagcc ttccagggcc tccggcccgt ggacccgagg aggatgagct 360
ggctttttcc cctgaccaag agcgcctcct cctccgcggc tgggtccccc ggtggcctca 420
ccagcctcca gcagcagaag cagcgcctga tcgagtccct ccggaactca cactccagat 480
tgcttcctcc acagtttcct caggaaaaac cagtgatcag tgtttatcca ccaatacgac 540
atcacttaat ggataaacaa ggagtgtatg ttacctctcc attagtaaac aattttacaa 600
tgcactcaga tcttggaaaa attattcaga gtctgttgga tgagttttgg aagaatcctc 660
cagttttagc tcctacttca acagcatttc cttatctata cagtaaccca agtgggatgt 720
ctccttatgc ttctcagggt tttccatttc ttcctccata tcctccacaa gaagcaaaca 780
ggagtatcac ttctttatct gttgctgaca ctgtttcttc ttcaacaaca agtcatacca 840
cagccaagcc tgccgctcct tcatttggtg tcctttcaaa tctgccatta cccattccca 900
cagtggatgc ttcaataccg acaagccaaa atggttttgg gtacaagatg ccagatgtcc 960
ctgatgcatt tccagaactc tcagaactaa gtgtgtcaca actcacagat atgaatgaac 1020
aagaggaggt attactagaa cagtttctga ctttgcctca actaaaacaa attattaccg 1080
acaaagatga cttagtaaaa agtattgagg aactagcaag aaaaaatctc cttttggagc 1140
ccagcttgga agccaaaaga caaactgttt tagataagta tgaattactt acacagatga 1200
agtccacttt cgaaaagaag atgcaaaggc agcatgaact tagtgagagc tgtagtgcaa 1260
gtgcccttca ggcaagattg aaagtagctg cacatgaagc tgaggaagaa tctgataata 1320
ttgcagaaga cttcttggag ggaaagatgg aaatagatga ttttctcagt agcttcatgg 1380
aaaagagaac aatttgccac tgtagaagag ccaaggaaga gaaacttcag caggcgatag 1440
caatgcacag ccaatttcat gctccactat agattttcct ggaaacatga actgccaaga 1500
gaggaatggg acacaaaacc aaacactgtt ttatatttat ggtttgcaaa ctggcatttc 1560
atcagtggct aaattcacag atatcctata tagattgtat acagaactga gactgatttt 1620
gtaccgatta gaatgattgc tatgatcttt gagaaatttt tctgcactat ttgcactgaa 1680
atgtttattt attgttgata aattgtatca tatttaagtt ccactgctgt tcctcttacc 1740
ttgattaaat gcctatgcat gtacttttag ctagttttta atattttata aaacttcatt 1800
taaatttgta tttttaactt gaagttccat ttctttatca aggatggtat ttagattttt 1860

-continued ttcctcttaa cctttttca aaaactattt tcaactgtga ggaaaccctt atttttcttt 1920
ctttgtggat aaaactttca aaagcaattt aagatattca tagtgttagg aaacaccaaa 1980
cctgcctatg tgccatctca caaaagaaac ttttaatacc tacaataaat caaaagaata 2040
aaccagctgt tcttatatat tgtttcattt ttaaaactaa agatgcattt aagaagcaat 2100
acaagtaaat attttaccta ataggaaaaa aaaaagttgc ctttcattta aaccattcca 2160
acagaaattc ttatgctaat ttaaaacata tatatatctg gtaggtttgt ggttggatag 2220
gttttctaaa ttcctaatgt taaaaacaat ctttatgtta atatacacta aatctataca 2280
caaaaaaagt cagtgaactt ttctgacctt tactgtgagt taccttttcc taagaggaaa 2340
gctatagtaa taagtaaaat ttaattttta ggcaatcctg atttttaatg aatttaattg 2400
agtgttcttg tatactacat tgagcagttt gcttctatac cgtgtcacaa aattcatgta 2460
tttcttgaga agccctaaaa gctcataaag gaaaatgccg tgaactatgt agctcaggct 2520
tggtaaggtg ccatctaaat tacaaaacaa actaatgcat aattttgctt aaatttcatc 2580
ccagtatgat tgtcttccca acaccagcat atagtataga ttgtctgtct tttttatatt 2640
ttttagttct tcctgtacat gtttttggca ataaagttat aggaagaaca aaattatttt 2700
gttagaatta aaacatgctt aatatttagt ctgtttgtgg agggcaggta ttcacgtgga 2760
ctgagataca atgttggata cagaaaataa ctttcattgt cttcctgaca ctgtgctaag 2820
gacatgctgt taaagcttca aagtgaccag atgaggaagg aataattaat tattactcct 2880
gatttgtaga taactgaggt aagagtgttt caaatttatg atagtctttt gggtattcag 2940
aaacctttcc ttatactgca ctggccacca gagcttaatt ttcccagcag ttacagcaat 3000
gggagataga acagtctcaa tcttttgcca accatcaggt tcctagaaac caggtaggtg 3060
tatcccataa caagggagga gcataccaca gcccctcatt tgattaattc atttgatcta 3120
tctatgttat taagtaccta ctaggaataa ggcattgtgg aaatactata caaagataaa 3180
cattgtttag atgcttatct actttccttt tcaccagaaa aacagaaaaa aaagaaacat 3240
tttcttacag agtaaaaatg ttctacataa tcacatgagt agttcatctc agtgtttttt 3300
attctttaaa gttgaactat cccagtttca ttctatacca ttcattggat aaccttgtta 3360
caacccagtc atgaaacaga gcagtgtgat cagttatctg catttaacaa atagacaaat 3420
cagtttacat aaaggttatg tatgtcaccc acgatgaaaa gaatctgcat ttgaatatgc 3480
ccgtatgaat gtgggttctg tttttgcaac agagattaag tgaccatttt ttctaatttt 3540
atggctatat attttcttca taaaaattgg tcacatcgga gaagcagtgc cacaggaaaa 3600
atgaaatgca tgtgaaagtt tgtattctga ttttacaaga tgagatagaa atcagaatta 3660
aagaggaata cttaggagtt actaggctaa tcagtgtacg aatttgtcat aggtagagat 3720
ttaaaggtta atatcttaaa atagaagaaa attctaaatc aatcaatcag tgagatataa 3780
actaaacaga cccacttcaa agttgaaaga aatttctagg cataaattga gactaggaaa 3840
tttatatcag aatagagggt gcttgacaca tatatatgct taaattgaag gacagctcag 3900
attcattttt aggagaagaa agtaaactaa tgtgctctta aagaataaaa atttattcta 3960
tggtttctgt ctctgatcat caccttccat tctataaaaa gctcagttac tgatttgctg 4020
ggtcatggtc aaaattctta cctatttatt tcatatcaac tttaaaaaat aaattacttg 4080
cattctatat attactaatt gggaagtaat atgcctcaaa tcagttttat actggattat 4140
tccctatgct ttaaaccact gctctcaata aaacacttcc tgattaatgt ttgattatta 4200
gatattttag tcttgttggg gatattttag tcttgttggg ttagccatgc tctgaagaat 4260
ctgtgaaagt acagtaaagt tttaataagc aataaatgta accttttata taaatctcag 4320
tgctaggtta acttctaata agcagacgaa catgttacat aaattataat gtctgtcttg 4380
taaaaaagtt gaggggacta aaagtttatg actctgatat ggaagttgtc atattaaaaa 4440
actacatttt aaaacatcaa atatttatac tatttgcttt tcaaataaaa gcatagtgct 4500
gtttggcata 4510

<210> SEQ ID NO 32
<211> LENGTH: 11062
<212> TYPE: DNA
<213> ORGANISM: Homo sapiens

<400> SEQUENCE: 32
gcagatcggg agcggtgccg agaaaaattt ccttactaga tgacatttca tcgcaatgtc 60
cgatcgtttg gggcaaatta ccaagggcaa ggatgggaaa agcaagtact cgactctcag 120
cctgtttgat aagtataaag gaaaatcagt agacgcgatt agatcctcag ttattcctag 180
acatggctta cagagtcttg ggaaagttgc tgcagcccgg cgcatgccac cgcctgcaaa 240
cctgccaagc ttgaagtctg aaaacaaagg aaacgacccc aacatcgtga tagtacccaa 300
ggacgggacg ggatgggcaa acaagcagga tcagcaagac ccaaagagtt ccagtgcgac 360
ggcctctcag ccgccggagt cgctgccgca gccgggtttg cagaaatctg tctccaattt 420
gcagaaaccg acacagtcaa tcagtcagga gaatacaaat tcagtgccag gtggaccaaa 480
gtcatgggca cagctgaatg gaaagccagt aggacacgaa ggtggtttaa ggggctcaag 540
ccgactgtta tccttctctc ccgaggaatt tccgacgctg aaagcagctg gagggcagga 600
caaggctggc aaagaaaagg gcgtcttaga tctgtcgtat gggccaggac caagcctccg 660
ccctcagaat gtgacaagct ggagggaggg cggtgggcga cacataattt ctgccacgtc 720
tctgagcacc tccccaactg agctgggcag caggaactcg agtacgggag atggagcccc 780
ctcctcggca tgtaccagcg attctaagga cccctctctc cgcccggctc agcctgtccg 840
aaaaggggct tcacagttca tgggaaatgt ataccaccca cctacatacc atgacatgct 900
tcctgctttt atgtgttcgc cgaagtcatc agaaaaccag ggtacagtgg aacgaggctc 960
ttttcccctt cctcagctcc gccttgaacc tcgagttcct tttagacagt tccagatgaa 1020
tgaccaagac ggaaaagaaa acaggctggg attgtctcgc ccactccgcc cactaaggca 1080
gctggtggag cgggcaccac ggcccaccat tatcaatgcg gaaaacctga agggccttga 1140
cgatctggac gccgatgccg atgatggctg ggcaggcctc catgaagaag tggactattc 1200
tgagaaactg aagttcagtg atgatgaaga ggaggaagaa gttgtgaagg acggcaggcc 1260
aaagtggaac agttgggacc ctaggaggca gcggcagttg tcaatgagct ctgcagacag 1320
tgcggacgct aagcggactc gagaggaagg gaaggactgg gctgaagcag tgggtgcgtc 1380
ccgtgtggtc cgaaaggcgc cagaccctca gccaccgccc aggaagcttc atggctgggc 1440
accaggccct gactaccaga agtcatcaat gggcagcatg ttccggcaac agtccatcga 1500
ggacaaggag gacaagcccc caccaaggca gaagttcatt cagtcagaga tgtccgaggc 1560
ggtggagcga gcccgaaagc gccgggaaga agaggagcgc cgagcccggg aggagaggct 1620
ggccgcctgt gctgccaaac tcaagcagct ggaccagaag tgtaagcagg cacgaaaggc 1680
aggtgaggcc cggaagcagg cagagaagga agtgccctgg tctccaagtg ctgagaaggc 1740
atctccccag gaaaacggcc ctgctgtcca caaaggctcc ccagaattcc ctgcccaaga 1800

-continued

```
gacccccacc acattcccag aagaggcacc cacagtgtcc ccagcagtgg cacagagcaa   1860
cagcagtgag gaagaggcca gagaggctgg gtcccctgca caggagttca agtatcagaa   1920
gtcccttcct ccccgattcc agcgccagca gcagcaacaa cagcaggagc agctgtacaa   1980
gatgcagcac tggcagccgg tgtacccccc gccgtcccac ccccagcgca ccttttaccc   2040
acaccacccc cagatgttgg gcttcgatcc caggtggatg atgatgcctt cctacatgga   2100
cccacgtatc acgcccactc ggaccccggt ggacttctac cctccgcccc tgcatccctc   2160
aggactgatg aagcccatga tgccccagga gtccctcaat gggacaggct gtcgctctga   2220
ggatcagaac tgtgtgcccc cactccaaga aagaaaagtg acccccatcg actcaccccc   2280
tgtgtggagc ccagagggct acatggcact gcagagcaag ggctacccgc tcccgcaccc   2340
gaagtcgagt gacaccttgg ctatggacat gcgtgtcagg aatgaaagct ctttctctgc   2400
ctcactcgga agggcagggg gcgtaagtgc tcagcgcgat ctctttgagg agagagggga   2460
ggagtacttg agtgcttttg acaagaaggc ccaagcagac tttgacagct gtatctcttc   2520
tcaaagaata ggccaggagc ttttgtttcc accccaagaa aatgttcagg atgcaggtgc   2580
tcctgggggt cacacccaaa acctcaggtg ttccccattg gagcctgact ttgtcccaga   2640
tgagaaaaag ccagagtgtg gcagttggga tgttagccac cagccagaga ccgctgacac   2700
agcccatggt gttgagcggg agacaccccg ggaggggacg gcctttaaca tctcctcctg   2760
ggacaagaac gggagcccca acaaacagcc atcctcggag cctgaatgga ctcccgagcc   2820
ccggagctcc agcagccagc acccggagca gacgggcagg acccggaggt cgggacccat   2880
caagaaacca gtcctgaaag ccctcaaggt ggaagacaag gagaaggagc ttgagaagat   2940
taagcaggag ctaggggagg agagtacccg gctggccaag gagaaggagc agagccccac   3000
ggcagaaaag gatgaggacg aagagaacga tgcctctctg gccaactcct ccaccaccac   3060
tttggaggac aaaggccctg gccatgccac ttttggccgc gaggccacca aatttgaaga   3120
ggaggagaaa cctgacaagg cctgggaagc cagacccccca cgagagtcca gcgatgttcc   3180
ccccatgaag agaaataact ggatctttat tgatgaggag caagcctttg ggtcagagg   3240
acaggcccgg ggccggggcc gtggtttcag agagttcact tttcgtggtc ggcctgctgg   3300
cggaaatggg agcggcctct gtggtggggg ggtcctgggg gcccgcagca tctactgcag   3360
cagtcagcgc agcggccgtg gccggggcct gcgagagttt gcgcggccag aggactgccc   3420
cagagccaag ccccgacgga gagttgccag tgagacccat agcgagggct cagagtatga   3480
agaacttccc aagcgccgcc ggcagagggg ctccgagaac gggaatgaag gctcgctcct   3540
ggagagggag gagagcacct tgaagaaggg cgactgcaga gattcttggc ggtccaacaa   3600
ggggtgctct gaggaccaca gcggtctaga tgccaagagc cgaggccctc gggcctttgg   3660
gcgagccctc cctccccggc tgagcaattg cgggtatgga cggagaacct tcgtctccaa   3720
agagtcaccc cactggcaga gcaaaagtcc aggcagctct tggcaggaat atggcccttc   3780
cgacacatgc ggatcccggc gacctacaga cagagactat gtcccagatt cctacagaca   3840
ccctgacgca tttggtggcc ggggctttga ggacagccgc gcggaggaca agagatcctt   3900
cttccaagat gaacacgtgg cagattctga aaatgcagag aaccggccct tcaggagaag   3960
gcgcccccca cgccaagata agccccctcg attccggcgc ctccggcaag agcgggagtc   4020
cctgggcctg tggggacccg aggaggagcc ccacctgctg gcaggtcagt ggccaggcag   4080
gcccaaactg tgttctgggg acaagagtgg cactgtgggc cgcaggtccc ctgagctctc   4140
ctaccagaac tcctccgatc acgccaatga ggagtgggag acggcctccg aaagcagcga   4200
```

-continued

```
cttcagcgag cggcgggagc ggcgggaagg ccctgggtcc gagcccgact cccaggtgga   4260
tggtggcctg tcgggggcta gtttgggtga gaagaaggag ctggccaaga ggagcttctc   4320
cagtcagaga cccgtggttg acagacagag ccgaaagctg gagccgggag ggtttgggga   4380
gaagcccgtt aggccaggtg gtggtgacac ctcccctcgc tatgagagcc aacagaatgg   4440
gacgcctttg aaagtgaaaa gatccccaga cgaggccttg cctggaggtc ttagtggctg   4500
cagcagtggg agtggccact cccccctatgc cctggagcgg gcagcccatg ccagtgctga   4560
ccttcccgaa gcctccagta aaaaggcaga gaaggaggcc aagttggctg ctccgagggc   4620
aggtgaacag ggagaggcca tgaaacagtt tgacctgaac tatggaagtg ccatcattga   4680
aaattgcggg tccagccccg gggaggagag tgaggtgggt tctatggtgg gcgaaggctt   4740
catcgaagtc ctgaccaaga agcagcgccg cctgctggag gaagagagaa gaaagaagga   4800
gcaggccgtg caggtgcctg tcaaaggtcg aggcctttcc tcccgtattc ctcctcgatt   4860
tgcaaaaaag cagaacaact tatgtctgga gcaaggtgac gtgaccgtgc ctggcagcag   4920
cctgggcact gagatctggg agagcagcag ccaggctctc cctgtgcagg ccccagccaa   4980
cgactcctgg aggaaagctg tcactgcctt cagcagcacc gagactggct ctgcggagca   5040
gggttttaag agcagccagg gagatagtgg cgttgacttg agtgccgagt ctcgggagtc   5100
gtctgcgacc tcctcgcagc gcagctcccc atatgggact ctgaagccag aggagatgag   5160
cgggcccggc ctggcggaac ccaaggccga cagccacaag gagcaggctc caaagccatc   5220
tgagcagaag gattcagaac aaggctctgg acagagcaag gagcacagac caggacccat   5280
cggcaacgag cgttctctga aaaacagaaa gggctcggag ggggccgagc ggctgcaagg   5340
ggctgtcgtc ccgcctgtta acggggtgga gattcacgtg gactccgtgc tgcctgtgcc   5400
acccattgaa tttggagtca gtccaaaaga ctccgatttc agcttgccac ctggttctgc   5460
ctctggtcct actgggagtc cagttgttaa acttcaggat gccttggcca gtaatgcagg   5520
gttaacacag agtatcccca tcctgcggcg ggaccatcac atccagaggg ccatcggtct   5580
ctccccaatg tccttcccca ccgccgacct tactctgaag atggagtctg cgcgcaaggc   5640
ttgggaaaac tcccccagtt tgccggagca gagctctcca ggcggcgctg gctcaggcat   5700
ccagcctcca tcctctgtgg gtgcctccag cggggtcaac tacagctcct tcggtggagt   5760
gtccatgcca cccatgcctg tggcctctgt agcaccttct gcttctatgc caggcagcca   5820
cctcccgccc ctgtacctgg atggccatgt gtttgcaagt cagccccggc tggttcctca   5880
aacgatacct cagcagcaga gttaccaaca ggccgccgct gcccagcaga tcccgatctc   5940
ccttcacaca tctctgcagg cacaagctca gcttggactg aggggtgggc ttcctgtgtc   6000
ccagtcccag gagatcttca gctccttgca gcccttcaga tctcaggtgt acatgcaccc   6060
cagcctgtca ccgcccagca ccatgatcct ctctgggggc acagccttga agcctccata   6120
ctcggcgttc ccaggcatgc agcccttgga gatggtgaag ccgcagtctg gctcacccta   6180
ccagcccatg agcgggaacc aagccctggt ctacgagggc cagctcagcc aggctgctgg   6240
cctgggtgcc tcccagatgt tggactccca gctcccacag ctgaccatgc cactgcctcg   6300
gtacggctcc gggcagcagc cactgatcct gccccagtct attcagctgc cacctgggca   6360
gagcctctcc gttggggccc cccgaaggat tcctccgccc gggtcccagc cgccagtcct   6420
gaacaccagc agagagccct ctcagatgga gatgaaaggc ttccactttg ccgacagtaa   6480
acagaatgtc ccttcaggag gccccgtgcc atcgccacag acctacaggc ctagctctgc   6540
```

-continued tagccccagt gggaagccct ctggatcagc agttaacatg ggctctgtgc agggacacta 6600
cgtgcaacag gcaaaacaac gagtggatga gaaacccagc ctgggagccg tgaagctgca 6660
ggaggccccc tcggctgcct cccagatgaa gcgaaccgga gcgatcaagc ctcgggctgt 6720
caaagtggag gagagtaagg cctgacagtg cctggctgcc acctcgcctc tccctactga 6780
ggacggtgcc gccatgcggc ctcgacacag ccgacactcg ggagcctcac cagatccacc 6840
gtccaaatgc gtggcccaga ctgagagacc tccctcctct ccactcccga aagctccgtt 6900
gtcaaccagc ttgcacccgt ggatatatgg cattgacccg cttgctttga tacgaaacaa 6960
aaaagcagac gactccttca tcccatctgc tcctaccgtg actgtggagt gacgcctcct 7020
gtgcagtgca gatttgccct ccctgcctcc tccctgtcct gccgcgcagc cagggcgcct 7080
tctcagcagt gcttccggcc cagccgccca tccctaggca cagtgatttg gcagcagggt 7140
cattttactt tgaggctttt tgttttaaaa tgtagccaag gtttttacaa aggggaaagg 7200
aaaagaaaac aaaaacgcaa gctccatgtg tatagctgaa cttttatatg tttcttgcca 7260
gcccctccgc tcccttccat ctctagcctc tgtcctgttt agtttgatac gtcactgcag 7320
taccttaaga ggtgactctt aagaatgcat cccctcctga ttcctcagct ggttcaccct 7380
tgaggttatt tgcaaaaaga aaaggaggtt cttgagggca ccgattgcga gcattctggt 7440
gcctggctcc ccgcctggga agcgatgggg tgctcagagc agcaggcagg ttgggggagg 7500
gggggggtca tagttgggtt ccagctcctg gcttgatgag cccagggcgc ttacaggcag 7560
cccatgaagt tgatgacagt tttagcatga gaatcacaca gggtccctgt cctgggctcc 7620
tctaaagcca gtggatgtgc tgggcaccag agacaaatca tggagatggc tgctggtggc 7680
tcccaggttg gcccagatgg ggtgagctga cataccacag gcccatccca ggccccgtgg 7740
gctctgcttc tggggctcca taccctgccc tgcaggggtg ctgtgttttt cacacatttc 7800
tttccctgaa gccttctgta acctgtcatt ttccttcctt cctcttccgg agcctgctgc 7860
tttctctgga cctgtctcca cctcccacac agctcatcgt gaacaccact tggtgatgga 7920
gggagtggac ccgtgtgtgg tccccaagtg aggccactgg gagtttgtcc ttttcctcct 7980
ttgcttcact cccagcagca gacccaggtt gtcaggacag gagggcctga gctaagcagt 8040
aggcatcagt ctcgtttgtc ttcagacggc gggggcaggt ccagggtgag gctgggtgga 8100
gggctgacca aggtccaaag ggcctgcgca gcctccggga gggcagcttc tccagccaga 8160
ggcttgtgtg agccatcgtg tgctgggctt gtttttaagt aagaaacaag gaaatcactc 8220
cagattctgt cattccaagg aaagggaagg ggacagttca ggtttctcag ctgttcttag 8280
gggtcactga gcgtctacct cctcctccag aggaggctgg ctcagaacac ctagaggagg 8340
gggccgggga tgcacccccc accagaggct gccttcagcg tctcacgggt gcaggacagc 8400
gctcaggctt gggctctaag ctctgtgtct agtgtagaac atggggaagg agcatcttag 8460
gaactgctga agtaacttct tactgctctc acaattctaa ggaagcggga gaacggcctc 8520
ctaccaacag cgcccacccc agagctgcct gggaaagggc agttttactg aaaggtgctt 8580
tactgttcac ctgcatcttt cagcagctcc cctcctgccc tcacctggtc ttttccctct 8640
ttatcccaag cctttatgct tgagtccctt ccccaggggc tgcccacccg acagttccag 8700
gcattcccta cctgagcttc ttgtctgctt ttccttctcc cactgcaagc ggctgcttgt 8760
ggggcctggg atgagccctc tctgtcccca ccggccctcc ttgccaagcc attcctgggt 8820
gagttcaggc ctgcgggagc cacacattca tctccacctg gacacttgag ccgcatggcc 8880
agacccctcc cacctgatgc ggtggtgcgt gtgatttgtc aaaagaaagc cttctggatg 8940

```
ctgttaagat gtacccttca ggtgaacctg gtatcagacc cacagtactt gctgtttgag   9000
aaaaaataaa aacaaaaagg tcacctgttc tccagccctt ttctcttacc tggtatttcc   9060
ttcctttctc ctcccccacc ccaaataaaa aaacaaaaaa cactagaatt tatttatatg   9120
tattgatgtt gtaggtctag gtgaaaaaaa aagaagtaaa tgtttcactg ctctatttat   9180
atataatgtc tgaattaatt ctgtgcagga aaggccagga aattgcatgt gaagttcggt   9240
gcagtcacca cctgtgtgtg acctgagctg cagtctcttc gctgagatgc aggttttaaa   9300
tgagacttgg ggggctgagg gcaggcctca ggcctcccag cgccccaacc cctccttggt   9360
ctaatgaaat gcagttctta gtgcagagat gttttaaggt gcaatatatc tcttcctttc   9420
ccgtggtttt agagccaagc tcaaggtagt aggacgtagg gtcttatttt gttttcaaac   9480
ccccatcctc agagcgcaga tacatgcaga ggcttctgcc aggataccac ggggccttag   9540
tgggaacagg tggagaccag cacttccctt tcctgctgct gaggtaggga ttggggggtc   9600
agaacccact cacttttgcc tgttaaagtt gccctcctga cgctggcagc tctgccttgg   9660
tcactgggga tgcggctcgt tgctcagcca ccagtggcct tgcggtattg tccaccatcc   9720
actagagtgg gatgaagtcc agagtgtggg tatacatctc agatgcccat ctacccactg   9780
gggacttcaa tgccagctgc atttggtttg gttttcttaa ctgttggctt ctccccacag   9840
cgtttttttgt ttttttttaa acattcatat tgttttcaaa cttggaattc atagacactc   9900
tggctctagg ttccttaagg gggaaaacaa aagatgactt tatttcacat tcaagaaaat   9960
cagttcagtt ccaaagctgt ggtccttcca gccacttcta gggacactgg ggaaccttgt  10020
taaacgttga catcagtgct ctccagccgt gctgtcaccc tcctatcttc tggatctgcc  10080
ttcgcgatgg tcagtgacag cttctggaag ctgagcacac acaggtgcac agccatgctg  10140
tggtctggcc tgctacggca gcatggcagc tctggtggag ccttctccct tgccatttgg  10200
ttcccctgtg ccaagtagct gcaggctgcc cctcaaatct tcatttgtcc cttttcactt  10260
cctgcagaac aagcctgggt tagagggtct gctggaaatg gcctttgaag accaaggata  10320
ccaggatgtg tgcactctgt cgtgttctgt gatgaatggg aaacgtaggc ttccagaaag  10380
ccagctctct tctgaaatgt gacggaccta agcaggaagt catccaggac aggagtggct  10440
cagtgttggg gatggacgct gtcgcccagc catgctccac cagggccacc aatgtgtagt  10500
tggctggtgg tcttcgggca tgtgagacct gctcttcact gtttccaccc cacttggtgg  10560
cctccaggat ggtagtggca ccctcagagc cccatcttca gcatgttctg aagcctcaga  10620
gtggaaattc ctgctaaggc tctgtgtgga cgcctttctc ccgtgatcta aaggggacac  10680
tgtactcaag cttttgacct catgccttgt gtagtaaaaa aggatttggg ggttttgttt  10740
ggttcctgag agggttgtgt tttgtttttg tttccttttg tttatgtttt ggcctttcct  10800
ctttgtcttt ccatgtagac cagatatttg aaagggcaga cgatggctag aggtgtaatg  10860
tgcagcttgt ttatacggta ttttgggaaa cttaccttgg atgggaaatc gaatcgtgga  10920
ttcaccaggc cggtgctggc acactcaccc tcgccctttc cctccggttc agtacctatt  10980
gtttctcctt tcaaatatgt gattgtacta gctctttcca tatgaaagaa ttctccttat  11040
ttaaataaaa aaagtttaaa aa                                             11062
```

<210> SEQ ID NO 33
<211> LENGTH: 7689
<212> TYPE: DNA
<213> ORGANISM: Homo sapiens -continued

<400> SEQUENCE: 33

```
tcccacagtg cctggcccag aagccttgct aaatatttga acaggattgc ccaatacttt     60
tctgctgtga gaatgtaaga tggatccaga agagcaggag ctcttaaatg attacagata    120
cagaagctac tcttcagtga ttgaaaaggc tttgagaaat tttgagtcct cgagtgaatg    180
ggcggatctc atatcttcac ttggcaaact caacaaggct cttcagagta acctgaggta    240
ctccttgttg ccaagacggc tcctcatcag caaaagatta gctcagtgtt tgcaccctgc    300
cctgcccagt ggtgtccact taaaagctct ggaaacctac gagattatct ttaaaatcgt    360
ggggaccaaa tggctggcca aggacttgtt tctgtacagc tgcgggttat ttcctctcct    420
ggcacacgcg gcggtgtcgg tgaggccggt gctgctcacc ctgtacgaga agtacttcct    480
cccactgcag aagctgctcc tgcccagtct gcaggccttc atcgtgggcc tgctgcccgg    540
ccttgaagag ggctccgaga tctccgacag aacggatgct ctgctcctga gactgtcgct    600
ggtggttggc aaagaggtgt tttacaccgc cctctggggg agcgtcctgg ccagcccgtc    660
catccgcctc cctgcctcag tcttcgtggt gggccacatc aacagggatg cccccggccg    720
ggagcagaag tacatgctgg ggaccaatca ccaactcacg gtgaagtctt tgcgtgcctc    780
cctgttggac tcaaatgttc ttgtgcaaag aaataatctg gaaatcgttc tgtttttctt    840
cccattttat acctgtctgg attccaatga gagagccatc cccctcctca gatctgacat    900
cgtgcgcatt ctctcagccg ccacccagac cctactgaga agggacatgt ccctgaacag    960
aagactgtat gcatggttac taggctcaga cataaaagga aataccgttg tgccagaatc   1020
tgaaatctca aattcttatg aagaccagtc gtcttatttt tttgaaaaat actccaagga   1080
tcttttagtt gagggtttgg ctgagatatt gcatcagaag ttcatagatg ctgacgtgga   1140
ggaacgccat catgcatacc tgaagccttt tcgcgtcctc atcagtctgc ttgacaagcc   1200
agaaataggg cctcaagtgg ttgggaattt gtttctcgaa gtcatcaggg ccttttattc   1260
ttactgcaga gatgcccttg gctctgatct taaacttagc tacacccaga gtggaaattc   1320
gctgataagt gcaatcaagg aaaacagaaa tgcctctgag attgtcaaaa cggtaaattt   1380
gctgataact tctctaagca cagactttct ctgggattat atgacaaggt gttttgagga   1440
atgctttaga ccagtgaagc agcgttacag cgtgaggaac agcgtcagcc ctcccccccac   1500
ggtctcggag ctctgcgccc tcctggtctt cctgctggat gtcattcctt tggaacttta   1560
ctctgaggtg caaacccagt atctccctca ggtgctcggc tgcctggtgc agcctcttgc   1620
tgaggacatg gaggccttaa gtttacctga actcacgcat gccttgaaga cgtgtttcaa   1680
ggtgctcagc aaagtccaga tgcctccttc ctacctcgac acggagtcca ccagcggaac   1740
ctcgagtcca gtaaaaggtg aaaacggcaa aataattttg gaaacaaagg cagtgattcc   1800
cggtgacgaa gatgcttcgt ttcccccctct gaagtctgag gacagtggga tcgggctcag   1860
tgcctcgtca ccggagctct ctgagcactt gagggttcct cgagtttctc tggaaaggga   1920
cgacgtttgg aagaagggcg ggagcatgca gaggacgttt ctttgcatcc aagagctaat   1980
cgccaacttt gccagcaaga acatttttgg agtacagctg acagcgtcag gagaagaaag   2040
caagtccgag gagcctgcag ggaagaggga cagggatggg acgcagagcc tggcagccaa   2100
tgattccagc aggaagaact cttgggagcc caagcccatc actgtgcctc agttcaagca   2160
gatgctgtca gacttgttca cagcacgagg gtctccattc aagacaaaaa gttcagagtc   2220
accatcgtct tcgcccagca gccctgccag gaaaaacggg ggagaatggg atgttgagaa   2280
ggtggtcatt gacctggggg gttccaggga ggaacgcagg gaggcctttg ccgccgcctg   2340
```

-continued

```
ccacctgctg ctggattgtg ccactttccc tgtctacctg tccgaggaag agaccgagca   2400
gctctgtgca acgctcttcc agctgccagg agccggtgat tccagttttc catcttggct   2460
gaagtccctc atgactattt gctgctgtgt gactgactgc tacctccaga acgtggccat   2520
ttccactctg ctggaagtga taaaccattc ccagtccctg gcgcttgtca ttgaagacaa   2580
gatgaaacgc tataagagct ctggacacaa cccttttttt ggcaagctgc agatggtgac   2640
ggttcctccc attgctccag ggatattgaa agtcattgca gagaaaacag atttctatca   2700
gagggtggct cgtgtgcttt ggaatcagct gaacaaagag acccgggagc atcacgtcac   2760
ctgcgtagaa ttgttctacc ggctgcactg cctggcccct acggccaaca tctgcgagga   2820
catcatctgc catgccctcc tggaccctga caagggaaca aggctggaag ctctgtttag   2880
attttccgtg atctggcatc tgacaagaga gatccaaggc agtcgagtaa catctcacaa   2940
tcgctccttt gataggtcct tgtttgtcgt gctggacagc ctggcctgca cggatggtgc   3000
catcggtgcg gcagcccagg gctggctggt gcgtgcgctc tccctcgggg acgtggctcg   3060
catcctcgaa cccgtgctcc tgctgctgct gcagccaaaa acccagagaa cctccatcca   3120
ctgcctcaag caggagaact cggccgatga cttgcaccgt tggtttaaca ggaagaaaac   3180
ctctttcaga gaggcatgcg cagtgcccga gcctcaggag agcggctctg aagagcacct   3240
gcctctgagc cagttcacca cagtggaccg tgaagccatt tgggccgaag tggagaagga   3300
gcccgagaag tacccgctgc gaggcgagct gagcgaggaa gagctgccct actacgtgga   3360
gcttccagac aggacggccc acggcgcccc ggacagcagc gagcacaccg agtctgcaga   3420
tacaagctcc tgccacacgg acagcgagaa cacgtcctcc ttctcctccc cttcccacga   3480
cctgcaggag ctgagcaacg aagagaactg ctgtgcaccc atccccatgg ggggcagggc   3540
gtaccccaag cgctcggccc tgctggcggc cttccagtca gaaagcttca aggctggggc   3600
caagttaagc ctggtgcggg tggactcgga caagacgcag gcttctgagt cgttctccag   3660
cgacgaggag gcggacttgg agctccaggc cctcaccaca tccaggctgc taaagcagca   3720
gcgggaaagg caggaggccg tcgaggcctt gttcaagcac atcctgctct acctgcagcc   3780
ctacgactct cggcgggtcc tctatgcctt ctcggtgctg gaggctgtgc tcaaaaccaa   3840
ccctaaggaa ttcatcgagg ctgtgtccag gactagcatg gataccagct ccaccgcgca   3900
cctcaacctc atctccaacc tcctcgctcg ccaccaggag gccctcattg gccagagttt   3960
ctacggaaag ctccagaccc aggtccccaa cgtgtgcccc cactctctgc tcctggagct   4020
gctcacctac ctctgcctga gcttcctgcg ctcctactac ccttgctatt tgaaggtctc   4080
gcaccgagac attctcggca accgggacgt gcaggtcaaa agtgtcgagg ttttgatcag   4140
gataatgatg cagctggtct cagtggccaa gtcttcggaa gggaagaacg tggagttcat   4200
ccacagcttg ctgcagaggt gcaaagttca ggagtttgtc ctgctctccc tgtcggcgtc   4260
catgtacacg agccagaagc gctacgggct ggccaccgcc caccacggca gggccctgcc   4320
agaggacagc ctctttgagg agagtctcat taacttgggt caggaccaga tctggagtga   4380
gcacccgctg cagattgagc tgctgaagct gctgcaggtg ctgattgtct tggaacacca   4440
cctgggtcgg gcccatgagg aggcggaaaa ccagcccgac ctgtcccggg agtggcagag   4500
agccctgaac ttccagcagg ccatcagcgc cctgcagtac gtgcagcccc accccctcac   4560
ctcccagggt cttctggtct ctgcggtggt gaggggtctg cagcccgcct acggttacgg   4620
catgcatccg gcctgggtga gcttggtcac gcattccttg ccctacttcg gaaagtccct   4680
```

-continued

```
gggctggacg gtgacaccct ttgttgtcca gatttgcaaa aacttggatg acttggtcaa   4740
gcagtatgaa agcgaatctg tgaagctctc tgtcagcaca acctccaaga gggaaaacat   4800
ttctccagat tatccactca cccttctaga aggtctaacg accattagtc atttttgtct   4860
tttggaacaa gccaaccaaa acaaaaagac catggctgca ggtgatcctg ccaacttgag   4920
gaatgccaga aatgccattt tggaagagct gcctcgaact gttaacacca tggcccttct   4980
ctggaatgtt ctcagaaagg aggagactca aaagagacct gtcgatctcc taggggccac   5040
gaagggatcc tcttccgttt actttaaaac caccaaaacc ataagacaaa aaattttaga   5100
cttcttaaac cccttgacgg cccatcttgg ggttcagttg acagcggctg ttgcggcagt   5160
gtggagcaga aagaaagccc agcgtcacag taagatgaag attatcccaa cggcaagtgc   5220
atcccagcta acccttgtcg acttggtgtg tgcactcagc accctgcaga ctgacacgct   5280
gctgcacctg gtgaaggagg tggtgaagag gccaccccaa gtcaaagggg gtgatgagaa   5340
atcgccccta gtggacattc ctgtgttgca gttttgctat gcttttctcc aaaggctccc   5400
agtaccagcc ttgcaagaga acttttcttc actgttggga gtattgaaag agtctgtaca   5460
gttgaatcta gccccacctg ggtattttct gcttctcagc atgctgaatg actttgtaac   5520
aagaactccc aacctggaaa acaagaagga ccaaaaagac ctgcaggaaa tcactcagaa   5580
aatcctagaa gctgtgggga acattgccgg ctcttccttg gagcaaacca gctggctaag   5640
cagaaacctg gaagtgaagg cccaacctca ggcctctcta gaagaatctg atgctgagga   5700
ggacctgtat gatgctgctg cagcttcagc aatggtgtct tcatccgccc cgtcggtgta   5760
cagcgtgcaa gccctctctc tcctggcaga ggtactggct tccctcctgg acatggttta   5820
tcgaagtgat gagaaggaga aagctgtgcc gttaatctcc cgtctgcttt actatgtttt   5880
tccatactta cgcaaccaca gtgcctacaa tgctcccagc ttccgggctg gcgctcagct   5940
gctgagctcc ctgagtggct atgcctacac aaagcgagcc tggaggaagg aggtcctgga   6000
gctgtttctc gaccccgctt tctttcagat ggatacttcc tgtgttcatt ggaagtccat   6060
tattgaccat cttttgactc atgagaaaac aatgtttaag gatttaatga acatgcagag   6120
cagttctttg aaactattct caagttttga acagaaagcc atgctgttaa agcgccaggc   6180
ttttgctgtc ttcagtggag aacttgatca ataccacctt taccttccac tgatacaaga   6240
acgcctgaca gacaatctca gagttggaca gacatcccata gttgctgctc agatgtttct   6300
ttttttcaga gttttgctgc taagaatatc tcctcaacat ttgacttcat tgtggccaat   6360
aatggtctct gaattgattc agacattcac acagcttgaa gaagatctaa aagatgaaga   6420
tgagtcattg agaagcacca acaaagtaaa cagaacgaaa gtttcagtcc cggatgcaaa   6480
tggaccctca gtgggggaga taccccagag tgaactcatc ttgtatttat cagcttgcaa   6540
attcttggac acagcgcttt cttttccacc tgacaagatg ccattatttc aaatttatag   6600
gtgggcattt attccagaag tggacacaga gggccctgcc ttcctgtcgg atgtagagga   6660
gaatcaccaa gaatgcaaac cccacactgt caggattcta gaacttctaa aattaaagtt   6720
tggggaaatc agtagctctg atgagatcac catgaagagt gaattcccgc ttctgcgcca   6780
acattctgtt tccagcatca ggcagttgat gccattcttc atgactctaa atggtgcatt   6840
taagacccag agacagctgc ctgctgatag cccaggaact ccattcttgg actttcctgt   6900
cacagatagc ccaaggatct taaaacaact ggaagaatgc atcgaatatg attttctgga   6960
acatccagaa tgttaaccat gtgagagaga atatgtttaa tccatgtatt ggtactttac   7020
tgaaaaccag gttatattct aaagaagaaa gaaggcagga tagtgctttt gaacaagcct   7080
```

atttccattt tgaaagtaga tttcaggcta ggtgcggtgg ctcacacctg taatctcagc 7140
actttgggag gccaaggcag gcagatcact tgaggtcagg agttcgagac cagcctgacc 7200
aacatggtga gaccctgtct ctactaaaaa tacaaaaatt agctgggtgt ggtggcggcg 7260
cctgtaatcc cagctacttg ggaggctaag gcatgagaat tgcttgaacc caggaggtgg 7320
aggctgcagt gagccgagat cacgacactg cactccagct gtgtgacaga atgagaccat 7380
ctccaaaaaa aaaaaaaagt agatttcaga taatttactg ttcagcaaca ggacacacct 7440
ccctaaatgc cttgtaatat atttgaatct gattctgcat ttcttcctca atttatgtaa 7500
tgaaaataaa attaatatat catctaacag tagcacaaaa tttgtaatat gaagtaaagt 7560
atgaagataa tgaagaagtt gttttctttg ttgaagcagt tatatgggtc tttctcagta 7620
tatttctctt ttctctaaaa gtttaaactt attaaaagaa tgttattttt aacctttcaa 7680
aaaaaaaaa 7689

<210> SEQ ID NO 34
<211> LENGTH: 1138
<212> TYPE: DNA
<213> ORGANISM: Homo sapiens

<400> SEQUENCE: 34
gctctggccg gccccggcga ttggtcaccg cccgctaggg gacagccctg gcctcctctg 60
attggcaagc gctggccacc tccccacacc ccttgcgaac gctcccctag tggagaaaag 120
gagtagctat tagccaattc ggcagggccc gctttttaga agcttgattt cctttgaaga 180
tgaaagacta gcggaagctc tgcctctttc cccagtgggc gagggaactc ggggcgattg 240
gctgggaact gtatccaccc aaatgtcacc gatttcttcc tatgcaggaa atgagcagac 300
ccatcaataa gaaatttctc agcctggccg aaaatggttg gccccacgaa gccacgacaa 360
ctggaggcaa agagggttgc tcaacgcccc gcctcattgg aaaaccaaat cagatctggg 420
acctatatag cgtggcggag gcggggcgat gattgtcgcg ctcgcaccca ctgcagctgc 480
gcacagtcgc atttctttcc ccgcccctga gaccctgcag caccatctgt catggcggct 540
gggctgtttg gtttgagcgc tcgccgtctt ttggcggcag cggcgacgcg agggctcccg 600
gccgcccgcg tccgctggga atctagcttc tccaggactg tggtcgcccc gtccgctgtg 660
gcgggaaagc ggcccccaga accgaccaca ccgtggcaag aggacccaga acccgaggac 720
gaaaacttgt atgagaagaa cccagactcc catggttatg acaaggaccc cgttttggac 780
gtctggaaca tgcgacttgt cttcttcttt ggcgtctcca tcatcctggt ccttggcagc 840
acctttgtgg cctatctgcc tgactacagg tgcacagggt gtccaagagc gtgggatggg 900
atgaaagagt ggtcccgccg cgaagctgag aggcttgtga aataccgaga ggccaatggc 960
cttcccatca tggaatccaa ctgcttcgac cccagcaaga tccagctgcc agaggatgag 1020
tgaccagttg ctaagtgggg ctcaagaagc accgccttcc ccaccccctg cctgccattc 1080
tgacctcttc tcagagcacc taattaaagg ggctgaaagt ctgaaaaaaa aaaaaaaa 1138

<210> SEQ ID NO 35
<211> LENGTH: 1377
<212> TYPE: DNA
<213> ORGANISM: Homo sapiens

<400> SEQUENCE: 35
atgctaaaac taatcgtccc aacaattata ttactaccac tgacatgact ttccaaaaaa 60

```
cacataattt gaatcaacac aaccacccac agcctaatta ttagcatcat ccctctacta    120
tttttaacc aaatcaacaa caacctattt agctgttccc caaccttttc ctccgacccc    180
ctaacaaccc ccctcctaat actaactacc tgactcctac ccctcacaat catggcaagc    240
caacgccact tatccagtga accactatca cgaaaaaaac tctacctctc tatactaatc    300
tccctacaaa tctccttaat tataacattc acagccacag aactaatcat attttatatc    360
ttcttcgaaa ccacacttat ccccaccttg gctatcatca cccgatgagg caaccagcca    420
gaacgcctga acgcaggcac atacttccta ttctacaccc tagtaggctc ccttccccta    480
ctcatcgcac taatttacac tcacaacacc ctaggctcac taaacattct actactcact    540
ctcactgccc aagaactatc aaactcctga gccaacaact taatatgact agcttacaca    600
atagctttta tagtaaagat acctctttac ggactccact tatgactccc taaagcccat    660
gtcgaagccc ccatcgctgg gtcaatagta cttgccgcag tactcttaaa actaggcggc    720
tatggtataa tacgcctcac actcattctc aaccccctga caaaacacat agcctacccc    780
ttccttgtac tatccctatg aggcataatt ataacaagct ccatctgcct acgacaaaca    840
gacctaaaat cgctcattgc atactcttca atcagccaca tagccctcgt agtaacagcc    900
attctcatcc aaaccccctg aagcttcacc ggcgcagtca ttctcataat cgcccacggg    960
cttacatcct cattactatt ctgcctagca aactcaaact acgaacgcac tcacagtcgc   1020
atcataatcc tctctcaagg acttcaaact tactcccact aatagctttt tgatgacttc   1080
tagcaagcct cgctaacctc gccttacccc ccactattaa cctactggga gaactctctg   1140
tgctagtaac cacgttctcc tgatcaaata tcactctcct acttacagga ctcaacatac   1200
tagtcacagc cctatactcc ctctacatat ttaccacaac acaatggggc tcactcaccc   1260
accacattaa caacataaaa ccctcattca cacgagaaaa caccctcatg ttcatacacc   1320
tatcccccat tctcctccta tccctcaacc ccgacatcat taccgggttt tcctctt      1377
```

<210> SEQ ID NO 36
<211> LENGTH: 1779
<212> TYPE: DNA
<213> ORGANISM: Homo sapiens

<400> SEQUENCE: 36

```
cggcgtgccc tggggcggcg cgggcgcagg ggcgcgtgcg cggcgggctg tcgttggctg     60
gagcagcggc tgcgcgggtc gcggtgctgt gaggtctgcg ggcgctggca aatccggccc    120
aggatgtaga gctggcagtg cctgacggcg cgtctgacgc ggagttgggt ggggtagaga    180
gtagggggcg gtagtcgggg gtggtgggag aaggaggagg cggcgaatca cttataaatg    240
gcgccgaagc aggacccgaa gcctaaattc caggaggttg ggatgaatgg gttccggaga    300
gcagagtact caaatacgtg gacaccaatt tgcagaaaca gcgagaactt caaaaagcca    360
atcaggagca gtatgcagag gggaagatga gaggggctgc cccaggaaag aagacatctg    420
gtctgcaaca gaaaaatgtt gaagtgaaaa cgaaaaagaa caaacagaaa acacctggaa    480
atggagatgg tggcagtacc agtgagaccc ctcagcctcc tcggaagaaa agggcccggg    540
tagatcctac tgttgaaaat gaggaaacat tcatgaacag agttgaagtt aaagtaaaga    600
ttcctgaaga gctaaaaccg tggcttgttg atgactggga cttaattacc aggcaaaaac    660
agctctttta tcttcctgcc aagaagaatg tggattccat tcttgaggat tatgcaaatt    720
acaagaaatc tcgtggaaac acagataata aggagtatgc ggttaatgaa gttgtggcag    780
ggataaaaga atacttcaac gtaatgttgg gtacccagct actctataaa tttgagagac    840
```

cacagtatgc tgaaattctt gcagatcatc ccgatgcacc catgtcccag gtgtatggag 900
cgccacatct cctgagatta tttgtacgaa ttggagcaat gttggcttat acacctctgg 960
atgagaagag ccttgcttta ttactcaatt atcttcacga tttcctaaag tacctggcaa 1020
agaattctgc aactttgttc agtgccagcg attatgaagt ggctcctcct gagtaccatc 1080
ggaaagctgt gtgagaggca ctctcactca cttatgtttg gatctccgta aacacatttt 1140
tgttcttagt ctatctcttg tacaaacgat gtgctttgaa gatgttagtg tataacaatt 1200
gatgtttgtt ttctgtttga ttttaaacag agaaaaaata aaagggggta atagctcctt 1260
ttttcttctt tcttttttt tttcatttca aaattgctgc cagtgttttc aatgatggac 1320
aacagaggga tatgctgtag agtgttttat tgcctagttg acaaagctgc ttttgaatgc 1380
tggtggttct attcctttga cactacgcac ttttataata catgttaatg ctatatgaca 1440
aaatgctctg attcctagtg ccaaaggttc aattcagtgt atataactga acacactcat 1500
ccatttgtgc ttttgttttt ttttatggtg cttaaagtaa agagcccatc ctttgcaagt 1560
catccatgtt gttacttagg cattttatct tggctcaaat tgttgaagaa tggtggcttg 1620
tttcatggtt tttgtatttg tgtctaatgc acgttttaac atgatagacg caatgcattg 1680
tgtagctagt tttctggaaa agtcaatctt ttaggaattg tttttcagat cttcaataaa 1740
ttttttcttt aaatttcaaa gaacaaaaaa aaaaaaaaa 1779

<210> SEQ ID NO 37
<211> LENGTH: 7827
<212> TYPE: DNA
<213> ORGANISM: Homo sapiens

<400> SEQUENCE: 37
gtagtcttga cgtgagctag ctggcatggc ggcctgcatt gcagcggggc actgggctgc 60
aatgggccta ggccggagtt tccaagccgc caggactctg ctccccccgc cggcctctat 120
cgcctgcagg gtccacgcgg ggcctgtccg gcagcagagc actgggcctt ccgagcccgg 180
tgcgttccaa ccgccgccga aaccggtcat cgtggacaag caccgccccg tggaaccgga 240
acgcaggttc ttgagtcctg aattcattcc tcgaagggga agaacagatc ctctgaaatt 300
tcaaatagaa agaaaagata tgttagaaag gagaaaagta ctccacattc cagagttcta 360
tgttggaagt attcttcgtg ttactacagc tgacccatat gccagtggaa aaatcagcca 420
gtttctgggg atttgcattc agagatcagg aagaggactt ggagctactt tcatccttag 480
gaatgttatc gaaggacaag gtgtcgagat ttgctttgaa ctttataatc ctcgggtcca 540
ggagattcag gtggtcaaat tagagaaacg gctggatgat agcttgctat acttacgaga 600
tgcccttcct gaatatagca cttttgatgt gaatatgaag ccagtagtac aagagcctaa 660
ccaaaaagtt cctgttaatg agctgaaagt aaaaaatgaag cctaagccct ggtctaaacg 720
ctgggaacgt ccaaatttta atattaaagg aatcagattt gatctttgtt taactgaaca 780
gcaaatgaaa gaagctcaga agtggaatca gccatggctt gaatttgata tgatgaggga 840
atatgatact tcaaaaattg aagctgcaat atggaaggaa attgaagcgt cgaaaaggtc 900
ttgattctga gaatgaattt ggttagttgc agaagataca ttggctctaa gaggatatat 960
tttgagacca atttaatttc atttataaga acatagtaat taagtgaact aagcattcat 1020
tgttttatta atactttttt tctaaaataa aacttgtaca ccagtttatt actctaaaaa 1080
gagaattaca catgccaaat ggaccaatgt ccatttgctt attggaggca aagctacaat 1140
agaagtcaga gcatcaccag aatggtcttt aatgagcatg gaacctgagc aaagggaata 1200
ggtgggatga attttttttt taattgtgaa acaattcata agcacaatat gatttacaga 1260
ataataaaca ttcatgtacc cactatcagg ttaagaaata gaacatttat taatatgtag 1320
gaatgttaag aaataaaaca tttaataaga tctcagaaga ctccagtaaa tctgcaattg 1380
tatctctctc ctttttaaat gtaaatatca tcttgacttg ttaattattc ccttgcattt 1440
cttttagttt actgccaaca catatattct tcaacaatat atttaatttt gaaaaacctg 1500
aaaaaaaaaa cctgttagca agtataaagg ggcagtatta ctattattgc atgaaggctt 1560
caagggaaac gttacagtct ttgggtcata gtctggcttc agcttcctct gagagtttac 1620
agaggccaat tttgagcaaa ttcatggcta aggttatgag tgagttctgc taaacagaag 1680
gctcaccaca aggtatctgg caggattata ctgggtagct ggatgttgca gaaatgtggt 1740
tagaggaagt aaactgtttt ttgatgctca cagcatgatg aatcaaactc tgtatcttag 1800
gattaggtta aaacaatacc tttggtatga tatgagtgtt gttgctgatc catgcagcat 1860
ggattggaaa gctggggtat aagcacacat gctaaagaaa aacatgtaat ttggtccata 1920
ctcacctgga tatactgttc ctcaggttaa aaaatacagt actatcctaa atcttgaagg 1980
caactctcag cctatccatt gagttacctt cagatctgcc ctctggttcc tagctgtctt 2040
gggactaact tctttcctgc gctcagctgt tttctggatt ccatgttttc cattttattg 2100
agtactaact tgttttgctg cagcacatcc tttggtagct tctagaggaa gtttgtgtgg 2160
aggtaaaatt tttgagacct tgcatgtctc atgtttgatt gatactttat acgtttaggt 2220
aggaggtaat tttccttcag gactttaaaa atattgttgc tccattttct ttgtttctat 2280
tgttgtattg agaaatccaa tgccattttg atttccccat cataaatttc atgatgatgt 2340
gtcttggtgt gggtctatat ttatccattg tattgggttt taggtgaacc cttccagata 2400
gtaactcatt tctgtcagtt ctgggaaaca cttagcattg gttgatgatt tattctctgc 2460
tgctttgttc tcccaactat tatttggatg ttggatatcc agcactgggt atctattttc 2520
ttacctccct cccttgaccc cagtctctgt tttttagctc tttagctcaa tcttccaact 2580
ctttgctatt gtattttaaa atcttaagac cccttcttga tttgtagaag ttccttttct 2640
tacaaccaaa aagcctttat ctatggattt gttcacagat aaggggtatt caatatagtg 2700
tatttttttt tcatttaaaa ttgtttgcgc atctatttcc tccaaatttc tttctgtatt 2760
tatttttttgt tgtctatatt tcagactttt ccaggatatc tgataatctt tggctgtctt 2820
cttatggttg aaagagggac taaaaagctt ggaaagcctt tgggttgtgg gaaggggctg 2880
tctttaggat tatctgaatg ggcttttttg ggagtcccct cctccacatg aatattttgg 2940
ttttgtcaga ttccctagaa tagaggcttc caatctcctt cctggagggg tctgtccagg 3000
aaggagattg tctaggggtc tgtcagacag cagctttcag ctacttcctt gatctttttc 3060
actaatgatt atatagtcat ctaactactg tcaacaagta atagatatcc tatccttcac 3120
ttgtttagat tatttgctga gataacctct caaaagaacc tctcaaaata aaaggttaac 3180
aagagcctat atcttatatt tttcttctct ttatcttgtt agaagatagc tattaaaacc 3240
tgttcttttt ctgtcttgat aaacacactt caatcttggt agaatggtag atgggacagt 3300
atattttagg acctaaagct ctgcaaatgt atgatcagct tgtaagtaca ggtgctcaaa 3360
aacatgtaaa caatcatgct ttttactctg taggaatatc tttaaaattc ttgtgaattt 3420
ttccccagaa gtaaagcaaa tcttccccca gaaataaaat taaatgtgca taatctaaag 3480
cttttttttt ttattgtggt aggatatata tataaaacat aatttgccat tgtaaacatt 3540

```
ttaaatttac aagtcagagg cattaattac atcacaatgt tgtgaaatta ttactactat   3600
ttccaaaatt ttctcatcac cccaaactga aactctgtaa ctgttgagca ataacctcat   3660
tcctgtatct ctcccaaccc caggtaacct caaatctttc tttttatctt tgagacaagg   3720
tctcattcta tcactcaggt aggagtgcag tggtgtgatc atagctcatt gcagcctcaa   3780
aatcctgggc tcaagcaatc ctccttgagt agctaagact ataggcacac attaactgcg   3840
cctggctgat tttgtttttt gtagagatgt ggtcttgcta tgtttcccat gctggtcttg   3900
agttcctggc ctcaagcagt ccttaagatt catccatgtt gtggcatgtg tcagaatttc   3960
atttgttttt atgactaaat aatattccat tgtatgtata tacattttgt tcatccatct   4020
tctgatgaac actgggatat gtctaccttt tggctattgt gaataatgct gcagtaaaca   4080
ttgacataac aagtatgtat ttgattgcct gtttctaagt tcttttgggt atacatcttg   4140
agtagaattg ctagataatg tcatgtttta tttctcttgt gatttcttct tcgatcccct   4200
ggttgagtgt gttaatttct acatgtttat gaatttccca ctgttttttt gttattgatt   4260
tccaagttca ttccattgtg attagagaag atacttagta tgattttaat gtttttgaga   4320
attggtgtgt ggcctgatag atggtctgtc ctggagaatg ttcctcatac acttgagcaa   4380
aatatttatc atgctattgt tgactgtagt tttctatatg tctcttaggt caaggtggtt   4440
tacaatgtgt taaggttctc ttttttaaa aaaatttttg cacagagtat ctttttctat   4500
gtgttccatg tatttgtgtc tttggagcta tagtctcttg tagacagcat atcactatct   4560
tgttttgttt tgtttttct gtccattctg ccaatttctg ccttttgatt ggaaaattta   4620
atccatttgc atttaaagta attaaggaag gactttcttc taccatttaa cacttcttct   4680
atatgtcata tacttttttg gcccctcatt tcctctttat ggccttcttt tctgtttttt   4740
tgtagtgaac tagtctgatt ctctttccac tccccttttgt gtatatttgt tagatgtttt   4800
atttgtggtt gctatgggga ttatagttaa catcctacac ttaaaacaat ctaatttaaa   4860
ctgataccaa tttaccttca atagcataca aaatctctac tcctgtaaag ctctgcccct   4920
gcccccctta tgttattgat ggcacaaatt gcctaataaa taatttatag ttatttgtat   4980
gagtttgtct tttaaatcat ttaggaaata aaaagtggag ttagaaaaca gtatgatagt   5040
aatactgact tttatatttg tcaatatatt tatcttattt tggatcctta tttcattata   5100
tagatttgag ttactgtcta gtgcccttcc atttcggccc aaaggattcc cttatgcatt   5160
tcttgcaggg caagtctaat tgtaataaac tccctcagct tttgttttat ctgagaatgt   5220
cttgatttct cccttatttt tgatggataa ttttgccaga tacatgaatt tttggtaaca   5280
gtatttttct ttcagcactt taaatatgtc atcccactac cttctgactt catggtttct   5340
catgagatat tagatgttat aaaatttgag gattcctcat tcttgatgag tcagttctgt   5400
cttattgctt ttcggatttg ctcagctttt gtcttttgac agtttgatta taacgcggct   5460
cagtgtgggt ctctgagttt atcccactta gagtttgttg agtttcttgg agtcatagat   5520
ttatgtcttt tatcaaattt tggacatatt tggctattat ttcttcaatt tttttcactg   5580
cttctttctt ttccttctga aatattctta atgtatatgt tggtctgttt gatgctgtct   5640
caccagtttc ttaggctgtg ttctcttttg ttcctcagac ttgattattg cagttgccct   5700
tctttttatt tttttcaagt ttgttgattc ttctccctgt tcagatcaac tgttgaactc   5760
ctctagtgaa tttatttcag ttactgtact tttcagctcc aagatttatc tttggttcct   5820
ttttataacg tctgtgtctt tattgatatt ctcattttgt tcatatgtct ctttcttcct   5880
```

-continued

```
ttagttcttt gtccatgttt tcctttagct ctttgggctt atttaagaca attgtttaaa   5940

gtctttgcat agtaagtcca atgtctgtgt ttcttcaggg atggttttca ttattttgtt   6000

ttcaatgagc catactttcc tgtgtctttg tatgctgtct ttttgttgtt gaaaactgta   6060

tgtttgaaca tcataacgtg gtggccctga aaatcagata ttcccccctt cctgagagtt   6120

agttttattt ttattattga agattgtagc agtctattgc tacatgtgca gtcatttcca   6180

aactattttt gcaaagactg tattccttct gtgtgtcatc actgaagtct ctgttcctta   6240

gtttgtgttt aatagtttga catagatttc cttgaaagga gttaaaacta gcagaaaaat   6300

ctctctccca gtctttccag tctttgtaga ttggttctgt gctgggcttt tccattaata   6360

cttagccagg cttgtactga gcctaacaat caggcccaaa agcgtagggt ctttgcagat   6420

cttgtctgag catgcttctt gctgtgtatg cacgtagttt tctaaatctc cctgtatgtg   6480

ctgttgaata ttctaatttc ccaaagaaac tcctttgcag ctttttctca cagaacatag   6540

atggtttttt ggatatcttg accatagtct ttcgacccag gtgtttgcgg ttgttagttc   6600

accttacact tttttcaagc attgcctact gcttacgatg agtgctctgt caatccttta   6660

agtagcccca gacaggctac cagagactta aacaagaatt tgtaagttct gctcagcttc   6720

ctctagaaat ggggatcagg gtccaagaca gaatgcagtt gctgatttca agactgctgc   6780

aacaccaggg agcttgtggg ggaagggcaa gcagaaatgt cacaaagctt tcttgccatt   6840

ttaaagttgc ctgttcttga ctcagcattt gcttcattgc tataaacttt ttactgtttt   6900

tcagagttct gataaaattg gctatgcctg ttcctgcttt aaaaaatata tatatatttt   6960

ttagggattg gggtctcact atactgacca ggctggtctt gaacttctgg cctcaagcca   7020

tcctctcatt tcagcttccc aaagtgctgc aattacacgc gtgaaccacc acacccagcc   7080

cctgcttgtt tttcaatgtg cctactccac catgttgctc aagtatgtat attttctaaa   7140

ctaccttgta gtgttgtgat gggaaataaa tccctgagcc ttttgaataa ctcagagaga   7200

tcaaaaactt agtttatcct attcgaagga ttagaaaaat gatatatctt tcactttttc   7260

agggataggc tcctcattag aaggctccta tgtgccgatg ctgtacaaga catttcattt   7320

ctcttaatgt ttacaacaag cttgttgcca aggctgatct tgaactcctg gcctcaaacg   7380

atcctcccag ctcagtctca caaagtgttg ggatgtctgg ccaactaatg actatcttaa   7440

ctcttgtgtt tcaatgttta tgccttcttt tatcttgact gattgtatga ctatgtcttc   7500

tagaacaatg ttgaacagaa atggtgagag cagacatcct tgctttaata tttcaccatt   7560

atatatgatg ttaggtatag atttttctca cagatgcctt ttatcagatt gaggaattta   7620

tattcctact ttgccgaaag gtttttgtag tatgaggggg tgctgaattt tgtcaaacac   7680

tttttcggta ataattgaga tgattggttc tgcagtcatc gagatgtgga ttttctcctt   7740

tattctgttc gtgagtgatt acactggttg actaatgtta aaacaacctt actttccagg   7800

aataaaccct attatctttt ttataca                                       7827
```

<210> SEQ ID NO 38
<211> LENGTH: 1821
<212> TYPE: DNA
<213> ORGANISM: Homo sapiens

<400> SEQUENCE: 38

```
tgcgggtacg gacagcgcat gagcttatgt tgagggcgga gcccagacca gcccttcgtc     60

ctatcctgcc cttccagcac ctctcagccg taacttaaac tacacttccc agaagcctcc    120

tcagccaggg acttccgttg tcgtcagcgg aagcggtgac agatcatccc aggccacaca    180
```

```
gaggccggct tggtcactat ggaggagata ggcatcttgg tggagaaggc tcaggatgag    240
atcccagcac tgtccgtgtc ccggccccag accggcctgt ccttcctggg ccctgagcct    300
gaggacctgg aggacctgta cagccgctac aaggaggagg tgaagcgaat ccaaagcatc    360
ccgctggtca tcggacaatt tctggaggct gtggatcaga atacagccat cgtgggctct    420
accacaggct ccaactatta tgtgcgcatc ctgagcacca tcgatcggga gctgctcaag    480
cccaacgcct cagtggccct ccacaagcac agcaatgcac tggtggacgt gctgcccccc    540
gaagccgaca gcagcatcat gatgctcacc tcagaccaga agccagatgt gatgtacgcg    600
gacatcggag gcatggacat ccagaagcag gaggtgcggg aggccgtgga gctcccgctc    660
acgcatttcg agctctacaa gcagatcggc atcgatcccc cccgaggcgt cctcatgtat    720
ggcccacctg gctgtgggaa gaccatgttg gcaaaggcgg tggcacatca cacaacagct    780
gcattcatcc gggtcgtggg ctcggagttt gtacagaagt atctgggtga gggcccccgc    840
atggtccggg atgtgttccg cctggccaag gagaatgcac ctgccatcat cttcatagac    900
gagattgatg ccatcgccac caagagattc gatgctcaga caggggccga cagggaggtt    960
cagaggatcc tgctggagct gctgaatcag atggatggat ttgatcagaa tgtcaatgtc   1020
aaggtaatca tggccacaaa cagagcagac accctggatc cggccctgct acggccagga   1080
cggctggacc gtaaaattga atttccactt cctgaccgcc gccagaagag attgattttc   1140
tccactatca ctagcaagat gaacctctct gaggaggttg acttggaaga ctatgtggcc   1200
cggccagata agatttcagg agctgatatt aactccatct gtcaggagag tggaatgttg   1260
gctgtccgtg aaaaccgcta cattgtcctg gccaaggact tcgagaaagc atacaagact   1320
gtcatcaaga aggacgagca ggagcatgag ttttacaagt gacccttccc ttccctccac   1380
cacaccactc aggggctggg gcttctctcg cacccccagc acctctgtcc caaaacctca   1440
ttcccttttt tctttaccca ggattggttt cttcaataaa tagataagat cgaatccatt   1500
taatttcttc ttagaagttt aactcctttg gagaatgtgg gccttgaata ggatcctctg   1560
ggtccctctt aatctgacag atgagcagac gaggtgcatg gcctgggttg cagcttgaga   1620
gaaccaaaat attcaaacca gatgacttcc aaaatgtggg gaaagggatg gaaaatgaac   1680
ctgagatgga gtccttaatc acgggataaa gccctgtgca tctccctcat ttcctacagg   1740
taaaagacag taaagaaatt caggtcacag gccttgggag ttcataggaa ggagatgtcc   1800
agtgctgtcc agtagaactt t                                             1821
```

<210> SEQ ID NO 39
<211> LENGTH: 5159
<212> TYPE: DNA
<213> ORGANISM: Homo sapiens

<400> SEQUENCE: 39

```
ggtcccggaa gtgcgccagt cgtaccttcg cggccgcaac tcgctcggcc gccgccatct     60
tgcgagctcg tcgtactgac cgagcgggga ggctgtcttg aggcggcacc gctcaccgac    120
accgaggcgg actggcagcc ctgagcgtcg cagtcatgcc ggccggaccc gtgcaggcgg    180
tgcccccgcc gccgcccgtg cccacggagc ccaaacagcc cacagaagaa gaagcatctt    240
caaaggagga ttctgcacct tctaagccag ttgtggggat tatttaccct cctccagagg    300
tcagaaatat tgttgacaag actgccagct ttgtggccag aaacgggcct gaatttgaag    360
ctaggatccg acagaacgag atcaacaacc ccaagttcaa ctttctgaac cccaatgacc    420
```

```
cttaccatgc ctactaccgc cacaaggtca gcgagttcaa ggaagggaag gctcaggagc    480
cgtccgccgc catccccaag gtcatgcagc agcagcagca gaccacccag cagcagctgc    540
cccagaaggt ccaagcccaa gtaatccaag agaccatcgt gcccaaagag cctcctcctg    600
agtttgagtt cattgctgat cctccctcta tctcagcctt cgacttggat gtggtgaagc    660
tgacggctca gtttgtggcc aggaatgggc gccagtttct gacccagctg atgcagaaag    720
agcagcgcaa ctaccagttt gactttctcc gcccacagca cagcctcttc aactacttca    780
cgaagctagt ggaacagtac accaagatct tgattccacc caaaggttta ttttcaaagc    840
tcaagaaaga ggctgaaaac ccccgagaag ttttggatca ggtgtgttac cgagtggaat    900
gggccaaatt ccaggaacgt gagaggaaga aggaagaaga ggagaaggag aaggagcggg    960
tggcctatgc tcagatcgac tggcatgatt ttgtggtggt ggaaacagtg gacttccaac   1020
ccaatgagca agggaacttc cctccccca ccacgccaga ggagctgggg gcccgaatcc   1080
tcattcagga gcgctatgaa aagtttgggg agagtgagga agttgagatg gaggtcgagt   1140
ctgatgagga ggatgacaaa caggagaagg cggaggagcc tccttcccag ctggaccagg   1200
acacccaagt acaagatatg gatgagggtt cagatgatga agaagaaggg cagaaagtgc   1260
ccccaccccc agagacaccc atgcctccac ctctgccccc aactccagac caagtcattg   1320
tccgcaagga ttatgatccc aaagcctcca agcccttgcc tccagcccct gctccagatg   1380
agtatcttgt gtcccccatt actggggaga agatccccgc cagcaaaatg caggaacaca   1440
tgcgcattgg acttcttgac cctcgctggc tggagcagcg ggatcgctcc atccgtgaga   1500
agcagagcga tgatgaggtg tacgcaccag gtctggatat tgagagcagc ttgaagcagt   1560
tggctgagcg gcgtactgac atcttcggtg tagaggaaac agccattggt aagaagatcg   1620
gtgaggagga gatccagaag ccagaggaaa aggtgacctg ggatggccac tcaggcagca   1680
tggcccggac ccagcaggct gcccaggcca acatcaccct ccaggagcag attgaggcca   1740
ttcacaaggc caaaggcctg gtgccagagg atgacactaa agagaagatt ggccccagca   1800
agcccaatga aatccctcaa cagccaccgc caccatcttc agccaccaac atccccagct   1860
cggctccacc catcacttca gtgccccgac cacccacaat gccacctcca gttcgtacta   1920
cagttgtctc cgcagtaccc gtcatgcccc ggccccccat ggcatctgtg gtccggctgc   1980
ccccaggctc agtgatcgcc cccatgccgc ccatcatcca cgcgcccaga atcaacgtgg   2040
tgcccatgcc tccctcggcc cctcctatta tggcccccg cccaccccc atgattgtgc   2100
caacagcctt tgtgcctgct ccacctgtgg cacctgtccc agctccagcc ccaatgcccc   2160
ctgtgcatcc cccacctccc atggaagatg agcccacctc caaaaaactg aagacagagg   2220
acagcctcat gccagaggag gagttcctgc gcagaaacaa gggtccagtg tccatcaaag   2280
tccaggtgcc caacatgcag gataagacgg aatggaaact gaatgggcag gtgctggtct   2340
tcaccctccc actcacggac caggtctctg tcattaaggt gaagattcat gaagccacag   2400
gcatgcctgc agggaaacag aagctacagt atgagggtat cttcatcaaa gattccaact   2460
cactggctta ctacaacatg gccaatggcg cagtcatcca cctggccctc aaggagagag   2520
gcgggaggaa gaagtagaca agaggaacct gctgtcaagt ccctgccatt ttgcctctcc   2580
tgtctcccac cccctgcccc agacccagga gcccccctga ggctttgcct tgcctgcata   2640
tttgtttcgc tcttactcag tttgggaatt caaattgtcc tgcagaggtt cattcccctg   2700
acccttccc cacattggta agagtagctg ggttttctaa gccactctct ggaatctctt   2760
tgtgttaggg tctcgatttg aggacattca tttcttcagc agcccattag caactgagag   2820
```

```
cccagggatg tcctacagga tagtttcata gtgacaggtg gcacttggct aatagaatat   2880
ggctgatatt gtcattaatc attttgtacc ttgacatggg ttgtctaata aaactcggac   2940
ccttcttgtg aaatcagtta aataagactt gtctcggtca cctgtgccct gtccagactc   3000
gaggcagtgg taacactgca cagtgctatg tggcttctct ttgaggattt ttgggttttg   3060
taactaaatt cttgctgccc tcatactttt tatgtattag aatcatattc gtattgccct   3120
tttaaaacat tgggatcctc caaaggcctg ccccatgtat ttaacagtaa tacaggaagc   3180
atggcaggca ccatgcaaac caaggatgga tggtgcagtc cctgtgtcag tgggcggtgg   3240
tttcctgctg gcctggaatc actcatcacc tgattgattg gctctgtggt cctgggcagg   3300
tgcctcatag gtgtgtggat atgatgacgt ttctttaaaa tgtatgtatt taacaaatac   3360
ttaattgtat taaggtcatg taccaaggat ttgataaagt ttaaataatt tactctctac   3420
ttttatccat tttatccatt ttaactcatg taatcctcat gtgagtattc ctgtttaaca   3480
cttgagtaaa ctgaggcaca gagaacataa gttgcatgcc atagtcacac actgtgaaag   3540
tgaaaagaga atgtgtgcaa aacacgtcac agtcctggtt tctgagtaaa ggcaggctgt   3600
tatctttaga atcaagctat cacagggaga taggcaatgc tgtgggtgtt ggaggaaggt   3660
gagagcctgt tgctaacaat ttcctggttt taaagctaag gctgatttta ttgggaagat   3720
ctcacatgtg tgtggcccct gagagttccc agtgcctttt atttgcagtc cttccatttg   3780
gacctcctag ctgccccatc aggtcatctc cagggctcag aggggtgaga ccatttccca   3840
aggtcacaga accagctctc tagtcaccac cctgcctctc cctctcaccc agagtcagta   3900
ccagttttat ggctttatta caaactgctg ggtccctccc attttcaact tgattgatgg   3960
gatgtcatcc cttatcctgt ctgacatttg cctctggcct ggttgctaga agtttgcccc   4020
aggggcaaga gttgaaattt ggcttcctga ggtgggcttt gtggtttgcg tccctaaagt   4080
gagcccacta ctggttgctt gtccatggcc aacaccagaa atcccctgag cactacctgg   4140
gtctcattcc aagaaggaag agggtcagga gacctgggga gtctcatatt ccaagttctt   4200
ctttctttct gggagcagtg ggcagttcat ggtgttaggg cactcacccc cacagactgg   4260
caaaccctgc aggacttccg tggctgaggc tgtgaccgga ggccaggaat gccgttgggt   4320
ggattgtgag tgaatgggcc ctttgagctg ccctctagag agcaaatcca gtttcctgga   4380
gctcctgaat gaatatctgt actggctcgc tcagatgcag aagctccatt gaccatgagg   4440
ccttgtgaac atcagtggcc acaggcccag tgtgctgctt ggcactgcac tagtttagga   4500
cctgcagcat gtaggtagcg tcctagtgtt tataatacaa agctgctctg cacagctttt   4560
ctgattcttc ttgcaatctc ctgaggatta tctgccccat ttttaaaacg aggtggaata   4620
cccaaggtca tgtagccagt gagtgctctg gaaagccaaa gcagctcatc ccttcctggg   4680
gaccacactg ctctgctcca ccagaccaca ctatgaaata ggaataagtg ctcctgttgc   4740
aggactgctg ggaaaacagg tggtgtggga cttaagtcac cataattttg aagacttgca   4800
tgcagagggc tccaggaatt gtagacatta aggaatttca ctttcagttc tacccactac   4860
ttaagtactt gtcatgtact cttagaggag gccagtaatg atcagaacca ttttacttta   4920
aaattaataa tattgtatta gagaatatat taaatggtta tattgggtta tgttaggata   4980
tatacttgaa tggaaataca tgtactatta gcaatcatat ttcatttatc cctgtaatta   5040
gacaagaaag cataatatag ctctactcat gggtacacat accagtgtat aagattttta   5100
gaagtttact ttttaaaaat aaaagcaaaa tgtaagatct taaaaaaaaa aaaaaaaaa    5159
```

<210> SEQ ID NO 40
<211> LENGTH: 5416
<212> TYPE: DNA
<213> ORGANISM: Homo sapiens

<400> SEQUENCE: 40
agtgggccgc catgttgtcg gagtgaaagg taagggggag cgagagcgcc agagagagaa 60
gatcgggggg ctgaaatcca tcttcatcct accgctccgc ccgtgttggt ggaatgagcg 120
ttgcatgtgt cttgaagaga aaagcagtgc tttggcagga ctctttcagc cccacctga 180 aacatcaccc tcaagaacca gctaatccca acatgcctgt tgttttgaca tctggaacag 240
ggtcgcaagc gcagccacaa ccagctgcaa atcaggctct tgcagctggg actcactcca 300
gccctgtccc aggatctata ggagttgcag gccgttccca ggacgacgct atggtggact 360
acttctttca gaggcagcat ggtgagcagc ttgggggagg aggaagtgga ggaggcggct 420
ataataatag caaacatcga tggcctactg ggataacat tcatgcagaa catcaggtgc 480
gttccatgga tgaactgaat catgattttc aagcacttgc tctggaggga agagcgatgg 540
gagagcagct cttgccaggt aaaaagtttt gggaaacaga tgaatccagc aaagatggac 600
caaaaggaat attcctgggt gatcaatggc gagacagtgc ctggggaaca tcagatcatt 660
cagtttccca gccaatcatg gtgcagagaa gacctggtca gagtttccat gtgaacagtg 720
aggtcaattc tgtactgtcc ccacgatcgg agagtggggg actaggcgtt agcatggtgg 780
agtatgtgtt gagctcatcc ccgggcgatt cctgtctaag aaaaggagga tttggcccaa 840
gggatgcaga cagtgatgaa aacgacaaag gtgaaaagaa gaacaagggt acgtttgatg 900
gagataagct aggagatttg aaggaggagg gtgatgtgat ggacaagacc aatggtttac 960
cagtgcagaa tgggattgat gcagacgtca aagattttag ccgtacccct ggtaattgcc 1020
agaactctgc taatgaagtg gatcttctgg gtccaaacca gaatggttct gagggcttag 1080
cccagctgac cagcaccaat ggtgccaagc ctgtggagga tttctccaac atggagtccc 1140
agagtgtccc cttggacccc atggaacatg tgggcatgga gcctcttcag tttgattatt 1200
caggcacgca ggtacctgtg gactcagcag cagcaactgt gggacttttt gactacaatt 1260
ctcaacaaca gctgttccaa agacctaatg cgcttgctgt ccagcagttg acagctgctc 1320
agcagcagca gtatgcactg gcagctgctc atcagccgca catcggttta gctcccgctg 1380
cgtttgtccc caatccatac atcatcagcg ctgctccccc agggacggac ccctacacag 1440
ctggattggc tgcagcagcg acactaggcc cagctgtggt ccctcaccag tattatggag 1500
ttactccctg gggagtctac cctgccagtc ttttccagca gcaagctgcc gctgccgctg 1560
cagcaactaa ttcagctaat caacagacca ccccacaggc tcagcaagga cagcagcagg 1620
ttctccgtgg aggagccagc caacgtcctt tgaccccaaa ccagaaccag cagggacagc 1680
aaacggatcc ccttgtggca gctgcagcag tgaattctgc ccttgcattt ggacaaggtc 1740
tggcagcagg catgccaggt tatccggtgt tggctcctgc tgcttactat gaccaaactg 1800
gtgcccttgt agtgaatgca ggcgcgagaa atggtcttgg agctcctgtt cgacttgtag 1860
ctcctgcccc agtcatcatt agttcctcag ctgcacaagc agctgttgca gcagccgcag 1920
cttcagcaaa tggagcagct ggtggtcttg ctggaacaac aaatggacca tttcgccctt 1980
taggaacaca gcagcctcag ccccagcccc agcagcagcc caataacaac ctggcatcca 2040
gttctttcta cggcaacaac tctctgaaca gcaattcaca gagcagctcc ctcttctccc 2100
agggctctgc ccagcctgcc aacacatcct tgggattcgg aagtagcagt tctctcggcg 2160

```
ccaccctggg atccgccctt ggagggtttg gaacagcagt tgcaaactcc aacactggca   2220
gtggctcccg ccgtgactcc ctgactggca gcagtgacct ttataagagg acatcgagca   2280
gcttgacccc cattggacac agtttttata acggccttag cttttcctcc tctcctggac   2340
ccgtgggcat gcctctccct agtcagggac caggacattc acagacacca cctccttccc   2400
tctcttcaca tggatcctct tcaagcttaa acctgggagg actcacgaat ggcagtggaa   2460
gatacatctc tgctgctcca ggcgctgaag ccaagtaccg cagtgcaagc agcgcctcca   2520
gcctcttcag cccgagcagc actcttttct cttcctctcg tttgcgatat ggaatgtctg   2580
atgtcatgcc ttctggcagg agcaggcttt tggaagattt tcgaaacaac cggtacccca   2640
atttacaact gcgggagatt gctggacata taatggaatt ttcccaagac cagcatgggt   2700
ccagattcat tcagctgaaa ctggagcgtg ccacaccagc tgagcgccag cttgtcttca   2760
atgaaatcct ccaggctgcc taccaactca tggtggatgt gtttggtaat tacgtcattc   2820
agaagttctt tgaatttggc agtcttgaac agaagctggc tttggcagaa cggattcgag   2880
gccacgtcct gtcattggca ctacagatgt atggctgccg tgttatccag aaagctcttg   2940
agtttattcc ttcagaccag caggtaatta atgagatggt tcgggaacta gatggccatg   3000
tcttgaagtg tgtgaaagat cagaatggca atcacgtggt tcagaaatgc attgaatgtg   3060
tacagcccca gtctttgcaa tttatcatcg atgcgtttaa gggacaggta tttgccttat   3120
ccacacatcc ttatggctgc cgagtgattc agagaatcct ggagcactgt ctccctgacc   3180
agacactccc tattttagag gagcttcacc agcacacaga gcagcttgta caggatcaat   3240
atggaaatta tgtaatccaa catgtactgg agcacggtcg tcctgaggat aaaagcaaaa   3300
ttgtagcaga aatccgaggc aatgtacttg tattgagtca gcacaaattt gcaagcaatg   3360
ttgtggagaa gtgtgttact cacgcctcac gtacggagcg cgctgtgctc atcgatgagg   3420
tgtgcaccat gaacgacggt ccccacagtg ccttatacac catgatgaag gaccagtatg   3480
ccaactacgt ggtccagaag atgattgacg tggcggagcc aggccagcgg aagatcgtca   3540
tgcataagat ccggccccac atcgcaactc ttcgtaagta cacctatggc aagcacattc   3600
tggccaagct ggagaagtac tacatgaaga acggtgttga cttagggccc atctgtggcc   3660
cccctaatgg tatcatctga ggcagtgtca cccgctgttc cctcattccc gctgacctca   3720
ctggcccact ggcaaatcca accagcaacc agaaatgttc tagtgtagag tctgagacgg   3780
gcaagtggtt gctccaggat tactccctcc tccaaaaaag gaatcaaatc cacgagtgga   3840
aaagcctttg taaatttaat tttattacac ataacatgta ctattttttt taattgacta   3900
attgccctgc tgttttactg gtgtatagga tacttgtaca taggtaacca atgtacatgg   3960
gaggccacat attttgttca ctgttgtatc tatatttcac atgtggaaac tttcagggtg   4020
gttggtttaa caaaaaaaaa aagctttaaa aaaaaaagaa aaaaaggaaa aggtttttag   4080
ctcatttgcc tggccggcaa gttttgcaaa tagctcttcc ccacctcctc attttagtaa   4140
aaaacaaaca aaaacaaaaa aacctgagaa gtttgaattg tagttaaatg accccaaact   4200
ggcatttaac actgtttata aaaaatatat atatatatat atatatatat aatgaaaaag   4260
gtttcagagt tgctaaagct tcagtttgtg acattaagtt tatgaaattc taaaaaatgc   4320
ctttttttgga gactatatta tgctgaagaa ggctgttcgt gaggaggaga tgcgagcacc   4380
cagaacgtct tttgaggctg ggcgggtgtg attgtttact gcctactgga tttttttcta   4440
ttaacattga aaggtaaaat ctgattattt agcatgagaa aaaaaaatcc aactctgctt   4500
```

ttggtcttgc ttctataaat atatagtgta tacttggtgt agactttgca tatatacaaa 4560
tttgtagtat tttcttgttt tgatgtctaa tctgtatcta taatgtaccc tagtagtcga 4620
acatactttt gattgtacaa ttgtacattt gtatacctgt aatgtaaatg tggagaagtt 4680
tgaatcaaca taaacacgtt ttttggtaag aaaagagaat tagccagccc tgtgcattca 4740
gtgtatattc tcacctttta tggtcgtagc atatagtgtt gtatattgta aattgtaatt 4800
tcaaccagaa gtaaattttt ttctttttgaa ggaataaatg ttctttatac agcctagtta 4860
atgtttaaaa agaaaaaaat agcttggttt tatttgtcat ctagtctcaa gtatagcgag 4920
attctttcta aatgttattc aagattgagt tctcactagt gtttttttaa tcctaaaaaa 4980
gtaatgtttt gattttgtga cagtcaaaag gacgtgcaaa agtctagcct tgcccgagct 5040
ttccttacaa tcagagcccc tctcaccttg taaagtgtga atcgcccttc ccttttgtac 5100
agaagatgaa ctgtattttg cattttgtct acttgtaagt gaatgtaaca tactgtcaat 5160
tttccttgtt tgaatataga attgtaacac tacacggtgt acatttccag agccttgtgt 5220
atatttccaa tgaacttttt tgcaagcaca cttgtaacca tatgtgtata attaacaaac 5280
ctgtgtatgc ttatgcctgg gcaactattt tttgtaactc ttgtgtagat tgtctctaaa 5340
caatgtgtga tctttatttt gaaaaataca gaactttgga atctgaaaaa aaaaaaaaaa 5400
aaaaaaaaaa aaaaaa 5416

<210> SEQ ID NO 41
<211> LENGTH: 1940
<212> TYPE: DNA
<213> ORGANISM: Homo sapiens

<400> SEQUENCE: 41
gagtgagcgg cgcggggcca atcagcgtgc gccgttccga aagttgcctt ttatggctcg 60
agcggccgcg gcggcgccct ataaaaccca gcggcgcgac gcgccaccac cgccgagacc 120
gcgtccgccc cgcgagcaca gagcctcgcc tttgccgatc cgccgcccgt ccacacccgc 180
cgccagctca ccatggatga tgatatcgcc gcgctcgtcg tcgacaacgg ctccggcatg 240
tgcaaggccg gcttcgcggg cgacgatgcc ccccgggccg tcttcccctc catcgtgggg 300
cgccccaggc accagggcgt gatggtgggc atgggtcaga aggattccta tgtgggcgac 360
gaggcccaga gcaagagagg catcctcacc ctgaagtacc ccatcgagca cggcatcgtc 420
accaactggg acgacatgga gaaaatctgg caccacacct tctacaatga gctgcgtgtg 480
gctcccgagg agcaccccgt gctgctgacc gaggcccccc tgaaccccaa ggccaaccgc 540
gagaagatga cccagatcat gtttgagacc ttcaacaccc cagccatgta cgttgctatc 600
caggctgtgc tatccctgta cgcctctggc cgtaccactg gcatcgtgat ggactccggt 660
gacggggtca cccacactgt gcccatctac gaggggtatg ccctccccca tgccatcctg 720
cgtctggacc tggctggccg ggacctgact gactacctca tgaagatcct caccgagcgc 780
ggctacagct tcaccaccac ggccgagcgg gaaatcgtgc gtgacattaa ggagaagctg 840
tgctacgtcg ccctggactt cgagcaagag atggccacgg ctgcttccag ctcctccctg 900
gagaagagct acgagctgcc tgacggccag gtcatcacca ttggcaatga gcggttccgc 960
tgccctgagg cactcttcca gccttccttc ctgggcatgg agtcctgtgg catccacgaa 1020
actaccttca actccatcat gaagtgtgac gtggacatcc gcaaagacct gtacgccaac 1080
acagtgctgt ctggcggcac caccatgtac cctggcattg ccgacaggat gcagaaggag 1140
atcactgccc tggcacccag cacaatgaag atcaagatca ttgctcctcc tgagcgcaag 1200

```
tactccgtgt ggatcggcgg ctccatcctg gcctcgctgt ccaccttcca gcagatgtgg   1260

atcagcaagc aggagtatga cgagtccggc ccctccatcg tccaccgcaa atgcttctag   1320

gcggactatg acttagttgc gttacaccct ttcttgacaa aacctaactt gcgcagaaaa   1380

caagatgaga ttggcatggc tttatttgtt tttttgttt tgttttggtt ttttttttt   1440

ttttggcttg actcaggatt taaaaactgg aacggtgaag gtgacagcag tcggttggag   1500

cgagcatccc ccaaagttca caatgtggcc gaggactttg attgcacatt gttgtttttt   1560

taatagtcat tccaaatatg agatgcgttg ttacaggaag tcccttgcca tcctaaaagc   1620

caccccactt ctctctaagg agaatggccc agtcctctcc caagtccaca caggggaggt   1680

gatagcattg ctttcgtgta aattatgtaa tgcaaaattt ttttaatctt cgccttaata   1740

ctttttttatt ttgttttatt ttgaatgatg agccttcgtg cccccccttc cccctttttt   1800

gtcccccaac ttgagatgta tgaaggcttt tggtctccct gggagtgggt ggaggcagcc   1860

agggcttacc tgtacactga cttgagacca gttgaataaa agtgcacacc ttaaaaatga   1920

ggaaaaaaaa aaaaaaaaaa                                                1940
```

<210> SEQ ID NO 42
<211> LENGTH: 1309
<212> TYPE: DNA
<213> ORGANISM: Homo sapiens

<400> SEQUENCE: 42

```
gctctctgct cctcctgttc gacagtcagc cgcatcttct tttgcgtcgc cagccgagcc     60

acatcgctca gacaccatgg ggaaggtgaa ggtcggagtc aacggatttg gtcgtattgg    120

gcgcctggtc accagggctg cttttaactc tggtaaagtg gatattgttg ccatcaatga    180

ccccttcatt gacctcaact acatggttta catgttccaa tatgattcca cccatggcaa    240

attccatggc accgtcaagg ctgagaacgg gaagcttgtc atcaatggaa atcccatcac    300

catcttccag gagcgagatc cctccaaaat caagtggggc gatgctggcg ctgagtacgt    360

cgtggagtcc actggcgtct tcaccaccat ggagaaggct ggggctcatt tgcagggggg    420

agccaaaagg gtcatcatct ctgccccctc tgctgatgcc cccatgttcg tcatgggtgt    480

gaaccatgag aagtatgaca acagcctcaa gatcatcagc aatgcctcct gcaccaccaa    540

ctgcttagca cccctggcca aggtcatcca tgacaacttt ggtatcgtgg aaggactcat    600

gaccacagtc catgccatca ctgccaccca gaagactgtg gatggcccct ccgggaaact    660

gtggcgtgat ggccgcgggg ctctccagaa catcatccct gcctctactg gcgctgccaa    720

ggctgtgggc aaggtcatcc ctgagctgaa cgggaagctc actggcatgg ccttccgtgt    780

ccccactgcc aacgtgtcag tggtggacct gacctgccgt ctagaaaaac ctgccaaata    840

tgatgacatc aagaaggtgg tgaagcaggc gtcggagggc cccctcaagg gcatcctggg    900

ctacactgag caccaggtgg tctcctctga cttcaacagc gacacccact cctccacctt    960

tgacgctggg gctggcattg ccctcaacga ccactttgtc aagctcattt cctggtatga   1020

caacgaattt ggctacagca acagggtggt ggacctcatg gcccacatgg cctccaagga   1080

gtaagacccc tggaccacca gccccagcaa gagcacaaga ggaagagaga gaccctcact   1140

gctggggagt ccctgccaca ctcagtcccc caccacactg aatctcccct cctcacagtt   1200

gccatgtaga ccccttgaag aggggagggg cctagggagc cgcaccttgt catgtaccat   1260

caataaagta ccctgtgctc aaccagttaa aaaaaaaaaa aaaaaaaaa                1309
```

<210> SEQ ID NO 43
<211> LENGTH: 2321
<212> TYPE: DNA
<213> ORGANISM: Homo sapiens

<400> SEQUENCE: 43
gtcctcaacc aagatggcgc ggatggcttc aggcgcatca cgacaccggc gcgtcacgcg 60
acccgcccta cgggcacctc ccgcgctttt cttagcgccg cagacggtgg ccgagcgggg 120
gaccgggaag catggcccgg gggtcggcgg ttgcctgggc ggcgctcggg ccgttgttgt 180
ggggctgcgc gctggggctg cagggcggga tgctgtaccc ccaggagagc ccgtcgcggg 240
agtgcaagga gctggacggc ctctggagct tccgcgccga cttctctgac aaccgacgcc 300
ggggcttcga ggagcagtgg taccggcggc cgctgtggga gtcaggcccc accgtggaca 360
tgccagttcc ctccagcttc aatgacatca gccaggactg gcgtctgcgg cattttgtcg 420
gctgggtgtg gtacgaacgg gaggtgatcc tgccggagcg atggacccag gacctgcgca 480
caagagtggt gctgaggatt ggcagtgccc attcctatgc catcgtgtgg gtgaatgggg 540
tcgacacgct agagcatgag gggggctacc tccccttcga ggccgacatc agcaacctgg 600
tccaggtggg gcccctgccc tcccggctcc gaatcactat cgccatcaac aacacactca 660
cccccaccac cctgccacca gggaccatcc aatacctgac tgacacctcc aagtatccca 720
agggttactt tgtccagaac acatattttg actttttcaa ctacgctgga ctgcagcggt 780
ctgtacttct gtacacgaca cccaccacct acatcgatga catcaccgtc accaccagcg 840
tggagcaaga cagtgggctg gtgaattacc agatctctgt caagggcagt aacctgttca 900
agttggaagt gcgtcttttg gatgcagaaa acaaagtcgt ggcgaatggg actgggaccc 960
agggccaact taaggtgcca ggtgtcagcc tctggtggcc gtacctgatg cacgaacgcc 1020
ctgcctatct gtattcattg gaggtgcagc tgactgcaca gacgtcactg gggcctgtgt 1080
ctgacttcta cacactccct gtggggatcc gcactgtggc tgtcaccaag agccagttcc 1140
tcatcaatgg gaaacctttc tatttccacg gtgtcaacaa gcatgaggat gcggacatcc 1200
gagggaaggg cttcgactgg ccgctgctgg tgaaggactt caacctgctt cgctggcttg 1260
gtgccaacgc tttccgtacc agccactacc cctatgcaga ggaagtgatg cagatgtgtg 1320
accgctatgg gattgtggtc atcgatgagt gtcccggcgt gggcctggcg ctgccgcagt 1380
tcttcaacaa cgtttctctg catcaccaca tgcaggtgat ggaagaagtg gtgcgtaggg 1440
acaagaacca ccccgcggtc gtgatgtggt ctgtggccaa cgagcctgcg tcccacctag 1500
aatctgctgg ctactacttg aagatggtga tcgctcacac caaatccttg gacccctccc 1560
ggcctgtgac ctttgtgagc aactctaact atgcagcaga caagggggct ccgtatgtgg 1620
atgtgatctg tttgaacagc tactactctt ggtatcacga ctacgggcac ctggagttga 1680
ttcagctgca gctggccacc cagtttgaga actggtataa gaagtatcag aagcccatta 1740
ttcagagcga gtatggagca gaaacgattg cagggtttca ccaggatcca cctctgatgt 1800
tcactgaaga gtaccagaaa agtctgctag agcagtacca tctgggtctg gatcaaaaac 1860
gcagaaaata cgtggttgga gagctcattt ggaattttgc cgatttcatg actgaacagt 1920
caccgacgag agtgctgggg aataaaaagg ggatcttcac tcggcagaga caaccaaaaa 1980
gtgcagcgtt ccttttgcga gagagatact ggaagattgc caatgaaacc aggtatcccc 2040
actcagtagc caagtcacaa tgtttggaaa acagcctgtt tacttgagca agactgatac 2100
cacctgcgtg tcccttcctc cccgagtcag ggcgacttcc acagcagcag aacaagtgcc 2160
tcctggactg ttcacggcag accagaacgt ttctggcctg ggttttgtgg tcatctattc 2220
tagcagggaa cactaaaggt ggaaataaaa gattttctat tatggaaata aagagttggc 2280
atgaaagtgg ctactgaaaa aaaaaaaaaa aaaaaaaaaa a 2321

<210> SEQ ID NO 44
<211> LENGTH: 1229
<212> TYPE: DNA
<213> ORGANISM: Homo sapiens

<400> SEQUENCE: 44
gtctgacggg cgatggcgca gccaatagac aggagcgcta tccgcggttt ctgattggct 60
actttgttcg cattataaaa ggcacgcgcg ggcgcgaggc ccttctctcg ccaggcgtcc 120
tcgtggaagt gacatcgtct ttaaaccctg cgtggcaatc cctgacgcac cgccgtgatg 180
cccagggaag acagggcgac ctggaagtcc aactacttcc ttaagatcat ccaactattg 240
gatgattatc cgaaatgttt cattgtggga gcagacaatg tgggctccaa gcagatgcag 300
cagatccgca tgtcccttcg cgggaaggct gtggtgctga tgggcaagaa caccatgatg 360
cgcaaggcca tccgagggca cctggaaaac aacccagctc tggagaaact gctgcctcat 420
atccggggga atgtgggctt tgtgttcacc aaggaggacc tcactgagat cagggacatg 480
ttgctggcca ataaggtgcc agctgctgcc cgtgctggtg ccattgcccc atgtgaagtc 540
actgtgccag cccagaacac tggtctcggg cccgagaaga cctccttttt ccaggcttta 600
ggtatcacca ctaaaatctc caggggcacc attgaaatcc tgagtgatgt gcagctgatc 660
aagactggag acaaagtggg agccagcgaa gccacgctgc tgaacatgct caacatctcc 720
cccttctcct ttgggctggt catccagcag gtgttcgaca atggcagcat ctacaaccct 780
gaagtgcttg atatcacaga ggaaactctg cattctcgct tcctggaggg tgtccgcaat 840
gttgccagtg tctgtctgca gattggctac ccaactgttg catcagtacc ccattctatc 900
atcaacgggt acaaacgagt cctggccttg tctgtggaga cggattacac cttcccactt 960
gctgaaaagg tcaaggcctt cttggctgat ccatctgcct ttgtggctgc tgcccctgtg 1020
gctgctgcca ccacagctgc tcctgctgct gctgcagccc cagctaaggt tgaagccaag 1080
gaagagtcgg aggagtcgga cgaggatatg ggatttggtc tctttgacta atcaccaaaa 1140
agcaaccaac ttagccagtt ttatttgcaa aacaaggaaa taaaggctta cttctttaaa 1200
aagtaaaaaa aaaaaaaaaa aaaaaaaaa 1229

<210> SEQ ID NO 45
<211> LENGTH: 5234
<212> TYPE: DNA
<213> ORGANISM: Homo sapiens

<400> SEQUENCE: 45
agagcgtcgg gatatcgggt ggcggctcgg gacggaggac gcgctagtgt gagtgcgggc 60
ttctagaact acaccgaccc tcgtgtcctc ccttcatcct gcggggctgg ctggagcggc 120
cgctccggtg ctgtccagca gccataggga gccgcacggg gagcgggaaa gcggtcgcgg 180
ccccaggcgg ggcggccggg atggagcggg gccgcgagcc tgtggggaag gggctgtggc 240
ggcgcctcga gcggctgcag gttcttctgt gtggcagttc agaatgatgg atcaagctag 300
atcagcattc tctaacttgt ttggtggaga accattgtca tatacccggt tcagcctggc 360
tcggcaagta gatggcgata acagtcatgt ggagatgaaa cttgctgtag atgaagaaga 420

-continued

```
aaatgctgac aataacacaa aggccaatgt cacaaaacca aaaaggtgta gtggaagtat    480
ctgctatggg actattgctg tgatcgtctt tttcttgatt ggatttatga ttggctactt    540
gggctattgt aaaggggtag aaccaaaaac tgagtgtgag agactggcag gaaccgagtc    600
tccagtgagg gaggagccag gagaggactt ccctgcagca cgtcgcttat attgggatga    660
cctgaagaga aagttgtcgg agaaactgga cagcacagac ttcaccggca ccatcaagct    720
gctgaatgaa aattcatatg tccctcgtga ggctggatct caaaaagatg aaaatcttgc    780
gttgtatgtt gaaaatcaat ttcgtgaatt taaactcagc aaagtctggc gtgatcaaca    840
ttttgttaag attcaggtca aagacagcgc tcaaaactcg gtgatcatag ttgataagaa    900
cggtagactt gtttacctgg tggagaatcc tgggggttat gtggcgtata gtaaggctgc    960
aacagttact ggtaaactgg tccatgctaa ttttggtact aaaaaagatt ttgaggattt   1020
atacactcct gtgaatggat ctatagtgat tgtcagagca gggaaaatca cctttgcaga   1080
aaaggttgca aatgctgaaa gcttaaatgc aattggtgtg ttgatataca tggaccagac   1140
taaatttccc attgttaacg cagaactttc attctttgga catgctcatc tggggacagg   1200
tgacccttac acacctggat tcccttcctt caatcacact cagtttccac catctcggtc   1260
atcaggattg cctaatatac ctgtccagac aatctccaga gctgctgcag aaaagctgtt   1320
tgggaatatg gaaggagact gtccctctga ctggaaaaca gactctacat gtaggatggt   1380
aacctcagaa agcaagaatg tgaagctcac tgtgagcaat gtgctgaaag agataaaaat   1440
tcttaacatc tttggagtta ttaaaggctt tgtagaacca gatcactatg ttgtagttgg   1500
ggcccagaga gatgcatggg gccctggagc tgcaaaatcc ggtgtaggca cagctctcct   1560
attgaaactt gcccagatgt tctcagatat ggtcttaaaa gatgggtttc agcccagcag   1620
aagcattatc tttgccagtt ggagtgctgg agactttgga tcggttggtg ccactgaatg   1680
gctagaggga tacctttcgt ccctgcattt aaaggctttc acttatatta atctggataa   1740
agcggttctt ggtaccagca acttcaaggt ttctgccagc ccactgttgt atacgcttat   1800
tgagaaaaca atgcaaaatg tgaagcatcc ggttactggg caatttctat atcaggacag   1860
caactgggcc agcaaagttg agaaactcac tttagacaat gctgctttcc ctttccttgc   1920
atattctgga atcccagcag tttctttctg tttttgcgag gacacagatt atccttattt   1980
gggtaccacc atggacacct ataaggaact gattgagagg attcctgagt tgaacaaagt   2040
ggcacgagca gctgcagagg tcgctggtca gttcgtgatt aaactaaccc atgatgttga   2100
attgaacctg gactatgaga ggtacaacag ccaactgctt tcatttgtga gggatctgaa   2160
ccaatacaga gcagacataa aggaaatggg cctgagttta cagtggctgt attctgctcg   2220
tggagacttc ttccgtgcta cttccagact aacaacagat ttcgggaatg ctgagaaaac   2280
agacagattt gtcatgaaga aactcaatga tcgtgtcatg agagtggagt atcacttcct   2340
ctctccctac gtatctccaa aagagtctcc tttccgacat gtcttctggg gctccggctc   2400
tcacacgctg ccagctttac tggagaactt gaaactgcgt aaacaaaata acggtgcttt   2460
taatgaaacg ctgttcagaa accagttggc tctagctact tggactattc agggagctgc   2520
aaatgccctc tctggtgacg tttgggacat tgacaatgag ttttaaatgt gatacccata   2580
gcttccatga gaacagcagg gtagtctggt ttctagactt gtgctgatcg tgctaaattt   2640
tcagtagggc tacaaaacct gatgttaaaa ttccatccca tcatcttggt actactagat   2700
gtctttaggc agcagctttt aatacagggt agataacctg tacttcaagt taaagtgaat   2760
aaccacttaa aaaatgtcca tgatggaata ttcccctatc tctagaattt taagtgcttt   2820
```

```
gtaatgggaa ctgcctcttt cctgttgttg ttaatgaaaa tgtcagaaac cagttatgtg   2880
aatgatctct ctgaatccta agggctggtc tctgctgaag gttgtaagtg gtcgcttact   2940
ttgagtgatc ctccaacttc atttgatgct aaataggaga taccaggttg aaagaccttc   3000
tccaaatgag atctaagcct ttccataagg aatgtagctg gtttcctcat tcctgaaaga   3060
aacagttaac tttcagaaga gatgggcttg ttttcttgcc aatgaggtct gaaatggagg   3120
tccttctgct ggataaaatg aggttcaact gttgattgca ggaataaggc cttaatatgt   3180
taacctcagt gtcatttatg aaaagagggg accagaagcc aaagacttag tatattttct   3240
tttcctctgt cccttccccc ataagcctcc atttagttct ttgttatttt tgtttcttcc   3300
aaagcacatt gaaagagaac cagtttcagg tgtttagttg cagactcagt ttgtcagact   3360
ttaaagaata atatgctgcc aaattttggc caaagtgtta atcttagggg agagctttct   3420
gtccttttgg cactgagata tttattgttt atttatcagt gacagagttc actataaatg   3480
gtgttttttt aatagaatat aattatcgga agcagtgcct tccataatta tgacagttat   3540
actgtcggtt tttttaaat  aaaagcagca tctgctaata aaacccaaca gatactggaa   3600
gttttgcatt tatggtcaac acttaagggt tttagaaaac agccgtcagc caaatgtaat   3660
tgaataaagt tgaagctaag atttagagat gaattaaatt taattagggg ttgctaagaa   3720
gcgagcactg accagataag aatgctggtt ttcctaaatg cagtgaattg tgaccaagtt   3780
ataaatcaat gtcacttaaa ggctgtggta gtactcctgc aaaattttat agctcagttt   3840
atccaaggtg taactctaat tcccattttg caaaatttcc agtacctttg tcacaatcct   3900
aacacattat cgggagcagt gtcttccata atgtataaag aacaaggtag tttttaccta   3960
ccacagtgtc tgtatcggag acagtgatct ccatatgtta cactaagggt gtaagtaatt   4020
atcgggaaca gtgtttccca taattttctt catgcaatga catcttcaaa gcttgaagat   4080
cgttagtatc taacatgtat cccaactcct ataattccct atcttttagt tttagttgca   4140
gaaacatttt gtggtcatta agcattgggt gggtaaattc aaccactgta aaatgaaatt   4200
actacaaaat ttgaaattta gcttgggttt ttgttacctt tatggtttct ccaggtcctc   4260
tacttaatga gatagtagca tacatttata atgtttgcta ttgacaagtc attttaactt   4320
tatcacatta tttgcatgtt acctcctata aacttagtgc ggacaagttt taatccagaa   4380
ttgacctttt gacttaaagc agagggactt tgtatagaag gtttgggggc tgtggggaag   4440
gagagtcccc tgaaggtctg acacgtctgc ctacccattc gtggtgatca attaaatgta   4500
ggtatgaata agttcgaagc tccgtgagtg aaccatcatt ataaacgtga tgatcagctg   4560
tttgtcatag ggcagttgga aacggcctcc tagggaaaag ttcatagggt ctcttcaggt   4620
tcttagtgtc acttacctag atttacagcc tcacttgaat gtgtcactac tcacagtctc   4680
tttaatcttc agttttatct ttaatctcct cttttatctt ggactgacat ttagcgtagc   4740
taagtgaaaa ggtcatagct gagattcctg gttcgggtgt tacgcacacg tacttaaatg   4800
aaagcatgtg gcatgttcat cgtataacac aatatgaata cagggcatgc attttgcagc   4860
agtgagtctc ttcagaaaac ccttttctac agttagggtt gagttacttc ctatcaagcc   4920
agtacgtgct aacaggctca atattcctga atgaaatatc agactagtga caagctcctg   4980
gtcttgagat gtcttctcgt taaggagatg ggccttttgg aggtaaagga taaaatgaat   5040
gagttctgtc atgattcact attctagaac ttgcatgacc tttactgtgt tagctctttg   5100
aatgttcttg aaattttaga ctttctttgt aaacaaatga tatgtcctta tcattgtata   5160
```

-continued aaagctgtta tgtgcaacag tgtggagatt ccttgtctga tttaataaaa tacttaaaca 5220
ctgaaaaaaa aaaa 5234

<210> SEQ ID NO 46
<211> LENGTH: 1869
<212> TYPE: DNA
<213> ORGANISM: Homo sapiens

<400> SEQUENCE: 46
tacctggttg atcctgccag tagcatatgc ttgtctcaaa gattaagcca tgcatgtcta 60
agtacgcacg gccggtacag tgaaactgcg aatggctcat taaatcagtt atggttcctt 120
tggtcgctcg ctcctctccc acttggataa ctgtggtaat tctagagcta atacatgccg 180
acgggcgctg accccttcg cggggggat gcgtgcattt atcagatcaa aaccaacccg 240
gtcagcccct ctccggcccc ggccgggggg cgggcgccgg cggctttggt gactctagat 300
aacctcgggc cgatcgcacg ccccccgtgg cggcgacgac ccattcgaac gtctgcccta 360
tcaactttcg atggtagtcg ccgtgcctac catggtgacc acgggtgacg gggaatcagg 420
gttcgattcc ggagagggag cctgagaaac ggctaccaca tccaaggaag gcagcaggcg 480
cgcaaattac ccactcccga cccggggagg tagtgacgaa aaataacaat acaggactct 540
ttcgaggccc tgtaattgga atgagtccac tttaaatcct ttaacgagga tccattggag 600
ggcaagtctg gtgccagcag ccgcggtaat tccagctcca atagcgtata ttaaagttgc 660
tgcagttaaa aagctcgtag ttggatcttg ggagcgggcg ggcggtccgc cgcgaggcga 720
gccaccgccc gtccccgccc cttgcctctc ggcgcccccct cgatgctctt agctgagtgt 780
cccgcggggc ccgaagcgtt tactttgaaa aaattagagt gttcaaagca ggcccgagcc 840
gcctggatac cgcagctagg aataatggaa taggaccgcg gttctatttt gttggttttc 900
ggaactgagg ccatgattaa gagggacggc cgggggcatt cgtattgcgc cgctagaggt 960
gaaattcttg gaccggcgca agacggacca gagcgaaagc atttgccaag aatgttttca 1020
ttaatcaaga acgaaagtcg gaggttcgaa gacgatcaga taccgtcgta gttccgacca 1080
taaacgatgc cgaccggcga tgcggcggcg ttattcccat gacccgccgg gcagcttccg 1140
ggaaaccaaa gtctttgggt tccgggggga gtatggttgc aaagctgaaa cttaaaggaa 1200
ttgacggaag ggcaccacca ggagtggagc ctgcggctta atttgactca acacgggaaa 1260
cctcacccgg cccggacacg gacaggattg acagattgat agctctttct cgattccgtg 1320
ggtggtggtg catggccgtt cttagttggt ggagcgattt gtctggttaa ttccgataac 1380
gaacgagact ctggcatgct aactagttac gcgacccccg agcggtcggc gtcccccaac 1440
ttcttagagg gacaagtggc gttcagccac ccgagattga gcaataacag gtctgtgatg 1500
cccttagatg tccggggctg cacgcgcgct acactgactg gctcagcgtg tgcctaccct 1560
acgccggcag gcgcgggtaa cccgttgaac cccattcgtg atggggatcg gggattgcaa 1620
ttattcccca tgaacgagga attcccagta agtgcgggtc ataagcttgc gttgattaag 1680
tccctgccct ttgtacacac cgcccgtcgc tactaccgat tggatggttt agtgaggccc 1740
tcggatcggc cccgccgggg tcggcccacg gccctggcgg agcgctgaga agacggtcga 1800
acttgactat ctagaggaag taaaagtcgt aacaaggttt ccgtaggtga acctgcggaa 1860
ggatcatta 1869

<210> SEQ ID NO 47
<211> LENGTH: 2288

<212> TYPE: DNA
<213> ORGANISM: Homo sapiens

<400> SEQUENCE: 47
ggggccgaac gtggtataaa aggggcggga ggccaggctc gtgccgtttt gcagacgcca 60
ccgccgagga aaaccgtgta ctattagcca tggtcaaccc caccgtgttc ttcgacattg 120
ccgtcgacgg cgagcccttg ggccgcgtct cctttgagct gtttgcagac aaggtcccaa 180
agacagcaga aaattttcgt gctctgagca ctggagagaa aggatttggt tataagggtt 240
cctgctttca cagaattatt ccagggttta tgtgtcaggg tggtgacttc acacgccata 300
atggcactgg tggcaagtcc atctatgggg agaaatttga agatgagaac ttcatcctaa 360
agcatacggg tcctggcatc ttgtccatgg caaatgctgg acccaacaca aatggttccc 420
agtttttcat ctgcactgcc aagactgagt ggttggatgg caagcatgtg gtgtttggca 480
aagtgaaaga aggcatgaat attgtggagg ccatggagcg ctttgggtcc aggaatggca 540
agaccagcaa gaagatcacc attgctgact gtggacaact cgaataagtt tgacttgtgt 600
tttatcttaa ccaccagatc attccttctg tagctcagga gagcacccct ccaccccatt 660
tgctcgcagt atcctagaat ctttgtgctc tcgctgcagt tccctttggg ttccatgttt 720
tccttgttcc ctcccatgcc tagctggatt gcagagttaa gtttatgatt atgaaataaa 780
aactaaataa caattgtcct cgtttgagtt aagagtgttg atgtaggctt tattttaagc 840
agtaatgggt tacttctgaa acatcacttg tttgcttaat tctacacagt acttagattt 900
tttttacttt ccagtcccag gaagtgtcaa tgtttgttga gtggaatatt gaaaatgtag 960
gcagcaactg ggcatggtgg ctcactgtct gtaatgtatt acctgaggca gaagaccacc 1020
tgagggtagg agtcaagatc agcctgggca acatagtgag acgctgtctc tacaaaaaat 1080
aattagcctg gcctggtggt gcatgcctag tcctagctga tctggaggct gacgtgggag 1140
gattgcttga gcctagagtg agctattatc atgccactgt acagcctggg tgttcacaga 1200
tcttgtgtct caaaggtagg cagaggcagg aaaagcaagg agccagaatt aagaggttgg 1260
gtcagtctgc agtgagttca tgcatttaga ggtgttcttc aagatgacta atgtcaaaaa 1320
ttgagacatc tgttgcggtt tttttttttt tttttccccc tggaatgcag tggcgtgatc 1380
tcagctcact gcagcctccg cctcctgggt tcaagtgatt ctagtgcctc agcctcctga 1440
gtagctggga taatgggcgt gtgccaccat gcccagctaa tttttgtatt tttagtatag 1500
atggggtttc atcattttga ccaggctggt ctcaaactct tgacctcagc tgatgcgcct 1560
gccttggcct cccaaactgc tgagattaca gatgtgagcc accgcaccct acctcatttt 1620
ctgtaacaaa gctaagcttg aacactgttg atgttcttga gggaagcata ttgggcttta 1680
ggctgtaggt caagtttata catcttaatt atggtggaat tcctatgtag agtctaaaaa 1740
gccaggtact tggtgctaca gtcagtctcc ctgcagaggg ttaaggcgca gactacctgc 1800
agtgaggagg tactgcttgt agcatataga gcctctccct agctttggtt atggaggctt 1860
tgaggttttg caaacctgac caatttaagc cataagatct ggtcaaaggg ataccettcc 1920 cactaaggac ttggtttctc aggaaattat atgtacagtg cttgctggca gttagatgtc 1980
aggacaatct aagctgagaa aaccccttct ctgcccacct taacagacct ctagggttct 2040
taacccagca atcaagtttg cctatcctag aggtggcgga tttgatcatt tggtgtgttg 2100
ggcaattttt gttttactgt ctggttcctt ctgcgtgaat taccaccacc accacttgtg 2160
catctcagtc ttgtgtgttg tctggttacg tattccctgg gtgataccat tcaatgtctt 2220
aatgtacttg tggctcagac ctgagtgcaa ggtggaaata aacatcaaac atcttttcat 2280
tatcccta 2288

<210> SEQ ID NO 48
<211> LENGTH: 2439
<212> TYPE: DNA
<213> ORGANISM: Homo sapiens

<400> SEQUENCE: 48
gagagcagcg gccgggaagg ggcggtgcgg gaggcggggt gtggggcggt agtgtgggcc 60
ctgttcctgc ccgcgcggtg ttccgcattc tgcaagcctc cggagcgcac gtcggcagtc 120
ggctccctcg ttgaccgaat caccgacctc tctccccagc tgtatttcca aaatgtcgct 180
ttctaacaag ctgacgctgg acaagctgga cgttaaaggg aagcgggtcg ttatgagagt 240
cgacttcaat gttcctatga agaacaacca gataacaaac aaccagagga ttaaggctgc 300
tgtcccaagc atcaaattct gcttggacaa tggagccaag tcggtagtcc ttatgagcca 360
cctaggccgg cctgatggtg tgcccatgcc tgacaagtac tccttagagc cagttgctgt 420
agaactcaaa tctctgctgg gcaaggatgt tctgttcttg aaggactgtg taggcccaga 480
agtggagaaa gcctgtgcca acccagctgc tgggtctgtc atcctgctgg agaacctccg 540
ctttcatgtg gaggaagaag ggaagggaaa agatgcttct gggaacaagg ttaaagccga 600
gccagccaaa atagaagctt tccgagcttc actttccaag ctaggggatg tctatgtcaa 660
tgatgctttt ggcactgctc acagagccca cagctccatg gtaggagtca atctgccaca 720
gaaggctggt gggtttttga tgaagaagga gctgaactac tttgcaaagg ccttggagag 780
cccagagcga cccttcctgg ccatcctggg cggagctaaa gttgcagaca agatccagct 840
catcaataat atgctggaca aagtcaatga gatgattatt ggtggtggaa tggcttttac 900
cttccttaag gtgctcaaca acatggagat tggcacttct ctgtttgatg aagagggagc 960
caagattgtc aaagacctaa tgtccaaagc tgagaagaat ggtgtgaaga ttaccttgcc 1020
tgttgacttt gtcactgctg acaagtttga tgagaatgcc aagactggcc aagccactgt 1080
ggcttctggc atacctgctg gctggatggg cttggactgt ggtcctgaaa gcagcaagaa 1140
gtatgctgag gctgtcactc gggctaagca gattgtgtgg aatggtcctg tgggggtatt 1200
tgaatgggaa gcttttgccc ggggaaccaa agctctcatg gatgaggtgg tgaaagccac 1260
ttctaggggc tgcatcacca tcataggtgg tggagacact gccacttgct gtgccaaatg 1320
gaacacggag gataaagtca gccatgtgag cactgggggt ggtgccagtt tggagctcct 1380
ggaaggtaaa gtccttcctg gggtggatgc tctcagcaat atttagtact ttcctgcctt 1440
ttagttcctg tgcacagccc ctaagtcaac ttagcatttt ctgcatctcc acttggcatt 1500
agctaaaacc ttccatgtca agattcagct agtggccaag agatgcagtg ccaggaaccc 1560
ttaaacagtt gcacagcatc tcagctcatc ttcactgcac cctggatttg catacattct 1620
tcaagatccc atttgaattt tttagtgact aaaccattgt gcattctaga gtgcatatat 1680
ttatattttg cctgttaaaa agaaagtgag cagtgttagc ttagttctct tttgatgtag 1740
gttattatga ttagctttgt cactgtttca ctactcagca tggaaacaag atgaaattcc 1800
atttgtaggt agtgagacaa aattgatgat ccattaagta aacaataaaa gtgtccattg 1860
aaaccgtgat tttttttttt ttcctgtcat actttgttag gaagggtgag aatagaatct 1920
tgaggaacgg atcagatgtc tatattgctg aatgcaagaa gtggggcagc agcagtggag 1980
agatgggaca attagataaa tgtccattct ttatcaaggg cctactttat ggcagacatt 2040
gtgctagtgc ttttattcta acttttattt ttatcagtta cacatgatca taatttaaaa 2100
agtcaaggct tataacaaaa aagccccagc ccattcctcc cattcaagat tcccactccc 2160
cagaggtgac cactttcaac tcttgagttt ttcaggtata tacctccatg tttctaagta 2220
atatgcttat attgttcact tctttttttt ttatttttta aagaaatcta tttcatacca 2280
tggaggaagg ctctgttcca catatatttc cacttcttca ttctctcggt atagttttgt 2340
cacaattata gattagatca aaagtctaca taactaatac agctgagcta tgtagtatgc 2400
tatgattaaa tttacttatg taaaaaaaaa aaaaaaaaa 2439

<210> SEQ ID NO 49
<211> LENGTH: 1196
<212> TYPE: DNA
<213> ORGANISM: Homo sapiens

<400> SEQUENCE: 49
cacttctgcc gcccctgttt caagggataa gaaaccctgc gacaaaacct cctccttttc 60
caagcggctg ccgaagatgg cggaggtgca ggtcctggtg cttgatggtc gaggccatct 120
cctgggccgc ctggcggcca tcgtggctaa acaggtactg ctgggccgga aggtggtggt 180
cgtacgctgt gaaggcatca acatttctgg caatttctac agaaacaagt tgaagtacct 240
ggctttcctc cgcaagcgga tgaacaccaa cccttcccga ggcccctacc acttccgggc 300
ccccagccgc atcttctggc ggaccgtgcg aggtatgctg ccccacaaaa ccaagcgagg 360
ccaggccgct ctggaccgtc tcaaggtgtt tgacggcatc ccaccgccct acgacaagaa 420
aaagcggatg gtggttcctg ctgccctcaa ggtcgtgcgt ctgaagccta caagaaagtt 480
tgcctatctg gggcgcctgg ctcacgaggt tggctggaag taccaggcag tgacagccac 540
cctggaggag aagaggaaag agaaagccaa gatccactac cggaagaaga aacagctcat 600
gaggctacgg aaacaggccg agaagaacgt ggagaagaaa attgacaaat acacagaggt 660
cctcaagacc cacggactcc tggtctgagc ccaataaaga ctgttaattc ctcatgcgtt 720
gcctgccctt cctccattgt tgccctggaa tgtacgggac ccaggggcag cagcagtcca 780
ggtgccacag gcagccctgg gacataggaa gctgggagca aggaaagggt cttagtcact 840
gcctcccgaa gttgcttgaa agcactcgga gaattgtgca ggtgtcattt atctatgacc 900
aataggaaga gcaaccagtt actatgagtg aaagggagcc agaagactga ttggagggcc 960
ctatcttgtg agtggggcat ctgttggact ttccacctgg tcatatactc tgcagctgtt 1020
agaatgtgca agcacttggg gacagcatga gcttgctgtt gtacacaggg tatttctaga 1080
agcagaaata gactgggaag atgcacaacc aaggggttac aggcatcgcc catgctcctc 1140
acctgtattt tgtaatcaga aataaattgc ttttaaagaa aaaaaaaaaa aaaaaa 1196

<210> SEQ ID NO 50
<211> LENGTH: 987
<212> TYPE: DNA
<213> ORGANISM: Homo sapiens

<400> SEQUENCE: 50
aatataagtg gaggcgtcgc gctggcgggc attcctgaag ctgacagcat tcgggccgag 60
atgtctcgct ccgtggcctt agctgtgctc gcgctactct ctctttctgg cctggaggct 120
atccagcgta ctccaaagat tcaggtttac tcacgtcatc cagcagagaa tggaaagtca 180
aatttcctga attgctatgt gtctgggttt catccatccg acattgaagt tgacttactg 240

-continued

```
aagaatggag agagaattga aaaagtggag cattcagact tgtctttcag caaggactgg    300
tctttctatc tcttgtacta cactgaattc acccccactg aaaaagatga gtatgcctgc    360
cgtgtgaacc atgtgacttt gtcacagccc aagatagtta agtgggatcg agacatgtaa    420
gcagcatcat ggaggtttga agatgccgca tttggattgg atgaattcca aattctgctt    480
gcttgctttt taatattgat atgcttatac acttacactt tatgcacaaa atgtagggtt    540
ataataatgt taacatggac atgatcttct ttataattct actttgagtg ctgtctccat    600
gtttgatgta tctgagcagg ttgctccaca ggtagctcta ggagggctgg caacttagag    660
gtggggagca gagaattctc ttatccaaca tcaacatctt ggtcagattt gaactcttca    720
atctcttgca ctcaaagctt gttaagatag ttaagcgtgc ataagttaac ttccaattta    780
catactctgc ttagaatttg ggggaaaatt tagaaatata attgacagga ttattggaaa    840
tttgttataa tgaatgaaac attttgtcat ataagattca tatttacttc ttatacattt    900
gataaagtaa ggcatggttg tggttaatct ggtttatttt tgttccacaa gttaaataaa    960
tcataaaact tgatgtgtta tctctta                                        987
```

<210> SEQ ID NO 51
<211> LENGTH: 3003
<212> TYPE: DNA
<213> ORGANISM: Homo sapiens

<400> SEQUENCE: 51

```
ctttctcctt ccccttcttc cgggctcccg tcccggctca tcacccggcc tgtggcccac     60
tcccaccgcc agctggaacc ctggggacta cgacgtccct caaaccttgc ttctaggaga    120
taaaaagaac atccagtcat ggataaaaat gagctggttc agaaggccaa actggccgag    180
caggctgagc gatatgatga catggcagcc tgcatgaagt ctgtaactga gcaaggagct    240
gaattatcca atgaggagag gaatcttctc tcagttgctt ataaaaatgt tgtaggagcc    300
cgtaggtcat cttggagggt cgtctcaagt attgaacaaa agacggaagg tgctgagaaa    360
aaacagcaga tggctcgaga atacagagag aaaattgaga cggagctaag agatatctgc    420
aatgatgtac tgtctctttt ggaaaagttc ttgatcccca atgcttcaca agcagagagc    480
aaagtcttct atttgaaaat gaaaggagat tactaccgtt acttggctga ggttgccgct    540
ggtgatgaca agaaagggat tgtcgatcag tcacaacaag cataccaaga agcttttgaa    600
atcagcaaaa aggaaatgca accaacacat cctatcagac tgggtctggc ccttaacttc    660
tctgtgttct attatgagat tctgaactcc ccagagaaag cctgctctct tgcaaagaca    720
gcttttgatg aagccattgc tgaacttgat acattaagtg aagagtcata caaagacagc    780
acgctaataa tgcaattact gagagacaac ttgacattgt ggacatcgga tacccaagga    840
gacgaagctg aagcaggaga aggaggggaa aattaaccgg ccttccaact tttgtctgcc    900
tcattctaaa atttacacag tagaccattt gtcatccatg ctgtcccaca aatagttttt    960
tgtttacgat ttatgacagg tttatgttac ttctatttga atttctatat ttcccatgtg   1020
gtttttatgt ttaatattag gggagtagag ccagttaaca tttagggagt tatctgtttt   1080
catcttgagg tggccaatat ggggatgtgg aatttttata caagttataa gtgtttggca   1140
tagtactttt ggtacattgt ggcttcaaaa gggccagtgt aaaactgctt ccatgtctaa   1200
gcaaagaaaa ctgcctacat actggtttgt cctggcgggg aataaaaggg atcattggtt   1260
ccagtcacag gtgtagtaat tgtgggtact ttaaggtttg gagcacttac aaggctgtgg   1320
tagaatcata ccccatggat accacatatt aaaccatgta tatctgtgga atactcaatg   1380
```

```
tgtacacctt tgactacagc tgcagaagtg ttcctttaga caaagttgtg acccatttta   1440

ctctggataa gggcagaaac ggttcacatt ccattatttg taaagttacc tgctgttagc   1500

tttcattatt tttgctacac tcattttatt tgtatttaaa tgttttaggc aacctaagaa   1560

caaatgtaaa agtaaagatg caggaaaaat gaattgcttg gtattcatta cttcatgtat   1620

atcaagcaca gcagtaaaac aaaaacccat gtatttaact ttttttagg atttttgctt    1680

ttgtgatttt ttttttttg atacttgcct aacatgcatg tgctgtaaaa atagttaaca    1740

gggaaataac ttgagatgat ggctagcttt gtttaatgtc ttatgaaatt ttcatgaaca   1800

atccaagcat aattgttaag aacacgtgta ttaaattcat gtaagtggaa taaaagtttt   1860

atgaatggac ttttcaacta ctttctctac agcttttcat gtaaattagt cttggttctg   1920

aaacttctct aaaggaaatt gtacattttt tgaaatttat tccttattcc ctcttggcag   1980

ctaatgggct cttaccaagt ttaaacacaa aatttatcat aacaaaaata ctactaatat   2040

aactactgtt tccatgtccc atgatcccct ctcttcctcc ccaccctgaa aaaaatgagt   2100

tcctattttt tctgggagag ggggggattg attagaaaaa aatgtagtgt gttccattta   2160

aaattttggc atatggcatt ttctaactta ggaagccaca atgttcttgg cccatcatga   2220

cattgggtag cattaactgt aagttttgtg cttccaaatc actttttggt ttttaagaat   2280

ttcttgatac tcttatagcc tgccttcaat tttgatcctt tattctttct atttgtcagg   2340

tgcacaagat taccttcctg ttttagcctt ctgtcttgtc accaaccatt cttacttggt   2400

ggccatgtac ttggaaaaag gccgcatgat ctttctggct ccactcagtg tctaaggcac   2460

cctgcttcct ttgcttgcat cccacagact atttccctca tcctatttac tgcagcaaat   2520

ctctccttag ttgatgagac tgtgtttatc tccctttaaa accctaccta tcctgaatgg   2580

tctgtcattg tctgccttta aaatccttcc tctttcttcc tcctctattc tctaaataat   2640

gatggggcta agttataccc aaagctcact ttacaaaata tttcctcagt actttgcaga   2700

aaacaccaaa caaaaatgcc attttaaaaa aggtgtattt tttcttttag aatgtaagct   2760

cctcaagagc agggacaatg ttttctgtat gttctattgt gcctagtaca ctgtaaatgc   2820

tcaataaata ttgatgatgg gaggcagtga gtcttgatga taagggtgag aaactgaaat   2880

cccaaacact gttttgttgc ttgttttatt atgacctcag attaaattgg gaaatattgg   2940

cccttttgaa taattgtccc aaatattaca ttcaaataaa agtgcaatgg agaaaaaaaa   3000

aaa                                                                 3003
```

<210> SEQ ID NO 52
<211> LENGTH: 2803
<212> TYPE: DNA
<213> ORGANISM: Homo sapiens

<400> SEQUENCE: 52

```
actgcagccc cgctcgactc cggcgtggtg cgcaggcgcg gtatcccccc tcccccgcca     60

gctcgacccc ggtgtggtgc gcaggcgcag tctgcgcagg gactggcggg actgcgcggc    120

ggcaacagca gacatgtcgg gggtccgggg cctgtcgcgg ctgctgagcg ctcggcgcct    180

ggcgctggcc aaggcgtggc caacagtgtt gcaaacagga acccgaggtt ttcacttcac    240

tgttgatggg aacaagaggg catctgctaa agtttcagat tccatttctg ctcagtatcc    300

agtagtggat catgaatttg atgcagtggt ggtaggcgct ggaggggcag gcttgcgagc    360

tgcatttggc ctttctgagg cagggtttaa tacagcatgt gttaccaagc tgtttcctac    420
```

```
caggtcacac actgttgcag cacagggagg aatcaatgct gctctgggga acatggagga    480
ggacaactgg aggtggcatt tctacgacac cgtgaagggc tccgactggc tgggggacca    540
ggatgccatc cactacatga cggagcaggc cccgccgcc gtggtcgagc tagaaaatta    600
tggcatgccg tttagcagaa ctgaagatgg gaagatttat cagcgtgcat ttggtggaca    660
gagcctcaag tttggaaagg gcgggcaggc ccatcggtgc tgctgtgtgg ctgatcggac    720
tggccactcg ctattgcaca ccttatatgg aaggtctctg cgatatgata ccagctattt    780
tgtggagtat tttgccttgg atctcctgat ggagaatggg gagtgccgtg gtgtcatcgc    840
actgtgcata gaggacgggt ccatccatcg cataagagca aagaacactg ttgttgccac    900
aggaggctac gggcgcacct acttcagctg cacgtctgcc cacaccagca ctggcgacgg    960
cacggccatg atcaccaggg caggccttcc ttgccaggac ctagagtttg ttcagttcca   1020
ccctacaggc atatatggtg ctggttgtct cattacggaa ggatgtcgtg gagagggagg   1080
cattctcatt aacagtcaag gcgaaaggtt tatggagcga tacgcccctg tcgcgaagga   1140
cctggcgtct agagatgtgg tgtctcggtc catgactctg gagatccgag aaggaagagg   1200
ctgtggccct gagaaagatc acgtctacct gcagctgcac cacctacctc cagagcagct   1260
ggccacgcgc ctgcctggca tttcagagac agccatgatc ttcgctggcg tggacgtcac   1320
gaaggagccg atccctgtcc tccccaccgt gcattataac atgggcggca ttcccaccaa   1380
ctacaagggg caggtcctga ggcacgtgaa tggccaggat cagattgtgc ccggcctgta   1440
cgcctgtggg gaggccgcct gtgcctcggt acatggtgcc aaccgcctcg ggcaaactc   1500
gctcttggac ctggttgtct ttggtcgggc atgtgccctg agcatcgaag agtcatgcag   1560
gcctggagat aaagtccctc caattaaacc aaacgctggg gaagaatctg tcatgaatct   1620
tgacaaattg agatttgctg atggaagcat aagaacatcg gaactgcgac tcagcatgca   1680
gaagtcaatg caaaatcatg ctgccgtgtt ccgtgtggga agcgtgttgc aagaaggttg   1740
tgggaaaatc agcaagctct atggagacct aaagcacctg aagacgttcg accggggaat   1800
ggtctggaac acggacctgg tggagaccct ggagctgcag aacctgatgc tgtgtgcgct   1860
gcagaccatc tacggagcag aggcacggaa ggagtcacgg ggcgcgcatg ccagggaaga   1920
ctacaaggtg cggattgatg agtacgatta ctccaagccc atccaggggc aacagaagaa   1980
gccctttgag gagcactgga ggaagcacac cctgtcctat gtggacgttg gcactgggaa   2040
ggtcactctg gaatatagac ccgtgatcga caaaactttg aacgaggctg actgtgccac   2100
cgtcccgcca gccattcgct cctactgatg agacaagatg tggtgatgac agaatcagct   2160
tttgtaatta tgtataatag ctcatgcatg tgtccatgtc ataactgtct tcatacgctt   2220
ctgcactctg gggaagaagg agtacattga agggagattg gcacctagtg gctgggagct   2280
tgccaggaac ccagtggcca gggagcgtgg cacttacctt tgtcccttgc ttcattcttg   2340
tgagatgata aaactgggca cagctcttaa ataaaatata aatgaacaaa ctttctttta   2400
tttccaaatc catttgaaat attttactgt tgtgacttta gtcatatttg ttgacctaaa   2460
aatcaaatgt aatctttgta ttgtgttaca tcaaaatcca gatattttgt atagtttctt   2520
ttttcttttt cttttctttt tttttttga gacaggatcg gtgcagtagt acaatcacag   2580
ctcactgcag cctcaaactc ctgggcagct caggtgatct tcctgactca gccttctgag   2640
tagttggggc tacaggtgtg caccaccatg cccagctcat ttattttgta attgtaggga   2700
cagggtctca ctgtgttgcc taggctggtc tcaagtgatc ctccctcctt ggcctcccaa   2760
ggtgctggaa ttataggtgt gaacaaacca aaaaaaaaaa aaa                     2803
```

<210> SEQ ID NO 53
<211> LENGTH: 1435
<212> TYPE: DNA
<213> ORGANISM: Homo sapiens

<400> SEQUENCE: 53
ggcggggcct gcttctcctc agcttcaggc ggctgcgacg agccctcagg cgaacctctc 60
ggctttcccg cgcggcgccg cctcttgctg cgcctccgcc tcctcctctg ctccgccacc 120
ggcttcctcc tcctgagcag tcagcccgcg cgccggccgg ctccgttatg gcgacccgca 180
gccctggcgt cgtgattagt gatgatgaac caggttatga ccttgattta ttttgcatac 240
ctaatcatta tgctgaggat ttggaaaggg tgtttattcc tcatggacta attatggaca 300
ggactgaacg tcttgctcga gatgtgatga aggagatggg aggccatcac attgtagccc 360
tctgtgtgct caagggggc tataaattct ttgctgacct gctggattac atcaaagcac 420
tgaatagaaa tagtgataga tccattccta tgactgtaga ttttatcaga ctgaagagct 480
attgtaatga ccagtcaaca ggggacataa aagtaattgg tggagatgat ctctcaactt 540
taactggaaa gaatgtcttg attgtggaag atataattga cactggcaaa acaatgcaga 600
ctttgctttc cttggtcagg cagtataatc caaagatggt caaggtcgca agcttgctgg 660
tgaaaaggac cccacgaagt gttggatata agccagactt tgttggattt gaaattccag 720
acaagtttgt tgtaggatat gcccttgact ataatgaata cttcagggat ttgaatcatg 780
tttgtgtcat tagtgaaact ggaaaagcaa aatacaaagc ctaagatgag agttcaagtt 840
gagtttggaa acatctggag tcctattgac atcgccagta aaattatcaa tgttctagtt 900
ctgtggccat ctgcttagta gagctttttg catgtatctt ctaagaattt tatctgtttt 960
gtactttaga aatgtcagtt gctgcattcc taaactgttt atttgcacta tgagcctata 1020
gactatcagt tccctttggg cggattgttg tttaacttgt aaatgaaaaa attctcttaa 1080
accacagcac tattgagtga aacattgaac tcatatctgt aagaaataaa gagaagatat 1140
attagttttt taattggtat tttaattttt atatatgcag gaaagaatag aagtgattga 1200
atattgttaa ttataccacc gtgtgttaga aaagtaagaa gcagtcaatt ttcacatcaa 1260
agacagcatc taagaagttt tgttctgtcc tggaattatt ttagtagtgt ttcagtaatg 1320
ttgactgtat tttccaactt gttcaaatta ttaccagtga atctttgtca gcagttccct 1380
tttaaatgca aatcaataaa ttcccaaaaa tttaaaaaaa aaaaaaaaaa aaaaa 1435

<210> SEQ ID NO 54
<211> LENGTH: 4476
<212> TYPE: DNA
<213> ORGANISM: Homo sapiens

<400> SEQUENCE: 54
agcagagaga acacacgtcc ttgcggaagt gacggcagtt ccgagtccag tgggggcggt 60
gggagcgatg agggtctgag acggtgggag cggttgtgtg aagatggaga cattccatac 120
accaagcttg ggtgatgagg aatttgaaat cccacctatc tccttggatt ctgatccctc 180
attggctgtc tcagatgtgg ttggccactt tgatgacctg gcagaccctt cctcttcaca 240
ggatggcagt tttttcagccc agtatggggt ccagacattg gacatgcctg tgggcatgac 300
ccatggcttg atggagcagg gcggggggct cctgagtggg ggcttgacca tggacttgga 360
ccactctata ggaactcagt atagtgccaa cccacctgtt acaattgatg taccaatgac 420

-continued

```
agacatgaca tctggcttga tggggcatag ccagttgacc accattgatc agtcagaact    480
gagttcccag ctgggtttga gcctaggggg tggcaccatc ctgccacctg cccagtcacc    540
tgaagatcgt ctttcaacca ccccttcacc tactagttca cttcacgagg atggtgttga    600
ggatttccgg aggcaacttc ccagccagaa gacagtcgtg gtggaagcag ggaaaaagca    660
gaaggcccca aagaagagaa aaaagaaaga tcctaatgaa cctcagaaac cagtttcagc    720
atatgcttta ttctttcgtg atacacaggc tgccatcaag ggacagaatc ctaatgccac    780
ttttggtgag gtttcaaaaa ttgtggcctc catgtgggat agtcttggag aggagcaaaa    840
acaggtatat aagaggaaaa ctgaggctgc caagaaagag tatctgaagg cactggctgc    900
ttacaaagac aaccaggagt gtcaggccac tgtggaaaca gtggaattgg atccagcacc    960
accatcacaa actccttctc cacctcctat ggctactgtt gacccagcat ctccagcacc   1020
agcttcaata gagcccctg ccctgtcccc atccattgtt gttaactcca ccctttcatc   1080
ctatgtggca aaccaggcat cttctggagc tgggggtcag cccaatatca ccaagttgat   1140
tattaccaaa caaatgttgc cctcttctat tactatgtct caaggaggga tggttactgt   1200
tatcccagcc acagtggtga cctcccgggg gctccaacta ggccaaacca gtacagctac   1260
tatccagccc agtcaacaag cccagattgt cactcggtca gtgttgcagg cagcagcagc   1320
tgctgctgct gctgcttcta tgcaactgcc tccaccccga ctacagcccc ctccattaca   1380
acagatgcca cagcccccga ctcagcagca agttaccatt ctgcagcagc ctcctccact   1440
ccaggccatg caacagcctc cacctcagaa agttcgaatc aatttacagc aacagcctcc   1500
tcctctgcag atcaagagtg tgcctctacc cactttgaaa atgcagacta ccttagtccc   1560
accaactgtg gaaagtagtc ctgagcggcc tatgaacaac agccctgagg cccatacagt   1620
ggaggcacct tctcctgaga ctatctgtga gatgatcaca gatgtagttc ctgaggttga   1680
gtctccttct cagatggatg ttgaattggt gagtgggtct cctgtggcac tctcacccca   1740
gcctcgatgt gtgaggtctg gttgtgagaa ccctcccatt gtgagtaagg actgggacaa   1800
tgaatactgc agcaatgagt gtgtggtgaa gcactgcagg gatgtattct tggcctgggt   1860
agcctctaga aattcaaaca cagtggtgtt tgtgaaatag tccttcctgt tctccaagcc   1920
agtgaagagt tatctgctgg gaaagtgtcc aagagcctgt tttgaaaca caagctgggc   1980
ttctggtagt gcctcatcac aacccatgat ggctgttcat gtttcacccc ttttcttcct   2040
tcagcagagg ccaggctatg gagcagggcc actgaatttg ctgtaatctg gagatgcttt   2100
ttactttcaa ccataagcgg taatagcaga ggaaagggtg aagggagtct gggcaagcaa   2160
agcatagaga tggtggggtg gtggtggggt tgaagaaact tgttggtata attgtcatag   2220
gacttgccta aaatattatt aaaattacgg gagtgtactc agctttgagc ctaggagaaa   2280
atgccactgt gtgcatccat tttaaagggt tccctcataa aaaaatgtta ttccccatta   2340
tcacatcagt acactgcttt gaaaacaaaa cttttcaaca tgggcatact gggctacatg   2400
gaaaatgaca tcacccagga gtgatttctc tttatatata ttatttctgc agttaccatc   2460
cttatctgag ttatcacagt tcatgaatct aagaggcgga actctacatc attagtaaga   2520
ggttccacca aagtctaaag ttgtattcac ttgtgtttga tgaactatct ttaaaagacc   2580
ataggtctat cattatttct tagacataat ctaaagaaaa acagactaga gaagccacct   2640
ggttgtaaca gaataagcag aagtttacag catgatagtc caagtggtga taactttaaa   2700
taaaactcaa atttttactg tttgtagaca ggaatgctgt cctagagaac ctcctcctca   2760
accagctacg tacatagttt tatcctatgc attcctgttt tctgtgtgtt ttttgttttt   2820
```

-continued

```
ttttttttt ttttttttg agacagagtc tcgctctgtc acccaggctg gagtgcagtg   2880

gtgcgacctc agctcactga aacctctgcc tcccgggttc aagcgattct cctgcatcag   2940

cctcccgagt agctaggatt acaggcgccc gccactacgc ccagctaatt tgtggtattt   3000

ttagtagaga cagggtttca ccatgttggc caggctggtc tcgaactcct gacctcatga   3060

tccgcccgcc ttgacctccc aaagtgctgg gattacaggc atgagccacc gcacccagcc   3120

tgcattcctg tttttttaat ggttttggag ggtagcagta gagatggggt ctcactatgt   3180

tgcccagtct agtcttgaac tcctgggcta cagttaccct cctacctcgg cttcccaaag   3240

tgctcggatt acaggtgtga gccactgtgc ctagcctata atgatcattt taatgtttcc   3300

catgcactca tttagtttga accttcacag caacccaatg aggtaatact cccatttcac   3360

atataatact gagagatgag ttgcacaaga ttatacactg ttaagtagca gagccagaat   3420

ggacttcaga atcccaacta caatacaaat gtttatttaa ataaagaaga aagctattgt   3480

acaaatatca ctcttcaggt ttagcttaca gagccatggc tatggattct tagctctgta   3540

aggaagtgct tctataaatt cttaggttta gagatgatac catctgggta cctttgcttg   3600

aaccgtgcaa ccacatctgg gtctagtagg tggatcccat ccagttggtt tccaagggtg   3660

atcctgaaac agtgtaaaag gaggggcaaa ccagaaatcc tggaattaga gggtttaata   3720

ttgttaaaaa atgcatacca aatgaagact gcctatcatc atatcaaata tgccaattct   3780

aaaaagagct taacattaga atagtatatg gtagaattac tagttcagaa ttggcataga   3840

ttctggtgtt aaaatagact ggatctgtat tatctgaggg ttagtaacta atgcttagcc   3900

aggcctgctt cacagagttg ctaccaggga gtattctttg gataagcaaa atgctagcag   3960

catgtgtttt aagctctgtt aaggggtgaa agatgtaatt attgacagat taaatagata   4020

acttcgtaac caccaggggg cagattcaat acatcacaga atggctgagg aagatccttg   4080

ggttgtgaag agagtagaaa ccctagggag cagtgctttt gggtcctaga acctgttgag   4140

tttctaatga atatttgtag aatctcataa aacagtttaa atacaagctt aagtggctta   4200

tgaatcctgt gaagctcatt tatggactag tgtaaaacaa tgtgaagctc tactaagttc   4260

tgtccttaat cataaataat agccccttga ggactagcct gttctctggt caccttacca   4320

gttgggttgc acattgtgtg gtcgtccaaa taactcaatc ttgcgagtgc caggagatag   4380

tctttcaatc atgccataga tttcatctgg tttatgactg gtggaacgaa cctaggaaat   4440

aaaaactagc tgctttttaa gttacacaag aaaaaa                             4476
```

CHEMICAL COMPOSITIONS AND METHODS OF USE

CROSS-REFERENCE TO RELATED APPLICATIONS

This application is a Continuation of U.S. patent application Ser. No. 16/039,041, filed on Jul. 18, 2018, which claims the benefit of and priority to U.S. Provisional Application No. 62/535,419, filed Jul. 21, 2017. The contents of each of the aforementioned patent applications are hereby incorporated by reference in their entireties for all purposes.

INCORPORATION BY REFERENCE OF SEQUENCE LISTING

The instant application contains a Sequence Listing which has been submitted in ASCII format via EFS-Web and is hereby incorporated by reference in its entirety. Sai ASCII copy, created on Sep. 28, 2021, is named "LBIO-002_C01US_SeqList.txt", and is about 283,182 bytes in size.

FIELD OF THE INVENTION

The present invention relates to plasma cell dyscrasia detection.

BACKGROUND OF THE INVENTION

Multiple myeloma is an incurable hematological malignancy of end-stage B-lineage or plasma cells. This clonal plasma cell malignancy accounts for ~2% of all cancer cases and approximately 10% of hematologic malignancies. It is the third most common B cell malignancy after diffuse B-cell lymphoma and chronic lymphocytic leukemia. The incidence is estimated at (~1/100,000 incidence in the US). In 2017, more than 12,500 deaths resulted from the disease. Patients older than 65 years account for >80% of those diagnosed; there is a twofold increased incidence in blacks compared with whites. There has been a significant rise in the incidence of the disease over the last fifty years. Moreover, overall survival has improved in the last two decades from a median of ~3.5 years to ~6 years with an average 5-year survival of ~50%. This is attributed to innovative treatments and the widespread use of proteasome inhibitors and immunomodulatory drugs but many patients exhibit low progression-free survival rates and have a poor overall survival. This reflects tumor heterogeneity, drug resistance and the immunosuppressive nature of the tumor within the osteo-microenvironment.

Multiple myelomas typically progress from asymptomatic precursor stages (monoclonal gammopathy of undetermined significance: MGUS) and smoldering multiple myeloma (SMM) to frank disease. Some exhibit rapid progression to MM, whilst others have life-long indolent disease. The heterogeneity and genomic complexity of the disease, and particularly intraclonal heterogeneity, underpins the heterogeneous evolution of disease, responses to therapy as well as progression after "successful" treatment.

Multiple myelomas exhibit notable inter- and intrapatient heterogeneity. This is reflected in copy number variations including hyperdiploidy and focal or Chromosome (Chr) arm gains or amplifications e.g., Chr 1q or loss e.g., Chr 17p, and translocations involving the immunoglobulin heavy chain locus on chromosome 14. These are all hallmarks of multiple myeloma pathogenesis. Hyperdiploidy and chromosomal translocations are the most common genetic aberrations and both are considered primary events. Secondary events that are associated with disease progression include activating translocations e.g., in the MYC oncogene, but these occur in subsets of patients. For example, a MYC translocations either alone, or in conjunction with Chr1q amplification identifies a poor prognostic subtype in hyperdiploid myeloma. While useful, cytogenetic approaches become problematic when two markers predicting opposing outcomes coexist in the same patient. They are also only of modest assistance in indicating appropriate therapeutic strategies and none of them provide predictive information.

Standard blood-based biomarkers e.g., lactate dehydrogenase, albumin or (32 microglobulin (prognostic markers) or serum free light chain (FLC) assays (for disease monitoring) while important in diagnosis and management, are affected by numerous factors including renal failure and other comorbidities or by the cytogenetic profile of an individual disease. They do not measure or encompass the biologic determinants of multiple myeloma.

A number of gene expression assays have been developed from isolated plasma cells. These have involved isolating transformed B-cells from bone marrow aspirates or capturing CD138-positive cells from blood and then undertaking transcriptome-based arrays. These studies have identified gene expression profiles in MM cells that identify high risk patients. GEP70 (70 genes, 30% located at the prognostic Chr1 loci) is a prognostic; CTNI is a multigene centromere amplification-associated prognostic signature; IFM15 includes 15 genes linked to control of the cell cycle (prognostic); HZDC (97 genes—linked to cell death)—prognostic; the PI signature (50 proliferation-associated genes)—prognostic; a signature derived from myeloma cell lines (HMCL—248 genes—"high risk signature"); EMC92 is a 92-gene prognostic signature; CINGEC—a measure of chromosome instability (160 genes—prognostic) and a 17 gene set that may identify patients at risk of early relapse. A number of these signatures have identified the same genes or pathways of activation; all of them require isolation of plasma cells; all require undertaking gene expression array studies. The prognostic utility of these signatures either alone, in combination with other prognostic gene expression signatures or staging systems, have been demonstrated but they function poorly for defining minimal residual disease and do not provide predictive value.

The complex nature of cancer and therapeutic responsiveness comprises a series of "hallmarks", that include canonical pathways, e.g., RAS and NFκB pathway activation, as well as other features e.g., response to immunotherapy etc. For example, the mutational landscape of newly diagnosed multiple myeloma is dominated by mutations in the RAS (43%) and NFκB (17%) pathways. These are not prognostic but because they can be therapeutically targeted, may be predictive. Identifying prognostic and predictive blood gene signatures without the requirement for isolating plasma cells or the use of bone marrow aspirates therefore is an attractive liquid biopsy approach for this disease.

Recently, such an approach (the NETest) has been developed for tumors with a neuroendocrine phenotype. This blood-based 51-specific mRNA target assay does not require isolation of a specific population of target cells. Gene expression measurements in whole blood correlates with tissue levels and therefore provide direct information about the tumor, its pathophysiology and its state of evolution from stability to progression. This functions as a diagnostic tool and as a surrogate marker of neuroendocrine tumor behavior. Expression of all genes is prognostic; while a subset of genes, those involved in metabolism and the RAS/RAF pathway, predict the response to peptide receptor radiotherapy for this tumor type.

For myelomas, there are no whole blood-derived transcript biomarker panel that functions as a diagnostic or as a prognostic for disease recurrence. A biomarker that can be used to determine minimal residual disease and identify those who will relapse is currently lacking. Moreover, early detection of changes in clonality or the identification of molecular markers of poor prognosis are required.

SUMMARY OF THE INVENTION

Among other things, disclosed herein is a 32-gene expression tool for plasma cell dyscrasias like MGUS and myeloma. It can have high sensitivity and specificity (>95%) for the detection of a plasma cell dyscrasia and can differentiate minimal residual disease from progressive, active disease. In addition, it can detect patients who are no longer responding to a therapy. Patient clinical status (newly diagnosed, stable/remission or relapsed/refractory) can be predicted with an overall accuracy of >90%.

One aspect of the present disclosure relates to a method for detecting a plasma cell dyscrasia in a subject in need thereof, comprising: (a) determining the expression level of at least 32 biomarkers from a test sample from the subject by contacting the test sample with a plurality of agents specific to detect the expression of the at least 32 biomarkers, wherein the at least 32 biomarkers comprise ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, UBE2J1, and at least one housekeeping gene; (b) normalizing the expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2JI to the expression level of the at least one housekeeping gene, thereby obtaining a normalized expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1; (c) inputting each normalized expression level into an algorithm to generate a score; (d) comparing the score with a first predetermined cutoff value; and (e) producing a report, wherein the report identifies the presence of a plasma cell dyscrasia in the subject when the score is equal to or greater than the first predetermined cutoff value or determining the absence of a plasma cell dyscrasia in the subject when the score is below the first predetermined cutoff value, wherein the first predetermined cutoff value is 20 on a scale of 0 to 100.

In some embodiments, the method further comprises treating the subject identified as having a plasma cell dyscrasia with drug therapy.

In some embodiments, the first predetermined cutoff value is derived from a plurality of reference samples obtained from subjects free of a neoplastic disease. The reference sample can be blood, serum, plasma, or a non-neoplastic tissue.

Another aspect of the present disclosure relates to a method for determining whether a plasma cell dyscrasia in a subject is stable or progressive, comprising: (a) determining the expression level of at least 32 biomarkers from a test sample from the subject by contacting the test sample with a plurality of agents specific to detect the expression of the at least 32 biomarkers, wherein the at least 32 biomarkers comprise ASXL1, BHLHE40, BTG2, COPA, FBXW7, GNA13, IL8, JMJD1C, LARS2, MALAT1, MBNL1, MCL1, NFKBIZ (2 splice variants), NR4A1(2 splice variants), PDE4B, P1AS2, PRKAA1 (2 splice variants), SCYL2(2 splice variants), SMARCD2, SP1 (2 splice variants), SRSF5, TAGAP, TANK, TLE4, TSC22D3, UBE2J1, and at least one housekeeping gene; (b) normalizing the expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1 to the expression level of the at least one housekeeping gene, thereby obtaining a normalized expression level of each of ASXL1, BHLHE40, BTG2, COPA, FBXW7, GNA13, IL8, JMJD1C LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1; (c) inputting each normalized expression level into an algorithm to generate a score; (d) comparing the score with a second predetermined cutoff value; and (e) producing a report, wherein the report identifies that the plasma cell dyscrasia is progressive when the score is equal to or greater than the second predetermined cutoff value or identifies that the plasma cell dyscrasia is stable when the score is below the second predetermined cutoff value, wherein the second predetermined cutoff value is 40 on a scale of 0 to 100.

Another aspect of the present disclosure relates to a method for determining a risk of disease relapse in a subject having a plasma cell dyscrasia, comprising: (a) determining the expression level of at least 32 biomarkers from a test sample from the subject after treatment by contacting the test sample with a plurality of agents specific to detect the expression of the at least 32 biomarkers, wherein the at least 32 biomarkers comprise ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, UBE2J1, and at least one housekeeping gene; (b) normalizing the expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1 to the expression level of the at least one housekeeping gene, thereby obtaining a normalized expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1; (c) inputting each normalized expression level into an algorithm to generate a score; (d)

comparing the score with a third predetermined cutoff value; and (e) producing a report, wherein the report identifies that the subject has a high risk of disease relapse when the score is equal to or greater than the third predetermined cutoff value or identifies that the subject has a low risk of disease relapse when the score is below the third predetermined cutoff value, wherein the third predetermined cutoff value is 40 on a scale of 0 to 100.

Yet another aspect of the present disclosure relates to a method for determining a response by a subject having a plasma cell dyscrasia to a therapy, comprising: (a) determining a first expression level of at least 31 biomarkers from a first test sample from the subject at a first time point by contacting the first test sample with a plurality of agents specific to detect the expression of the at least 31 biomarkers, wherein the at least 31 biomarkers comprise ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1; (b) determining a second expression level of the at least 31 biomarkers from a second test sample from the subject at a second time point by contacting the second test sample with a plurality of agents specific to detect the expression of the at least 31 biomarkers, wherein the second time point is after the first time point and after the administration of the therapy to the subject; (c) comparing the first expression level with the second expression level; and (d) producing a report, wherein the report identifies that the subject is responsive to the therapy when the second expression level is significantly decreased as compared to the first expression level.

In some embodiments, the first time point is prior to the administration of the therapy to the subject. In some embodiments, the first time point is after the administration of the therapy to the subject. In some embodiments, the therapy comprises a targeted therapy (e.g., a proteasome inhibitor).

In some embodiments of any one of the above aspects, the plasma cell dyscrasia is MGUS or myeloma.

In some embodiments of any one of the above aspects, the at least one housekeeping gene is selected from the group consisting of ALG9, SEPN, YWHAQ, VPS37A, PRRC2B, DOPEY2, NDUFB11, ND4, MRPL19, PSMC4, SF3A1, PUM1, ACTB, GAPD, GUSB, RPLP0, TFRC, MORF4L1, 18S, PPIA, PGK1, RPL13A, B2M, YWHAZ, SDHA, HPRT1, TOX4, and TPT1.

In some embodiments of any one of the above aspects, the method can have a specificity, sensitivity, and/or accuracy of at least 75%, 80%, 85%, 90%, 91%, 92%, 93%, 94%, 95%, 96%, 97%, 98%, or 99%. In some embodiments of any one of the above aspects, the method has a sensitivity of greater than 90%. In some embodiments of any one of the above aspects, the method has a specificity of greater than 90%.

In some embodiments of any one of the above aspects, at least one of the at least 32 biomarkers is RNA, cDNA, or protein. When the biomarker is RNA, the RNA can be reverse transcribed to produce cDNA, and the produced cDNA expression level is detected. In some embodiments of any one of the above aspects, the expression level of the biomarker is detected by forming a complex between the biomarker and a labeled probe or primer. When the biomarker is RNA or cDNA, the RNA or cDNA can be detected by forming a complex between the RNA or cDNA and a labeled nucleic acid probe or primer. When the biomarker is protein, the protein can be detected by forming a complex between the protein and a labeled antibody. The label can be a fluorescent label.

In some embodiments of any one of the above aspects, the test sample is blood, serum, plasma, or a neoplastic tissue. In some embodiments, the reference sample is blood, serum, plasma, or a non-neoplastic tissue.

In some embodiments of any one of the above aspects, the subject in need thereof is a subject diagnosed with a plasma cell dyscrasia, a subject having at least one plasma cell dyscrasia symptom, or a subject have a predisposition or familial history for developing a plasma cell dyscrasia. In some embodiments, the subject is a human.

In some embodiments of any one of the above aspects, the algorithm is XGB, RF, glmnet, cforest, CART, treebag, knn, nnet, SVM-radial, SVM-linear, NB, NNET, mlp, or logistic regression modelling.

BRIEF DESCRIPTION OF THE DRAWINGS

FIG. 2A is a graph showing that the area under the curve (AUC) was 0.99±0.005 ($p<0.0001$) for differentiating between myeloma (n=57) and controls (n=23). FIG. 2B is a graph showing that the metrics for MelanomX as a diagnostic has sensitivity >95%, specificity 100%, PPV 100%, NPV 88.5%. The overall accuracy was 96% in Test Set I.

FIG. 3A is a graph showing that MGUS patients (n=18) exhibited significantly higher (39±9%, $p<0.0001$) scores than controls. Control levels were 12±8%. FIG. 3B is a graph showing that the AUC for differentiating MGUS from controls was 0.97±0.01 ($p<0.0001$).

FIG. 4A is a graph showing that newly diagnosed patients (n=53) exhibited significantly higher (75±25; $p<0.0001$) scores than in those with clinically stable disease (n=56; 31±20). Patients with refractory disease (n=26) also presented with higher scores (92±17; $p<0.0001$ vs. stable disease). FIG. 4B is a graph showing that the AUC for differentiating stable from refractory disease was 0.97±0.03 ($p<0.0001$).

FIG. 5A is a graph showing that the mean MyelomX score in multiple myelomas (n=81) was significantly higher (47±14, $p<0.0001$) than the control group (n=155; 12±8). FIG. 5B is a graph showing that the AUC was 0.97±0.01 ($p<0.0001$) for differentiating between myeloma and controls. FIG. 5C is a graph showing that the metrics for MelanomX as a diagnostic (using 20 as a cut-off)

has sensitivity 97.5%, specificity 93.6%, PPV 88.8%, NPV 98.6%. The overall accuracy was 94% in Test Set II.

Figure 6:
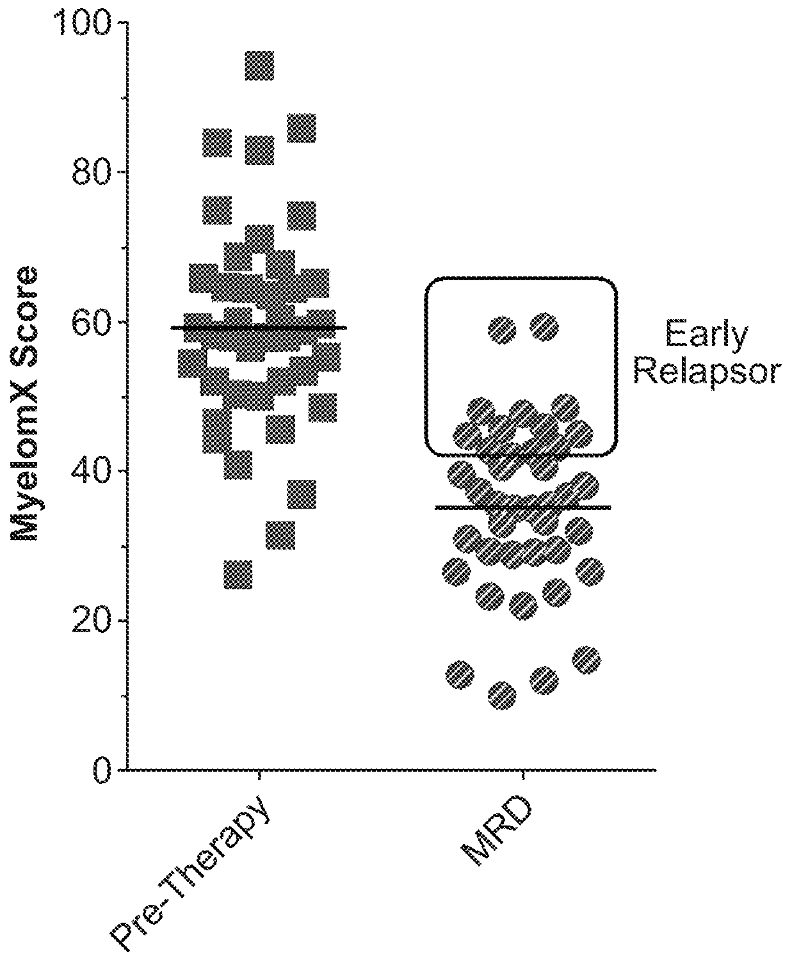

FIG. 6 is a graph showing the effect of therapy on MelanomX. Therapy significantly ($p<0.0001$) decreased the score from 59±14 (pre-therapy) to 35±12 in 40 patients. Ten patients all with high scores (>40) relapsed at an early time point (within one year).

Figure 7:
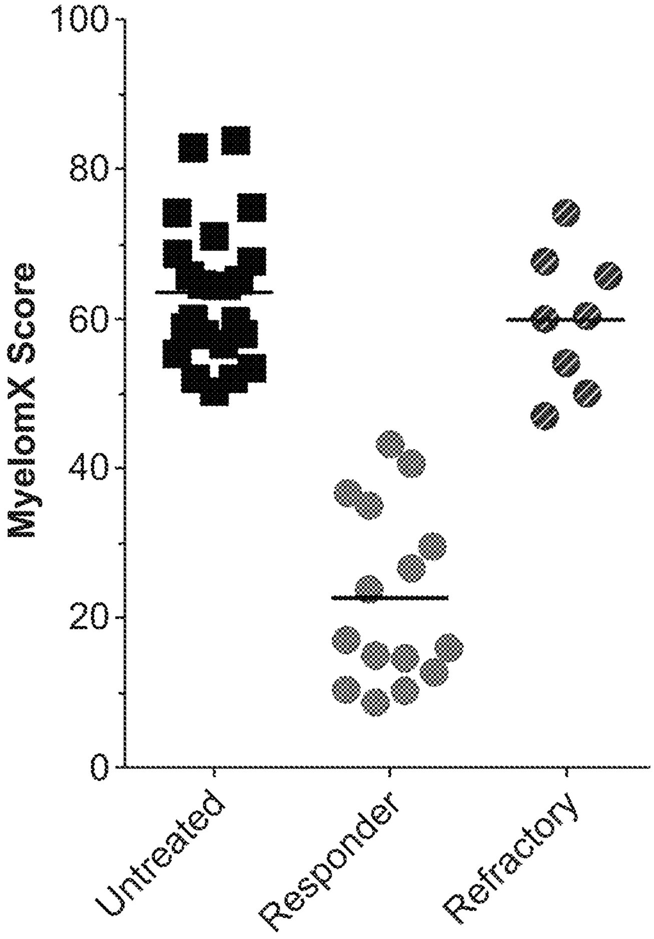

FIG. 7 is a graph showing the effect of 3 months bortemozib therapy on MelanomX. Therapy significantly ($p<0.0001$) decreased the score from 64±9 (pre-therapy) to 23±12 in 15 patients who responded to therapy. Eight patients who were refractory exhibited elevated scores (60±9, p=NS vs. pre-treatment).

Figure 8A:
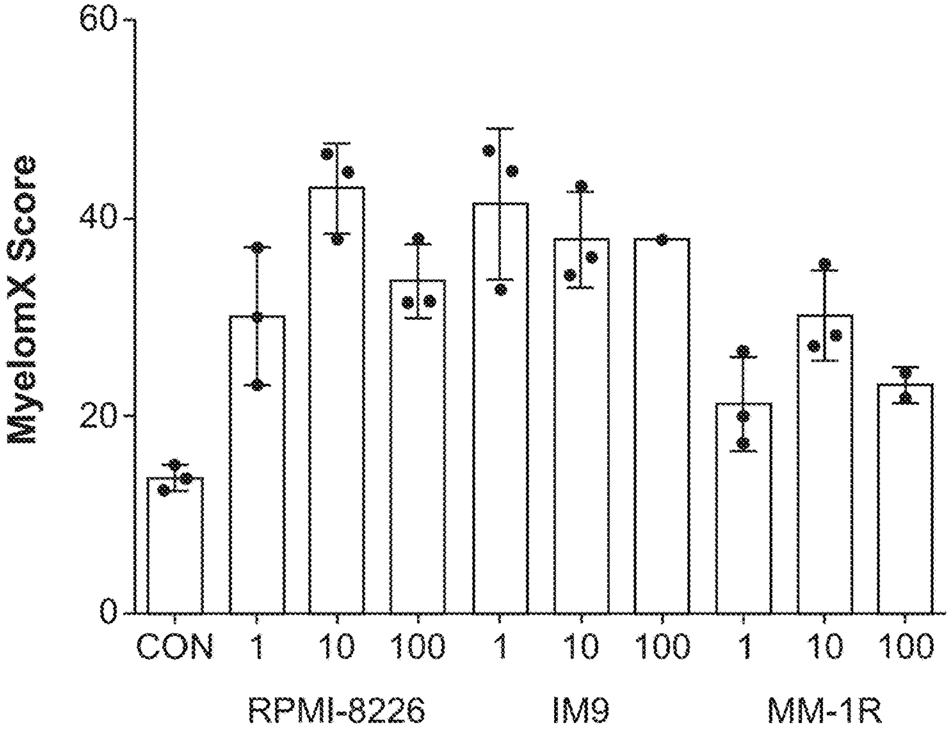
Figure 8B:
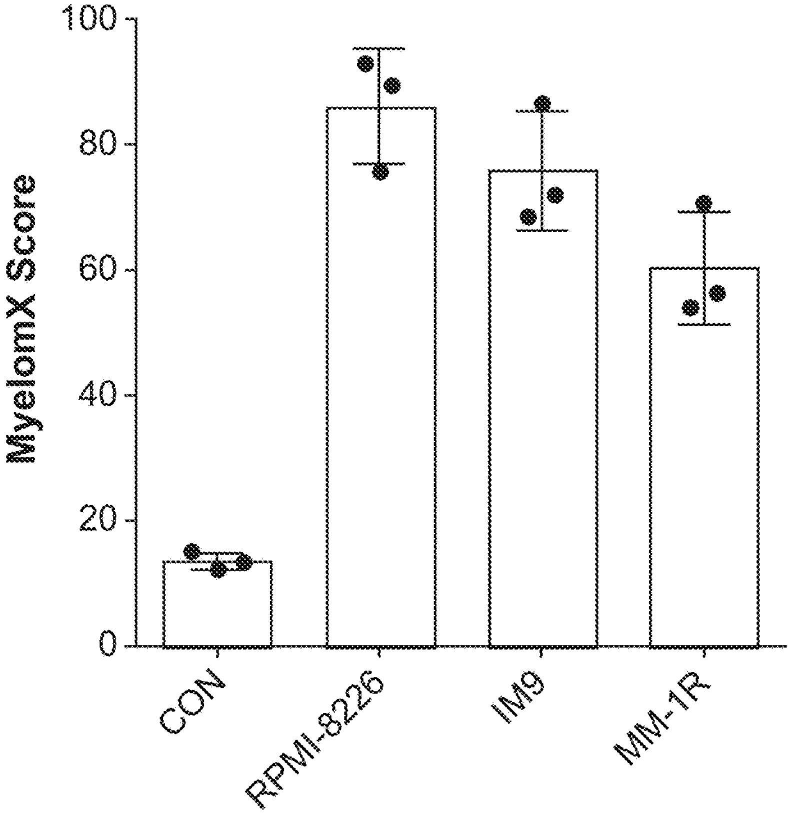

FIG. 8A and FIG. 8B are a set of graphs showing MyelomX score in 3 different myeloma cell lines. FIG. 8A identifies the cell lines demonstrate elevated expression—MyelomX score ranging from 60 (MM-1R) to 86 (RPMI-8226). FIG. 8B identifies that spiking these cells into blood from a subject that does not have a myeloma or other plasma cell dyscrasia, resulted in detectable gene expression and scores. A minimum of 1 cell/ml of blood could be consistently identified.

Figure 9A:
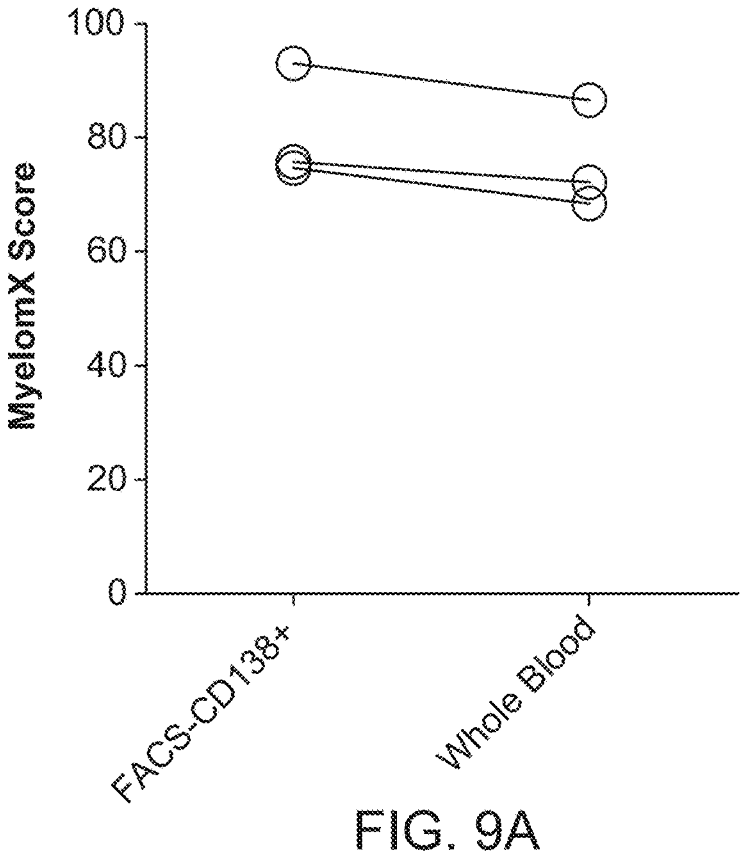
Figure 9B:
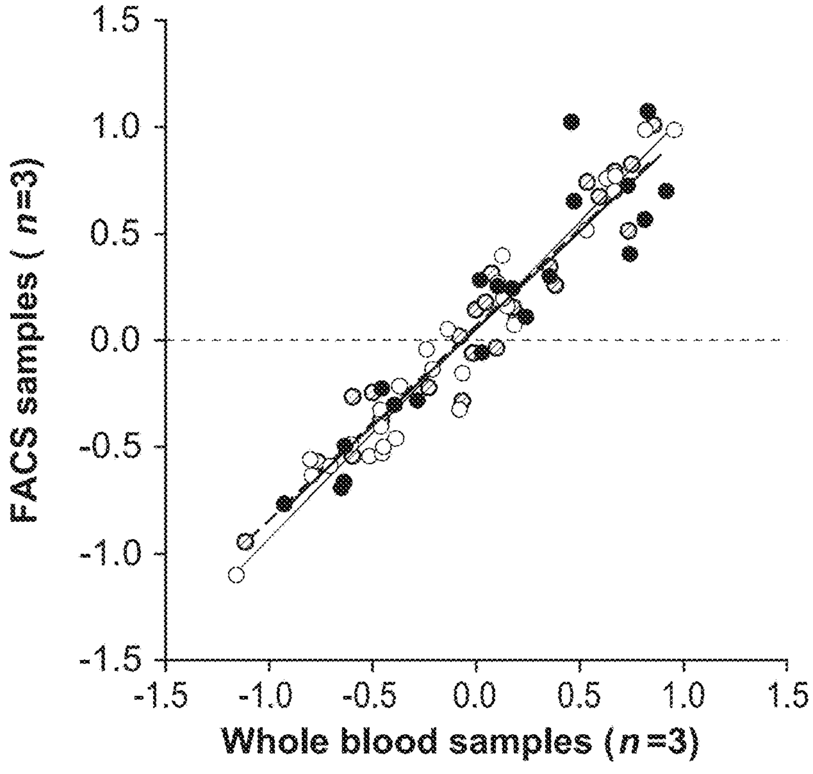

FIG. 9A and FIG. 9B are a set of graphs showing the MyelomX score in different FAC-sorted (CD138+) and matched whole blood samples from 3 different multiple myeloma patients. FIG. 9A identifies the scores from FACS samples and whole bloods and identifies the scores are positive and identical. FIG. 9B identifies that gene expression in FACS samples compared to matched blood samples is highly concordant (correlation ~0.90) consistent with the assay detecting circulating multiple myeloma cells.

DETAILED DESCRIPTION OF THE INVENTION

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Plasma cell dyscrasias (also termed plasma cell disorders and plasma cell proliferative diseases) are a spectrum of progressively more severe monoclonal gammopathies in which a clone or multiple clones of pre-malignant or malignant plasma cells over-produce and secrete into the blood stream a myeloma protein, i.e., an abnormal monoclonal antibody or portion thereof. A plasma cell dyscrasia can develop in different stages. The MGUS stage can be non-IgM MGUS, IgM MGUS, light chain MGUS, or monoclonal gammopathy of renal significance. The smoldering multiple myeloma (SMM) stage can be non-IgM SMM, smoldering Waldenstrom's macroglobulinemia, or light chain SMM. The malignant sgate can be solitary plasmacytoma, non-secretory multiple myeloma, plasma cell myeloma with concomitant chronic lymphocytic leukemia/monoclonal B-Cell lymphocytosis, Waldenström's macroglobulinemia, multiple myeloma, light chain multiple myeloma, or plasma cell leukemia. In some embodiments, the plasma cell dyscrasia is MGUS. In some embodiments, the plasma cell dyscrasia is myeloma.

The symptoms and signs can vary greatly for patients having myelomas, as many organs can be affected by myelomas. Symptoms can include, but are not limited to, bone pain, anemia, kidney failure, infection, and neurological symptoms (e.g., weakness, confusion, fatigue, headache, visual changes, retinopathy, radicular pain, loss of bowel, bladder control, or carpal tunnel syndrome).

Traditionally, myelomas can be diagnosed through a blood test or urine test. Myeloma cells produce M proteins and beta-2 microglobulin, which can be detected by a blood test. M proteins can also be detected by urine tests. Myelomas can be diagnosed through examination of the bone marrow. Specifically, a sample of bone marrow is removed, and the sample is examined for myeloma cells. Specialized tests, such as fluorescence in situ hybridization (FISH) can analyze myeloma cells to understand their chromosome abnormalities. Tests are also done to measure the rate at which the myeloma cells are dividing. Imaging tests can also be performed to detect bone problems associated with multiple myeloma. Tests may include X-ray, MRI, CT or positron emission tomography (PET).

The present disclosure provides a MyelomX score that can be used for, inter alia, identifying active disease, providing an assessment of treatment responses, predicting risk of relapse, or identifying minimal residual in conjunction with standard clinical assessment and imaging. Measurements of circulating plasma cell dyscrasia transcripts—the MyelomX—can identify plasma cell dyscrasias, and decreases in the MyelomX score correlate with the efficacy of therapeutic interventions such as proteasome inhibitors and immunomodulators. Targeted gene expression profile of RNA can be isolated from the biological samples (e.g., peripheral blood) of patients with plasma cell dyscrasias. This expression profile can be evaluated in an algorithm and converted to an output (prediction).

In one aspect, the present disclosure relates to a method for detecting a plasma cell dyscrasia in a subject in need thereof, comprising: (a) determining the expression level of at least 32 biomarkers from a test sample from the subject by contacting the test sample with a plurality of agents specific to detect the expression of the at least 32 biomarkers, wherein the at least 32 biomarkers comprise ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, UBE2R, and at least one housekeeping gene; (b) normalizing the expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1 to the expression level of the at least one housekeeping gene, thereby obtaining a normalized expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1; (c) inputting each normalized expression level into an algorithm to generate a score; (d) comparing the score with a first predetermined cutoff value; and (e) producing a report, wherein the report identifies the presence of a plasma cell dyscrasia in the subject when the score is equal to or greater than the first predetermined cutoff value or determining the absence of a plasma cell dyscrasia in the subject when the score is below the first predetermined cutoff value, wherein the first predetermined cutoff value is 20 on a scale of 0 to 100.

The identity of the splice variants for NFKBIZ, NR4A 1, PRKAA1, SCYL2, and SP1 can be found at Table 2.

Among the provided methods are those that are able to classify or detect a plasma cell dyscrasia such as MGUS and myeloma. In some embodiments, the provided methods can identify or classify a plasma cell dyscrasia in a human biological sample. In some embodiments, the biological sample is a blood, serum, plasma, or a neoplastic tissue. In some examples, the methods can provide such information with a specificity, sensitivity, and/or accuracy of at least 75%, 80%, 85%, 90%, 91%, 92%, 93%, 94%, 95%, 96%, 97%, 98%, or 99%.

The agents can be any agents for detection of the biomarkers, and typically are isolated polynucleotides or isolated polypeptides or proteins, such as antibodies, for example, those that specifically hybridize to or bind to the at least 32 biomarkers.

The biomarker can be RNA, cDNA, or protein. When the biomarker is RNA, the RNA can be reverse transcribed to produce cDNA (such as by RT-PCR), and the produced cDNA expression level is detected. The expression level of the biomarker can be detected by forming a complex between the biomarker and a labeled probe or primer. When the biomarker is RNA or cDNA, the RNA or cDNA can be detected by forming a complex between the RNA or cDNA and a labeled nucleic acid probe or primer. The complex between the RNA or cDNA and the labeled nucleic acid probe or primer can be a hybridization complex.

When the biomarker is protein, the protein can be detected by forming a complex between the protein and a labeled antibody. The label can be any label, for example a fluorescent label, chemiluminescence label, radioactive label, etc. The protein level can be measured by methods including, but not limited to, immunoprecipitation, ELISA, Western blot analysis, or immunohistochemistry using an agent, e.g., an antibody, that specifically detects the protein encoded by the gene.

In some embodiments, the methods are performed by contacting the test sample with one of the provided agents, more typically with a plurality of the provided agents, for example, a set of polynucleotides that specifically bind to the at least 32 biomarkers. In some embodiments, the set of polynucleotides includes DNA, RNA, cDNA, PNA, genomic DNA, or synthetic oligonucleotides. In some embodiments, the methods include the step of isolating RNA from the test sample prior to detection, such as by RT-PCR, e.g., QPCR. Thus, in some embodiments, detection of the biomarkers, such as expression levels thereof, includes detecting the presence, absence, or amount of RNA. In one example, the RNA is detected by PCR or by hybridization.

In some embodiments, the polynucleotides include sense and antisense primers, such as a pair of primers that is specific to each of the at least 32 biomarkers. In one aspect of this embodiment, the detection of the at least 32 biomarkers is carried out by PCR, typically quantitative or real-time PCR. For example, in one aspect, detection is carried out by producing cDNA from the test sample by reverse transcription; then amplifying the cDNA using the pairs of sense and antisense primers that specifically hybridize to the panel of at least 32 biomarkers, and detecting products of the amplification.

The test sample can be any biological fluid obtained from the subject. Preferably, the test sample is blood, serum, plasma, or a neoplastic tissue. In some embodiments, the test sample is a blood sample.

The first predetermined cutoff value can be derived from a plurality of reference samples obtained from subjects free of a neoplastic disease. Preferably, the reference sample is blood, serum, plasma, or non-neoplastic tissue.

The subject in need thereof can be a subject diagnosed with a plasma cell dyscrasia, a subject having at least one plasma cell dyscrasia symptom, or a subject have a predisposition or familial history for developing a plasma cell dyscrasia. The subject can be any mammal. Preferably, the subject is human. The terms "subject" and "patient" are used interchangeably herein.

In some embodiments, the method can further include determining a mathematically-derived expression level score of the at least 32 biomarkers in the test sample. This is the MyelomX score, which has a scale of 0 to 100. The MyelomX score is the product of a classifier built from a predictive classification algorithm, e.g., XGB, RF, glmnet, cforest, CART, treebag, knn, nnet, SVM-radial, SVM-linear, NB, mlp, or logistic regression modelling. In some embodiments, the predictive classification algorithm used is XGB.

The method can further include treating the subject identified as having a plasma cell dyscrasia with targeted therapy, biological therapy, chemotherapy, corticosteroids, stem cell transplantation, radiation therapy, or a combination thereof. Targeted therapy can include the use of proteasome inhibitors. In some embodiments, the targeted therapy can include bortezomib and/or carfilzomib. Biological therapy can include immunomodulators. In some embodiments, the biological therapy can include thalidomide, lenalidomide, and/or pomalidomide. Chemotherapy can include any known chemotherapeutic drugs. Corticosteroids can be prednisone or dexamethasone.

The present disclosure also provides a method for determining whether a plasma cell dyscrasia in a subject is stable or progressive, comprising: (a) determining the expression level of at least 32 biomarkers from a test sample from the subject by contacting the test sample with a plurality of agents specific to detect the expression of the at least 32 biomarkers, wherein the at least 32 biomarkers comprise ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, UBE2J1, and at least one housekeeping gene; (b) normalizing the expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1 to the expression level of the at least one housekeeping gene, thereby obtaining a normalized expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1; (c) inputting each normalized expression level into an algorithm to generate a score; (d) comparing the score with a second predetermined cutoff value; and (e) producing a report, wherein the report identifies that the plasma cell dyscrasia is progressive when the score is equal to or greater than the second predetermined cutoff value or identifies that the plasma cell dyscrasia is stable when the score is below the second predetermined cutoff value, wherein the second predetermined cutoff value is 40 on a scale of 0 to 100.

The second predetermined cutoff value can be derived from a plurality of reference samples obtained from subjects whose plasma cell dyscrasias are demonstrating disease progression.

The present disclosure also provides a method for determining a risk of disease relapse in a subject having a plasma cell dyscrasia, comprising: (a) determining the expression level of at least 32 biomarkers from a test sample from the subject after treatment by contacting the test sample with a plurality of agents specific to detect the expression of the at least 32 biomarkers, wherein the at least 32 biomarkers comprise ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, UBE2J1, and at least one housekeeping gene; (b) normalizing the expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1 to the expression level of the at least one housekeeping gene, thereby obtaining a normalized expression level of each of ASXL1, BHLHE40, BTG2, COPA, FBXW7, GNA13, IL8, JMJD1C LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1; (c) inputting each normalized expression level into an algorithm to generate a score; (d) comparing the score with a third predetermined cutoff value; and (e) producing a report, wherein the report identifies that the subject has a high risk of disease relapse when the score is equal to or greater than the third predetermined cutoff value or identifies that the subject has a low risk of disease relapse when the score is below the third predetermined cutoff value, wherein the third predetermined cutoff value is 40 on a scale of 0 to 100.

The third predetermined cutoff value can be derived from a plurality of reference samples obtained from subjects whose plasma cell dyscrasias are being adequately controlled by therapies.

The present disclosure also provides a method for determining a response by a subject having a plasma cell dyscrasia to a therapy, comprising: (a) determining a first expression level of at least 31 biomarkers from a first test sample from the subject at a first time point by contacting the first test sample with a plurality of agents specific to detect the expression of the at least 31 biomarkers, wherein the at least 31 biomarkers comprise ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1; (b) determining a second expression level of the at least 31 biomarkers from a second test sample from the subject at a second time point by contacting the second test sample with a plurality of agents specific to detect the expression of the at least 31 biomarkers, wherein the second time point is after the first time point and after the administration of the therapy to the subject; (c) comparing the first expression level with the second expression level; and (d) producing a report, wherein the report identifies that the subject is responsive to the therapy when the second expression level is significantly decreased as compared to the first expression level.

In some embodiments, the methods can predict treatment responsiveness to, or determine whether a patient has become clinically stable following, or is responsive or non-responsive to, a plasma cell dyscrasia treatment, such as a drug therapy (for example, an immunotherapy or targeted therapy). In some cases, the methods can do so with a specificity, sensitivity, and/or accuracy of at least 75%, 80%, 85%, 90%, 91%, 92%, 93%, 94%, 95%, 96%, 97%, 98%, or 99%.

In some embodiments, the first and second test samples can be of the same type. In some embodiments, the first and second test samples can be of different types.

In some embodiments, the therapy can be a drug therapy. The drug therapy can be an immunotherapy, a targeted therapy, a chemotherapy, or a combination thereof. In some embodiments, the therapy can be a radiation therapy.

In some embodiments, the first time point is prior to the administration of the therapy to the subject. In some embodiments, the first time point is after the administration of the therapy to the subject. The second time point can be a few days, a few weeks, or a few months after the first time point. For example, the second time point can be at least 1 day, at least 7 days, at least 14 days, at least 30 days, at least 60 days, or at least 90 days after the first time point.

In some embodiments, the second expression level is significantly decreased as compared to the first expression level when the second expression level is at least 10% less than the first expression level. In some embodiments, the second expression level is significantly decreased as compared to the first expression level when the second expression level is at least 20% less than the first expression level. In some embodiments, the second expression level is significantly decreased as compared to the first expression level when the second expression level is at least 25% less than the first expression level. In some embodiments, the second expression level is significantly decreased as compared to the first expression level when the second expression level is at least 30% less than the first expression level. In some embodiments, the second expression level is significantly decreased as compared to the first expression level when the second expression level is at least 40% less than the first expression level. In some embodiments, the second expression level is significantly decreased as compared to the first expression level when the second expression level is at least 50% less than the first expression level. In some embodiments, the second expression level is significantly decreased as compared to the first expression level when the second expression level is at least 60% less than the first expression level. In some embodiments, the second expression level is significantly decreased as compared to the first expression level when the second expression level is at least 70% less than the first expression level. In some embodiments, the second expression level is significantly decreased as compared to the first expression level when the second expression level is at least 80% less than the first expression level. In some embodiments, the second expression level is significantly decreased as compared to the first expression level when the second expression level is at least 90% less than the first expression level.

In some embodiments, the method further comprises determining a third expression level of the at least 32 biomarkers from a third test sample from the subject at a third time point by contacting the third test sample with a plurality of agents specific to detect the expression of the at least 32 biomarkers, wherein the third time point is after the second time point. The method can further comprise creating a plot showing the trend of the expression level change.

The present disclosure also provides an assay comprising: (a) determining the expression level of biomarkers consisting essentially of the following 32 biomarkers from a test sample from a patient diagnosed of a plasma cell dyscrasia or a subject suspected of having a plasma cell dyscrasia: ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, UBE2R, and at least one housekeeping gene; (b) normalizing the expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1 to the expression level of the at least one housekeeping gene, thereby obtaining a normalized expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1; (c) inputting each normalized expression level into an algorithm to generate a score; and (d) comparing the score with a first predetermined cutoff value.

The present disclosure also provides an assay comprising: (a) determining the expression level of biomarkers consisting of the following 32 biomarkers from a test sample from patient diagnosed of a plasma cell dyscrasia or a subject suspected of having a plasma cell dyscrasia: ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, UBE2R, and at least one housekeeping gene; (b) normalizing the expression level of each of ASXL1, BHLHE40, BTG2, COPA, FBXW7, GNA13, IL8, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1 to the expression level of the at least one housekeeping gene, thereby obtaining a normalized expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1; (c) inputting each normalized expression level into an algorithm to generate a score; and (d) comparing the score with a first predetermined cutoff value.

In some embodiments, the at least one housekeeping gene is selected from the group consisting of ALG9, SEPN, YWHAQ, VPS37A, PRRC2B, DOPEY2, NDUFB11, ND4, MRPL19, PSMC4, SF3A1, PUM1, ACTB, GAPD, GUSB, RPLP0, TFRC, MORF4L1, 18S, PPIA, PGK1, RPL13A, B2M, YWHAZ, SDHA, HPRT1, TOX4, and TPT1. In some embodiments, the housekeeping gene is TPT1.

In some embodiments, two or more housekeeping genes can be used in normalizing the expression levels. For example, when two housekeeping genes are used, the method can comprise: (1) normalizing the expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1 to the expression level of a first housekeeping gene; (2) normalizing the expression level of each of ASXL1, BHLHE40, BTG2, COPA, FBXW7, GNA13, IL8, JMJD1C, LARS2, MALAT1, MBNL1, MCL1, NFKBIZ (2 splice variants), NR4A1 (2 splice variants), PDE4B, P1AS2, PRKAA1 (2 splice variants), SCYL2 (2 splice variants), SMARCD2, SP1 (2 splice variants), SRSF5, TAGAP, TANK, TLE4, TSC22D3, and UBE2J1 to the expression level of a second housekeeping gene; and (3) averaging the first normalized expression level and the second normalized expression level to obtain an averaged normalized expression level.

The sequence information of the plasma cell dyscrasia biomarkers and housekeepers is shown in Table 1.

TABLE 1

Plasma cell dyscrasia Biomarker/Housekeeper Sequence Information

| Gene Name | RefSeq Accession | Sequence | SEQ ID NO: |
|---|---|---|---|
| ASXL1 | NM_001164603.1 | CACACCCACG GCAGACACGC ACGCACCCGG GCGCCGAAGG GAAAGCCGCG TCTCGCCCTC CCGCCCCGCC GTCGGTCCTG TCTCAGTCCC TCAGCAGAGC GGGAAAGCGG AGGCCGGAGC CGTGACCTCT GACCCCGTGG TTATGCGGAG CCGCCGCATT CCTTAGCGAT CGCGGGGCAG CCGCCGCTGC CGCCGTGGGC GACTGACGCA GCGCGGGCGC GTGGAGCCGC CGCCGCCCCT CCCCCACCGC CGCTCTCGCG CCAGCCGGTC CCCGCGTGCC CGCCCCTTCT CCCCGGCCGC ACCCGAGACC TCGCGCGCCG CCGCTGCCAC GCGCCCCCCC CACCGCCGCC GCCGCCCCAG CCCCGCGCCA CCGCCCCAGC CCGCCCAGCC CGGAGGTCCC | 1 |

TABLE 1-continued

Plasma cell dyscrasia Biomarker/Housekeeper Sequence Information

| Gene Name | RefSeq Accession | Sequence | SEQ ID NO: |
|---|---|---|---|
| | | GCGTGGAGCT GCCGCCGCCG CCGGGGAGAA GGATGAAGGA | |
| | | CAAACAGAAG AAGAAGAAGG AGCGCACGTG GGCCGAGGCC | |
| | | GCGCGCCTGG TATTAGAAAA CTACTCGGAT GCTCCAATGA | |
| | | CACCAAAACA GATTCTGCAG GTCATAGAGG CAGAAGGACT | |
| | | AAAGGAAATG AGAAGTGGGA CTTCCCCTCT CGCATGCCTC | |
| | | AATGCTATGC TACATTCCAA TTCAAGAGGA GGAGAGGGGT | |
| | | TGTTTTATAA ACTGCCTGGC CGAATCAGCC TTTTCACGCT | |
| | | CAAGGTGTGA GCCACTGCAC CAGGCCCCTT CATCTTAATT | |
| | | TTAATATATC TTTGAATAAA CACCATTGTA TGAACCTGCT | |
| | | GTAAGCTTGG GAGTGGTCTG TTAGTCTACA GCTTGTGTCT | |
| | | GAGATGTGCT AATTGAATAT TTGCTCAGTA CCTCATCTTA | |
| | | ACTGCCTTTG GCTTTATGTT GCTTATCCTT CATAGTATCT | |
| | | TGTTCATTGG CCTTTTACAT CCATAGGCAT CACTTCTCTG | |
| | | ATATTCGTTG TGCTCTTTTA ATGGATTAAT GGTTTGCTTG | |
| | | GTTGGTTCCT CTAGTTAGAC TGTAAACTCC TTGAGAGCAG | |
| | | AGTCTGTATT TTATTAATTA CCCACAGTAC TAGGTACATA | |
| | | GTTGCCTTCA ATAAATATAT ATTTAATGAA AAAAAAAAAA | |
| | | AAAA | |
| BHLHE40 | NM_003670.2 | CGCCTCCCCG CCCGCCCCAC TTCTCATTCA CTTGGCTCGC | 2 |
| | | ACGGCGCAGA CAGACCGCGC AGGGAGCACA CACCGCCAGT | |
| | | CTGTGCGCTG AGTCGGAGCC AGAGGCCGCG GGGACACCGG | |
| | | GCCATGCACG CCCCCAACTG AAGCTGCATC TCAAAGCCGA | |
| | | AGATTCCAGC AGCCCAGGGG ATTTCAAAGA GCTCAGACTC | |
| | | AGAGGAACAT CTGCGGAGAG ACCCCCGAAG CCCTCTCCAG | |
| | | GGCAGTCCTC ATCCAGACGC TCCGCTAGTG CAGACAGGAG | |
| | | CGCGCAGTGG CCCCGGCTCG CCGCGCCATG GAGCGGATCC | |
| | | CCAGCGCGCA ACCACCCCCC GCCTGCCTGC CCAAAGCACC | |
| | | GGGACTGGAG CACGGAGACC TACCAGGGAT GTACCCTGCC | |
| | | CACATGTACC AAGTGTACAA GTCAAGACGG GGAATAAAGC | |
| | | GGAGCGAGGA CAGCAAGGAG ACCTACAAAT TGCCGCACCG | |
| | | GCTCATCGAG AAAAAGAGAC GTGACCGGAT TAACGAGTGC | |
| | | ATCGCCCAGC TGAAGGATCT CCTACCCGAA CATCTCAAAC | |
| | | TTACAACTTT GGGTCACTTG GAAAAAGCAG TGGTTCTTGA | |
| | | ACTTACCTTG AAGCATGTGA AAGCACTAAC AAACCTAATT | |
| | | GATCAGCAGC AGCAGAAAAT CATTGCCCTG CAGAGTGGTT | |
| | | TACAAGCTGG TGAGCTGTCA GGGAGAAATG TCGAAACAGG | |
| | | TCAAGAGATG TTCTGCTCAG GTTTCCAGAC ATGTGCCCGG | |
| | | GAGGTGCTTC AGTATCTGGC CAAGCACGAG AACACTCGGG | |
| | | ACCTGAAGTC TTCGCAGCTT GTCACCCACC TCCACCGGGT | |
| | | GGTCTCGGAG CTGCTGCAGG GTGGTACCTC CAGGAAGCCA | |
| | | TCAGACCCAG CTCCCAAAGT GATGGACTTC AAGGAAAAAC | |
| | | CCAGCTCTCC GGCCAAAGGT TCGGAAGGTC CTGGGAAAAA | |
| | | CTGCGTGCCA GTCATCCAGC GGACTTTCGC TCACTCGAGT | |
| | | GGGGAGCAGA GCGGCAGCGA CACGGACACA GACAGTGGCT | |
| | | ATGGAGGAGA ATCGGAGAAG GGCGACTTGC GCAGTGAGCA | |
| | | GCCGTGCTTC AAAAGTGACC ACGGACGCAG GTTCACGATG | |
| | | GGAGAAAGGA TCGGCGCAAT TAAGCAAGAG TCCGAAGAAC | |
| | | CCCCCACAAA AAAGAACCGG ATGCAGCTTT CGGATGATGA | |
| | | AGGCCATTTC ACTAGCAGTG ACCTGATCAG CTCCCCGTTC | |
| | | CTGGGCCCAC ACCCACACCA GCCTCCTTTC TGCCTGCCCT | |
| | | TCTACCTGAT CCCACCTTCA GCGACTGCCT ACCTGCCCAT | |
| | | GCTGGAGAAG TGCTGGTATC CCACCTCAGT GCCAGTGCTA | |
| | | TACCCAGGCC TCAACGCCTC TGCCGCAGCC CTCTCTAGCT | |
| | | TCATGAACCC AGACAAGATC TCGGCTCCCT TGCTCATGCC | |
| | | CCAGAGACTC CCTTCTCCCT TGCCAGCTCA TCCGTCCGTC | |
| | | GACTCTTCTG TCTTGCTCCA AGCTCTGAAG CCAATCCCCC | |
| | | CTTTAAACTT AGAAACCAAA GACTAAACTC TCTAGGGGAT | |
| | | CCTGCTGCTT TGCTTTCCTT CCTCGCTACT TCCTAAAAAG | |
| | | CAACAAAAAA GTTTTTGTGA ATGCTGCAAG ATTGTTGCAT | |
| | | TGTGTATACT GAGATAATCT GAGGCATGGA GAGCAGATTC | |
| | | AGGGTGTGTG TGTGTGTGTG TGTGTGTGTA TGTGCGTGTG | |
| | | CGTGCACATG TGTGCCTGCG TGTTGGTATA GGACTTTAAA | |
| | | GCTCCTTTTG GCATAGGGAA GTCACGAAGG ATTGCTTGAC | |
| | | ATCAGGAGAC TTGGGGGGGA TTGTAGCAGA CGTCTGGGCT | |
| | | TTTCCCCACC CAGAGAATAG CCCCCTTCGA TACACATCAG | |
| | | CTGGATTTTC AAAAGCTTCA AAGTCTTGGT CTGTGAGTCA | |
| | | CTCTTCAGTT TGGGAGCTGG GTCTGTGGCT TTGATCAGAA | |
| | | GGTACTTTCA AAAGAGGGCT TTCCAGGGCT CAGCTCCCAA | |
| | | CCAGCTGTTA GGACCCCACC CTTTTGCCTT TATTGTCGAC | |
| | | GTGACTCACC AGACGTCGGG GAGAGAGAGC AGTCAGACCG | |
| | | AGCTTTCTGC TAACATGGGG AGGTAGCAGG CACTGGCATA | |
| | | GCACGGTAGT GGTTTGGGGA GGTTTCCGCA GGTCTGCTCC | |
| | | CCACCCCTGC CTCGGAAGAA TAAAGAGAAT GTAGTTCCCT | |

TABLE 1-continued

Plasma cell dyscrasia Biomarker/Housekeeper Sequence Information

| Gene Name | RefSeq Accession | Sequence | SEQ ID NO: |
|---|---|---|---|
| | | ACTCAGGCTT TCGTAGTGAT TAGCTTACTA AGGAACTGAA AATGGGCCCC TTGTACAAGC TGAGCTGCCC CGGAGGGAGG GAGGAGTTCC CTGGGCTTCT GGCACCTGTT TCTAGGCCTA ACCATTAGTA CTTACTGTGC AGGGAACCAA ACCAAGGTCT GAGAAATGCG GACACCCCGA GCGAGCACCC CAAAGTGCAC AAAGCTGAGT AAAAAGCTGC CCCCTTCAAA CAGAACTAGA CTCAGTTTTC AATTCCATCC TAAAACTCCT TTTAACCAAG CTTAGCTTCT CAAAGGCCTA ACCAAGCCTT GGCACCGCCA GATCCTTTCT GTAGGCTAAT TCCTCTTGCC CAACGGCATA TGGAGTGTCC TTATTGCTAA AAAGGATTCC GTCTCCTTCA AAGAAGTTTT ATTTTTGGTC CAGAGTACTT GTTTTCCCGA TGTGTCCAGC CAGCTCCGCA GCAGCTTTTC AAAATGCACT ATGCCTGATT GCTGATCGTG TTTTAACTTT TTCTTTTCCT GTTTTTATTT TGGTATTAAG TCGTTGCCTT TATTTGTAAA GCTGTTATAA ATATATATTA TATAAATATA TTAAAAAGGA AAATGTTTCA GATGTTTATT TGTATAATTA CTTGATTCAC ACAGTGAGAA AAAATGAATG TATTCCTGTT TTTGAAGAGA AGAATAATTT TTTTTTTCTC TAGGGAGAGG TACAGTGTTT ATATTTTGGA GCCTTCCTGA AGGTGTAAAA TTGTAAATAT TTTTATCTAT GAGTAAATGT TAAGTAGTTG TTTTAAAATA CTTAATAAAA TAATTCTTTT CCTGTGGAAG AGAAAAAAAA AAAAAAAAAA AAAAAAAAAA A | |
| BTG2 | NM_006763.2 | CAGGGTAACG CTGTCTTGTG GACCCGCACT TCCCACCCGA GACCTCTCAC TGAGCCCGAG CCGCGCGCGA CATGAGCCAC GGGAAGGGAA CCGACATGCT CCCGGAGATC GCCGCCGCCG TGGGCTTCCT CTCCAGCCTC CTGAGGACCC GGGGCTGCGT GAGCGAGCAG AGGCTTAAGG TCTTCAGCGG GGCGCTCCAG GAGGCACTCA CAGAGCACTA CAAACACCAC TGGTTTCCCG AAAAGCCGTC CAAGGGCTCC GGCTACCGCT GCATTCGCAT CAACCACAAG ATGGACCCCA TCATCAGCAG GGTGGCCAGC CAGATCGGAC TCAGCCAGCC CCAGCTGCAC CAGCTGCTGC CCAGCGAGCT GACCCTGTGG GTGGACCCCT ATGAGGTGTC CTACCGCATT GGGGAGGACG GCTCCATCTG CGTCTTGTAC GAGGAGGCCC CACTGGCCGC CTCCTGTGGG CTCCTCACCT GCAAGAACCA AGTGCTGCTG GGCCGGAGCA GCCCCTCCAA GAACTACGTG ATGGCAGTCT CCAGCTAGGC CCTTCCGCCC CCGCCCTGGG CGCCGCCGTG CTCATGCTGC CGTGACAACA GGCCACCACA TACCTCAACC TGGGGAACTG TATTTTTAAA TGAAGAGCTA TTTATATATA TTATTTTTTT TTAAGAAAGG AGGAAAAGAA ACCAAAAGTT TTTTTTAAGA AAAAAAATCC TTCAAGGGAG CTGCTTGGAA GTGGCCTCCC CAGGTGCCTT TGGAGAGAAC TGTTGCGTGC TTGAGTCTGT GAGCCAGTGT CTGCCTATAG GAGGGGGAGC TGTTAGGGGG TAGACCTAGC CAAGGAGAAG TGGGAGACGT TTGGCTAGCA CCCCAGGAAG ATGTGAGAGG GAGCAAGCAA GGTTAGCAAC TGTGAACAGA GAGGTCGGGA TTTGCCCTGG GGGAGGAAGA GAGGCCAAGT TCAGAGCTCT CTGTCTCCCC CAGCCAGACA CCTGCATCCC TGGCTCCTCT ATTACTCAGG GGCATTCATG CCTGGACTTA AACAATACTA TGTTATCTTT TCTTTTATTT TTCTAATGAG GTCCTGGGCA GAGAGTGAAA AGGCCTCTCC TGATTCCTAC TGTCCTAAGC TGCTTTTCTT GAAATCATGA CTTGTTTCTA ATTCTACCCT CAGGGGCCTG TAGATGTTGC TTTCCAGCCA GGAATCTAAA GCTTTGGGTT TTCTGAGGGG GGGGAGGAGG GAACTGGAGG TTATTGGGGT TAGGATGGAA GGGAACTCTG CACAAAACCT TTGCTTTGCT AGTGCTGCTT TGTGTGTATG TGTGGCAAAT AATTTGGGGG TGATTTGCAA TGAAATTTTG GGACCCAAAG AGTATCCACT GGGGATGTTT TTTGGCCAAA ACTCTTCCTT TTGGAACCAC ATGAAAGTCT TGATGCTGCT GCCATGATCC CTTTGAGAGG TGGCTCAAAA GCTACAGGGA ACTCCAGGTC CTTTATTACT GCCTTCTTTT CAAAAGCACA ACTCTCCTCT AACCCTCCCC TCCCCCTTCC CTTCTGGTCG GGTCATAGAG CTACCGTATT TTCTAGGACA AGAGTTCTCA GTCACTGTGC AATATGCCCC CTGGGTCCCA GGAGGGTCTG GAGGAAAACT GGCTATCAGA ACCTCCTGAT GCCCTGGTGG GCTTAGGGAA CCATCTCTCC TGCTCTCCTT GGGATGATGG CTGGCTAGTC AGCCTTGCAT GTATTCCTTG GCTGAATGGG AGAGTGCCCC ATGTTCTGCA AGACTACTTG GTATTCTTGT AGGGCCGACA CTAAATAAAA GCCAAACCTT GGGCACTGTT TTTTCTCCCT GGTGCTCAGA GCACCTGTGG GAAAGGTTGC TGTCTGTCTC AGTACAATCC AAATTTGTCG TAGACTTGTG CAATATATAC TGTTGTGGGT TGGAGAAAAG TGGAAAGCTA CACTGGGAAG AAACTCCCTT CCTTCAATTT CTCAGTGACA TTGATGAGGG GTCCTCAAAA GACCTCGAGT TTCCCAAACC | 3 |

TABLE 1-continued

Plasma cell dyscrasia Biomarker/Housekeeper Sequence Information

| Gene Name | RefSeq Accession | Sequence | SEQ ID NO: |
|---|---|---|---|
| | | GAATCACCTT AAGAAGGACA GGGCTAGGGC ATTTGGCCAG | |
| | | GATGGCCACC CTCCTGCTGT TGCCCCTTAG TGAGGAATCT | |
| | | TCACCCCACT TCCTCTACCC CCAGGTTCTC CTCCCCACAG | |
| | | CCAGTCCCCT TTCCTGGATT TCTAAACTGC TCAATTTTGA | |
| | | CTCAAAGGTG CTATTTACCA AACACTCTCC CTACCCATTC | |
| | | CTGCCAGCTC TGCCTCCTTT TCAACTCTCC ACATTTTGTA | |
| | | TTGCCTTCCC AGACCTGCTT CCAGTCTTTA TTGCTTTAAA | |
| | | GTTCACTTTG GGCCCACAGA CCCAAGAGCT AATTTTCTGG | |
| | | TTTGTGGGTT GAAACAAAGC TGTGAATCAC TGCAGGCTGT | |
| | | GTTCTTGCAT CTTGTCTGCA AACAGGTCCC TGCCTTTTTA | |
| | | GAAGCAGCCT CATGGTCTCA TGCTTAATCT TGTCTCTCTT | |
| | | CTCTTCTTTA TGATGTTCAC TTTAAAAACA ACAAAACCCC | |
| | | TGAGCTGGAC TGTTGAGCAG GCCTGTCTCT CCTATTAAGT | |
| | | AAAAATAAAT AGTAGTAGTA TGTTTGTAAG CTATTCTGAC | |
| | | AGAAAAGACA AAGGTTACTA ATTGTATGAT AGTGTTTTTA | |
| | | TATGGAAGAA TGTACAGCTT ATGGACAAAT GTACACCTTT | |
| | | TTGTTACTTT AATAAAAATG TAGTAGGATA AAAAAAA | |
| COPA | NM_001098398.1 | AGAAGGGAGA CAGTGGCGGT CGCGGCGGGG CCGATCCGAG | 4 |
| | | AGTTCCCCTT AGAGAACGGA GCTCACGGGC GGGGAGGCCT | |
| | | CACCTGCTAG TAGGACGCAG AAAGACAGAA GGCGAAGGAG | |
| | | ACCCCGACTT CCCGGGTCAG CCCCAGAGCC ACCCCCTGCC | |
| | | GTAGCCATCT TGCCTCTCTG CTGAGCGGAA GCCCCCGTTC | |
| | | GGCTCCTGTC TGTTAGCGGC CTCTCTAGGC TACCACTGAC | |
| | | ACCGTCTCTG TGGCCCGGAG CCTAAGAGAC CGGAAGTTCG | |
| | | TGTTTCCAGG CGCTTCCGGA AACCGCGGGA GAGGGTCGCT | |
| | | GACGTGGAGG CGTCCGAAGG GCAGCAGGGT GTGTCGGGGC | |
| | | TCGGATTAAG ACATCGGAGT CGGAGACCTG AGAGATGTTA | |
| | | ACCAAATTCG AGACCAAGAG CGCGCGGGTC AAAGGGCTCA | |
| | | GCTTTCACCC CAAAAGACCT TGGATCCTGA CTAGTTTACA | |
| | | TAATGGGGTC ATCCAGTTAT GGGACTATCG GATGTGCACT | |
| | | CTCATTGACA AGTTTGATGA ACATGATGGT CCAGTGCGAG | |
| | | GCATTGACTT CCATAAGCAG CAGCCACTGT TCGTCTCTGG | |
| | | AGGAGATGAC TATAAGATTA AGGTTTGGAA TTACAAGCTT | |
| | | CGGCGCTGTC TTTTCACATT GCTTGGGCAC TTAGATTATA | |
| | | TTCGCACCAC GTTTTTTCAT CATGAATATC CCTGGATTCT | |
| | | GAGTGCCTCC GATGATCAGA CCATCCGAGT GTGGAACTGG | |
| | | CAATCTAGAA CCTGTGTTTG TGTGTTAACA GGGCACAACC | |
| | | ATTATGTGAT GTGTGCTCAG TTCCACCCCA CAGAAGACTT | |
| | | GGTAGTATCA GCCAGCCTGG ACCAGACTGT GCGCGTTTGG | |
| | | GATATTTCTG GTCTGAGGAA AAAAAACCTG TCCCCTGGTG | |
| | | CGGTGGAATC GGATGTGAGA GGAATAACTG GGGTTGATCT | |
| | | ATTTGGAACT ACAGATGCAG TGGTGAAGCA TGTACTAGAG | |
| | | GGTCACGATC GTGGAGTAAA CTGGGCTGCC TTCCACCCCA | |
| | | CTATGCCCCT TATTGTATCT GGGGCAGATG ATCGTCAAGT | |
| | | GAAGATCTGG CGCATGAATG AATCAAAGGC ATGGGAGGTT | |
| | | GATACCTGCC GGGGCCATTA CAACAATGTA TCTTGTGCCG | |
| | | TCTTCCACCC TCGCCAAGAG TTGATCCTCA GCAATTCTGA | |
| | | GGACAAGAGT ATTCGAGTCT GGGATATGTC TAAGCGGACT | |
| | | GGGGTTCAGA CTTTCCGCAG AGACCATGAT CGTTTCTGGG | |
| | | TCCTAGCTGC TCACCCTAAC CTTAACCTCT TTGCAGCAGG | |
| | | CCATGATGGT GGTATGATTG TGTTTAAGCT GGAACGGGAA | |
| | | CGGCCAGCCT ATGCTGTTCA TGGCAATATG CTACACTATG | |
| | | TCAAGGACCG ATTCTTACGA CAGCTGGATT TCAACAGCTC | |
| | | CAAAGATGTA GCTGTGATGC AGTTGCGGAG TGGTTCCAAG | |
| | | TTTCCAGTAT TCAATATGTC ATACAATCCA GCAGAAAATG | |
| | | CAGTCCTGCT TTGTACAAGA GCTAGCAATC TAGAGAATAG | |
| | | TACCTATGAC CTGTACACCA TCCCTAAAGA TGCTGACTCC | |
| | | CAGAATCCTG ATGCGCCTGA AGGGAAACGA TCCTCAGGCC | |
| | | TGACAGCCGT TTGGGTCGCT CGAAATCGGT TTGCTGTCCT | |
| | | AGATCGGATG CATTCGCTTC TGATCAAGAA TCTGAAGAAT | |
| | | GAGATCACCA AAAAGGTACA GGTGCCCAAC TGTGATGAGA | |
| | | TCTTCTATGC TGGCACAGGC AATCTCCTGC TTCGAGATGC | |
| | | GGACTCTATC ACACTCTTTG ACGTACAGCA GAAGCGGACT | |
| | | CTGGCATCTG TGAAGATTTC TAAAGTGAAA TACGTTATCT | |
| | | GGTCAGCAGA CATGTCACAT GTAGCACTAC TAGCCAAACA | |
| | | CGAACACTCA TGCCCTTTGC CTCTTACAGC CATTGTGATC | |
| | | TGTAACCGCA AACTGGATGC TTTATGTAAC ATTCATGAGA | |
| | | ACATTCGTGT CAAGAGTGGG GCCTGGGATG AGAGTGGGGT | |
| | | ATTTATCTAT ACCACAAGCA ACCACATCAA ATATGCTGTC | |
| | | ACCACTGGGG ACCACGGGAT CATTCGAACT CTGGATTTAC | |
| | | CCATCTATGT CACACGGGTG AAGGGCAACA ATGTATACTG | |
| | | CCTAGACAGG GAGTGTCGTC CCCGGGTACT CACCATTGAT | |
| | | CCCACTGAGT TCAAATTCAA GCTGGCCCTG ATCAACAGAA | |

TABLE 1-continued

Plasma cell dyscrasia Biomarker/Housekeeper Sequence Information

| Gene Name | RefSeq Accession | Sequence | SEQ ID NO: |
|---|---|---|---|
| | | AATATGATGA GGTACTGCAC ATGGTGAGGA ATGCCAAACT | |
| | | AGTTGGCCAG TCTATTATTG CTTATCTCCA GAAGAAGGGC | |
| | | TATCCTGAAG TGGCACTGCA TTTTGTCAAG GATGAGAAAA | |
| | | CTCGCTTTAG TCTGGCACTG GAGTGTGGAA ACATTGAGAT | |
| | | TGCTCTGGAA GCAGCCAAAG CACTGGATGA CAAGAACTGC | |
| | | TGGGAAAAGC TGGGAGAAGT GGCCCTGCTG CAGGGGAACC | |
| | | ACCAGATTGT GGAAATGTGC TATCAGCGTA CCAAAAACTT | |
| | | TGACAAACTT TCCTTCCTGT ATCTTATCAC TGGCAACTTA | |
| | | GAAAAACTTC GCAAGATGAT GAAGATTGCT GAGATCAGAA | |
| | | AGGACATGAG TGGCCACTAT CAGAATGCCC TATACCTGGG | |
| | | TGATGTGTCA GAGCGTGTGC GGATCCTGAA GAACTGTGGA | |
| | | CAGAAGTCCC TGGCCTATCT CACAGCTGCT ACCCATGGCT | |
| | | TAGATGAAGA AGCTGAGAGC CTAAAGGAGA CATTTGACCC | |
| | | AGAGAAGGAG ACAATCCCAG ACATTGACCC TAATGCCAAG | |
| | | CTGCTCCAGC CACCTGCACC TATCATGCCA TTGGATACCA | |
| | | ATTGGCCTTT ATTGACTGTA TCCAAAGGAT TTTTTGAAGG | |
| | | CACCATTGCC AGCAAAGGGA AGGGAGGAGC ACTGGCTGCT | |
| | | GACATTGACA TTGACACTGT TGGTACAGAG GGCTGGGGAG | |
| | | AGGATGCAGA GCTGCAGTTG GATGAAGATG GGTTTGTGGA | |
| | | GGCTACAGAA GGTTTGGGGG ATGATGCTCT TGGCAAGGGA | |
| | | CAGGAAGAAG GAGGTGGCTG GGATGTAGAA GAAGATCTGG | |
| | | AGCTCCCTCC TGAGCTGGAT ATATCCCCTG GGGCAGCTGG | |
| | | TGGGGCTGAA GATGGTTTCT TTGTGCCCCC AACCAAGGGA | |
| | | ACAAGTCCAA CTCAGATCTG GTGTAATAAC TCTCAGCTTC | |
| | | CAGTTGATCA CATCCTGGCA GGCTCTTTCG AAACAGCCAT | |
| | | GCGGCTCCTT CATGACCAAG TAGGGGTAAT CCAGTTTGGC | |
| | | CCCTACAAGC AACTGTTCCT ACAGACATAC GCCCGAGGCC | |
| | | GCACAACCTA TCAGGCTCTG CCCTGCCTAC CCTCCATGTA | |
| | | TGGCTATCCT AATCGCAACT GGAAGGATGC AGGGCTGAAG | |
| | | AATGGTGTAC CAGCTGTGGG CCTGAAGCTT AATGACCTCA | |
| | | TCCAACGGTT GCAGCTGTGC TACCAGCTCA CCACAGTTGG | |
| | | CAAATTTGAG GAGGCTGTGG AAAAATTCCG TTCCATCCTT | |
| | | CTCAGTGTGC CACTTCTTGT TGTGGACAAT AAACAAGAGA | |
| | | TTGCAGAGGC CCAGCAGCTC ATCACCATTT GCCGTGAGTA | |
| | | CATTGTGGGT TTGTCCGTGG AGACAGAAAG GAAGAAGCTG | |
| | | CCCAAAGAGA CTCTAGAACA GCAGAAGCGC ATCTGTGAGA | |
| | | TGGCAGCCTA TTTCACCCAC TCAAACCTGC AGCCTGTGCA | |
| | | CATGATCCTG GTGCTGCGTA CAGCCCTCAA TCTGTTCTTC | |
| | | AAGCTCAAGA ACTTCAAGAC AGCTGCCACC TTTGCTCGGC | |
| | | GCCTACTAGA ACTCGGGCCC AAGCCTGAGG TGGCCCAACA | |
| | | GACCCGAAAA ATCCTGTCTG CCTGTGAGAA GAATCCCACA | |
| | | GATGCCTACC AGCTCAATTA TGACATGCAC AACCCCTTTG | |
| | | ACATTTGTGC TGCATCATAT CGGCCCATCT ACCGTGGAAA | |
| | | GCCAGTAGAA AAGTGTCCAC TCAGTGGGGC CTGCTATTCC | |
| | | CCTGAGTTCA AAGGTCAAAT CTGCAGGGTC ACCACAGTGA | |
| | | CAGAGATTGG CAAAGATGTG ATTGGTTTAA GGATCAGTCC | |
| | | TCTGCAGTTT CGCTAAGGCC CCCTTTGTGT GCATGGGTCA | |
| | | GTCACCATAT GTTCCCCCCA GAGAATGTGT CTATATCCTC | |
| | | CTTCTAACAG CACCTTCCCC CTGCAGCTAC TCTTCAGATC | |
| | | TGGCTCTCTG TACCCTAAAA CCTAGTATCT TTTTCTCTTC | |
| | | TATGGAAAAT CCGAAGGTCT AAACTTGACT TTTTTGAGGT | |
| | | CTTCTCAACT TGACTACAGT TGTGCTCATA ATTGTCCTTG | |
| | | CCTTTCCAGC TTAATTATTT TAAGGAACAA ATGAAAACTC | |
| | | TGGGCTGGGT GGAGTGGCTC ATACCTGTAA TCCCAGCACT | |
| | | TTGGGAGGCT ACGGTGGGCA GATCATCTGA GGCCAGGAGT | |
| | | TCGAGACCTG CCTGGCCAAC ATGGCAACAC CCCGTCTCTA | |
| | | ATAAAAATAT AAAAATTAGC CTGGCATGGT AGCATGCGCC | |
| | | TATAGTCCCA GCTGCTCAGG AGGCTGAGGC ATGAGAATCG | |
| | | CTTGAACCTA GGAGGTGGAG GTTGCATTCA ACTGAGATCA | |
| | | TACCACTTCA TTCCAGCCTG GGTGACAGAG CAAGACTCTG | |
| | | TCTCAAAAAA AAAAAAAAGG AAAACTCTGT GATGGACATT | |
| | | TGTTTAGTAA ATCCCTTCAG TATTTATCCC TCCTTTCCCC | |
| | | ACAGCAGCTT TCTTTCCTGT CAACTAGAAA GGAGCAGGAT | |
| | | GTAATAAATA CATTTTGGTG TGACTAGGCC ACACCAACTC | |
| | | TTAATCATCT CCCATTTTCC TTAGACATTT AAATTTCAAG | |
| | | GCAGGTACCC TCTGTGTACT CAGAAATTTG AAGAAGTTAT | |
| | | TTGGTTTTCC AAAATGCACA CTGCGGGTTA TTGATTTGTT | |
| | | CTTTACAACT ATTGTTCTCA TATTTCTCAC ACTAAATAAA | |
| | | TCTCTATGAG AGCTTCTTGA CTTGGCCATT TATTTCTTGG | |
| | | ACACTCTCAT GTTCTTGTTC ACCCATGCAG GCACCCCACC | |
| | | AAAGTACATA TCTTCCTTCC AGTAATAATT TTTAATTACA | |
| | | AAATAAACAT CCACTATTGG AAAAAAAAAA AAAAAGCTAG | |
| | | CCGGGCATGG TGGTGGGTGC CTGTAATCCC AGCTACTCTG | |
| | | GAGGCTGAGG CAGAGGATTG CTTGAACCCG GGAGGCGGAG | |

TABLE 1-continued

Plasma cell dyscrasia Biomarker/Housekeeper Sequence Information

| Gene Name | RefSeq Accession | Sequence | SEQ ID NO: |
|---|---|---|---|
| | | GTTGCAGTAA GCTGAGATCG CGCCACCGCA CTCCAGCCTG | |
| | | GGCGACAGAG TGAGACTCCA TCTCAAAAAA AAAGAAAGAA | |
| | | AAAAAGAAGC ACATGTTTTT CATAGGGTAT ATATGAGGAC | |
| | | CTAAACTGCT GTGAAAATGA TAGAAAGCAA GTAGCTCCCT | |
| | | TATTCTGTTT TTGATTGCAG CCTTTTATCT TTTGCTAATT | |
| | | ATAGCAATAT TTATTGAGCA CCTGCCATGT GACTGTCACT | |
| | | GTTCTAGATA TTTTACATGT AATATACAGA TAAAAGAATA | |
| | | GTACTTTATA TATATTACAA TGATACAATG ATTACATTAA | |
| | | CAATACAATA TTTTGCTTGT CATATGCTAA GAATAATTGG | |
| | | GTAGAGTGAC ATTACTGTGC CTTCGATTAA AATAAGTACT | |
| | | TTTTTGCGTG TTAAATTCAT GTTTTCAATA AATAATAAAT | |
| | | GCATATAGTT GAAAAATCAG TAAATA | |
| FBXW7 | NM_001013415.1 | AGACAGGTCA GGACATTTGG TAGGGGAAGG TTGAAAGACA | 5 |
| | | AAAGCAGCAG GCCTTGGGTT CTCAGCCTTT TAAAAACTAT | |
| | | TATTAAATAT ATATTTTTAA AATTTAGTGG TTAGAGCTTT | |
| | | TAGTAATGTG CCTGTATTAC ATGTAGAGAG TATTCGTCAA | |
| | | CCAAGAGGAG TTTTAAAATG TCAAAACCGG GAAAACCTAC | |
| | | TCTAAACCAT GGCTTGGTTC CTGTTGATCT TAAAAGTGCA | |
| | | AAAGAGCCTC TACCACATCA AACTGTGATG AAGATATTTA | |
| | | GCATTAGCAT CATTGCCCAA GGCCTCCCTT TTTGTCGAAG | |
| | | ACGGATGAAA AGAAAGTTGG ACCATGGTTC TGAGGTCCGC | |
| | | TCTTTTTCTT TGGGAAAGAA ACCATGCAAA GTCTCAGAAT | |
| | | ATACAAGTAC CACTGGGCTT GTACCATGTT CAGCAACACC | |
| | | AACAACTTTT GGGGACCTCA GAGCAGCCAA TGGCCAAGGG | |
| | | CAACAACGAC GCCGAATTAC ATCTGTCCAG CCACCTACAG | |
| | | GCCTCCAGGA ATGGCTAAAA ATGTTTCAGA GCTGGAGTGG | |
| | | ACCAGAGAAA TTGCTTGCTT TAGATGAACT CATTGATAGT | |
| | | TGTGAACCAA CACAAGTAAA ACATATGATG CAAGTGATAG | |
| | | AACCCCAGTT TCAACGAGAC TTCATTTCAT TGCTCCCTAA | |
| | | AGAGTTGGCA CTCTATGTGC TTTCATTCCT GGAACCCAAA | |
| | | GACCTGCTAC AAGCAGCTCA GACATGTCGC TACTGGAGAA | |
| | | TTTTGGCTGA AGACAACCTT CTCTGGAGAG AGAAATGCAA | |
| | | AGAAGAGGGG ATTGATGAAC CATTGCACAT CAAGAGAAGA | |
| | | AAAGTAATAA AACCAGGTTT CATACACAGT CCATGGAAAA | |
| | | GTGCATACAT CAGACAGCAC AGAATTGATA CTAACTGGAG | |
| | | GCGAGGAGAA CTCAAATCTC CTAAGGTGCT GAAAGGACAT | |
| | | GATGATCATG TGATCACATG CTTACAGTTT TGTGGTAACC | |
| | | GAATAGTTAG TGGTTCTGAT GACAACACTT TAAAAGTTTG | |
| | | GTCAGCAGTC ACAGGCAAAT GTCTGAGAAC ATTAGTGGGA | |
| | | CATACAGGTG GAGTATGGTC ATCACAAATG AGAGACAACA | |
| | | TCATCATTAG TGGATCTACA GATCGGACAC TCAAAGTGTG | |
| | | GAATGCAGAG ACTGGAGAAT GTATACACAC CTTATATGGG | |
| | | CATACTTCCA CTGTGCGTTG TATGCATCTT CATGAAAAAA | |
| | | GAGTTGTTAG CGGTTCTCGA GATGCCACTC TTAGGGTTTG | |
| | | GGATATTGAG ACAGGCCAGT GTTTACATGT TTTGATGGGT | |
| | | CATGTTGCAG CAGTCCGCTG TGTTCAATAT GATGGCAGGA | |
| | | GGGTTGTTAG TGGAGCATAT GATTTTATGG TAAAGGTGTG | |
| | | GGATCCAGAG ACTGAAACCT GTCTACACAC GTTGCAGGGG | |
| | | CATACTAATA GAGTCTATTC ATTACAGTTT GATGGTATCC | |
| | | ATGTGGTGAG TGGATCTCTT GATACATCAA TCCGTGTTTG | |
| | | GGATGTGGAG ACAGGGAATT GCATTCACAC GTTAACAGGG | |
| | | CACCAGTCGT TAACAAGTGG AATGGAACTC AAAGACAATA | |
| | | TTCTTGTCTC TGGGAATGCA GATTCTACAG TTAAAATCTG | |
| | | GGATATCAAA ACAGGACAGT GTTTACAAAC ATTGCAAGGT | |
| | | CCCAACAAGC ATCAGAGTGC TGTGACCTGT TTACAGTTCA | |
| | | ACAAGAACTT TGTAATTACC AGCTCAGATG ATGGAACTGT | |
| | | AAAACTATGG GACTTGAAAA CGGGTGAATT TATTCGAAAC | |
| | | CTAGTCACAT TGGAGAGTGG GGGGAGTGGG GGAGTTGTGT | |
| | | GGCGGATCAG AGCCTCAAAC ACAAAGCTGG TGTGTGCAGT | |
| | | TGGGAGTCGG AATGGGACTG AAGAAACCAA GCTGCTGGTG | |
| | | CTGGACTTTG ATGTGGACAT GAAGTGAAGA GCAGAAAAGA | |
| | | TGAATTTGTC CAATTGTGTA GACGATATAC TCCCTGCCCT | |
| | | TCCCCCTGCA AAAAGAAAAA AAGAAAAGAA AAAGAAAAAA | |
| | | ATCCCTTGTT CTCAGTGGTG CAGGATGTTG GCTTGGGGCA | |
| | | ACAGATTGAA AAGACCTACA GACTAAGAAG GAAAAGAAGA | |
| | | AGAGATGACA AACCATAACT GACAAGAGAG GCGTCTGCTG | |
| | | TCTCATCACA TAAAAGGCTT CACTTTTGAC TGAGGGCAGC | |
| | | TTTGCAAAAT GAGACTTTCT AAATCAAACC AGGTGCAATT | |
| | | ATTTCTTTAT TTTCTTCTCC AGTGGTCATT GGGCAGTGTT | |
| | | AATGCTGAAA CATCATTACA GATTCTGCTA GCCTGTTCTT | |
| | | TTACCACTGA CAGCTAGACA CCTAGAAAGG AACTGCAATA | |
| | | ATATCAAAAC AAGTACTGGT TGACTTTCTA ATTAGAGAGC | |
| | | ATCTGCAACA AAAAGTCATT TTTCTGGAGT GGAAAAGCTT | |

TABLE 1-continued

Plasma cell dyscrasia Biomarker/Housekeeper Sequence Information

| Gene Name | RefSeq Accession | Sequence | SEQ ID NO: |
|---|---|---|---|
| | | AAAAAAATTA CTGTGAATTG TTTTTGTACA GTTATCATGA<br>AAAGCTTTTT TTTTTTTTTT TTTGCCAACC ATTGCCAATG<br>TCAATCAATC ACAGTATTAG CCTCTGTTAA TCTATTTACT<br>GTTGCTTCCA TATACATTCT TCAATGCATA TGTTGCTCAA<br>AGGTGGCAAG TTGTCCTGGG TTCTGTGAGT CCTGAGATGG<br>ATTTAATTCT TGATGCTGGT GCTAGAAGTA GGTCTTCAAA<br>TATGGGATTG TTGTCCCAAC CCTGTACTGT ACTCCCAGTG<br>GCCAAACTTA TTTATGCTGC TAAATGAAAG AAAGAAAAAA<br>GCAAATTATT TTTTTTTATT TTTTTTCTGC TGTGACGTTT<br>TAGTCCCAGA CTGAATTCCA AATTTGCTCT AGTTTGGTTA<br>TGGAAAAAAG ACTTTTTGCC ACTGAAACTT GAGCCATCTG<br>TGCCTCTAAG AGGCTGAGAA TGGAAGAGTT TCAGATAATA<br>AAGAGTGAAG TTTGCCTGCA AGTAAAGAAT TGAGAGTGTG<br>TGCAAAGCTT ATTTTCTTTT ATCTGGGCAA AAATTAAAAC<br>ACATTCCTTG GAACAGAGCT ATTACTTGCC TGTTCTGTGG<br>AGAAACTTTT CTTTTTGAGG GCTGTGGTGA ATGGATGAAC<br>GTACATCGTA AAACTGACAA AATATTTTAA AAATATATAA<br>AACACAAAAT TAAAATAAAG TTGCTGGTCA GTCTTAGTGT<br>TTTACAGTAT TTGGGAAAAC AACTGTTACA GTTTTATTGC<br>TCTGAGTAAC TGACAAAGCA GAAACTATTC AGTTTTTGTA<br>GTAAAGGCGT CACATGCAAA CAAACAAAAT GAATGAAACA<br>GTCAAATGGT TTGCCTCATT CTCCAAGAGC CACAACTCAA<br>GCTGAACTGT GAAAGTGGTT TAACACTGTA TCCTAGGCGA<br>TCTTTTTTCC TCCTTCTGTT TATTTTTTTG TTTGTTTTAT<br>TTATAGTCTG ATTTAAAACA ATCAGATTCA AGTTGGTTAA<br>TTTTAGTTAT GTAACAACCT GACATGATGG AGGAAAACAA<br>CCTTTAAAGG GATTGTGTCT ATGGTTTGAT TCACTTAGAA<br>ATTTTATTTT CTTATAACTT AAGTGCAATA AAATGTGTTT<br>TTTCATGTTA | |
| GNA13 | NM_006572.5 | CTCCTTCCCT CCCTCCCTCC CCCGCTGTCC TGGCCCGCCC<br>TGCCCGGCCC GCCCTGCGAG TCAGTTCGCT GGTTCCCTCC<br>CTCCCTGGGC GCGCTCGGGC CGCCGCCGCG CTCCCCGCCC<br>TCGAGCCTCG GTGCCGGAGC CGCCCGCCGC CGGAGGAGGA<br>GGTGGAGGGA GCCGGAGGGG CCCGCCGAGG CGGCGGCGGC<br>GGCGGCAAGA TGGCGGACTT CCTGCCGTCG CGGTCCGTGC<br>TGTCCGTGTG CTTCCCCGGC TGCCTGCTGA CGAGTGGCGA<br>GGCCGAGCAG CAACGCAAGT CCAAGGAGAT CGACAAATGC<br>CTGTCTCGGG AAAAGACCTA TGTGAAGCGG CTGGTGAAGA<br>TCCTGCTGCT GGGCGCGGGC GAGAGCGGCA AGTCCACCTT<br>CCTGAAGCAG ATGCGGATCA TCCACGGGCA GGACTTCGAC<br>CAGCGCGCGC GCGAGGAGTT CCGCCCCACC ATCTACAGCA<br>ACGTGATCAA AGGTATGAGG GTGCTGGTTG ATGCTCGAGA<br>GAAGCTTCAT ATTCCCTGGG GAGACAACTC AAACCAACAA<br>CATGGAGATA AGATGATGTC GTTTGATACC CGGGCCCCCA<br>TGGCAGCCCA AGGAATGGTG GAAACAAGGG TTTTCTTACA<br>ATATCTTCCT GCTATAAGAG CATTATGGGC AGACAGCGGC<br>ATACAGAATG CCTATGACCG GCGTCGAGAA TTTCAACTGG<br>GTGAATCTGT AAAATATTTC CTGGATAACT TGGATAAACT<br>TGGAGAACCA GATTATATTC CATCACAACA AGATATTCTG<br>CTTGCCAGAA GACCCACCAA AGGCATCCAT GAATACGACT<br>TTGAAATAAA AAATGTTCCT TTCAAAATGG TTGATGTAGG<br>TGGTCAGAGA TCAGAAAGGA AACGTTGGTT TGAATGTTTC<br>GACAGTGTGA CATCAATACT TTTCCTTGTT TCCTCAAGTG<br>AATTTGACCA GGTGCTTATG GAAGATCGAC TGACCAATCG<br>CCTTACAGAG TCTCTGAACA TTTTTGAAAC AATCGTCAAT<br>AACCGGGTTT TCAGCAATGT CTCCATAATT CTGTTCTTAA<br>ACAAGACAGA CTTGCTTGAG GAGAAGGTGC AAATTGTGAG<br>CATCAAAGAC TATTTCCTAG AATTTGAAGG GGATCCCCAC<br>TGCTTAAGAG ACGTCCAAAA ATTCCTGGTG GAATGTTTCC<br>GGAACAAACG CCGGGACCAG CAACAGAAGC CCTTATACCA<br>CCACTTCACC ACTGCTATCA ACACGGAGAA CATCCGCCTT<br>GTTTTCCGTG ACGTGAAGGA TACTATTCTG CATGACAACC<br>TCAAGCAGCT TATGCTACAG TGATGTACAA AAGACTTGCT<br>GTTTTAATAT CTTTTTGTGT TTTTGATGTT TTCTGTTTGT<br>TTTGTTTTTT AAAATAGCAG TTTACAACCA GAATTAGAAC<br>AATCTTAATT CTACGTTTAA CTTCTTGAAA ATCTTAGTAC<br>TTTTTCTGCG GCCTTTGGTT TGTGGCTGAA AGCTGTTGAG<br>TGACTCATCG CCAAGATTTG CTGTAATGCA GGCTTTGATC<br>TGTTTCACCA TGGCTTCTAT TCAAGTCCAG TTAAAACCTC<br>CCAGCTGACC TCAGACTAGG CATATTTCAG GCTTTAAATT<br>ATTCTACTTT CCAAACTGAA TTCTCCTGCA GTGCCAAGTA<br>TCAAAGGTGT CCTTAAATAC TTGTAGGGAT GAGGTTAGGA<br>ATATTCAGTT CCAAAACAAG ATATCTTCTG TCCGCCTTAC | 6 |

TABLE 1-continued

| Gene Name | RefSeq Accession | Sequence | SEQ ID NO: |
|---|---|---|---|
| | | ATATAGCAGT GACACTTGTT GCCTAACTTT ATGGTGACCT<br>CCTATTTTGT AAGGGCTGTT AGAAGTTCTA TCTAAGAAAT<br>GGCATTCTGT AGGTTTATAG AAGGTTTAGC CTTCATATTT<br>TAATTGCTTG TATACACAAC AGCTGTTTTG CTTTTAGATT<br>TCTGTGTTTC TGAAGGTAAT GTTCTTCCTG TTTTCAAGTT<br>TACATAAGGA TCTTTGGTCT GATGCTGATG AAGAGTTCAC<br>AGGTGGTATG GGAGAGCAAA AGGCAAGCTA ATGCTGTTTA<br>CCGTGTTTTG GTCAAACGTA ACGAGTGAAA TAGAATTTGC<br>CTTTCTCATA TTTAATTATC ATGTAGTTTA ATGTACCATA<br>TGTGAAACAT TCTGGCCATA GCAGCAACTA AAAACTGCAA<br>GCAACTTGGT AACAGAACTT TCTAAATAAA CTTAACCTGT<br>TCCAGAATGT CATGTATTTG ACTTTTAAGC CCTATCTCAG<br>TTGGTCAGTA AAGACCAATC CTTACTGTAG GAAATCATTG<br>TTGTATCATC ACAAACATCT ATCTTTTGCT GTCCTGTCCA<br>GTCCCATCAA CTCCACACTG TGCCATTTGT GGCATCGTTT<br>TGTTTATTTG GAGTTTGCTA AGGGCAGTAT TTTTCTGTCA<br>AGACTATTCA AGAAGGCATT ATTTGAGATT CCTGTTCATT<br>CTTGGTGTGT CTCTAACAGA TACAGTATGT ATACATTTGT<br>ATAATTGTTG TTGTTGAAAG TCCAGCTTTT TTGAGGTATA<br>TTTTAAATGT TTTAAGGATG CTTCTAAGGA TCAGTAGTAA<br>TTTTTTTAGT TCGCACCTAA AGATGATTAC ATTGACCTCC<br>CCCGACTGCT TACCAAATTA AAATGTGTCC ACGAAGTAGC<br>TTTGTGATCG CAGATACATT CATAGTGAAC TCATCAGAAT<br>GGCTGGTTTG CAGTACTGAA ATACTATCTT CTAGGCTGTA<br>TGTAGTGCTA CAATTAGAGA AACAGAAGTC CAAGGCTGGC<br>GACAGCTTGA AAAGTCTGAC AGCTTTTCTA CTTTTCCTGA<br>AAATTTTAAG ACTGTGATAT CTGTCATTTT ACTGTATAGC<br>TGACTGTGTA CTCAGGTATT TTATTGGTCC TTGAAAGATT<br>GGTCGTTATG GATCACCCAG CCTTTCCAAG TCAGTGGCTG<br>TTGTTCTGTC TTGCTGTCTG ATACGAGAGT GGGGCTTTTC<br>AGTGAACTAA CCAGGGATTG TTCTTGACAT ACCTGACTTT<br>TCTCACATTT GAACTTCCAC TATCATTGTA TCCATATAAC<br>TTCTAGCATT TTCATGCCAT GGTAATCCAT GAGCTACACA<br>TACGTAGCCC GGCACCGTGA TGCAAGTTCA TGGTATCGTG<br>CATGTTCGTG GTATCATGGT ATCATTCATG CGTGTTTGAA<br>TAGTTCTACA TCTAGTGCTT CTTGCCAAAA AGAATACATT<br>GTTTAAATTC ACAAAATTAG CATAATTGCA GTGCTAATGA<br>ATATCGGAAT ATGTGCACAG TAACATTTGG ACTATTCATT<br>GGAGAGTTTA CCCATACATT TAGCAAATTG AATGGCCAAA<br>ACATTTGACT CCAGTGAGGG CTCAAGTTAG ATCCCTATAG<br>AAAGAGGACA CTTCATCTTA CTTAAGTCAT AGTTAAGATC<br>TGTGATACGA ACCATAGATA TTGCCTGACA AAGCAGAAAT<br>CACCAAGTTT CCCCCTTTTG AATTACCACC AAGAAGTGTT<br>GAAACACCAA ATAGATATCA TGTTATTTTG GGCATTTGCA<br>GTTTTCTTCC CTGCTGCATG TAATGTCTCA GAATCAACAT<br>TCTTTTAAAA TCTAGACTAT ATTTTGAGGC AATGAATTAC<br>TTATATTCAA CTTAGGCTTG TTTTGACATT CAGTAGAACT<br>TTAAGTTCAA TCTAAAGGCT TCAGTCCACA TTTTTTTATA<br>CGTTGTATTT TAAAAACGTT TGAAAGGAGT CTTACACCTG<br>TATCATGAAA ACTGAATCCT TTTGAAATAC CACTATATGA<br>AGAGAGAGAT GAAATTTAGT GAACAGAATT GAAAAGGTGC<br>TCATAATTTC ACTATGCAAA CTTACCCCAG TCTCTAAAAA<br>AGTAATTTAG ATTTAAAGTT CTTTGATGTA TTTGATTTTC<br>TAAATCTTTA TGGTTATGAT TTGGAATAAA ATGTGCCTAA<br>TCCTGTGTTA CATTCTGTTC TTAAATCTGA ATGCCTTCTC<br>ATTTAATTCT GAGGAAATAT CACACAAGTG TCTTCATTGA<br>CCTTGAAGAA ATGTATATAC AGTTGCCTTA TAAAACAACA<br>TAAATTTAGA CCATAACTTT TATAGAGAAA GGGTTTTGTC<br>AAATGTTTTC TGAAAATCTG AGTAATTCAA AGCATGCCTC<br>TGCCCCTTTA ATATTTTTAA TAACCTGCAT TGTTGCTGTC<br>TGCCAAATAT TAAATTGAAA TCTTCATTTC AATTTTATTA<br>TCTGGAAAGG GCACTGGATT GCTCTGCAAC CAAAGAAAGC<br>AATATGGAAT GAAAAAACTC ATTCACTTTT GTCTTATTTT<br>CTTTTAAGGT GTATTGGCAT GTAATTTGCA TAGAGAAGGT<br>CCTCTGGTTA GTCTCTCAAA TTGAGGCTGT TTAGGGAAAT<br>CCTTATTCAG TTGGTGGCAG TGGTTGGTTT AAAGTAGAAG<br>GAAATAAGAT CGCCTTAATA CCAGAAATGA TTAGAAGTGC<br>TGATTTAGAT TCAACAAATA CCATATGTCC TTATCATTTT<br>TTGTAAGAAG AAATTGGTTA AGTCCTAACT TTCAATGTGT<br>ACCCAAATAC TTGTATTTAT GCTTTTGATA AAATGTATTT<br>TCAGCATTAA TACACATCCG ATTATGCCTT ATTTATATAT<br>GAAGAATAAA GTTACCATGT TACACTGTTA TGTCCTAAAA<br>TTCAAATCAC TATTTGAGAA ACCCTCAAAT TGGTGCTTTC<br>ATTATATAAT GATACATTTA GACAAAACCC CAAACTAAGC | |

TABLE 1-continued

Plasma cell dyscrasia Biomarker/Housekeeper Sequence Information

| Gene Name | RefSeq Accession | Sequence | SEQ ID NO: |
|---|---|---|---|
| | | CATTTGAAAC AAGATTCTCT CCATTGCAGT TTGTAGCAAT | |
| | | GTTATTTCTG TGTATGTCAT GAGAAGGCTA AATATCAGTG | |
| | | TTAATTTCTT GTTTGAATCC GTGAAATCAT GCCTGTAAAG | |
| | | CCCAAACATT TGTAACAAAC TCCCTAATAA ATTTAGAGAA | |
| | | AGTCACTCTG TTACCATTTC ATTTATTTTA GTTTTATTTG | |
| | | AGAAATTAAG ACCAGAAGTT TTGCTCATGT CTTTTTCACT | |
| | | TGGAAATCTG ACTTAGTACC TAGTTAATTT GTCTCTCTCC | |
| | | CATCATTTTA AGGCGTTCGC TTCTGTTAAT CACAGATGAT | |
| | | CTGTCCTTGT GTTGTGCTGC TTGACTAAAA GCACTGTTTT | |
| | | GTTTTGTTTT GTTTTGTTTT TTAATGATAG GATACAGGGT | |
| | | GGCTTTTCAG TCTAGTAAAC ATGAGGAGGG GAGAGATTGT | |
| | | GGGTGGGTGT GGGTGTGTCC GCATGTCCCA AATACAGCAC | |
| | | ATGCCCATTT TTTTATGGTA CGAGGTTAGG GCTTATTAAT | |
| | | AAATGTATAC TAGATCTTGA AGTGTAAGTC TAAGTCTGAA | |
| | | CATTTTAAAC AAGTTGGACT TTATGGCTTT TTCAAGTTCC | |
| | | ATCAAGTAGA TACTAGTCTT AGGCTGGTAG GTGATTAACA | |
| | | ACATCATTTG GAGTACAGTG TTTGTACCAC TAGCATTCTT | |
| | | ATGTCTGTAC TTGAACGTGT AGTTAGCATT TAAGTTATGT | |
| | | TCACTCTTGT AGCATTCAGG TCTTACCATC TGGTTTCAAA | |
| | | TGCGAGAGCT TATATGAACA TTGTTTTGAA AGCATGAATG | |
| | | ATATGGCAAT ATTTTATGTC TTGATAAGGA GAGTTTTGTG | |
| | | ACATATACAA ATCTGCTGTT GATGATGAAA GTTTACAGGT | |
| | | GGATCAGAGT ATGCTGGAAC TCAGTGTGCA TAAAATTTCA | |
| | | GTCAGTGAAT ATCACTGAAC GTCATATACT ACTTGGTATG | |
| | | TGACTTTGGT TTGTGTTAAG AAAGCTTGTA TATAATATTT | |
| | | TTTGCCATAG TAAGTGAGAA ATTGTCCTTA ATCATGCCTG | |
| | | TTTGATGGTA CTAGGAAAGA AAGGGGTAGA GATTAATTCT | |
| | | TGCACAGTAT AAGCAACAGT GCAACAAACT ATGCCATTTA | |
| | | CCTTTTACCT CTTACTTGAA GGCAGAATCG CAAAACGTTT | |
| | | GAAATGGCTT TTCTAAACTA CTCTACTCTG GTGAGAGCTC | |
| | | ATTTACCACA AGAAGCCTTA TAAAAAAGTA TATTTTGTAA | |
| | | TAACCCCGTA GATACTGTAC CTAACAAAAC ATGACTCGTA | |
| | | TTAGCTCTAT AAAATATTTG TGGCTTAGGA TTTTTTTTTT | |
| | | ACATATATCT TTTTATAACT TTCCAGGAAC TAAGCACATT | |
| | | ATCTGATAAT TGTTGTAAAT TTTTTTGTCA GTGCTTTAGT | |
| | | TCAGGATGGG CAATAAATTA TTTCTAAAGG AGGTCTAAAA | |
| | | GTGGAAAGAA TGGTTTGATT TTATAAAATG AGTTGCTAGT | |
| | | TCATTACAGC TTTTTACTTT TGTACATATT TTGCAAAACA | |
| | | TTTGCCTCTT GCTATTAATA TTTGCTTTGT AAAAATTACT | |
| | | GACATTTAAT AAACATTTGT AAACAATTCA AAAAAAAAAA | |
| | | AAAAAA | |
| IL8 | NM_000584.3 | GAGGGTGCAT AAGTTCTCTA GTAGGGTGAT GATATAAAAA | 7 |
| | | GCCACCGGAG CACTCCATAA GGCACAAACT TTCAGAGACA | |
| | | GCAGAGCACA CAAGCTTCTA GGACAAGAGC CAGGAAGAAA | |
| | | CCACCGGAAG GAACCATCTC ACTGTGTGTA AACATGACTT | |
| | | CCAAGCTGGC CGTGGCTCTC TTGGCAGCCT TCCTGATTTC | |
| | | TGCAGCTCTG TGTGAAGGTG CAGTTTTGCC AAGGAGTGCT | |
| | | AAAGAACTTA GATGTCAGTG CATAAAGACA TACTCCAAAC | |
| | | CTTTCCACCC CAAATTTATC AAAGAACTGA GAGTGATTGA | |
| | | GAGTGGACCA CACTGCGCCA ACACAGAAAT TATTGTAAAG | |
| | | CTTTCTGATG GAAGAGAGCT CTGTCTGGAC CCCAAGGAAA | |
| | | ACTGGGTGCA GAGGGTTGTG GAGAAGTTTT TGAAGAGGGC | |
| | | TGAGAATTCA TAAAAAAATT CATTCTCTGT GGTATCCAAG | |
| | | AATCAGTGAA GATGCCAGTG AAACTTCAAG CAAATCTACT | |
| | | TCAACACTTC ATGTATTGTG TGGGTCTGTT GTAGGGTTGC | |
| | | CAGATGCAAT ACAAGATTCC TGGTTAAATT TGAATTTCAG | |
| | | TAAACAATGA ATAGTTTTTC ATTGTACCAT GAAATATCCA | |
| | | GAACATACTT ATATGTAAAG TATTATTTAT TTGAATCTAC | |
| | | AAAAAACAAC AAATAATTTT TAAATATAAG GATTTTCCTA | |
| | | GATATTGCAC GGGAGAATAT ACAAATAGCA AAATTGAGGC | |
| | | CAAGGGCCAA GAGAATATCC GAACTTTAAT TTCAGGAATT | |
| | | GAATGGGTTT GCTAGAATGT GATATTTGAA GCATCACATA | |
| | | AAAATGATGG GACAATAAAT TTTGCCATAA AGTCAAATTT | |
| | | AGCTGGAAAT CCTGGATTTT TTTCTGTTAA ATCTGGCAAC | |
| | | CCTAGTCTGC TAGCCAGGAT CCACAAGTCC TTGTTCCACT | |
| | | GTGCCTTGGT TTCTCCTTTA TTTCTAAGTG GAAAAAGTAT | |
| | | TAGCCACCAT CTTACCTCAC AGTGATGTTG TGAGGACATG | |
| | | TGGAAGCACT TTAAGTTTTT TCATCATAAC ATAAATTATT | |
| | | TTCAAGTGTA ACTTATTAAC CTATTTATTA TTTATGTATT | |
| | | TATTTAAGCA TCAAATATTT GTGCAAGAAT TTGGAAAAAT | |
| | | AGAAGATGAA TCATTGATTG AATAGTTATA AAGATGTTAT | |
| | | AGTAAATTTA TTTTATTTTA GATATTAAAT GATGTTTTAT | |
| | | TAGATAAATT TCAATCAGGG TTTTTAGATT AAACAAACAA | |

TABLE 1-continued

| Plasma cell dyscrasia Biomarker/Housekeeper Sequence Information | | | |
|---|---|---|---|
| Gene Name | RefSeq Accession | Sequence | SEQ ID NO: |
| | | ACAATTGGGT ACCCAGTTAA ATTTTCATTT CAGATAAACA<br>ACAAATAATT TTTTAGTATA AGTACATTAT TGTTTATCTG<br>AAATTTTAAT TGAACTAACA ATCCTAGTTT GATACTCCCA<br>GTCTTGTCAT TGCCAGCTGT GTTGGTAGTG CTGTGTTGAA<br>TTACGGAATA ATGAGTTAGA ACTATTAAAA CAGCCAAAAC<br>TCCACAGTCA ATATTAGTAA TTTCTTGCTG GTTGAAACTT<br>GTTTATTATG TACAAATAGA TTCTTATAAT ATTATTTAAA<br>TGACTGCATT TTTAAATACA AGGCTTTATA TTTTTAACTT<br>TAAGATGTTT TTATGTGCTC TCCAAATTTT TTTTACTGTT<br>TCTGATTGTA TGGAAATATA AAAGTAAATA TGAAACATTT<br>AAAATATAAT TTGTTGTCAA AGTAAAAAAA AAAAAAAA | |
| JMJD1C | NM_001282948.1 | CTCGTTCTCA TTTGGGTGTC TGCACTGTTG GAAGCTACTG<br>CACTGTGTTT CCACGCAGAC AGAGTACAGT GGGAAAGGCT<br>TTCTCCAGCT GATGGATGGC TGTTCTCTTT ATTTGGAGTA<br>TCTTACTGGT TATGTAAGCG ACCTCGAGAG AAATTATCCT<br>GACCCAGATC GGAGGATGCA GTAGTGCTTC AGCTGCAGGA<br>TTTCTTAGTC GTTAACACCA CAGTGCTGAT GACAAAGAGC<br>GAGTTGTAAT CCTCATCACT GCCAGGGCTG AGCCAGAGCA<br>GACAGAAAAT CGTCATTTGC TCGTTGGAGA CTTGTTAGGT<br>TACAGCTCCT GCTTCGTTCT GTGGTCTTGG CTTTTCTTCC<br>TATACAATGA CGCCGCTGCA AGTGAGCTCA GAAATGCTTG<br>GTTTGAGAGC CATTTGCCTG TGATTTTTGA AGACTAAAGA<br>AGTATTTACA CTAGATACTC TTCCAGAACA AAATAGAAAT<br>TTCAGCAAAT ACTTACTGAC CTTTAAAGCC TTGTTGTGGA<br>TTTCTGAGAT TTAAAGATAC TTTAAAATTC TCAAGAACAA<br>AACTTTCAAA CCTCTGGTTG AAAGAAATAT ACCCAGTTCA<br>GTCACTGCAG TAGAATTCCT TGTAGATAAG CAACTGGATT<br>TTTTAACTGA AGATAGTGCC TTTCAGCCCT ACCAGGACGA<br>CATAGACAGC CTAAACCCAG TTCTCAGGGA CAACCCGCAG<br>CTTCATGAGG AAGTGAAAGT CTGGGTAAAG GAACAAAAGG<br>TTCAGGAGAT TTTTATGCAA GGTCCTTATT CCTTAAATGG<br>ATACAGAGTG AGAGTATATA GACAAGACTC TGCCACCCAG<br>TGGTTTACTG GCATAATTAC TCATCATGAT CTCTTCACCC<br>GCACCATGAT CGTTATGAAT GATCAGGTAC TAGAACCACA<br>GAATGTCGAT CCTTCTATGG TTCAAATGAC CTTTCTAGAT<br>GATGTTGTTC ACTCTTTGTT AAAAGGTGAA AATATTGGCA<br>TTACATCACG ACGCAGGTCT CGTGCCAATC AAAACGTCAA<br>CGCTGTTCAC AGCCATTATA CACGTGCCCA AGCAAATAGT<br>CCCAGACCAG CAATGAACTC CCAAGCTGCT GTACCAAAAC<br>AGAATACACA CCAGCAACAG CAACAAAGAA GTATCCGTCC<br>AAATAAGAGG AAGGGCTCAG ATAGCAGTAT ACCAGATGAA<br>GAGAAGATGA AGGAGGAAAA ATATGATTAT ATATCACGAG<br>GAGAAAATCC TAAAGGTAAA AACAAACACT TGATGAATAA<br>AAGAAGGAAA CCTGAGGAGG ATGAAAAGAA ACTAAATATG<br>AAAAGACTTC GAACTGACAA TGTTTCAGAC TTTTCTGAGA<br>GCAGTGACTC AGAAAATTCA AATAAGAGAA TAATAGATAA<br>TTCCTCAGAA CAGAAGCCAG AGAATGAATT GAAAAATAAA<br>AATACTTCAA AAATAAATGG AGAAGAAGGA AAACCCCATA<br>ATAATGAGAA GGCAGGAGAA GAGACCCTAA AAAATAGCCA<br>GCCTCCCTGG GATCAAATAC AGGAAGATAA AAAACATGAA<br>GAAGCAGAGA AGCGGAAGTC TGTTGACACT CAGCTTCAAG<br>AAGATATGAT TATTCATTCG TCAGAACAGT CCACAGTTTC<br>TGATCATAAT TCTAATGATT TACTTCCTCA GGAATGCAAT<br>ATGGATAAAA CACATACCAT GGAATTGCTA CCAAAGGAGA<br>AGTTTGTATC CAGACCACCC ACACCAAAAT GTGTTATTGA<br>TATTACAAAT GACACTAATT TAGAAAAGGT GGCTCAGGAA<br>AACTCAAGTA CCTTTGGCCT TCAGACACTT CAGAAAATGG<br>ATCCTAATGT TAGTGATTCA AAACACTCTA TTGCAAATGC<br>AAAATTCTTG GAAACAGCAA AAAAAGATTC TGACCAGAGC<br>TGGGTCAGTG ATGTAGTTAA AGTGGATCTA ACCCAATCAA<br>GTGTTACAAA TGCTTCTTCA GGAAATGATC ACTTGAACAT<br>GGAAAAAGAG AAGTATGTCT CTTACATTTC TCCTTTAAGT<br>GCAGTTTCTG TCATGGAAGA TAAGCTGCAT AAGCGAAGTC<br>CACCTCCAGA GACTATAAAA TCTAAACTTA ATACTTCAGT<br>AGATACTCAC AAGATAAAAT CCAGCCCATC ACCTGAAGTT<br>GTTAAACCCA AAATAACTCA TTCTCCTGAT TCTGTAAAGT<br>CTAAGGCCAC TTATGTGAAC AGCCAAGCTA CTGGTGAAAG<br>AAGATTGGCA AATAAGATAG AACATGAGCT ATCAAGATGC<br>AGTTTTCATC CAATTCCTAC TCGAAGCAGT ACATTAGAAA<br>CTACAAAGAG TCCTCTTATC ATTGATAAAA ATGAGCATTT<br>TACAGTTTAC AGAGATCCTG CACTTATTGG GTCAGAAACA<br>GGAGCTAATC ATATTTCACC TTTCCTAAGC CAGCATCCTT<br>TTCCTCTTCA CTCCTCATCT CATAGAACCT GTTTAAATCC | 8 |

TABLE 1-continued

Plasma cell dyscrasia Biomarker/Housekeeper Sequence Information

| Gene Name | RefSeq Accession | Sequence | SEQ ID NO: |
|---|---|---|---|
| | | AGGTACCCAT CATCCTGCCT TAACTCCTGC ACCCCATTTA<br>CTAGCCGGAT CATCTAGTCA AACTCCATTA CCTACCATTA<br>ACACTCATCC TCTGACTAGT GGTCCACACC ATGCTGTTCA<br>TCACCCTCAT TTACTTCCCA CTGTGTTACC TGGAGTGCCT<br>ACTGCCTCCT TACTTGGTGG CCACCCACGA CTAGAGAGTG<br>CTCATGCCAG CAGCTTGAGC CACTTAGCGC TAGCACACCA<br>GCAACAACAA CAGTTGTTAC AGCACCAGTC ACCTCATCTT<br>CTTGGACAAG CCCATCCTTC TGCTTCATAT AATCAGCTTG<br>GACTTTATCC AATTATTTGG CAGTATCCAA ATGGAACACA<br>TGCATACTCA GGACTTGGTT TGCCTTCTTC TAAGTGGGTT<br>CACCCAGAAA ATGCAGTTAA TGCTGAAGCT TCATTAAGGA<br>GGAATTCTCC CAGTCCTTGG CTACATCAGC CCACCCCTGT<br>GACCTCAGCA GATGGTATTG GATTACTTAG TCACATTCCT<br>GTCAGACCTT CCAGTGCAGA GCCTCATCGG CCTCTTAAAA<br>TTACAGCCCA TTCCAGTCCA CCATTGACAA AAACTTTAGT<br>AGATCATCAT AAGGAAGAAT TAGAAAGAAA AGCTTTTATG<br>GAACCATTAC GGTCTGTTGC ATCCACATCA GCCAAAAATG<br>ACCTGGATCT AAATAGGTCA CAGACTGGAA AAGATTGTCA<br>CTTACATAGG CATTTTGTGG ATCCAGTATT AAATCAGTTA<br>CAGAGGCCAC CCCAGGAGAC TGGAGAGAGG TTAAACAAAT<br>ACAAAGAGGA ACACCGTCGA ATTCTTCAAG AAAGTATTGA<br>TGTTGCTCCC TTTACAACTA AAATCAAGGG ACTTGAGGGT<br>GAGAGAGAGA ATTATTCCAG AGTGGCATCA TCATCTTCCA<br>GTCCTAAAAG CCATATCATC AAACAAGATA TGGATGTAGA<br>ACGCTCAGTA TCAGATCTTT ATAAAATGAA GCACTCAGTG<br>CCTCAGAGTT TACCCCAAAG TAACTATTTC ACTACATTGT<br>CTAATAGTGT GGTCAATGAA CCACCAAGAT CATACCCATC<br>CAAAGAAGTT TCAAATATTT ACGGTGATAA ACAGAGTAAT<br>GCCCTTGCAG CGGCAGCAGC TAATCCTCAA ACTCTGACTT<br>CATTTATAAC ATCTCTTTCA AAGCCTCCAC CTTTGATTAA<br>ACACCAACCA GAAAGTGAAG GTTTAGTAGG CAAGATACCA<br>GAACATCTTC CACATCAGAT TGCATCTCAC TCAGTAACAA<br>CCTTCAGAAA TGATTGTAGG AGTCCTACCC ATTTGACAGT<br>TTCTTCTACA AATACACTCC GCAGTATGCC TGCATTACAT<br>AGAGCACCAG TATTTCACCC ACCAATCCAT CACAGCCTGG<br>AAAGAAAGGA AGGCAGCTAT AGTAGTCTTT CCCCTCCAAC<br>TTTAACTCCG GTGATGCCAG TAAATGCTGG TGGTAAAGTT<br>CAAGAATCAC AGAAGCCTCC AACTCTAATA CCCGAACCAA<br>AAGACTCCCA GGCAAATTTT AAGAGTTCTT CAGAACAGAG<br>TTTGACGGAG ATGTGGAGAC CTAATAATAA CCTCAGCAAA<br>GAGAAAACTG AATGGCATGT GGAGAAAAGC AGCGGAAAGT<br>TACAGGCTGC TATGGCATCT GTCATTGTGC GTCCATCTTC<br>TAGTACAAAA ACTGATAGTA TGCCAGCAAT GCAGTTAGCT<br>TCTAAAGATC GAGTTAGTGA AAGATCTTCA GCTGGGGCAC<br>ATAAAACAGA TTGCCTCAAA CTAGCAGAAG CCGGAGAAAC<br>TGGAAGAATC ATTTTGCCAA ATGTGAATTC AGACAGTGTT<br>CACACAAAAT CTGAAAAAAA CTTTCAGGCT GTCTCACAGG<br>GCAGTGTTCC CAGTTCAGTC ATGTCTGCTG TAAATACGAT<br>GTGTAATACC AAAACGGATG TAATCACATC TGCTGCCGAT<br>ACTACCAGTG TTTCCAGCTG GGGTGGTTCA GAAGTAATTT<br>CCTCTTTATC AAATACCATT TTGGCCTCTA CATCATCAGA<br>ATGTGTATCT TCAAAAAGTG TCAGTCAGCC AGTGGCTCAA<br>AAACAAGAAT GCAAGGTCAG CACCACAGCA CCAGTTACAT<br>TAGCCAGTAG TAAGACAGGA AGTGTTGTTC AACCCAGTTC<br>TGGGTTCTCA GGCACAACTG ATTTTATCCA TTTAAAAAAG<br>CACAAGGCAG CATTGGCTGC AGCTCAGTAT AAAAGTAGTA<br>ATGCCAGTGA GACTGAACCT AATGCTATAA AAAATCAGAC<br>ACTTTCAGCC TCCCTTCCTC TGGATAGCAC TGTAATCTGT<br>AGTACAATTA ACAAAGCAAA CTCTGTAGGA AATGGGCAAG<br>CTTCCCAGAC AAGTCAACCA AACTACCATA CTAAACTGAA<br>AAAGGCCTGG CTCACCAGAC ACTCAGAAGA AGATAAAAAT<br>ACTAATAAAA TGGAAAATTC AGGGAATTCT GTATCAGAAA<br>TTATTAAGCC ATGTTCTGTC AACTTAATAG CCTCTACATC<br>TAGTGATATA CAAAATAGTG TAGATAGTAA GATCATAGTT<br>GATAAATATG TAAAAGATGA TAAAGTCAAC AGGAGAAAAG<br>CCAAAAGAAC TTATGAATCT GGCTCTGAAA GTGGAGACTC<br>AGATGAAAGT GAAAGCAAGT CAGAGCAAAG GACTAAAAGA<br>CAACCTAAGC CAACTTACAA AAAGAAGCAA AATGATTTGC<br>AAAAGAGAAA AGGTGAAATA GAAGAAGATT TGAAACCCAA<br>TGGAGTTCTC AGCAGGAGTG CCAAAGAAAG AAGTAAACTG<br>AAGTTGCAAA GCAACAGTAA TACTGGCATT CCTCGTTCAG<br>TATTGAAAGA TTGGCGTAAA GTCAAGAAGC TGAAGCAAAC<br>TGGGGAATCC TTTTTACAGG ATGACTCCTG CTGTGAGATA<br>GGGCCTAATT TACAAAAGTG TCGAGAATGT AGACTTATTC | |

TABLE 1-continued

Plasma cell dyscrasia Biomarker/Housekeeper Sequence Information

| Gene Name | RefSeq Accession | Sequence | SEQ ID NO: |
|---|---|---|---|
| | | GCAGTAAAAA AGGAGAAGAA CCAGCTCACT CACCAGTATT<br>TTGTAGATTT TACTACTTTA GACGGTTGTC ATTTAGTAAA<br>AACGGAGTAG TTAGAATAGA TGGTTTCTCT TCTCCTGACC<br>AATATGATGA TGAAGCTATG AGTTTGTGGA CACATGAAAA<br>TTTTGAAGAT GATGAACTAG ATATAGAGAC TTCTAAATAT<br>ATCTTGGATA TAATAGGTGA TAAGTTCTGT CAATTAGTAA<br>CATCTGAAAA AACAGCTTTG TCCTGGGTGA AAAAGGATGC<br>CAAAATTGCC TGGAAAAGAG CAGTGAGAGG AGTCCGGGAG<br>ATGTGTGATG CATGTGAAGC AACATTGTTT AACATTCACT<br>GGGTCTGCCA AAAATGTGGA TTTGTGGTCT GCTTAGATTG<br>TTACAAGGCA AAGGAAAGGA AGAGTTCTAG AGATAAAGAA<br>CTATATGCTT GGATGAAGTG TGTGAAGGGA CAGCCTCATG<br>ATCACAAACA TTTAATGCCA ACCCAAATTA TACCTGGTTC<br>TGTTTTGACA GATCTTCTAG ATGCCATGCA CACTCTTAGG<br>GAAAAATATG GTATTAAATC CCATTGTCAT TGTACTAACA<br>AACAGAATTT ACAAGTTGGA AATTTTCCTA CAATGAATGG<br>TGTATCTCAA GTTTTACAGA ATGTTCTTAA TCACAGTAAT<br>AAAATTTCTC TGTGCATGCC TGAGTCTCAG CAGCAAAATA<br>CTCCTCCGAA GTCTGAGAAA AATGGTGGCA GCAGCCCAGA<br>GAGTGATGTA GGCACAGATA ACAAGTTAAC TCCTCCAGAA<br>TCCCAGTCAC CACTGCACTG GTTAGCAGAT CTTGCAGAGC<br>AAAAAGCCAG AGAGGAAAAA AAAGAAAACA AAGAACTTAC<br>CCTTGAAAAC CAAATTAAAG AAGAAAGAGA ACAAGACAAC<br>TCTGAATCTC CAAATGGCAG AACATCACCT CTTGTGTCCC<br>AGAATAATGA ACAAGGCTCA ACCTTACGGG ATTTGCTGAC<br>TACAACAGCT GGAAAGCTAC GTGTGGGGTC TACAGATGCT<br>GGCATTGCCT TTGCCCCAGT ATATTCAATG GGAGCCCCAA<br>GTAGCAAAAG TGGACGGACT ATGCCTAACA TTCTTGATGA<br>CATAATTGCT TCAGTTGTTG AAAACAAAAT TCCACCAAGT<br>AAAACCTCCA AGATAAATGT AAAACCAGAG CTTAAAGAAG<br>AGCCTGAAGA AAGCATAATA TCTGCAGTGG ATGAAAATAA<br>TAAATTATAC AGTGATATAC CACATTCTTG GATCTGTGAG<br>AAGCATATTT TATGGCTTAA GGATTATAAG AATAGCAGTA<br>ATTGGAAGCT TTTCAAAGAA TGTTGGAAAC AAGGACAGCC<br>TGCAGTGGTT TCTGGTGTGC ATAAGAAAAT GAACATTAGC<br>CTATGGAAGG CGGAATCAAT TAGTCTTGAT TTTGGAGACC<br>ACCAAGCTGA TCTCCTGAAC TGCAAAGATA GCATCATTTC<br>AAATGCCAAT GTTAAGGAAT TCTGGGATGG TTTTGAAGAA<br>GTTTCAAAAC GGCAGAAAAA CAAGAGTGGA GAAACAGTTG<br>TTTTAAAATT GAAAGACTGG CCTTCAGGAG AAGACTTCAA<br>GACTATGATG CCAGCAAGAT ACGAAGATCT TTTAAAAAGT<br>CTGCCATTGC CAGAATATTG TAATCCAGAA GGAAAATTCA<br>ATTTGGCCTC TCATTTGCCA GGATTTTTTG TACGTCCTGA<br>TCTAGGACCC AGGTTGTGCA GTGCCTATGG TGTAGTTGCT<br>GCTAAAGATC ATGATATAGG AACAACAAAT CTCCATATTG<br>AAGTTTCTGA TGTTGTAAAT ATACTAGTTT ATGTTGGCAT<br>AGCAAAAGGA AATGGCATTC TCTCAAAAGC AGGAATTCTC<br>AAGAAATTTG AGGAAGAAGA TTTGGATGAC ATTTTAAGGA<br>AAAGATTGAA GGACTCAAGT GAAATACCTG GTGCTCTGTG<br>GCATATTTAT GCTGGGAAAG ATGTTGACAA GATAAGGGAA<br>TTTCTTCAAA AGATTTCAAA AGAACAAGGC CTTGAAGTTC<br>TACCAGAACA TGATCCAATA CGTGACCAAA GTTGGTATGT<br>GAACAAAAAG CTCCGTCAAA GGCTGCTTGA AGAATATGGA<br>GTCAGAACCT GTACTCTTAT TCAGTTCCTT GGTGATGCTA<br>TTGTTTTGCC AGCGGGAGCA CTTCATCAGG TTCAGAATTT<br>TCACAGCTGT ATTCAGGTAA CTGAAGATTT TGTGTCTCCA<br>GAACATCTTG TAGAGTCATT TCATTTAACA CAGGAACTGA<br>GACTTTTGAA GGAAGAAATC AATTATGATG ATAAACTACA<br>GGTTAAAAAT ATTTTGTATC ATGCAGTCAA AGAAATGGTG<br>AGAGCCTTGA AGATACACGA GGATGAAGTA GAGGATATGG<br>AAGAAAATTA AGTGTGATCC AGTTTGATAT TTTTAGGTTG<br>TTGAACTGGG ATTACTTAAC CTTGAATGAT GATATGTATG<br>CACACTGACT TTAAGCTTCA TAAAACCATC AGTGCCAAGA<br>AATTCTCTTT GTAGTAATTA CTTGTTACTG ACACCACAGC<br>AGTATAGCAT ATGTCACAGC TCCTGTGATT CAATGTTATA<br>AAACAAGCAG AATTTTAAAA GCAGCACTAT ATAGCTGTTT<br>TGTATTATAG TGTATATGAT GTTTGTGAAA ATGCCAGATT<br>TAAAATGATG TATTTATTTT TGGTAAAAAA TAAAAAATTC<br>TATGCTATAT TGTTGATCAA GTGTAAATGT GACCTTGTAC<br>AGTTTACTAA AATTACTGAT ATTTTTCACT ACATTGAGAC<br>AGTTACTGTG AGAATAGGAC ACAAACACCA GCTATTGCCT<br>GCATCTGGGA AATTGCTGAA TCGCACAGCA GTCATGTCAT<br>AATCAGAAAA TTACTGCCAA ATAATTGTAA AATTTGTAAA<br>GTATAAAGTA TATAAAGTAG ATACTAAATA CAGACACTTC | |

TABLE 1-continued

| Plasma cell dyscrasia Biomarker/Housekeeper Sequence Information | | | |
|---|---|---|---|
| Gene Name | RefSeq Accession | Sequence | SEQ ID NO: |
| | | AATATTTTGT TGAAGCTATT GACTGTACAA TTAAACATTT TCAAAAGGTG TAATTTATTT AAAATTGTCT CATTTTGGTA AAATTTATGT GAACTTTTAA AGCTAAATAT TAAACTTAAT ATGCTATGTA AATATATACA TATATACATT TAATGATGTA TTTTTTTAAA ACATTGGCTT GCTTTTGTTA AAGTGCAAGT GTTACATATG GCTTTGTACA TTAAAGTTGA AAGGGGTTTT ACATTTTCCA TTAAAAGGAC TTTATCAAAA ATTGA | |
| LARS2 | NM_015340.3 | TGACAACATG GCGGCGCCCA TGGTCCGTGG CCCGGCAGTG CTCGCCTAAA GGTGGAGAAC GAGGAGTAGA GGAGCCGCAG GCCAGAGCCT GTGAGCAGAT CCAGACCTAC AGATAAAAAA CATTATTTAA TCTATCTGGG ATTTACTCCG GCTTATGATT TGAGGGCCTT CTCACCTTCT GAAGAATGGC TTCTGTTTGG CAGAGATTGG GTTTTTATGC CTCTCTTCTG AAAAGACAGC TAAATGGTGG GCCAGATGTC ATCAAGTGGG AAAGGAGAGT AATTCCCGGA TGTACCAGAA GCATCTACAG TGCCACGGGA AAGTGGACAA AAGAGTATAC ATTGCAGACA AGAAAGGATG TTGAGAAATG GTGGCATCAA CGAATAAAAG AACAGGCCTC CAAAATTTCA GAAGCTGATA AATCGAAGCC AAAATTTTAC GTGCTTTCCA TGTTCCCTTA TCCTTCTGGT AAGCTGCACA TGGGCCATGT GCGTGTCTAC ACCATCAGCG ACACCATAGC ACGGTTCCAG AAGATGAGAG GGATGCAGGT CATCAACCCC ATGGGATGGG ATGCTTTTGG ATTGCCTGCT GAAAATGCCG CAGTCGAGAG GAATCTACAT CCACAAAGTT GGACACAAAG TAATATTAAA CACATGAGGA AACAGCTTGA TCGTCTGGGC CTGTGTTTCA GCTGGGATAG GGAAATAACT ACGTGTTTGC CAGATTACTA CAAGTGGACT CAGTATCTCT TTATTAAACT GTATGAGGCT GGGCTGGCCT ATCAAAAGGA GGCCCTGGTT AACTGGGACC CAGTGGATCA AACAGTGCTT GCCAATGAGC AGGTGGATGA ACATGGCTGT TCATGGCGTT CTGGAGCAAA GGTGGAACAG AAGTACCTCA GACAATGGTT TATTAAGACA ACCGCTTATG CAAAGGCCAT GCAGGACGCG TTGGCAGACC TTCCAGAATG GTATGGAATA AAAGGCATGC AAGCCCACTG GATTGGGGAC TGTGTGGGCT GCCACCTGGA CTTCACATTA AAGGTTCATG GGCAAGCCAC GGGCGAAAAG CTGACTGCCT ATACGGCCAC CCCTGAAGCC ATTTATGGCA CCTCCCACGT GGCCATCTCG CCCAGCCACA GACTCCTACA TGGGCACAGC TCTCTGAAGG AAGCCTTGAG GATGGCCCTT GTCCCTGGCA AAGATTGCCT CACGCCTGTA ATGGCTGTGA ACATGCTTAC CCAGCAGGAG GTCCCTGTCG TTATTTTGGC CAAAGCTGAC TTGGAAGGCT CTCTGGATTC AAAAATAGGA ATTCCCAGTA CTAGCTCAGA GGACACCATC TTAGCCCAAA CCCTGGGCCT GGCCTACTCT GAAGTCATTG AAACTTTGCC AGATGGCACA GAGAGACTGA GCAGCTCTGC TGAGTTCACA GGTATGACCC GGCAGGATGC TTTTCTAGCC CTGACTCAGA AAGCCCGGGG GAAGAGAGTG GGTGGAGACG TGACAAGTGA TAAACTGAAA GACTGGCTGA TTTCACGGCA GCGGTACTGG GGCACACCAA TCCCCATTGT CCACTGCCCA GTCTGTGGCC CCACACCTGT GCCCCTGGAG GACTTGCCTG TGACCCTGCC CAACATCGCG TCTTTCACTG GCAAGGGAGG CCCCCCACTG GCCATGGCTT CAGAGTGGGT GAACTGCTCC TGCCCAAGGT GCAAGGGAGC AGCCAAGAGA GAGACAGACA CGATGGATAC CTTTGTTGAT TCTGCTTGGT ACTACTTCAG ATACACTGAC CCTCATAATC CACACAGCCC TTTTAACACA GCAGTGGCCG ATTACTGGAT GCCTGTGGAT TTGTACATTG GAGGGAAAGA ACATGCCGTC ATGCACTTGT TCTATGCAAG ATTCTTTAGT CATTTTTGCC ATGATCAAAA AATGGTTAAA CATAGGGAGC CTTTTCATAA GCTGCTGGCC CAAGGCCTTA TCAAGGGGCA GACATTCCGC CTACCATCTG GACAGTATCT ACAGAGAGAG GAAGTGGATC TCACAGGTTC CGTTCCTGTT CATGCAAAAA CGAAAGAGAA GTTAGAGGTG ACGTGGGAGA AGATGAGTAA GTCCAAACAC AACGGGGTGG ACCCAGAGGA AGTTGTGGAG CAGTATGGGA TCGACACGAT TCGGCTCTAC ATCCTTTTTG CTGCCCCTCC TGAGAAGGAT ATCTTGTGGG ATGTGAAAAC TGATGCTCTC CCTGGGGTGC TGAGATGGCA ACAACGACTG TGGACCTTGA CAACTCGGTT TATTGAGGCC AGGGCTTCTG GGAAGTCTCC CCAGCCTCAG CTGCTGAGTA ACAAGGAGAA AGCTGAGGCC AGGAAGCTCT GGGAGTACAA GAACTCCGTC ATCTCTCAGG TGACCACCCA TTTCACAGAG GACTTCTCAC TGAATTCTGC AATTTCTCAG CTGATGGGAC TCAGCAATGC CCTCTCGCAA GCCTCTCAGA GCGTCATTCT CCACAGCCCC GAGTTTGAGG ATGCTTTGTG TGCCCTGATG GTAATGGCTG CTCCACTGGC CCCTCATGTA ACCTCAGAGA TCTGGGCAGG CCTGGCGCTG GTGCCGAGGA AGCTCTGTGC CCACTACACT TGGGATGCCA | 9 |

TABLE 1-continued

Plasma cell dyscrasia Biomarker/Housekeeper Sequence Information

| Gene Name | RefSeq Accession | Sequence | SEQ ID NO: |
|---|---|---|---|
| | | GTGTGCTGCT CCAGGCATGG CCTGCTGTGG ACCCGGAGTT | |
| | | CCTGCAGCAG CCTGAGGTTG TCCAGATGGC AGTTCTGATC | |
| | | AACAATAAAG CTTGTGGCAA AATTCCTGTG CCCCAACAAG | |
| | | TTGCCCGGGA CCAGGACAAA GTCCACGAAT TTGTTCTTCA | |
| | | AAGCGAGCTG GGTGTCAGGC TTTTGCAAGG ACGAAGCATC | |
| | | AAGAAGTCCT TCCTTTCCCC GAGAACTGCC CTCATCAACT | |
| | | TCCTGGTGCA AGATTGACAG CCAGGAGGCT GCAGCTACCA | |
| | | CGAGGGCCTC TGAGGAACCT CCTTCCAGGC CTGGGATGAG | |
| | | GGGGCGATGT CTGCTGGCCC AGGGGAAGGG AAAAGACAAA | |
| | | TGTCTTGACT GTTGACCTCG GTCCTGTGGC AGACTGCAGT | |
| | | CAACAGTGTG CCTCTGTAGT GTGGCCTGGT GCTGGGGTGA | |
| | | AGGTGAGCTG GGCAAAGGAG AAATATGAGC TACTGAGGAG | |
| | | GGGGTTGGAC ATCCTGCCCC TCACCCCCCA CCCACACTGC | |
| | | AGGTAGAGGA GGCCATCTGA TCCCATGGGA AGCCATCAGA | |
| | | GACACTGCTG GTGGGAGCAG GAAGGAGCAG TGCCCCTCGA | |
| | | GCAGCCAGGA AGCCTGCGGA TCTGGGAAAT GGCTCTGCCT | |
| | | TAGGCACTTC TCGGGAATTT GAGGCCAGCC TGAGGAACTG | |
| | | CAGGACTCAG GTGCAATGTG CCAGCCACTT GGAACTGCTA | |
| | | ACTGAGCCTC CAGATGGTAG TGAATGGTCT CTTTGCCTTC | |
| | | AGGCTGGATG AGGAAGTCAT TTAGGAAATG TTCAAATAAC | |
| | | CAATATGTGG AAATGGACAC AGGGATCTTC TGAAGTTGCT | |
| | | TTGAATCAAA AGGCAGGCAG TGCTGGTTCC TCTGCCTGTG | |
| | | TCCCCACCAC TCCCCAGCTC TGTCATGCAG GCCTGTCCTC | |
| | | CCCAACCCCA GCTGGATGTG CCTCCCAGGC CTGCTGTGGT | |
| | | TCTGACACAC AGGATCCCAG GCAAGGCACC ACTTCCTCAC | |
| | | ATGAATGAGG AGCAGCAAGT CATAACCACT CCCTTGGGTA | |
| | | TACAATTTGC TGTGTAGTGA AGTGGAACCA GGCTCAGGCT | |
| | | GCTGGTCCCA ACCTCAGAGC CCCACCGCAG CCCAGTAGGG | |
| | | ATGCAGCACG CCCCAGAGGG CTCATGTGGG CCCCAGATGG | |
| | | CAATGCCACC ATTGTTGATG TGACTCCAGA GCCAGTTATT | |
| | | AGGAAGAGCA AGCTCACCAC AGAGGAGTGG AACTGAGGCC | |
| | | CCCCAGATGT TGCCTCCGGT GTCCAAGCCA CAGCGGTCTG | |
| | | GCTGTTGGGA AGATGGCCAG GAATGGACTC ATACCATTGG | |
| | | CACATTAGGC TAATCCTGGT TTTATGTGAA GTCAGCAATT | |
| | | AAGTGTTCCC ACTAGAACTG ACCTAAGCCA CTGATTAATA | |
| | | TTTAATGAGG GAAGGTAGGG GAGAATCTAG CCATTTTATA | |
| | | ATGCCAGAAA TCTATATATG TTATCTGATG CCATTTTTCT | |
| | | GAAGTAGCCT CACATGTGGT CCCCCTGCAG TTCAGCAGTT | |
| | | AACAGATGAC TTTTTTAGTG TAATAAAATG TTTATCATCT | |
| | | ATG | |
| MALAT1 | NR_002819.2 | GTAAAGGACT GGGGCCCCGC AACTGGCCTC TCCTGCCCTC | 10 |
| | | TTAAGCGCAG CGCCATTTTA GCAACGCAGA AGCCCGGCGC | |
| | | CGGGAAGCCT CAGCTCGCCT GAAGGCAGGT CCCCTCTGAC | |
| | | GCCTCCGGGA GCCCAGGTTT CCCAGAGTCC TTGGGACGCA | |
| | | GCGACGAGTT GTGCTGCTAT CTTAGCTGTC CTTATAGGCT | |
| | | GGCCATTCCA GGTGGTGGTA TTTAGATAAA ACCACTCAAA | |
| | | CTCTGCAGTT TGGTCTTGGG GTTTGGAGGA AAGCTTTTAT | |
| | | TTTTCTTCCT GCTCCGGTTC AGAAGGTCTG AAGCTCATAC | |
| | | CTAACCAGGC ATAACACAGA ATCTGCAAAA CAAAAACCCC | |
| | | TAAAAAAGCA GACCCAGAGC AGTGTAAACA CTTCTGGGTG | |
| | | TGTCCCTGAC TGGCTGCCCA AGGTCTCTGT GTCTTCGGAG | |
| | | ACAAAGCCAT TCGCTTAGTT GGTCTACTTT AAAAGGCCAC | |
| | | TTGAACTCGC TTTCCATGGC GATTTGCCTT GTGAGCACTT | |
| | | TCAGGAGAGC CTGGAAGCTG AAAAACGGTA GAAAAATTTC | |
| | | CGTGCGGGCC GTGGGGGGCT GGCGGCAACT GGGGGGCCGC | |
| | | AGATCAGAGT GGGCCACTGG CAGCCAACGG CCCCCGGGGC | |
| | | TCAGGCGGGG AGCAGCTCTG TGGTGTGGGA TTGAGGCGTT | |
| | | TTCCAAGAGT GGGTTTTCAC GTTTCTAAGA TTTCCCAAGC | |
| | | AGACAGCCCG TGCTGCTCCG ATTTCTCGAA CAAAAAAGCA | |
| | | AAACGTGTGG CTGTCTTGGG AGCAAGTCGC AGGACTGCAA | |
| | | GCAGTTGGGG GAGAAAGTCC GCCATTTTGC CACTTCTCAA | |
| | | CCGTCCCTGC AAGGCTGGGG CTCAGTTGCG TAATGGAAAG | |
| | | TAAAGCCCTG AACTATCACA CTTTAATCTT CCTTCAAAAG | |
| | | GTGGTAAACT ATACCTACTG TCCCTCAAGA GAACACAAGA | |
| | | AGTGCTTTAA GAGGTATTTT AAAAGTTCCG GGGGTTTTGT | |
| | | GAGGTGTTTG ATGACCCGTT TAAAATATGA TTTCCATGTT | |
| | | TCTTTTGTCT AAAGTTTGCA GCTCAAATCT TTCCACACGC | |
| | | TAGTAATTTA AGTATTTCTG CATGTGTAGT TTGCATTCAA | |
| | | GTTCCATAAG CTGTTAAGAA AAATCTAGAA AAGTAAAACT | |
| | | AGAACCTATT TTTAACCGAA GAACTACTTT TTGCCTCCCT | |
| | | CACAAAGGCG GCGGAAGGTG ATCGAATTCC GGTGATGCGA | |
| | | GTTGTTCTCC GTCTATAAAT ACGCCTCGCC CGAGCTGTGC | |
| | | GGTAGGCATT GAGGCAGCCA GCGCAGGGGC TTCTGCTGAG | |

TABLE 1-continued

Plasma cell dyscrasia Biomarker/Housekeeper Sequence Information

| Gene Name | RefSeq Accession | Sequence | SEQ ID NO: |
|---|---|---|---|
| | | GGGGCAGGCG GAGCTTGAGG AAACCGCAGA TAAGTTTTTT<br>TCTCTTTGAA AGATAGAGAT TAATACAACT ACTTAAAAAA<br>TATAGTCAAT AGGTTACTAA GATATTGCTT AGCGTTAAGT<br>TTTTAACGTA ATTTTAATAG CTTAAGATTT TAAGAGAAAA<br>TATGAAGACT TAGAAGAGTA GCATGAGGAA GGAAAAGATA<br>AAAGGTTTCT AAAACATGAC GGAGGTTGAG ATGAAGCTTC<br>TTCATGGAGT AAAAAATGTA TTTAAAAGAA AATTGAGAGA<br>AAGGACTACA GAGCCCCGAA TTAATACCAA TAGAAGGGCA<br>ATGCTTTTAG ATTAAAATGA AGGTGACTTA AACAGCTTAA<br>AGTTTAGTTT AAAAGTTGTA GGTGATTAAA ATAATTTGAA<br>GGCGATCTTT TAAAAAGAGA TTAAACCGAA GGTGATTAAA<br>AGACCTTGAA ATCCATGACG CAGGGAGAAT TGCGTCATTT<br>AAAGCCTAGT TAACGCATTT ACTAAACGCA GACGAAAATG<br>GAAAGATTAA TTGGGAGTGG TAGGATGAAA CAATTTGGAG<br>AAGATAGAAG TTTGAAGTGG AAAACTGGAA GACAGAAGTA<br>CGGGAAGGCG AAGAAAAGAA TAGAGAAGAT AGGGAAATTA<br>GAAGATAAAA ACATACTTTT AGAAGAAAAA AGATAAATTT<br>AAACCTGAAA AGTAGGAAGC AGAAGAAAAA AGACAAGCTA<br>GGAAACAAAA AGCTAAGGGC AAAATGTACA AACTTAGAAG<br>AAAATTGGAA GATAGAAACA AGATAGAAAA TGAAAATATT<br>GTCAAGAGTT TCAGATAGAA AATGAAAAAC AAGCTAAGAC<br>AAGTATTGGA GAAGTATAGA AGATAGAAAA ATATAAAGCC<br>AAAAATTGGA TAAAATAGCA CTGAAAAAAT GAGGAAATTA<br>TTGGTAACCA ATTTATTTTA AAAGCCCATC AATTTAATTT<br>CTGGTGGTGC AGAAGTTAGA AGGTAAAGCT TGAGAAGATG<br>AGGGTGTTTA CGTAGACCAG AACCAATTTA GAAGAATACT<br>TGAAGCTAGA AGGGGAAGTT GGTTAAAAAT CACATCAAAA<br>AGCTACTAAA AGGACTGGTG TAATTTAAAA AAAACTAAGG<br>CAGAAGGCTT TTGGAAGAGT TAGAAGAATT TGGAAGGCCT<br>TAAATATAGT AGCTTAGTTT GAAAAATGTG AAGGACTTTC<br>GTAACGGAAG TAATTCAAGA TCAAGAGTAA TTACCAACTT<br>AATGTTTTTG CATTGGACTT TGAGTTAAGA TTATTTTTTA<br>AATCCTGAGG ACTAGCATTA ATTGACAGCT GACCCAGGTG<br>CTACACAGAA GTGGATTCAG TGAATCTAGG AAGACAGCAG<br>CAGACAGGAT TCCAGGAACC AGTGTTTGAT GAAGCTAGGA<br>CTGAGGAGCA AGCGAGCAAG CAGCAGTTCG TGGTGAAGAT<br>AGGAAAAGAG TCCAGGAGCC AGTGCGATTT GGTGAAGGAA<br>GCTAGGAAGA AGGAAGGAGC GCTAACGATT TGGTGGTGAA<br>GCTAGGAAAA AGGATTCCAG GAAGGAGCGA GTGCAATTTG<br>GTGATGAAGG TAGCAGGCGG CTTGGCTTGG CAACCACACG<br>GAGGAGGCGA GCAGGCGTTG TGCGTAGAGG ATCCTAGACC<br>AGCATGCCAG TGTGCCAAGG CCACAGGGAA AGCGAGTGGT<br>TGGTAAAAAT CCGTGAGGTC GGCAATATGT TGTTTTTCTG<br>GAACTTACTT ATGGTAACCT TTTATTTATT TTCTAATATA<br>ATGGGGGAGT TTCGTACTGA GGTGTAAAGG GATTTATATG<br>GGGACGTAGG CCGATTTCCG GGTGTTGTAG GTTTCTCTTT<br>TTCAGGCTTA TACTCATGAA TCTTGTCTGA AGCTTTTGAG<br>GGCAGACTGC CAAGTCCTGG AGAAATAGTA GATGGCAAGT<br>TTGTGGGTTT TTTTTTTTTA CACGAATTTG AGGAAAACCA<br>AATGAATTTG ATAGCCAAAT TGAGACAATT TCAGCAAATC<br>TGTAAGCAGT TTGTATGTTT AGTTGGGGTA ATGAAGTATT<br>TCAGTTTTGT GAATAGATGA CCTGTTTTTA CTTCCTCACC<br>CTGAATTCGT TTTGTAAATG TAGAGTTTGG ATGTGTAACT<br>GAGGCGGGGG GGAGTTTTCA GTATTTTTTT TTGTGGGGGT<br>GGGGGCAAAA TATGTTTTCA GTTCTTTTTC CCTTAGGTCT<br>GTCTAGAATC CTAAAGGCAA ATGACTCAAG GTGTAACAGA<br>AAACAAGAAA ATCCAATATC AGGATAATCA GACCACCACA<br>GGTTTACAGT TTATAGAAAC TAGAGCAGTT CTCACGTTGA<br>GGTCTGTGGA AGAGATGTCC ATTGGAGAAA TGGCTGGTAG<br>TTACTCTTTT TTCCCCCCAC CCCCTTAATC AGACTTTAAA<br>AGTGCTTAAC CCCTTAAACT TGTTATTTTT TACTTGAAGC<br>ATTTTGGGAT GGTCTTAACA GGGAAGAGAG AGGGTGGGGG<br>AGAAAATGTT TTTTTCTAAG ATTTTCCACA GATGCTATAG<br>TACTATTGAC AAACTGGGTT AGAGAAGGAG TGTACCGCTG<br>TGCTGTTGGC ACGAACACCT TCAGGGACTG GAGCTGCTTT<br>TATCCTTGGA AGAGTATTCC CAGTTGAAGC TGAAAAGTAC<br>AGCACAGTGC AGCTTTGGTT CATATTCAGT CATCTCAGGA<br>GAACTTCAGA AGAGCTTGAG TAGGCCAAAT GTTGAAGTTA<br>AGTTTTCCAA TAATGTGACT TCTTAAAAGT TTTATTAAAG<br>GGGAGGGGCA AATATTGGCA ATTAGTTGGC AGTGGCCTGT<br>TACGGTTGGG ATTGGTGGGG TGGGTTTAGG TAATTGTTTA<br>GTTTATGATT GCAGATAAAC TCATGCCAGA GAACTTAAAG<br>TCTTAGAATG GAAAAAGTAA AGAAATATCA ACTTCCAAGT<br>TGGCAAGTAA CTCCCAATGA TTTAGTTTTT TTCCCCCCAG | |

TABLE 1-continued

Plasma cell dyscrasia Biomarker/Housekeeper Sequence Information

| Gene Name | RefSeq Accession | Sequence | SEQ ID NO: |
|---|---|---|---|
| | | TTTGAATTGG GAAGCTGGGG GAAGTTAAAT ATGAGCCACT<br>GGGTGTACCA GTGCATTAAT TTGGGCAAGG AAAGTGTCAT<br>AATTTGATAC TGTATCTGTT TTCCTTCAAA GTATAGAGCT<br>TTTGGGGAAG GAAAGTATTG AACTGGGGGT TGGTCTGGCC<br>TACTGGGCTG ACATTAACTA CAATTATGGG AAATGCAAAA<br>GTTGTTTGGA TATGGTAGTG TGTGGTTCTC TTTTGGAATT<br>TTTTTCAGGT GATTTAATAA TAATTTAAAA CTACTATAGA<br>AACTGCAGAG CAAAGGAAGT GGCTTAATGA TCCTGAAGGG<br>ATTTCTTCTG ATGGTAGCTT TTGTATTATC AAGTAAGATT<br>CTATTTTCAG TTGTGTGTAA GCAAGTTTTT TTTTAGTGTA<br>GGAGAAATAC TTTTCCATTG TTTAACTGCA AAACAAGATG<br>TTAAGGTATG CTTCAAAAAT TTTGTAAATT GTTTATTTTA<br>AACTTATCTG TTTGTAAATT GTAACTGATT AAGAATTGTG<br>ATAGTTCAGC TTGAATGTCT CTTAGAGGGT GGGCTTTTGT<br>TGATGAGGGA GGGGAAACTT TTTTTTTTTC TATAGACTTT<br>TTTCAGATAA CATCTTCTGA GTCATAACCA GCCTGGCAGT<br>ATGATGGCCT AGATGCAGAG AAAACAGCTC CTTGGTGAAT<br>TGATAAGTAA AGGCAGAAAA GATTATATGT CATACCTCCA<br>TTGGGGAATA AGCATAACCC TGAGATTCTT ACTACTGATG<br>AGAACATTAT CTGCATATGC CAAAAAATTT TAAGCAAATG<br>AAAGCTACCA ATTTAAAGTT ACGGAATCTA CCATTTTAAA<br>GTTAATTGCT TGTCAAGCTA TAACCACAAA AATAATGAAT<br>TGATGAGAAA TACAATGAAG AGGCAATGTC CATCTCAAAA<br>TACTGCTTTT ACAAAAGCAG AATAAAAGCG AAAAGAAATG<br>AAAATGTTAC ACTACATTAA TCCTGGAATA AAAGAAGCCG<br>AAATAAATGA GAGATGAGTT GGGATCAAGT GGATTGAGGA<br>GGCTGTGCTG TGTGCCAATG TTTCGTTTGC CTCAGACAGG<br>TATCTCTTCG TTATCAGAAG AGTTGCTTCA TTTCATCTGG<br>GAGCAGAAAA CAGCAGGCAG CTGTTAACAG ATAAGTTTAA<br>CTTGCATCTG CAGTATTGCA TGTTAGGGAT AAGTGCTTAT<br>TTTTAAGAGC TGTGGAGTTC TTAAATATCA ACCATGGCAC<br>TTTCTCCTGA CCCCTTCCCT AGGGGATTTC AGGATTGAGA<br>AATTTTTCCA TCGAGCCTTT TTAAAATTGT AGGACTTGTT<br>CCTGTGGGCT TCAGTGATGG GATAGTACAC TTCACTCAGA<br>GGCATTTGCA TCTTTAAATA ATTTCTTAAA AGCCTCTAAA<br>GTGATCAGTG CCTTGATGCC AACTAAGGAA ATTTGTTTAG<br>CATTGAATCT CTGAAGGCTC TATGAAAGGA ATAGCATGAT<br>GTGCTGTTAG AATCAGATGT TACTGCTAAA ATTTACATGT<br>TGTGATGTAA ATTGTGTAGA AAACCATTAA ATCATTCAAA<br>ATAATAAACT ATTTTTATTA GAGAATGTAT ACTTTTAGAA<br>AGCTGTCTCC TTATTTAAAT AAAATAGTGT TTGTCTGTAG<br>TTCAGTGTTG GGGCAATCTT GGGGGGGATT CTTCTCTAAT<br>CTTTCAGAAA CTTTGTCTGC GAACACTCTT TAATGGACCA<br>GATCAGGATT TGAGCGGAAG AACGAATGTA ACTTTAAGGC<br>AGGAAAGACA AATTTTATTC TTCATAAAGT GATGAGCATA<br>TAATAATTCC AGGCACATGG CAATAGAGGC CCTCTAAATA<br>AGGAATAAAT AACCTCTTAG ACAGGTGGGA GATTATGATC<br>AGAGTAAAAG GTAATTACAC ATTTTATTTC CAGAAAGTCA<br>GGGGTCTATA AATTGACAGT GATTAGAGTA ATACTTTTTC<br>ACATTTCCAA AGTTTGCATG TTAACTTTAA ATGCTTACAA<br>TCTTAGAGTG GTAGGCAATG TTTTACACTA TTGACCTTAT<br>ATAGGGAAGG GAGGGGGTGC CTGTGGGGTT TTAAAGAATT<br>TTCCTTTGCA GAGGCATTTC ATCCTTCATG AAGCCATTCA<br>GGATTTTGAA TTGCATATGA GTGCTTGGCT CTTCCTTCTG<br>TTCTAGTGAG TGTATGAGAC CTTGCAGTGA GTTTATCAGC<br>ATACTCAAAA TTTTTTTCCT GGAATTTGGA GGGATGGGAG<br>GAGGGGGTGG GGCTTACTTG TTGTAGCTTT TTTTTTTTTT<br>ACAGACTTCA CAGAGAATGC AGTTGTCTTG ACTTCAGGTC<br>TGTCTGTTCT GTTGGCAAGT AAATGCAGTA CTGTTCTGAT<br>CCCGCTGCTA TTAGAATGCA TTGTGAAACG ACTGGAGTAT<br>GATTAAAAGT TGTGTTCCCC AATGCTTGGA GTAGTGATTG<br>TTGAAGGAAA AAATCCAGCT GAGTGATAAA GGCTGAGTGT<br>TGAGGAAATT TCTGCAGTTT TAAGCAGTCG TATTTGTGAT<br>TGAAGCTGAG TACATTTTGC TGGTGTATTT TTAGGTAAAA<br>TGCTTTTTGT TCATTTCTGG TGGTGGGAGG GGACTGAAGC<br>CTTTAGTCTT TTCCAGATGC AACCTTAAAA TCAGTGACAA<br>GAAACATTCC AAACAAGCAA CAGTCTTCAA GAAATTAAAC<br>TGGCAAGTGG AAATGTTTAA ACAGTTCAGT GATCTTTAGT<br>GCATTGTTTA TGTGTGGGTT TCTCTCTCCC CTCCCTTGGT<br>CTTAATTCTT ACATGCAGGA ACACTCAGCA GACACACGTA<br>TGCGAAGGGC CAGAGAAGCC AGACCCAGTA AGAAAAAATA<br>GCCTATTTAC TTTAAATAAA CCAAACATTC CATTTTAAAT<br>GTGGGGATTG GGAACCACTA GTTCTTTCAG ATGGTATTCT<br>TCAGACTATA GAAGGAGCTT CCAGTTGAAT TCACCAGTGG | |

TABLE 1-continued

| Plasma cell dyscrasia Biomarker/Housekeeper Sequence Information | | | |
|---|---|---|---|
| Gene Name | RefSeq Accession | Sequence | SEQ ID NO: |
| | | ACAAAATGAG GAAAACAGGT GAACAAGCTT TTTCTGTATT | |
| | | TACATACAAA GTCAGATCAG TTATGGGACA ATAGTATTGA | |
| | | ATAGATTTCA GCTTTATGCT GGAGTAACTG GCATGTGAGC | |
| | | AAACTGTGTT GGCGTGGGGG TGGAGGGGTG AGGTGGGCGC | |
| | | TAAGCCTTTT TTTAAGATTT TTCAGGTACC CCTCACTAAA | |
| | | GGCACCGAAG GCTTAAAGTA GGACAACCAT GGAGCCTTCC | |
| | | TGTGGCAGGA GAGACAACAA AGCGCTATTA TCCTAAGGTC | |
| | | AAGAGAAGTG TCAGCCTCAC CTGATTTTTA TTAGTAATGA | |
| | | GGACTTGCCT CAACTCCCTC TTTCTGGAGT GAAGCATCCG | |
| | | AAGGAATGCT TGAAGTACCC CTGGGCTTCT CTTAACATTT | |
| | | AAGCAAGCTG TTTTTATAGC AGCTCTTAAT AATAAAGCCC | |
| | | AAATCTCAAG CGGTGCTTGA AGGGGAGGGA AAGGGGGAAA | |
| | | GCGGGCAACC ACTTTTCCCT AGCTTTTCCA GAAGCCTGTT | |
| | | AAAAGCAAGG TCTCCCCACA AGCAACTTCT CTGCCACATC | |
| | | GCCACCCCGT GCCTTTTGAT CTAGCACAGA CCCTTCACCC | |
| | | CTCACCTCGA TGCAGCCAGT AGCTTGGATC CTTGTGGGCA | |
| | | TGATCCATAA TCGGTTTCAA GGTAACGATG GTGTCGAGGT | |
| | | CTTTGGTGGG TTGAACTATG TTAGAAAAGG CCATTAATTT | |
| | | GCCTGCAAAT TGTTAACAGA AGGGTATTAA AACCACAGCT | |
| | | AAGTAGCTCT ATTATAATAC TTATCCAGTG ACTAAAACCA | |
| | | ACTTAAACCA GTAAGTGGAG AAATAACATG TTCAAGAACT | |
| | | GTAATGCTGG GTGGGAACAT GTAACTTGTA GACTGGAGAA | |
| | | GATAGGCATT TGAGTGGCTG AGAGGGCTTT TGGGTGGGAA | |
| | | TGCAAAAATT CTCTGCTAAG ACTTTTTCAG GTGAACATAA | |
| | | CAGACTTGGC CAAGCTAGCA TCTTAGCGGA AGCTGATCTC | |
| | | CAATGCTCTT CAGTAGGGTC ATGAAGGTTT TTCTTTTCCT | |
| | | GAGAAAACAA CACGTATTGT TTTCTCAGGT TTTGCTTTTT | |
| | | GGCCTTTTTC TAGCTTAAAA AAAAAAAAAG CAAAAGATGC | |
| | | TGGTGGTTGG CACTCCTGGT TTCCAGGACG GGGTTCAAAT | |
| | | CCCTGCGGCG TCTTTGCTTT GACTACTAAT CTGTCTTCAG | |
| | | GACTCTTTCT GTATTTCTCC TTTTCTCTGC AGGTGCTAGT | |
| | | TCTTGGAGTT TTGGGGAGGT GGGAGGTAAC AGCACAATAT | |
| | | CTTTGAACTA TATACATCCT TGATGTATAA TTTGTCAGGA | |
| | | GCTTGACTTG ATTGTATATT CATATTTACA CGAGAACCTA | |
| | | ATATAACTGC CTTGTCTTTT TCAGGTAATA GCCTGCAGCT | |
| | | GGTGTTTTGA GAAGCCCTAC TGCTGAAAAC TTAACAATTT | |
| | | TGTGTAATAA AAATGGAGAA GCTCTAAA | |
| MBNL1 | NM_001314057.1 | CTTGCCGGCT TCCTTGCAAA GCCCGGTGCA AGGGCCTCTT | 11 |
| | | TCAAAATGAA CCCACTGGTG TGCCTAGCAG TCGGTAGAAG | |
| | | AAGCGGGAGG GCGTCCGGTC TGCACGCCCG CCGCGAGGTT | |
| | | ACAATGCTGA ACGCATGAGA TGGAAGATAC CAACGGGAGG | |
| | | CCGAGGGGAT CCACGGCGCC CGCGCGGGCT CCGGCTTCCT | |
| | | CCTGCTCTCG GCGCCGCTGG GCGACCGCCC ATGACCCGCT | |
| | | CTTGCGGGCT CTGTCCGGTT GACAGGCGAC CCTGTGGCCC | |
| | | GGGGAAGCGC GGGAGGGCGC CGGCGGAAAG TTGAAGAGCG | |
| | | TTTTTCTCGC CGCCGCGTGC ATTAGGAGCT CGACGAGTCC | |
| | | GCCCTGGGCT TCCTGGTGGG GCTGGGCGGG CGGGGGAGGG | |
| | | GCCGCGCAGC AGCAGCGGAA GCCAGACCTC GGCGATAAGA | |
| | | GGCTGCACAG CGACATGCAA CAGTCTTTTC ACTGCAGCTG | |
| | | AATGAGTTGT GGCGCCCACA ATGCTCCCAT GACAAGGAGC | |
| | | TGACAAGTTC CATTTTCCGT CGCGGGCATC TTGGAATCAT | |
| | | GACTCCCACA ATGCCTTGGG CACTTGGTCG ACAGTGGGGC | |
| | | CGCCTCTGAA AAAAAAATGT GAGAGCAGTC ACTCAGGAAA | |
| | | TGTTGTTTAA GGGGAACCTT CTGGATCCTT TTCATGGCAC | |
| | | CATGGCAAGA AGAAGCTGTA TCTTATCTAT GGAAGATAAA | |
| | | GCATGGAGTT GGCTAATGGA TGCTGATAGG ACCATCTAGT | |
| | | TGCAGGAAAA CAAGCTCAGG GCTCCCACTG ATTCTACATT | |
| | | ATGGGCCGTT GCTCCAGGGA GAACTGCAAA TATCTTCATC | |
| | | CACCCCCACA TTTAAAAACG CAGTTGGAGA TAAATGGACG | |
| | | CAATAACTTG ATTCAGCAGA AGAACATGGC CATGTTGGCC | |
| | | CAGCAAATGC AACTAGCCAA TGCCATGATG CCTGGTGCCC | |
| | | CATTACAACC CGTGCCAATG TTTTCAGTTG CACCAAGCTT | |
| | | AGCCACCAAT GCATCAGCAG CCGCCTTTAA TCCCTATCTG | |
| | | GGACCTGTTT CTCCAAGCCT GGTCCCGGCA GAGATCTTGC | |
| | | CGACTGCACC AATGTTGGTT ACAGGGAATC CGGGTGTCCC | |
| | | TGTACCTGCA GCTGCTGCAG CTGCTGCACA GAAATTAATG | |
| | | CGAACAGACA GACTTGAGGT ATGTCGAGAG TACCAACGTG | |
| | | GCAATTGCAA CCGAGGAGAA AATGATTGTC GGTTTGCTCA | |
| | | TCCTGCTGAC AGCACAATGA TTGACACCAA TGACAACACA | |
| | | GTCACTGTGT GTATGGATTA CATCAAAGGG AGATGCTCTC | |
| | | GGGAAAAGTG CAAATACTTT CATCCCCCTG CACATTTGCA | |
| | | AGCCAAGATC AAGGCTGCCC AATACCAGGT CAACCAGGCT | |
| | | GCAGCTGCAC AGGCTGCAGC CACCGCAGCT GCCATGACTC | |

TABLE 1-continued

Plasma cell dyscrasia Biomarker/Housekeeper Sequence Information

| Gene Name | RefSeq Accession | Sequence | SEQ ID NO: |
|---|---|---|---|
| | | AGTCGGCTGT CAAATCACTG AAGCGACCCC TCGAGGCAAC<br>CTTTGACCTG GGAATTCCTC AAGCTGTACT TCCCCCATTA<br>CCAAAGAGGC CTGCTCTTGA AAAAACCAAC GGTGCCACCG<br>CAGTCTTTAA CACTGGTATT TTCCAATACC AACAGGCTCT<br>AGCCAACATG CAGTTACAAC AGCATACAGC ATTTCTCCCA<br>CCAGGCTCAA TATTGTGCAT GACACCCGCT ACAAGTGTTG<br>TTCCCATGGT GCACGGTGCT ACGCCAGCCA CTGTGTCCGC<br>AGCAACAACA TCTGCCACAA GTGTTCCCTT CGCTGCAACA<br>GCCACAGCCA ACCAGATACC CATAATATCT GCCGAACATC<br>TGACTAGCCA CAAGTATGTT ACCCAGATGT AGAATTTTCA<br>TCACTAAACA ATCATGCTAA AGAGGAAAGG ACAGTGTGCT<br>TGGTTAGAGT AAAGGACGAG GTCATTAGCC ATATTGTATA<br>TATCGTCAAG CAACACACAC AAAAGTTCCT CAGCCACAAG<br>ACATCCACAT ATTGCATGTT AACCAGAAGA AAAGACAACA<br>TTTTCCGGAA ATCCACTGCA CACTGTTGCC TATACACTTT<br>GTACATTTAA TTGATATTTG TGCTGAGGTG ATATTCCTGT<br>CTAAAAGAAC AACATTGTCT TTCTTTTCTA GCACAGAGTT<br>ATGCATTCAA AGATGCATAC CTAGTTAGTT TCCTATATAT<br>TCATGCCATC TTGAAAAGAC AGACTATGGT GTAACCATGA<br>TTCTATTATG TATTGGTACG TCTGTAGACC AAGATATAAT<br>TTTTTAAAAA TAAGTTTATT TCTTTCAAGG TTTACAAATA<br>ACAAAGGTGC ACCTTGTATT TAAAATTGCC ATTATAGATG<br>AGAGCGTGCA TGCACAGTCA TTTTTGTTTA AGAGTAATAT<br>TTTTAATGTA ATAGATTGTA AGACGTGGTG AGGGAGGGAT<br>CTGACAGAGA TGAATGTGCC AAGCAAAACC ACAACTGTGT<br>ATATTTTAAA GCACATCATG GCTTTAAGTA CCATGTTGTT<br>AAGGATTCTC ATGAAGTGCC ATAGACTGTA CATCAAATTA<br>GAGTATTATT TCTTCAGTGT TATTGTTTTC AGAGCCACAT<br>TTTGTTGCAT ATTTGCTAGT ACTAATCAGT CAAAGGGCAC<br>CATTCTTTTT TTTTTTTTTT GAAACCAAAG CTGTCTCAGA<br>AATGGCCAAT TTAACTTTAC AGTAACAATA GACAGCACAA<br>CACAAACTCT CTCAATACAG ATAAACTCAC ACATACTGGA<br>GATATATATA TAATAGATAT ATATAAAATT ATTTTAATGC<br>ATTGTAGTGT AATATTTATG CATACTATAC TGTATAACAT<br>GTTATTCAAA AGGGATTGCC ATTTCTGAGA CACAGTAACA<br>AAAAAATGAG GAAATTATTT TGCTTCTATT TATAGCCTCT<br>GTCAAAAGTC AAAAGACTAT AAATGCTTTG CAAAAATGGT<br>TTCACGTTTG CTTAAATGCT TCATCACAGT CACATTCAAA<br>ATAGTGACTC TAAACAAAGA AGAAAGCAGC ACTGTCATCA<br>GATGCATGAT AAACCAAAAT ATGAAAATGG GAAATGTTTA<br>ATTAACCTAG TAATTGGGTG GGTTAAGTAC ATGGGTGAAT<br>TTTATATGTG ATTTTTGTTT TGTTTTGTTT TGTTCAGATT<br>AACTGCTTAT AGCCTTAGAA AGCCTTTTAC AAAATTAAAA<br>AAAAAATAGA TGTGCATTCA GTTTTTAAGA ATGGAATCAT<br>CCAAAGGAAT TCCTTTTTTT GAGGTTTGGA TGTTGCAGCT<br>AGTAAAGGAT ATTTTTGCTC TGTTCAGCAG TTCTAAAAAT<br>TGCTGAAGTA GGGGCCAGGT CACTGGTAGT TATAGTATGG<br>AATGGGAGAA GTGAAAGTTC AGTTATAGAA CTTTCCATAC<br>TTCCAAGTTT ACTGCAAGTT TTTATGCTTG AGAGAGATGC<br>TTTCTAATAT AAGACTGATG TGTTGATTTT ACTGATTGTA<br>CTGTACATCT ATTAAAGCCT TAGATTATTA CATTACGGGT<br>TGGAACCCAT ACCAATGTAA TTTCAATCGT GTTAAGAAAG<br>TAATGGTGAC TTCACATGTT ATTGTAGTTA GTTACATTAT<br>AGAATATTAC TTATTTTTCT TGTTAAAATG TAGTTTTTCA<br>TTTCCTACAT TTATTAGATT TTCATTTTCT ATTAACAATT<br>GAATACCATT TCAGTTTATA GACTTGTTTT ATTAGATTTT<br>ACCAATGAAT TTTTCAAAAT ACAAAAAAAA GTAGTTTTTC<br>CTTCATAACA TACTCAGTTT TGAATTACAT GTAGTGTCAC<br>ATGAATATTC GTATTGTTAA CTAAATGATT TATATTTTAC<br>TGATTTAATA TTACAGTGTA AGAATGTCAG TCATTGTTAG<br>TTCTTGTCTA GTTTTCATTA AAAGAACAAA GATCTTTTAT<br>ATGGATATCT TATAAATATA TAATCATTGC TAAGTAAGAA<br>GTTAAGTTGT TGCTATCGCA ACAATCCTGG CAGACAATTG<br>AGTAATATTT TGATGATTTA TTTTGTTTGT AATTAGTTAT<br>TATAAGAAGA TCTAGATCCT AGATATTAGA ATAAAATTTA<br>TTTTCTACTG TATCCATTTC AAATGTTAAA ATATTGTTTA<br>ATATTTTTGA AATCCCTGAG TATCAGGCCT TGTTATAAAT<br>AAGCTGCATA ATCAATAAAT AGAACAAGGG ACTTTTTGTT<br>GATAATCCAA ATACTCAAAG TTTACGTAAT GAAAATTATA<br>GCGTGTGTGC AAACTCTTGA GGGTTGATTA TGCTGCAATT<br>TAGCATGTTG GAACGTCTAG GGAGAAGGTT GACTTTTTGC<br>ACTTCTGTAT ATAGTCAAAA GAGAGAAACC TGTATAATAG<br>TAAGATCTTA TTTTGAATAA AAACGTCTAT AATTACAAGG<br>AGTTTTGTTA AGGCTAATAC AATGACAGAC TGAGCAAAAT | |

TABLE 1-continued

| Plasma cell dyscrasia Biomarker/Housekeeper Sequence Information | | | |
|---|---|---|---|
| Gene Name | RefSeq Accession | Sequence | SEQ ID NO: |
| | | TGCTTGCAAA AGTGGCACAG AGTTAGCACT CCATACCCCT TCAAACATGT TGCTTTGCTT TCTTGTGGAC AGCTTGTAGT TTGCCAGGAT TTTTTCAGCT GGAAAGATAC GCCATCCTTT CAAACCCTCA TGACTGACAA AAACTCCATG GGGCCAAATC TGCCTGAAGA TCATTACCAA AAATAGCAGG TACTTCTACC ATTAAGGTGA AATCATGGAT CAGATATTCC TTACATTTTT CAAAACTACT GCATGTTTAA AACTTCAACA AAAAAAGAGA GAAAGAACTA TACTAAGAAC ATATATTATT CAGATCAGTT TCTGCCAATT TCAGTGGTTT ATTGTTCACA AAAAAATCTT CAAAACAAGT ATTGACTTTC ACAAAATTTA AATCATAAAC AGGCAAACCA AACAGCACAC TGTAGCTATA GTTGTTATGT GATTGTTTTT TAATTGCTGT AGGATCCTGT TCTTTCAGCA GGTGAAAAAT AAAACGCAGT TCAAATTTCA TGGTTTTAAT TTTCAACTCA GAAGCACTCA AAAATGCAAA ATGTGATAAT GGGCACTTGT TTAAAAGAAT TAGTGTATCC AGCCTTCACT CCAGCTGGTT AAAAATGTTG CACTTATCAG CAACCCTACC ACTTTCATCT GCTGAAAGGA CAAATGTGCT TGGTTTTACT ATTATGTAAT CACAACTTAC TTTCTGCTTG TAGTTGCTTA AAATTATGTA TTTTGTCTTG GGCTGCAATT TGTTTTATGC TTATTTTATT ATTACTGCAG TAGTTGACTT TGCTGTATGG AAAAATAAAG TGAAATTGCC CTAATAAAAC TTCTCTTTCT TAAGTAAAAA AAAAAAAAAA AAAAAA | |
| MCL1 | NM_001197320.1 | GCGCAACCCT CCGGAAGCTG CCGCCCCTTT CCCCTTTTAT GGGAATACTT TTTTTAAAAA AAAAGAGTTC GCTGGCGCCA CCCCGTAGGA CTGGCCGCCC TAAAACCGTG ATAAAGGAGC TGCTCGCCAC TTCTCACTTC CGCTTCCTTC CAGTAAGGAG TCGGGGTCTT CCCCAGTTTT CTCAGCCAGG CGGCGGCGGC GACTGGCAAT GTTTGGCCTC AAAAGAAACG CGGTAATCGG ACTCAACCTC TACTGTGGGG GGGCCGGCTT GGGGGCCGGC AGCGGCGGCG CCACCCGCCC GGGAGGGCGA CTTTTGGCCA CCGGCGCCAA GGACACAAAG CCAATGGGCA GGTCTGGGGC CACCAGCAGG AAGGCGCTGG AGACCTTACG ACGGGTTGGG GATGGCGTGC AGCGCAACCA CGAGACGGCC TTCCAAGGCA TGCTTCGGAA ACTGGACATC AAAAACGAAG ACGATGTGAA ATCGTTGTCT CGAGTGATGA TCCATGTTTT CAGCGACGGC GTAACAAACT GGGGCAGGAT TGTGACTCTC ATTTCTTTTG GTGCCTTTGT GGCTAAACAC TTGAAGACCA TAAACCAAGA AAGCTGCATC GAACCATTAG CAGAAAGTAT CACAGACGTT CTCGTAAGGA CAAAACGGGA CTGGCTAGTT AAACAAAGAG GCTGGGATGG GTTTGTGGAG TTCTTCCATG TAGAGGACCT AGAAGGTGGC ATCAGGAATG TGCTGCTGGC TTTTGCAGGT GTTGCTGGAG TAGGAGCTGG TTTGGCATAT CTAATAAGAT AGCCTTACTG TAAGTGCAAT AGTTGACTTT TAACCAACCA CCACCACCAC CAAAACCAGT TTATGCAGTT GGACTCCAAG CTGTAACTTC CTAGAGTTGC ACCCTAGCAA CCTAGCCAGA AAAGCAAGTG GCAAGAGGAT TATGGCTAAC AAGAATAAAT ACATGGGAAG AGTGCTCCCC ATTGATTGAA GAGTCACTGT CTGAAAGAAG CAAAGTTCAG TTTCAGCAAC AAACAAACTT TGTTTGGGAA GCTATGGAGG AGGACTTTTA GATTTAGTGA AGATGGTAGG GTGGAAAGAC TTAATTTCCT TGTTGAGAAC AGGAAAGTGG CCAGTAGCCA GGCAAGTCAT AGAATTGATT ACCCGCCGAA TTCATTAATT TACTGTAGTG TTAAGAGAAG CACTAAGAAT GCCAGTGACC TGTGTAAAAG TTACAAGTAA TAGAACTATG ACTGTAAGCC TCAGTACTGT ACAAGGGAAG CTTTTCCTCT CTCTAATTAG CTTTCCCAGT ATACTTCTTA GAAAGTCCAA GTGTTCAGGA CTTTTATACC TGTTATACTT TGGCTTGGTT TCCATGATTC TTACTTTATT AGCCTAGTTT ATCACCAATA ATACTTGACG GAAGGCTCAG TAATTAGTTA TGAATATGGA TATCCTCAAT TCTTAAGACA GCTTGTAAAT GTATTTGTAA AAATTGTATA TATTTTTACA GAAAGTCTAT TTCTTTGAAA CGAAGGAAGT ATCGAATTTA CATTAGTTTT TTTCATACCC TTTTGAACTT TGCAACTTCC GTAATTAGGA ACCTGTTTCT TACAGCTTTT CTATGCTAAA CTTTGTTCTG TTCAGTTCTA GAGTGTATAC AGAACGAATT GATGTGTAAC TGTATGCAGA CTGGTTGTAG TGGAACAAAT CTGATAACTA TGCAGGTTTA AATTTTCTTA TCTGATTTTG GTAAGTATTC CTTAGATAGG TTTTTCTTTG AAAACCTGGG ATTGAGAGGT TGATGAATGG AAATTCTTTC ACTTCATTAT ATGCAAGTTT TCAATAATTA GGTCTAAGTG GAGTTTTAAG GTTACTGATG ACTTACAAAT AATGGGCTCT GATTGGGCAA TACTCATTTG AGTTCCTTCC ATTTGACCTA ATTTAACTGG TGAAATTTAA AGTGAATTCA TGGGCTCATC TTTAAAGCTT TTACTAAAAG ATTTTCAGCT GAATGGAACT CATTAGCTGT GTGCATATAA | 12 |

TABLE 1-continued

Plasma cell dyscrasia Biomarker/Housekeeper Sequence Information

| Gene Name | RefSeq Accession | Sequence | SEQ ID NO: |
|---|---|---|---|
| | | AAAGATCACA TCAGGTGGAT GGAGAGACAT TTGATCCCTT GTTTGCTTAA TAAATTATAA AATGATGGCT TGGAAAAGCA GGCTAGTCTA ACCATGGTGC TATTATTAGG CTTGCTTGTT ACACACACAG GTCTAAGCCT AGTATGTCAA TAAAGCAAAT ACTTACTGTT TTGTTTCTAT TAATGATTCC CAAACCTTGT TGCAAGTTTT TGCATTGGCA TCTTTGGATT TCAGTCTTGA TGTTTGTTCT ATCAGACTTA ACCTTTTATT TCCTGTCCTT CCTTGAAATT GCTGATTGTT CTGCTCCCTC TACAGATATT TATATCAATT CCTACAGCTT TCCCCTGCCA TCCCTGAACT CTTTCTAGCC CTTTTAGATT TTGGCACTGT GAAACCCCTG CTGGAAACCT GAGTGACCCT CCCTCCCCAC CAAGAGTCCA CAGACCTTTC ATCTTTCACG AACTTGATCC TGTTAGCAGG TGGTAATACC ATGGGTGCTG TGACACTAAC AGTCATTGAG AGGTGGGAGG AAGTCCCTTT TCCTTGGACT GGTATCTTTT CAACTATTGT TTTATCCTGT CTTTGGGGGC AATGTGTCAA AAGTCCCCTC AGGAATTTTC AGAGGAAAGA ACATTTTATG AGGCTTTCTC TAAAGTTTCC TTTGTATAGG AGTATGCTCA CTTAAATTTA CAGAAAGAGG TGAGCTGTGT TAAACCTCAG AGTTTAAAAG CTACTGATAA ACTGAAGAAA GTGTCTATAT TGGAACTAGG GTCATTTGAA AGCTTCAGTC TCGGAACATG ACCTTTAGTC TGTGGACTCC ATTTAAAAAT AGGTATGAAT AAGATGACTA AGAATGTAAT GGGGAAGAAC TGCCCTGCCT GCCCATCTCA GAGCCATAAG GTCATCTTTG CTAGAGCTAT TTTTACCTAT GTATTTATCG TTCTTGATCA TAAGCCGCTT ATTTATATCA TGTATCTCTA AGGACCTAAA AGCACTTTAT GTAGTTTTTA ATTAATCTTA AGATCTGGTT ACGGTAACTA AAAAAGCCTG TCTGCCAAAT CCAGTGGAAA CAAGTGCATA GATGTGAATT GGTTTTTAGG GGCCCCACTT CCCAATTCAT TAGGTATGAC TGTGGAAATA CAGACAAGGA TCTTAGTTGA TATTTTGGGC TTGGGGCAGT GAGGGCTTAG GACACCCCAA GTGGTTTGGG AAAGGAGGAG GGGAGTGGTG GGTTTATAGG GGGAGGAGGA GGCAGGTGGT CTAAGTGCTG ACTGGCTACG TAGTTCGGGC AAATCCTCCA AAAGGGAAAG GGAGGATTTG CTTAGAAGGA TGGCGCTCCC AGTGACTACT TTTTGACTTC TGTTTGTCTT ACGCTTCTCT CAGGGAAAAA CATGCAGTCC TCTAGTGTTT CATGTACATT CTGTGGGGGG TGAACACCTT GGTTCTGGTT AAACAGCTGT ACTTTTGATA GCTGTGCCAG GAAGGGTTAG GACCAACTAC AAATTAATGT TGGTTGTCAA ATGTAGTGTG TTTCCCTAAC TTTCTGTTTT TCCTGAGAAA AAAAAATAAA TCTTTTATTC AAATACAGGG AAAAAAAAAA AAAAAAAA | |
| NFKBIZ | NM_001005474.2 | CTCCTCTTGC CACGAGGTCA GACGGCGAGT TCTTAGAGAA AAAGGCTGCT TAGCTGCTGC TTATCATGTA ACCTCAAAAG GAAACTGATC GTCTTTCTCA TGCTGTCACG TACTTGGGTT ATTATCGCTG ATTACAGCTG GAAACAATTG ATTTGCTCTT ACGTATTTGT GTGACTTGAC TCTTCAAACA CAAAGGTTAA CAGGAAGATC TCGAGGGCCC TGGCTGAACT TCACCTTTTG GCTTTCTTGG CCTGATGCTG AACTCTCGAG GTTGAGCCCC ATATGGGGGT TGGCAGGCAG CAGAGAGGCC CCTTTCAAGG TGTTCGGGTA AAGAACTCAG TGAAGGAACT CCTGTTGCAC ATCCGAAGTC ATAAACAGAA GGCTTCTGGC CAAGCTGTGG ATGATTTTAA GACACAAGGT GTGAACATAG AACAGTTCAG AGAATTGAAG AACACAGTAT CATACAGTGG GAAAAGGAAA GGGCCCGATT CGTTGTCTGA TGGACCTGCT TGCAAAAGGC CAGCTCTGTT GCATTCCCAA TTTTTGACAC CACCTCAAAC ACCAACGCCC GGGGAGAGCA TGGAAGATGT TCATCTCAAT GAACCCAAAC AGGAGAGCAG TGCTGATCTG CTTCAGAACA TTATCAACAT TAAGAATGAA TGCAGCCCCG TTTCCCTGAA CACAGTTCAA GTTAGCTGGC TGAACCCCGT GGTGGTCCCT CAGAGCTCCC CCGCAGAGCA GTGTCAGGAC TTCCATGGAG GGCAGGTCTT TTCTCCACCT CAGAAATGCC AACCATTCCA AGTCAGGGGC TCCCAACAAA TGATAGACCA GGCTTCCCTG TACCAGTATT CTCCACAGAA CCAGCATGTA GAGCAGCAGC CACACTACAC CCACAAACCA ACTCTGGAAT ACAGTCCTTT TCCCATACCT CCCCAGTCCC CCGCTTATGA ACCAAACCTC TTTGATGGTC CAGAATCACA GTTTTGCCCA AACCAAAGCT TAGTTTCCCT TCTTGGTGAT CAAAGGGAAT CTGAGAATAT TGCTAATCCC ATGCAGACTT CCTCCAGTGT TCAGCAGCAA AATGATGCTC ACTTGCACAG CTTCAGCATG ATGCCCAGCA GCGCCTGTGA GGCCATGGTG GGGCACGAGA TGGCCTCTGA CTCTTCAAAC ACTTCACTGC CATTCTCAAA CATGGGAAAT CCAATGAACA CCACACAGTT AGGGAAATCA CTTTTTCAGT GGCAGGTGGA GCAGGAAGAA AGCAAATTGG CAAATATTTC | 13 |

TABLE 1-continued

Plasma cell dyscrasia Biomarker/Housekeeper Sequence Information

| Gene Name | RefSeq Accession | Sequence | SEQ ID NO: |
|---|---|---|---|
| | | CCAAGACCAG TTTCTTTCAA AGGATGCAGA TGGTGACACG | |
| | | TTCCTTCATA TTGCTGTTGC CCAAGGGAGA AGGGCACTTT | |
| | | CCTATGTTCT TGCAAGAAAG ATGAATGCAC TTCACATGCT | |
| | | GGATATTAAA GAGCACAATG GACAGAGTGC CTTTCAGGTG | |
| | | GCAGTGGCTG CCAATCAGCA TCTCATTGTG CAGGATCTGG | |
| | | TGAACATCGG GGCACAGGTG AACACCACAG ACTGCTGGGG | |
| | | AAGAACACCT CTGCATGTGT GTGCTGAGAA GGGCCACTCC | |
| | | CAGGTGCTTC AGGCGATTCA GAAGGGAGCA GTGGGAAGTA | |
| | | ATCAGTTTGT GGATCTTGAG GCAACTAACT ATGATGGCCT | |
| | | GACTCCCCTT CACTGTGCAG TCATAGCCCA CAATGCTGTG | |
| | | GTCCATGAAC TCCAGAGAAA TCAACAGCCT CATTCACCTG | |
| | | AAGTTCAGGA GCTTTTACTG AAGAATAAGA GTCTGGTTGA | |
| | | TACCATTAAG TGCCTAATTC AAATGGGAGC AGCGGTGGAA | |
| | | GCGAAGGATC GCAAAAGTGG CCGCACAGCC CTGCATTTGG | |
| | | CAGCTGAAGA AGCAAATCTG GAACTCATTC GCCTCTTTTT | |
| | | GGAGCTGCCC AGTTGCCTGT CTTTTGTGAA TGCAAAGGCT | |
| | | TACAATGGCA ACACTGCCCT CCATGTTGCT GCCAGCTTGC | |
| | | AGTATCGGTT GACACAATTA GATGCTGTCC GCCTGTTGAT | |
| | | GAGGAAGGGA GCAGACCCAA GTACTCGGAA CTTGGAGAAC | |
| | | GAACAGCCAG TGCATTTGGT TCCCGATGGC CCTGTGGGAG | |
| | | AACAGATCCG ACGTATCCTG AAGGGAAAGT CCATTCAGCA | |
| | | GAGAGCTCCA CCGTATTAGC TCCATTAGCT TGGAGCCTGG | |
| | | CTAGCAACAC TCACTGTCAG TTAGGCAGTC CTGATGTATC | |
| | | TGTACATAGA CCATTTGCCT TATATTGGCA AATGTAAGTT | |
| | | GTTTCTATGA AACAAACATA TTTAGTTCAC TATTATATAG | |
| | | TGGGTTATAT TAAAAGAAAA GAAGAAAAAT ATCTAATTTC | |
| | | TCTTGGCAGA TTTGCATATT TCATACCCAG GTATCTGGGA | |
| | | TCTAGACATC TGAATTTGAT CTCAATGGTA ACATTGCCTT | |
| | | CAATTAACAG TAGCTTTTGA GTAGGAAAGG ACTTTGATTT | |
| | | GTGGCACAAA ACATTATTAA TATAGCTATT GACAGTTTCA | |
| | | AAGCAGGTAA ATTGTAAATG TTTCTTTAAG AAAAAGCATG | |
| | | TGAAAGGAAA AAGGTAAATA CAGCATTGAG GCTTCATTTG | |
| | | GCCTTAGTCC CTGGGAGTTA CTGGCGTTGG ACAGGCTTCA | |
| | | GTCATTGGAC TAGATGAAAG GTGTCCATGG TTAGAATTTG | |
| | | ATCTTTGCAA ACTGTATATA ATTGTTATTT TTGTCCTTAA | |
| | | AAATATTGTA CATACTTGGT TGTTAACATG GTCATATTTG | |
| | | AAATGTATAA GTCCATAAAA TAGAAAAGAA CAAGTGAATT | |
| | | GTTGCTATTT AAAAAAATTT TACAATTCTT ACTAAGGAGT | |
| | | TTTTATTGTG TAATCACTAA GTCTTTGTAG ATAAAGCAGA | |
| | | TGGGGAGTTA CGGAGTTGTT CCTTTACTGG CTGAAAGATA | |
| | | TATTCGAATT GTAAAGATGC TTTTTCTCAT GCATTGAAAT | |
| | | TATACATTAT TTGTAGGGAA TTGCATGCTT TTTTTTTTTT | |
| | | TTCTCCCGAG ACAGGGTCTT GCTCTGGCGC CCAGGCTGGA | |
| | | GTACAGTGGC ATGATCTTGG CTCACTTCAG CCTTGACTTG | |
| | | GGCTCAAGTG ATCCTCCTAC CTGAGCCTTC TGAGTAACTG | |
| | | GAACTACAGG TGTGCACTCC TCGCCTGGCT AATTTTTTAT | |
| | | TTTTTGTACA GGCAGGATCT TGCCACCTTG CCCAGGCTGG | |
| | | TCTTGAACTC CTGAGCTCAT GCCATCTGCC TGCCTTAGTC | |
| | | TCCCAAAATG CTGGGATTAC AGGAGTGAGC CACCATGCCC | |
| | | GGCTGGCAGT TGCATGGAAG AGAACACCTC TTTATGGCTT | |
| | | ACCCTCTAGA ATTTCTAATT TATGTGTTCT GTTGAAATTT | |
| | | TTGTTTTTTT ACCTTTATTG AAACAACAAA AAGTCAGTAT | |
| | | TGAAACATAT CTTCCTGTTT TCTGTTGTCA AATGATGATA | |
| | | ATGTGCCATG ATGTTTTATA TATATCATTC AGAAAAAGTT | |
| | | TTATTTTTTA ATAACATTCT ATTAACATTA TTTTGCTTGC | |
| | | CGCTGGCATG CCTGAGGAAT GTATTTGGCT TTGATTACAC | |
| | | ACTAAGTTTT TGTAATAAAT TTGACTCATT AAAAACCTTT | |
| | | TTTTTTTAAA AAAAAAAAAA AAGAAAATCT CATTAGTGAA | |
| | | CTTATCTTTG CAGCTGAGTA CTTAAATTCT TTTTAAAAAG | |
| | | ATACCCTTTG GATTGATCAC ATTGTTTGAC CCAGTATGTC | |
| | | TTGTAGACAC GTTAGTTATA ATCACCTTGT ATCTCTAAAT | |
| | | ATGGTGTGAT ATGAACCAGT CCATTCACAT TGGAAAAACT | |
| | | GATGGTTTTA AATAAACTAA TTCACTAATA TTAAAAAAAA A | |
| NR4A1 | NM_001202233.1 | TTCCTGGTGT AAGCTTTGGT ATGGATGGTG GCCGTCTCCC | 14 |
| | | TACAGACTGG GAGCTGTTAG AGGGCAGGGA TCCTAGCTGA | |
| | | CACATCTATG TCCTCGCCTT GGTTGGAGGC CTCCACCATG | |
| | | GACAGAGGCC AGGCCCTGCC CCTCCCAGGC AGCCTGGCTC | |
| | | CTTCTGCTGG GCCCTGAAGG CAGACGGGAT AATGTGGTTG | |
| | | GCCAAGGCCT GTTGGTCCAT CCAGAGTGAG ATGCCCTGTA | |
| | | TCCAAGCCCA ATATGGGACA CCAGCACCGA GTCCGGGACC | |
| | | CCGTGACCAC CTGGCAAGCG ACCCCCTGAC CCCTGAGTTC | |
| | | ATCAAGCCCA CCATGGACCT GGCCAGCCCC GAGGCAGCCC | |
| | | CCGCTGCCCC CACTGCCCTG CCCAGCTTCA GCACCTTCAT | |

TABLE 1-continued

Plasma cell dyscrasia Biomarker/Housekeeper Sequence Information

| Gene Name | RefSeq Accession | Sequence | SEQ ID NO: |
|---|---|---|---|
| | | GGACGGCTAC ACAGGAGAGT TTGACACCTT CCTCTACCAG CTGCCAGGAA CAGTCCAGCC ATGCTCCTCA GCCTCCTCCT CGGCCTCCTC CACATCCTCG TCCTCAGCCA CCTCCCCTGC CTCTGCCTCC TTCAAGTTCG AGGACTTCCA GGTGTACGGC TGCTACCCCG GCCCCCTGAG CGGCCCAGTG GATGAGGCCC TGTCCTCCAG TGGCTCTGAC TACTATGGCA GCCCCTGCTC GGCCCCGTCG CCCTCCACGC CCAGCTTCCA GCCGCCCCAG CTCTCTCCCT GGGATGGCTC CTTCGGCCAC TTCTCGCCCA GCCAGACTTA CGAAGGCCTG CGGGCATGGA CAGAGCAGCT GCCCAAAGCC TCTGGGCCCC CACAGCCTCC AGCCTTCTTT TCCTTCAGTC CTCCCACCGG CCCCAGCCCC AGCCTGGCCC AGAGCCCCCT GAAGTTGTTC CCCTCACAGG CCACCCACCA GCTGGGGGAG GGAGAGAGCT ATTCCATGCC TACGGCCTTC CCAGGTTTGG CACCCACTTC TCCACACCTT GAGGGCTCGG GGATACTGGA TACACCCGTG ACCTCAACCA AGGCCCGGAG CGGGGCCCCA GGTGGAAGTG AAGGCCGCTG TGCTGTGTGT GGGGACAACG CTTCATGCCA GCATTATGGT GTCCGCACAT GTGAGGGCTG CAAGGGCTTC TTCAAGCGCA CAGTGCAGAA AAACGCCAAG TACATCTGCC TGGCTAACAA GGACTGCCCT GTGGACAAGA GGCGGCGAAA CCGCTGCCAG TTCTGCCGCT TCCAGAAGTG CCTGGCGGTG GGCATGGTGA AGGAAGTTGT CCGAACAGAC AGCCTGAAGG GGCGGCGGGG CCGGCTACCT TCAAAACCCA AGCAGCCCCC AGATGCCTCC CCTGCCAATC TCCTCACTTC CCTGGTCCGT GCACACCTGG ACTCAGGGCC CAGCACTGCC AAACTGGACT ACTCCAAGTT CCAGGAGCTG GTGCTGCCCC ACTTTGGGAA GGAAGATGCT GGGGATGTAC AGCAGTTCTA CGACCTGCTC TCCGGTTCTC TGGAGGTCAT CCGCAAGTGG GCGGAGAAGA TCCCTGGCTT TGCTGAGCTG TCACCGGCTG ACCAGGACCT GTTGCTGGAG TCGGCCTTCC TGGAGCTCTT CATCCTCCGC CTGGCGTACA GGTCTAAGCC AGGCGAGGGC AAGCTCATCT TCTGCTCAGG CCTGGTGCTA CACCGGCTGC AGTGTGCCCG TGGCTTCGGG GACTGGATTG ACAGTATCCT GGCCTTCTCA AGGTCCCTGC ACAGCTTGCT TGTCGATGTC CCTGCCTTCG CCTGCCTCTC TGCCCTTGTC CTCATCACCG ACCGGCATGG GCTGCAGGAG CCGCGGCGGG TGGAGGAGCT GCAGAACCGC ATCGCCAGCT GCCTGAAGGA GCACGTGGCA GCTGTGGCGG GCGAGCCCCA GCCAGCCAGC TGCCTGTCAC GTCTGTTGGG CAAACTGCCC GAGCTGCGGA CCCTGTGCAC CCAGGGCCTG CAGCGCATCT TCTACCTCAA GCTGGAGGAC TTGGTGCCCC CTCCACCCAT CATTGACAAG ATCTTCATGG ACACGCTGCC CTTCTGACCC CTGCCTGGGA ACACGTGTGC ACATGCGCAC TCTCATATGC CACCCCATGT GCCTTTAGTC CACGGACCCC CAGAGCACCC CCAAGCCTGG GCTTGAGCTG CAGAATGACT CCACCTTCTC ACCTGCTCCA GGAGGTTTGC AGGGAGCTCA AGCCCTTGGG GAGGGGGATG CCTTCATGGG GGTGACCCCA CGATTTGTCT TATCCCCCCC AGCCTGGCCC CGGCCTTTAT GTTTTTTGTA AGATAAACCG TTTTTAACAC ATAGCGCCGT GCTGTAAATA AGCCCAGTGC TGCTGTAAAT ACAGGAAGAA AGAGCTTGAG GTGGGAGCGG GGCTGGGAGG AAGGGATGGG CCCCGCCTTC CTGGGCAGCC TTTCCAGCCT CCTGCTGGCT CTCTCTTCCT ACCCTCCTTC CACATGTACA TAAACTGTCA CTCTAGGAAG AAGACAAATG ACAGATTCTG ACATTTATAT TTGTGTATTT TCCTGGATTT ATAGTATGTG ACTTTTCTGA TTAATATATT TAATATATTG AATAAAAAAT AGACATGTAG TTGGAACTGA AAAAAAAAAA AAA | |
| PDE4B | NM_001037339.2 | ATCACATACC CTAAAGAACC CTGGGATGAC TAAGGCAGAG AGAGTCTGAG AAAACTCTTT GGTGCTTCTG CCTTTAGTTT TAGGACACAT TTATGCAGAT GAGCTTATAA GAGACCGTTC CCTCCGCCTT CTTCCTCAGA GGAAGTTTCT TGGTAGATCA CCGACACCTC ATCCAGGCGG GGGGTTGGGG GGAAACTTGG CACCAGCCAT CCCAGGCAGA GCACCACTGT GATTTGTTCT CCTGGTGGAG AGAGCTGGAA GGAAGGAGCC AGCGTGCAAA TAATGAAGGA GCACGGGGGC ACCTTCAGTA GCACCGGAAT CAGCGGTGGT AGCGGTGACT CTGCTATGGA CAGCCTGCAG CCGCTCCAGC CTAACTACAT GCCTGTGTGT TTGTTTGCAG AAGAATCTTA TCAAAAATTA GCAATGGAAA CGCTGGAGGA ATTAGACTGG TGTTTAGACC AGCTAGAGAC CATACAGACC TACCGGTCTG TCAGTGAGAT GGCTTCTAAC AAGTTCAAAA GAATGCTGAA CCGGGAGCTG ACACACCTCT CAGAGATGAG CCGATCAGGG AACCAGGTGT CTGAATACAT TTCAAATACT TTCTTAGACA AGCAGAATGA TGTGGAGATC CCATCTCCTA CCCAGAAAGA CAGGGAGAAA AAGAAAAAGC AGCAGCTCAT | 15 |

TABLE 1-continued

Plasma cell dyscrasia Biomarker/Housekeeper Sequence Information

| Gene Name | RefSeq Accession | Sequence | SEQ ID NO: |
|---|---|---|---|
| | | GACCCAGATA AGTGGAGTGA AGAAATTAAT GCATAGTTCA<br>AGCCTAAACA ATACAAGCAT CTCACGCTTT GGAGTCAACA<br>CTGAAAATGA AGATCACCTG GCCAAGGAGC TGGAAGACCT<br>GAACAAATGG GGTCTTAACA TCTTTAATGT GGCTGGATAT<br>TCTCACAATA GACCCCTAAC ATGCATCATG TATGCTATAT<br>TCCAGGAAAG AGACCTCCTA AAGACATTCA GAATCTCATC<br>TGACACATTT ATAACCTACA TGATGACTTT AGAAGACCAT<br>TACCATTCTG ACGTGGCATA TCACAACAGC CTGCACGCTG<br>CTGATGTAGC CCAGTCGACC CATGTTCTCC TTTCTACACC<br>AGCATTAGAC GCTGTCTTCA CAGATTTGGA GATCCTGGCT<br>GCCATTTTTG CAGCTGCCAT CCATGACGTT GATCATCCTG<br>GAGTCTCCAA TCAGTTTCTC ATCAACACAA ATTCAGAACT<br>TGCTTTGATG TATAATGATG AATCTGTGTT GGAAAATCAT<br>CACCTTGCTG TGGGTTTCAA ACTGCTGCAA GAAGAACACT<br>GTGACATCTT CATGAATCTC ACCAAGAAGC AGCGTCAGAC<br>ACTCAGGAAG ATGGTTATTG ACATGGTGTT AGCAACTGAT<br>ATGTCTAAAC ATATGAGCCT GCTGGCAGAC CTGAAGACAA<br>TGGTAGAAAC GAAGAAAGTT ACAAGTTCAG GCGTTCTTCT<br>CCTAGACAAC TATACCGATC GCATTCAGGT CCTTCGCAAC<br>ATGGTACACT GTGCAGACCT GAGCAACCCC ACCAAGTCCT<br>TGGAATTGTA TCGGCAATGG ACAGACCGCA TCATGGAGGA<br>ATTTTTCCAG CAGGGAGACA AAGAGCGGGA GAGGGGAATG<br>GAAATTAGCC CAATGTGTGA TAAACACACA GCTTCTGTGG<br>AAAAATCCCA GGTTGGTTTC ATCGACTACA TTGTCCATCC<br>ATTGTGGGAG ACATGGGCAG ATTTGGTACA GCCTGATGCT<br>CAGGACATTC TCGATACCTT AGAAGATAAC AGGAACTGGT<br>ATCAGAGCAT GATACCTCAA AGTCCCTCAC CACCACTGGA<br>CGAGCAGAAC AGGGACTGCC AGGGTCTGAT GGAGAAGTTT<br>CAGTTTGAAC TGACTCTCGA TGAGGAAGAT TCTGAAGGAC<br>CTGAGAAGGA GGGAGAGGGA CACAGCTATT TCAGCAGCAC<br>AAAGACGCTT TGTGTGATTG ATCCAGAAAA CAGAGATTCC<br>CTGGGAGAGA CTGACATAGA CATTGCAACA GAAGACAAGT<br>CCCCCGTGGA TACATAATCC CCCTCTCCCT GTGGAGATGA<br>ACATTCTATC CTTGATGAGC ATGCCAGCTA TGTGGTAGGG<br>CCAGCCCACC ATGGGGGCCA AGACCTGCAC AGGACAAGGG<br>CCACCTGGCC TTTCAGTTAC TTGAGTTTGG AGTCAGAAAG<br>CAAGACCAGG AAGCAAATAG CAGCTCAGGA AATCCCACGG<br>TTGACTTGCC TTGATGGCAA GCTTGGTGGA GAGGGCTGAA<br>GCTGTTGCTG GGGGCCGATT CTGATCAAGA CACATGGCTT<br>GAAAATGGAA GACACAAAAC TGAGAGATCA TTCTGCACTA<br>AGTTTCGGGA ACTTATCCCC GACAGTGACT GAACTCACTG<br>ACTAATAACT TCATTTATGA ATCTTCTCAC TTGTCCCTTT<br>GTCTGCCAAC CTGTGTGCCT TTTTTGTAAA ACATTTTCAT<br>GTCTTTAAAA TGCCTGTTGA ATACCTGGAG TTTAGTATCA<br>ACTTCTACAC AGATAAGCTT TCAAAGTTGA CAAACTTTTT<br>TGACTCTTTC TGGAAAAGGG AAAGAAAATA GTCTTCCTTC<br>TTTCTTGGGC AATATCCTTC ACTTTACTAC AGTTACTTTT<br>GCAAACAGAC AGAAAGGATA CACTTCTAAC CACATTTTAC<br>TTCCTTCCCC TGTTGTCCAG TCCAACTCCA CAGTCACTCT<br>TAAAACTTCT CTCTGTTTGC CTGCCTCCAA CAGTACTTTT<br>AACTTTTTGC TGTAAACAGA ATAAAATTGA ACAAATTAGG<br>GGGTAGAAAG GAGCAGTGGT GTCGTTCACC GTGAGAGTCT<br>GCATAGAACT CAGCAGTGTG CCCTGCTGTG TCTTGGACCC<br>TGCCCCCCAC AGGAGTTGTA CAGTCCCTGG CCCTGTTCCC<br>TACCTCCTCT CTTCACCCCG TTAGGCTGTT TTCAATGTAA<br>TGCTGCCGTC CTTCTCTTGC ACTGCCTTCT GCGCTAACAC<br>CTCCATTCCT GTTTATAACC GTGTATTTAT TACTTAATGT<br>ATATAATGTA ATGTTTTGTA AGTTATTAAT TTATATATCT<br>AACATTGCCT GCCAATGGTG GTGTTAAATT TGTGTAGAAA<br>ACTCTGCCTA AGAGTTACGA CTTTTTCTTG TAATGTTTTG<br>TATTGTGTAT TATATAACCC AAACGTCACT TAGTAGAGAC<br>ATATGGCCCC CTTGGCAGAG AGGACAGGGG TGGGCTTTTG<br>TTCAAAGGGT CTGCCCTTTC CCTGCCTGAG TTGCTACTTC<br>TGCACAACCC CTTTATGAAC CAGTTTTGGA AACAATATTC<br>TCACATTAGA TACTAAATGG TTTATACTGA GCTTTTACTT<br>TTGTATAGCT TGATAGGGGC AGGGGGCAAT GGGATGTAGT<br>TTTTACCCAG GTTCTATCCA AATCTATGTG GGCATGAGTT<br>GGGTTATAAC TGGATCCTAC TATCATTGTG GCTTTGGTTC<br>AAAAGGAAAC ACTACATTTG CTCACAGATG ATTCTTCTGA<br>ATGCTCCCGA ACTACTGACT TTGAAGAGGT AGCCTCCTGC<br>CTGCCATTAA GCAGGAATGT CATGTTCCAG TTCATTACAA<br>AAGAAAACAA TAAAACAATG TGAATTTTTA TAATAAAATG<br>TGAACTGATG TAGCAAATTA CGCAAATGTG AAGCCTCTTC<br>TGATAACACT TGTTAGGCCT CTTACTGATG TCAGTTTCAG | |

TABLE 1-continued

Plasma cell dyscrasia Biomarker/Housekeeper Sequence Information

| Gene Name | RefSeq Accession | Sequence | SEQ ID NO: |
|---|---|---|---|
| | | TTTGTAAAAT ATGTTTCATG CTTTCAGTTC AGCATTGTGA | |
| | | CTCAGTAATT ACAGAAAATG GCACAAATGT GCATGACCAA | |
| | | TGTATGTCTA TGAACACTGC ATTGTTTCAG GTGGACATTT | |
| | | TATCATTTTC AAATGTTTCT CACAATGTAT GTTATAGTAT | |
| | | TATTATTATA TATTGTGTTC AAATGCATTC TAAAGAGACT | |
| | | TTTATATGAG GTGAATAAAG AAAAGCATGA TTAGATTAAA | |
| | | AAAA | |
| PLAS2 | NM_001324046.1 | CGGAGGCGGA GCTCCCGCGC CGTTCACGTG ACGGGCCCGG | 16 |
| | | CTGTAGCGGC GGCGGCCGCG GCGTCTTAAG CGGCGCCCAG | |
| | | TGCAGGATGG TGCTGGAGGC GGCGGCGGCC GTGGTGGCGG | |
| | | CAGCGTCGTT GGCGGCAGCG GGAGTGGGTG CGGCGGCAGC | |
| | | GGCGGCGGCG CCCGCGGGTG GTATAAAATG GCGGATTTCG | |
| | | AAGAGTTGAG GGATCTCCAG TACAATGTTG AATAGAAGCT | |
| | | GTGATGGGGG CATCCTGATC TTGTTCCTGA TTTTAAAGGG | |
| | | AATGCTTTCA AAGTTTCACA AGTGGCTGTA CCATTTTACA | |
| | | TCCCTACCAG CAATGTATGG AGTGATCCAG TTTCTCAGCA | |
| | | TCCTCGCCAG CATTTGGTGT TATCAGTGTT TTTCATTTTA | |
| | | GCCATTCTGA ATATGGTTTC TAGTTTTAGG GTTTCTGAAC | |
| | | TACAAGTATT ACTAGGCTTT GCTGGACGGA ATAAAAGTGG | |
| | | ACGCAAGCAT GACCTCCTGA TGAGGGCGCT GCATTTATTG | |
| | | AAGAGCGGCT GCAGCCCTGC GGTTCAGATT AAAATCCGAG | |
| | | AATTGTATAG ACGCCGATAT CCACGAACTC TTGAAGGACT | |
| | | TTCTGATTTA TCCACAATCA AATCATCGGT TTTCAGTTTG | |
| | | GATGGTGGCT CATCACCTGT AGAACCTGAC TTGGCCGTGG | |
| | | CTGGAATCCA CTCGTTGCCT TCCACTTCAG TTACACCTCA | |
| | | CTCACCATCC TCTCCTGTTG GTTCTGTGCT GCTTCAAGAT | |
| | | ACTAAGCCCA CATTTGAGAT GCAGCAGCCA TCTCCCCCAA | |
| | | TTCCTCCTGT CCATCCTGAT GTGCAGTTAA AAAATCTGCC | |
| | | CTTTTATGAT GTCCTTGATG TTCTCATCAA GCCCACGAGT | |
| | | TTAGTTCAAA GCAGTATTCA GCGATTTCAA GAGAAGTTTT | |
| | | TTATTTTTGC TTTGACACCT CAACAAGTTA GAGAGATATG | |
| | | CATATCCAGG GATTTTTTGC CAGGTGGTAG GAGAGATTAT | |
| | | ACAGTCCAAG TTCAGTTGAG ACTTTGCCTG GCAGAGACAA | |
| | | GTTGCCCTCA AGAAGATAAC TATCCAAATA GTCTATGTAT | |
| | | AAAAGTAAAT GGGAAGCTAT TTCCTTTGCC TGGCTATGCA | |
| | | CCACCGCCTA AAAATGGGAT TGAACAGAAG CGCCCTGGAC | |
| | | GCCCCTTGAA TATTACATCT TTAGTTAGGT TATCTTCAGC | |
| | | TGTGCCAAAC CAAATTTCCA TTTCTTGGGC ATCAGAAATT | |
| | | GGGAAGAATT ACTCTATGTC TGTATATCTT GTACGGCAGC | |
| | | TTACATCAGC CATGTTATTA CAGAGATTAA AAATGAAAGG | |
| | | TATTAGAAAC CCTGATCATT CCAGAGCACT AATTAAAGAA | |
| | | AAACTTACTG CAGATCCTGA TAGTGAAATT GCTACAACTA | |
| | | GCCTTCGGGT ATCCTTGATG TGCCCTTTAG GAAAAATGAG | |
| | | GCTGACAATC CCATGCCGTG CAGTGACTTG TACACATCTG | |
| | | CAGTGTTTTG ATGCTGCCCT CTATCTACAA ATGAATGAGA | |
| | | AAAAGCCCAC CTGGATTTGT CCTGTGTGTG ACAAAAAAGC | |
| | | TGCCTATGAA AGTCTAATAT TAGATGGGCT TTTTATGGAA | |
| | | ATTCTCAATG ACTGTTCTGA TGTAGATGAG ATCAAATTCC | |
| | | AAGAAGATGG TTCTTGGTGT CCAATGAGAC CGAAGAAAGA | |
| | | AGCTATGAAA GTATCCAGCC AACCGTGTAC AAAAATAGAA | |
| | | AGTTCAAGCG TCCTCAGTAA GCCTTGTTCA GTGACTGTAG | |
| | | CCAGTGAGGC AAGCAAGAAG AAAGTAGATG TTATTGATCT | |
| | | TACAATAGAA AGCTCTTCTG ACGAAGAGGA AGACCCTCCT | |
| | | GCCAAAAGGA AATGCATCTT TATGTCAGAA ACACAAAGCA | |
| | | GCCCAACCAA AGGGGTTCTC ATGTATCAGC CATCTTCTGT | |
| | | AAGGGTGCCC AGTGTGACTT CGGTTGATCC TGCTGCTATT | |
| | | CCGCCTTCAT TAACAGACTA CTCAGTACCA TTCCACCATA | |
| | | CGCCAATATC AAGCATGTCA TCAGATTTGC CAGGTTTGGA | |
| | | TTTTCTTTCC CTTATTCCAG TTGATCCCCA GTCTCACCTC | |
| | | ACCCTTAACA GCAAGCAGTA CGTCTGTCAC CACCACCAGC | |
| | | TCCCATGAAA GCAGTACTCA TGTTAGTTCA TCCAGCAGCA | |
| | | GGAGTGAGAC AGGGGTCATA ACCAGCAGTG GAAGTAACAT | |
| | | TCCTGACATC ATCTCATTGG ACTAAAGGAG GACTCACTTG | |
| | | ATTCTGGGAA TCATTCATCA GAACTGCTTT TTCTTGGATC | |
| | | TCTAGTCTGT GGAAACGTTC TTTTTTTTTT TTTTTTAATA | |
| | | ATTTGGTATT TATTGAAAGT CAGATGGATT CTTTTGCTTT | |
| | | CTGAGGGGTG AACACAGAAG ACTGCAACAA GAACCAAATG | |
| | | ACATGCAAGG ATTTTTCTTA ATTATGCTGT ACTCTCAGCA | |
| | | TCAGATACAT TCAACCATAA CTGTATCTTC CTGAGAGATG | |
| | | GATTTCACTT TCATACGTTA ATGGATGGAG TCTACAAATC | |
| | | AGTGAAAAAA GTTTTTGTTA AAATAAAGAG CAATAAAATT | |
| | | ATGTAAATAT TCAAGTAACC TTTTTCTAA TTAAAAAAAA | |
| | | AATTGTAATC ACTGATTCTA GAATGACAGC AACTTCTGTT | |

TABLE 1-continued

Plasma cell dyscrasia Biomarker/Housekeeper Sequence Information

| Gene Name | RefSeq Accession | Sequence | SEQ ID NO: |
|---|---|---|---|
| | | TAACCTTACG TGAAGGAAAA AAAATATATG GAAAGAACTT | |
| | | AATGTTTGCT GAATGAGTCC TTTCCATGGA GATTTGCTCT | |
| | | GTTTCATTGA AGTAATGAAG TTTCAGTACG TGGCCAAAGC | |
| | | TTGGATTCCA CTTTTCGTCC TGCATTTCCA CTTTTCTTCG | |
| | | TGATTGCATC AAAGAAAAAT GGCATTCGTG TTACTTGGTT | |
| | | TTTTTCCTGC TTATCATTTA CACTTTGACG TTGTTTGCTA | |
| | | ATGAGTGCTG TGTGAAGTTC TGGGATTTGG CTACTCTTCA | |
| | | TTGGTGATTA TGTTTAAAAG CACTATGCAG ATTCTGCCCT | |
| | | GACATAAAGT GTGTTATTAT GTTTTTAGTA ATTGTACATT | |
| | | TTTCATTCTA GAGTTTTCTA TAAATTTGAG GCTTGCCTTC | |
| | | TCAAAAAAGA AACTATGCAG CCATTGAATG AAATGTCTTT | |
| | | GGGGTACGGT GTGACTGGAA TGTTTGTTAG AAATTTGTTC | |
| | | ACACTATCAA ATATTGATAT CTTGGAGCCA GCAGAAGAGC | |
| | | AGATTTTGGG AGGTGGTAAT AACAAAATTT AATTTCTTCC | |
| | | CAACAACTTA ATTTTCTCAT TTATTTTACA GAATAGTAGT | |
| | | GAAATATTTG ATGAAACTTT GTATTTTGGT AGCACTACAT | |
| | | AGAAAATGTG TTTTAGATTT ATGATGATCA TATTTCTCAC | |
| | | CAATGTAATT TCAGTCTCAG CAGTGATTTT CAAACTTAGG | |
| | | GAAAGGGACA GCATTAGATT TTTTTTTTTT TTCATTTTTT | |
| | | TAAAATGATA TCTTACCTGA AACTACAAAC GACAAAAGAG | |
| | | AATTAGAAAT GTTTGAATTA AAGTGAAGAA GGGTTGGGGG | |
| | | AGATGGGCCT GAACCCACTT CCTGTCTCAA TCCATGCTAC | |
| | | CCCAAACACT CCAGGGAACC TCTGAGGTTT TATTGGGTGC | |
| | | ACTTTGAAAA TTTCTCTTCT ATAGTGTGTT TGTTTGATTT | |
| | | TAAATCACAG AGAAAACTGG GTTTTACTCT TAGAGAAACA | |
| | | TTTTCATCCA GTTTTTTAGT TTGCTTCATT TGACTTCCTA | |
| | | AATCATTTTT GAGTTCACAA GGATTTGGTA CTTTTCTGTT | |
| | | TAGCTTTCTC TCTCTAAGCT TTATCTACCT TAAAAACAAA | |
| | | GTCCTTTTTT TAATGGCCAG TCCAACCAAT TGATTTCTCA | |
| | | AACTGAAGTG CCCAGGTGTG GACTCATCAA TTTCCGTTAG | |
| | | AATAGGGACA TCCTACTTAA GAGTTGGTGC AGCTCCAAGG | |
| | | AGCTGACTTG TCCTTGCTTG GGGTTTTTTT TTTTTTTCTT | |
| | | TCACCTTCTC AAGTTTCCAT GGCCTTTGTG TGTTCTTTTT | |
| | | ATGTTGATTT AAATTCATAT GGTTTTCCAC AAATCCCTTC | |
| | | TTTGGCTACA TTGTCTCCTT ATTCAATGGA TTATCCCTTT | |
| | | GTGGGGGCTG CTTATTTTAA AGATGTTGGG GGGGAAACAA | |
| | | ACCCAAATCT ACGAGCAGTA GTTGCACATA GTTGCCAGTT | |
| | | TTACCTTCTT AGTCATTAGA TTTCCAAACC ATGTTGCAGT | |
| | | TTTTTGGTCC AGATATAGTA TTTCTTTCTA ATAAAGTTTT | |
| | | ATGTTGCTGC TCTAAATACA GATGCAATAT TTATTGACTC | |
| | | TGTAATCAGA TAGAAAAAAC TTAACTTGGT TTGTGTGGTA | |
| | | TGACTTATAA AGAAATGATG TATATTTGTT ATTTTGTTAC | |
| | | CCTTTAGATT GTCAGAGACT CCCCCAATTT AATCAACAAA | |
| | | GTTTTATAAA GTAAATGAAA ATATTAATAG AAATTAGTTT | |
| | | ATTTACTTGG TTCTTATAAC TGATATCTCT GTGCTTTTAT | |
| | | AATTGTGATT TGTTTTTTTG TTTTTTTTTC TATTTTCTGT | |
| | | GAACAGTTTT AATGTTCGGT TTTGGTGTTT TACACTGAAA | |
| | | TTACATATAA ATTTTTAATT TATTTCATAC AGGCAACTTG | |
| | | CATTTTAAAA AATACACTTT GAAGTTTATC ATCTTGAAAT | |
| | | TGGGGCTTAC GTTGTTTATC TGTCTTGAGC ATTAGTACTT | |
| | | TATGACTTTG GCCTTATGGC AACATCATGA TTATTAATCC | |
| | | GTCAGCCTTT AATGTGGTCA CTGTTTCTTA TCCAGACCCT | |
| | | GACTTTCTAG TAGTTTATTT TGCTAGCCCA GATTTCTGCT | |
| | | TAACCAAATA TAAGGGAGTT TCAGAGGGGT GATCTTAGCT | |
| | | GTCACCTAGA TTCTGTCAGC CAACCAGTGA TTGTCTGGAA | |
| | | TATCTTAGGA AATGAACTGT AATTGTCAGC CTCCTAAAAT | |
| | | CAATTTTTTT TTTTTTTTTT TTGAGGCTGA GTCTTGCTCT | |
| | | TGTTGCCCGG GATGGAGTGC AATGGTGCGA TCTTGGCTCA | |
| | | CCGCAACCTC CACCTACAGG GTTCAAGCGA TTCTCCTGCC | |
| | | TCAGCCTCCC GAGTAGCTGG GATTACAGGC ATGTATCACC | |
| | | ACGCCCAGCT AATTTTGTAT TTTTAGTAGA TACGGGGTTT | |
| | | CTCCATTTTG GTCAGGCTGG TCTCGAACTC CCGACCTCAG | |
| | | GTGATCCGCC TGCCTTGGCC TCCCAAAGTG CTGGGATTTA | |
| | | CAGGCGTGAG CCACCGCGCC TGGCCAAAAT AAAATGTTTT | |
| | | TATCTTTCTT CACTTAGAAC TATGAAGGCC TTTTCTTGTT | |
| | | CTGGTAACCC CCCACAGTGT AATTGGTGCT GAAAATAGTT | |
| | | TCGTGCCTGA GGTCTGTTGT CACTCACTCA CTTTCTGACA | |
| | | ATTAGGTGAG CCACTTGAGG ATTTTCTGGC CTGAAGTTAT | |
| | | AAAAACTTGG CATCTGTCCT AAGGTAATTG TAAAGGCAAA | |
| | | ATGAAAGCAT TGAGGTGAAT TTAGGTTATA TGGCATTTAT | |
| | | CTGGTAATGT GTTTCAGAAA AGCTAGAATG AAAATGTGAT | |
| | | GTAAGGGATA GCAAGTGTAG GTTGATTCAT AATTCTTGGT | |
| | | ATAAAACCAA GTTTTCCTTA GTCTTGAGGA ATTTGAAGAA | |
| | | AGGTAAAATG TTGGATTTTA AGCAAAGTAG GATTGACCAG | |

TABLE 1-continued

Plasma cell dyscrasia Biomarker/Housekeeper Sequence Information

| Gene Name | RefSeq Accession | Sequence | SEQ ID NO: |
|---|---|---|---|
| | | AGACTGTTCT GACTTTGACA TTCAGACCTT TCAGATGTTC | |
| | | TTCCTTCAGA CCAGTCCAAG ACACTCAGCA TTTCCAGCCA | |
| | | AGTTGTCTTT TTTTTCTGCC AATAAAGTAT TCATTAGTTG | |
| | | ACGTTTGTTT GTATTTTAAG TAAAGTCAAT TTTTTTTAAA | |
| | | GCATTAATTT AATTCACGGG TATGCCTTTC ATTTCTCTGG | |
| | | CCTTCAGTTG GTTTAAAAAA AAAAAAAAAA AAAAAAGCAC | |
| | | TTAGCCGGAC CATTCTTTCT TTAGTAAACA TTTTTATTTT | |
| | | CTTAATTTTT CCTGAAAGAT TTTCTTCATT TTCATGGAAT | |
| | | GTCATAATGA CACTACCATT ATTTTCTAGC TCTTTGCATA | |
| | | ATAGAAAAAT GTAGAGCAGT GCACCATTTA AACACGTCTG | |
| | | ACATTGGATT TAGTGGTCCT AGGTTCATGT GATTTGGGAG | |
| | | CCTTAAGTTG TTATTTAGAT TGATTCAGCC TGATTCACCA | |
| | | TCTTTTTTAC TACAGTTCTA CATGAATGTG GTGAAACAGG | |
| | | TAGAAGAAAA TTAAGCATTT CTCTGCTTTT GGAGTCTAAT | |
| | | GTTCCTGCCT AGTGACTGGT TTGTAACACC CCCCTCACCC | |
| | | CTACTTTGTT AGGAACCTGC AATTCCTAAA AGAAATAAAT | |
| | | AAAGCTGTAC CCAATGTCCA TTCTTTAATG CTTGCCTGGT | |
| | | TGAATAATGT TTGTTTTTTC TGTTTATGTC AGTAGTACAT | |
| | | GCTTATTGTG GAAAATTTAG ACAATACAGA AAAGTATAAC | |
| | | AATTAATTGC CTATGATTCT GTCACCAGAA AAAATCACTT | |
| | | GATATTTTTG CATCTTCCTT GCCATTGTCT TTGCTACTTC | |
| | | TGCATATTTT TACTTAGTTT CATCATTCTC AGTGTAATTT | |
| | | ATATCTTGGG GTTTTTCCCC GCAACCTACA GGCATTATTC | |
| | | CATGTCATTA AAACTGTGTC AACTATTATT AATTTTATGG | |
| | | TACTCCATTG TTATGGATGT GCCATGTTTC ATATAACCTT | |
| | | TACTTATTTT GAACAGTTTA GATTATATCT CATAATGCCA | |
| | | CAATGAATGT CTTTGTGTAT AAATTATTTT CTTAGGATAA | |
| | | AATACTGGAG GTGGAATTTC TAGTCAAGGG TATATGAACA | |
| | | CTTTTGTAGT TCTTGATTCA TACCACTTTT CCACATGGGT | |
| | | ATGTTAATTT ATACTGCAGC TAGATGGTAT GGGAAGGGTG | |
| | | GTCTAGCCAT ATTTTCCAAG AACATGCAAC GTTTTATCTT | |
| | | TATGCAGGCA TCTGCACTAA GACCCTCTGC CTTTCTGACT | |
| | | CTATGGAACG GGGTTAACTG ATATGGAGAT CATTGGCAGA | |
| | | GATTTTCCCA AGCTTTCTTA GTTTTAAATA TATCTGACAT | |
| | | GGGCCGGGTA TGGAGGCTCA CGCCTGTAAT CCCAGCACTT | |
| | | TGGGAGGCCA AGGCGGGCAG ATAATCTGAA GTCAGGAGTT | |
| | | GGAGACCAGC CTGGCTAACA TGGAACATGG TGAAACCCCA | |
| | | TCTCTAGCAA AAACATAAAT TAGGTGGGTG TGATGGCAGG | |
| | | CGCCTGTAGT CCCAGCTACT TGGGAGACCG AGGCAGGAGA | |
| | | ATCGCTTGAA CCCAGGAGGC GGAGGATTTG CAGTGATCCG | |
| | | AGATTGTGCC ACTGCACTCC AGCCTGGGTA ACAAAGCAAG | |
| | | ACTCTCTAAA AAAAAAAAAA AAAAAAAAAA AAAATATATA | |
| | | TATATATATA TATATATATA TAAAATCTGA CATGTTTCAG | |
| | | AAACACCTAC GTATGGCTAT CCAAGCTTTT CCCATGATTT | |
| | | TACTGGCACT GTAAAGTTGC ACAAATATTC TTTGTCAGAC | |
| | | TACGTTTTCC ATCTTTAGTT CAAAAGTTTT GTCACTTTTT | |
| | | AAAAAAAGCC TCTTGTACCT AAGGCCTGCC CTTAAGAGGT | |
| | | CAGCTCTCTT TTTCCTCTTC CTGTAGGCCC CATTATGGCC | |
| | | TTTCTGAGCT CCCCAAAGCC AGTAGAATCT ACTGAGCCAA | |
| | | AGGCATTCCA TCCCCAAACT GAAAAGTGGT AAGGCTAAAA | |
| | | GCTATAAAAA CAGGCAAACA TTGCCTGTTT TCACTTTATA | |
| | | TTCCCTTATG TTTCCAATAA GGGTAGCTGC AGGGAAAGAA | |
| | | AAAAACAGAT TGCTACCTTC AGATGTTTGA GGTACAACAT | |
| | | TTTCTTGATT GGCGTAGCAC AATCATTTCC CAAACTGCTT | |
| | | CCTATTTCTG AATGGCTTTT TTAAAAAGCT TTATTTTGTG | |
| | | TTCTCAAAGC TTAATTATTT TAAGTGACGA AGAGTGTTAC | |
| | | CGTGTTGTAG AATAGCATAT GCCTCTTATT TTGGCCTTCA | |
| | | TCAAACTGTT TAATAAATGT TTAGAGTGTT TTGTAAGTAC | |
| | | ACGTGGAATA GAGTGTTACA GAAGTTTTGG TTCCAGACAT | |
| | | CAGGCAGCTT ATAATCAAGG TTCCAAAAAT CAAGAATTCT | |
| | | TAAGCTGGGC ATGGTGGCTC ATGCCTGTAA TCCCAGCACT | |
| | | TTGGGAAGCC AAGGCAGGCA AATCACTTGA GGCCAGGAGT | |
| | | TTGAGACCAG CCTGGCCAAC TTGGTAAAAC CCCATCTCTA | |
| | | CTAAAAATAC AAAAAATTAG GGCATGATGG CTCATGTCTG | |
| | | TAATCCCAGC TACTTGGGAG GCTGAGGGAT GAGAATTGCT | |
| | | TGAACCTGAG AGGCGGAGGT TGCAGTGACT CAGGATCATG | |
| | | ACCCTGTACT CCAGCCTGGG TGACAGAGTG AGACCAAAAA | |
| | | AAAAAAAAAA AAAAAAAAAA AAAAGTAACA GGCATTGTGC | |
| | | AAAGAATTTT CCAAGAATGT CTCATTCTTG CAATGGCTTC | |
| | | TCAGAGGAAA GTGGTGTTAT TCCCCATTTT ACAAATGAAA | |
| | | CAGGTTTAGG TAAGTTTCCC AAGGTCACAG TGAATGAGTA | |
| | | GTGGACTTGG GAGTCTGACC TAGACTTACC CCAAAAGCTC | |
| | | TCTGCGTAAA CTGAAGTGAC GTTAATTAGC TGTGCTATCT | |
| | | AGGAGACTGA TATGGGAATC TAGACTTAAA ATTATGAGAA | |

TABLE 1-continued

Plasma cell dyscrasia Biomarker/Housekeeper Sequence Information

| Gene Name | RefSeq Accession | Sequence | SEQ ID NO: |
|---|---|---|---|
| | | CTGGTTTCAG ATGATGGCCA GAGTAATAAG GAAGGAGTGG<br>ATGCTGAAGC CATTTCAAAG GAAGACTCAA GATTCAGTGA<br>CTGAATATAG GAGTAAGGGT TGAGTGCATT TTTCATCCAT<br>TTTTCAAGCC TGGGTAACTT GGATGTTAAT GGCACTATCT<br>ACAGAGACAG GAGGCAGTTT AGAGTGAAGA CGAATCATGT<br>ATGGGAGACA GTGATGAATG TTAAGCATGG GATTTCAGAA<br>ATGAAGCATC CATGAGGCTC ATTCCTGGTT TTTCTGCAGT<br>CTTTTAAATA AAAGTACAAA CCTCCCTTGT CATCCATTTT<br>TGCCTTCACT TATCTCCATT CTGTATTATG TTCTAGTCAC<br>GCCCCAGTCA CTGATCCCTT CCTAGGCCAT ACTTGGCTAC<br>ATCTTAGCCT TTTCTTTTGA TTTTTCTCTT CACTGCCTTG<br>CCCATTACAA ATTTGGCTGC CACCTGAGGC CCTGCCATAC<br>CCTACAGCTC ACACCAGCGT GGGCTGTGTT CACATTCTAC<br>ATATCTCAAG ATACAGTGGT TGCTGTCCTT CCCCCCTACT<br>GCATCGTTAC ACGTCTCTAA AAAATCTCTG CCTCTGAAGC<br>TCATGCCAAG AGGTTATACT ATCAGCTACC TCTAGTCTTA<br>TAACTGCCTG ATCATTCCCT TTGATTTGCT GGAAGCTTTG<br>ACTCACAGTG TTCCTTGCCT TCCTTGATTC TGGTCATTAT<br>TATTAATATC TTGAACATTC TATAGATGAT TTATCCAAGT<br>TGGTCTGTGA GGTATTGGTT ACTTTACCTC CAGCATTTTC<br>GTCTACTGAA CCACGCTTTC TGTTTTCCTC TTTGCTACTT<br>GTCCAGACTG TTCTTTCATT ATTGCAGCCT TGAAGAAATC<br>CTCAGTAACC TATCCATCCT CCGACATGAC GTAGCATAGT<br>TCCTTTGCCC ATTCTCATCA GTTATAACAA ATGTTATTGC<br>CCTCTTTTCA GGCCACTTCC TTCTCAGAAG ATGACTTTGC<br>TGCTTAATTC AAACAGAAGG GACAGTCCGA AAGCATGATT<br>TCTTCCCCAC CTATGACCAC CTCCATCCTT TTTTGTTTCC<br>AGTTTCAGAG AATGAGGTAG GCCTTTAAGG CCAACTGACT<br>CTGGTCTCCT CCTGTCATCT TCAGGACCTT CCTCTGTCAG<br>ACTTCCCCTC TCTTATCTCC ATGTCTCTCA CCTCTCTACT<br>GCTGCTTTTC TTGGCTTACA AATGGTCTCA GTCATCCAGT<br>ATTTGAGATT ATATTAGGTG CCAGGCATTG TATCAGGCAC<br>TTGGAACACA AGGCAGGATC CTGCCCCCAC CAAAGTTGTG<br>CTCCAATAGC GTCAACAGAG GTGTGAAATA GGGAGATTAC<br>AATGTTAATG GTAAAAGACA AAGTATAGGG TGCTACAAGA<br>GCATGTAAAT GAGGCACCTC AATGATTTAA TAGAAGTAAT<br>GTGGAGAAAT GTGAGGATTG ATGAAAAGCT TGTCCAAAAA<br>GGGCCAGAAA TGTTTAGAAT TGCTGGAAGT TTGCTAAGGA<br>ATATTGAGAA ATATGCATAG ATAGATCGTG AAGGGCCTTG<br>TAAAACAGTG ATGAGACATT GAAGAGTTTT CATGATCATT<br>AGTAGTAATG AGAATTTGTT GAGTTTGGCA TGATTATCTC<br>CATATTACAA ATGTGGAAAC AGATTCTGAC AGGATAAGCG<br>ACTTACTTGC CCAGGGTCAT GCAGCTTGTA ATTGAGGAGT<br>CAGGTTTCAA ATCCAGTTTT AACTACTTTC TCAGAGGCCT<br>TTCTTGATCA TTCTATCTAA AAAGCAAGTG TTCCCTAACT<br>ATTATCCCAG TACCCTGGTT TATATACTCT TAATACATAA<br>AATAATCCCT GCATATTGTG TGTTTCCCCT ACTAGATTGT<br>AAGCTCCATG AGGGCAGAGG TGATAACTTT TTTCACTTGC<br>ATCCCAGAGC CTAACATGAT ATGGGCTACA TAGAAGGTGC<br>CCAGTAAATA TTGGTGGATG AAGAAATGGT GGATAACCAT<br>TTGCATTTGA CTTATGCTGA CTGGAAATTC AATACCTTTG<br>GAATATATAA TACCTCAGCA GTAAGCATTC ACCAAGAGAG<br>GAAAACAGAA GGAGGTGCAT GTTTAGGGTA GGTGGTACGG<br>GAGATGGATG CTGAGGTGTT GAAAGGCAGC ATACTCACCT<br>TCTGAACTCC AAAACTTACA GGGGCAAGGG CCATTAATGA<br>GGGGTGGGTA GAGCAGTGCA CAGTGGGGAT AATATGGGAG<br>TAGGTGTATT AAACCTGGAA GTGTAAGCAA CTCCTTGTAG<br>ACCCACCCTA CTGTGTATAA AAGGCTGGAG AAATTCTTCA<br>TATGATCTAC TCTAGGTTAT GTACTGAGGA CCACCTTATC<br>TGGGTCAGGT ACACTACACA GAGTGCTACA ATATAATTGT<br>AAACATAATT TATCCTCACT GTGATGGCTA GCCACCTGAC<br>CCAAATCATT ATTAGACTCA ATACTTTGGA ACTGGAACAA<br>AAATCAGTTG ACCTGATGTC TGAAAGACAT GCCCACCTGC<br>TATTTGACAA GCTATAGACA TATCCTACCA ATTGATGGGT<br>AGTAGCACTG AAACTATGAA AGTGGATGAA CTCATCCAGA<br>GGAGTTGATG AGTGAGAAAA GAAGACTGGA AAAGGAACAC<br>AAGGAAATCA AGAAGCAGCA GCTGAGACTG AAGGAAAATA<br>ACGTGGTATT ACAGAGGCCA AAAAATAGAG TATTTCAAGA<br>AGCAAGTGGT TAGTGGAGTT AAAAGCTGCT GATACAACCT<br>AAAAAAGTAA GTATCCATTT TTTAAAAAAC TTTCATTTAA<br>AATACCACCA TATTTTATTG AATCTAAGTA CCTGATTGTA<br>AGACATTAAA GAAAAATTAA ACCTGCTAAT TAAA | |

TABLE 1-continued

Plasma cell dyscrasia Biomarker/Housekeeper Sequence Information

| Gene Name | RefSeq Accession | Sequence | SEQ ID NO: |
|---|---|---|---|
| PRKAA1 | NM_006251.5 | AGCGCCATGC GCAGACTCAG TTCCTGGAGA AAGATGGCGA | 17 |
| | | CAGCCGAGAA GCAGAAACAC GACGGGCGGG TGAAGATCGG | |
| | | CCACTACATT CTGGGTGACA CGCTGGGGGT CGGCACCTTC | |
| | | GGCAAAGTGA AGGTTGGCAA ACATGAATTG ACTGGGCATA | |
| | | AAGTAGCTGT GAAGATACTC AATCGACAGA AGATTCGGAG | |
| | | CCTTGATGTG GTAGGAAAAA TCCGCAGAGA AATTCAGAAC | |
| | | CTCAAGCTTT TCAGGCATCC TCATATAATT AAACTGTACC | |
| | | AGGTCATCAG TACACCATCT GATATTTTCA TGGTGATGGA | |
| | | ATATGTCTCA GGAGGAGAGC TATTTGATTA TATCTGTAAG | |
| | | AATGGAAGGC TGGATGAAAA AGAAAGTCGG CGTCTGTTCC | |
| | | AACAGATCCT TTCTGGTGTG GATTATTGTC ACAGGCATAT | |
| | | GGTGGTCCAT AGAGATTTGA AACCTGAAAA TGTCCTGCTT | |
| | | GATGCACACA TGAATGCAAA GATAGCTGAT TTTGGTCTTT | |
| | | CAAACATGAT GTCAGATGGT GAATTTTTAA GAACAAGTTG | |
| | | TGGCTCACCC AACTATGCTG CACCAGAAGT AATTTCAGGA | |
| | | AGATTGTATG CAGGCCCAGA GGTAGATATA TGGAGCAGTG | |
| | | GGGTTATTCT CTATGCTTTA TTATGTGGAA CCCTTCCATT | |
| | | TGATGATGAC CATGTGCCAA CTCTTTTTAA GAAGATATGT | |
| | | GATGGGATCT TCTATACCCC TCAATATTTA AATCCTTCTG | |
| | | TGATTAGCCT TTTGAAACAT ATGCTGCAGG TGGATCCCAT | |
| | | GAAGAGGGCC ACAATCAAAG ATATCAGGGA ACATGAATGG | |
| | | TTTAAACAGG ACCTTCCAAA ATATCTCTTT CCTGAGGATC | |
| | | CATCATATAG TTCAACCATG ATTGATGATG AAGCCTTAAA | |
| | | AGAAGTATGT GAAAAGTTTG AGTGCTCAGA AGAGGAAGTT | |
| | | CTCAGCTGTC TTTACAACAG AAATCACCAG GATCCTTTGG | |
| | | CAGTTGCCTA CCATCTCATA ATAGATAACA GGAGAATAAT | |
| | | GAATGAAGCC AAAGATTTCT ATTTGGCGAC AAGCCCACCT | |
| | | GATTCTTTTC TTGATGATCA TCACCTGACT CGGCCCCATC | |
| | | CTGAAAGAGT ACCATTCTTG GTTGCTGAAA CACCAAGGGC | |
| | | ACGCCATACC CTTGATGAAT TAAATCCACA GAAATCCAAA | |
| | | CACCAAGGTG TAAGGAAAGC AAAATGGCAT TTAGGAATTA | |
| | | GAAGTCAAAG TCGACCAAAT GATATTATGG CAGAAGTATG | |
| | | TAGAGCAATC AAACAATTGG ATTATGAATG GAAGGTTGTA | |
| | | AACCCATATT ATTTGCGTGT ACGAAGGAAG AATCCTGTGA | |
| | | CAAGCACTTA CTCCAAAATG AGTCTACAGT TATACCAAGT | |
| | | GGATAGTAGA ACTTATCTAC TGGATTTCCG TAGTATTGAT | |
| | | GATGAAATTA CAGAAGCCAA ATCAGGGACT GCTACTCCAC | |
| | | AGAGATCGGG ATCAGTTAGC AACTATCGAT CTTGCCAAAG | |
| | | GAGTGATTCA GATGCTGAGG CTCAAGGAAA ATCCTCAGAA | |
| | | GTTTCTCTTA CCTCATCTGT GACCTCACTT GACTCTTCTC | |
| | | CTGTTGACCT AACTCCAAGA CCTGGAAGTC ACACAATAGA | |
| | | ATTTTTTGAG ATGTGTGCAA ATCTAATTAA AATTCTTGCA | |
| | | CAATAAACAG AAAACTTTGC TTATTTCTTT TGCAGCAATA | |
| | | AGCATGCATA ATAAGTCACA GCCAAATGCT TCCATTTGTA | |
| | | ATCAAGTTAT ACATAATTAT AACCGAGGGC TGGCGTTTTG | |
| | | GAATGCAATT TGCACAGGGA TTGGAACATG ATTTATAGTT | |
| | | AAAAGCCTAA TATGCAGAAA TGAATTAAGA TCATTTTGTT | |
| | | GTTCATTGTG CAGTATGTAT ATAGCATAAT ATACACAGTG | |
| | | AATTATAGGT CTCAGGCTTA CTTGATTTTT GGCTATTTTA | |
| | | TATTTAGTGT ACACAGGGCT TTGAAATATT AATTTACATA | |
| | | AAGGCCTTCA TATATTATTA CGTGTTATAT ATTACGTGTT | |
| | | ATAAATTTAT TCAATAAATA TTTGCCTAGA ATTCCCAAGA | |
| | | CCTTTATAGG TGATTTTGTT TTCTGGGCTC CTTAACTTCA | |
| | | TAAATAGCTA GTATCTTCCA GCAGTAGTAA CAGTCTGGAT | |
| | | AACTTCTTCC ATATCCCTCC CTCTTTGTTT TTTTGAGACA | |
| | | GTGTCACTTT GTCACCCAGG CTGGAGTGCA ATGGTGTGGT | |
| | | CTCGGCTCAC TGCAACCTCC ACCTCCCGGG TTCAAGTGAT | |
| | | TCTCCCGCCT CAGCTTCCTG AGTAGCTGGA ACTACAGGCG | |
| | | TGTGCCACCA CACCCGGCTA ATTTTTCGTA TTTTTAGTGT | |
| | | AGACGGGGTT TCACTATGTT GCCCAGGCTG GTCTCGAACT | |
| | | CCTGACCGCG TGATCCACCA CCTCAGCTTC CCAAAGTGGT | |
| | | GGGATTACAG GCGTGAGCCA CCGCACCCGG CCTCCATATC | |
| | | CCCCTTTTAA AATTCTGTAG TGTATGGTAA GTCATATCAG | |
| | | ATATCAGACC TAATTTAAAT TTCATTTTAG CTTTACAAGT | |
| | | CCAAAAACAC AGAATTTATA TATTCAGATA CTCTAGCACT | |
| | | AATTTTAGTC TTAAAATATT CCCACGATAT TCTGTACACA | |
| | | AAATGTTCTT TTTGTTACAA GAGCTGAGTT GCATATACTG | |
| | | TAGATAAATC ATATTATTTT TGCCAATTTC ACAAATTCCT | |
| | | CTGGCCCATC ATGTCAGTCA TTATTGAGTA TATGCACACA | |
| | | TTGCTACTTA TTTGATTATG TATCTTTTAA ATTGATTCAG | |
| | | TGCATAGAAA ACTATCTCTT ACAAACTTTA AGTGCTCTGA | |
| | | TATGACTTCC CCCCCAAATT TTATTATGAA CATTTTTAAA | |
| | | AACAGAAAAA TTGAAAAACT GTTTGGTAAG CACATGTATA | |

TABLE 1-continued

Plasma cell dyscrasia Biomarker/Housekeeper Sequence Information

| Gene Name | RefSeq Accession | Sequence | SEQ ID NO: |
|---|---|---|---|
| | | TCTACCATTT AGATTCAGCA GTTGTTAATG TTTTGTCATT TGTTTTCTCT ATACCTATAT ATGTATAGAT ACAGCTAGTT ATGCATATAT ATGCATATAT GTGTTTGTTT GTGTATGTAT ATATGCTTTT TTCCCCCTGA ACCATTTGGA TGTTACAGAC ATACTTATCA CCGTGAAAAT ACTTCAAGTA TCTCCTACAG ATAATGACAT TCTCCTAAAA ATCCGTAATA CCATTGTAAA AGTAATAATT CCCCAATATC ATCTAATCAA GCCATATTTA AATTTCTGAA GTTAACTCCA AATTTCTTTA TAGCTGATTA TTTCAAACTA GGATCCAATT AAAGTTTACA TATGACACTT GGTTATAACT CTTTAGTTGG ATATAACATT ATTATTATTT TGATAAAATA TGGAACAAAT CAATTCTATT AATAAGTGGT CACATTTGTT TTGGGCTTAA ATTACTTTTT AAAGATACTG GATTTTCCTA AGATTTCTGA TTTACACTGA TATTTTTTTT TGTCATTCTT AATTGCATCA CACAATAGAT GTAAATGAAG ATGTAGTCAC CTCAGATAAA ATTGGTATCG TGTATGATAA TATTGTATCA TTTATATTTG CCTTATGTTA ACTTTAAGAA ATTGATTTTT TTGTATTAAT CATTTTCCCA TTGCAACAGA GCTATATTTT TTCTATTTTA AGAATCATAT TTTAGGATTA TTTTTGGCAA ATACAGTGAG CACTTATGTA ACCAGATGAT AATGAACTCA AATGTCATGA TAGCTTGCAT AAATGGTGAC TCTAGTAGAT TTGACTCAAG CACTTCTAGA ATCATGCACT GAATTCAAAA GAAAAATCTT GCTGCTTTTT GTCCAGGGCT TGTTCTATTC AACTTCTAAT TTGAAAGCTG TACAAAGTAA TAGAAGTTCC ATTTAAATAT GAGTTCAAAA CTGTATTTAC TTTTTATGTG GCCCTCTCTT TAGGGGATTC TAATTTTACT TAGGGTCTCT AAGTGCAGCA TAATGTTCCT GATGTTAACA GAAGACTGTA TTTTTAAAGT TACAAATTTG TATATGGAAT TAAGTAATGG CGCTATATAC GCTGTTGTGG GGAGGGGGGA AGAAAAGGAG GAACCAATTA AATAGGACCT TTTAAAAATT GTTAATTTTG TAAACTTTGC TTCTCTTATA AGTTATTGTG ATTCATTTTA GTTACTGTGT TTTATTTTGA AAATATTTAA ATATTGCACT TCTATAAATA GTATGATAAA TGCACAGACA ATTGCAGTAA ATTCTTTTTT AAGCTAGGAT ATTTGAAATG ACAACCTTTG GTTAAGTGTG TCAAGGTTGC AACAGAATTT TCACAATTTT TTTGTTGTTT GCAAATTGTT ACTAATATTG AAGAGGTAAG GGAGGCAATG CAAATGATTT TTAATCTTTT TTTATTATCT TTTCAGCAGT TTTATATTTT TGTGACTTTA TGCAACCATA TTTTTACTTT GTCTTGACAA CTGAAAGATG TATAAGGTTT TTTGCCAGAA ATGTACTGTA TACATAGTTT TAAGTATAAC AGATTTTACT GATATGTAAA AATTTTGCCA TTAAAATAAA TGATTTCTCA CTGAGAGGAA CTTTTCTACC AGGTTGGGGC ATATGGGAGC TTAATATATC ATATCTAATT TAAAATAATT TCACTGAAAT AAACTCCATT GCTTTTACCT AATTTTTTTC TTGAGATGCT TTTGTAGTTT TTCAGAGTTT TAGATGATTT TATACAAAAT CCTCTGCCTA GCACTGCTCT TTTTGATGTT GTAGTGACAC CATTTACATT GAATTAATGC TTGGTAGCCT GGGGCTAGAT GTGGAACTCC ATGGATCTGT GTTCTGACTG GCACCTTTGG AATGAAAGAA AAGTGTGTGC TGTCCAAATT TTTTCCCCTT AATTCTTTCC CTCATCTTCT CACCCATAAT AGAAATTTTA TTTCCATTGT GAGTTCTGAC AAGAATGAAA TTCCACATAC AACATAACTG TAAATTGTTG GTAGGTAGAA GTTAATATTT GTGGTTCATG TATATTTTGA CCAGAGTATA TTTAAGTATA TAATTTCAGC TTCCTTGATT TAGAAATATG ATATAATAAA GAAAAACTCC ATTTATCATC TGTTA | |
| SCYL2 | NM_001317784.1 | AGGAAGTGAC GTCATGCCCC CGGCCGGCAG GTCTTTTAGT CTTTTTCCCC CTCCCTTACT CTTCGTCCCC GGTCCCTCCC CTCCCCACCC CTTTCCTTCT AGCTCCGACG TTTGCGGCCG CGGGGGCGGC GGAGGATATG GAGTAAAGCC AGAGTCAGTG GCCAGGCACG AAGGCAGAGC AGGAACAGCC AGGAGGCGTT TATTAGGGGG GCGGGGGGAA AGAGCCCCAG CACCGCCCCT CCTGGAAGAA GGAAGAGGTA ACTATAACTA CCCAATATTG CAGCCATGGA GTCCATGCTT AATAAATTGA AGAGTACTGT TACAAAAGTA ACAGCTGATG TCACTAGTGC TGTAATGGGA AATCCTGTCA CTAGAGAATT TGATGTTGGT CGACACATTG CCAGTGGTGG CAATGGGCTA GCTTGGAAGA TTTTTAATGG CACAAAAAAG TCAACAAAGC AGGAAGTGGC AGTTTTTGTC TTTGATAAAA AACTGATTGA CAAGTATCAA AAATTTGAAA AGGATCAAAT CATTGATTCT CTAAAACGAG GAGTCCAACA GTTAACTCGG CTTCGACACC CTCGACTTCT TACTGTCCAG CATCCTTTAG AAGAATCCAG GGATTGCTTG GCATTTTGTA CAGAACCAGT TTTTGCCAGT TTAGCCAATG TTCTTGGTAA CTGGGAAAAT CTACCTTCCC CTATATCTCC AGACATTAAG | 18 |

TABLE 1-continued

Plasma cell dyscrasia Biomarker/Housekeeper Sequence Information

| Gene Name | RefSeq Accession | Sequence | SEQ ID NO: |
|---|---|---|---|
| | | GATTATAAAC TTTATGATGT AGAAACCAAA TATGGTTTGC | |
| | | TTCAGGTTTC TGAAGGATTG TCATTCTTGC ATAGCAGTGT | |
| | | GAAAATGGTG CATGGAAATA TCACTCCTGA AAATATAATT | |
| | | TTGAATAAAA GTGGAGCCTG GAAAATAATG GGTTTTGATT | |
| | | TTTGTGTATC ATCAACCAAT CCTTCTGAAC AAGAGCCTAA | |
| | | ATTTCCTTGT AAAGAATGGG ACCCAAATTT ACCTTCATTG | |
| | | TGTCTTCCAA ATCCTGAATA TTTGGCTCCT GAATACATAC | |
| | | TTTCTGTGAG CTGTGAAACA GCCAGTGATA TGTATTCTTT | |
| | | AGGAACTGTT ATGTATGCTG TATTTAATAA AGGGAAACCT | |
| | | ATATTTGAAG TCAACAAGCA AGATATTTAC AAGAGTTTCA | |
| | | GTAGGCAGTT GGATCAGTTG AGTCGTTTAG GATCTAGTTC | |
| | | ACTTACAAAT ATACCTGAGG AAGTTCGTGA ACATGTAAAG | |
| | | CTACTGTTAA ATGTAACTCC GACTGTAAGA CCAGATGCAG | |
| | | ATCAAATGAC AAAGATTCCC TTCTTTGATG ATGTTGGTGC | |
| | | AGTAACACTG CAATATTTTG ATACCTTATT CCAAAGAGAT | |
| | | AATCTTCAGA AATCACAGTT TTTCAAAGGA CTGCCAAAGG | |
| | | TTCTACCAAA ACTGCCCAAG CGTGTCATTG TGCAGAGAAT | |
| | | TTTGCCTTGT TTGACTTCAG AATTTGTAAA CCCTGACATG | |
| | | GTACCTTTTG TTTTGCCCAA TGTTCTACTT ATTGCTGAGG | |
| | | AATGCACCAA AGAAGAATAT GTCAAATTAA TTCTTCCTGA | |
| | | ACTTGGCCCT GTGTTTAAGC AGCAGGAGCC AATCCAGATT | |
| | | TTGTTAATTT TCCTACAAAA AATGGATTTG CTACTAACCA | |
| | | AAACCCCTCC TGATGAGATA AAGAACAGTG TTCTACCCAT | |
| | | GGTTTACAGA GCACTAGAAG CTCCTTCCAT TCAGATCCAG | |
| | | GAGCTCTGTC TAAACATCAT TCCAACCTTT GCAAATCTTA | |
| | | TAGACTACCC ATCCATGAAA AACGCTTTGA TACCAAGAAT | |
| | | TAAAAATGCT TGTCTACAAA CATCTTCCCT TGCGGTTCGT | |
| | | GTAAATTCAT TAGTGTGCTT AGGAAAGATT TTGGAATACT | |
| | | TGGATAAGTG GTTTGTACTT GATGATATCC TACCCTTCTT | |
| | | ACAACAAATT CCATCCAAGG AACCTGCGGT CCTCATGGGA | |
| | | ATTTTAGGTA TTTACAAATG TACTTTTACT CATAAGAAGT | |
| | | TGGGAATCAC CAAAGAGCAG CTGGCCGGAA AAGTGTTGCC | |
| | | TCATCTTATT CCCCTGAGTA TTGAAAACAA TCTTAATCTT | |
| | | AATCAGTTCA ATTCTTTCAT TTCCGTCATA AAAGAAATGC | |
| | | TTAATAGATT GGAGTCTGAA CATAAGACTA AACTGGAGCA | |
| | | ACTTCATATA ATGCAAGAAC AGCAGAAATC TTTGGATATA | |
| | | GGAAATCAAA TGAATGTTTC TGAGGAGATG AAAGTTACAA | |
| | | ATATTGGGAA TCAGCAAATT GACAAAGTTT TTAACAACAT | |
| | | TGGAGCAGAC CTTCTGACTG GCAGTGAGTC CGAAAATAAA | |
| | | GAGGACGGGT TACAGAATAA ACATAAAAGA GCATCACTTA | |
| | | CACTTGAAGA AAAACAAAAA TTAGCAAAAG AACAAGAGCA | |
| | | GGCACAGAAG CTGAAAAGCC AGCAGCCTCT TAAACCCCAA | |
| | | GTGCACACAC CTGTTGCTAC TGTTAAACAG ACTAAGGACT | |
| | | TGACAGACAC ACTGATGGAT AATATGTCAT CCTTGACCAG | |
| | | CCTTTCTGTT AGTACCCCTA AATCTTCTGC TTCAAGTACT | |
| | | TTCACTTCTG TTCCTTCCAT GGGCATTGGT ATGATGTTTT | |
| | | CTACACCAAC TGATAATACA AAGAGAAATT TGACAAATGG | |
| | | CCTAAATGCC AATATGGGCT TTCAGACTTC AGGATTCAAC | |
| | | ATGCCCGTTA ATACAAACCA GAACTTCTAC AGTAGTCCAA | |
| | | GCACAGTTGG AGTGACCAAG ATGACTCTGG GAACACCTCC | |
| | | CACTTTGCCA AACTTCAATG CTTTGAGTGT TCCTCCTGCT | |
| | | GGTGCAAAGC AGACCCAACA AAGACCCACA GATATGTCTG | |
| | | CCCTTAATAA TCTCTTTGGC CCTCAGAAAC CCAAAGTTAG | |
| | | CATGAACCAG TTATCACAAC AGAAACCAAA TCAGTGGCTT | |
| | | AATCAGTTTG TACCTCCTCA AGGTTCTCCA ACTATGGGCA | |
| | | GTTCAGTAAT GGGGACACAG ATGAACGTGA TAGGACAATC | |
| | | TGCTTTTGGT ATGCAGGGTA ATCCTTTCTT TAACCCACAG | |
| | | AACTTTGCAC AGCCACCAAC TACTATGACC AATAGCAGTT | |
| | | CAGCTAGCAA TGATTTAAAA GATCTTTTTG GGTGAGGTGT | |
| | | CTTACTTCTA TTTTGAAGGA TTATTTCAGT TTCAATCATG | |
| | | GGTGAGCTGA TTTACATCTT TATATAGTTG GCTTGGAGGA | |
| | | AGTACTTCTA TGGGAAAGTG AACAGTTCTG TGACAGGAAA | |
| | | CATCTCTGTC CATGCCAGCA TAGTAGTTGT ATGGACTTCT | |
| | | AACCAGTTGA GTTTTTTAAA GCATTGAGGA TTTTTTCCTC | |
| | | TTACCAACTC CTCTTCAGGT TTTTAAAGAC CCAGCCCTTC | |
| | | CCAATCTCAA AGAGAAAAAG GAAACTGAGT TATCTTGAAT | |
| | | AACATAACTT TTTAATCAAA TGTTTATTTT GGCTTGTGGA | |
| | | TCTTGGTGTT ATTTAAAAAA TTGAGGTGAT GGTCATTGCA | |
| | | AGCTCATCTA TTAAGTACTA TATGGTACAC AGTCTATGAG | |
| | | TCATTAGTCT TCATTTTAAT ATGTAAAAAA TCTTGATGCT | |
| | | GTATTGATTT GTTTGCATTT AAGATGACAG TGAGAAAATG | |
| | | ATAAGCATAA AGAGAAGTAT CAGGTTATTT GCTTTTTCCA | |
| | | AACTTTTCAG ATGAACTATT GTTTAGTACA GAGACTGAGC | |
| | | AAATACTACA AAATTCAACT TAACCTTCAT TTCATTGGTT | |

TABLE 1-continued

Plasma cell dyscrasia Biomarker/Housekeeper Sequence Information

| Gene Name | RefSeq Accession | Sequence | SEQ ID NO: |
|---|---|---|---|
| | | TAAATGCGTT ATTAACCATC TTAAGTGCAA ACTAATCATT<br>GTAAATTATA TTTTAGCATG GTCTGCCTCA AATAGTAATG<br>TATTTTTCTG CATTCACTTG GATATATTTA GAATCACTTT<br>TTTCCTCCTG TATCAAGGAA GAGGTATGTG CTGATTTGTT<br>TGGATATTTG ACAAGGCACT CTGATGTGAC TTCCCTGACT<br>ACTACCTTCA TATTTCATTT CAAATTCAAA CTTCTGAGGT<br>TGCAGCATAT ATGAATTGCA TTTTCAAAAG AAGATTTGTA<br>AGAATTAAAC TATATTTATG AGTAAACTTT TGAGGTTTCT<br>GCTGTATTGT TTCAAATGTA ATAAACTTTA CTTCTGTAAA<br>AATTGAGCAG TTGTATCTTC TGACCACCAA CAGATTTTCA<br>GCTTGCCATG ATAGTCTGAC CTCATTAATT ACTGCTACTG<br>AAGTTCAATT TTTTTCTAGG AATTTTAGGA ACCTTTTGTT<br>TAAATATTTT AATTTCTATT AGCCATTTTT AGGAAGGAAA<br>GAATCAATTC TCTTAACAGG AAACATGCTT TATTTTTCAA<br>AACCTTTCTC TGATATTTTT CTTTAATTTG CTGATTATTC<br>AACCACAGAG CCTTATGCTA TAAATGTCAT TTGTATTTTA<br>AAAAATAATA TTCCACTCAT AAAACTTTAA AACCATCTTT<br>CAACGAACTA TATATGTATT ATAGTTGCTG CCATAGAGTT<br>GATGGTTTTT AATTATCTGG AACCAGCAAT CATTTAAAAT<br>AAACCATATT AAGTTTAGTA TGCTGGTATT GTTTATTCAT<br>TTTATATGAA TATTCATTGA AAATATATAC ACAATATATG<br>TAATACACAG CACTTGATTA CAAAATGTAA TTTAATTATA<br>TTATTGCTGG CAGCATTCAG TTAAGAGGGT ACTTTAAAAA<br>ATAGAAGTCA GCTTTCACAT CTGATTTCTG TATGGGCTGT<br>ACTTGGTTAA CTTGATTTTA GAAAAAGGAC TAACAGAATT<br>GCTAAAGAAA TGCATCCAAT AAATGAAAAA CAGTAGGAAG<br>ATCAAATGTT TTTGTCAAAT ATATTCACAA CTTGACCAGA<br>TTAGCTGTCC TGTTTGTAAT GCAATATTAA TATGTCTTTT<br>GGGAAAAAGC CTACATATGG AATAAAATAA GTATTGAAGA<br>ATTTTTCTTT GTAACAATTT AGTAGTCACT GTTTATTGAG<br>AAATTGTTTT TTATTTTGTA AAATAACATG ATGTTAGTGT<br>TGAACTCTTA AACAGAAAGA AAGCTTAATA TAACAGCTTA<br>TAGAACTTGA ACTACTAAAT ATGAAAATAA GTCATTTGAA<br>AAAAATACAG TATGTAAAAT TTGTTCATTC GTTGAGGTAA<br>TGGTGCTATG TTTTTACAAA ATTGTTCCTA CACCTTTTTT<br>CTACTTCAGG TATTTTATTT CAACCATTTC CATCAATTGA<br>ACTGTTACCA TTGCCTTTTT CTGTTGAGAA ATTGCCTCTG<br>AAAAATAGTG CTATTTTTCA GCTTAAGTGT TCTTAAGTGA<br>ATGAAATTTT CAAAGTACTA GATCACCTTA AAATTATTTC<br>ACGTACTGAA GACAATTAAG TCCGTTATGT TTAGAGTAGA<br>AAATGTTTAG GTTAAAGAGC ATCTGTCAAC AGAATCTACA<br>AAAAAGATTC CCTTGCATTT GAATTAGTTC TCTATTCTCC<br>TATTGCTAAA TGTGTGATAT ATAGAGAGGA TGTATAAAAG<br>GAAATGGAAA TAGACTATGT ACTTGTCTGG TTTTTGTTTG<br>TTTTTATTTT GGAATGCTTA TAAGCCTCCT TTACACTGAA<br>TAAGGAAGTA GTTTTTGTTT TCTTTTGACC TGTAAAATAC<br>CTCACATGGT TGTTTTTACA CATGAAAGAA AAAGGTATAT<br>GCGAACATAC CTGATATCAA GAGGAGTATG CACCAAATAA<br>ATTTTAGCTT TGATAAAACT TTCCATAAAA AAAAAA | |
| SMARCD2 | NM_001098426.1 | GTTGGGCGGG GCAGGGAGTT CGTAGCCGCC TCTGGGTAAC<br>TCGACTCGGG CGGCCAAACC TCCGGAGGCC GGGGACGGAA<br>GGCGGGCCCG CAGCAGATCC TGGATCCGGA ATCTCCCGGG<br>CAGGAGCGGA ATCTGTCCCG AACCGGGTCT GTGAGGAACT<br>CGCGAACTTG GATTAGGAAA TCCCGGAGCC CGGATCGACA<br>AATCCCGGAA CCCGGAATTA AGATCGCCAA GTCCCGGATC<br>GCGGAGCACA GAGCACGGAG TGGACTCGAC GCGGAGCCCG<br>GAGTCCGGAT CGCGGCACCG CGGGACGGGA CGGAGCGATG<br>TCGGGCCGAG GCGCGGGCGG GTTCCCGCTG CCCCCGCTAA<br>GCCCTGGCGG CGGCGCCGTG GCTGCGGCCC TGGGAGCGCC<br>GCCTCCCCCC GCGGGACCCG GCATGCTGCC CGGACCGGCG<br>CTCCGGGGAC CGGGTCCGGC AGGAGGCGTG GGGGGCCCCG<br>GGGCCGCCGC CTTCCGCCCC ATGGGCCCCG CGGGCCCCGC<br>GGCGCAGTAC CAGCGACCTG GCATGTCACC AGGGAACCGG<br>ATGCCCATGG CTGGCTTGCA GGTGGGACCC CCTGCTGGCT<br>CCCCATTTGG TGCAGCAGCT CCGCTTCGAC CTGGCATGCC<br>ACCCACCATG ATGGATCCAT TCCGAAAACG CCTGCTTGTG<br>CCCCAGGCGC AGCCTCCCAT GCCTGCCCAG CGCCGGGGGT<br>TAAAGAGGAG GAAGATGGCA GATAAGGTTC TACCTCAGCG<br>AATCCGGGAG CTTGTTCCAG AGTCTCAGGC GTACATGGAT<br>CTCTTGGCTT TTGAGCGGAA GCTGGACCAG ACCATTGCTC<br>GCAAGCGGAT GGAGATCCAG GAGGCCATCA AAAAGCCTCT<br>GACACAAAAG CGAAAGCTTC GGATCTACAT TTCCAATACG<br>TTCAGTCCCA GCAAGGCGGA AGGCGATAGT GCAGGAACTG | 19 |

TABLE 1-continued

Plasma cell dyscrasia Biomarker/Housekeeper Sequence Information

| Gene Name | RefSeq Accession | Sequence | SEQ ID NO: |
|---|---|---|---|
| | | CAGGGACCCC TGGGGGAACC CCAGCAGGGG ACAAGGTGGC | |
| | | TTCCTGGGAA CTCCGAGTGG AAGGAAAACT GCTGGATGAT | |
| | | CCTAGCAAAC AGAAGAGGAA GTTTTCTTCA TTCTTTAAGA | |
| | | GCCTCGTCAT TGAGCTGGAC AAGGAGCTGT ACGGGCCTGA | |
| | | CAATCACCTG GTGGAGTGGC ACCGGATGCC CACCACCCAG | |
| | | GAGACAGATG GCTTCCAAGT AAAACGGCCT GGAGACCTCA | |
| | | ACGTCAAGTG CACCCTCCTG CTCATGCTGG ATCATCAGCC | |
| | | TCCCCAGTAC AAATTGGACC CCCGATTGGC AAGGCTGCTG | |
| | | GGAGTGCACA CGCAGACGAG GGCCGCCATC ATGCAGGCCC | |
| | | TGTGGCTTTA CATCAAGCAC AACCAGCTGC AGGATGGGCA | |
| | | CGAGCGGGAG TACATCAACT GCAACCGTTA CTTCCGCCAG | |
| | | ATCTTCAGTT GTGGCCGACT CCGTTTCTCC GAGATTCCCA | |
| | | TGAAGCTGGC AGGGTTGCTG CAGCATCCAG ACCCCATTGT | |
| | | CATCAACCAT GTCATTAGTG TCGACCCTAA CGACCAGAAG | |
| | | AAGACAGCCT GTTACGACAT CGATGTGGAG GTGGACGACC | |
| | | CACTGAAGGC CCAAATGAGC AATTTTCTGG CCTCTACCAC | |
| | | CAATCAGCAG GAGATCGCCT CCCTTGATGT CAAGATCCAT | |
| | | GAGACCATTG AGTCCATCAA CCAGCTGAAG ACCCAGAGAG | |
| | | ATTTCATGCT CAGTTTTAGC ACCGACCCCC AGGACTTCAT | |
| | | CCAGGAATGG CTCCGTTCCC AGCGCCGAGA CCTCAAGATC | |
| | | ATCACTGATG TGATTGGAAA TCCTGAGGAG GAGAGACGAG | |
| | | CTGCTTTCTA CCACCAGCCC TGGGCCCAGG AAGCAGTAGG | |
| | | CAGGCACATC TTTGCCAAGG TGCAGCAGCG AAGGCAGGAA | |
| | | CTGGAACAGG TGCTGGGAAT TCGCCTGACC TAACTGCTCA | |
| | | GGGATCTTTC TTCCCAGCCC TGGAGCCTGG AGGGAGACCA | |
| | | CCCTCTGGGT CCTTGCTGGG GCCGCAGACA CGTAGGCTGG | |
| | | GGTGAGGAGT GTCTGCTGTC ACCCTCTACT CTCCAGCTTT | |
| | | AGTCTTATAA ATGTAGTGAT AGGATTCCTT GTTGCTTGGT | |
| | | CCCCAAAGCC TTATACTTTT TGCATTGGCT TTAATTGGGT | |
| | | TCAGCAGATG CCTCCTCTGC CCCCCTGCAG GCAGGCCCAA | |
| | | GTAGGACTGC TGGAGGCTGT GCTTTGACAT TGTAAGACAT | |
| | | TTCCGAACCA AAGGCTGCTG GGTTTGCATG TTTACAGACT | |
| | | CCCCCTGGGG CGAGGGTCAG AGCTGGCTCT GGGGAGCTGG | |
| | | GCTAGGAAGA GGAGGTGCAG CCCAGACTCT TCCTAGCCTT | |
| | | TCTAAACCAA AGTTCTTTGC CATTCCTACA AGCCCAGCCT | |
| | | TGCTGCTGGT TTTTTCCTTT CCTTTGGGTA TTTGCACTAT | |
| | | TTTGGGAGCA AGTTTTCTAT GTGGGAGCCA CTTTTTTTGT | |
| | | ACAGGGGTAA GTTGGGGGTT TTCAGGGAGC CTGTTAGGTG | |
| | | CCTCCTTCTT TTCTTTCCTC AATCTATGCA AGCGGCTCTG | |
| | | GCCGCCATCA TCTCCTGGGA TGCCAGAGGG CTGCCTCTCC | |
| | | AGCGGCTTGG GCCGGGGAGG GGACACTCCA GTTCTCTAGC | |
| | | ATGGCCTGAG GTATGGGGTA TGTGCATGTG GAGGCCAGGG | |
| | | TAAGGTGAAT GGGGAGGCTG GGAGGACTGG TGTTGCCCTT | |
| | | TGGAGCTTGG TGAGGAGGGT GGGCCTAGGG CTTGGCGAGT | |
| | | GCCACATCTG GCAGGTTTGG AAATTTCCAA ATAAATCCTT | |
| | | TTGTCTATTG | |
| SP1 | NM_001251825.1 | GTCCGGGTTC GCTTGCCTCG TCAGCGTCCG CGTTTTTCCC | 20 |
| | | GGCCCCCCCC AACCCCCCCG GACAGGACCC CCTTGAGCTT | |
| | | GTCCCTCAGC TGCCACCATG AGCGACCAAG ATCACTCCAT | |
| | | GGATGAAATG ACAGCTGTGG TGAAAATTGA AAAAGGAGTT | |
| | | GGTGGCAATA ATGGGGGCAA TGGTAATGGT GGTGGTGCCT | |
| | | TTTCACAGGC TCGAAGTAGC AGCACAGGCA GTAGCAGCAG | |
| | | CACTGGAGGA GGAGGGCAGG GTGCCAATGG CTGGCAGATC | |
| | | ATCTCTTCCT CCTCTGGGGC TACCCCTACC TCAAAGGAAC | |
| | | AGAGTGGCAG CAGTACCAAT GGCAGCAATG GCAGTGAGTC | |
| | | TTCCAAGAAT CGCACAGTCT CTGGTGGGCA GTATGTTGTG | |
| | | GCTGCCGCTC CCAACTTACA GAACCAGCAA GTTCTGACAG | |
| | | GACTACCTGG AGTGATGCCT AATATTCAGT ATCAAGTAAT | |
| | | CCCACAGTTC CAGACCGTTG ATGGGCAACA GCTGCAGTTT | |
| | | GCTGCCACTG GGGCCCAAGT GCAGCAGGAT GGTTCTGGTC | |
| | | AAATACAGAT CATACCAGGT GCAAACCAAC AGATTATCAC | |
| | | AAATCGAGGA AGTGGAGGCA ACATCATTGC TGCTATGCCA | |
| | | AACCTACTCC AGCAGGCTGT CCCCCTCCAA GGCCTGGCTA | |
| | | ATAATGTACT CTCAGGACAG ACTCAGTATG TGACCAATGT | |
| | | ACCAGTGGCC CTGAATGGGA ACATCACCTT GCTACCTGTC | |
| | | AACAGCGTTT CTGCAGCTAC CTTGACTCCC AGCTCTCAGG | |
| | | CAGTCACGAT CAGCAGCTCT GGGTCCCAGG AGAGTGGCTC | |
| | | ACAGCCTGTC ACCTCAGGGA CTACCATCAG TTCTGCCAGC | |
| | | TTGGTATCAT CACAAGCCAG TTCCAGCTCC TTTTTCACCA | |
| | | ATGCCAATAG CTACTCAACT ACTACTACCA CCAGCAACAT | |
| | | GGGAATTATG AACTTTACTA CCAGTGGATC ATCAGGGACC | |
| | | AACTCTCAAG GCCAGACACC CCAGAGGGTC AGTGGGCTAC | |
| | | AGGGGTCTGA TGCTCTGAAC ATCCAGCAAA ACCAGACATC | |

TABLE 1-continued

Plasma cell dyscrasia Biomarker/Housekeeper Sequence Information

| Gene Name | RefSeq Accession | Sequence | SEQ ID NO: |
|---|---|---|---|
| | | TGGAGGCTCA TTGCAAGCAG GCCAGCAAAA AGAAGGAGAG | |
| | | CAAAACCAGC AGACACAGCA GCAACAAATT CTTATCCAGC | |
| | | CTCAGCTAGT TCAAGGGGGA CAGGCCCTCC AGGCCCTCCA | |
| | | AGCAGCACCA TTGTCAGGGC AGACCTTTAC AACTCAAGCC | |
| | | ATCTCCCAGG AAACCCTCCA GAACCTCCAG CTTCAGGCTG | |
| | | TTCCAAACTC TGGTCCCATC ATCATCCGGA CACCAACAGT | |
| | | GGGGCCCAAT GGACAGGTCA GTTGGCAGAC TCTACAGCTG | |
| | | CAGAACCTCC AAGTTCAGAA CCCACAAGCC CAAACAATCA | |
| | | CCTTAGCCCC AATGCAGGGT GTTTCCTTGG GGCAGACCAG | |
| | | CAGCAGCAAC ACCACTCTCA CACCCATTGC CTCAGCTGCT | |
| | | TCCATTCCTG CTGGCACAGT CACTGTGAAT GCTGCTCAAC | |
| | | TCTCCTCCAT GCCAGGCCTC CAGACCATTA ACCTCAGTGC | |
| | | ATTGGGTACT TCAGGAATCC AGGTGCACCC AATTCAAGGC | |
| | | CTGCCGTTGG CTATAGCAAA TGCCCCAGGT GATCATGGAG | |
| | | CTCAGCTTGG TCTCCATGGG GCTGGTGGTG ATGGAATACA | |
| | | TGATGACACA GCAGGTGGAG AGGAAGGAGA AAACAGCCCA | |
| | | GATGCCCAAC CCCAAGCCGG TCGGAGGACC CGGCGGGAAG | |
| | | CATGCACCTG CCCCTACTGT AAAGACAGTG AAGGAAGGGG | |
| | | CTCGGGGGAT CCTGGCAAAA AGAAACAGCA TATTTGCCAC | |
| | | ATCCAAGGCT GTGGGAAAGT GTATGGCAAG ACCTCTCACC | |
| | | TGCGGGCACA CTTGCGCTGG CATACAGGCG AGAGGCCATT | |
| | | TATGTGTACC TGGTCATACT GTGGGAAACG CTTCACACGT | |
| | | TCGGATGAGC TACAGAGGCA CAAACGTACA CACACAGGTG | |
| | | AGAAGAAATT TGCCTGCCCT GAGTGTCCTA AGCGCTTCAT | |
| | | GAGGAGTGAC CACCTGTCAA AACATATCAA GACCCACCAG | |
| | | AATAAGAAGG GAGGCCCAGG TGTAGCTCTG AGTGTGGGCA | |
| | | CTTTGCCCCT GGACAGTGGG GCAGGTTCAG AAGGCAGTGG | |
| | | CACTGCCACT CCTTCAGCCC TTATTACCAC CAATATGGTA | |
| | | GCCATGGAGG CCATCTGTCC AGAGGGCATT GCCCGTCTTG | |
| | | CCAACAGTGG CATCAACGTC ATGCAGGTGG CAGATCTGCA | |
| | | GTCCATTAAT ATCAGTGGCA ATGGCTTCTG AGATCAGGCA | |
| | | CCCGGGGCCA GAGACATATG GGCCATACCC CTTAACCCCG | |
| | | GGATGCAAGG TAGCATGGGT CCAAGAGACA TGGAAGAGAG | |
| | | AGCCATGAAG CATTAAAATG CATGGTGTTG AGAAGAATCA | |
| | | GGAGAGGGAT ACAAGAGAGG AGATGGGGTC CCGGCACCCA | |
| | | TCTGTATCAT CAGTGCCTCT TTGAAGGTGG GAAACATTAG | |
| | | TGAAAATTCT GTTGGTGCCA CGCTTTGATG AGCATTTGTT | |
| | | TGACCCCAGT TTCTTCTTAC ACTTCTTACC CCAGCCTACC | |
| | | CTTCCTGCAT TTCTCTTCTC AGCTCTTCCA TGATGGATTC | |
| | | CCCCCCCTTT CCTAAAGCCA TCATGCCTTG ATAAATATAT | |
| | | ATGATCATTG AAATACTTTT TAACAAAAAA CAGATTCTAT | |
| | | ATTATTATAT ATATATATAT ATATATAAAG ATATATAGAG | |
| | | ATGCATTCAC AGGGGTTGGC TGGGAGGAGG AAGACCATTC | |
| | | TGTGACCAAA ATACCTTGGT CATTTTTTTT ATATTGCCTT | |
| | | ATTTCCCTAT GGCTGAGCCT TGTTGTGACA CATCAAGCTT | |
| | | TTCTGTAGAT GTTGTCTTGG CTTCCCACCA GCTTAAGCGT | |
| | | TCATATGCTC TGCTTTTAGT TCATATATAC ATACATAATG | |
| | | TTTTTCCTTT CTTAATTTTG TCTTTTTGTT TGGGATCAGC | |
| | | TTCTTGCACT CCTTCCCTAA CTCAACTGTT GCCGTCTCAT | |
| | | CTTCTCTCAT CTGATCACTT CATGTTTTGT TTTTGTTACT | |
| | | GCCTGGATGA GGCACTTCTG TCAATTTTTT CAGGACCTTA | |
| | | GTTCCAGCAG CAGAATGGAA AAATCCTTGA AGCCCAGGCT | |
| | | GATGCTTGAA GTAACTGTGG AGGGAGTGTT CAAAATACTA | |
| | | CTGACGCAGG CACCTTCTTG GCGCTGGAGA GTCAAAGGCA | |
| | | TCTCCCTTCA TTAGCTGCTC TGAGCATCAA GAATTAGAAG | |
| | | TCTTTCAGTG GAATTGTACA AGAGTCCCTT TGAAGATAAT | |
| | | AATCTTGGCT CAGTTTGTAT AAACTGTCAA ATTTTCAAAT | |
| | | AATAGGTAGG GGGCTTTCAC TAGGAAAATC ATGTGCTCAG | |
| | | AAGAGGAAAT GACTCGTAGT CAGGTTCAGG AGTTAGTGGA | |
| | | GTATTTGGAC TTTGGTACTG CTGTCTTCCA AGGTAGCTCT | |
| | | AAGTTTTGAT GTGTGGGCTT CTGAGTTTAT ATTCTGAAAG | |
| | | GAAATACACT TCTTTTGAAC ATCCCCACTA GGTTCTTTTC | |
| | | CATTGTCAAT AAGGAGCATC AGCCAGTGAA TCTGTTTCAG | |
| | | GTTTCCATTC TGCAGAACTC CTCCAAAGCA TGTGCTAGTG | |
| | | GCAAGACAGT GGTTCTTATG ATGTTTTCCC TTAACTTTTC | |
| | | CTTGTATGTT CTTGGGTGGT TCCTAAGGGA AAGGGAAGCA | |
| | | CATGATCATG GGAATGATAG CCCAGAACAA AAAGAAATCT | |
| | | TGTCTTACCA CAGTGTTTTA TAGGAGAGAT TGGGAGAAAT | |
| | | CATCCTGTTT TCTCTGTGAC CTGATTTCAG AAGAGACTGA | |
| | | TCCAAAAAATT ATAACGGCAG GGAACCTAGT GCATTTGGCA | |
| | | CTGAGATTTA AATGCAACCA GAATTGTCCT CAAGGCCCAG | |
| | | CCATAAAAGC ATTGTCTCTC TCGACCTTCT GGTATCTTGT | |
| | | TAGAGAGCTT TTCACTGTGA GGAAGTGTGG AAAAATAGCT | |
| | | CTGTGTGTGT GTGTGTGTGT GTGTGTGTGT GTGTGTGTAA | |

TABLE 1-continued

Plasma cell dyscrasia Biomarker/Housekeeper Sequence Information

| Gene Name | RefSeq Accession | Sequence | SEQ ID NO: |
|---|---|---|---|
| | | TCTGTTAGGT TGGGGATAGG TTTTCTGCTA GCCAATATTA | |
| | | AAAGAGACCT GCAATAAAAA AATTACCCTG ATCTGATAGA | |
| | | AAGCAAGTGT TTTTGTATGT GTGGGTGAAT GTGTGTTCAT | |
| | | GCCCGTATAT GTCTACACAC AGATGACAAA TTATATTTGA | |
| | | AATCGTTGGA AAATAAATTC AGATCAAAAT GCCTTTCAGG | |
| | | CCCATTACCT AGAAATCTAT CTTAAAACCT GGGTATGTTC | |
| | | CTAAGGTCAT TTCTTTGCTT ATGCTAAATT AATTACAATT | |
| | | ATGAATGGAG GATATTCTAC TGTACTTTTT TAAAAAGAAA | |
| | | CTATTTTTGT GTTTGAAAGT GAAACCAACA TCCAGATCTA | |
| | | TAGCAGAGTC CTTATTCTTC TCATAAATCT TTTTACTTTG | |
| | | GCTACAAATA GATGATGGTA TGATTCTATT ATATATTTTA | |
| | | TATAAAATCC ATCCAAATTA AGTTTTGGGT AAGTGTGTTG | |
| | | TTTAATCTGA ACTATAGTAA CTTAATACTC TAAACAATAG | |
| | | TTCACTCCAT TTGGTCCTTT CTCCACAGAT GTAATTATGT | |
| | | TTTCAACTCA GGAACTATGG CAAGGAACTT TCCCCAGATC | |
| | | AAATTCTATT AACGCTGAGA TACAAGTCAT CCATGCACAG | |
| | | CCACTATCAT ACCCTTTATT CTCACTGAAA GGCAGAACTC | |
| | | AGAACCTGTT ATTTTATGTC TGTAATCATG TACTTTGGCA | |
| | | TCTTTTGGAG GAAAGGGGCA GGATAACTCA CTGGAATGTA | |
| | | CAGTATTTTG CTAGTGCATT TCAAGGAATG GAATCTTCTC | |
| | | CAGTATGAAA TTACCAGATA TAAAATAATG TAATGATGCT | |
| | | GAGGATATAA GCTTTTAGAA GGTAATTTGA TGGTATTTCT | |
| | | TTCTCGAATG AAAAGCTGCT GGTTTACCCT CAACCCTATT | |
| | | CATTAGCATT ACCATGAGTG AATTTATATC TAATTATTTC | |
| | | CACTTGCCCT GTTCTCTTCA CACCAAGGAA GCTCCAGATC | |
| | | CAGTATCTTG TTTGGCCTCA AAACAGAAGC AGCTTCTTTT | |
| | | GTCTCCCAGC AGTAGTGAGC CACTCAGTCT CTTCCACAGG | |
| | | AAGTTTGGAG CCTACATTCC TTGAGTCAGG AGCTTATTAC | |
| | | AGAAAAACCC CGTTTCCCTG AACTTTTGGC TAACAGAAAT | |
| | | TAATTTAACT GACATGCATA TTGATTCTGA AATTTTTTTC | |
| | | CTAAGTTTTT TTCATTTTTT TGAATGAGTT TTTTAAATTT | |
| | | TTTAGATGAC CAAAACTTGC AGGGCAGGGG ATGCCCAGAA | |
| | | GAGTGGTGAG ATAGTAAAAC ACTTATTCCC TCATCCTTTC | |
| | | AGGTTTTCAG GTTGCCCATT TATATTCATT TACATGTCAT | |
| | | TTGACTGTCT CACTTTTTAC CCAGAACAGT AACAACCCAC | |
| | | ACCGTCTTCC TTCAGGGATT TCCAACTGGC ACTCTGTGGG | |
| | | TGCTACACAG AATGCAATTT AATGGATATT TCTCAGCCTG | |
| | | GTTCAGAATA AATTGATCCT TTGATCCCAG AAAGTATATA | |
| | | CTGAAGTGTG GGATAAAGAT TATGATTAGG GGAGGGTTGG | |
| | | AGACAAAAGC TGTAAATTAC TATGGCTGAT TTATTTCTAC | |
| | | TATATACATA TATATTTTTT GCTTTTGTAT ATCCTATATA | |
| | | GGAAACTAAG CATTGTATTT TTTTTAACAA ATCTAAAAAA | |
| | | GCACTATGAA CTACAGGTGT TTGACTTTCA AAATATATTT | |
| | | TGTATTGTTA ATATCTTCAC ATTGTGTGAA TACTGGAAGC | |
| | | TGCAGATCTT TGCTAGGACG CAATAAATTT ATATACTTTT | |
| | | TGAGGGGTTC TTCTGGGGTG CTAATCAGGC CCCTGTTATG | |
| | | CTTAGGGGGA GCCCTGGTGC TACTTGCTTG AAGTTTTCAG | |
| | | TGTAAGTACC CTGATGCCTT TTGGACCTTG GGATCAGATC | |
| | | AAGAGTTTTG GAGATCAGGT ACCAAGGAAA TAAGGACAGT | |
| | | CTAGCTGCCT CAAGTGAGGG GCCCTTTGCA TAGCTCTCCT | |
| | | TCCCCCTCAC TGAAGCTGGG TAGCCTATTG GGGTTGAGAG | |
| | | GGAAAATGTG AAATCTCAGA ATTTATCTCC CTTAGAAGAG | |
| | | AGCCAGTAAC TTATGTACAA GGATGAAAGA AAGGTCGCAG | |
| | | CAGTAGCTTT GGGGAAAGGG AGGAAGATAT GGCACTTCTC | |
| | | CAACCCCGGA AAACATTGCT TTTGAAAACT GCTGATAAAA | |
| | | TATGAGCCGG TTATTACTTC TGTTTGGGAG ACTGTGCTCT | |
| | | CTGTGGTGCC TCTCTTGGCT CTACTCCACA GATACCAGAC | |
| | | CTCTTCTAAG AGGATGAGCA GACCAGCTTT GAGGTTGACC | |
| | | TGTTTCTCTT TGTCTGCCTT CCCAAAACAC CAGCCCCCAG | |
| | | GAAGACATTA AGCAGCCTTA AGCTTAAATT CCTACTCCCT | |
| | | CTTCCAAATT TGGCTCACTT GCCTTAGATC CAAGGCAGGG | |
| | | AAAGGAAAAG AAGGGGGGTC TCTGGCTTTA TTACTCCCCT | |
| | | AAGTCTTTAC TCTGACTTCC CCAAACCCAG AAAGATTTTC | |
| | | TCCACAGTGT TCATTTGAAA GAGGAGTATT TTGTCCCATT | |
| | | TTCCCCTTCC TCATTATCAA ACAGCCCCAG TCTTCCTTGT | |
| | | CTCTGCTAAG AAAGTAGAGG CATGATGATC TGCCTCTCAA | |
| | | CTGCCCTAAG TCCTAGCTAA GTATCAGGGG AAAAAAAAAA | |
| | | AAAAAAAGCC TAACAAATGG GATTAGACTA GGGCTGCAAG | |
| | | TAGTGAGGAT TTTGTTGATA CCTCTGCTGG GATGTGTGCT | |
| | | TTCCCATATC TTGCCTTCAG GAATTACACT GTGCCTTTTC | |
| | | CCCAGGGATA TGGGCTCTGT CTACCCAGTG CTCCAGTTTC | |
| | | CCGGTAACTG CTCTTGAACA TTGTGGACAA GGGCAGGTCT | |
| | | TCATATTTTT GATCATCCCT TTCTCCCAGT GAAATCCCAT | |
| | | AGCCCTTACC TAGAGTCTAG GGCACAAAGA CTTCGGGGAA | |

TABLE 1-continued

Plasma cell dyscrasia Biomarker/Housekeeper Sequence Information

| Gene Name | RefSeq Accession | Sequence | SEQ ID NO: |
|---|---|---|---|
| | | GATACACTGA GATTGACCTG AGGAGACATC TACACACACC AGTGGCAGCT GCCCCAGGGC CTGCTTCCCC TTCCTAAGTC TGTCATCCTC TGGAAGGGAT GGGTGGTGCT CCAATCTCTG GTGCCTAAAA ACCCAAGTTT ATTTCTCTCT TAACACTGGC AATAACCAGT CCACACCACT GTTGCCTTTT AAAACCTCTT AATAATCTCA TGCTGTGTTT GTTTTGATTC CAATCCAATT ATCACCAGGG CTGTGTGGGT AAATGCTTTT AAATGCTCTC TCATCTTGTT CTTCCCCCTC ACCCCCCACT CTTAGGTATG TATGATGCTA ATCTTGTCCC TAAGTAAGTT TCTTCCTGCT CCTTTTGTAT CTTCCTTTCT TGTCTTTCCT CCTACCTTTT GTCTCTTGGT GTTTTGGGAC TTTTTTTTTT TTTTTTTTGG CCTTTTGTAC AAAGATTAGT TTCAATGTAG TCTGTAGCCT CCTTTGTAAA CCAATTAAAA AGTTTTTTAA TAAAAAAAAA AAA | |
| SRSF5 | NM_001039465.1 | ATTTTGTGGA GCGCCAGAGC TGCTAAGTGC GTCAGTTGTG GAGTGGCGTA GACGAGTTAA GTCCTGGTCT GCGTGGAGGT CGACGACTCC GTCGCAGACT ACGGACCTGT CTGGGTCTCA GCCGCCAAAG ACCCCGTCCG GTAGGTGAGT GGCTCACTTT GAGGGCAAGC CTTCTCGGAT CGAGGCTTCT TCATGGCCGC TCAGATCGTG AGCGGCCGGG GCTGCTCTCT TTGCGGAGGA TGGCGTCTAA TGAGCGCAGT TGATTCGAGG AAGTACTAGC CGGACATCAT GAGTGGCTGT CGGGTATTCA TCGGGAGACT AAATCCAGCG GCCAGGGAGA AGGACGTGGA AAGATTCTTC AAGGGATATG GACGGATAAG AGATATTGAT CTGAAAAGAG GCTTTGGTTT TGTGGAATTT GAGGATCCAA GGGATGCAGA TGATGCTGTG TATGAGCTTG ATGGAAAAGA ACTCTGTAGT GAAAGGGTTA CTATTGAACA TGCTAGGGCT CGGTCACGAG GTGGAAGAGG TAGAGGACGA TACTCTGACC GTTTTAGTAG TCGCAGACCT CGAAATGATA GACGAAATGC TCCACCTGTA AGAACAGAAA ATCGTCTTAT AGTTGAGAAT TTATCCTCAA GAGTCAGCTG GCAGGATCTC AAAGATTTCA TGAGACAAGC TGGGGAAGTA ACGTTTGCGG ATGCACACCG ACCTAAATTA AATGAAGGGG TGGTTGAGTT TGCCTCTTAT GGTGACTTAA AGAATGCTAT TGAAAAACTT TCTGGAAAGG AAATAAATGG GAGAAAAATA AAATTAATTG AAGGCAGCAA AAGGCACAGT AGGTCAAGAA GCAGGTCTCG ATCCCGGACC AGAAGTTCCT CTAGGTCTCG TAGCCGATCC CGTTCCCGTA GTCGCAAATC TTACAGCCGG TCAAGAAGCA GGAGCAGGAG CCGGAGCCGG AGCAAGTCCC GTTCTGTTAG TAGGTCTCCC GTGCCTGAGA AGAGCCAGAA ACGTGGTTCT TCAAGTAGAT CTAAGTCTCC AGCATCTGTG GATCGCCAGA GGTCCCGGTC CCGATCAAGG TCCAGATCAG TTGACAGTGG CAATTAAACT GTAAATAACT TGCCCTGGGG GCCTTTTTTT AAAAAACAAA AACCACAAAA ATTCCCAAAC CATACTTGCT AAAAATTCTG GTAAGTATGT GCTTTTCTGT GGGGGTGGGA TTTGGAAGGG GGGTTGGGTT GGGCTGGATA TCTTTGTAGA TGTGGACCAC CAAGGGGTTG TTGAAAACTA ATTGTATTAA ATGTCTTTTG ATAAGCCTTC TGCTCACATT TTTGTGAATG TCTGAAGTAT ATAGTTTGTG TATATTGACA GAGCTCTTTT ATAACTAAAG CAAATTTAAT TTTTTTGTAC TAGAAAAAAA TTTGAACATT TTAGTTCTTG GTTATAAAAA TGTTAATTCA GAATTAGTTT AATGCCTTAA TTAAACTAAT TAATAGCTTT GGACACTTAA AAGAGCTCTA AATTTGCTTG TACATAAAGG CTTAATTTGT TTTCCTTGTT AGGGTCAAGG GTGTCCTCCA CTCTTTAACA GCTGCTGGAC AGACACATTA GAGCAGCTGT TTGTTATTGA TAATAAAATA TTATAAAACT A | 21 |
| TAGAP | NM_001278733.1 | ATACTATTGA CCACATTATG CGGCCAACGA TACCCATTTT CTTACCTGGA TCTTTGCTTC TTAACACTGT AGTCTAATTT TTCTCGTTGC CTTGTTTTCT TGGCTGTAGA AGTTAAGAAG AGAAAGAAGG TGCTGTCCTG GCCCTTTCTC ATGAGAAGGC TCTCCCCTGC ATCAGATTTT TCTGGGGCTT TGGAGACAGA CTTGAAAGCA TCGCTATTTG ATCAGCCCTT GTCAATTATC TGCGGTGACA GTGACACACT CCCCAGACCC ATCCAGGACA TTCTCACTAT TCTATGCCTT AAAGGCCCTT CAACGGAAGG GATATTCAGG AGAGCAGCCA ACGAGAAAGC CCGTAAGGAG CTGAAGGAGG AGCTCAACTC TGGGGATGCG GTGGATCTGG AGAGGCTCCC CGTGCACCTC CTCGCTGTGG TCTTTAAGGA CTTCCTCAGA AGTATCCCCC GGAAGCTACT TTCAAGCGAC CTCTTTGAGG AGTGGATGGG TGCTCTGGAG ATGCAGGACG AGGAGGACAG AATCGAGGCC CTGAAACAGG TTGCAGATAA GCTCCCCCGG CCCAACCTCC TGCTACTCAA GCACTTGGTC TATGTGCTGC ACCTCATCAG CAAGAACTCT GAGGTGAACA | 22 |

TABLE 1-continued

Plasma cell dyscrasia Biomarker/Housekeeper Sequence Information

| Gene Name | RefSeq Accession | Sequence | SEQ ID NO: |
|---|---|---|---|
| | | GGATGGACTC CAGCAATCTG GCCATCTGCA TTGGACCCAA<br>CATGCTCACC CTGGAGAATG ACCAGAGCCT GTCATTTGAA<br>GCCCAGAAGG ACCTGAACAA CAAGGTGAAG ACACTGGTGG<br>AATTCCTCAT TGATAACTGC TTTGAAATAT TTGGGGAGAA<br>CATTCCAGTG CATTCCAGTA TCACTTCTGA TGACTCCCTG<br>GAGCACACTG ACAGTTCAGA TGTGTCGACC CTGCAGAATG<br>ACTCAGCCTA CGACAGCAAC GACCCTGATG TGGAATCCAA<br>CAGCAGCAGT GGCATCAGCT CTCCCAGCAG GCAGCCCCAG<br>GTGCCCATGG CCACAGCTGC TGGCTTGGAT AGCGCGGGCC<br>CACAGGATGC CCGAGAGGTC AGCCCAGAGC CCATTGTGAG<br>CACCGTGGCC AGGCTGAAAA GCTCCCTCGC ACAGCCCGAT<br>AGGAGATACT CAGAGCCCAG CATGCCATCC TCCCAGGAGT<br>GCCTCGAGAG CCGGGTGACA AACCAAACAC TAACAAAGAG<br>TGAAGGGGAC TTCCCCGTGC CCCGGGTAGG CTCTCGTTTG<br>GAAAGTGAGG AGGCTGAAGA CCCATTTCCA GAGGAGGTCT<br>TCCCTGCAGT GCAAGGCAAA ACCAAGAGGC CGGTGGACCT<br>GAAGATCAAG AACTTGGCCC CGGGTTCGGT GCTCCCGCGG<br>GCACTGGTTC TCAAAGCCTT CTCCAGCAGC TCGCTGGACG<br>CGTCCTCTGA CAGCTCGCCC GTGGCTTCTC CTTCCAGTCC<br>CAAAAGAAAT TTCTTCAGCA GACATCAGTC TTTCACCACA<br>AAGACAGAGA AAGGCAAGCC CAGCCGAGAA ATTAAAAAGC<br>ACTCCATGTC TTTCACCTTT GCCCCTCACA AAAAAGTGCT<br>GACCAAAAAC CTCAGCGCGG GCTCTGGGAA ATCGCAAGAC<br>TTTACCAGGG ACCACGTCCC GAGGGGTGTC AGAAAGGAAA<br>GCCAGCTTGC CGGCCGAATC GTGCAGGAAA ATGGGTGTGA<br>AACCCACAAC CAAACAGCCC GCGGCTTCTG CCTGAGACCC<br>CACGCCCTCT CGGTGGATGA TGTGTTCCAG GGAGCTGACT<br>GGGAGAGGCC TGGAAGCCCA CCCTCTTATG AAGAGGCCAT<br>GCAGGGCCCG GCAGCCAGAC TAGTGGCCTC CGAGAGCCAG<br>ACCGTGGGGA GCATGACGGT GGGGAGCATG AGGGCGAGGA<br>TGCTGGAGGC GCACTGCCTC CTACCCCCTC TTCCACCTGC<br>TCACCACGTA GAGGACTCAA GACACAGGGG CAGCAAAGAG<br>CCACTCCCTG GCCACGGACT CTCTCCCCTG CCTGAGCGAT<br>GGAAACAGAG CAGAACTGTC CATGCTTCTG GGGACTCTCT<br>GGGGCACGTG TCTGGCCCAG GGAGACCTGA GCTCCTCCCG<br>CTGAGGACCG TCTCCGAGTC CGTGCAGAGG AATAAGCGGG<br>ACTGTCTCGT GCGACGATGT AGCCAGCCGG TCTTTGAGGC<br>TGACCAATTC CAATATGCCA AAGAATCGTA TATTTAGGAG<br>GGAGGCCATA CGCCATGCCA TAGCTTGTGC TATCTGTAAA<br>TATGAGACTT GTAAAGAACT GCCTGTAGAT TGTTTTTAAA<br>AGGTCTTGAA TAAGCTCCTT GAGAAAGTTG TGGAAAGCCC<br>TCCTCAGTGA GGATAGCTAC ACCATGGCCA TGGCGCATCA<br>GATAGTCTCT GTGTACCTGG ATTTGTGCAA TATGTAAAAA<br>TGTATCAAAT GTATTATAGA TAAGGTGTTA GGTGCAAAGG<br>ATGTCTAATA ATCCCTGCAC ACGTTTTGAA CTTGCAGTGA<br>AGTACACTGC TGTTCCTTGC TTCCTGGGGC ACTTTTCTCT<br>TGGTTAGTGT TTAAAAATTA TCTTCGCTTT TTTAATGTGG<br>CCTCAAATGT CATGCCAATT TTCACATCTT CCACAAACTC<br>CATTTAGGGA GAAATGTTTA AATCTCTGGT ATAAGTTTAC<br>TCCATACCAG AGTAAACTAT ATATTACTCT ATATAAGCAG<br>TCTTGCAATA ACTAATCACC ACCATAGAAG AAAGAAACAG<br>ACTGCAAGGA ACAGAGTTGA GTGTCTGGAG TCATCAAAGG<br>CATTAAAAAC TCCAGTAAAA GCTGGGGCCG TAGCAAAAAT<br>CATGAAAAAC ACTTCAACGT GTCCTTTCAA TCATCCAATT<br>AAATGTGGGT AGATTAATGA AAATGTATTA CATCAATATT<br>AACTCATCTA TAGCACTTTG AGTATCTTTG TAGTTCATGA<br>TATCCTATCC TATAATGTGG AGGTAAATGA TTTTATATGC<br>ATTGGGGGTC ATATATAAAA CTTCAATGTA ATTTCACTAC<br>AATAAATTGC CTTCCTTATT TGAAAGTAAA AATGTTCTTT<br>TTTTATTGAC ATGTTAACTC CTTTCCCTCA ATTAATAGAA<br>ATCCACTAAG AAAATCATTC ACATATTGGT TCACTCAACA<br>AGCATTTATT AAATATATAT TCACTATTCT AGACTAATAG<br>CAAGACCGGG GATCTTGTTT AGGAAGAAGC AGTCCCTGTT<br>CTCCAGAATT TGCAAAACCA TTAAAAAAGC ACCTACTTTA<br>AGCCATTTTT TTTCAGCAAG GAGTCATTCT GCCAGAAAAA<br>TGTAGTACAC AAATACAGGA TAATATAACA AATGTAAAAT<br>TTCTCATTTC TAGTGAATTA AACTTTCCAG TAATTTTACA<br>TCTCACCTCA TTCTTATGAT GCTCAGTTTG CTTAATTATT<br>GGCAAACATA ATGGTAAAAT GTTTGTACTG TATTAGAGCT<br>TTACTGTTCG ATTATTAAGA TATTTATCCA GTATCTTAGA<br>GATGCTGGAC TTCAATTTTC CTTATTTTAT CTTTTTAAAA<br>TAAAATATCA TGCATGCTTC TGATTTGTTA TAGAAA | |

TABLE 1-continued

Plasma cell dyscrasia Biomarker/Housekeeper Sequence Information

| Gene Name | RefSeq Accession | Sequence | SEQ ID NO: |
|---|---|---|---|
| TANK | NM_001199135.1 | ACTCGGCCAG GCGCCGGCGA CCTGAGGGGA GAGGGAACGC | 23 |
| | | AGCTGAAAGC GTGAACTGTA CCTGTCATTT ACTCCATCCT | |
| | | TTATAGTGAT GCTACAGGAC GAAGAGGAAT GGATAAAAAC | |
| | | ATTGGCGAGC AACTCAATAA AGCGTATGAA GCCTTCCGGC | |
| | | AGGCATGCAT GGATAGAGAT TCTGCAGTAA AAGAATTACA | |
| | | GCAAAAGACT GAGAACTATG AGCAGAGAAT ACGTGAACAA | |
| | | CAGGAACAGC TGTCACTTCA ACAGACTATT ATTGACAAGC | |
| | | TAAAATCTCA GTTACTTCTT GTGAATTCCA CTCAAGATAA | |
| | | CAATTATGGC TGTGTTCCTC TGCTTGAAGA CAGTGAAACA | |
| | | AGAAAGAATA ATTTGACTCT TGATCAGCCA CAAGATAAAG | |
| | | TGATTTCAGG AATAGCAAGA GAAAAACTAC CAAAGGTAAG | |
| | | AAGACAAGAG GTTTCTTCTC CTAGAAAAGA AACTTCAGCA | |
| | | AGGAGTCTTG GCAGTCCTTT GCTCCATGAA AGGGGTAATA | |
| | | TAGAGAAGAC TTTCTGGGAT CTGAAAGAAG AATTTCATAA | |
| | | AATATGCATG CTAGCAAAAG CACAGAAAGA CCACTTAAGC | |
| | | AAACTTAATA TACCAGACAC TGCAACTGAA ACACAGTGCT | |
| | | CTGTGCCTAT ACAGTGTACG GATAAAACAG ATAAACAAGA | |
| | | AGCGCTGTTT AAGCCTCAGG CTAAAGATGA TATAAATAGA | |
| | | GGTGCACCAT CCATCACATC TGTCACACCA AGAGGACTGT | |
| | | GCAGAGATGA GGAAGACACC TCTTTTGAAT CACTTTCTAA | |
| | | ATTCAATGTC AAGTTTCCAC CTATGGACAA TGACTCAACT | |
| | | TTCTTACATA GCACTCCAGA GAGACCCGGC ATCCTTAGTC | |
| | | CTGCCACGTC TGAGGCAGTG TGCCAAGAGA AATTTAATAT | |
| | | GGAGTTCAGA GACAACCCAG GGAACTTTGT TAAAACAGAA | |
| | | GAAACTTTAT TTGAAATTCA GGGAATTGAC CCCATAGCTT | |
| | | CAGCTATACA AAACCTTAAA ACAACTGACA AAACAAAGCC | |
| | | CTCAAATCTC GTAAACACTT GTATCAGGAC AACTCTGGAT | |
| | | AGAGCTGCGT GTTTGCCACC TGGAGACCAT AATGCATTAT | |
| | | ATGTAAATAG CTTCCCACTT CTGGACCCAT CTGATGCACC | |
| | | TTTTCCCTCA CTCGATTCCC CGGGAAAAGC AATCCGAGGA | |
| | | CCACAGCAGC CCATTTGGAA GCCCTTTCCT AATCAAGACA | |
| | | GTGACTCGGT GGTACTAAGT GGCACAGACT CAGAACTGCA | |
| | | TATACCTCGA GTATGTGAAT TCTGTCAAGC AGTTTTCCCA | |
| | | CCATCCATTA CATCCAGGGG GGATTTCCTT CGGCATCTTA | |
| | | ATTCACACTT CAATGGAGAG ACTTAAGACA CATTTGAAAA | |
| | | CAGACATATC AAGTTCTATG TGATGATTTT GGGTTTTTAA | |
| | | TACTATAAAT ACTTGATTGT AAACTAAATT CAAGATCATT | |
| | | TATAGGAAAA TCTAGTTTCA CAGCTATTTG AATTTTTTTC | |
| | | TGGATTTACT ATATAACTCT TATTTTTTAA AAGATCATTC | |
| | | TGTTCTTTCA AGGAGAAATA AGCCTAAAAG AAGAAAAACA | |
| | | AAAAAAATTC TGTATAAAAC TGTAATCCTT TGTATTCATG | |
| | | TTTACAGTGC TATTACTATA ATTCAAAATT ATGTATGTGA | |
| | | CTTAGAGTTA TATAATCATA ATTTATGTTT ATTTCAAATA | |
| | | TCTAAGTTTA TTGCTTGGAT TTCTAGTGAG AGCTGTTGAA | |
| | | TTTGGTGATG TCAAATGTTT CTAGGGTTTT TTTAGTTTGT | |
| | | TTTTATTGAA AAATTTAATT ATTTATGCTA TAGGTGATAT | |
| | | TCTCTTTGAA TAAACCTATA ATAGAAAATA GCAGACAACA | |
| | | TAAACATCTT TGTAAATATC AAACCTAATA CATTTCTTGT | |
| | | CCAGTGATAA AACAACTGGT AGAATTATTT AAACACTTTA | |
| | | GATTTTTAAA TAATATACAT GGCTTTAATT TTTACTGTGT | |
| | | GTATAGCTAC ATGATGAAAT TAATTAAATA TTAAGAGGTA | |
| | | AAAATAAAAA AAAAAAAAAA | |
| TLE4 | NM_001282748.1 | GGAGAGCTCG CCAGAGCGCT CGCATGGCGG GCCGGTGATT | 24 |
| | | GTAGTCAATC TGGCCGTATT CTCAGGCAGG GTCGCCCGGG | |
| | | GCGGACTACA TCTCCCGGGA TGCTGCGCGG CCGCCCCGCG | |
| | | GAAGATTGTG AATATGTATC AGAATGTTAA TGATTAGCTG | |
| | | CTGCTAAATT TGGTCAAAGA AGTCACCTAC ACAGAGCGTG | |
| | | TTGTTAGAGC TGTGCTGAGC GGGTGTTTGG GTTGTTGGCT | |
| | | GCTTTCTTCC CCCTTTCTCA CACACTTGTA TATTATTTTG | |
| | | AGGTGGTGTT CGCAGAGTTT GAAAGGAGAG AGAATTAAAA | |
| | | AAAAAAGCCG CAAGCGTTTC ACTCTTTTAT TTTTATAATC | |
| | | CCCTTCAATT TGGGGTTAAA AAAAAGACAA GAAAACAGGA | |
| | | AGGAAGAGAA ATAAGGAAAT GAGATGTGGT AAAAGAAGCT | |
| | | AAAAGGTGCC TTTTAAAAGA TCGTTGCTGT GAAGTGAAAA | |
| | | AAATCTCCAG AGAAACCAAA AAGCACCGCC GAGACCTCTT | |
| | | CCGAACCAAA GGAGTTTGTG TTTGCTTTTA GGGAAGAAGA | |
| | | AAGATCATTC ATTCGGAGGA ATAACAACCA ATTAAAAGAC | |
| | | AAATAAAAAA AGTTTGGAGT GGGACGCAGA GCGAGCGAGA | |
| | | GGAGCTGCCG GCGGGCGGTG GGGCGCGGAG CCCGCACTTT | |
| | | CCCGGCCGGG TGAGCGGCGG CCGCGGCGCC GGGCTCGGCG | |
| | | GGTGCGCCTC GGCGGAGCGA ACGTCGGAGC GTTGCCTTGG | |
| | | GAGACGCGCG CCGGACAATG CCCGCGGCGG GCCAGTGACG | |

TABLE 1-continued

Plasma cell dyscrasia Biomarker/Housekeeper Sequence Information

| Gene Name | RefSeq Accession | Sequence | SEQ ID NO: |
|---|---|---|---|
| | | CCCGCGGGGA ATGCGGAGCG GCCCGGCAGC CGGCACCCAG | |
| | | CCGCCGCCGC GCGTTCCTGC CGCCCGTGTC ACGCGAGACC | |
| | | CGGCGGGGGC CGGGACCGCC CGAGCCGCCC CTCAGACCGA | |
| | | GCCGGCCGCC TCCGCTGCCG CGGCCGCCTC CTCTTCGGGG | |
| | | TCATTAAAGC CAATGAGCCG CGCGCCTCTG CCGAGCGCAG | |
| | | CCAACTAAAT CGGCTTGGAT GATTCGCGAC CTGAGCAAGA | |
| | | TGTACCCGCA GACCAGACAC CCGGCACCGC ATCAGCCTGC | |
| | | TCAACCCTTT AAATTTACAA TTTCCGAATC CTGTGATCGG | |
| | | ATTAAGGAAG AGTTTCAGTT TTTACAGGCT CAATACCACA | |
| | | GTCTGAAGCT GGAATGTGAG AAACTCGCCA GTGAGAAGAC | |
| | | AGAGATGCAG CGGCATTATG TCATGTATTA TGAAATGTCC | |
| | | TATGGGTTGA ATATAGAAAT GCACAAGCAG GCAGAGATTG | |
| | | TCAAGAGGCT GAATGCTATC TGTGCACAAG TCATTCCTTT | |
| | | CCTGTCCCAA GAGCACCAGC AACAAGTGGT GCAGGCTGTG | |
| | | GAACGGGCCA AGCAGGTGAC CATGGCAGAA CTGAACGCCA | |
| | | TCATTGGGCA ACAACTCCAG GCCCAGCATT TATCACATGG | |
| | | ACATGGTCTC CCCGTACCTC TGACTCCACA CCCTTCAGGG | |
| | | CTCCAGCCCC CTGCCATTCC ACCCATCGGT AGCAGTGCCG | |
| | | GGCTTCTGGC CCTCTCCAGT GCTCTAGGAG GTCAGTCCCA | |
| | | TCTTCCAATT AAAGATGAGA AGAAGCACCA TGACAATGAT | |
| | | CACCAAAGAG ACAGAGACTC CATCAAGAGC TCTTCAGTAT | |
| | | CCCCATCAGC CAGTTTCCGA GGTGCTGAGA AGCACAGAAA | |
| | | CTCCGCAGAC TACTCCTCAG AGAGCAAAAA GCAGAAAACT | |
| | | GAAGAAAAGG AAATTGCAGC TCGTTATGAC AGCGATGGTG | |
| | | AGAAAAGTGA TGACAACTTG GTGGTTGACG TTTCCAATGA | |
| | | GGATCCATCT TCCCCTCGAG GGAGCCCAGC ACATTCCCCC | |
| | | AGAGAGAATG GCCTAGACAA GACACGCCTG CTCAAGAAAG | |
| | | ATGCCCCGAT TAGTCCAGCC TCTATTGCAT CTTCCAGCAG | |
| | | TACTCCCTCC TCCAAATCCA AAGAACTTAG CCTTAAGAGG | |
| | | GATATGGGGA AATTGAGTGA AACACGTCTT AGCGAAGATG | |
| | | AACAATGCAC ATTGGGGTTA CAGAGATGGT TTTGTCGCCT | |
| | | GTGGTTTATG AATGAAAAAT CTACTACTCC CGTCTCAAAG | |
| | | TCCAATACCC CTACTCCACG AACTGATGCG CCCACCCCAG | |
| | | GCAGTAACTC TACTCCCGGA TTGAGGCCTG TACCTGGAAA | |
| | | ACCACCAGGA GTTGACCCTT TGGCCTCAAG CCTAAGGACC | |
| | | CCAATGGCAG TACCTTGTCC ATATCCAACT CCATTTGGGA | |
| | | TTGTGCCCCA TGCTGGAATG AACGGAGAGC TGACCAGCCC | |
| | | CGGAGCGGCC TACGCTGGGC TCCACAACAT CTCCCCTCAG | |
| | | ATGAGCGCAG CTGCTGCCGC CGCCGCTGCT GCTGCTGCCT | |
| | | ATGGGAGATC ACCAGTGGTG GGATTTGATC CACACCATCA | |
| | | CATGCGTGTG CCAGCAATAC CTCCAAACCT GACAGGCATT | |
| | | CCAGGAGGAA AACCAGCATA CTCCTTCCAT GTTAGCGCAG | |
| | | ATGGTCAGAT GCAGCCTGTC CCTTTTCCAC CCGACGCCCT | |
| | | CATCGGACCT GGAATCCCCC GGCATGCTCG CCAGATCAAC | |
| | | ACCCTCAACC ACGGGGAGGT GGTGTGCGCG GTGACCATCA | |
| | | GCAACCCCAC GAGACACGTG TACACGGGTG GGAAGGGCTG | |
| | | CGTCAAGGTC TGGGACATCA GCCACCCAGG CAATAAGAGT | |
| | | CCTGTCTCCC AGCTCGACTG TCTGAACAGG GATAACTACA | |
| | | TCCGTTCCTG CAGATTGCTC CCTGATGGTC GCACCCTAAT | |
| | | TGTTGGAGGG GAAGCCAGTA CTTTGTCCAT TTGGGACCTG | |
| | | GCGGCTCCAA CCCCACGCAT CAAGGCAGAG CTGACATCCT | |
| | | CGGCCCCCGC CTGCTATGCC CTGGCCATCA GCCCCGATTC | |
| | | CAAGGTCTGC TTCTCATGCT GCAGCGACGG CAACATCGCT | |
| | | GTGTGGGATC TGCACAACCA GACCTTGGTG AGGCAATTCC | |
| | | AGGGCCACAC AGATGGAGCC AGCTGTATTG ACATTTCTAA | |
| | | TGATGGCACC AAGCTCTGGA CAGGTGGTTT GGACAACACG | |
| | | GTCAGGTCCT GGGACCTGCG CGAGGGGCGG CAGCTGCAGC | |
| | | AGCACGACTT CACCTCCCAG ATCTTTTCTC TGGGCTACTG | |
| | | CCCAACTGGA GAGTGGCTTG CAGTGGGGAT GGAGAACAGC | |
| | | AATGTGGAAG TTTTGCATGT CACCAAGCCA GACAAATACC | |
| | | AACTACATCT TCATGAGAGC TGTGTGCTGT CGCTCAAGTT | |
| | | TGCCCATTGT GGCAAATGGT TTGTAAGCAC TGGAAAGGAC | |
| | | AACCTTCTGA ATGCCTGGAG AACACCTTAT GGGGCCAGTA | |
| | | TATTCCAGTC CAAAGAATCC TCATCGGTGC TTAGCTGTGA | |
| | | CATCTCCGTG GACGACAAAT ACATTGTCAC TGGCTCTGGG | |
| | | GATAAGAAGG CCACAGTTTA TGAAGTTATT TATTAAAGAC | |
| | | AAATCTTCAT GCAGACTGGA CTTCTCCTCC TGGTAGCACT | |
| | | TTGCTCTGTC ATCCTTTTTG TTCACCCCCA TCCCCGCATC | |
| | | TAAAACCAAG GATTTCAGAT ACTCATTGCA GTTGTGGAGT | |
| | | TTAATCCCCT TTCTTAACCT CACTTCCCAC TTGCTATTGA | |
| | | ATTGTGAATA GTCATTAAAA ACCTGTGATA CCAAATCTTC | |
| | | AGCTGTCTAC TTGGAAGAAC ATGGAATAAG CATACTTAAC | |
| | | AGTGAAAAGA ATCTTTAATT ATGTATTATA TCTGTAATAT | |
| | | ATTTATTTTG TTTAAAGAAG GCTTTCTAAC AATGACTGAC | |

TABLE 1-continued

Plasma cell dyscrasia Biomarker/Housekeeper Sequence Information

| Gene Name | RefSeq Accession | Sequence | SEQ ID NO: |
|---|---|---|---|
| | | TAAATAAAGC TGTCTGCTCC TGCATTGATA ATGAAGGTGC | |
| | | GTTGTATTTG ATACCCCTCC CCCCCTTTTT TTGGCAAAGG | |
| | | AGGGGAAAGG AAGGTTTAAA ATAATTGATT TAAAATGTCA | |
| | | CTAAGTGTAG ACTGATGACT GTATAGAGAT GTGAAATGTA | |
| | | TAATTACACA TGGAAGCAAT ATGTTGCTGT GTTGTTATTA | |
| | | GGTTTTTTTT GTTTTTGTTT TCTACATCTT TTAAAGACTT | |
| | | TTGGAAATTT GGCTGAACAA TTAGAACACA ACAGGCCAAC | |
| | | TCATACTCAT TTGGATCTAT TTAGACAACG TTAACCAATA | |
| | | TATCTATAGC TTTAGATTAT ATTCGATAAA AGTAATTGGA | |
| | | CTTTTTTTCT TTTTTTGACT CGTTGACAAG TGTCTTTGTA | |
| | | ATATGTTTTT AGTTCCCTTT TTTTGTTGTA TTATAGGCAG | |
| | | ATGAACAAAT TAAATTTGGC CTCAAAGAGA GAACTTACTC | |
| | | CCTTCTGGAT ATTTTTGCCA CATTTCTTTG CAAAAGGAGA | |
| | | TATATATATC TTTAGTCAGT TTTGTTGTTA TGAGAAATTA | |
| | | TGGGTTATTT TGTGGCATGC TCTTTGGGAG CTGCACAGTT | |
| | | ATGGGGAGGA CTCCCACTGC TGTGCAAGTT AAGTCTTTTA | |
| | | CAAAACAAGG ACAGCAGAGG AGGGTTTGCA GAGACCTCCC | |
| | | TCTGAAAAAC ACAAAGAATG GACTCTCTCC TGGGATGAGG | |
| | | ACTTGCTTTC TTTACCTCCG GTTCTTTCCA TGTCTTAGTT | |
| | | GGATGTCCCT GAAATGGACA CAGGCTGTGC CATTGTGCCA | |
| | | GAAACATTGT GTTATCTTTT ATGTTGTTGT TGTTGCTGTT | |
| | | AAACTATAAT ATGTGACTTC TTTTTTTATT ATTTTTTGTT | |
| | | TGAATGCTTT AAAAATCTTT TAAGTCTGTG GATCTGCTGA | |
| | | TGTACAGTGC CTTTGCTGCT ATGGATCAAA ATCAAAAGAA | |
| | | CCGTGTAGAT ATACTTTATT GTATAAGTAG AAAATTACTT | |
| | | AATTTCATAC TAGAAATGGA TGGATGCTGC AAGTTGAAAT | |
| | | GGACTGTCCA TTGACGTTCC TAATGTGGTA GCAGAAAAAA | |
| | | AAAAATGGTG TCTTAAGTGC TTAGTGTTTG ATGTCATTAA | |
| | | CAGTTTCGTA AAACTCTACA GTGTAGAAAG ATTTTGATAC | |
| | | TAAACTGTGC GTTGTACATA GTTCTAATGC ATTGTATTGA | |
| | | CCACCAGTAC TTCTATAATG GTAGATTGTT TGTGAATTCA | |
| | | GACTTTTAAG CATTAAACAT AAATAACTTC TAGTATGCTT | |
| | | ATTTTTCTAA TTCTTTGTCT TGATGACATT AGTTTATTTT | |
| | | TTATCTTTGG CTGTGCCACT CCTATATATT AAAAATGCCT | |
| | | AGTTTTTTCA AGGGAGATTG TTGTTAAAGT AAAGTGGTTT | |
| | | TTTTTGTTGT TAAA | |
| TPT1 | NM_001286272.1 | CTTCGTGCCA CGTCACCGCC TGCGTCGCTT CCGGAGGCGC | 25 |
| | | AGCGGGCGAT GACGTAGAGG GACGTGCCCT CTATATGAGG | |
| | | TTGGGGAGCG GCTGAGTCGG CCTTTTCCGC CCGCTCCCCC | |
| | | CTCCCCCCGA GCGCCGCTCC GGCTGCACCG CGCTCGCTCC | |
| | | GAGTTTCAGG CTCGTGCTAA GCTAGCGCCG TCGTCGTCTC | |
| | | CCTTCAGTCG CCATCATGAT TATCTACCGG GACCTCATCA | |
| | | GCCACGATGA GATGTTCTCC GACATCTACA AGATCCGGGA | |
| | | GATCGCGGAC GGGTTGTGCC TGGAGGTGGA GGGGAAGATG | |
| | | GTCAGTAGGA CAGAAGGTAA CATTGATGAC TCGCTCATTG | |
| | | GTGGAAATGC CTCCGCTGAA GGCCCCGAGG GCGAAGGTAC | |
| | | CGAAAGCACA GTAATCACTG GTGTCGATAT TGTCATGAAC | |
| | | CATCACCTGC AGGAAACAAG TTTCACAAAA GAAGCCTACA | |
| | | AGAAGTACAT CAAAGATTAC ATGAAATCAA TCAAAGGGAA | |
| | | ACTTGAAGAA CAGAGACCAG AAAGAGTAAA ACCTTTTATG | |
| | | ACAGGGGCTG CAGAACAAAT CAAGCACATC CTTGCTAATT | |
| | | TCAAAAACTA CCAGTTCTTT ATTGGTGAAA ACATGAATCC | |
| | | AGATGGCATG GTTGCTCTAT TGGACTACCG TGAGGATGGT | |
| | | GTGACCCCAT ATATGATTTT CTTTAAGGAT GGTTTAGAAA | |
| | | TGGAAAAATG TGATGCAAAA GAAAGAAATC CCTGCGCTTT | |
| | | CTGTCTGTCT TTGTGGCGGC CCAGATTGAA TTGGGGAATA | |
| | | CATCTTTAGC CTGGAAATGT AGGCTGCATG TTAATGGTAA | |
| | | TGTAACTTTT GCAGTGTAAT GTTTGAAAAA TATTAATGTA | |
| | | GTTTTTGCTT TTACAGTAAC AAATGTGGCA ATTATTTTGG | |
| | | ATCTATCACC TGTCATCATA ACTGGCTTCT GCTTGTCATC | |
| | | CACACAACAC CAGGACTTAA GACAAATGGG ACTGATGTCA | |
| | | TCTTGAGCTC TTCATTTATT TTGACTGTGA TTTATTTGGA | |
| | | GTGGAGGCAT TGTTTTTAAG AAAAACATGT CATGTAGGTT | |
| | | GTCTAAAAAT AAAATGCATT TAAACTCATT TGAGAGAATG | |
| | | CCTTTTAGTT TAATGCATAT TTAAACTAAA TTGATCCTGT | |
| | | AGTGTTCCTG GAGAAGCTAG AGCCTGATTG TAGGCTACTA | |
| | | CTCATCAATT AACTTCTACA GTGGAGACTA CTTCTGGGAC | |
| | | TGGAATATAA AAAAGAATCA AAGGTTCTGA TTTTGAGTTG | |
| | | CAATAAAGGG AAAGACCATG CTCATAGCAG TGCCAACATC | |
| | | TGAAGTGTGG AGCCTTACCC ATTTCATCAC CTACAACGGA | |
| | | AGTAGTTAAC TGGAAGAGAT TACCAAGAGA ATAAAAAGAG | |
| | | ACTCATTCAG TGGAAGCAAC TTTGTCTCAG CTTATTTCAC | |
| | | ATAAAGAGAG CGAAGTCTTT TGGGATGAAT GTTAATTAAA | |

TABLE 1-continued

Plasma cell dyscrasia Biomarker/Housekeeper Sequence Information

| Gene Name | RefSeq Accession | Sequence | SEQ ID NO: |
|---|---|---|---|
| | | CTCCCTGGTA ACTAGAACAG GGACTGGCAA ACTAGCCTAT<br>CTGACCACCT GTTTTGTACA CTTTAAGGTG GTTGGTTGCC<br>TTTTTAAATG GTTGAGGGGA AAAGAATACC TTGTGGGATA<br>TGGAATTTAA GTTCGAGTCC AGTTTTATTG GAACGTGGCT<br>ATGCTTATTC ATTTATGGAT TGACTGTGGC TGTTGTCAGT<br>GCATGAGCAG AGTTGTGTCT AACAGACTAG AGCCTGCAAG<br>TTTGCCAGCC CCTGATTTAA AAGATGAAGG TACACAGAAT<br>GTGGGCTGGC TGGTGGGCAA AGGGGTAAAA ATGTTCTCTA<br>TATTGTATCT GAAAAGATGG GGTGTCTGAA TAAGAAAATG<br>CATCTATTTG ACAGACCTGG AGCAGTTGCT ATCTGCTGCT<br>ATGGTTTCCA CCACAGATGC AAGAAGAACA TGTCCTTGCG<br>CTTTCCGTCT GTCTAATTGT GGCAGCTGAG ATTGAATAGA<br>GGAATACAGG AGGAAAAAAA GCGGGAAGAG TTTTTGAGGC<br>AGGTCGGTCA CCCAGGCTTG TAGTGCAGTG GCACAAGCAA<br>CTCACTGCAT TCTCTGCATC CTGTGCTCAA GCCATTTTCC<br>CACCTCAGTC TCACTAGTTG CTGGGACTGC AGGCATGCAC<br>CCCTATGCCC AGCTAATTTT TGTAGAGACC GAGTATCGCT<br>TAGTTGCCCA GGGTGGTCTC AACTCCTGGG CTCAAGGAGA<br>TCTGCCCACC TCAGCCTCCC AAAGTGCAGG CCTAGCCTGG<br>GAGGGGAATT TTCAAAACGT GAGTTTTGGG AAATAGTCTA<br>TCAGCCTTAC CTGGTTGATT ACACTTGTAA AAGAAAGATT<br>AAAAGCAGGC CAGTGACTCT GGTCTGCTTG AACATGTGAA<br>TGTAGTGGTT TGAGCAATCT GGAGTTTGCC CTAGTGTCAA<br>ATTCCAGACT GTCCATAGTG TCCAAAACCT GAGGCAGATA<br>CTAATGTTAA CCCCCAGCAC CCCGTGATTG GAAACAAACC<br>TAAATACGTA TTGGGAACTT AATAGCAATT TTAAGCATTC<br>TGATAGATTT TTTGTAGGGA TGGGGTCATG CCATGTGGCC<br>CAGGCTGGTC TGAAAACTCT GGCCTCAAGT GATCTCAAGC<br>TTTGGCCTTC TAAAGTGTTG GGATTACAGG TGTGAGGCAT<br>TGCACCTGGC TTAGCGTTCT GATTTGACAT TGTAATGAAA<br>AGTGTGAGTC TCATCTACAG GGCCTTTTGT CCTCTGAAAT<br>GATAGCAGGA AGGGAATTTT CAGGCAGTGG TCAAAGCTGG<br>GGAAACCAGG ATAGTGAAGA AGGCCTTGAG GTGAGAGATG<br>GAAGCTAATT GGTGAACTAG CCTTGGAAGC CTGAAACAGA<br>CAAGTAGCAA TTCAGAGACT TTGTGGGCTC CACTGCTCCA<br>ACTTGTTTTG AAGATTTTCA GTTCTGCAGA AGAGGTATTT<br>CCCCAGTTGT CCTTTCAGTG CTCTTAGCTG TTTTCCCAAC<br>ATCCAGATCC AATCAAGGCT GGGACATAGC ATTTTATCAT<br>GTCTATTTAA GTCAGAAGTG ATGAACCCCA GCTGTTTACC<br>TCATGGTAAA CCTTTGAAGA TTCCAGGTAG AATCTTCTCA<br>GACTTTGAAG ACTGTCTCAT TTTATATCTT TTTCTCGTTA<br>TTCCTAGGGT CAAGACGTTT TGGGCAAGAA TAAGGATGTG<br>AACATCAGAA AGCTCATAAC ATTTTGTTTT TGATGCTAAG<br>TTTAACAAAG GCATGCTTTA GTAGCCTGTG GGCCCTAGGG<br>TTTGTTAAAG TGTGGAGAAC AACTGAGTGG AGCAAGAGGA<br>CTTTTCTAGG AAGGTCCTTG TAATGTGACA TTTGAAAACA<br>AATGAAGGTG TGGAAGTAGG CCATGTGGAT ATCAGGACAA<br>ACCATTCCAG GCCAAGACAA CAGCAGTTAG TCTGGAGTGT<br>GATGTGTTCT GGGAAAAAAG TGGCCACTTT GCTAACCCAA<br>GAAGACAGGA AGGGTTGTAA AGCAGTGGGA GTGTGCAAGG<br>AAGGAAGACC AGACCTCAAG GAAACCACAG GCGCTCTGAG<br>CAGAAGAGTT ACATGATATG ACTCAAATTT TTAAAGGATC<br>ACTTTGGCTG CCAGGTGGCA GGGTAAAAGC ATAGAATAAT<br>TGTGTATAAT GTGTTTTTAA GGCAAAGATA GTGGCTTAGT<br>CTAGGGTAGT AGACTGAGGT GGTAGGAAAT GAAGATAGAG<br>ACAACAGGAT ATGCTGGTGG GTGAGGATGG ATTTAATGTT<br>GATACAAGTA TTTTGGTCTG AGCGTTTGGA AGAAAGTTGG<br>CACTGAGGTG GGAAGTCGAG TTTAGTTTTG TTAGTTTTGG<br>ATGTGTTAAG TTTGAGATGC TGATTCTTCA GAGAAGTCTA<br>AGCTGGAGAA CTATATAGAG AGTGGAAAGA TAACAATAGA<br>CATTGAAAGC CATGATACAG GATAAGGTCA TTTGGAGAGA<br>GGATAGACTG CATTCCAACA TGAGATTGGT TGACAAAGAG<br>AAACCAACAA AGGTAATTAA GAGGTGCTCC CACTGCACTT<br>GTACTCAGAA GGCTGAGGTA GGATTGTTAG AGGCCAGCCT<br>GGGCACCACA GGGAGACCCC ATCTCTAAAA TTTAGCCAGG<br>AACCATGGCT CATGCCTGTA GCCCCAGGAA TTTGGGAGGC<br>TGAGTGGGGA GGATCGCTTG AGGTCAGGAG TTTGAGACCA<br>GCCTGGGCAA CATAGGGAGA CCTAAAAAAA TTAATTGGGC<br>ATCTGTAGTC CCAGCTACTC AGGCGGCTGA GCTGAGAGGA<br>TGGCTTGAGT CCGAGAGATT GAGGGTGCAG TGAGCTGTGA<br>TCATACCACT GCACTCCAGC CTGGGCGGCA GTGAGACACT<br>ATCTGAAAAA AGTTTAAAAA TTTTAAAAAA GAAGGAACTG<br>CCCCTGAGGT AAGAACCAAG GGAGGGCCTC CCAGAGGTCA<br>GGTGGAAAAA GTTTTAGGAA GGAGGAAGTA GTCAACAGGG | |

TABLE 1-continued

Plasma cell dyscrasia Biomarker/Housekeeper Sequence Information

| Gene Name | RefSeq Accession | Sequence | SEQ ID NO: |
|---|---|---|---|
| | | TTACCTGTTG CAAAGTACTT AAGTAATATG AGGCCTGATA GTGGTAAACT TGACTACCGT TGGATTTCAC TAGTGGGAAA GGAAGTCTAA TTAAAATGCA CTCAAGAGAC TAACAGTCGC AGGCATGAAA TACAATACAG GTACATGGTT TTTTATTATG TGTGCATCTG CTTCAGTAAT AGGTGTGAAT TACTCATTTG GATCATTAGG AGTTTCAAAA TCTAGTTAAA TGACTAGATT TTTGTTGATG TAAATTCTGT CATTCTGAAC TGCAGGGATT GTCAGTAACT TAACTGCAAA CTAAACTGGT GATAATTATG GTAAAATTGC AAGACGAGCA ATAAATCTCA ACCAACTTGA GAGAACACTG ATAA | |
| TSC22D3 | NM_001015881.1 | CGCCGTGAAA ACCAGCTGCT GCAGCCGCAG AGGCAGCCGG AGGCAGAGGG GCGGCGGGCA GGACCAGACA GGGCTGGGCA GGGGGCTGGC CGAGCGCCGT GCGCCGCTTG GGAGAAGGCC GGAAGCTTAC CAGCCGAGAA GGAATTCCTA GCTAGCTTCA GAGCCGGTGC CTCCGGAGCC AGCGTGGTGG CCATAGACAA CAAGATCGAA CAGGCCATGG ATCTGGTGAA GAATCATCTG ATGTATGCTG TGAGAGAGGA GGTGGAGATC CTGAAGGAGC AGATCCGAGA GCTGGTGGAG AAGAACTCCC AGCTAGAGCG TGAGAACACC CTGTTGAAGA CCCTGGCAAG CCCAGAGCAG CTGGAGAAGT TCCAGTCCTG TCTGAGCCCT GAAGAGCCAG CTCCCGAATC CCCACAAGTG CCCGAGGCCC CTGGTGGTTC TGCGGTGTAA GTGGCTCTGT CCTCAGGGTG GGCAGAGCCA CTAAACTTGT TTTACCTAGT TCTTTCCAGT TTGTTTTTGG CTCCCCAAGC ATCATCTCAC GAGGAGAACT TTACACCTAG CACAGCTGGT GCCAAGAGAT GTCCTAAGGA CATGGCCACC TGGGTCCACT CCAGCGACAG ACCCCTGACA AGAGCAGGTC TCTGGAGGCT GAGTTGCATG GGGCCTAGTA ACACCAAGCC AGTGAGCCTC TAATGCTACT GCGCCCTGGG GGCTCCCAGG GCCTGGGCAA CTTAGCTGCA ACTGGCAAAG GAGAAGGGTA GTTTGAGGTG TGACACCAGT TTGCTCCAGA AAGTTTAAGG GGTCTGTTTC TCATCTCCAT GGACATCTTC AACAGCTTCA CCTGACAACG ACTGTTCCTA TGAAGAAGCC ACTTGTGTTT TAAGCAGAGG CAACCTCTCT CTTCTCCTCT GTTTCGTGAA GGCAGGGGAC ACAGATGGGA GAGATTGAGC CAAGTCAGCC TTCTGTTGGT TAATATGGTA TAATGCATGG CTTTGTGCAC AGCCCAGTGT GGGATTACAG CTTTGGGATG ACCGCTTACA AAGTTCTGTT TGGTTAGTAT TGGCATAGTT TTTCTATATA GCCATAAATG CGTATATATA CCCATAGGGC TAGATCTGTA TCTTAGTGTA GCGATGTATA CATATACACA TCCACCTACA TGTTGAAGGG CCTAACCAGC CTTGGGAGTA TTGACTGGTC CCTTACCTCT TATGGCTAAG TCTTTGACTG TGTTCATTTA CCAAGTTGAC CCAGTTTGTC TTTTAGGTTA AGTAAGACTC GAGAGTAAAG GCAAGGAGGG GGGCCAGCCT CTGAATGCGG CCACGGATGC CTTGCTGCTG CAACCCTTTC CCCAGCTGTC CACTGAAACG TGAAGTCCTG TTTTGAATGC CAAACCCACC ATTCACTGGT GCTGACTACA TAGAATGGGG TTGAGAGAAG ATCAGTTTGG GCTTCACAGT GTCATTTGAA AACGTTTTTT GTTTTGTTTT GTAATTATTG TGGAAAACTT TCAAGTGAAC AGAAGGATGG TGTCCTACTG TGGATGAGGG ATGAACAAGG GGATGGCTTT GATCCAATGG AGCCTGGGAG GTGTGCCCAG AAAGCTTGTC TGTAGCGGGT TTTGTGAGAG TGAACACTTT CCACTTTTTG ACACCTTATC CTGATGTATG GTTCCAGGAT TTGGATTTTG ATTTTCCAAA TGTAGCTTGA AATTTCAATA AACTTTGCTC TGTTTTTCTA AAAATAAAAA AAAAAAAAAA AAAAAAAAAA AAAAAAAAAA A | 26 |
| UBE2J1 | NM_016021.2 | GCGGCCGCGG CAGGGCTGGG CCTGCGACTA CCCGAGGAGG CTGACCTCCA GCCCGGGCGC CCGGTTCAGC GCCGCCCCGG CCGGCGCCGG TGCCTGCCAG GCACTCAGGG AGGCGGGGGC GCAGTGGAGG AGGCGGCGCC ATCGCGAAGC GAGCGCCTCG CCCGCACTCA GCCTTGCCAC CCCGCCCGCA GTCCAGGCTG GACTGGGCGG CATTTGCCGA GGCTCCTCGG CCAGGCCCCG TCCGCCCGAG CCGCGCTGAG ACCCGGGCAG CGGCCGCGTG GAGAGGAGGT GGCAGCGGCC CGGGAGGCCG GAGCCAAGCC AGCGACCCAC CATGGAGACC CGCTACAACC TGAAGAGTCC GGCTGTTAAA CGTTTAATGA AAGAAGCGGC AGAATTGAAA GATCCAACAG ATCATTACCA TGCGCAGCCT TTAGAGGATA ACCTTTTTGA ATGGCACTTC ACGGTTAGAG GGCCCCCAGA CTCCGATTTT GATGGAGGAG TTTATCACGG GCGGATAGTA CTGCCACCAG AGTATCCCAT GAAACCACCA AGCATTATTC TCCTAACGGC TAATGGTCGA TTTGAAGTGG GCAAGAAAAT CTGTTTGAGC ATCTCAGGCC ATCATCCTGA AACTTGGCAG CCTTCGTGGA GTATAAGGAC AGCATTATTA GCCATCATTG | 27 |

TABLE 1-continued

Plasma cell dyscrasia Biomarker/Housekeeper Sequence Information

| Gene Name | RefSeq Accession | Sequence | SEQ ID NO: |
|---|---|---|---|
| | | GGTTTATGCC AACAAAAGGA GAGGGAGCCA TAGGTTCTCT<br>AGATTACACT CCTGAGGAAA GAAGAGCACT TGCCAAAAAA<br>TCACAAGATT TCTGTTGTGA AGGATGTGGC TCTGCCATGA<br>AGGATGTCCT GTTGCCTTTA AAATCTGGAA GCGATTCAAG<br>CCAAGCTGAC CAAGAAGCCA AAGAACTGGC TAGGCAAATA<br>AGCTTTAAGG CAGAAGTCAA TTCATCTGGA AAGACTATCT<br>CTGAGTCAGA CTTAAACCAC TCTTTTTCAC TAACTGATTT<br>ACAAGATGAT ATACCTACAA CATTCCAGGG TGCTACGGCC<br>AGTACATCGT ACGGACTCCA GAATTCCTCA GCAGCATCCT<br>TTCATCAACC TACCCAACCT GTAGCTAAGA ATACCTCCAT<br>GAGCCCTCGA CAGCGCCGGG CCCAGCAGCA GAGTCAGAGA<br>AGGTTGTCTA CTTCACCAGA TGTAATCCAG GGCCACCAGC<br>CAAGAGACAA CCACACTGAT CATGGTGGGT CAGCTGTACT<br>GATTGTCATC CTGACTTTGG CATTGGCAGC TCTTATATTC<br>CGACGAATAT ATCTGGCAAA CGAATACATA TTTGACTTTG<br>AGTTATAATA TGGTTTTGTG ACTTATGAGC TGTGACTCAA<br>CTGCTTCATT AAACATTCTG CATTGGGTAT AATCTAAGAA<br>TTGTTTACAA AAAGATTATT TTGTATTTAC CCTTCATTCC<br>TTTTTTTGAT CCTTGTAAGT TTAGTATAAA TATATCTAGA<br>CATTCAGACT GTGTCTAGCA GTTACGTCCT GCTTAAAGGG<br>ACTAGAAGTC AAAGTTCCTT GTCTCACTAT TTGATCTGCT<br>TTGCAGGGAA ATAACTTGTT TTTTCTCATG TTTCATCTTC<br>TTTTTATGTA AATTTGTAAT ACTTTCCTAT ATTGCCCTTT<br>GAAATTTTTG GATAAAAGAT GATGTTTTAA GTTCCAATGA<br>GTATTACTAG TTACTCAATA CCACTTATTG AGTACTCTGT<br>TTCTACGTAT GTAGAATGTA TAGGGATAGA AGAGTTGAAA<br>AGGGAAAGCA AAACTCCTCA AGTAGCTTCC TTAAAATGTC<br>ATTCATAGGA GATGTACTGG AATTGCTCAT TCTGTGACTT<br>TATTTGTGTC CTAAACATTC TTCAGTGAAA ATAATTTTAT<br>TTCAGTCAAA CATTTATGAG GAAATGAGAT CACATCTTTG<br>TCACTGGATG CTACTTGAAG AGGGAGTACT TTGTAACCAC<br>TTTGATATGC TGTTATCACC ACCCCCTGCC CTCTGCTGCC<br>ATAATCACAC AAATTTAAAA AGAAAGAAAA CAGTCTTCCA<br>TAGATTTTTA AGGAAGAAAG GGCCCAAGCC AGGAGATCGC<br>TTGGTTTTCT TCCAGAAGTT AAATGGGGGG ATCTGAAGAT<br>TTGAATGTTT GGTCTGCTTT GAAATGTATG TCTTTTGGGA<br>TGTATTATAT GCCTAGCTTT ATAATCAGTA TAAATTTTAA<br>TTATTCCAGG AATATGCATA ATATTGAAAT ATTTCATGTC<br>CTATTTTAAT AGAAAACCTC AGGGCCCAAG TAACAGTGAT<br>AGAAGTTAGA AAAACCTTTA CTTAGAATTG TCCACCTAGT<br>CAGAGCCCAA GAAAGAATTT TCAGTGGAAA AATCAATATA<br>TAACTTAGTG CTAGCTAGCG CCACAGACTC TAGTAGATAA<br>TATTATCATC ATAATGGCTG GTGAAACCAT ATAATCACAG<br>AAAAACATTG CCTTCAGCAT GTTCAGTTCG CAGCACTGAG<br>GGCACTCTTG AGGGTGTTGT TAATGAAGAT TTAATTTTTA<br>AATACAGGTG GTTCCAAGCT TTCAAATAGG TTATGCTCCA<br>AAAGTGTTAT TTGTAAGTTA ATTTTTTTAC AAGTCAAACA<br>ATGTTGGAAG TGGTATTTAG GTTCTAGATC GGTCCACGAA<br>AGTTAGCCCA TATGTATATC TTGAATAGTA TAGGGGAGGG<br>TATTCATAAA GTCCTTATGT GGTTTTAACT AAGTGAAATT<br>ATGGACAAGA GAAATAATTG TAAAATCGTC TTAAAGGAAA<br>ATTTAATTTT TACTCCTGTT TATGGGACAT TCGTTCTATT<br>AACTGTCAGA CACAATTTCT GTTTTCATCT GAGAGCCAGT<br>TTTCCTTTAT TTCTACATCT AAAATAAGAA CATATTGTAC<br>ACTATTATAT AATACAGAAT TGTCTTAAAC TTTAATAAAT<br>TCGCATTTTA AAGGTGTTTA CAGATTATTT TTTATATCTG<br>TAGCTGAATT TGTTAAAGTC TAAAAAGCTC AAGGACTTTA<br>TGAAGATCTC ATTATATGAG GAAAATCATA GGTTACCATT<br>TTATAACTCT ATTGCCATAA GAAAATACAC TCTAAAATCT<br>TGATTTGAAA CATATTAGAA ACCTTGATTC AGTGCTCAGT<br>GGTCTCCTAG TAAGAAGTCA CCGACGGTAG CGTCATATGA<br>GAAGAAAGAA ATCCCCACCA CCTCAACCTC TGCTGAGATT<br>GTGTGCTAGG AACAGCCTTC CCTCCGTTTC CCCTCAGTCA<br>AACTTGAGCC AGCCTCTGGA TCGATGTGAT CTTATTGCAT<br>GTTTCCATGG GGTGTACCTA TACTTTAAGC CAATCCTGCT<br>GCATTCACTG CTAAGTTAAA TAAAAAGCCA AGAAGATTTT<br>GCACTGTGCA GATCCTTTGC TATCTGACTT GCATCTCTTC<br>CCCCACCTGT CAGCTAGCCA CCTGCTTGTT TGTGTTGGGA<br>TATTTTTTAG CACCTGAAGC ACCATCTGAA AGGGGCACCA<br>TTTTCTTCTT CCCTTTGATC TCACATATGC TCCCTAAAAA<br>TCCTTAAGTT GTCAATCTGA TCCCCAGTGT GAGGTTAATG<br>AGCAAAATTG GTCTTTGGGG CCCTTTTTGT CCAAGCCCCA<br>CTGAAAGGCC TCTTCAGAAA ACTATTATCT TTAAAGCCCT<br>ACTTTAACTC CTTAATTCCA GCATACAGCT AAAACTGGAT | |

TABLE 1-continued

Plasma cell dyscrasia Biomarker/Housekeeper Sequence Information

| Gene Name | RefSeq Accession | Sequence | SEQ ID NO: |
|---|---|---|---|
| | | GTATATTCTG GCAAGTAAAG GCTGAGGACT CCTCTTTAAT CCTCAGATCT AGATAACTCA TGACATTTTA TTTGACCAAC ATAGCACATG ATGAGATATC AAGGTAATTA AAATAGCATG CTTGAAAAAA AAATACGTAA TCTGTTTCAC CTGTAACTGT TTAAGCCAAT AAACTTTTCA AAATTTATGT AATGTGGGGC TTTTATGTAG CACTTTACGT TTTCATGCTG CTTATTGTTT TATTCTACTG AAAAAAATGA ATTTCAAGAT TCTCAACTTT TTTAATTTCA AAAATTGTTT ATTGTTTTGA CTATAGGAAT ACAAAATTTC CTATTTTGGG AGAATAAGAA CTCTTTTTGT CATTTTTGGC TATGAATAAA CTTTCTGGTC TTTTGAGACC ACCCATTTTT ATAGATCAGA ATCAGAAAAC AGGTAAACCT CACTCACACA TTTGGACTCA TTTGAACAAA AATCTAGGCC AAAATACTGA AAAGCCTATG TGTTTTTTTA ATTGGAAGTA TATGTAAGGT TAATGCATTT AGTGAACGTG ACTAACAAAG ACTAATGTGC ACATTAACAG ATGTACTTTT TAAGGTTTTA TGGGAGGCTG TGCATTGCTC AAAAGCTGTT GGGAACGCCT TCTGAACAGT TGCCTTCAGA ACTAGTTTGA GCTGCTCAAT AAAACCAGTG ACTTTACTCA TAAAAAAAAA AAAAAAAAAA | |
| ALG9 | NM_001077690.1 | GTCTTTTGTC CCTCGGCGGA CACCGTTTGC CAGCCAAAGC TATGTCTGCG CGCTCACCGA CTTCATAGGG TGCCGAATTC TTTTTTCCCC AGGCTTGCCA TGGCTAGTCG AGGGGCTCGG CAGCGCCTGA AGGGCAGCGG GGCCAGCAGT GGGGATACGG CCCCGGCTGC GGACAAGCTG CGGGAGCTGC TGGGCAGCCG AGAGGCGGGC GGCGCGGAGC ACCGGACCGA GTTATCTGGG AACAAAGCAG GACAAGTCTG GGCACCTGAA GGATCTACTG CTTTCAAGTG TCTGCTTTCA GCAAGGTTAT GTGCTGCTCT CCTGAGCAAC ATCTCTGACT GTGATGAAAC ATTCAACTAC TGGGAGCCAA CACACTACCT CATCTATGGG GAAGGGTTTC AGACTTGGGA ATATTCCCCA GCATATGCCA TTCGCTCCTA TGCTTACCTG TTGCTTCATG CCTGGCCAGC TGCATTTCAT GCAAGAATTC TACAAACTAA TAAGATTCTT GTGTTTTACT TTTTGCGATG TCTTCTGGCT TTTGTGAGCT GTATTTGTGA ACTTTACTTT TACAAGGCTG TGTGCAAGAA GTTTGGGTTG CACGTGAGTC GAATGATGCT AGCCTTCTTG GTTCTCAGCA CTGGCATGTT TTGCTCATCA TCAGCATTCC TTCCTAGTAG CTTCTGTATG TACACTACGT TGATAGCCAT GACTGGATGG TATATGGACA AGACTTCCAT TGCTGTGCTG GGAGTAGCAG CTGGGGCTAT CTTAGGCTGG CCATTCAGTG CAGCTCTTGG TTTACCCATT GCCTTTGATT TGCTGGTCAT GAAACACAGG TGGAAGAGTT TCTTTCATTG GTCGCTGATG GCCCTCATAC TATTTCTGGT GCCTGTGGTG GTCATTGACA GCTACTATTA TGGGAAGTTG GTGATTGCAC CACTCAACAT TGTTTTGTAT AATGTCTTTA CTCCTCATGG ACCTGATCTT TATGGTACAG AACCCTGGTA TTTCTATTTA ATTAATGGAT TTCTGAATTT CAATGTAGCC TTTGCTTTGG CTCTCCTAGT CCTACCACTG ACTTCTCTTA TGGAATACCT GCTGCAGAGA TTTCATGTTC AGAATTTAGG CCACCCGTAT TGGCTTACCT TGGCTCCAAT GTATATTTGG TTTATAATTT TCTTCATCCA GCCTCACAAA GAGGAGAGAT TTCTTTTTCCC TGTGTATCCA CTTATATGTC TCTGTGGCGC TGTGGCTCTC TCTGCACTTC AGAAATGTTA CCACTTTGTG TTTCAACGAT ATCGCCTGGA GCACTATACT GTGACATCGA ATTGGCTGGC ATTAGGAACT GTCTTCCTGT TTGGGCTCTT GTCATTTTCT CGCTCTGTGG CACTGTTCAG AGGATATCAC GGGCCCCTTG ATTTGTATCC AGAATTTTAC CGAATTGCTA CAGACCCAAC CATCCACACT GTCCCAGAAG GCAGACCTGT GAATGTCTGT GTGGGAAAAG AGTGGTATCG ATTTCCCAGC AGCTTCCTTC TTCCTGACAA TTGGCAGCTT CAGTTCATTC CATCAGAGTT CAGAGGTCAG TTACCAAAAC CTTTTGCAGA AGGACCTCTG GCCACCCGGA TTGTTCCTAC TGACATGAAT GACCAGAATC TAGAAGAGCC ATCCAGATAT ATTGATATCA GTAAATGCCA TTATTTAGTG GATTTGGACA CCATGAGAGA AACACCCCGG GAGCCAAAAT ATTCATCCAA TAAAGAAGAA TGGATCAGCT TGGCCTATAG ACCATTCCTT GATGCTTCTA GATCTTCAAA GCTGCTGCGG GCATTCTATG TCCCCTTCCT GTCAGATCAG TATACAGTGT ACGTAAACTA CACCATCCTC AAACCCCGGA AAGCAAAGCA AATCAGGAAG AAAAGTGGAG GTTAGCAACA CACCTGTGGC CCCAAAGGAC AACCATCTTG TTAACTATTG ATTCCAGTGA CCTGACTCCC TGCAAGTCAT CGCCTGTAAC ATTTGTAATA AAGGTCTTCT GACATGAATA CTGGAATCTG GGTGCTCTGG GCTAGTCAAA GTCTATTTCA AAGTCTAATC AAAGTCACAT TTGCTCCCTG TGTGTGTCTC TGTTCTGCAT GTAAACTTTT TGCAGCTAGG CAGAGAAAGG CCCTAAAGCA CAGATAGATA TATTGCTCCA | 28 |

TABLE 1-continued

| Gene Name | RefSeq Accession | Sequence | SEQ ID NO: |
|---|---|---|---|
| | | CATCTCATTG TTTTTCCTCT GTTCAATTAT TTACTAGACC<br>GGAGAAGAGC AGAACCAACT TACAGGAAGA ATTGAAAATC<br>CTGGTACTGG ATGGCTGTGA TAAGCTGTTC TCCACACTCT<br>GGCCTGGCAT CTGAGAACTA GCAAGCCTCT CTTAGGCCAT<br>ATGGGCTTCT CCACCAAAGC TGTTTGGCAG CTCCTAGCAG<br>ACCTTCTTAT TGAAATCCTC ATGCTGAAAA TGAACACAGC<br>CTAGTTGCCA ACCCACATGT CCTTTTCACC TCCAGCAAGA<br>CTAAGCTTCT TTAAAGCACT TCACAGGACT AGGACCCTGT<br>CCTGGAGCTA TCTCAGGAAA AAGGTGACCA TTTGAGGAAC<br>TGTGACCTAA TTTTATTATA ATGATGCCTC TAATTTTCAT<br>TTCCTTTACA ACCAACTGTA ACTATAAGGT TGTATTGCTT<br>TTTTGTTCAG TTTTAGCATG CTATTTTTTG AATTCTAGAC<br>TCCTCCATGT GAAGATATCA ACAGACAAAA CTACAACTGT<br>ATAGGACATA TTTGGAGAAA ATTCTATCAA TTGATACATT<br>TGGATGACAT CACATTTTTA AGTAATGTAA TCTGAGGCCA<br>TTGCTGAGGA AATTAAGAAT TTTCCTTTTT TTTTAACCAC<br>CCCCAGTGAA AAGGATCAGT GTATATTTAT AGCACCTATT<br>TTTTAGTTCT GTCTGTTGTG AGGCACATCC TGCATGGGGC<br>ACTTCTAGTC AAATAGGCAA TGATAAGGAC CTAATTAAAA<br>TGTGATAAGT GTATACTATT ACTTTAAAAG CCTTTACAGT<br>CAGTACTTCA GTTTACAAGG CACTTTCACA GCATCTCGTT<br>TGATCCTCAC AGTCACAACA TGTGGTAGAC AAGGCAGGTG<br>ATTTTTATCC CCATTTTACA GATAAGGAAA CAGGCTGCGG<br>GTGGGGAGTG AGGGGAGGTA AAGATAGTTA GTTGCCTAAG<br>GTCACACAGC CAGTAAGTAA TAGAGCTGGG ACTGGAACCC<br>AGGTTTCCTT ACTCTCATCT ATTGCTCCTC CATATTCCTC<br>ACTCAACCAT GAAAACATTA CTTGAAAGGA CTGATGAGGT<br>TAACCAGAGA CCTAACTGAT ATTGTAACTT TCTATTTTAA<br>GGAAGAATTG TGTCTGTATT TGAGTTCTTT GGAGCCTCCA<br>GTCTGCCTGT GTGTTAGACC AGCACAGCAG TGCTGTGTGA<br>TGCAGCCTGA CCTGTGGCAG GAAAGTAGTG CTTCTGTTTG<br>GAAGTCATGT TCTTTTGCAG CCACACAGGA TCCAAATATC<br>AGTACTATTC CTGTAGTCAA TCTGGGGTCA CATTATAGGT<br>GCCTTATTTC CCTAAGGGTA ACTGATCTGA ATATCTGCAA<br>ATAGGATGAA TCTATTTTTC AGAAGTTCCA TCTTTCATTT<br>TTCTTTTTTT TTTTGAGACA GAGTCTCATT CTGTCGCCCA<br>TGCTGGAGTG CAGTGGCGCG ATCTCGGCTC GCTGCAACCT<br>CTGCCTCCCA GGTTGAAGCA ATTCTCATGC CTCAGCCACC<br>CGAGTAGCTG GGATTACAGG CATGCGCCAT CATGCCCAGC<br>TAATTTATGT ATTTTTAGTA GAGTTGGAGT TTCACCATGT<br>TGGCCAGGCT GGTCTTGGAC TCCTGACCTC AGGTCATCCA<br>CCCGCCTCAG CCTCCCAAAG TGCTGGTATT ACAGGCGTGA<br>GCCACCGCAC CCAGCCCCAT CTTTCATTTT CAAAGAGAAG<br>GGCATTCTAA TAGGAACTGG TGCCAAGAGA GAAGAAAAGA<br>AGTGATAACA GAAGAAATGG CTAGTTACAA TATTAAAAAG<br>CTCCTCTTTG AGATCTCCTC TGCAGGAATA TCAGAGACGG<br>AGTTGAAGCG CTGGAGAGGT AATAGGTCTA GACAGTACAG<br>AACAATAACT GGGGAGTGTG TGAGGATAGA CTGGGCTCCC<br>CCTTGCTTGA AAGATCTCTG GCATTTAATT CTCAATTCTT<br>GATTACTATT TTCCAGTGTA AAACTAGCAC ATATGATCTG<br>ACTACAGGAC AGAGAATTTT AAGTGAAACA TTTGCCTTAC<br>TTGCAGTAAT AATGTGCTGT TCTTCACAGT AGCTAAGGCC<br>CTCTATGTTT CCCAGAGGTA AATAAGAATC CAGGAATGGA<br>GGTCCATCTG TGATGAATGG CTTTTTTCTA ATCAAAGTAG<br>TATAATGCTG TTTTATCTGT TTTGTCATCT TGTTTTTTTT<br>TTTTTTTAAA AAAACAAAAC CTTAATTATA ATATAGCGCA<br>AAGAAAGGCC AGGACTGATG CAGGGATTCC TTGGAAATAT<br>CAGTTCCTAT CACTTTTAAA ACCTGATTTT GGATCTCTCT<br>GTTCTATGTA TGTCTTTAGT GAGAGCACAA TACATGGCAG<br>AACGCTGTGC CAAATGTTAT AGGTAAGGAA TATAGAAATG<br>AATGTTTTTT GTTGTGAAGG TGTTTTCATG TGATATTTTA<br>TAAACACATT TTAAAAAATC TCCATCACTT TTTAGTATAG<br>GAAGGATAGC TTTGCCTGGG AAAAACAGTT TCAACACACC<br>TGCTCAGAGT AGCAGTTCTC CCTCAAAAAA GCAGTGTTCA<br>GCCTGCACTG ACTGTTCTGC TTGCCAAAAG GAGGAAGCAT<br>GCAAGATACT TATTTCTCCA TAGATTGTGG AGTATAGAGG<br>GATGTGGGAC TACAGATTAT TATTTTTTTT CCCCGAGACA<br>GAGTCTTGCT CTGTCGCCCA GGTTGGAACA CAATGGCACG<br>ACCTCAGCTC ACTGCAACCT CTGTCTCCCG GGTTCAAGCA<br>ATTCTCCTGC TTCAGCCTCC TGAGTAGCTG GGATTACAGG<br>CACACACCAC CACCGCACTC AGCTAATTTT TGTATTTTTA<br>GTAGAGGTGG GGTTTTACCA TGTTGGCCAG GCTGGTCTTA<br>AACTCCTGAC CTTGTAATCA TCCCGCCTCG GCCTCCTAAA<br>GTGCTAGGAT TACAGGCATG AGCCACCGCA CCCGGCCCAG | |

TABLE 1-continued

Plasma cell dyscrasia Biomarker/Housekeeper Sequence Information

| Gene Name | RefSeq Accession | Sequence | SEQ ID NO: |
|---|---|---|---|
| | | ATAATTTTTA ATAGCCTTTG ATCATGGGGT GAGTGAGGGA<br>GTAGGTATAC TTGGCAAATG CATGGTTCTC TGATTTCTAG<br>CTCTAAAGCA GCCTTATCTG AATCCCCAAA TCTTGTGATG<br>CTGAGTACCA TTACTGAACC AGTCTGCACG GTAGGCATCT<br>GCTACCAAAA TTTACCTCCT ACCTGGTAGG TGTCATCTGA<br>TAAGAAAGAA GACAGGTTAT TTTAATTTTT TGAGATAATC<br>ACAGAAAATT GCAGCCCATA CTCTTTATTA CCGAATTCAA<br>GTTTGGAAAT AGACCCTTTG TTTTAAATCA TGATGGGTCT<br>TTATCCCAAT CATTTATCTG GGTCATTTTT CCAACTTTGG<br>AGTTCTAGGA AAGAACCTTG AAAACCTGAT ATGATTCTGC<br>AGCATGAGGT CTACGGTGAC CATTTGGGCA AAGCTCCAGT<br>GGCAATCATT TATTGTGTTT TGCATTTCCT GGGATTTATT<br>GAAATAAGAA TTCACTGTGA TTATGTAGTC TTCTGGCTAG<br>TATCAGGCAG CTCTGCTTTT AATTTGGTTA ATTTTATTTT<br>CTCTGAAGAG GGAGAAGAGG TACAATTTAA TCTTGGCCTC<br>CACAAGCATA TTAAAGCTCA CGTGTTAATC AGTGCATTCT<br>TATGCTCCTA CATTAAATGC CTTGGGTAAA TGGATAAATG<br>GACATGTGCC CAGCTTTAAT TTTTTTTGCA ACAGAAAGAT<br>CAGACTTCCG TATGGCATCG TTGGATTTCA GAGGCTTTCT<br>GGTGTATCTG TAAATCTGAA TGTTGCCTTC TGCCAGTCTG<br>TATAACCAGG TGATTCATGC TGCAAATGAA ATCAGGAAGC<br>AGTAAAGTGT TAAAGCAAGA GTATTGTCCA ATTCACTTGT<br>CTTCCTGATC CTTGTACTTT ATTTCACGTG TCGGTGTTTA<br>CATTACATAC TTATATTTCC TGTGAAAGAA AGAGTTAAAT<br>AAATTGTAGC AGTTTGA | |
| SEPN | NM_031475.2 | AGCGGAGCGC CAGGCAGCGC GGAGCGGAGG CCAGGCCCAC<br>AGCCGCTCCG CCTCCCGGCC CGCAGATCCC CGACGGCCGC<br>ACCGCGGGCT CCTCTGGCCC GCAAGAACAC GTGCATGGCG<br>TCCTGGGGAA GGCGCTGAGT GCGGAGTCGC GGCGCCGCAC<br>GCGGCACCAT GGCCCTGGAG CAGGCGCTGC AGGCGGCGCG<br>GCAGGGCGAG CTGGACGTGC TGAGGTCGCT GCACGCCGCA<br>GGCCTCCTGG GGCCCTCGCT GCGCGACCCG CTGGACGCGC<br>TGCCCGTGCA CCACGCGGCC CGCGCTGGGA AGCTGCACTG<br>TCTGCGCTTC CTGGTGGAGG AAGCCGCCCT CCCCGCCGCG<br>GCCCGCGCCC GCAACGGCGC CACACCGGCC CACGACGCCT<br>CCGCCACCGG CCACCTCGCC TGCCTGCAGT GGCTGCTGTC<br>GCAGGGCGGC TGCAGAGTGC AGGACAAAGA CAATTCTGGT<br>GCCACAGTCT TGCATCTGGC TGCCCGCTTC GGCCACCCCG<br>AGGTGGTGAA CTGGCTCTTG CATCATGGCG GTGGGGACCC<br>CACCGCGGCC ACAGACATGG GCGCCCTGCC TATCCACTAC<br>GCTGCCGCCA AAGGAGACTT CCCCTCCCTG AGGCTTCTCG<br>TCGAGCACTA CCCTGAGGGA GTGAATGCCC AAACCAAGAA<br>CGGTGCCACG CCCCTGTACC TGGCGTGCCA GGAGGGCCAC<br>CTGGAGGTGA CCCAGTACCT GGTGCAGGAA TGCGGCGCAG<br>ACCCGCACGC GCGCGCCCAC GACGGCATGA CCCCGCTGCA<br>CGCCGCGGCG CAGATGGGCC ACAGCCCAGT CATCGTGTGG<br>TTGGTGAGCT GCACCGACGT GAGCCTGTCC GAGCAGGACA<br>AAGACGGCGC CACCGCCATG CACTTCGCGG CGAGCCGCGG<br>CCACACCAAG GTGCTCAGCT GGCTGCTGCT GCACGGCGGG<br>GAGATCTCGG CTGACCTGTG GGGCGGGACC CCGCTGCACG<br>ACGCCGCCGA GAACGGGGAG CTAGAGTGCT GCCAGATCCT<br>GGTAGTGAAC GGCGCGGAGC TGGACGTCCG CGACCGCGAC<br>GGGTACACGG CCGCCGACCT GTCGGACTTC AACGGCCACA<br>GCCACTGCAC CCGCTACCTG CGCACGGTGG AGAACCTGAG<br>CGTGGAGCAC CGCGTGCTTT CCCGGGATCC ATCCGCAGAG<br>CTGGAGGCTA AGCAGCCGGA TTCAGGCATG TCCTCACCCA<br>ATACCACGGT GTCGGTCCAG CCGCTGAACT TTGACCTCAG<br>CTCGCCTACC AGCACCCTCT CCAACTACGA CTCCTGCTCC<br>TCCAGCCACT CCAGCATCAA GGGCCAGCAC CCTCCATGTG<br>GGCTTTCCAG CGCTAGAGCT GCAGACATAC AGAGCTACAT<br>GGACATGCTG AACCCGGAGC TGGGCCTGCC TCGGGGCACG<br>ATTGGGAAGC CCACACCCCC ACCACCCCCA CCCAGCTTCC<br>CCCCGCCACC CCCGCCCCCA GGCACCCAAC TGCCCCCACC<br>CCCACCTGGC TACCCAGCTC CCAAGCCTCC TGTAGGACCA<br>CAGGCAGCTG ACATCTACAT GCAGACCAAG AACAAACTCC<br>GCCACGTGGA GACAGAGGCC CTCAAGAAGG AGCTGAGCTC<br>CTGTGACGGC CACGACGGGC TGCGGAGGCA GGACTCCAGC<br>CGCAAGCCCC GCGCCTTCAG CAAGCAGCCC AGCACGGGGG<br>ACTACTACCG GCAGCTGGGC CGCTGCCCCG GCGAGACGCT<br>GGCCGCACGC CCGGGCATGG CGCACAGCGA GGAGGTGCGT<br>GCCCGCCAGC CCGCGCGCGC CGGCTGCCCG CGCCTCGGCC<br>CTGCCGCCCG CGGCTCACTC GAAGGCCCCT CCGCTCCCCC<br>GCAGGCGGCG CTGCTTCCTG GGAACCATGT TCCTAACGGC | 29 |

TABLE 1-continued

Plasma cell dyscrasia Biomarker/Housekeeper Sequence Information

| Gene Name | RefSeq Accession | Sequence | SEQ ID NO: |
|---|---|---|---|
| | | TGCGCCGCGG ACCCCAAGGC GTCCAGGGAG CTGCCACCGC<br>CGCCCCCACC GCCGCCGCCG CCCCTGCCGG AGGCCGCGAG<br>TTCGCCACCG CCGGCCCCGC CTCTGCCCCT CGAGAGCGCT<br>GGCCCTGGCT GCGGGCAGCG CCGCTCCTCC TCGTCCACCG<br>GCAGCACCAA GTCTTTCAAC ATGATGTCCC CGACGGGCGA<br>CAACTCGGAG CTACTGGCTG AGATTAAGGC AGGCAAGAGC<br>CTGAAGCCGA CGCCCCAGAG CAAGGGGCTG ACCACAGTGT<br>TCTCAGGCAT CGGGCAGCCG GCCTTCCAGC CCGATTCGCC<br>GCTGCCTTCT GTGTCACCTG CACTGTCACC AGTCCGGAGC<br>CCCACACCGC CAGCTGCGGG GTTTCAGCCG CTGCTCAATG<br>GAAGCTTGGT TCCCGTGCCG CCCACTACTC CTGCGCCGGG<br>AGTGCAGCTG GACGTGGAGG CTCTCATCCC CACGCACGAT<br>GAGCAGGGCC GGCCCATCCC CGAGTGGAAG CGCCAGGTGA<br>TGGTGCGCAA GATGCAGCTG AAGATGCAGG AGGAGGAGGA<br>GCAGAGGCGG AAGGAGGAGG AGGAGGAGGC CCGGCTGGCC<br>AGCATGCCCG CCTGGAGGCG GGACCTCCTG CGGAAGAAGC<br>TGGAAGAAGA GAGGGAGCAG AAGCGGAAAG AGGAGGAGCG<br>ACAGAAGCAG GAGGAGCTGC GGCGGGAGAA GGAACAGTCA<br>GAGAAGCTGC GGACGCTGGG CTACGATGAG AGCAAGCTGG<br>CGCCCTGGCA GCGACAGGTC ATCCTGAAGA AGGGGGACAT<br>CGCTAAGTAC TAGAGGCCGC AGACTCCTGT CCGCAGCCTC<br>GCAGCTCCGT GGGGCCCTCC GCCCCAGCCC CAGCCAGCCA<br>GGCCCTGGTG GAAAGGCTGG GAGCCGCACA GCCCTCCCCT<br>CCTGCGCTGG AAACCCTCCC TGACCCCCAC CCTGGCCCCC<br>CGTATCCCCA GCCCTTGGCA ACACTGGAGT GCACACGCCG<br>CCACGGTTGC CCAGAAAAAG TGCCCAAGCT GCTGACGCAA<br>ACAACAACAA ATGCTGCTTA TTTGCATGCC GACTTACATA<br>TATTTGCATG TTCGTTGACT ATCAAAGAGT GCAGAGCTCT<br>CCCCAGCCCC GTGGGTGGTG ACTTTGTTTT CCTGCGGGGC<br>TCAGCCCCCT CCAGGATGCA GCCCCCTCCC CCGCACCCCG<br>GAACCGGCGT CGCTGGCGCA TCCTGGGTGG AGGCAGGCCC<br>CGAGCTCGGG GAAGGGGTTT TCCCTTCCTC TCTGACCCAG<br>ATCTGCGCGC GGCCTAGCCC GGGCCTCATT TCTTATCCCC<br>GCCAAGGGTT TCCTCTCAGT CATTTGTTTA CCAGAAACAT<br>GAAAACTGCC TGTCTGGCCG GGCCGCACTT GTGGCCCCCG<br>GGACCCCACC TCTGGCCCCA CCTCCCTCAA GTCTGCGCCC<br>CGTCCCCAGC CAGACCCACT CGCTGCCGGG ACCCTTTCAC<br>TGCCCCGGTG GAGTGAATAG AGGATGAGGG GCCCTGACCC<br>TGTGTCTCCA ACTGCTGCAC CCCATCCCGA CCCTGTCTCC<br>GCCACCTCGC AGCCCCATTA AAGCGCTCTC ATCTGGGCTC<br>CGGTTCACTC A | |
| YWHAQ | NM_006826.3 | TTGGGCGGTG GACCGCCCCT CGGCCCCGGG GTAGGCTGAC<br>ACGGGAGGGT CCTCAGCTAA AGCCAAAAGC AGATCAAAGT<br>GGTGGGACTC GCGTCGCGGC CGCGGAGACG TGAAGCTCTC<br>GAGGCTCCTC CCGCTGCGGG TCGGCGCTCG CCCTCGCTCT<br>CCTCGCCCTC CGCCCCGGCC CCGGCCCCGC GCCCGCCATG<br>GAGAAGACTG AGCTGATCCA GAAGGCCAAG CTGGCCGAGC<br>AGGCCGAGCG CTACGACGAC ATGGCCACCT GCATGAAGGC<br>AGTGACCGAG CAGGGCGCCG AGCTGTCCAA CGAGGAGCGC<br>AACCTGCTCT CCGTGGCCTA CAAGAACGTG GTCGGGGGCC<br>GCAGGTCCGC CTGGAGGGTC ATCTCTAGCA TCGAGCAGAA<br>GACCGACACC TCCGACAAGA AGTTGCAGCT GATTAAGGAC<br>TATCGGGAGA AAGTGGAGTC CGAGCTGAGA TCCATCTGCA<br>CCACGGTGCT GGAATTGTTG GATAAATATT TAATAGCCAA<br>TGCAACTAAT CCAGAGAGTA AGGTCTTCTA TCTGAAAATG<br>AAGGGTGATT ACTTCCGGTA CCTTGCTGAA GTTGCGTGTG<br>GTGATGATCG AAAACAAACG ATAGATAATT CCCAAGGAGC<br>TTACCAAGAG GCATTTGATA TAAGCAAGAA AGAGATGCAA<br>CCCACACACC CAATCCGCCT GGGGCTTGCT CTTAACTTTT<br>CTGTATTTTA CTATGAGATT CTTAATAACC CAGAGCTTGC<br>CTGCACGCTG GCTAAAACGG CTTTTGATGA GGCCATTGCT<br>GAACTTGATA CACTGAATGA AGACTCATAC AAAGACAGCA<br>CCCTCATCAT GCAGTTGCTT AGAGACAACC TAACACTTTG<br>GACATCAGAC AGTGCAGGAG AAGAATGTGA TGCGGCAGAA<br>GGGGCTGAAA ACTAAATCCA TACAGGGTGT CATCCTTCTT<br>TCCTTCAAGA AACCTTTTTA CACATCTCCA TTCCTTATTC<br>CACTTGGATT TCCTATAGCA AAGAAACCCA TTCATGTGTA<br>TGGAATCAAC TGTTTATAGT CTTTTCACAC TGCAGCTTTG<br>GGAAAACTTC ATTCCTTGAT TTGTGTTTGT CTTGGCCTTC<br>CTGGTGTGCA GTACTGCTGT AGAAAAGTAT TAATAGCTTC<br>ATTTCATATA AACATAAGTA ACTCCCAAAC ACTTATGTAG<br>AGGACTAAAA ATGTATCTGG TATTTAAGTA ATCTGAACCA<br>GTTCTGCAAG TGACTGTGTT TTGTATTACT GTGAAAATAA | 30 |

TABLE 1-continued

Plasma cell dyscrasia Biomarker/Housekeeper Sequence Information

| Gene Name | RefSeq Accession | Sequence | SEQ ID NO: |
|---|---|---|---|
| | | GAAAATGTAG TTAATTACAA TTTAAAGAGT ATTCCACATA | |
| | | ACTTCTTAAT TTCTACATTC CCTCCCTTAC TCTTCGGGGG | |
| | | TTTCCTTTCA GTAAGCAACT TTTCCATGCT CTTAATGTAT | |
| | | TCCTTTTTAG TAGGAATCCG GAAGTATTAG ATTGAATGGA | |
| | | AAAGCACTTG CCATCTCTGT CTAGGGGTCA CAAATTGAAA | |
| | | TGGCTCCTGT ATCACATACG GAGGTCTTGT GTATCTGTGG | |
| | | CAACAGGGAG TTTCCTTATT CACTCTTTAT TTGCTGCTGT | |
| | | TTAAGTTGCC AACCTCCCCT CCCAATAAAA ATTCACTTAC | |
| | | ACCTCCTGCC TTTGTAGTTC TGGTATTCAC TTTACTATGT | |
| | | GATAGAAGTA GCATGTTGCT GCCAGAATAC AAGCATTGCT | |
| | | TTTGGCAAAT TAAAGTGCAT GTCATTTCTT AATACACTAG | |
| | | AAAGGGGAAA TAAATTAAAG TACACAAGTC CAAGTCTAAA | |
| | | ACTTTAGTAC TTTTCCATGC AGATTTGTGC ACATGTGAGA | |
| | | GGGTGTCCAG TTTGTCTAGT GATTGTTATT TAGAGAGTTG | |
| | | GACCACTATT GTGTGTTGCT AATCATTGAC TGTAGTCCCA | |
| | | AAAAAGCCTT GTGAAAATGT TATGCCCTAT GTAACAGCAG | |
| | | AGTAACATAA AATAAAAGTA CATTTTATAA ACCATTTACT | |
| | | ATGGCTTTGT AACAATTGCA TACCCATATT TTAAGGGACA | |
| | | GGTGAATTTA CTACTTTCTA AAGTTTATTG ATACTTCCCT | |
| | | TTTATGTAAA ATGTAGTAGT GATACCTATA TTTCCACATT | |
| | | GTGCATTGTG ACACACTTGT CTAGGGATGC CTGGAAGTGT | |
| | | ATAAAATTGG ACTGCATTTC TTAGAGTGTT TTACTATAGA | |
| | | TCAGTCTCAT GGGCCATCTC TTCCTCAGAT GTAAATGATA | |
| | | TCTGGTTAAG TGTTATATGG AATAAAGTGG ACATTTTAAA | |
| | | ACTAGCAAAG TTAAAAAAAA AAAAAAAAAA AA | |
| VPS37A | NM_001145152.1 | GCAGAGGGGG CGGAGAGCGC CCCCGGGGGC GGGGCACGCA | 31 |
| | | AGTGACGGCG GCGCGGGTGG TGGAGCGCTG GGCGGCCAGG | |
| | | CTCCCTGGCT GGCCGGTTTG GGCGTCTGGG CCGTGAAGGT | |
| | | GGGACCTCCT GTTCCGGGCC GCAAGTTTCC CTCTCCAGCC | |
| | | GCCCGCCGTT CGTAGCATGT CCCCCAGAAC TCGGGGAGCG | |
| | | CAGGCAGGAC AGGCTTAGAG AAGACGCGGT CCCCAGCGCT | |
| | | TGGGCCACGG ACGTCCCACC CCGCTCCTCT GTCGCTGGAG | |
| | | AACCGCCGGG CCGAGCCACT GGGAGAAGCA GGCCAGAGCC | |
| | | TTCCAGGGCC TCCGGCCCGT GGACCCGAGG AGGATGAGCT | |
| | | GGCTTTTTCC CCTGACCAAG AGCGCCTCCT CCTCCGCGGC | |
| | | TGGGTCCCCC GGTGGCCTCA CCAGCCTCCA GCAGCAGAAG | |
| | | CAGCGCCTGA TCGAGTCCCT CCGGAACTCA CACTCCAGAT | |
| | | TGCTTCCTCC ACAGTTTCCT CAGGAAAAAC CAGTGATCAG | |
| | | TGTTTATCCA CCAATACGAC ATCACTTAAT GGATAAACAA | |
| | | GGAGTGTATG TTACCTCTCC ATTAGTAAAC AATTTTACAA | |
| | | TGCACTCAGA TCTTGGAAAA ATTATTCAGA GTCTGTTGGA | |
| | | TGAGTTTTGG AAGAATCCTC CAGTTTTAGC TCCTACTTCA | |
| | | ACAGCATTTC CTTATCTATA CAGTAACCCA AGTGGGATGT | |
| | | CTCCTTATGC TTCTCAGGGT TTTCCATTTC TTCCTCCATA | |
| | | TCCTCCACAA GAAGCAAACA GGAGTATCAC TTCTTTATCT | |
| | | GTTGCTGACA CTGTTTCTTC TTCAACAACA AGTCATACCA | |
| | | CAGCCAAGCC TGCCGCTCCT TCATTTGGTG TCCTTTCAAA | |
| | | TCTGCCATTA CCCATTCCCA CAGTGGATGC TTCAATACCG | |
| | | ACAAGCCAAA ATGGTTTTGG GTACAAGATG CCAGATGTCC | |
| | | CTGATGCATT TCCAGAACTC TCAGAACTAA GTGTGTCACA | |
| | | ACTCACAGAT ATGAATGAAC AAGAGGAGGT ATTACTAGAA | |
| | | CAGTTTCTGA CTTTGCCTCA ACTAAAACAA ATTATTACCG | |
| | | ACAAAGATGA CTTAGTAAAA AGTATTGAGG AACTAGCAAG | |
| | | AAAAAATCTC CTTTTGGAGC CCAGCTTGGA AGCCAAAAGA | |
| | | CAAACTGTTT TAGATAAGTA TGAATTACTT ACACAGATGA | |
| | | AGTCCACTTT CGAAAAGAAG ATGCAAAGGC AGCATGAACT | |
| | | TAGTGAGAGC TGTAGTGCAA GTGCCCTTCA GGCAAGATTG | |
| | | AAAGTAGCTG CACATGAAGC TGAGGAAGAA TCTGATAATA | |
| | | TTGCAGAAGA CTTCTTGGAG GGAAAGATGG AAATAGATGA | |
| | | TTTTCTCAGT AGCTTCATGG AAAAGAGAAC AATTTGCCAC | |
| | | TGTAGAAGAG CCAAGGAAGA GAAACTTCAG CAGGCGATAG | |
| | | CAATGCACAG CCAATTTCAT GCTCCACTAT AGATTTTCCT | |
| | | GGAAACATGA ACTGCCAAGA GAGGAATGGG ACACAAAACC | |
| | | AAACACTGTT TTATATTTAT GGTTTGCAAA CTGGCATTTC | |
| | | ATCAGTGGCT AAATTCACAG ATATCCTATA TAGATTGTAT | |
| | | ACAGAACTGA GACTGATTTT GTACCGATTA GAATGATTGC | |
| | | TATGATCTTT GAGAAATTTT TCTGCACTAT TTGCACTGAA | |
| | | ATGTTTATTT ATTGTTGATA AATTGTATCA TATTTAAGTT | |
| | | CCACTGCTGT TCCTCTTACC TTGATTAAAT GCCTATGCAT | |
| | | GTACTTTTAG CTAGTTTTTA ATATTTTATA AAACTTCATT | |
| | | TAAATTTGTA TTTTTAACTT GAAGTTCCAT TTCTTTATCA | |
| | | AGGATGGTAT TTAGATTTTT TTCCTCTTAA CCTTTTTTCA | |
| | | AAAACTATTT TCAACTGTGA GGAAACCCTT ATTTTTCTTT | |

TABLE 1-continued

Plasma cell dyscrasia Biomarker/Housekeeper Sequence Information

| Gene Name | RefSeq Accession | Sequence | SEQ ID NO: |
|---|---|---|---|
| | | CTTTGTGGAT AAAACTTTCA AAAGCAATTT AAGATATTCA TAGTGTTAGG AAACACCAAA CCTGCCTATG TGCCATCTCA CAAAAGAAAC TTTTAATACC TACAATAAAT CAAAAGAATA AACCAGCTGT TCTTATATAT TGTTTCATTT TTAAAACTAA AGATGCATTT AAGAAGCAAT ACAAGTAAAT ATTTTACCTA ATAGGAAAAA AAAAAGTTGC CTTTCATTTA AACCATTCCA ACAGAAATTC TTATGCTAAT TTAAAACATA TATATATCTG GTAGGTTTGT GGTTGGATAG GTTTTCTAAA TTCCTAATGT TAAAAACAAT CTTTATGTTA ATATACACTA AATCTATACA CAAAAAAAGT CAGTGAACTT TTCTGACCTT TACTGTGAGT TACCTTTTCC TAAGAGGAAA GCTATAGTAA TAAGTAAAAT TTAATTTTTA GGCAATCCTG ATTTTTAATG AATTTAATTG AGTGTTCTTG TATACTACAT TGAGCAGTTT GCTTCTATAC CGTGTCACAA AATTCATGTA TTTCTTGAGA AGCCCTAAAA GCTCATAAAG GAAAATGCCG TGAACTATGT AGCTCAGGCT TGGTAAGGTG CCATCTAAAT TACAAAACAA ACTAATGCAT AATTTTGCTT AAATTTCATC CCAGTATGAT TGTCTTCCCA ACACCAGCAT ATAGTATAGA TTGTCTGTCT TTTTTATATT TTTTAGTTCT TCCTGTACAT GTTTTTGGCA ATAAAGTTAT AGGAAGAACA AAATTATTTT GTTAGAATTA AAACATGCTT AATATTTAGT CTGTTTGTGG AGGGCAGGTA TTCACGTGGA CTGAGATACA ATGTTGGATA CAGAAAATAA CTTTCATTGT CTTCCTGACA CTGTGCTAAG GACATGCTGT TAAAGCTTCA AAGTGACCAG ATGAGGAAGG AATAATTAAT TATTACTCCT GATTTGTAGA TAACTGAGGT AAGAGTGTTT CAAATTTATG ATAGTCTTTT GGGTATTCAG AAACCTTTCC TTATACTGCA CTGGCCACCA GAGCTTAATT TTCCCAGCAG TTACAGCAAT GGGAGATAGA ACAGTCTCAA TCTTTTGCCA ACCATCAGGT TCCTAGAAAC CAGGTAGGTG TATCCCATAA CAAGGGAGGA GCATACCACA GCCCCTCATT TGATTAATTC ATTTGATCTA TCTATGTTAT TAAGTACCTA CTAGGAATAA GGCATTGTGG AAATACTATA CAAAGATAAA CATTGTTTAG ATGCTTATCT ACTTTCCTTT TCACCAGAAA AACAGAAAAA AAAGAAACAT TTTCTTACAG AGTAAAAATG TTCTACATAA TCACATGAGT AGTTCATCTC AGTGTTTTTT ATTCTTTAAA GTTGAACTAT CCCAGTTTCA TTCTATACCA TTCATTGGAT AACCTTGTTA CAACCCAGTC ATGAAACAGA GCAGTGTGAT CAGTTATCTG CATTTAACAA ATAGACAAAT CAGTTTACAT AAAGGTTATG TATGTCACCC ACGATGAAAA GAATCTGCAT TTGAATATGC CCGTATGAAT GTGGGTTCTG TTTTTGCAAC AGAGATTAAG TGACCATTTT TTCTAATTTT ATGGCTATAT ATTTTCTTCA TAAAAATTGG TCACATCGGA GAAGCAGTGC CACAGGAAAA ATGAAATGCA TGTGAAAGTT TGTATTCTGA TTTTACAAGA TGAGATAGAA ATCAGAATTA AAGAGGAATA CTTAGGAGTT ACTAGGCTAA TCAGTGTACG AATTTGTCAT AGGTAGAGAT TTAAAGGTTA ATATCTTAAA ATAGAAGAAA ATTCTAAATC AATCAATCAG TGAGATATAA ACTAAACAGA CCCACTTCAA AGTTGAAAGA AATTTCTAGG CATAAATTGA GACTAGGAAA TTTATATCAG AATAGAGGGT GCTTGACACA TATATATGCT TAAATTGAAG GACAGCTCAG ATTCATTTTT AGGAGAAGAA AGTAAACTAA TGTGCTCTTA AAGAATAAAA ATTTATTCTA TGGTTTCTGT CTCTGATCAT CACCTTCCAT TCTATAAAAA GCTCAGTTAC TGATTTGCTG GGTCATGGTC AAAATTCTTA CCTATTTATT TCATATCAAC TTTAAAAAAT AAATTACTTG CATTCTATAT ATTACTAATT GGGAAGTAAT ATGCCTCAAA TCAGTTTTAT ACTGGATTAT TCCCTATGCT TTAAACCACT GCTCTCAATA AAACACTTCC TGATTAATGT TTGATTATTA GATATTTTAG TCTTGTTGGG GATATTTTAG TCTTGTTGGG TTAGCCATGC TCTGAAGAAT CTGTGAAAGT ACAGTAAAGT TTTAATAAGC AATAAATGTA ACCTTTTATA TAAATCTCAG TGCTAGGTTA ACTTCTAATA AGCAGACGAA CATGTTACAT AAATTATAAT GTCTGTCTTG TAAAAAAGTT GAGGGGACTA AAAGTTTATG ACTCTGATAT GGAAGTTGTC ATATTAAAAA ACTACATTTT AAAACATCAA ATATTTATAC TATTTGCTTT TCAAATAAAA GCATAGTGCT GTTTGGCATA | |
| PRRC2B | NM_013318.3 | GCAGATCGGG AGCGGTGCCG AGAAAAATTT CCTTACTAGA TGACATTTCA TCGCAATGTC CGATCGTTTG GGGCAAATTA CCAAGGGCAA GGATGGGAAA AGCAAGTACT CGACTCTCAG CCTGTTTGAT AAGTATAAAG GAAAATCAGT AGACGCGATT AGATCCTCAG TTATTCCTAG ACATGGCTTA CAGAGTCTTG GGAAAGTTGC TGCAGCCCGG CGCATGCCAC CGCCTGCAAA CCTGCCAAGC TTGAAGTCTG AAAACAAAGG AAACGACCCC AACATCGTGA TAGTACCCAA GGACGGGACG GGATGGGCAA | 32 |

TABLE 1-continued

Plasma cell dyscrasia Biomarker/Housekeeper Sequence Information

| Gene Name | RefSeq Accession | Sequence | SEQ ID NO: |
|---|---|---|---|
| | | ACAAGCAGGA TCAGCAAGAC CCAAAGAGTT CCAGTGCGAC<br>GGCCTCTCAG CCGCCGGAGT CGCTGCCGCA GCCGGGTTTG<br>CAGAAATCTG TCTCCAATTT GCAGAAACCG ACACAGTCAA<br>TCAGTCAGGA GAATACAAAT TCAGTGCCAG GTGGACCAAA<br>GTCATGGGCA CAGCTGAATG GAAAGCCAGT AGGACACGAA<br>GGTGGTTTAA GGGGCTCAAG CCGACTGTTA TCCTTCTCTC<br>CCGAGGAATT TCCGACGCTG AAAGCAGCTG GAGGGCAGGA<br>CAAGGCTGGC AAAGAAAAGG GCGTCTTAGA TCTGTCGTAT<br>GGGCCAGGAC CAAGCCTCCG CCCTCAGAAT GTGACAAGCT<br>GGAGGGAGGG CGGTGGGCGA CACATAATTT CTGCCACGTC<br>TCTGAGCACC TCCCCAACTG AGCTGGGCAG CAGGAACTCG<br>AGTACGGGAG ATGGAGCCCC CTCCTCGGCA TGTACCAGCG<br>ATTCTAAGGA CCCCTCTCTC CGCCCGGCTC AGCCTGTCCG<br>AAAAGGGGCT TCACAGTTCA TGGGAAATGT ATACCACCCA<br>CCTACATACC ATGACATGCT TCCTGCTTTT ATGTGTTCGC<br>CGAAGTCATC AGAAAACCAG GGTACAGTGG AACGAGGCTC<br>TTTTCCCCTT CCTCAGCTCC GCCTTGAACC TCGAGTTCCT<br>TTTAGACAGT TCCAGATGAA TGACCAAGAC GGAAAAGAAA<br>ACAGGCTGGG ATTGTCTCGC CCACTCCGCC CACTAAGGCA<br>GCTGGTGGAG CGGGCACCAC GGCCCACCAT TATCAATGCG<br>GAAAACCTGA AGGGCCTTGA CGATCTGGAC GCCGATGCCG<br>ATGATGGCTG GGCAGGCCTC CATGAAGAAG TGGACTATTC<br>TGAGAAACTG AAGTTCAGTG ATGATGAAGA GGAGGAAGAA<br>GTTGTGAAGG ACGGCAGGCC AAAGTGGAAC AGTTGGGACC<br>CTAGGAGGCA GCGGCAGTTG TCAATGAGCT CTGCAGACAG<br>TGCGGACGCT AAGCGGACTC GAGAGGAAGG GAAGGACTGG<br>GCTGAAGCAG TGGGTGCGTC CCGTGTGGTC CGAAAGGCGC<br>CAGACCCTCA GCCACCGCCC AGGAAGCTTC ATGGCTGGGC<br>ACCAGGCCCT GACTACCAGA AGTCATCAAT GGGCAGCATG<br>TTCCGGCAAC AGTCCATCGA GGACAAGGAG GACAAGCCCC<br>CACCAAGGCA GAAGTTCATT CAGTCAGAGA TGTCCGAGGC<br>GGTGGAGCGA GCCCGAAAGC GCCGGGAAGA AGAGGAGCGC<br>CGAGCCCGGG AGGAGAGGCT GGCCGCCTGT GCTGCCAAAC<br>TCAAGCAGCT GGACCAGAAG TGTAAGCAGG CACGAAAGGC<br>AGGTGAGGCC CGGAAGCAGG CAGAGAAGGA AGTGCCCTGG<br>TCTCCAAGTG CTGAGAAGGC ATCTCCCCAG GAAAACGGCC<br>CTGCTGTCCA CAAAGGCTCC CCAGAATTCC CTGCCCAAGA<br>GACCCCCACC ACATTCCCAG AAGAGGCACC CACAGTGTCC<br>CCAGCAGTGG CACAGAGCAA CAGCAGTGAG GAAGAGGCCA<br>GAGAGGCTGG GTCCCCTGCA CAGGAGTTCA AGTATCAGAA<br>GTCCCTTCCT CCCCGATTCC AGCGCCAGCA GCAGCAACAA<br>CAGCAGGAGC AGCTGTACAA GATGCAGCAC TGGCAGCCGG<br>TGTACCCCCC GCCGTCCCAC CCCCAGCGCA CCTTTTACCC<br>ACACCACCCC CAGATGTTGG GCTTCGATCC CAGGTGGATG<br>ATGATGCCTT CCTACATGGA CCCACGTATC ACGCCCACTC<br>GGACCCCGGT GGACTTCTAC CCCTCCGCCC TGCATCCCTC<br>AGGACTGATG AAGCCCATGA TGCCCCAGGA GTCCCTCAAT<br>GGGACAGGCT GTCGCTCTGA GGATCAGAAC TGTGTGCCCC<br>CACTCCAAGA AAGAAAAGTG ACCCCCATCG ACTCACCCCC<br>TGTGTGGAGC CCAGAGGGCT ACATGGCACT GCAGAGCAAG<br>GGCTACCCGC TCCCGCACCC GAAGTCGAGT GACACCTTGG<br>CTATGGACAT GCGTGTCAGG AATGAAAGCT CTTTCTCTGC<br>CTCACTCGGA AGGGCAGGGG GCGTAAGTGC TCAGCGCGAT<br>CTCTTTGAGG AGAGAGGGGA GGAGTACTTG AGTGCTTTTG<br>ACAAGAAGGC CCAAGCAGAC TTTGACAGCT GTATCTCTTC<br>TCAAAGAATA GGCCAGGAGC TTTTGTTTCC ACCCCAAGAA<br>AATGTTCAGG ATGCAGGTGC TCCTGGGGGT CACACCCAAA<br>ACCTCAGGTG TTCCCCATTG GAGCCTGACT TTGTCCCAGA<br>TGAGAAAAAG CCAGAGTGTG GCAGTTGGGA TGTTAGCCAC<br>CAGCCAGAGA CCGCTGACAC AGCCCATGGT GTTGAGCGGG<br>AGACACCCCG GGAGGGGACG GCCTTTAACA TCTCCTCCTG<br>GGACAAGAAC GGGAGCCCCA ACAAACAGCC ATCCTCGGAG<br>CCTGAATGGA CTCCCGAGCC CCGGAGCTCC AGCAGCCAGC<br>ACCCGGAGCA GACGGGCAGG ACCCGGAGGT CGGGACCCAT<br>CAAGAAACCA GTCCTGAAAG CCCTCAAGGT GGAAGACAAG<br>GAGAAGGAGC TTGAGAAGAT TAAGCAGGAG CTAGGGGAGG<br>AGAGTACCCG GCTGGCCAAG GAGAAGGAGC AGAGCCCCAC<br>GGCAGAAAAG GATGAGGACG AAGAGAACGA TGCCTCTCTG<br>GCCAACTCCT CCACCACCAC TTTGGAGGAC AAAGGCCCTG<br>GCCATGCCAC TTTTGGCCGC GAGGCCACCA AATTTGAAGA<br>GGAGGAGAAA CCTGACAAGG CCTGGGAAGC CAGACCCCCA<br>CGAGAGTCCA GCGATGTTCC CCCCATGAAG AGAAATAACT<br>GGATCTTTAT TGATGAGGAG CAAGCCTTTG GGGTCAGAGG<br>ACAGGCCCGG GGCCGGGGCC GTGGTTTCAG AGAGTTCACT | |

TABLE 1-continued

Plasma cell dyscrasia Biomarker/Housekeeper Sequence Information

| Gene Name | RefSeq Accession | Sequence | SEQ ID NO: |
|---|---|---|---|
| | | TTTCGTGGTC GGCCTGCTGG CGGAAATGGG AGCGGCCTCT<br>GTGGTGGGGG GGTCCTGGGG GCCCGCAGCA TCTACTGCAG<br>CAGTCAGCGC AGCGGCCGTG GCCGGGGCCT GCGAGAGTTT<br>GCGCGGCCAG AGGACTGCCC CAGAGCCAAG CCCCGACGGA<br>GAGTTGCCAG TGAGACCCAT AGCGAGGGCT CAGAGTATGA<br>AGAACTTCCC AAGCGCCGCC GGCAGAGGGG CTCCGAGAAC<br>GGGAATGAAG GCTCGCTCCT GGAGAGGGAG GAGAGCACCT<br>TGAAGAAGGG CGACTGCAGA GATTCTTGGC GGTCCAACAA<br>GGGGTGCTCT GAGGACCACA GCGGTCTAGA TGCCAAGAGC<br>CGAGGCCCTC GGGCCTTTGG GCGAGCCCTC CCTCCCCGGC<br>TGAGCAATTG CGGGTATGGA CGGAGAACCT TCGTCTCCAA<br>AGAGTCACCC CACTGGCAGA GCAAAAGTCC AGGCAGCTCT<br>TGGCAGGAAT ATGGCCCTTC CGACACATGC GGATCCCGGC<br>GACCTACAGA CAGAGACTAT GTCCCAGATT CCTACAGACA<br>CCCTGACGCA TTTGGTGGCC GGGGCTTTGA GGACAGCCGC<br>GCGGAGGACA AGAGATCCTT CTTCCAAGAT GAACACGTGG<br>CAGATTCTGA AAATGCAGAG AACCGGCCCT TCAGGAGAAG<br>GCGCCCCCCA CGCCAAGATA AGCCCCCTCG ATTCCGGCGC<br>CTCCGGCAAG AGCGGGAGTC CCTGGGCCTG TGGGGACCCG<br>AGGAGGAGCC CCACCTGCTG GCAGGTCAGT GGCCAGGCAG<br>GCCCAAACTG TGTTCTGGGG ACAAGAGTGG CACTGTGGGC<br>CGCAGGTCCC CTGAGCTCTC CTACCAGAAC TCCTCCGATC<br>ACGCCAATGA GGAGTGGGAG ACGGCCTCCG AAAGCAGCGA<br>CTTCAGCGAG CGGCGGGAGC GGCGGGAAGG CCCTGGGTCC<br>GAGCCCGACT CCCAGGTGGA TGGTGGCCTG TCGGGGGCTA<br>GTTTGGGTGA GAAGAAGGAG CTGGCCAAGA GGAGCTTCTC<br>CAGTCAGAGA CCCGTGGTTG ACAGACAGAG CCGAAAGCTG<br>GAGCCGGGAG GGTTTGGGGA GAAGCCCGTT AGGCCAGGTG<br>GTGGTGACAC CTCCCCTCGC TATGAGAGCC AACAGAATGG<br>GACGCCTTTG AAAGTGAAAA GATCCCCAGA CGAGGCCTTG<br>CCTGGAGGTC TTAGTGGCTG CAGCAGTGGG AGTGGCCACT<br>CCCCCTATGC CCTGGAGCGG GCAGCCCATG CCAGTGCTGA<br>CCTTCCCGAA GCCTCCAGTA AAAAGGCAGA GAAGGAGGCC<br>AAGTTGGCTG CTCCGAGGGC AGGTGAACAG GGAGAGGCCA<br>TGAAACAGTT TGACCTGAAC TATGGAAGTG CCATCATTGA<br>AAATTGCGGG TCCAGCCCCG GGGAGGAGAG TGAGGTGGGT<br>TCTATGGTGG GCGAAGGCTT CATCGAAGTC CTGACCAAGA<br>AGCAGCGCCG CCTGCTGGAG GAAGAGAGAA GAAAGAAGGA<br>GCAGGCCGTG CAGGTGCCTG TCAAAGGTCG AGGCCTTTCC<br>TCCCGTATTC CTCCTCGATT TGCAAAAAAG CAGAACAACT<br>TATGTCTGGA GCAAGGTGAC GTGACCGTGC CTGGCAGCAG<br>CCTGGGCACT GAGATCTGGG AGAGCAGCAG CCAGGCTCTC<br>CCTGTGCAGG CCCCAGCCAA CGACTCCTGG AGGAAAGCTG<br>TCACTGCCTT CAGCAGCACC GAGACTGGCT CTGCGGAGCA<br>GGGTTTTAAG AGCAGCCAGG GAGATAGTGG CGTTGACTTG<br>AGTGCCGAGT CTCGGGAGTC GTCTGCGACC TCCTCGCAGC<br>GCAGCTCCCC ATATGGGACT CTGAAGCCAG AGGAGATGAG<br>CGGGCCCGGC CTGGCGGAAC CCAAGGCCGA CAGCCACAAG<br>GAGCAGGCTC CAAAGCCATC TGAGCAGAAG GATTCAGAAC<br>AAGGCTCTGG ACAGAGCAAG GAGCACAGAC CAGGACCCAT<br>CGGCAACGAG CGTTCTCTGA AAAACAGAAA GGGCTCGGAG<br>GGGGCCGAGC GGCTGCAAGG GGCTGTCGTC CCGCCTGTTA<br>ACGGGGTGGA GATTCACGTG GACTCCGTGC TGCCTGTGCC<br>ACCCATTGAA TTTGGAGTCA GTCCAAAAGA CTCCGATTTC<br>AGCTTGCCAC CTGGTTCTGC CTCTGGTCCT ACTGGGAGTC<br>CAGTTGTTAA ACTTCAGGAT GCCTTGGCCA GTAATGCAGG<br>GTTAACACAG AGTATCCCCA TCCTGCGGCG GGACCATCAC<br>ATCCAGAGGG CCATCGGTCT CTCCCCAATG TCCTTCCCCA<br>CCGCCGACCT TACTCTGAAG ATGGAGTCTG CGCGCAAGGC<br>TTGGGAAAAC TCCCCCAGTT TGCCGGAGCA GAGCTCTCCA<br>GGCGGCGCTG GCTCAGGCAT CCAGCCTCCA TCCTCTGTGG<br>GTGCCTCCAG CGGGGTCAAC TACAGCTCCT TCGGTGGAGT<br>GTCCATGCCA CCCATGCCTG TGGCCTCTGT AGCACCTTCT<br>GCTTCTATGC CAGGCAGCCA CCTCCCGCCC CTGTACCTGG<br>ATGGCCATGT GTTTGCAAGT CAGCCCCGGC TGGTTCCTCA<br>AACGATACCT CAGCAGCAGA GTTACCAACA GGCCGCCGCT<br>GCCCAGCAGA TCCCGATCTC CCTTCACACA TCTCTGCAGG<br>CACAAGCTCA GCTTGGACTG AGGGGTGGGC TTCCTGTGTC<br>CCAGTCCCAG GAGATCTTCA GCTCCTTGCA GCCCTTCAGA<br>TCTCAGGTGT ACATGCACCC CAGCCTGTCA CCGCCCAGCA<br>CCATGATCCT CTCTGGGGGC ACAGCCTTGA AGCCTCCATA<br>CTCGGCGTTC CCAGGCATGC AGCCCTTGGA GATGGTGAAG<br>CCGCAGTCTG GCTCACCCTA CCAGCCCATG AGCGGGAACC<br>AAGCCCTGGT CTACGAGGGC CAGCTCAGCC AGGCTGCTGG | |

TABLE 1-continued

Plasma cell dyscrasia Biomarker/Housekeeper Sequence Information

| Gene Name | RefSeq Accession | Sequence | SEQ ID NO: |
|---|---|---|---|
| | | CCTGGGTGCC TCCCAGATGT TGGACTCCCA GCTCCCACAG | |
| | | CTGACCATGC CACTGCCTCG GTACGGCTCC GGGCAGCAGC | |
| | | CACTGATCCT GCCCCAGTCT ATTCAGCTGC CACCTGGGCA | |
| | | GAGCCTCTCC GTTGGGGCCC CCCGAAGGAT TCCTCCGCCC | |
| | | GGGTCCCAGC CGCCAGTCCT GAACACCAGC AGAGAGCCCT | |
| | | CTCAGATGGA GATGAAAGGC TTCCACTTTG CCGACAGTAA | |
| | | ACAGAATGTC CCTTCAGGAG GCCCCGTGCC ATCGCCACAG | |
| | | ACCTACAGGC CTAGCTCTGC TAGCCCCAGT GGGAAGCCCT | |
| | | CTGGATCAGC AGTTAACATG GGCTCTGTGC AGGGACACTA | |
| | | CGTGCAACAG GCAAAACAAC GAGTGGATGA GAAACCCAGC | |
| | | CTGGGAGCCG TGAAGCTGCA GGAGGCCCCC TCGGCTGCCT | |
| | | CCCAGATGAA GCGAACCGGA GCGATCAAGC CTCGGGCTGT | |
| | | CAAAGTGGAG GAGAGTAAGG CCTGACAGTG CCTGGCTGCC | |
| | | ACCTCGCCTC TCCCTACTGA GGACGGTGCC GCCATGCGGC | |
| | | CTCGACACAG CCGACACTCG GGAGCCTCAC CAGATCCACC | |
| | | GTCCAAATGC GTGGCCCAGA CTGAGAGACC TCCCTCCTCT | |
| | | CCACTCCCGA AAGCTCCGTT GTCAACCAGC TTGCACCCGT | |
| | | GGATATATGG CATTGACCCG CTTGCTTTGA TACGAAACAA | |
| | | AAAAGCAGAC GACTCCTTCA TCCCATCTGC TCCTACCGTG | |
| | | ACTGTGGAGT GACGCCTCCT GTGCAGTGCA GATTTGCCCT | |
| | | CCCTGCCTCC TCCCTGTCCT GCCGCGCAGC CAGGGCGCCT | |
| | | TCTCAGCAGT GCTTCCGGCC CAGCCGCCCA TCCCTAGGCA | |
| | | CAGTGATTTG GCAGCAGGGT CATTTTACTT TGAGGCTTTT | |
| | | TGTTTTAAAA TGTAGCCAAG GTTTTTACAA AGGGGAAAGG | |
| | | AAAAGAAAAC AAAAACGCAA GCTCCATGTG TATAGCTGAA | |
| | | CTTTTATATG TTTCTTGCCA GCCCCTCCGC TCCCTTCCAT | |
| | | CTCTAGCCTC TGTCCTGTTT AGTTTGATAC GTCACTGCAG | |
| | | TACCTTAAGA GGTGACTCTT AAGAATGCAT CCCCTCCTGA | |
| | | TTCCTCAGCT GGTTCACCCT TGAGGTTATT TGCAAAAAGA | |
| | | AAAGGAGGTT CTTGAGGGCA CCGATTGCGA GCATTCTGGT | |
| | | GCCTGGCTCC CCGCCTGGGA AGCGATGGGG TGCTCAGAGC | |
| | | AGCAGGCAGG TTGGGGGAGG GGGGGGGTCA TAGTTGGGTT | |
| | | CCAGCTCCTG GCTTGATGAG CCCAGGGCGC TTACAGGCAG | |
| | | CCCATGAAGT TGATGACAGT TTTAGCATGA GAATCACACA | |
| | | GGGTCCCTGT CCTGGGCTCC TCTAAAGCCA GTGGATGTGC | |
| | | TGGGCACCAG AGACAAATCA TGGAGATGGC TGCTGGTGGC | |
| | | TCCCAGGTTG GCCCAGATGG GGTGAGCTGA CATACCACAG | |
| | | GCCCATCCCA GGCCCCGTGG GCTCTGCTTC TGGGGCTCCA | |
| | | TACCCTGCCC TGCAGGGGTG CTGTGTTTTT CACACATTTC | |
| | | TTTCCCTGAA GCCTTCTGTA ACCTGTCATT TTCCTTCCTT | |
| | | CCTCTTCCGG AGCCTGCTGC TTTCTCTGGA CCTGTCTCCA | |
| | | CCTCCCACAC AGCTCATCGT GAACACCACT TGGTGATGGA | |
| | | GGGAGTGGAC CCGTGTGTGG TCCCCAAGTG AGGCCACTGG | |
| | | GAGTTTGTCC TTTTCCTCCT TTGCTTCACT CCCAGCAGCA | |
| | | GACCCAGGTT GTCAGGACAG GAGGGCCTGA GCTAAGCAGT | |
| | | AGGCATCAGT CTCGTTTGTC TTCAGACGGC GGGGGCAGGT | |
| | | CCAGGGTGAG GCTGGGTGGA GGGCTGACCA AGGTCCAAAG | |
| | | GGCCTGCGCA GCCTCCGGGA GGGCAGCTTC TCCAGCCAGA | |
| | | GGCTTGTGTG AGCCATCGTG TGCTGGGCTT GTTTTTAAGT | |
| | | AAGAAACAAG GAAATCACTC CAGATTCTGT CATTCCAAGG | |
| | | AAAGGGAAGG GGACAGTTCA GGTTTCTCAG CTGTTCTTAG | |
| | | GGGTCACTGA GCGTCTACCT CCTCCTCCAG AGGAGGCTGG | |
| | | CTCAGAACAC CTAGAGGAGG GGGCCGGGGA TGCACCCCCC | |
| | | ACCAGAGGCT GCCTTCAGCG TCTCACGGGT GCAGGACAGC | |
| | | GCTCAGGCTT GGGCTCTAAG CTCTGTGTCT AGTGTAGAAC | |
| | | ATGGGGAAGG AGCATCTTAG GAACTGCTGA AGTAACTTCT | |
| | | TACTGCTCTC ACAATTCTAA GGAAGCGGGA GAACGGCCTC | |
| | | CTACCAACAG CGCCCACCCC AGAGCTGCCT GGGAAAGGGC | |
| | | AGTTTTACTG AAAGGTGCTT TACTGTTCAC CTGCATCTTT | |
| | | CAGCAGCTCC CCTCCTGCCC TCACCTGGTC TTTTCCCTCT | |
| | | TTATCCCAAG CCTTTATGCT TGAGTCCCTT CCCCAGGGGC | |
| | | TGCCCACCCG ACAGTTCCAG GCATTCCCTA CCTGAGCTTC | |
| | | TTGTCTGCTT TTCCTTCTCC CACTGCAAGC GGCTGCTTGT | |
| | | GGGGCCTGGG ATGAGCCCTC TCTGTCCCCA CCGGCCCTCC | |
| | | TTGCCAAGCC ATTCCTGGGT GAGTTCAGGC CTGCGGGAGC | |
| | | CACACATTCA TCTCCACCTG GACACTTGAG CCGCATGGCC | |
| | | AGACCCCTCC CACCTGATGC GGTGGTGCGT GTGATTTGTC | |
| | | AAAAGAAAGC CTTCTGGATG CTGTTAAGAT GTACCCTTCA | |
| | | GGTGAACCTG GTATCAGACC CACAGTACTT GCTGTTTGAG | |
| | | AAAAAATAAA AACAAAAAGG TCACCTGTTC TCCAGCCCTT | |
| | | TTCTCTTACC TGGTATTTCC TTCCTTTCTC CTCCCCCACC | |
| | | CCAAATAAAA AAACAAAAAA CACTAGAATT TATTTATATG | |
| | | TATTGATGTT GTAGGTCTAG GTGAAAAAAA AAGAAGTAAA | |
| | | TGTTTCACTG CTCTATTTAT ATATAATGTC TGAATTAATT | |

TABLE 1-continued

| Gene Name | RefSeq Accession | Sequence | SEQ ID NO: |
|---|---|---|---|
| | | CTGTGCAGGA AAGGCCAGGA AATTGCATGT GAAGTTCGGT<br>GCAGTCACCA CCTGTGTGTG ACCTGAGCTG CAGTCTCTTC<br>GCTGAGATGC AGGTTTTAAA TGAGACTTGG GGGGCTGAGG<br>GCAGGCCTCA GGCCTCCCAG CGCCCCAACC CCTCCTTGGT<br>CTAATGAAAT GCAGTTCTTA GTGCAGAGAT GTTTTAAGGT<br>GCAATATATC TCTTCCTTTC CCGTGGTTTT AGAGCCAAGC<br>TCAAGGTAGT AGGACGTAGG GTCTTATTTT GTTTTCAAAC<br>CCCCATCCTC AGAGCGCAGA TACATGCAGA GGCTTCTGCC<br>AGGATACCAC GGGGCCTTAG TGGGAACAGG TGGAGACCAG<br>CACTTCCCTT TCCTGCTGCT GAGGTAGGGA TTGGGGGGTC<br>AGAACCCACT CACTTTTGCC TGTTAAAGTT GCCCTCCTGA<br>CGCTGGCAGC TCTGCCTTGG TCACTGGGGA TGCGGCTCGT<br>TGCTCAGCCA CCAGTGGCCT TGCGGTATTG TCCACCATCC<br>ACTAGAGTGG GATGAAGTCC AGAGTGTGGG TATACATCTC<br>AGATGCCCAT CTACCCACTG GGGACTTCAA TGCCAGCTGC<br>ATTTGGTTTG GTTTTCTTAA CTGTTGGCTT CTCCCCACAG<br>CGTTTTTTGT TTTTTTTTAA ACATTCATAT TGTTTTCAAA<br>CTTGGAATTC ATAGACACTC TGGCTCTAGG TTCCTTAAGG<br>GGGAAAACAA AAGATGACTT TATTTCACAT TCAAGAAAAT<br>CAGTTCAGTT CCAAAGCTGT GGTCCTTCCA GCCACTTCTA<br>GGGACACTGG GGAACCTTGT TAAACGTTGA CATCAGTGCT<br>CTCCAGCCGT GCTGTCACCC TCCTATCTTC TGGATCTGCC<br>TTCGCGATGG TCAGTGACAG CTTCTGGAAG CTGAGCACAC<br>ACAGGTGCAC AGCCATGCTG TGGTCTGGCC TGCTACGGCA<br>GCATGGCAGC TCTGGTGGAG CCTTCTCCCT TGCCATTTGG<br>TTCCCCTGTG CCAAGTAGCT GCAGGCTGCC CCTCAAATCT<br>TCATTTGTCC CTTTTCACTT CCTGCAGAAC AAGCCTGGGT<br>TAGAGGGTCT GCTGGAAATG GCCTTTGAAG ACCAAGGATA<br>CCAGGATGTG TGCACTCTGT CGTGTTCTGT GATGAATGGG<br>AAACGTAGGC TTCCAGAAAG CCAGCTCTCT TCTGAAATGT<br>GACGGACCTA AGCAGGAAGT CATCCAGGAC AGGAGTGGCT<br>CAGTGTTGGG GATGGACGCT GTCGCCCAGC CATGCTCCAC<br>CAGGGCCACC AATGTGTAGT TGGCTGGTGG TCTTCGGGCA<br>TGTGAGACCT GCTCTTCACT GTTTCCACCC CACTTGGTGG<br>CCTCCAGGAT GGTAGTGGCA CCCTCAGAGC CCCATCTTCA<br>GCATGTTCTG AAGCCTCAGA GTGGAAATTC CTGCTAAGGC<br>TCTGTGTGGA CGCCTTTCTC CCGTGATCTA AAGGGGACAC<br>TGTACTCAAG CTTTTGACCT CATGCCTTGT GTAGTAAAAA<br>AGGATTTGGG GGTTTTGTTT GGTTCCTGAG AGGGTTGTGT<br>TTTGTTTTTG TTTCCTTTTG TTTATGTTTT GGCCTTTCCT<br>CTTTGTCTTT CCATGTAGAC CAGATATTTG AAAGGGCAGA<br>CGATGGCTAG AGGTGTAATG TGCAGCTTGT TTATACGGTA<br>TTTTGGGAAA CTTACCTTGG ATGGGAAATC GAATCGTGGA<br>TTCACCAGGC CGGTGCTGGC ACACTCACCC TCGCCCTTTC<br>CCTCCGGTTC AGTACCTATT GTTTCTCCTT TCAAATATGT<br>GATTGTACTA GCTCTTTCCA TATGAAAGAA TTCTCCTTAT<br>TTAAATAAAA AAAGTTTAAA AA | |
| DOPEY2 | NM_005128.3 | TCCCACAGTG CCTGGCCCAG AAGCCTTGCT AAATATTTGA<br>ACAGGATTGC CCAATACTTT TCTGCTGTGA GAATGTAAGA<br>TGGATCCAGA AGAGCAGGAG CTCTTAAATG ATTACAGATA<br>CAGAAGCTAC TCTTCAGTGA TTGAAAAGGC TTTGAGAAAT<br>TTTGAGTCCT CGAGTGAATG GGCGGATCTC ATATCTTCAC<br>TTGGCAAACT CAACAAGGCT CTTCAGAGTA ACCTGAGGTA<br>CTCCTTGTTG CCAAGACGGC TCCTCATCAG CAAAAGATTA<br>GCTCAGTGTT TGCACCCTGC CCTGCCCAGT GGTGTCCACT<br>TAAAAGCTCT GGAAACCTAC GAGATTATCT TTAAAATCGT<br>GGGGACCAAA TGGCTGGCCA AGGACTTGTT TCTGTACAGC<br>TGCGGGTTAT TTCCTCTCCT GGCACACGCG GCGGTGTCGG<br>TGAGGCCGGT GCTGCTCACC CTGTACGAGA AGTACTTCCT<br>CCCACTGCAG AAGCTGCTCC TGCCCAGTCT GCAGGCCTTC<br>ATCGTGGGCC TGCTGCCCGG CCTTGAAGAG GGCTCCGAGA<br>TCTCCGACAG AACGGATGCT CTGCTCCTGA GACTGTCGCT<br>GGTGGTTGGC AAAGAGGTGT TTTACACCGC CCTCTGGGGG<br>AGCGTCCTGG CCAGCCCGTC CATCCGCCTC CCTGCCTCAG<br>TCTTCGTGGT GGGCCACATC AACAGGGATG CCCCCGGCCG<br>GGAGCAGAAG TACATGCTGG GGACCAATCA CCAACTCACG<br>GTGAAGTCTT TGCGTGCCTC CCTGTTGGAC TCAAATGTTC<br>TTGTGCAAAG AAATAATCTG GAAATCGTTC TGTTTTTCTT<br>CCCATTTTAT ACCTGTCTGG ATTCCAATGA GAGAGCCATC<br>CCCCTCCTCA GATCTGACAT CGTGCGCATT CTCTCAGCCG<br>CCACCCAGAC CCTACTGAGA AGGGACATGT CCCTGAACAG<br>AAGACTGTAT GCATGGTTAC TAGGCTCAGA CATAAAAGGA<br>AATACCGTTG TGCCAGAATC TGAAATCTCA AATTCTTATG | 33 |

TABLE 1-continued

Plasma cell dyscrasia Biomarker/Housekeeper Sequence Information

| Gene Name | RefSeq Accession | Sequence | SEQ ID NO: |
|---|---|---|---|
| | | AAGACCAGTC GTCTTATTTT TTTGAAAAAT ACTCCAAGGA<br>TCTTTTAGTT GAGGGTTTGG CTGAGATATT GCATCAGAAG<br>TTCATAGATG CTGACGTGGA GGAACGCCAT CATGCATACC<br>TGAAGCCTTT TCGCGTCCTC ATCAGTCTGC TTGACAAGCC<br>AGAAATAGGG CCTCAAGTGG TTGGGAATTT GTTTCTCGAA<br>GTCATCAGGG CCTTTTATTC TTACTGCAGA GATGCCCTTG<br>GCTCTGATCT TAAACTTAGC TACACCCAGA GTGGAAATTC<br>GCTGATAAGT GCAATCAAGG AAAACAGAAA TGCCTCTGAG<br>ATTGTCAAAA CGGTAAATTT GCTGATAACT TCTCTAAGCA<br>CAGACTTTCT CTGGGATTAT ATGACAAGGT GTTTTGAGGA<br>ATGCTTTAGA CCAGTGAAGC AGCGTTACAG CGTGAGGAAC<br>AGCGTCAGCC CTCCCCCCAC GGTCTCGGAG CTCTGCGCCC<br>TCCTGGTCTT CCTGCTGGAT GTCATTCCTT TGGAACTTTA<br>CTCTGAGGTG CAAACCCAGT ATCTCCCTCA GGTGCTCGGC<br>TGCCTGGTGC AGCCTCTTGC TGAGGACATG GAGGCCTTAA<br>GTTTACCTGA ACTCACGCAT GCCTTGAAGA CGTGTTTCAA<br>GGTGCTCAGC AAAGTCCAGA TGCCTCCTTC CTACCTCGAC<br>ACGGAGTCCA CCAGCGGAAC CTCGAGTCCA GTAAAAGGTG<br>AAAACGGCAA AATAATTTTG GAAACAAAGG CAGTGATTCC<br>CGGTGACGAA GATGCTTCGT TTCCCCCTCT GAAGTCTGAG<br>GACAGTGGGA TCGGGCTCAG TGCCTCGTCA CCGGAGCTCT<br>CTGAGCACTT GAGGGTTCCT CGAGTTTCTC TGGAAAGGGA<br>CGACGTTTGG AAGAAGGGCG GGAGCATGCA GAGGACGTTT<br>CTTTGCATCC AAGAGCTAAT CGCCAACTTT GCCAGCAAGA<br>ACATTTTTGG AGTACAGCTG ACAGCGTCAG GAGAAGAAAG<br>CAAGTCCGAG GAGCCTGCAG GGAAGAGGGA CAGGGATGGG<br>ACGCAGAGCC TGGCAGCCAA TGATTCCAGC AGGAAGAACT<br>CTTGGGAGCC CAAGCCCATC ACTGTGCCTC AGTTCAAGCA<br>GATGCTGTCA GACTTGTTCA CAGCACGAGG GTCTCCATTC<br>AAGACAAAAA GTTCAGAGTC ACCATCGTCT TCGCCCAGCA<br>GCCCTGCCAG GAAAAACGGG GGAGAATGGG ATGTTGAGAA<br>GGTGGTCATT GACCTGGGGG GTTCCAGGGA GGAACGCAGG<br>GAGGCCTTTG CCGCCGCCTG CCACCTGCTG CTGGATTGTG<br>CCACTTTCCC TGTCTACCTG TCCGAGGAAG AGACCGAGCA<br>GCTCTGTGCA ACGCTCTTCC AGCTGCCAGG AGCCGGTGAT<br>TCCAGTTTTC CATCTTGGCT GAAGTCCCTC ATGACTATTT<br>GCTGCTGTGT GACTGACTGC TACCTCCAGA ACGTGGCCAT<br>TTCCACTCTG CTGGAAGTGA TAAACCATTC CCAGTCCCTG<br>GCGCTTGTCA TTGAAGACAA GATGAAACGC TATAAGAGCT<br>CTGGACACAA CCCTTTTTTT GGCAAGCTGC AGATGGTGAC<br>GGTTCCTCCC ATTGCTCCAG GGATATTGAA AGTCATTGCA<br>GAGAAAACAG ATTTCTATCA GAGGGTGGCT CGTGTGCTTT<br>GGAATCAGCT GAACAAAGAG ACCCGGGAGC ATCACGTCAC<br>CTGCGTAGAA TTGTTCTACC GGCTGCACTG CCTGGCCCCT<br>ACGGCCAACA TCTGCGAGGA CATCATCTGC CATGCCCTCC<br>TGGACCCTGA CAAGGGAACA AGGCTGGAAG CTCTGTTTAG<br>ATTTTCCGTG ATCTGGCATC TGACAAGAGA GATCCAAGGC<br>AGTCGAGTAA CATCTCACAA TCGCTCCTTT GATAGGTCCT<br>TGTTTGTCGT GCTGGACAGC CTGGCCTGCA CGGATGGTGC<br>CATCGGTGCG GCAGCCCAGG GCTGGCTGGT GCGTGCGCTC<br>TCCCTCGGGG ACGTGGCTCG CATCCTCGAA CCCGTGCTCC<br>TGCTGCTGCT GCAGCCAAAA ACCCAGAGAA CCTCCATCCA<br>CTGCCTCAAG CAGGAGAACT CGGCCGATGA CTTGCACCGT<br>TGGTTTAACA GGAAGAAAAC CTCTTTCAGA GAGGCATGCG<br>CAGTGCCCGA GCCTCAGGAG AGCGGCTCTG AAGAGCACCT<br>GCCTCTGAGC CAGTTCACCA CAGTGGACCG TGAAGCCATT<br>TGGGCCGAAG TGGAGAAGGA GCCCGAGAAG TACCCGCTGC<br>GAGGCGAGCT GAGCGAGGAA GAGCTGCCCT ACTACGTGGA<br>GCTTCCAGAC AGGACGGCCC ACGGCGCCCC GGACAGCAGC<br>GAGCACACCG AGTCTGCAGA TACAAGCTCC TGCCACACGG<br>ACAGCGAGAA CACGTCCTCC TTCTCCTCCC CTTCCCACGA<br>CCTGCAGGAG CTGAGCAACG AAGAGAACTG CTGTGCACCC<br>ATCCCCATGG GGGGCAGGGC GTACCCCAAG CGCTCGGCCC<br>TGCTGGCGGC CTTCCAGTCA GAAAGCTTCA AGGCTGGGGC<br>CAAGTTAAGC CTGGTGCGGG TGGACTCGGA CAAGACGCAG<br>GCTTCTGAGT CGTTCTCCAG CGACGAGGAG GCGGACTTGG<br>AGCTCCAGGC CCTCACCACA TCCAGGCTGC TAAAGCAGCA<br>GCGGGAAAGG CAGGAGGCCG TCGAGGCCTT GTTCAAGCAC<br>ATCCTGCTCT ACCTGCAGCC CTACGACTCT CGGCGGGTCC<br>TCTATGCCTT CTCGGTGCTG GAGGCTGTGC TCAAAACCAA<br>CCCTAAGGAA TTCATCGAGG CTGTGTCCAG GACTAGCATG<br>GATACCAGCT CCACCGCGCA CCTCAACCTC ATCTCCAACC<br>TCCTCGCTCG CCACCAGGAG GCCCTCATTG GCCAGAGTTT<br>CTACGGAAAG CTCCAGACCC AGGTCCCCAA CGTGTGCCCC | |

TABLE 1-continued

Plasma cell dyscrasia Biomarker/Housekeeper Sequence Information

| Gene Name | RefSeq Accession | Sequence | SEQ ID NO: |
|---|---|---|---|
| | | CACTCTCTGC TCCTGGAGCT GCTCACCTAC CTCTGCCTGA | |
| | | GCTTCCTGCG CTCCTACTAC CCTTGCTATT TGAAGGTCTC | |
| | | GCACCGAGAC ATTCTCGGCA ACCGGGACGT GCAGGTCAAA | |
| | | AGTGTCGAGG TTTTGATCAG GATAATGATG CAGCTGGTCT | |
| | | CAGTGGCCAA GTCTTCGGAA GGGAAGAACG TGGAGTTCAT | |
| | | CCACAGCTTG CTGCAGAGGT GCAAAGTTCA GGAGTTTGTC | |
| | | CTGCTCTCCC TGTCGGCGTC CATGTACACG AGCCAGAAGC | |
| | | GCTACGGGCT GGCCACCGCC CACCACGGCA GGGCCCTGCC | |
| | | AGAGGACAGC CTCTTTGAGG AGAGTCTCAT TAACTTGGGT | |
| | | CAGGACCAGA TCTGGAGTGA GCACCCGCTG CAGATTGAGC | |
| | | TGCTGAAGCT GCTGCAGGTG CTGATTGTCT TGGAACACCA | |
| | | CCTGGGTCGG GCCCATGAGG AGGCGGAAAA CCAGCCCGAC | |
| | | CTGTCCCGGG AGTGGCAGAG AGCCCTGAAC TTCCAGCAGG | |
| | | CCATCAGCGC CCTGCAGTAC GTGCAGCCCC ACCCCCTCAC | |
| | | CTCCCAGGGT CTTCTGGTCT CTGCGGTGGT GAGGGGTCTG | |
| | | CAGCCCGCCT ACGGTTACGG CATGCATCCG GCCTGGGTGA | |
| | | GCTTGGTCAC GCATTCCTTG CCCTACTTCG GAAAGTCCCT | |
| | | GGGCTGGACG GTGACACCCT TTGTTGTCCA GATTTGCAAA | |
| | | AACTTGGATG ACTTGGTCAA GCAGTATGAA AGCGAATCTG | |
| | | TGAAGCTCTC TGTCAGCACA ACCTCCAAGA GGGAAAACAT | |
| | | TTCTCCAGAT TATCCACTCA CCCTTCTAGA AGGTCTAACG | |
| | | ACCATTAGTC ATTTTTGTCT TTTGGAACAA GCCAACCAAA | |
| | | ACAAAAAGAC CATGGCTGCA GGTGATCCTG CCAACTTGAG | |
| | | GAATGCCAGA AATGCCATTT TGGAAGAGCT GCCTCGAACT | |
| | | GTTAACACCA TGGCCCTTCT CTGGAATGTT CTCAGAAAGG | |
| | | AGGAGACTCA AAAGAGACCT GTCGATCTCC TAGGGGCCAC | |
| | | GAAGGGATCC TCTTCCGTTT ACTTTAAAAC CACCAAAACC | |
| | | ATAAGACAAA AAATTTTAGA CTTCTTAAAC CCCTTGACGG | |
| | | CCCATCTTGG GGTTCAGTTG ACAGCGGCTG TTGCGGCAGT | |
| | | GTGGAGCAGA AAGAAAGCCC AGCGTCACAG TAAGATGAAG | |
| | | ATTATCCCAA CGGCAAGTGC ATCCCAGCTA ACCCTTGTCG | |
| | | ACTTGGTGTG TGCACTCAGC ACCCTGCAGA CTGACACGCT | |
| | | GCTGCACCTG GTGAAGGAGG TGGTGAAGAG GCCACCCCAA | |
| | | GTCAAAGGGG GTGATGAGAA ATCGCCCCTA GTGGACATTC | |
| | | CTGTGTTGCA GTTTTGCTAT GCTTTTCTCC AAAGGCTCCC | |
| | | AGTACCAGCC TTGCAAGAGA ACTTTTCTTC ACTGTTGGGA | |
| | | GTATTGAAAG AGTCTGTACA GTTGAATCTA GCCCCACCTG | |
| | | GGTATTTTCT GCTTCTCAGC ATGCTGAATG ACTTTGTAAC | |
| | | AAGAACTCCC AACCTGGAAA ACAAGAAGGA CCAAAAAGAC | |
| | | CTGCAGGAAA TCACTCAGAA AATCCTAGAA GCTGTGGGGA | |
| | | ACATTGCCGG CTCTTCCTTG GAGCAAACCA GCTGGCTAAG | |
| | | CAGAAACCTG GAAGTGAAGG CCCAACCTCA GGCCTCTCTA | |
| | | GAAGAATCTG ATGCTGAGGA GGACCTGTAT GATGCTGCTG | |
| | | CAGCTTCAGC AATGGTGTCT TCATCCGCCC CGTCGGTGTA | |
| | | CAGCGTGCAA GCCCTCTCTC TCCTGGCAGA GGTACTGGCT | |
| | | TCCCTCCTGG ACATGGTTTA TCGAAGTGAT GAGAAGGAGA | |
| | | AAGCTGTGCC GTTAATCTCC CGTCTGCTTT ACTATGTTTT | |
| | | TCCATACTTA CGCAACCACA GTGCCTACAA TGCTCCCAGC | |
| | | TTCCGGGCTG GCGCTCAGCT GCTGAGCTCC CTGAGTGGCT | |
| | | ATGCCTACAC AAAGCGAGCC TGGAGGAAGG AGGTCCTGGA | |
| | | GCTGTTTCTC GACCCCGCTT TCTTTCAGAT GGATACTTCC | |
| | | TGTGTTCATT GGAAGTCCAT TATTGACCAT CTTTTGACTC | |
| | | ATGAGAAAAC AATGTTTAAG GATTTAATGA ACATGCAGAG | |
| | | CAGTTCTTTG AAACTATTCT CAAGTTTTGA ACAGAAAGCC | |
| | | ATGCTGTTAA AGCGCCAGGC TTTTGCTGTC TTCAGTGGAG | |
| | | AACTTGATCA ATACCACCTT TACCTTCCAC TGATACAAGA | |
| | | ACGCCTGACA GACAATCTCA GAGTTGGACA GACATCCATA | |
| | | GTTGCTGCTC AGATGTTTCT TTTTTTCAGA GTTTTGCTGC | |
| | | TAAGAATATC TCCTCAACAT TTGACTTCAT TGTGGCCAAT | |
| | | AATGGTCTCT GAATTGATTC AGACATTCAC ACAGCTTGAA | |
| | | GAAGATCTAA AAGATGAAGA TGAGTCATTG AGAAGCACCA | |
| | | ACAAAGTAAA CAGAACGAAA GTTTCAGTCC CGGATGCAAA | |
| | | TGGACCCTCA GTGGGGGAGA TACCCCAGAG TGAACTCATC | |
| | | TTGTATTTAT CAGCTTGCAA ATTCTTGGAC ACAGCGCTTT | |
| | | CTTTTCCACC TGACAAGATG CCATTATTTC AAATTTATAG | |
| | | GTGGGCATTT ATTCCAGAAG TGGACACAGA GGGCCCTGCC | |
| | | TTCCTGTCGG ATGTAGAGGA GAATCACCAA GAATGCAAAC | |
| | | CCCACACTGT CAGGATTCTA GAACTTCTAA AATTAAAGTT | |
| | | TGGGGAAATC AGTAGCTCTG ATGAGATCAC CATGAAGAGT | |
| | | GAATTCCCGC TTCTGCGCCA ACATTCTGTT TCCAGCATCA | |
| | | GGCAGTTGAT GCCATTCTTC ATGACTCTAA ATGGTGCATT | |
| | | TAAGACCCAG AGACAGCTGC CTGCTGATAG CCCAGGAACT | |
| | | CCATTCTTGG ACTTTCCTGT CACAGATAGC CCAAGGATCT | |
| | | TAAAACAACT GGAAGAATGC ATCGAATATG ATTTTCTGGA | |

TABLE 1-continued

Plasma cell dyscrasia Biomarker/Housekeeper Sequence Information

| Gene Name | RefSeq Accession | Sequence | SEQ ID NO: |
|---|---|---|---|
| | | ACATCCAGAA TGTTAACCAT GTGAGAGAGA ATATGTTTAA | |
| | | TCCATGTATT GGTACTTTAC TGAAAACCAG GTTATATTCT | |
| | | AAAGAAGAAA GAAGGCAGGA TAGTGCTTTT GAACAAGCCT | |
| | | ATTTCCATTT TGAAAGTAGA TTTCAGGCTA GGTGCGGTGG | |
| | | CTCACACCTG TAATCTCAGC ACTTTGGGAG GCCAAGGCAG | |
| | | GCAGATCACT TGAGGTCAGG AGTTCGAGAC CAGCCTGACC | |
| | | AACATGGTGA GACCCTGTCT CTACTAAAAA TACAAAAATT | |
| | | AGCTGGGTGT GGTGGCGGCG CCTGTAATCC CAGCTACTTG | |
| | | GGAGGCTAAG GCATGAGAAT TGCTTGAACC CAGGAGGTGG | |
| | | AGGCTGCAGT GAGCCGAGAT CACGACACTG CACTCCAGCT | |
| | | GTGTGACAGA ATGAGACCAT CTCCAAAAAA AAAAAAAAGT | |
| | | AGATTTCAGA TAATTTACTG TTCAGCAACA GGACACACCT | |
| | | CCCTAAATGC CTTGTAATAT ATTTGAATCT GATTCTGCAT | |
| | | TTCTTCCTCA ATTTATGTAA TGAAAATAAA ATTAATATAT | |
| | | CATCTAACAG TAGCACAAAA TTTGTAATAT GAAGTAAAGT | |
| | | ATGAAGATAA TGAAGAAGTT GTTTTCTTTG TTGAAGCAGT | |
| | | TATATGGGTC TTTCTCAGTA TATTTCTCTT TTCTCTAAAA | |
| | | GTTTAAACTT ATTAAAAGAA TGTTATTTTT AACCTTTCAA | |
| | | AAAAAAAAA | |
| NDUFB11 | NM_019056.6 | GCTCTGGCCG GCCCCGGCGA TTGGTCACCG CCCGCTAGGG | 34 |
| | | GACAGCCCTG GCCTCCTCTG ATTGGCAAGC GCTGGCCACC | |
| | | TCCCCACACC CCTTGCGAAC GCTCCCCTAG TGGAGAAAAG | |
| | | GAGTAGCTAT TAGCCAATTC GGCAGGGCCC GCTTTTTAGA | |
| | | AGCTTGATTT CCTTTGAAGA TGAAAGACTA GCGGAAGCTC | |
| | | TGCCTCTTTC CCCAGTGGGC GAGGGAACTC GGGGCGATTG | |
| | | GCTGGGAACT GTATCCACCC AAATGTCACC GATTTCTTCC | |
| | | TATGCAGGAA ATGAGCAGAC CCATCAATAA GAAATTTCTC | |
| | | AGCCTGGCCG AAAATGGTTG GCCCCACGAA GCCACGACAA | |
| | | CTGGAGGCAA AGAGGGTTGC TCAACGCCCC GCCTCATTGG | |
| | | AAAACCAAAT CAGATCTGGG ACCTATATAG CGTGGCGGAG | |
| | | GCGGGGCGAT GATTGTCGCG CTCGCACCCA CTGCAGCTGC | |
| | | GCACAGTCGC ATTTCTTTCC CCGCCCCTGA GACCCTGCAG | |
| | | CACCATCTGT CATGGCGGCT GGGCTGTTTG GTTTGAGCGC | |
| | | TCGCCGTCTT TTGGCGGCAG CGGCGACGCG AGGGCTCCCG | |
| | | GCCGCCCGCG TCCGCTGGGA ATCTAGCTTC TCCAGGACTG | |
| | | TGGTCGCCCC GTCCGCTGTG GCGGGAAAGC GGCCCCCAGA | |
| | | ACCGACCACA CCGTGGCAAG AGGACCCAGA ACCCGAGGAC | |
| | | GAAAACTTGT ATGAGAAGAA CCCAGACTCC CATGGTTATG | |
| | | ACAAGGACCC CGTTTTGGAC GTCTGGAACA TGCGACTTGT | |
| | | CTTCTTCTTT GGCGTCTCCA TCATCCTGGT CCTTGGCAGC | |
| | | ACCTTTGTGG CCTATCTGCC TGACTACAGG TGCACAGGGT | |
| | | GTCCAAGAGC GTGGGATGGG ATGAAAGAGT GGTCCCGCCG | |
| | | CGAAGCTGAG AGGCTTGTGA AATACCGAGA GGCCAATGGC | |
| | | CTTCCCATCA TGGAATCCAA CTGCTTCGAC CCCAGCAAGA | |
| | | TCCAGCTGCC AGAGGATGAG TGACCAGTTG CTAAGTGGGG | |
| | | CTCAAGAAGC ACCGCCTTCC CCACCCCCTG CCTGCCATTC | |
| | | TGACCTCTTC TCAGAGCACC TAATTAAAGG GGCTGAAAGT | |
| | | CTGAAAAAAA AAAAAAAA | |
| ND4 | NC_012920.1 | ATGCTAAAACTAATCGTCCCAACAATTATATTACTACCACTGAC | 35 |
| | | ATGACTTTCCAAAAAACACATAATTTGAATCAACACAACCACCC | |
| | | ACAGCCTAATTATTAGCATCATCCCTCTACTATTTTTTAACCAAA | |
| | | TCAACAACAACCTATTTAGCTGTTCCCCAACCTTTTCCTCCGACC | |
| | | CCCTAACAACCCCCCTCCTAATACTAACTACCTGACTCCTACCC | |
| | | CTCACAATCATGGCAAGCCAACGCCACTTATCCAGTGAACCACT | |
| | | ATCACGAAAAAAACTCTACCTCTCTATACTAATCTCCCTACAAA | |
| | | TCTCCTTAATTATAACATTCACAGCCACAGAACTAATCATATTT | |
| | | TATATCTTCTTCGAAACCACACTTATCCCCACCTTGGCTATCATC | |
| | | ACCCGATGAGGCAACCAGCCAGAACGCCTGAACGCAGGCACAT | |
| | | ACTTCCTATTCTACACCCTAGTAGGCTCCCTTCCCCTACTCATCG | |
| | | CACTAATTTACACTCACAACACCCTAGGCTCACTAAACATTCTA | |
| | | CTACTCACTCTCACTGCCCAAGAACTATCAAACTCCTGAGCCAA | |
| | | CAACTTAATATGACTAGCTTACACAATAGCTTTTATAGTAAAGA | |
| | | TACCTCTTTACGGACTCCACTTATGACTCCCTAAAGCCCATGTC | |
| | | GAAGCCCCCATCGCTGGGTCAATAGTACTTGCCGCAGTACTCTT | |
| | | AAAACTAGGCGGCTATGGTATAATACGCCTCACACTCATTCTCA | |
| | | ACCCCCTGACAAAACACATAGCCTACCCCTTCCTTGTACTATCC | |
| | | CTATGAGGCATAATTATAACAAGCTCCATCTGCCTACGACAAAC | |
| | | AGACCTAAAATCGCTCATTGCATACTCTTCAATCAGCCACATAG | |
| | | CCCTCGTAGTAACAGCCATTCTCATCCAAACCCCCTGAAGCTTC | |
| | | ACCGGCGCAGTCATTCTCATAATCGCCCACGGGCTTACATCCTC | |
| | | ATTACTATTCTGCCTAGCAAACTCAAACTACGAACGCACTCACA | |
| | | GTCGCATCATAATCCTCTCTCAAGGACTTCAAACTTACTCCCAC | |

TABLE 1-continued

Plasma cell dyscrasia Biomarker/Housekeeper Sequence Information

| Gene Name | RefSeq Accession | Sequence | SEQ ID NO: |
|---|---|---|---|
| | | TAATAGCTTTTTGATGACTTCTAGCAAGCCTCGCTAACCTCGCC TTACCCCCCACTATTAACCTACTGGGAGAACTCTCTGTGCTAGT AACCACGTTCTCCTGATCAAATATCACTCTCCTACTTACAGGAC TCAACATACTAGTCACAGCCCTATACTCCCTCTACATATTTACC ACAACACAATGGGGCTCACTCACCCACCACATTAACAACATAA AACCCTCATTCACACGAGAAAACACCCTCATGTTCATACACCTA TCCCCCATTCTCCTCCTATCCCTCAACCCCGACATCATTACCGGG TTTTCCTCTT | |
| MORF4L1 | NM_001265603.1 | CGGCGTGCCC TGGGGCGGCG CGGGCGCAGG GGCGCGTGCG CGGCGGGCTG TCGTTGGCTG GAGCAGCGGC TGCGCGGGTC GCGGTGCTGT GAGGTCTGCG GGCGCTGGCA AATCCGGCCC AGGATGTAGA GCTGGCAGTG CCTGACGGCG CGTCTGACGC GGAGTTGGGT GGGGTAGAGA GTAGGGGGCG GTAGTCGGGG GTGGTGGGAG AAGGAGGAGG CGGCGAATCA CTTATAAATG GCGCCGAAGC AGGACCCGAA GCCTAAATTC CAGGAGGTTG GGATGAATGG GTTCCGGAGA GCAGAGTACT CAAATACGTG GACACCAATT TGCAGAAACA GCGAGAACTT CAAAAAGCCA ATCAGGAGCA GTATGCAGAG GGGAAGATGA GAGGGGCTGC CCCAGGAAAG AAGACATCTG GTCTGCAACA GAAAAATGTT GAAGTGAAAA CGAAAAAGAA CAAACAGAAA ACACCTGGAA ATGGAGATGG TGGCAGTACC AGTGAGACCC CTCAGCCTCC TCGGAAGAAA AGGGCCCGGG TAGATCCTAC TGTTGAAAAT GAGGAAACAT TCATGAACAG AGTTGAAGTT AAAGTAAAGA TTCCTGAAGA GCTAAAACCG TGGCTTGTTG ATGACTGGGA CTTAATTACC AGGCAAAAAC AGCTCTTTTA TCTTCCTGCC AAGAAGAATG TGGATTCCAT TCTTGAGGAT TATGCAAATT ACAAGAAATC TCGTGGAAAC ACAGATAATA AGGAGTATGC GGTTAATGAA GTTGTGGCAG GGATAAAAGA ATACTTCAAC GTAATGTTGG GTACCCAGCT ACTCTATAAA TTTGAGAGAC CACAGTATGC TGAAATTCTT GCAGATCATC CCGATGCACC CATGTCCCAG GTGTATGGAG CGCCACATCT CCTGAGATTA TTTGTACGAA TTGGAGCAAT GTTGGCTTAT ACACCTCTGG ATGAGAAGAG CCTTGCTTTA TTACTCAATT ATCTTCACGA TTTCCTAAAG TACCTGGCAA AGAATTCTGC AACTTTGTTC AGTGCCAGCG ATTATGAAGT GGCTCCTCCT GAGTACCATC GGAAAGCTGT GTGAGAGGCA CTCTCACTCA CTTATGTTTG GATCTCCGTA AACACATTTT TGTTCTTAGT CTATCTCTTG TACAAACGAT GTGCTTTGAA GATGTTAGTG TATAACAATT GATGTTTGTT TTCTGTTTGA TTTTAAACAG AGAAAAAATA AAAGGGGGTA ATAGCTCCTT TTTTCTTCTT TCTTTTTTTT TTTCATTTCA AAATTGCTGC CAGTGTTTTC AATGATGGAC AACAGAGGGA TATGCTGTAG AGTGTTTTAT TGCCTAGTTG ACAAAGCTGC TTTTGAATGC TGGTGGTTCT ATTCCTTTGA CACTACGCAC TTTTATAATA CATGTTAATG CTATATGACA AAATGCTCTG ATTCCTAGTG CCAAAGGTTC AATTCAGTGT ATATAACTGA ACACACTCAT CCATTTGTGC TTTTGTTTTT TTTTATGGTG CTTAAAGTAA AGAGCCCATC CTTTGCAAGT CATCCATGTT GTTACTTAGG CATTTTATCT TGGCTCAAAT TGTTGAAGAA TGGTGGCTTG TTTCATGGTT TTTGTATTTG TGTCTAATGC ACGTTTTAAC ATGATAGACG CAATGCATTG TGTAGCTAGT TTTCTGGAAA AGTCAATCTT TTAGGAATTG TTTTTCAGAT CTTCAATAAA TTTTTTCTTT AAATTTCAAA GAACAAAAAA AAAAAAAAA | 36 |
| MRPL19 | NM_014763.3 | GTAGTCTTGA CGTGAGCTAG CTGGCATGGC GGCCTGCATT GCAGCGGGGC ACTGGGCTGC AATGGGCCTA GGCCGGAGTT TCCAAGCCGC CAGGACTCTG CTCCCCCCGC CGGCCTCTAT CGCCTGCAGG GTCCACGCGG GGCCTGTCCG GCAGCAGAGC ACTGGGCCTT CCGAGCCCGG TGCGTTCCAA CCGCCGCCGA AACCGGTCAT CGTGGACAAG CACCGCCCCG TGGAACCGGA ACGCAGGTTC TTGAGTCCTG AATTCATTCC TCGAAGGGGA AGAACAGATC CTCTGAAATT TCAAATAGAA AGAAAAGATA TGTTAGAAAG GAGAAAAGTA CTCCACATTC CAGAGTTCTA TGTTGGAAGT ATTCTTCGTG TTACTACAGC TGACCCATAT GCCAGTGGAA AAATCAGCCA GTTTCTGGGG ATTTGCATTC AGAGATCAGG AAGAGGACTT GGAGCTACTT TCATCCTTAG GAATGTTATC GAAGGACAAG GTGTCGAGAT TTGCTTTGAA CTTTATAATC CTCGGGTCCA GGAGATTCAG GTGGTCAAAT TAGAGAAACG GCTGGATGAT AGCTTGCTAT ACTTACGAGA TGCCCTTCCT GAATATAGCA CTTTTGATGT GAATATGAAG CCAGTAGTAC AAGAGCCTAA CCAAAAAGTT CCTGTTAATG AGCTGAAAGT AAAAATGAAG CCTAAGCCCT GGTCTAAACG CTGGGAACGT CCAAATTTTA ATATTAAAGG AATCAGATTT | 37 |

TABLE 1-continued

Plasma cell dyscrasia Biomarker/Housekeeper Sequence Information

| Gene Name | RefSeq Accession | Sequence | SEQ ID NO: |
|---|---|---|---|
| | | GATCTTTGTT TAACTGAACA GCAAATGAAA GAAGCTCAGA | |
| | | AGTGGAATCA GCCATGGCTT GAATTTGATA TGATGAGGGA | |
| | | ATATGATACT TCAAAAATTG AAGCTGCAAT ATGGAAGGAA | |
| | | ATTGAAGCGT CGAAAAGGTC TTGATTCTGA GAATGAATTT | |
| | | GGTTAGTTGC AGAAGATACA TTGGCTCTAA GAGGATATAT | |
| | | TTTGAGACCA ATTTAATTTC ATTTATAAGA ACATAGTAAT | |
| | | TAAGTGAACT AAGCATTCAT TGTTTTATTA ATACTTTTTT | |
| | | TCTAAAATAA AACTTGTACA CCAGTTTATT ACTCTAAAAA | |
| | | GAGAATTACA CATGCCAAAT GGACCAATGT CCATTTGCTT | |
| | | ATTGGAGGCA AAGCTACAAT AGAAGTCAGA GCATCACCAG | |
| | | AATGGTCTTT AATGAGCATG GAACCTGAGC AAAGGGAATA | |
| | | GGTGGGATGA ATTTTTTTTT TAATTGTGAA ACAATTCATA | |
| | | AGCACAATAT GATTTACAGA ATAATAAACA TTCATGTACC | |
| | | CACTATCAGG TTAAGAAATA GAACATTTAT TAATATGTAG | |
| | | GAATGTTAAG AAATAAAACA TTTAATAAGA TCTCAGAAGA | |
| | | CTCCAGTAAA TCTGCAATTG TATCTCTCTC CTTTTTAAAT | |
| | | GTAAATATCA TCTTGACTTG TTAATTATTC CCTTGCATTT | |
| | | CTTTTAGTTT ACTGCCAACA CATATATTCT TCAACAATAT | |
| | | ATTTAATTTT GAAAAACCTG AAAAAAAAAA CCTGTTAGCA | |
| | | AGTATAAAGG GGCAGTATTA CTATTATTGC ATGAAGGCTT | |
| | | CAAGGGAAAC GTTACAGTCT TTGGGTCATA GTCTGGCTTC | |
| | | AGCTTCCTCT GAGAGTTTAC AGAGGCCAAT TTTGAGCAAA | |
| | | TTCATGGCTA AGGTTATGAG TGAGTTCTGC TAAACAGAAG | |
| | | GCTCACCACA AGGTATCTGG CAGGATTATA CTGGGTAGCT | |
| | | GGATGTTGCA GAAATGTGGT TAGAGGAAGT AAACTGTTTT | |
| | | TTGATGCTCA CAGCATGATG AATCAAACTC TGTATCTTAG | |
| | | GATTAGGTTA AAACAATACC TTTGGTATGA TATGAGTGTT | |
| | | GTTGCTGATC CATGCAGCAT GGATTGGAAA GCTGGGGTAT | |
| | | AAGCACACAT GCTAAAGAAA AACATGTAAT TTGGTCCATA | |
| | | CTCACCTGGA TATACTGTTC CTCAGGTTAA AAAATACAGT | |
| | | ACTATCCTAA ATCTTGAAGG CAACTCTCAG CCTATCCATT | |
| | | GAGTTACCTT CAGATCTGCC CTCTGGTTCC TAGCTGTCTT | |
| | | GGGACTAACT TCTTTCCTGC GCTCAGCTGT TTTCTGGATT | |
| | | CCATGTTTTC CATTTTATTG AGTACTAACT TGTTTTGCTG | |
| | | CAGCACATCC TTTGGTAGCT TCTAGAGGAA GTTTGTGTGG | |
| | | AGGTAAAATT TTTGAGACCT TGCATGTCTC ATGTTTGATT | |
| | | GATACTTTAT ACGTTTAGGT AGGAGGTAAT TTTCCTTCAG | |
| | | GACTTTAAAA ATATTGTTGC TCCATTTTCT TTGTTTCTAT | |
| | | TGTTGTATTG AGAAATCCAA TGCCATTTTG ATTTCCCCAT | |
| | | CATAAATTTC ATGATGATGT GTCTTGGTGT GGGTCTATAT | |
| | | TTATCCATTG TATTGGGTTT TAGGTGAACC CTTCCAGATA | |
| | | GTAACTCATT TCTGTCAGTT CTGGGAAACA CTTAGCATTG | |
| | | GTTGATGATT TATTCTCTGC TGCTTTGTTC TCCCAACTAT | |
| | | TATTTGGATG TTGGATATCC AGCACTGGGT ATCTATTTTC | |
| | | TTACCTCCCT CCCTTGACCC CAGTCTCTGT TTTTTAGCTC | |
| | | TTTAGCTCAA TCTTCCAACT CTTTGCTATT GTATTTTAAA | |
| | | ATCTTAAGAC CCCTTCTTGA TTTGTAGAAG TTCCTTTTCT | |
| | | TACAACCAAA AAGCCTTTAT CTATGGATTT GTTCACAGAT | |
| | | AAGGGGTATT CAATATAGTG TATTTTTTTT TCATTTAAAA | |
| | | TTGTTTGCGC ATCTATTTCC TCCAAATTTC TTTCTGTATT | |
| | | TATTTTTTGT TGTCTATATT TCAGACTTTT CCAGGATATC | |
| | | TGATAATCTT TGGCTGTCTT CTTATGGTTG AAAGAGGGAC | |
| | | TAAAAAGCTT GGAAAGCCTT TGGGTTGTGG GAAGGGGCTG | |
| | | TCTTTAGGAT TATCTGAATG GGCTTTTTTG GGAGTCCCCT | |
| | | CCTCCACATG AATATTTTGG TTTTGTCAGA TTCCCTAGAA | |
| | | TAGAGGCTTC CAATCTCCTT CCTGGAGGGG TCTGTCCAGG | |
| | | AAGGAGATTG TCTAGGGGTC TGTCAGACAG CAGCTTTCAG | |
| | | CTACTTCCTT GATCTTTTTC ACTAATGATT ATATAGTCAT | |
| | | CTAACTACTG TCAACAAGTA ATAGATATCC TATCCTTCAC | |
| | | TTGTTTAGAT TATTTGCTGA GATAACCTCT CAAAAGAACC | |
| | | TCTCAAAATA AAAGGTTAAC AAGAGCCTAT ATCTTATATT | |
| | | TTTCTTCTCT TTATCTTGTT AGAAGATAGC TATTAAAACC | |
| | | TGTTCTTTTT CTGTCTTGAT AAACACACTT CAATCTTGGT | |
| | | AGAATGGTAG ATGGGACAGT ATATTTTAGG ACCTAAAGCT | |
| | | CTGCAAATGT ATGATCAGCT TGTAAGTACA GGTGCTCAAA | |
| | | AACATGTAAA CAATCATGCT TTTTACTCTG TAGGAATATC | |
| | | TTTAAAATTC TTGTGAATTT TTCCCCAGAA GTAAAGCAAA | |
| | | TCTTCCCCCA GAAATAAAAT TAAATGTGCA TAATCTAAAG | |
| | | CTTTTTTTTT TTATTGTGGT AGGATATATA TATAAAACAT | |
| | | AATTTGCCAT TGTAAACATT TTAAATTTAC AAGTCAGAGG | |
| | | CATTAATTAC ATCACAATGT TGTGAAATTA TTACTACTAT | |
| | | TTCCAAAATT TTCTCATCAC CCCAAACTGA AACTCTGTAA | |
| | | CTGTTGAGCA ATAACCTCAT TCCTGTATCT CTCCCAACCC | |
| | | CAGGTAACCT CAAATCTTTC TTTTTATCTT TGAGACAAGG | |

TABLE 1-continued

Plasma cell dyscrasia Biomarker/Housekeeper Sequence Information

| Gene Name | RefSeq Accession | Sequence | SEQ ID NO: |
|---|---|---|---|
| | | TCTCATTCTA TCACTCAGGT AGGAGTGCAG TGGTGTGATC | |
| | | ATAGCTCATT GCAGCCTCAA AATCCTGGGC TCAAGCAATC | |
| | | CTCCTTGAGT AGCTAAGACT ATAGGCACAC ATTAACTGCG | |
| | | CCTGGCTGAT TTTGTTTTTT GTAGAGATGT GGTCTTGCTA | |
| | | TGTTTCCCAT GCTGGTCTTG AGTTCCTGGC CTCAAGCAGT | |
| | | CCTTAAGATT CATCCATGTT GTGGCATGTG TCAGAATTTC | |
| | | ATTTGTTTTT ATGACTAAAT AATATTCCAT TGTATGTATA | |
| | | TACATTTTGT TCATCCATCT TCTGATGAAC ACTGGGATAT | |
| | | GTCTACCTTT TGGCTATTGT GAATAATGCT GCAGTAAACA | |
| | | TTGACATAAC AAGTATGTAT TTGATTGCCT GTTTCTAAGT | |
| | | TCTTTTGGGT ATACATCTTG AGTAGAATTG CTAGATAATG | |
| | | TCATGTTTTA TTTCTCTTGT GATTTCTTCT TCGATCCCCT | |
| | | GGTTGAGTGT GTTAATTTCT ACATGTTTAT GAATTTCCCA | |
| | | CTGTTTTTTT GTTATTGATT TCCAAGTTCA TTCCATTGTG | |
| | | ATTAGAGAAG ATACTTAGTA TGATTTTAAT GTTTTTGAGA | |
| | | ATTGGTGTGT GGCCTGATAG ATGGTCTGTC CTGGAGAATG | |
| | | TTCCTCATAC ACTTGAGCAA AATATTTATC ATGCTATTGT | |
| | | TGACTGTAGT TTTCTATATG TCTCTTAGGT CAAGGTGGTT | |
| | | TACAATGTGT TAAGGTTCTC TTTTTTTAAA AAAATTTTTG | |
| | | CACAGAGTAT CTTTTTCTAT GTGTTCCATG TATTTGTGTC | |
| | | TTTGGAGCTA TAGTCTCTTG TAGACAGCAT ATCACTATCT | |
| | | TGTTTTGTTT TGTTTTTTCT GTCCATTCTG CCAATTTCTG | |
| | | CCTTTTGATT GGAAAATTTA ATCCATTTGC ATTTAAAGTA | |
| | | ATTAAGGAAG GACTTTCTTC TACCATTTAA CACTTCTTCT | |
| | | ATATGTCATA TACTTTTTTG GCCCCTCATT TCCTCTTTAT | |
| | | GGCCTTCTTT TCTGTTTTTT TGTAGTGAAC TAGTCTGATT | |
| | | CTCTTTCCAC TCCCCTTTGT GTATATTTGT TAGATGTTTT | |
| | | ATTTGTGGTT GCTATGGGGA TTATAGTTAA CATCCTACAC | |
| | | TTAAAACAAT CTAATTTAAA CTGATACCAA TTTACCTTCA | |
| | | ATAGCATACA AAATCTCTAC TCCTGTAAAG CTCTGCCCCT | |
| | | GCCCCCCTTA TGTTATTGAT GGCACAAATT GCCTAATAAA | |
| | | TAATTTATAG TTATTTGTAT GAGTTTGTCT TTTAAATCAT | |
| | | TTAGGAAATA AAAAGTGGAG TTAGAAAACA GTATGATAGT | |
| | | AATACTGACT TTTATATTTG TCAATATATT TATCTTATTT | |
| | | TGGATCCTTA TTTCATTATA TAGATTTGAG TTACTGTCTA | |
| | | GTGCCCTTCC ATTTCGGCCC AAAGGATTCC CTTATGCATT | |
| | | TCTTGCAGGG CAAGTCTAAT TGTAATAAAC TCCCTCAGCT | |
| | | TTTGTTTTAT CTGAGAATGT CTTGATTTCT CCCTTATTTT | |
| | | TGATGGATAA TTTTGCCAGA TACATGAATT TTTGGTAACA | |
| | | GTATTTTTCT TTCAGCACTT TAAATATGTC ATCCCACTAC | |
| | | CTTCTGACTT CATGGTTTCT CATGAGATAT TAGATGTTAT | |
| | | AAAATTTGAG GATTCCTCAT TCTTGATGAG TCAGTTCTGT | |
| | | CTTATTGCTT TTCGGATTTG CTCAGCTTTT GTCTTTTGAC | |
| | | AGTTTGATTA TAACGCGGCT CAGTGTGGGT CTCTGAGTTT | |
| | | ATCCCACTTA GAGTTTGTTG AGTTTCTTGG AGTCATAGAT | |
| | | TTATGTCTTT TATCAAATTT TGGACATATT TGGCTATTAT | |
| | | TTCTTCAATT TTTTTCACTG CTTCTTTCTT TTCCTTCTGA | |
| | | AATATTCTTA ATGTATATGT TGGTCTGTTT GATGCTGTCT | |
| | | CACCAGTTTC TTAGGCTGTG TTCTCTTTTG TTCCTCAGAC | |
| | | TTGATTATTG CAGTTGCCCT TCTTTTTATT TTTTTCAAGT | |
| | | TTGTTGATTC TTCTCCCTGT TCAGATCAAC TGTTGAACTC | |
| | | CTCTAGTGAA TTTATTTCAG TTACTGTACT TTTCAGCTCC | |
| | | AAGATTTATC TTTGGTTCCT TTTTATAACG TCTGTGTCTT | |
| | | TATTGATATT CTCATTTTGT TCATATGTCT CTTTCTTCCT | |
| | | TTAGTTCTTT GTCCATGTTT TCCTTTAGCT CTTTGGGCTT | |
| | | ATTTAAGACA ATTGTTTAAA GTCTTTGCAT AGTAAGTCCA | |
| | | ATGTCTGTGT TTCTTCAGGG ATGGTTTTCA TTATTTTGTT | |
| | | TTCAATGAGC CATACTTTCC TGTGTCTTTG TATGCTGTCT | |
| | | TTTTGTTGTT GAAAACTGTA TGTTTGAACA TCATAACGTG | |
| | | GTGGCCCTGA AAATCAGATA TTCCCCCCTT CCTGAGAGTT | |
| | | AGTTTTATTT TTATTATTGA AGATTGTAGC AGTCTATTGC | |
| | | TACATGTGCA GTCATTTCCA AACTATTTTT GCAAAGACTG | |
| | | TATTCCTTCT GTGTGTCATC ACTGAAGTCT CTGTTCCTTA | |
| | | GTTTGTGTTT AATAGTTTGA CATAGATTTC CTTGAAAGGA | |
| | | GTTAAAACTA GCAGAAAAAT CTCTCTCCCA GTCTTTCCAG | |
| | | TCTTTGTAGA TTGGTTCTGT GCTGGGCTTT TCCATTAATA | |
| | | CTTAGCCAGG CTTGTACTGA GCCTAACAAT CAGGCCCAAA | |
| | | AGCGTAGGGT CTTTGCAGAT CTTGTCTGAG CATGCTTCTT | |
| | | GCTGTGTATG CACGTAGTTT TCTAAATCTC CCTGTATGTG | |
| | | CTGTTGAATA TTCTAATTTC CCAAAGAAAC TCCTTTGCAG | |
| | | CTTTTTCTCA CAGAACATAG ATGGTTTTTT GGATATCTTG | |
| | | ACCATAGTCT TTCGACCCAG GTGTTTGCGG TTGTTAGTTC | |
| | | ACCTTACACT TTTTTCAAGC ATTGCCTACT GCTTACGATG | |
| | | AGTGCTCTGT CAATCCTTTA AGTAGCCCCA GACAGGCTAC | |

TABLE 1-continued

Plasma cell dyscrasia Biomarker/Housekeeper Sequence Information

| Gene Name | RefSeq Accession | Sequence | SEQ ID NO: |
|---|---|---|---|
| | | CAGAGACTTA AACAAGAATT TGTAAGTTCT GCTCAGCTTC<br>CTCTAGAAAT GGGGATCAGG GTCCAAGACA GAATGCAGTT<br>GCTGATTTCA AGACTGCTGC AACACCAGGG AGCTTGTGGG<br>GGAAGGGCAA GCAGAAATGT CACAAAGCTT TCTTGCCATT<br>TTAAAGTTGC CTGTTCTTGA CTCAGCATTT GCTTCATTGC<br>TATAAACTTT TTACTGTTTT TCAGAGTTCT GATAAAATTG<br>GCTATGCCTG TTCCTGCTTT AAAAAATATA TATATATTTT<br>TTAGGGATTG GGGTCTCACT ATACTGACCA GGCTGGTCTT<br>GAACTTCTGG CCTCAAGCCA TCCTCTCATT TCAGCTTCCC<br>AAAGTGCTGC AATTACACGC GTGAACCACC ACACCCAGCC<br>CCTGCTTGTT TTTCAATGTG CCTACTCCAC CATGTTGCTC<br>AAGTATGTAT ATTTTCTAAA CTACCTTGTA GTGTTGTGAT<br>GGGAAATAAA TCCCTGAGCC TTTTGAATAA CTCAGAGAGA<br>TCAAAAACTT AGTTTATCCT ATTCGAAGGA TTAGAAAAAT<br>GATATATCTT TCACTTTTTC AGGGATAGGC TCCTCATTAG<br>AAGGCTCCTA TGTGCCGATG CTGTACAAGA CATTTCATTT<br>CTCTTAATGT TTACAACAAG CTTGTTGCCA AGGCTGATCT<br>TGAACTCCTG GCCTCAAACG ATCCTCCCAG CTCAGTCTCA<br>CAAAGTGTTG GGATGTCTGG CCAACTAATG ACTATCTTAA<br>CTCTTGTGTT TCAATGTTTA TGCCTTCTTT TATCTTGACT<br>GATTGTATGA CTATGTCTTC TAGAACAATG TTGAACAGAA<br>ATGGTGAGAG CAGACATCCT TGCTTTAATA TTTCACCATT<br>ATATATGATG TTAGGTATAG ATTTTTCTCA CAGATGCCTT<br>TTATCAGATT GAGGAATTTA TATTCCTACT TTGCCGAAAG<br>GTTTTTGTAG TATGAGGGGG TGCTGAATTT TGTCAAACAC<br>TTTTTCGGTA ATAATTGAGA TGATTGGTTC TGCAGTCATC<br>GAGATGTGGA TTTTCTCCTT TATTCTGTTC GTGAGTGATT<br>ACACTGGTTG ACTAATGTTA AAACAACCTT ACTTTCCAGG<br>AATAAACCCT ATTATCTTTT TTATACA | |
| PSMC4 | NM_153001.2 | TGCGGGTACG GACAGCGCAT GAGCTTATGT TGAGGGCGGA<br>GCCCAGACCA GCCCTTCGTC CTATCCTGCC CTTCCAGCAC<br>CTCTCAGCCG TAACTTAAAC TACACTTCCC AGAAGCCTCC<br>TCAGCCAGGG ACTTCCGTTG TCGTCAGCGG AAGCGGTGAC<br>AGATCATCCC AGGCCACACA GAGGCCGGCT TGGTCACTAT<br>GGAGGAGATA GGCATCTTGG TGGAGAAGGC TCAGGATGAG<br>ATCCCAGCAC TGTCCGTGTC CCGGCCCCAG ACCGGCCTGT<br>CCTTCCTGGG CCCTGAGCCT GAGGACCTGG AGGACCTGTA<br>CAGCCGCTAC AAGGAGGAGG TGAAGCGAAT CCAAAGCATC<br>CCGCTGGTCA TCGGACAATT TCTGGAGGCT GTGGATCAGA<br>ATACAGCCAT CGTGGGCTCT ACCACAGGCT CCAACTATTA<br>TGTGCGCATC CTGAGCACCA TCGATCGGGA GCTGCTCAAG<br>CCCAACGCCT CAGTGGCCCT CCACAAGCAC AGCAATGCAC<br>TGGTGGACGT GCTGCCCCCC GAAGCCGACA GCAGCATCAT<br>GATGCTCACC TCAGACCAGA AGCCAGATGT GATGTACGCG<br>GACATCGGAG GCATGGACAT CCAGAAGCAG GAGGTGCGGG<br>AGGCCGTGGA GCTCCCGCTC ACGCATTTCG AGCTCTACAA<br>GCAGATCGGC ATCGATCCCC CCCGAGGCGT CCTCATGTAT<br>GGCCCACCTG GCTGTGGGAA GACCATGTTG GCAAAGGCGG<br>TGGCACATCA CACAACAGCT GCATTCATCC GGGTCGTGGG<br>CTCGGAGTTT GTACAGAAGT ATCTGGGTGA GGGCCCCCGC<br>ATGGTCCGGG ATGTGTTCCG CCTGGCCAAG GAGAATGCAC<br>CTGCCATCAT CTTCATAGAC GAGATTGATG CCATCGCCAC<br>CAAGAGATTC GATGCTCAGA CAGGGGCCGA CAGGGAGGTT<br>CAGAGGATCC TGCTGGAGCT GCTGAATCAG ATGGATGGAT<br>TTGATCAGAA TGTCAATGTC AAGGTAATCA TGGCCACAAA<br>CAGAGCAGAC ACCCTGGATC CGGCCCTGCT ACGGCCAGGA<br>CGGCTGGACC GTAAAATTGA ATTTCCACTT CCTGACCGCC<br>GCCAGAAGAG ATTGATTTTC TCCACTATCA CTAGCAAGAT<br>GAACCTCTCT GAGGAGGTTG ACTTGGAAGA CTATGTGGCC<br>CGGCCAGATA AGATTTCAGG AGCTGATATT AACTCCATCT<br>GTCAGGAGAG TGGAATGTTG GCTGTCCGTG AAAACCGCTA<br>CATTGTCCTG GCCAAGGACT TCGAGAAAGC ATACAAGACT<br>GTCATCAAGA AGGACGAGCA GGAGCATGAG TTTTACAAGT<br>GACCCTTCCC TTCCCTCCAC CACACCACTC AGGGGCTGGG<br>GCTTCTCTCG CACCCCCAGC ACCTCTGTCC CAAAACCTCA<br>TTCCCTTTTT TCTTTACCCA GGATTGGTTT CTTCAATAAA<br>TAGATAAGAT CGAATCCATT TAATTTCTTC TTAGAAGTTT<br>AACTCCTTTG GAGAATGTGG GCCTTGAATA GGATCCTCTG<br>GGTCCCTCTT AATCTGACAG ATGAGCAGAC GAGGTGCATG<br>GCCTGGGTTG CAGCTTGAGA GAACCAAAAT ATTCAAACCA<br>GATGACTTCC AAAATGTGGG GAAAGGGATG GAAAATGAAC<br>CTGAGATGGA GTCCTTAATC ACGGGATAAA GCCCTGTGCA<br>TCTCCCTCAT TTCCTACAGG TAAAAGACAG TAAAGAAATT | 38 |

TABLE 1-continued

Plasma cell dyscrasia Biomarker/Housekeeper Sequence Information

| Gene Name | RefSeq Accession | Sequence | SEQ ID NO: |
|---|---|---|---|
| | | CAGGTCACAG GCCTTGGGAG TTCATAGGAA GGAGATGTCC AGTGCTGTCC AGTAGAACTT T | |
| SF3A1 | NM_005877.5 | GGTCCCGGAA GTGCGCCAGT CGTACCTTCG CGGCCGCAAC TCGCTCGGCC GCCGCCATCT TGCGAGCTCG TCGTACTGAC CGAGCGGGGA GGCTGTCTTG AGGCGGCACC GCTCACCGAC ACCGAGGCGG ACTGGCAGCC CTGAGCGTCG CAGTCATGCC GGCCGGACCC GTGCAGGCGG TGCCCCCGCC GCCGCCCGTG CCCACGGAGC CCAAACAGCC CACAGAAGAA GAAGCATCTT CAAAGGAGGA TTCTGCACCT TCTAAGCCAG TTGTGGGGAT TATTTACCCT CCTCCAGAGG TCAGAAATAT TGTTGACAAG ACTGCCAGCT TTGTGGCCAG AAACGGGCCT GAATTTGAAG CTAGGATCCG ACAGAACGAG ATCAACAACC CCAAGTTCAA CTTTCTGAAC CCCAATGACC CTTACCATGC CTACTACCGC CACAAGGTCA GCGAGTTCAA GGAAGGGAAG GCTCAGGAGC CGTCCGCCGC CATCCCCAAG GTCATGCAGC AGCAGCAGCA GACCACCCAG CAGCAGCTGC CCCAGAAGGT CCAAGCCCAA GTAATCCAAG AGACCATCGT GCCCAAAGAG CCTCCTCCTG AGTTTGAGTT CATTGCTGAT CCTCCCTCTA TCTCAGCCTT CGACTTGGAT GTGGTGAAGC TGACGGCTCA GTTTGTGGCC AGGAATGGGC GCCAGTTTCT GACCCAGCTG ATGCAGAAAG AGCAGCGCAA CTACCAGTTT GACTTTCTCC GCCCACAGCA CAGCCTCTTC AACTACTTCA CGAAGCTAGT GGAACAGTAC ACCAAGATCT TGATTCCACC CAAAGGTTTA TTTTCAAAGC TCAAGAAAGA GGCTGAAAAC CCCCGAGAAG TTTTGGATCA GGTGTGTTAC CGAGTGGAAT GGGCCAAATT CCAGGAACGT GAGAGGAAGA AGGAAGAAGA GGAGAAGGAG AAGGAGCGGG TGGCCTATGC TCAGATCGAC TGGCATGATT TTGTGGTGGT GGAAACAGTG GACTTCCAAC CCAATGAGCA AGGGAACTTC CCTCCCCCCA CCACGCCAGA GGAGCTGGGG GCCCGAATCC TCATTCAGGA GCGCTATGAA AAGTTTGGGG AGAGTGAGGA AGTTGAGATG GAGGTCGAGT CTGATGAGGA GGATGACAAA CAGGAGAAGG CGGAGGAGCC TCCTTCCCAG CTGGACCAGG ACACCCAAGT ACAAGATATG GATGAGGGTT CAGATGATGA AGAAGAAGGG CAGAAAGTGC CCCCACCCCC AGAGACACCC ATGCCTCCAC CTCTGCCCCC AACTCCAGAC CAAGTCATTG TCCGCAAGGA TTATGATCCC AAAGCCTCCA AGCCCTTGCC TCCAGCCCCT GCTCCAGATG AGTATCTTGT GTCCCCCATT ACTGGGGAGA AGATCCCCGC CAGCAAAATG CAGGAACACA TGCGCATTGG ACTTCTTGAC CCTCGCTGGC TGGAGCAGCG GGATCGCTCC ATCCGTGAGA AGCAGAGCGA TGATGAGGTG TACGCACCAG GTCTGGATAT TGAGAGCAGC TTGAAGCAGT TGGCTGAGCG GCGTACTGAC ATCTTCGGTG TAGAGGAAAC AGCCATTGGT AAGAAGATCG GTGAGGAGGA GATCCAGAAG CCAGAGGAAA AGGTGACCTG GGATGGCCAC TCAGGCAGCA TGGCCCGGAC CCAGCAGGCT GCCCAGGCCA ACATCACCCT CCAGGAGCAG ATTGAGGCCA TTCACAAGGC CAAAGGCCTG GTGCCAGAGG ATGACACTAA AGAGAAGATT GGCCCCAGCA AGCCCAATGA AATCCCTCAA CAGCCACCGC CACCATCTTC AGCCACCAAC ATCCCCAGCT CGGCTCCACC CATCACTTCA GTGCCCCGAC CACCCACAAT GCCACCTCCA GTTCGTACTA CAGTTGTCTC CGCAGTACCC GTCATGCCCC GGCCCCCAAT GGCATCTGTG GTCCGGCTGC CCCCAGGCTC AGTGATCGCC CCCATGCCGC CCATCATCCA CGCGCCCAGA ATCAACGTGG TGCCCATGCC TCCCTCGGCC CCTCCTATTA TGGCCCCCCG CCCACCCCCC ATGATTGTGC CAACAGCCTT TGTGCCTGCT CCACCTGTGG CACCTGTCCC AGCTCCAGCC CCAATGCCCC CTGTGCATCC CCCACCTCCC ATGGAAGATG AGCCCACCTC CAAAAAACTG AAGACAGAGG ACAGCCTCAT GCCAGAGGAG GAGTTCCTGC GCAGAAACAA GGGTCCAGTG TCCATCAAAG TCCAGGTGCC CAACATGCAG GATAAGACGG AATGGAAACT GAATGGGCAG GTGCTGGTCT TCACCCTCCC ACTCACGGAC CAGGTCTCTG TCATTAAGGT GAAGATTCAT GAAGCCACAG GCATGCCTGC AGGGAAACAG AAGCTACAGT ATGAGGGTAT CTTCATCAAA GATTCCAACT CACTGGCTTA CTACAACATG GCCAATGGCG CAGTCATCCA CCTGGCCCTC AAGGAGAGAG GCGGGAGGAA GAAGTAGACA AGAGGAACCT GCTGTCAAGT CCCTGCCATT TTGCCTCTCC TGTCTCCCAC CCCCTGCCCC AGACCCAGGA GCCCCCCTGA GGCTTTGCCT TGCCTGCATA TTTGTTTCGC TCTTACTCAG TTTGGGAATT CAAATTGTCC TGCAGAGGTT CATTCCCCTG ACCCTTTCCC CACATTGGTA AGAGTAGCTG GGTTTTCTAA GCCACTCTCT GGAATCTCTT TGTGTTAGGG TCTCGATTTG AGGACATTCA TTTCTTCAGC AGCCCATTAG CAACTGAGAG CCCAGGGATG TCCTACAGGA | 39 |

TABLE 1-continued

| Plasma cell dyscrasia Biomarker/Housekeeper Sequence Information | | | |
|---|---|---|---|
| Gene Name | RefSeq Accession | Sequence | SEQ ID NO: |
| | | TAGTTTCATA GTGACAGGTG GCACTTGGCT AATAGAATAT<br>GGCTGATATT GTCATTAATC ATTTTGTACC TTGACATGGG<br>TTGTCTAATA AAACTCGGAC CCTTCTTGTG AAATCAGTTA<br>AATAAGACTT GTCTCGGTCA CCTGTGCCCT GTCCAGACTC<br>GAGGCAGTGG TAACACTGCA CAGTGCTATG TGGCTTCTCT<br>TTGAGGATTT TTGGGTTTTG TAACTAAATT CTTGCTGCCC<br>TCATACTTTT TATGTATTAG AATCATATTC GTATTGCCCT<br>TTTAAAACAT TGGGATCCTC CAAAGGCCTG CCCCATGTAT<br>TTAACAGTAA TACAGGAAGC ATGGCAGGCA CCATGCAAAC<br>CAAGGATGGA TGGTGCAGTC CCTGTGTCAG TGGGCGGTGG<br>TTTCCTGCTG GCCTGGAATC ACTCATCACC TGATTGATTG<br>GCTCTGTGGT CCTGGGCAGG TGCCTCATAG GTGTGTGGAT<br>ATGATGACGT TTCTTTAAAA TGTATGTATT TAACAAATAC<br>TTAATTGTAT TAAGGTCATG TACCAAGGAT TTGATAAAGT<br>TTAAATAATT TACTCTCTAC TTTTATCCAT TTTATCCATT<br>TTAACTCATG TAATCCTCAT GTGAGTATTC CTGTTTAACA<br>CTTGAGTAAA CTGAGGCACA GAGAACATAA GTTGCATGCC<br>ATAGTCACAC ACTGTGAAAG TGAAAAGAGA ATGTGTGCAA<br>AACACGTCAC AGTCCTGGTT TCTGAGTAAA GGCAGGCTGT<br>TATCTTTAGA ATCAAGCTAT CACAGGGAGA TAGGCAATGC<br>TGTGGGTGTT GGAGGAAGGT GAGAGCCTGT TGCTAACAAT<br>TTCCTGGTTT TAAAGCTAAG GCTGATTTTA TTGGGAAGAT<br>CTCACATGTG TGTGGCCCCT GAGAGTTCCC AGTGCCTTTT<br>ATTTGCAGTC CTTCCATTTG GACCTCCTAG CTGCCCCATC<br>AGGTCATCTC CAGGGCTCAG AGGGGTGAGA CCATTTCCCA<br>AGGTCACAGA ACCAGCTCTC TAGTCACCAC CCTGCCTCTC<br>CCTCTCACCC AGAGTCAGTA CCAGTTTTAT GGCTTTATTA<br>CAAACTGCTG GGTCCCTCCC ATTTTCAACT TGATTGATGG<br>GATGTCATCC CTTATCCTGT CTGACATTTG CCTCTGGCCT<br>GGTTGCTAGA AGTTTGCCCC AGGGGCAAGA GTTGAAATTT<br>GGCTTCCTGA GGTGGGCTTT GTGGTTTGCG TCCCTAAAGT<br>GAGCCCACTA CTGGTTGCTT GTCCATGGCC AACACCAGAA<br>ATCCCCTGAG CACTACCTGG GTCTCATTCC AAGAAGGAAG<br>AGGGTCAGGA GACCTGGGGA GTCTCATATT CCAAGTTCTT<br>CTTTCTTTCT GGGAGCAGTG GGCAGTTCAT GGTGTTAGGG<br>CACTCACCCC CACAGACTGG CAAACCCTGC AGGACTTCCG<br>TGGCTGAGGC TGTGACCGGA GGCCAGGAAT GCCGTTGGGT<br>GGATTGTGAG TGAATGGGCC CTTTGAGCTG CCCTCTAGAG<br>AGCAAATCCA GTTTCCTGGA GCTCCTGAAT GAATATCTGT<br>ACTGGCTCGC TCAGATGCAG AAGCTCCATT GACCATGAGG<br>CCTTGTGAAC ATCAGTGGCC ACAGGCCCAG TGTGCTGCTT<br>GGCACTGCAC TAGTTTAGGA CCTGCAGCAT GTAGGTAGCG<br>TCCTAGTGTT TATAATACAA AGCTGCTCTG CACAGCTTTT<br>CTGATTCTTC TTGCAATCTC CTGAGGATTA TCTGCCCCAT<br>TTTTAAAACG AGGTGGAATA CCCAAGGTCA TGTAGCCAGT<br>GAGTGCTCTG GAAAGCCAAA GCAGCTCATC CCTTCCTGGG<br>GACCACACTG CTCTGCTCCA CCAGACCACA CTATGAAATA<br>GGAATAAGTG CTCCTGTTGC AGGACTGCTG GGAAAACAGG<br>TGGTGTGGGA CTTAAGTCAC CATAATTTTG AAGACTTGCA<br>TGCAGAGGGC TCCAGGAATT GTAGACATTA AGGAATTTCA<br>CTTTCAGTTC TACCCACTAC TTAAGTACTT GTCATGTACT<br>CTTAGAGGAG GCCAGTAATG ATCAGAACCA TTTTACTTTA<br>AAATTAATAA TATTGTATTA GAGAATATAT TAAATGGTTA<br>TATTGGGTTA TGTTAGGATA TATACTTGAA TGGAAATACA<br>TGTACTATTA GCAATCATAT TTCATTTATC CCTGTAATTA<br>GACAAGAAAG CATAATATAG CTCTACTCAT GGGTACACAT<br>ACCAGTGTAT AAGATTTTTA GAAGTTTACT TTTTAAAAAT<br>AAAAGCAAAA TGTAAGATCT TAAAAAAAAA AAAAAAAAA | |
| PUM1 | NM_001020658.1 | AGTGGGCCGC CATGTTGTCG GAGTGAAAGG TAAGGGGGAG<br>CGAGAGCGCC AGAGAGAGAA GATCGGGGGG CTGAAATCCA<br>TCTTCATCCT ACCGCTCCGC CCGTGTTGGT GGAATGAGCG<br>TTGCATGTGT CTTGAAGAGA AAAGCAGTGC TTTGGCAGGA<br>CTCTTTCAGC CCCCACCTGA AACATCACCC TCAAGAACCA<br>GCTAATCCCA ACATGCCTGT TGTTTTGACA TCTGGAACAG<br>GGTCGCAAGC GCAGCCACAA CCAGCTGCAA ATCAGGCTCT<br>TGCAGCTGGG ACTCACTCCA GCCCTGTCCC AGGATCTATA<br>GGAGTTGCAG GCCGTTCCCA GGACGACGCT ATGGTGGACT<br>ACTTCTTTCA GAGGCAGCAT GGTGAGCAGC TTGGGGGAGG<br>AGGAAGTGGA GGAGGCGGCT ATAATAATAG CAAACATCGA<br>TGGCCTACTG GGGATAACAT TCATGCAGAA CATCAGGTGC<br>GTTCCATGGA TGAACTGAAT CATGATTTTC AAGCACTTGC<br>TCTGGAGGGA AGAGCGATGG GAGAGCAGCT CTTGCCAGGT<br>AAAAAGTTTT GGGAAACAGA TGAATCCAGC AAAGATGGAC | 40 |

TABLE 1-continued

Plasma cell dyscrasia Biomarker/Housekeeper Sequence Information

| Gene Name | RefSeq Accession | Sequence | SEQ ID NO: |
|---|---|---|---|
| | | CAAAAGGAAT ATTCCTGGGT GATCAATGGC GAGACAGTGC | |
| | | CTGGGGAACA TCAGATCATT CAGTTTCCCA GCCAATCATG | |
| | | GTGCAGAGAA GACCTGGTCA GAGTTTCCAT GTGAACAGTG | |
| | | AGGTCAATTC TGTACTGTCC CCACGATCGG AGAGTGGGGG | |
| | | ACTAGGCGTT AGCATGGTGG AGTATGTGTT GAGCTCATCC | |
| | | CCGGGCGATT CCTGTCTAAG AAAAGGAGGA TTTGGCCCAA | |
| | | GGGATGCAGA CAGTGATGAA AACGACAAAG GTGAAAAGAA | |
| | | GAACAAGGGT ACGTTTGATG GAGATAAGCT AGGAGATTTG | |
| | | AAGGAGGAGG GTGATGTGAT GGACAAGACC AATGGTTTAC | |
| | | CAGTGCAGAA TGGGATTGAT GCAGACGTCA AAGATTTTAG | |
| | | CCGTACCCCT GGTAATTGCC AGAACTCTGC TAATGAAGTG | |
| | | GATCTTCTGG GTCCAAACCA GAATGGTTCT GAGGGCTTAG | |
| | | CCCAGCTGAC CAGCACCAAT GGTGCCAAGC CTGTGGAGGA | |
| | | TTTCTCCAAC ATGGAGTCCC AGAGTGTCCC CTTGGACCCC | |
| | | ATGGAACATG TGGGCATGGA GCCTCTTCAG TTTGATTATT | |
| | | CAGGCACGCA GGTACCTGTG GACTCAGCAG CAGCAACTGT | |
| | | GGGACTTTTT GACTACAATT CTCAACAACA GCTGTTCCAA | |
| | | AGACCTAATG CGCTTGCTGT CCAGCAGTTG ACAGCTGCTC | |
| | | AGCAGCAGCA GTATGCACTG GCAGCTGCTC ATCAGCCGCA | |
| | | CATCGGTTTA GCTCCCGCTG CGTTTGTCCC CAATCCATAC | |
| | | ATCATCAGCG CTGCTCCCCC AGGGACGGAC CCCTACACAG | |
| | | CTGGATTGGC TGCAGCAGCG ACACTAGGCC CAGCTGTGGT | |
| | | CCCTCACCAG TATTATGGAG TTACTCCCTG GGGAGTCTAC | |
| | | CCTGCCAGTC TTTTCCAGCA GCAAGCTGCC GCTGCCGCTG | |
| | | CAGCAACTAA TTCAGCTAAT CAACAGACCA CCCCACAGGC | |
| | | TCAGCAAGGA CAGCAGCAGG TTCTCCGTGG AGGAGCCAGC | |
| | | CAACGTCCTT TGACCCCAAA CCAGAACCAG CAGGGACAGC | |
| | | AAACGGATCC CCTTGTGGCA GCTGCAGCAG TGAATTCTGC | |
| | | CCTTGCATTT GGACAAGGTC TGGCAGCAGG CATGCCAGGT | |
| | | TATCCGGTGT TGGCTCCTGC TGCTTACTAT GACCAAACTG | |
| | | GTGCCCTTGT AGTGAATGCA GGCGCGAGAA ATGGTCTTGG | |
| | | AGCTCCTGTT CGACTTGTAG CTCCTGCCCC AGTCATCATT | |
| | | AGTTCCTCAG CTGCACAAGC AGCTGTTGCA GCAGCCGCAG | |
| | | CTTCAGCAAA TGGAGCAGCT GGTGGTCTTG CTGGAACAAC | |
| | | AAATGGACCA TTTCGCCCTT TAGGAACACA GCAGCCTCAG | |
| | | CCCCAGCCCC AGCAGCAGCC CAATAACAAC CTGGCATCCA | |
| | | GTTCTTTCTA CGGCAACAAC TCTCTGAACA GCAATTCACA | |
| | | GAGCAGCTCC CTCTTCTCCC AGGGCTCTGC CCAGCCTGCC | |
| | | AACACATCCT TGGGATTCGG AAGTAGCAGT TCTCTCGGCG | |
| | | CCACCCTGGG ATCCGCCCTT GGAGGGTTTG GAACAGCAGT | |
| | | TGCAAACTCC AACACTGGCA GTGGCTCCCG CCGTGACTCC | |
| | | CTGACTGGCA GCAGTGACCT TTATAAGAGG ACATCGAGCA | |
| | | GCTTGACCCC CATTGGACAC AGTTTTTATA ACGGCCTTAG | |
| | | CTTTTCCTCC TCTCCTGGAC CCGTGGGCAT GCCTCTCCCT | |
| | | AGTCAGGGAC CAGGACATTC ACAGACACCA CCTCCTTCCC | |
| | | TCTCTTCACA TGGATCCTCT TCAAGCTTAA ACCTGGGAGG | |
| | | ACTCACGAAT GGCAGTGGAA GATACATCTC TGCTGCTCCA | |
| | | GGCGCTGAAG CCAAGTACCG CAGTGCAAGC AGCGCCTCCA | |
| | | GCCTCTTCAG CCCGAGCAGC ACTCTTTTCT CTTCCTCTCG | |
| | | TTTGCGATAT GGAATGTCTG ATGTCATGCC TTCTGGCAGG | |
| | | AGCAGGCTTT TGGAAGATTT TCGAAACAAC CGGTACCCCA | |
| | | ATTTACAACT GCGGGAGATT GCTGGACATA TAATGGAATT | |
| | | TTCCCAAGAC CAGCATGGGT CCAGATTCAT TCAGCTGAAA | |
| | | CTGGAGCGTG CCACACCAGC TGAGCGCCAG CTTGTCTTCA | |
| | | ATGAAATCCT CCAGGCTGCC TACCAACTCA TGGTGGATGT | |
| | | GTTTGGTAAT TACGTCATTC AGAAGTTCTT TGAATTTGGC | |
| | | AGTCTTGAAC AGAAGCTGGC TTTGGCAGAA CGGATTCGAG | |
| | | GCCACGTCCT GTCATTGGCA CTACAGATGT ATGGCTGCCG | |
| | | TGTTATCCAG AAAGCTCTTG AGTTTATTCC TTCAGACCAG | |
| | | CAGGTAATTA ATGAGATGGT TCGGGAACTA GATGGCCATG | |
| | | TCTTGAAGTG TGTGAAAGAT CAGAATGGCA ATCACGTGGT | |
| | | TCAGAAATGC ATTGAATGTG TACAGCCCCA GTCTTTGCAA | |
| | | TTTATCATCG ATGCGTTTAA GGGACAGGTA TTTGCCTTAT | |
| | | CCACACATCC TTATGGCTGC CGAGTGATTC AGAGAATCCT | |
| | | GGAGCACTGT CTCCCTGACC AGACACTCCC TATTTTAGAG | |
| | | GAGCTTCACC AGCACACAGA GCAGCTTGTA CAGGATCAAT | |
| | | ATGGAAATTA TGTAATCCAA CATGTACTGG AGCACGGTCG | |
| | | TCCTGAGGAT AAAAGCAAAA TTGTAGCAGA AATCCGAGGC | |
| | | AATGTACTTG TATTGAGTCA GCACAAATTT GCAAGCAATG | |
| | | TTGTGGAGAA GTGTGTTACT CACGCCTCAC GTACGGAGCG | |
| | | CGCTGTGCTC ATCGATGAGG TGTGCACCAT GAACGACGGT | |
| | | CCCCACAGTG CCTTATACAC CATGATGAAG GACCAGTATG | |
| | | CCAACTACGT GGTCCAGAAG ATGATTGACG TGGCGGAGCC | |
| | | AGGCCAGCGG AAGATCGTCA TGCATAAGAT CCGGCCCCAC | |

TABLE 1-continued

Plasma cell dyscrasia Biomarker/Housekeeper Sequence Information

| Gene Name | RefSeq Accession | Sequence | SEQ ID NO: |
|---|---|---|---|
| | | ATCGCAACTC TTCGTAAGTA CACCTATGGC AAGCACATTC<br>TGGCCAAGCT GGAGAAGTAC TACATGAAGA ACGGTGTTGA<br>CTTAGGGCCC ATCTGTGGCC CCCCTAATGG TATCATCTGA<br>GGCAGTGTCA CCCGCTGTTC CCTCATTCCC GCTGACCTCA<br>CTGGCCCACT GGCAAATCCA ACCAGCAACC AGAAATGTTC<br>TAGTGTAGAG TCTGAGACGG GCAAGTGGTT GCTCCAGGAT<br>TACTCCCTCC TCCAAAAAAG GAATCAAATC CACGAGTGGA<br>AAAGCCTTTG TAAATTTAAT TTTATTACAC ATAACATGTA<br>CTATTTTTTT TAATTGACTA ATTGCCCTGC TGTTTTACTG<br>GTGTATAGGA TACTTGTACA TAGGTAACCA ATGTACATGG<br>GAGGCCACAT ATTTTGTTCA CTGTTGTATC TATATTTCAC<br>ATGTGGAAAC TTTCAGGGTG GTTGGTTTAA CAAAAAAAAA<br>AAGCTTTAAA AAAAAAAGAA AAAAAGGAAA AGGTTTTTAG<br>CTCATTTGCC TGGCCGGCAA GTTTTGCAAA TAGCTCTTCC<br>CCACCTCCTC ATTTTAGTAA AAAACAAACA AAAACAAAAA<br>AACCTGAGAA GTTTGAATTG TAGTTAAATG ACCCCAAACT<br>GGCATTTAAC ACTGTTTATA AAAAATATAT ATATATATAT<br>ATATATATAT AATGAAAAAG GTTTCAGAGT TGCTAAAGCT<br>TCAGTTTGTG ACATTAAGTT TATGAAATTC TAAAAAATGC<br>CTTTTTTGGA GACTATATTA TGCTGAAGAA GGCTGTTCGT<br>GAGGAGGAGA TGCGAGCACC CAGAACGTCT TTTGAGGCTG<br>GGCGGGTGTG ATTGTTTACT GCCTACTGGA TTTTTTTCTA<br>TTAACATTGA AAGGTAAAAT CTGATTATTT AGCATGAGAA<br>AAAAAAATCC AACTCTGCTT TTGGTCTTGC TTCTATAAAT<br>ATATAGTGTA TACTTGGTGT AGACTTTGCA TATATACAAA<br>TTTGTAGTAT TTTCTTGTTT TGATGTCTAA TCTGTATCTA<br>TAATGTACCC TAGTAGTCGA ACATACTTTT GATTGTACAA<br>TTGTACATTT GTATACCTGT AATGTAAATG TGGAGAAGTT<br>TGAATCAACA TAAACACGTT TTTTGGTAAG AAAAGAGAAT<br>TAGCCAGCCC TGTGCATTCA GTGTATATTC TCACCTTTTA<br>TGGTCGTAGC ATATAGTGTT GTATATTGTA AATTGTAATT<br>TCAACCAGAA GTAAATTTTT TTCTTTTGAA GGAATAAATG<br>TTCTTTATAC AGCCTAGTTA ATGTTTAAAA AGAAAAAAAT<br>AGCTTGGTTT TATTTGTCAT CTAGTCTCAA GTATAGCGAG<br>ATTCTTTCTA AATGTTATTC AAGATTGAGT TCTCACTAGT<br>GTTTTTTTAA TCCTAAAAAA GTAATGTTTT GATTTTGTGA<br>CAGTCAAAAG GACGTGCAAA AGTCTAGCCT TGCCCGAGCT<br>TTCCTTACAA TCAGAGCCCC TCTCACCTTG TAAAGTGTGA<br>ATCGCCCTTC CCTTTTGTAC AGAAGATGAA CTGTATTTTG<br>CATTTTGTCT ACTTGTAAGT GAATGTAACA TACTGTCAAT<br>TTTCCTTGTT TGAATATAGA ATTGTAACAC TACACGGTGT<br>ACATTTCCAG AGCCTTGTGT ATATTTCCAA TGAACTTTTT<br>TGCAAGCACA CTTGTAACCA TATGTGTATA ATTAACAAAC<br>CTGTGTATGC TTATGCCTGG GCAACTATTT TTTGTAACTC<br>TTGTGTAGAT TGTCTCTAAA CAATGTGTGA TCTTTATTTT<br>GAAAAATACA GAACTTTGGA ATCTGAAAAA AAAAAAAAAA<br>AAAAAAAAAA AAAAAA | |
| ACTB | NM_001101.4 | GAGTGAGCGG CGCGGGGCCA ATCAGCGTGC GCCGTTCCGA<br>AAGTTGCCTT TTATGGCTCG AGCGGCCGCG GCGGCGCCCT<br>ATAAAACCCA GCGGCGCGAC GCGCCACCAC CGCCGAGACC<br>GCGTCCGCCC CGCGAGCACA GAGCCTCGCC TTTGCCGATC<br>CGCCGCCCGT CCACACCCGC CGCCAGCTCA CCATGGATGA<br>TGATATCGCC GCGCTCGTCG TCGACAACGG CTCCGGCATG<br>TGCAAGGCCG GCTTCGCGGG CGACGATGCC CCCCGGGCCG<br>TCTTCCCCTC CATCGTGGGG CGCCCCAGGC ACCAGGGCGT<br>GATGGTGGGC ATGGGTCAGA AGGATTCCTA TGTGGGCGAC<br>GAGGCCCAGA GCAAGAGAGG CATCCTCACC CTGAAGTACC<br>CCATCGAGCA CGGCATCGTC ACCAACTGGG ACGACATGGA<br>GAAAATCTGG CACCACACCT TCTACAATGA GCTGCGTGTG<br>GCTCCCGAGG AGCACCCCGT GCTGCTGACC GAGGCCCCCC<br>TGAACCCCAA GGCCAACCGC GAGAAGATGA CCCAGATCAT<br>GTTTGAGACC TTCAACACCC CAGCCATGTA CGTTGCTATC<br>CAGGCTGTGC TATCCCTGTA CGCCTCTGGC CGTACCACTG<br>GCATCGTGAT GGACTCCGGT GACGGGGTCA CCCACACTGT<br>GCCCATCTAC GAGGGGTATG CCCTCCCCCA TGCCATCCTG<br>CGTCTGGACC TGGCTGGCCG GGACCTGACT GACTACCTCA<br>TGAAGATCCT CACCGAGCGC GGCTACAGCT TCACCACCAC<br>GGCCGAGCGG GAAATCGTGC GTGACATTAA GGAGAAGCTG<br>TGCTACGTCG CCCTGGACTT CGAGCAAGAG ATGGCCACGG<br>CTGCTTCCAG CTCCTCCCTG GAGAAGAGCT ACGAGCTGCC<br>TGACGGCCAG GTCATCACCA TTGGCAATGA GCGGTTCCGC<br>TGCCCTGAGG CACTCTTCCA GCCTTCCTTC CTGGGCATGG<br>AGTCCTGTGG CATCCACGAA ACTACCTTCA ACTCCATCAT | 41 |

TABLE 1-continued

Plasma cell dyscrasia Biomarker/Housekeeper Sequence Information

| Gene Name | RefSeq Accession | Sequence | SEQ ID NO: |
|---|---|---|---|
| | | GAAGTGTGAC GTGGACATCC GCAAAGACCT GTACGCCAAC ACAGTGCTGT CTGGCGGCAC CACCATGTAC CCTGGCATTG CCGACAGGAT GCAGAAGGAG ATCACTGCCC TGGCACCCAG CACAATGAAG ATCAAGATCA TTGCTCCTCC TGAGCGCAAG TACTCCGTGT GGATCGGCGG CTCCATCCTG GCCTCGCTGT CCACCTTCCA GCAGATGTGG ATCAGCAAGC AGGAGTATGA CGAGTCCGGC CCCTCCATCG TCCACCGCAA ATGCTTCTAG GCGGACTATG ACTTAGTTGC GTTACACCCT TTCTTGACAA AACCTAACTT GCGCAGAAAA CAAGATGAGA TTGGCATGGC TTTATTTGTT TTTTTTGTTT TGTTTTGGTT TTTTTTTTTT TTTTGGCTTG ACTCAGGATT TAAAAACTGG AACGGTGAAG GTGACAGCAG TCGGTTGGAG CGAGCATCCC CCAAAGTTCA CAATGTGGCC GAGGACTTTG ATTGCACATT GTTGTTTTTT TAATAGTCAT TCCAAATATG AGATGCGTTG TTACAGGAAG TCCCTTGCCA TCCTAAAAGC CACCCCACTT CTCTCTAAGG AGAATGGCCC AGTCCTCTCC CAAGTCCACA CAGGGGAGGT GATAGCATTG CTTTCGTGTA AATTATGTAA TGCAAAATTT TTTTAATCTT CGCCTTAATA CTTTTTTATT TTGTTTTATT TTGAATGATG AGCCTTCGTG CCCCCCCTTC CCCCTTTTTT GTCCCCCAAC TTGAGATGTA TGAAGGCTTT TGGTCTCCCT GGGAGTGGGT GGAGGCAGCC AGGGCTTACC TGTACACTGA CTTGAGACCA GTTGAATAAA AGTGCACACC TTAAAAATGA GGAAAAAAAA AAAAAAAAAA | |
| GAPD | NM_002046.6 | GCTCTCTGCT CCTCCTGTTC GACAGTCAGC CGCATCTTCT TTTGCGTCGC CAGCCGAGCC ACATCGCTCA GACACCATGG GGAAGGTGAA GGTCGGAGTC AACGGATTTG GTCGTATTGG GCGCCTGGTC ACCAGGGCTG CTTTTAACTC TGGTAAAGTG GATATTGTTG CCATCAATGA CCCCTTCATT GACCTCAACT ACATGGTTTA CATGTTCCAA TATGATTCCA CCCATGGCAA ATTCCATGGC ACCGTCAAGG CTGAGAACGG GAAGCTTGTC ATCAATGGAA ATCCCATCAC CATCTTCCAG GAGCGAGATC CCTCCAAAAT CAAGTGGGGC GATGCTGGCG CTGAGTACGT CGTGGAGTCC ACTGGCGTCT TCACCACCAT GGAGAAGGCT GGGGCTCATT TGCAGGGGGG AGCCAAAAGG GTCATCATCT CTGCCCCCTC TGCTGATGCC CCCATGTTCG TCATGGGTGT GAACCATGAG AAGTATGACA ACAGCCTCAA GATCATCAGC AATGCCTCCT GCACCACCAA CTGCTTAGCA CCCCTGGCCA AGGTCATCCA TGACAACTTT GGTATCGTGG AAGGACTCAT GACCACAGTC CATGCCATCA CTGCCACCCA GAAGACTGTG GATGGCCCCT CCGGGAAACT GTGGCGTGAT GGCCGCGGGG CTCTCCAGAA CATCATCCCT GCCTCTACTG GCGCTGCCAA GGCTGTGGGC AAGGTCATCC CTGAGCTGAA CGGGAAGCTC ACTGGCATGG CCTTCCGTGT CCCCACTGCC AACGTGTCAG TGGTGGACCT GACCTGCCGT CTAGAAAAAC CTGCCAAATA TGATGACATC AAGAAGGTGG TGAAGCAGGC GTCGGAGGGC CCCCTCAAGG GCATCCTGGG CTACACTGAG CACCAGGTGG TCTCCTCTGA CTTCAACAGC GACACCCACT CCTCCACCTT TGACGCTGGG GCTGGCATTG CCCTCAACGA CCACTTTGTC AAGCTCATTT CCTGGTATGA CAACGAATTT GGCTACAGCA ACAGGGTGGT GGACCTCATG GCCCACATGG CCTCCAAGGA GTAAGACCCC TGGACCACCA GCCCCAGCAA GAGCACAAGA GGAAGAGAGA GACCCTCACT GCTGGGGAGT CCCTGCCACA CTCAGTCCCC CACCACACTG AATCTCCCCT CCTCACAGTT GCCATGTAGA CCCCTTGAAG AGGGGAGGGG CCTAGGGAGC CGCACCTTGT CATGTACCAT CAATAAAGTA CCCTGTGCTC AACCAGTTAA AAAAAAAAAA AAAAAAAAA | 42 |
| GUSB | NM_000181.3 | GTCCTCAACC AAGATGGCGC GGATGGCTTC AGGCGCATCA CGACACCGGC GCGTCACGCG ACCCGCCCTA CGGGCACCTC CCGCGCTTTT CTTAGCGCCG CAGACGGTGG CCGAGCGGGG GACCGGGAAG CATGGCCCGG GGGTCGGCGG TTGCCTGGGC GGCGCTCGGG CCGTTGTTGT GGGGCTGCGC GCTGGGGCTG CAGGGCGGGA TGCTGTACCC CCAGGAGAGC CCGTCGCGGG AGTGCAAGGA GCTGGACGGC CTCTGGAGCT TCCGCGCCGA CTTCTCTGAC AACCGACGCC GGGGCTTCGA GGAGCAGTGG TACCGGCGGC CGCTGTGGGA GTCAGGCCCC ACCGTGGACA TGCCAGTTCC CTCCAGCTTC AATGACATCA GCCAGGACTG GCGTCTGCGG CATTTTGTCG GCTGGGTGTG GTACGAACGG GAGGTGATCC TGCCGGAGCG ATGGACCCAG GACCTGCGCA CAAGAGTGGT GCTGAGGATT GGCAGTGCCC ATTCCTATGC CATCGTGTGG GTGAATGGGG TCGACACGCT AGAGCATGAG GGGGGCTACC TCCCCTTCGA GGCCGACATC AGCAACCTGG TCCAGGTGGG GCCCCTGCCC TCCCGGCTCC GAATCACTAT | 43 |

TABLE 1-continued

Plasma cell dyscrasia Biomarker/Housekeeper Sequence Information

| Gene Name | RefSeq Accession | Sequence | SEQ ID NO: |
|---|---|---|---|
| | | CGCCATCAAC AACACACTCA CCCCCACCAC CCTGCCACCA GGGACCATCC AATACCTGAC TGACACCTCC AAGTATCCCA AGGGTTACTT TGTCCAGAAC ACATATTTTG ACTTTTTCAA CTACGCTGGA CTGCAGCGGT CTGTACTTCT GTACACGACA CCCACCACCT ACATCGATGA CATCACCGTC ACCACCAGCG TGGAGCAAGA CAGTGGGCTG GTGAATTACC AGATCTCTGT CAAGGGCAGT AACCTGTTCA AGTTGGAAGT GCGTCTTTTG GATGCAGAAA ACAAAGTCGT GGCGAATGGG ACTGGGACCC AGGGCCAACT TAAGGTGCCA GGTGTCAGCC TCTGGTGGCC GTACCTGATG CACGAACGCC CTGCCTATCT GTATTCATTG GAGGTGCAGC TGACTGCACA GACGTCACTG GGGCCTGTGT CTGACTTCTA CACACTCCCT GTGGGGATCC GCACTGTGGC TGTCACCAAG AGCCAGTTCC TCATCAATGG GAAACCTTTC TATTTCCACG GTGTCAACAA GCATGAGGAT GCGGACATCC GAGGGAAGGG CTTCGACTGG CCGCTGCTGG TGAAGGACTT CAACCTGCTT CGCTGGCTTG GTGCCAACGC TTTCCGTACC AGCCACTACC CCTATGCAGA GGAAGTGATG CAGATGTGTG ACCGCTATGG GATTGTGGTC ATCGATGAGT GTCCCGGCGT GGGCCTGGCG CTGCCGCAGT TCTTCAACAA CGTTTCTCTG CATCACCACA TGCAGGTGAT GGAAGAAGTG GTGCGTAGGG ACAAGAACCA CCCCGCGGTC GTGATGTGGT CTGTGGCCAA CGAGCCTGCG TCCCACCTAG AATCTGCTGG CTACTACTTG AAGATGGTGA TCGCTCACAC CAAATCCTTG GACCCCTCCC GGCCTGTGAC CTTTGTGAGC AACTCTAACT ATGCAGCAGA CAAGGGGGCT CCGTATGTGG ATGTGATCTG TTTGAACAGC TACTACTCTT GGTATCACGA CTACGGGCAC CTGGAGTTGA TTCAGCTGCA GCTGGCCACC CAGTTTGAGA ACTGGTATAA GAAGTATCAG AAGCCCATTA TTCAGAGCGA GTATGGAGCA GAAACGATTG CAGGGTTTCA CCAGGATCCA CCTCTGATGT TCACTGAAGA GTACCAGAAA AGTCTGCTAG AGCAGTACCA TCTGGGTCTG GATCAAAAAC GCAGAAAATA CGTGGTTGGA GAGCTCATTT GGAATTTTGC CGATTTCATG ACTGAACAGT CACCGACGAG AGTGCTGGGG AATAAAAAGG GGATCTTCAC TCGGCAGAGA CAACCAAAAA GTGCAGCGTT CCTTTTGCGA GAGAGATACT GGAAGATTGC CAATGAAACC AGGTATCCCC ACTCAGTAGC CAAGTCACAA TGTTTGGAAA ACAGCCTGTT TACTTGAGCA AGACTGATAC CACCTGCGTG TCCCTTCCTC CCCGAGTCAG GGCGACTTCC ACAGCAGCAG AACAAGTGCC TCCTGGACTG TTCACGGCAG ACCAGAACGT TTCTGGCCTG GGTTTTGTGG TCATCTATTC TAGCAGGGAA CACTAAAGGT GGAAATAAAA GATTTTCTAT TATGGAAATA AAGAGTTGGC ATGAAAGTGG CTACTGAAAA AAAAAAAAAA AAAAAAAAAA A | |
| RPLP0 | NM_001002.3 | GTCTGACGGG CGATGGCGCA GCCAATAGAC AGGAGCGCTA TCCGCGGTTT CTGATTGGCT ACTTTGTTCG CATTATAAAA GGCACGCGCG GGCGCGAGGC CCTTCTCTCG CCAGGCGTCC TCGTGGAAGT GACATCGTCT TTAAACCCTG CGTGGCAATC CCTGACGCAC CGCCGTGATG CCCAGGGAAG ACAGGGCGAC CTGGAAGTCC AACTACTTCC TTAAGATCAT CCAACTATTG GATGATTATC CGAAATGTTT CATTGTGGGA GCAGACAATG TGGGCTCCAA GCAGATGCAG CAGATCCGCA TGTCCCTTCG CGGGAAGGCT GTGGTGCTGA TGGGCAAGAA CACCATGATG CGCAAGGCCA TCCGAGGGCA CCTGGAAAAC AACCCAGCTC TGGAGAAACT GCTGCCTCAT ATCCGGGGGA ATGTGGGCTT TGTGTTCACC AAGGAGGACC TCACTGAGAT CAGGGACATG TTGCTGGCCA ATAAGGTGCC AGCTGCTGCC CGTGCTGGTG CCATTGCCCC ATGTGAAGTC ACTGTGCCAG CCCAGAACAC TGGTCTCGGG CCCGAGAAGA CCTCCTTTTT CCAGGCTTTA GGTATCACCA CTAAAATCTC CAGGGGCACC ATTGAAATCC TGAGTGATGT GCAGCTGATC AAGACTGGAG ACAAAGTGGG AGCCAGCGAA GCCACGCTGC TGAACATGCT CAACATCTCC CCCTTCTCCT TTGGGCTGGT CATCCAGCAG GTGTTCGACA ATGGCAGCAT CTACAACCCT GAAGTGCTTG ATATCACAGA GGAAACTCTG CATTCTCGCT TCCTGGAGGG TGTCCGCAAT GTTGCCAGTG TCTGTCTGCA GATTGGCTAC CCAACTGTTG CATCAGTACC CCATTCTATC ATCAACGGGT ACAAACGAGT CCTGGCCTTG TCTGTGGAGA CGGATTACAC CTTCCCACTT GCTGAAAAGG TCAAGGCCTT CTTGGCTGAT CCATCTGCCT TTGTGGCTGC TGCCCCTGTG GCTGCTGCCA CCACAGCTGC TCCTGCTGCT GCTGCAGCCC CAGCTAAGGT TGAAGCCAAG GAAGAGTCGG AGGAGTCGGA CGAGGATATG GGATTTGGTC TCTTTGACTA ATCACCAAAA AGCAACCAAC TTAGCCAGTT TTATTTGCAA AACAAGGAAA TAAAGGCTTA CTTCTTTAAA AAGTAAAAAA AAAAAAAAAA AAAAAAAAA | 44 |

TABLE 1-continued

Plasma cell dyscrasia Biomarker/Housekeeper Sequence Information

| Gene Name | RefSeq Accession | Sequence | SEQ ID NO: |
|---|---|---|---|
| TFRC | NM_003234.3 | AGAGCGTCGG GATATCGGGT GGCGGCTCGG GACGGAGGAC GCGCTAGTGT GAGTGCGGGC TTCTAGAACT ACACCGACCC TCGTGTCCTC CCTTCATCCT GCGGGGCTGG CTGGAGCGGC CGCTCCGGTG CTGTCCAGCA GCCATAGGGA GCCGCACGGG GAGCGGGAAA GCGGTCGCGG CCCCAGGCGG GGCGGCCGGG ATGGAGCGGG GCCGCGAGCC TGTGGGGAAG GGGCTGTGGC GGCGCCTCGA GCGGCTGCAG GTTCTTCTGT GTGGCAGTTC AGAATGATGG ATCAAGCTAG ATCAGCATTC TCTAACTTGT TTGGTGGAGA ACCATTGTCA TATACCCGGT TCAGCCTGGC TCGGCAAGTA GATGGCGATA ACAGTCATGT GGAGATGAAA CTTGCTGTAG ATGAAGAAGA AAATGCTGAC AATAACACAA AGGCCAATGT CACAAAACCA AAAAGGTGTA GTGGAAGTAT CTGCTATGGG ACTATTGCTG TGATCGTCTT TTTCTTGATT GGATTTATGA TTGGCTACTT GGGCTATTGT AAAGGGGTAG AACCAAAAAC TGAGTGTGAG AGACTGGCAG GAACCGAGTC TCCAGTGAGG GAGGAGCCAG GAGAGGACTT CCCTGCAGCA CGTCGCTTAT ATTGGGATGA CCTGAAGAGA AAGTTGTCGG AGAAACTGGA CAGCACAGAC TTCACCGGCA CCATCAAGCT GCTGAATGAA AATTCATATG TCCCTCGTGA GGCTGGATCT CAAAAAGATG AAAATCTTGC GTTGTATGTT GAAAATCAAT TTCGTGAATT TAAACTCAGC AAAGTCTGGC GTGATCAACA TTTTGTTAAG ATTCAGGTCA AAGACAGCGC TCAAAACTCG GTGATCATAG TTGATAAGAA CGGTAGACTT GTTTACCTGG TGGAGAATCC TGGGGGTTAT GTGGCGTATA GTAAGGCTGC AACAGTTACT GGTAAACTGG TCCATGCTAA TTTTGGTACT AAAAAAGATT TTGAGGATTT ATACACTCCT GTGAATGGAT CTATAGTGAT TGTCAGAGCA GGGAAAATCA CCTTTGCAGA AAAGGTTGCA AATGCTGAAA GCTTAAATGC AATTGGTGTG TTGATATACA TGGACCAGAC TAAATTTCCC ATTGTTAACG CAGAACTTTC ATTCTTTGGA CATGCTCATC TGGGGACAGG TGACCCTTAC ACACCTGGAT TCCCTTCCTT CAATCACACT CAGTTTCCAC CATCTCGGTC ATCAGGATTG CCTAATATAC CTGTCCAGAC AATCTCCAGA GCTGCTGCAG AAAAGCTGTT TGGGAATATG GAAGGAGACT GTCCCTCTGA CTGGAAAACA GACTCTACAT GTAGGATGGT AACCTCAGAA AGCAAGAATG TGAAGCTCAC TGTGAGCAAT GTGCTGAAAG AGATAAAAAT TCTTAACATC TTTGGAGTTA TTAAAGGCTT TGTAGAACCA GATCACTATG TTGTAGTTGG GGCCCAGAGA GATGCATGGG GCCCTGGAGC TGCAAAATCC GGTGTAGGCA CAGCTCTCCT ATTGAAACTT GCCCAGATGT TCTCAGATAT GGTCTTAAAA GATGGGTTTC AGCCCAGCAG AAGCATTATC TTTGCCAGTT GGAGTGCTGG AGACTTTGGA TCGGTTGGTG CCACTGAATG GCTAGAGGGA TACCTTTCGT CCCTGCATTT AAAGGCTTTC ACTTATATTA ATCTGGATAA AGCGGTTCTT GGTACCAGCA ACTTCAAGGT TTCTGCCAGC CCACTGTTGT ATACGCTTAT TGAGAAAACA ATGCAAAATG TGAAGCATCC GGTTACTGGG CAATTTCTAT ATCAGGACAG CAACTGGGCC AGCAAAGTTG AGAAACTCAC TTTAGACAAT GCTGCTTTCC CTTTCCTTGC ATATTCTGGA ATCCCAGCAG TTTCTTTCTG TTTTTGCGAG GACACAGATT ATCCTTATTT GGGTACCACC ATGGACACCT ATAAGGAACT GATTGAGAGG ATTCCTGAGT TGAACAAAGT GGCACGAGCA GCTGCAGAGG TCGCTGGTCA GTTCGTGATT AAACTAACCC ATGATGTTGA ATTGAACCTG GACTATGAGA GGTACAACAG CCAACTGCTT TCATTTGTGA GGGATCTGAA CCAATACAGA GCAGACATAA AGGAAATGGG CCTGAGTTTA CAGTGGCTGT ATTCTGCTCG TGGAGACTTC TTCCGTGCTA CTTCCAGACT AACAACAGAT TTCGGGAATG CTGAGAAAAC AGACAGATTT GTCATGAAGA AACTCAATGA TCGTGTCATG AGAGTGGAGT ATCACTTCCT CTCTCCCTAC GTATCTCCAA AAGAGTCTCC TTTCCGACAT GTCTTCTGGG GCTCCGGCTC TCACACGCTG CCAGCTTTAC TGGAGAACTT GAAACTGCGT AAACAAAATA ACGGTGCTTT TAATGAAACG CTGTTCAGAA ACCAGTTGGC TCTAGCTACT TGGACTATTC AGGGAGCTGC AAATGCCCTC TCTGGTGACG TTTGGGACAT TGACAATGAG TTTTAAATGT GATACCCATA GCTTCCATGA GAACAGCAGG GTAGTCTGGT TTCTAGACTT GTGCTGATCG TGCTAAATTT TCAGTAGGGC TACAAAACCT GATGTTAAAA TTCCATCCCA TCATCTTGGT ACTACTAGAT GTCTTTAGGC AGCAGCTTTT AATACAGGGT AGATAACCTG TACTTCAAGT TAAAGTGAAT AACCACTTAA AAAATGTCCA TGATGGAATA TTCCCCTATC TCTAGAATTT TAAGTGCTTT GTAATGGGAA CTGCCTCTTT CCTGTTGTTG TTAATGAAAA TGTCAGAAAC CAGTTATGTG AATGATCTCT CTGAATCCTA AGGGCTGGTC TCTGCTGAAG | 45 |

TABLE 1-continued

Plasma cell dyscrasia Biomarker/Housekeeper Sequence Information

| Gene Name | RefSeq Accession | Sequence | SEQ ID NO: |
|---|---|---|---|
| | | GTTGTAAGTG GTCGCTTACT TTGAGTGATC CTCCAACTTC<br>ATTTGATGCT AAATAGGAGA TACCAGGTTG AAAGACCTTC<br>TCCAAATGAG ATCTAAGCCT TTCCATAAGG AATGTAGCTG<br>GTTTCCTCAT TCCTGAAAGA AACAGTTAAC TTTCAGAAGA<br>GATGGGCTTG TTTTCTTGCC AATGAGGTCT GAAATGGAGG<br>TCCTTCTGCT GGATAAAATG AGGTTCAACT GTTGATTGCA<br>GGAATAAGGC CTTAATATGT TAACCTCAGT GTCATTTATG<br>AAAAGAGGGG ACCAGAAGCC AAAGACTTAG TATATTTTCT<br>TTTCCTCTGT CCCTTCCCCC ATAAGCCTCC ATTTAGTTCT<br>TTGTTATTTT TGTTTCTTCC AAAGCACATT GAAAGAGAAC<br>CAGTTTCAGG TGTTTAGTTG CAGACTCAGT TTGTCAGACT<br>TTAAAGAATA ATATGCTGCC AAATTTTGGC CAAAGTGTTA<br>ATCTTAGGGG AGAGCTTTCT GTCCTTTTGG CACTGAGATA<br>TTTATTGTTT ATTTATCAGT GACAGAGTTC ACTATAAATG<br>GTGTTTTTTT AATAGAATAT AATTATCGGA AGCAGTGCCT<br>TCCATAATTA TGACAGTTAT ACTGTCGGTT TTTTTTAAAT<br>AAAAGCAGCA TCTGCTAATA AAACCCAACA GATACTGGAA<br>GTTTTGCATT TATGGTCAAC ACTTAAGGGT TTTAGAAAAC<br>AGCCGTCAGC CAAATGTAAT TGAATAAAGT TGAAGCTAAG<br>ATTTAGAGAT GAATTAAATT TAATTAGGGG TTGCTAAGAA<br>GCGAGCACTG ACCAGATAAG AATGCTGGTT TTCCTAAATG<br>CAGTGAATTG TGACCAAGTT ATAAATCAAT GTCACTTAAA<br>GGCTGTGGTA GTACTCCTGC AAAATTTTAT AGCTCAGTTT<br>ATCCAAGGTG TAACTCTAAT TCCCATTTTG CAAAATTTCC<br>AGTACCTTTG TCACAATCCT AACACATTAT CGGGAGCAGT<br>GTCTTCCATA ATGTATAAAG AACAAGGTAG TTTTTACCTA<br>CCACAGTGTC TGTATCGGAG ACAGTGATCT CCATATGTTA<br>CACTAAGGGT GTAAGTAATT ATCGGGAACA GTGTTTCCCA<br>TAATTTTCTT CATGCAATGA CATCTTCAAA GCTTGAAGAT<br>CGTTAGTATC TAACATGTAT CCCAACTCCT ATAATTCCCT<br>ATCTTTTAGT TTTAGTTGCA GAAACATTTT GTGGTCATTA<br>AGCATTGGGT GGGTAAATTC AACCACTGTA AAATGAAATT<br>ACTACAAAAT TTGAAATTTA GCTTGGGTTT TTGTTACCTT<br>TATGGTTTCT CCAGGTCCTC TACTTAATGA GATAGTAGCA<br>TACATTTATA ATGTTTGCTA TTGACAAGTC ATTTTAACTT<br>TATCACATTA TTTGCATGTT ACCTCCTATA AACTTAGTGC<br>GGACAAGTTT TAATCCAGAA TTGACCTTTT GACTTAAAGC<br>AGAGGGACTT TGTATAGAAG GTTTGGGGGC TGTGGGGAAG<br>GAGAGTCCCC TGAAGGTCTG ACACGTCTGC CTACCCATTC<br>GTGGTGATCA ATTAAATGTA GGTATGAATA AGTTCGAAGC<br>TCCGTGAGTG AACCATCATT ATAAACGTGA TGATCAGCTG<br>TTTGTCATAG GGCAGTTGGA AACGGCCTCC TAGGGAAAAG<br>TTCATAGGGT CTCTTCAGGT TCTTAGTGTC ACTTACCTAG<br>ATTTACAGCC TCACTTGAAT GTGTCACTAC TCACAGTCTC<br>TTTAATCTTC AGTTTTATCT TTAATCTCCT CTTTTATCTT<br>GGACTGACAT TTAGCGTAGC TAAGTGAAAA GGTCATAGCT<br>GAGATTCCTG GTTCGGGTGT TACGCACACG TACTTAAATG<br>AAAGCATGTG GCATGTTCAT CGTATAACAC AATATGAATA<br>CAGGGCATGC ATTTTGCAGC AGTGAGTCTC TTCAGAAAAC<br>CCTTTTCTAC AGTTAGGGTT GAGTTACTTC CTATCAAGCC<br>AGTACGTGCT AACAGGCTCA ATATTCCTGA ATGAAATATC<br>AGACTAGTGA CAAGCTCCTG GTCTTGAGAT GTCTTCTCGT<br>TAAGGAGATG GGCCTTTTGG AGGTAAAGGA TAAAATGAAT<br>GAGTTCTGTC ATGATTCACT ATTCTAGAAC TTGCATGACC<br>TTTACTGTGT TAGCTCTTTG AATGTTCTTG AAATTTTAGA<br>CTTTCTTTGT AAACAAATGA TATGTCCTTA TCATTGTATA<br>AAAGCTGTTA TGTGCAACAG TGTGGAGATT CCTTGTCTGA<br>TTTAATAAAA TACTTAAACA CTGAAAAAAA AAAA | |
| 18S | X03205.1 | TACCTGGTTG ATCCTGCCAG TAGCATATGC TTGTCTCAAA<br>GATTAAGCCA TGCATGTCTA AGTACGCACG GCCGGTACAG<br>TGAAACTGCG AATGGCTCAT TAAATCAGTT ATGGTTCCTT<br>TGGTCGCTCG CTCCTCTCCC ACTTGGATAA CTGTGGTAAT<br>TCTAGAGCTA ATACATGCCG ACGGGCGCTG ACCCCCTTCG<br>CGGGGGGGAT GCGTGCATTT ATCAGATCAA AACCAACCCG<br>GTCAGCCCCT CTCCGGCCCC GGCCGGGGGG CGGGCGCCGG<br>CGGCTTTGGT GACTCTAGAT AACCTCGGGC CGATCGCACG<br>CCCCCCGTGG CGGCGACGAC CCATTCGAAC GTCTGCCCTA<br>TCAACTTTCG ATGGTAGTCG CCGTGCCTAC CATGGTGACC<br>ACGGGTGACG GGGAATCAGG GTTCGATTCC GGAGAGGGAG<br>CCTGAGAAAC GGCTACCACA TCCAAGGAAG GCAGCAGGCG<br>CGCAAATTAC CCACTCCCGA CCCGGGGAGG TAGTGACGAA<br>AAATAACAAT ACAGGACTCT TTCGAGGCCC TGTAATTGGA<br>ATGAGTCCAC TTTAAATCCT TTAACGAGGA TCCATTGGAG | 46 |

TABLE 1-continued

Plasma cell dyscrasia Biomarker/Housekeeper Sequence Information

| Gene Name | RefSeq Accession | Sequence | SEQ ID NO: |
|---|---|---|---|
| | | GGCAAGTCTG GTGCCAGCAG CCGCGGTAAT TCCAGCTCCA ATAGCGTATA TTAAAGTTGC TGCAGTTAAA AAGCTCGTAG TTGGATCTTG GGAGCGGGCG GGCGGTCCGC CGCGAGGCGA GCCACCGCCC GTCCCCGCCC CTTGCCTCTC GGCGCCCCCT CGATGCTCTT AGCTGAGTGT CCCGCGGGGC CCGAAGCGTT TACTTTGAAA AAATTAGAGT GTTCAAAGCA GGCCCGAGCC GCCTGGATAC CGCAGCTAGG AATAATGGAA TAGGACCGCG GTTCTATTTT GTTGGTTTTC GGAACTGAGG CCATGATTAA GAGGGACGGC CGGGGGCATT CGTATTGCGC CGCTAGAGGT GAAATTCTTG GACCGGCGCA AGACGGACCA GAGCGAAAGC ATTTGCCAAG AATGTTTTCA TTAATCAAGA ACGAAAGTCG GAGGTTCGAA GACGATCAGA TACCGTCGTA GTTCCGACCA TAAACGATGC CGACCGGCGA TGCGGCGGCG TTATTCCCAT GACCCGCCGG GCAGCTTCCG GGAAACCAAA GTCTTTGGGT TCCGGGGGGA GTATGGTTGC AAAGCTGAAA CTTAAAGGAA TTGACGGAAG GGCACCACCA GGAGTGGAGC CTGCGGCTTA ATTTGACTCA ACACGGGAAA CCTCACCCGG CCCGGACACG GACAGGATTG ACAGATTGAT AGCTCTTTCT CGATTCCGTG GGTGGTGGTG CATGGCCGTT CTTAGTTGGT GGAGCGATTT GTCTGGTTAA TTCCGATAAC GAACGAGACT CTGGCATGCT AACTAGTTAC GCGACCCCCG AGCGGTCGGC GTCCCCCAAC TTCTTAGAGG GACAAGTGGC GTTCAGCCAC CCGAGATTGA GCAATAACAG GTCTGTGATG CCCTTAGATG TCCGGGGCTG CACGCGCGCT ACACTGACTG GCTCAGCGTG TGCCTACCCT ACGCCGGCAG GCGCGGGTAA CCCGTTGAAC CCCATTCGTG ATGGGGATCG GGGATTGCAA TTATTCCCCA TGAACGAGGA ATTCCCAGTA AGTGCGGGTC ATAAGCTTGC GTTGATTAAG TCCCTGCCCT TTGTACACAC CGCCCGTCGC TACTACCGAT TGGATGGTTT AGTGAGGCCC TCGGATCGGC CCCGCCGGGG TCGGCCCACG GCCCTGGCGG AGCGCTGAGA AGACGGTCGA ACTTGACTAT CTAGAGGAAG TAAAAGTCGT AACAAGGTTT CCGTAGGTGA ACCTGCGGAA GGATCATTA | |
| PPIA | NM_021130.4 | GGGGCCGAAC GTGGTATAAA AGGGGCGGGA GGCCAGGCTC GTGCCGTTTT GCAGACGCCA CCGCCGAGGA AAACCGTGTA CTATTAGCCA TGGTCAACCC CACCGTGTTC TTCGACATTG CCGTCGACGG CGAGCCCTTG GGCCGCGTCT CCTTTGAGCT GTTTGCAGAC AAGGTCCCAA AGACAGCAGA AAATTTTCGT GCTCTGAGCA CTGGAGAGAA AGGATTTGGT TATAAGGGTT CCTGCTTTCA CAGAATTATT CCAGGGTTTA TGTGTCAGGG TGGTGACTTC ACACGCCATA ATGGCACTGG TGGCAAGTCC ATCTATGGGG AGAAATTTGA AGATGAGAAC TTCATCCTAA AGCATACGGG TCCTGGCATC TTGTCCATGG CAAATGCTGG ACCCAACACA AATGGTTCCC AGTTTTTCAT CTGCACTGCC AAGACTGAGT GGTTGGATGG CAAGCATGTG GTGTTTGGCA AAGTGAAAGA AGGCATGAAT ATTGTGGAGG CCATGGAGCG CTTTGGGTCC AGGAATGGCA AGACCAGCAA GAAGATCACC ATTGCTGACT GTGGACAACT CGAATAAGTT TGACTTGTGT TTTATCTTAA CCACCAGATC ATTCCTTCTG TAGCTCAGGA GAGCACCCCT CCACCCCATT TGCTCGCAGT ATCCTAGAAT CTTTGTGCTC TCGCTGCAGT TCCCTTTGGG TTCCATGTTT TCCTTGTTCC CTCCCATGCC TAGCTGGATT GCAGAGTTAA GTTTATGATT ATGAAATAAA AACTAAATAA CAATTGTCCT CGTTTGAGTT AAGAGTGTTG ATGTAGGCTT TATTTTAAGC AGTAATGGGT TACTTCTGAA ACATCACTTG TTTGCTTAAT TCTACACAGT ACTTAGATTT TTTTTACTTT CCAGTCCCAG GAAGTGTCAA TGTTTGTTGA GTGGAATATT GAAAATGTAG GCAGCAACTG GGCATGGTGG CTCACTGTCT GTAATGTATT ACCTGAGGCA GAAGACCACC TGAGGGTAGG AGTCAAGATC AGCCTGGGCA ACATAGTGAG ACGCTGTCTC TACAAAAAAT AATTAGCCTG GCCTGGTGGT GCATGCCTAG TCCTAGCTGA TCTGGAGGCT GACGTGGGAG GATTGCTTGA GCCTAGAGTG AGCTATTATC ATGCCACTGT ACAGCCTGGG TGTTCACAGA TCTTGTGTCT CAAAGGTAGG CAGAGGCAGG AAAAGCAAGG AGCCAGAATT AAGAGGTTGG GTCAGTCTGC AGTGAGTTCA TGCATTTAGA GGTGTTCTTC AAGATGACTA ATGTCAAAAA TTGAGACATC TGTTGCGGTT TTTTTTTTTT TTTTTTCCCC TGGAATGCAG TGGCGTGATC TCAGCTCACT GCAGCCTCCG CCTCCTGGGT TCAAGTGATT CTAGTGCCTC AGCCTCCTGA GTAGCTGGGA TAATGGGCGT GTGCCACCAT GCCCAGCTAA TTTTTGTATT TTTAGTATAG ATGGGGTTTC ATCATTTTGA CCAGGCTGGT CTCAAACTCT TGACCTCAGC TGATGCGCCT GCCTTGGCCT CCCAAACTGC TGAGATTACA GATGTGAGCC ACCGCACCCT ACCTCATTTT CTGTAACAAA GCTAAGCTTG | 47 |

TABLE 1-continued

| Plasma cell dyscrasia Biomarker/Housekeeper Sequence Information | | | |
|---|---|---|---|
| Gene Name | RefSeq Accession | Sequence | SEQ ID NO: |
| | | AACACTGTTG ATGTTCTTGA GGGAAGCATA TTGGGCTTTA GGCTGTAGGT CAAGTTTATA CATCTTAATT ATGGTGGAAT TCCTATGTAG AGTCTAAAAA GCCAGGTACT TGGTGCTACA GTCAGTCTCC CTGCAGAGGG TTAAGGCGCA GACTACCTGC AGTGAGGAGG TACTGCTTGT AGCATATAGA GCCTCTCCCT AGCTTTGGTT ATGGAGGCTT TGAGGTTTTG CAAACCTGAC CAATTTAAGC CATAAGATCT GGTCAAAGGG ATACCCTTCC CACTAAGGAC TTGGTTTCTC AGGAAATTAT ATGTACAGTG CTTGCTGGCA GTTAGATGTC AGGACAATCT AAGCTGAGAA AACCCCTTCT CTGCCCACCT TAACAGACCT CTAGGGTTCT TAACCCAGCA ATCAAGTTTG CCTATCCTAG AGGTGGCGGA TTTGATCATT TGGTGTGTTG GGCAATTTTT GTTTTACTGT CTGGTTCCTT CTGCGTGAAT TACCACCACC ACCACTTGTG CATCTCAGTC TTGTGTGTTG TCTGGTTACG TATTCCCTGG GTGATACCAT TCAATGTCTT AATGTACTTG TGGCTCAGAC CTGAGTGCAA GGTGGAAATA AACATCAAAC ATCTTTTCAT TATCCCTA | |
| PGK1 | NM_000291.3 | GAGAGCAGCG GCCGGGAAGG GGCGGTGCGG GAGGCGGGGT GTGGGGCGGT AGTGTGGGCC CTGTTCCTGC CCGCGCGGTG TTCCGCATTC TGCAAGCCTC CGGAGCGCAC GTCGGCAGTC GGCTCCCTCG TTGACCGAAT CACCGACCTC TCTCCCCAGC TGTATTTCCA AAATGTCGCT TTCTAACAAG CTGACGCTGG ACAAGCTGGA CGTTAAAGGG AAGCGGGTCG TTATGAGAGT CGACTTCAAT GTTCCTATGA AGAACAACCA GATAACAAAC AACCAGAGGA TTAAGGCTGC TGTCCCAAGC ATCAAATTCT GCTTGGACAA TGGAGCCAAG TCGGTAGTCC TTATGAGCCA CCTAGGCCGG CCTGATGGTG TGCCCATGCC TGACAAGTAC TCCTTAGAGC CAGTTGCTGT AGAACTCAAA TCTCTGCTGG GCAAGGATGT TCTGTTCTTG AAGGACTGTG TAGGCCCAGA AGTGGAGAAA GCCTGTGCCA ACCCAGCTGC TGGGTCTGTC ATCCTGCTGG AGAACCTCCG CTTTCATGTG GAGGAAGAAG GGAAGGGAAA AGATGCTTCT GGGAACAAGG TTAAAGCCGA GCCAGCCAAA ATAGAAGCTT TCCGAGCTTC ACTTTCCAAG CTAGGGGATG TCTATGTCAA TGATGCTTTT GGCACTGCTC ACAGAGCCCA CAGCTCCATG GTAGGAGTCA ATCTGCCACA GAAGGCTGGT GGGTTTTTGA TGAAGAAGGA GCTGAACTAC TTTGCAAAGG CCTTGGAGAG CCCAGAGCGA CCCTTCCTGG CCATCCTGGG CGGAGCTAAA GTTGCAGACA AGATCCAGCT CATCAATAAT ATGCTGGACA AAGTCAATGA GATGATTATT GGTGGTGGAA TGGCTTTTAC CTTCCTTAAG GTGCTCAACA ACATGGAGAT TGGCACTTCT CTGTTTGATG AAGAGGGAGC CAAGATTGTC AAAGACCTAA TGTCCAAAGC TGAGAAGAAT GGTGTGAAGA TTACCTTGCC TGTTGACTTT GTCACTGCTG ACAAGTTTGA TGAGAATGCC AAGACTGGCC AAGCCACTGT GGCTTCTGGC ATACCTGCTG GCTGGATGGG CTTGGACTGT GGTCCTGAAA GCAGCAAGAA GTATGCTGAG GCTGTCACTC GGGCTAAGCA GATTGTGTGG AATGGTCCTG TGGGGGTATT TGAATGGGAA GCTTTTGCCC GGGGAACCAA AGCTCTCATG GATGAGGTGG TGAAAGCCAC TTCTAGGGGC TGCATCACCA TCATAGGTGG TGGAGACACT GCCACTTGCT GTGCCAAATG GAACACGGAG GATAAAGTCA GCCATGTGAG CACTGGGGGT GGTGCCAGTT TGGAGCTCCT GGAAGGTAAA GTCCTTCCTG GGGTGGATGC TCTCAGCAAT ATTTAGTACT TTCCTGCCTT TTAGTTCCTG TGCACAGCCC CTAAGTCAAC TTAGCATTTT CTGCATCTCC ACTTGGCATT AGCTAAAACC TTCCATGTCA AGATTCAGCT AGTGGCCAAG AGATGCAGTG CCAGGAACCC TTAAACAGTT GCACAGCATC TCAGCTCATC TTCACTGCAC CCTGGATTTG CATACATTCT TCAAGATCCC ATTTGAATTT TTTAGTGACT AAACCATTGT GCATTCTAGA GTGCATATAT TTATATTTTG CCTGTTAAAA AGAAAGTGAG CAGTGTTAGC TTAGTTCTCT TTTGATGTAG GTTATTATGA TTAGCTTTGT CACTGTTTCA CTACTCAGCA TGGAAACAAG ATGAAATTCC ATTTGTAGGT AGTGAGACAA AATTGATGAT CCATTAAGTA AACAATAAAA GTGTCCATTG AAACCGTGAT TTTTTTTTTT TTCCTGTCAT ACTTTGTTAG GAAGGGTGAG AATAGAATCT TGAGGAACGG ATCAGATGTC TATATTGCTG AATGCAAGAA GTGGGGCAGC AGCAGTGGAG AGATGGGACA ATTAGATAAA TGTCCATTCT TTATCAAGGG CCTACTTTAT GGCAGACATT GTGCTAGTGC TTTTATTCTA ACTTTTATTT TTATCAGTTA CACATGATCA TAATTTAAAA AGTCAAGGCT TATAACAAAA AAGCCCCAGC CCATTCCTCC CATTCAAGAT TCCCACTCCC CAGAGGTGAC CACTTTCAAC TCTTGAGTTT TTCAGGTATA TACCTCCATG TTTCTAAGTA ATATGCTTAT ATTGTTCACT | 48 |

TABLE 1-continued

Plasma cell dyscrasia Biomarker/Housekeeper Sequence Information

| Gene Name | RefSeq Accession | Sequence | SEQ ID NO: |
|---|---|---|---|
| | | TCTTTTTTTT TTATTTTTTA AAGAAATCTA TTTCATACCA TGGAGGAAGG CTCTGTTCCA CATATATTTC CACTTCTTCA TTCTCTCGGT ATAGTTTTGT CACAATTATA GATTAGATCA AAAGTCTACA TAACTAATAC AGCTGAGCTA TGTAGTATGC TATGATTAAA TTTACTTATG TAAAAAAAAA AAAAAAAAA | |
| RPL13A | NM_012423.3 | CACTTCTGCC GCCCCTGTTT CAAGGGATAA GAAACCCTGC GACAAAACCT CCTCCTTTTC CAAGCGGCTG CCGAAGATGG CGGAGGTGCA GGTCCTGGTG CTTGATGGTC GAGGCCATCT CCTGGGCCGC CTGGCGGCCA TCGTGGCTAA ACAGGTACTG CTGGGCCGGA AGGTGGTGGT CGTACGCTGT GAAGGCATCA ACATTTCTGG CAATTTCTAC AGAAACAAGT TGAAGTACCT GGCTTTCCTC CGCAAGCGGA TGAACACCAA CCCTTCCCGA GGCCCCTACC ACTTCCGGGC CCCCAGCCGC ATCTTCTGGC GGACCGTGCG AGGTATGCTG CCCCACAAAA CCAAGCGAGG CCAGGCCGCT CTGGACCGTC TCAAGGTGTT TGACGGCATC CCACCGCCCT ACGACAAGAA AAAGCGGATG GTGGTTCCTG CTGCCCTCAA GGTCGTGCGT CTGAAGCCTA CAAGAAAGTT TGCCTATCTG GGGCGCCTGG CTCACGAGGT TGGCTGGAAG TACCAGGCAG TGACAGCCAC CCTGGAGGAG AAGAGGAAAG AGAAAGCCAA GATCCACTAC CGGAAGAAGA AACAGCTCAT GAGGCTACGG AAACAGGCCG AGAAGAACGT GGAGAAGAAA ATTGACAAAT ACACAGAGGT CCTCAAGACC CACGGACTCC TGGTCTGAGC CCAATAAAGA CTGTTAATTC CTCATGCGTT GCCTGCCCTT CCTCCATTGT TGCCCTGGAA TGTACGGGAC CCAGGGGCAG CAGCAGTCCA GGTGCCACAG GCAGCCCTGG GACATAGGAA GCTGGGAGCA AGGAAAGGGT CTTAGTCACT GCCTCCCGAA GTTGCTTGAA AGCACTCGGA GAATTGTGCA GGTGTCATTT ATCTATGACC AATAGGAAGA GCAACCAGTT ACTATGAGTG AAAGGGAGCC AGAAGACTGA TTGGAGGGCC CTATCTTGTG AGTGGGGCAT CTGTTGGACT TTCCACCTGG TCATATACTC TGCAGCTGTT AGAATGTGCA AGCACTTGGG GACAGCATGA GCTTGCTGTT GTACACAGGG TATTTCTAGA AGCAGAAATA GACTGGGAAG ATGCACAACC AAGGGGTTAC AGGCATCGCC CATGCTCCTC ACCTGTATTT TGTAATCAGA AATAAATTGC TTTTAAAGAA AAAAAAAAAA AAAAAA | 49 |
| B2M | NM_004048.2 | AATATAAGTG GAGGCGTCGC GCTGGCGGGC ATTCCTGAAG CTGACAGCAT TCGGGCCGAG ATGTCTCGCT CCGTGGCCTT AGCTGTGCTC GCGCTACTCT CTCTTTCTGG CCTGGAGGCT ATCCAGCGTA CTCCAAAGAT TCAGGTTTAC TCACGTCATC CAGCAGAGAA TGGAAAGTCA AATTTCCTGA ATTGCTATGT GTCTGGGTTT CATCCATCCG ACATTGAAGT TGACTTACTG AAGAATGGAG AGAGAATTGA AAAAGTGGAG CATTCAGACT TGTCTTTCAG CAAGGACTGG TCTTTCTATC TCTTGTACTA CACTGAATTC ACCCCCACTG AAAAAGATGA GTATGCCTGC CGTGTGAACC ATGTGACTTT GTCACAGCCC AAGATAGTTA AGTGGGATCG AGACATGTAA GCAGCATCAT GGAGGTTTGA AGATGCCGCA TTTGGATTGG ATGAATTCCA AATTCTGCTT GCTTGCTTTT TAATATTGAT ATGCTTATAC ACTTACACTT TATGCACAAA ATGTAGGGTT ATAATAATGT TAACATGGAC ATGATCTTCT TTATAATTCT ACTTTGAGTG CTGTCTCCAT GTTTGATGTA TCTGAGCAGG TTGCTCCACA GGTAGCTCTA GGAGGGCTGG CAACTTAGAG GTGGGGAGCA GAGAATTCTC TTATCCAACA TCAACATCTT GGTCAGATTT GAACTCTTCA ATCTCTTGCA CTCAAAGCTT GTTAAGATAG TTAAGCGTGC ATAAGTTAAC TTCCAATTTA CATACTCTGC TTAGAATTTG GGGGAAAATT TAGAAATATA ATTGACAGGA TTATTGGAAA TTTGTTATAA TGAATGAAAC ATTTTGTCAT ATAAGATTCA TATTTACTTC TTATACATTT GATAAAGTAA GGCATGGTTG TGGTTAATCT GGTTTATTTT TGTTCCACAA GTTAAATAAA TCATAAAACT TGATGTGTTA TCTCTTA | 50 |
| YWHAZ | NM_003406.3 | CTTTCTCCTT CCCCTTCTTC CGGGCTCCCG TCCCGGCTCA TCACCCGGCC TGTGGCCCAC TCCCACCGCC AGCTGGAACC CTGGGGACTA CGACGTCCCT CAAACCTTGC TTCTAGGAGA TAAAAAGAAC ATCCAGTCAT GGATAAAAAT GAGCTGGTTC AGAAGGCCAA ACTGGCCGAG CAGGCTGAGC GATATGATGA CATGGCAGCC TGCATGAAGT CTGTAACTGA GCAAGGAGCT GAATTATCCA ATGAGGAGAG GAATCTTCTC TCAGTTGCTT ATAAAAATGT TGTAGGAGCC CGTAGGTCAT CTTGGAGGGT CGTCTCAAGT ATTGAACAAA AGACGGAAGG TGCTGAGAAA AAACAGCAGA TGGCTCGAGA ATACAGAGAG AAAATTGAGA CGGAGCTAAG AGATATCTGC AATGATGTAC TGTCTCTTTT | 51 |

TABLE 1-continued

Plasma cell dyscrasia Biomarker/Housekeeper Sequence Information

| Gene Name | RefSeq Accession | Sequence | SEQ ID NO: |
|---|---|---|---|
| | | GGAAAAGTTC TTGATCCCCA ATGCTTCACA AGCAGAGAGC AAAGTCTTCT ATTTGAAAAT GAAAGGAGAT TACTACCGTT ACTTGGCTGA GGTTGCCGCT GGTGATGACA AGAAAGGGAT TGTCGATCAG TCACAACAAG CATACCAAGA AGCTTTTGAA ATCAGCAAAA AGGAAATGCA ACCAACACAT CCTATCAGAC TGGGTCTGGC CCTTAACTTC TCTGTGTTCT ATTATGAGAT TCTGAACTCC CCAGAGAAAG CCTGCTCTCT TGCAAAGACA GCTTTTGATG AAGCCATTGC TGAACTTGAT ACATTAAGTG AAGAGTCATA CAAAGACAGC ACGCTAATAA TGCAATTACT GAGAGACAAC TTGACATTGT GGACATCGGA TACCCAAGGA GACGAAGCTG AAGCAGGAGA AGGAGGGGAA AATTAACCGG CCTTCCAACT TTTGTCTGCC TCATTCTAAA ATTTACACAG TAGACCATTT GTCATCCATG CTGTCCCACA AATAGTTTTT TGTTTACGAT TTATGACAGG TTTATGTTAC TTCTATTTGA ATTTCTATAT TTCCCATGTG GTTTTTATGT TTAATATTAG GGGAGTAGAG CCAGTTAACA TTTAGGGAGT TATCTGTTTT CATCTTGAGG TGGCCAATAT GGGGATGTGG AATTTTTATA CAAGTTATAA GTGTTTGGCA TAGTACTTTT GGTACATTGT GGCTTCAAAA GGGCCAGTGT AAAACTGCTT CCATGTCTAA GCAAAGAAAA CTGCCTACAT ACTGGTTTGT CCTGGCGGGG AATAAAAGGG ATCATTGGTT CCAGTCACAG GTGTAGTAAT TGTGGGTACT TTAAGGTTTG GAGCACTTAC AAGGCTGTGG TAGAATCATA CCCCATGGAT ACCACATATT AAACCATGTA TATCTGTGGA ATACTCAATG TGTACACCTT TGACTACAGC TGCAGAAGTG TTCCTTTAGA CAAAGTTGTG ACCCATTTTA CTCTGGATAA GGGCAGAAAC GGTTCACATT CCATTATTTG TAAAGTTACC TGCTGTTAGC TTTCATTATT TTTGCTACAC TCATTTTATT TGTATTTAAA TGTTTTAGGC AACCTAAGAA CAAATGTAAA AGTAAAGATG CAGGAAAAAT GAATTGCTTG GTATTCATTA CTTCATGTAT ATCAAGCACA GCAGTAAAAC AAAAACCCAT GTATTTAACT TTTTTTTAGG ATTTTTGCTT TTGTGATTTT TTTTTTTTTG ATACTTGCCT AACATGCATG TGCTGTAAAA ATAGTTAACA GGGAAATAAC TTGAGATGAT GGCTAGCTTT GTTTAATGTC TTATGAAATT TTCATGAACA ATCCAAGCAT AATTGTTAAG AACACGTGTA TTAAATTCAT GTAAGTGGAA TAAAAGTTTT ATGAATGGAC TTTTCAACTA CTTTCTCTAC AGCTTTTCAT GTAAATTAGT CTTGGTTCTG AAACTTCTCT AAAGGAAATT GTACATTTTT TGAAATTTAT TCCTTATTCC CTCTTGGCAG CTAATGGGCT CTTACCAAGT TTAAACACAA AATTTATCAT AACAAAAATA CTACTAATAT AACTACTGTT TCCATGTCCC ATGATCCCCT CTCTTCCTCC CCACCCTGAA AAAAATGAGT TCCTATTTTT TCTGGGAGAG GGGGGGATTG ATTAGAAAAA AATGTAGTGT GTTCCATTTA AAATTTTGGC ATATGGCATT TTCTAACTTA GGAAGCCACA ATGTTCTTGG CCCATCATGA CATTGGGTAG CATTAACTGT AAGTTTTGTG CTTCCAAATC ACTTTTTGGT TTTTAAGAAT TTCTTGATAC TCTTATAGCC TGCCTTCAAT TTTGATCCTT TATTCTTTCT ATTTGTCAGG TGCACAAGAT TACCTTCCTG TTTTAGCCTT CTGTCTTGTC ACCAACCATT CTTACTTGGT GGCCATGTAC TTGGAAAAAG GCCGCATGAT CTTTCTGGCT CCACTCAGTG TCTAAGGCAC CCTGCTTCCT TTGCTTGCAT CCCACAGACT ATTTCCCTCA TCCTATTTAC TGCAGCAAAT CTCTCCTTAG TTGATGAGAC TGTGTTTATC TCCCTTTAAA ACCCTACCTA TCCTGAATGG TCTGTCATTG TCTGCCTTTA AAATCCTTCC TCTTTCTTCC TCCTCTATTC TCTAAATAAT GATGGGGCTA AGTTATACCC AAAGCTCACT TTACAAAATA TTTCCTCAGT ACTTTGCAGA AAACACCAAA CAAAAATGCC ATTTTAAAAA AGGTGTATTT TTTCTTTTAG AATGTAAGCT CCTCAAGAGC AGGGACAATG TTTTCTGTAT GTTCTATTGT GCCTAGTACA CTGTAAATGC TCAATAAATA TTGATGATGG GAGGCAGTGA GTCTTGATGA TAAGGGTGAG AAACTGAAAT CCCAAACACT GTTTTGTTGC TTGTTTTATT ATGACCTCAG ATTAAATTGG GAAATATTGG CCCTTTTGAA TAATTGTCCC AAATATTACA TTCAAATAAA AGTGCAATGG AGAAAAAAAA AAA | |
| SDHA | NM_004168.3 | ACTGCAGCCC CGCTCGACTC CGGCGTGGTG CGCAGGCGCG GTATCCCCCC TCCCCCGCCA GCTCGACCCC GGTGTGGTGC GCAGGCGCAG TCTGCGCAGG GACTGGCGGG ACTGCGCGGC GGCAACAGCA GACATGTCGG GGGTCCGGGG CCTGTCGCGG CTGCTGAGCG CTCGGCGCCT GGCGCTGGCC AAGGCGTGGC CAACAGTGTT GCAAACAGGA ACCCGAGGTT TTCACTTCAC TGTTGATGGG AACAAGAGGG CATCTGCTAA AGTTTCAGAT TCCATTTCTG CTCAGTATCC AGTAGTGGAT CATGAATTTG | 52 |

TABLE 1-continued

Plasma cell dyscrasia Biomarker/Housekeeper Sequence Information

| Gene Name | RefSeq Accession | Sequence | SEQ ID NO: |
|---|---|---|---|
| | | ATGCAGTGGT GGTAGGCGCT GGAGGGGCAG GCTTGCGAGC<br>TGCATTTGGC CTTTCTGAGG CAGGGTTTAA TACAGCATGT<br>GTTACCAAGC TGTTTCCTAC CAGGTCACAC ACTGTTGCAG<br>CACAGGGAGG AATCAATGCT GCTCTGGGGA ACATGGAGGA<br>GGACAACTGG AGGTGGCATT TCTACGACAC CGTGAAGGGC<br>TCCGACTGGC TGGGGGACCA GGATGCCATC CACTACATGA<br>CGGAGCAGGC CCCCGCCGCC GTGGTCGAGC TAGAAAATTA<br>TGGCATGCCG TTTAGCAGAA CTGAAGATGG GAAGATTTAT<br>CAGCGTGCAT TTGGTGGACA GAGCCTCAAG TTTGGAAAGG<br>GCGGGCAGGC CCATCGGTGC TGCTGTGTGG CTGATCGGAC<br>TGGCCACTCG CTATTGCACA CCTTATATGG AAGGTCTCTG<br>CGATATGATA CCAGCTATTT TGTGGAGTAT TTTGCCTTGG<br>ATCTCCTGAT GGAGAATGGG GAGTGCCGTG GTGTCATCGC<br>ACTGTGCATA GAGGACGGGT CCATCCATCG CATAAGAGCA<br>AAGAACACTG TTGTTGCCAC AGGAGGCTAC GGGCGCACCT<br>ACTTCAGCTG CACGTCTGCC CACACCAGCA CTGGCGACGG<br>CACGGCCATG ATCACCAGGG CAGGCCTTCC TTGCCAGGAC<br>CTAGAGTTTG TTCAGTTCCA CCCTACAGGC ATATATGGTG<br>CTGGTTGTCT CATTACGGAA GGATGTCGTG GAGAGGGAGG<br>CATTCTCATT AACAGTCAAG GCGAAAGGTT TATGGAGCGA<br>TACGCCCCTG TCGCGAAGGA CCTGGCGTCT AGAGATGTGG<br>TGTCTCGGTC CATGACTCTG GAGATCCGAG AAGGAAGAGG<br>CTGTGGCCCT GAGAAAGATC ACGTCTACCT GCAGCTGCAC<br>CACCTACCTC CAGAGCAGCT GGCCACGCGC CTGCCTGGCA<br>TTTCAGAGAC AGCCATGATC TTCGCTGGCG TGGACGTCAC<br>GAAGGAGCCG ATCCCTGTCC TCCCCACCGT GCATTATAAC<br>ATGGGCGGCA TTCCCACCAA CTACAAGGGG CAGGTCCTGA<br>GGCACGTGAA TGGCCAGGAT CAGATTGTGC CCGGCCTGTA<br>CGCCTGTGGG GAGGCCGCCT GTGCCTCGGT ACATGGTGCC<br>AACCGCCTCG GGGCAAACTC GCTCTTGGAC CTGGTTGTCT<br>TTGGTCGGGC ATGTGCCCTG AGCATCGAAG AGTCATGCAG<br>GCCTGGAGAT AAAGTCCCTC CAATTAAACC AAACGCTGGG<br>GAAGAATCTG TCATGAATCT TGACAAATTG AGATTTGCTG<br>ATGGAAGCAT AAGAACATCG GAACTGCGAC TCAGCATGCA<br>GAAGTCAATG CAAAATCATG CTGCCGTGTT CCGTGTGGGA<br>AGCGTGTTGC AAGAAGGTTG TGGGAAAATC AGCAAGCTCT<br>ATGGAGACCT AAAGCACCTG AAGACGTTCG ACCGGGGAAT<br>GGTCTGGAAC ACGGACCTGG TGGAGACCCT GGAGCTGCAG<br>AACCTGATGC TGTGTGCGCT GCAGACCATC TACGGAGCAG<br>AGGCACGGAA GGAGTCACGG GGCGCGCATG CCAGGGAAGA<br>CTACAAGGTG CGGATTGATG AGTACGATTA CTCCAAGCCC<br>ATCCAGGGGC AACAGAAGAA GCCCTTTGAG GAGCACTGGA<br>GGAAGCACAC CCTGTCCTAT GTGGACGTTG GCACTGGGAA<br>GGTCACTCTG GAATATAGAC CCGTGATCGA CAAAACTTTG<br>AACGAGGCTG ACTGTGCCAC CGTCCCGCCA GCCATTCGCT<br>CCTACTGATG AGACAAGATG TGGTGATGAC AGAATCAGCT<br>TTTGTAATTA TGTATAATAG CTCATGCATG TGTCCATGTC<br>ATAACTGTCT TCATACGCTT CTGCACTCTG GGGAAGAAGG<br>AGTACATTGA AGGGAGATTG GCACCTAGTG GCTGGGAGCT<br>TGCCAGGAAC CCAGTGGCCA GGGAGCGTGG CACTTACCTT<br>TGTCCCTTGC TTCATTCTTG TGAGATGATA AAACTGGGCA<br>CAGCTCTTAA ATAAAATATA AATGAACAAA CTTTCTTTTA<br>TTTCCAAATC CATTTGAAAT ATTTTACTGT TGTGACTTTA<br>GTCATATTTG TTGACCTAAA AATCAAATGT AATCTTTGTA<br>TTGTGTTACA TCAAAATCCA GATATTTTGT ATAGTTTCTT<br>TTTTCTTTTT CTTTTCTTTT TTTTTTTTGA GACAGGATCG<br>GTGCAGTAGT ACAATCACAG CTCACTGCAG CCTCAAACTC<br>CTGGGCAGCT CAGGTGATCT TCCTGACTCA GCCTTCTGAG<br>TAGTTGGGGC TACAGGTGTG CACCACCATG CCCAGCTCAT<br>TTATTTTGTA ATTGTAGGGA CAGGGTCTCA CTGTGTTGCC<br>TAGGCTGGTC TCAAGTGATC CTCCCTCCTT GGCCTCCCAA<br>GGTGCTGGAA TTATAGGTGT GAACAAACCA AAAAAAAAAA<br>AAA | |
| HPRT1 | NM_000194.2 | GGCGGGGCCT GCTTCTCCTC AGCTTCAGGC GGCTGCGACG<br>AGCCCTCAGG CGAACCTCTC GGCTTTCCCG CGCGGCGCCG<br>CCTCTTGCTG CGCCTCCGCC TCCTCCTCTG CTCCGCCACC<br>GGCTTCCTCC TCCTGAGCAG TCAGCCCGCG CGCCGGCCGG<br>CTCCGTTATG GCGACCCGCA GCCCTGGCGT CGTGATTAGT<br>GATGATGAAC CAGGTTATGA CCTTGATTTA TTTTGCATAC<br>CTAATCATTA TGCTGAGGAT TTGGAAAGGG TGTTTATTCC<br>TCATGGACTA ATTATGGACA GGACTGAACG TCTTGCTCGA<br>GATGTGATGA AGGAGATGGG AGGCCATCAC ATTGTAGCCC<br>TCTGTGTGCT CAAGGGGGGC TATAAATTCT TTGCTGACCT | 53 |

TABLE 1-continued

| Gene Name | RefSeq Accession | Sequence | SEQ ID NO: |
|---|---|---|---|
| | | GCTGGATTAC ATCAAAGCAC TGAATAGAAA TAGTGATAGA TCCATTCCTA TGACTGTAGA TTTTATCAGA CTGAAGAGCT ATTGTAATGA CCAGTCAACA GGGGACATAA AAGTAATTGG TGGAGATGAT CTCTCAACTT TAACTGGAAA GAATGTCTTG ATTGTGGAAG ATATAATTGA CACTGGCAAA ACAATGCAGA CTTTGCTTTC CTTGGTCAGG CAGTATAATC CAAAGATGGT CAAGGTCGCA AGCTTGCTGG TGAAAAGGAC CCCACGAAGT GTTGGATATA AGCCAGACTT TGTTGGATTT GAAATTCCAG ACAAGTTTGT TGTAGGATAT GCCCTTGACT ATAATGAATA CTTCAGGGAT TTGAATCATG TTTGTGTCAT TAGTGAAACT GGAAAAGCAA AATACAAAGC CTAAGATGAG AGTTCAAGTT GAGTTTGGAA ACATCTGGAG TCCTATTGAC ATCGCCAGTA AAATTATCAA TGTTCTAGTT CTGTGGCCAT CTGCTTAGTA GAGCTTTTTG CATGTATCTT CTAAGAATTT TATCTGTTTT GTACTTTAGA AATGTCAGTT GCTGCATTCC TAAACTGTTT ATTTGCACTA TGAGCCTATA GACTATCAGT TCCCTTTGGG CGGATTGTTG TTTAACTTGT AAATGAAAAA ATTCTCTTAA ACCACAGCAC TATTGAGTGA AACATTGAAC TCATATCTGT AAGAAATAAA GAGAAGATAT ATTAGTTTTT TAATTGGTAT TTTAATTTTT ATATATGCAG GAAAGAATAG AAGTGATTGA ATATTGTTAA TTATACCACC GTGTGTTAGA AAAGTAAGAA GCAGTCAATT TTCACATCAA AGACAGCATC TAAGAAGTTT TGTTCTGTCC TGGAATTATT TTAGTAGTGT TTCAGTAATG TTGACTGTAT TTTCCAACTT GTTCAAATTA TTACCAGTGA ATCTTTGTCA GCAGTTCCCT TTTAAATGCA AATCAATAAA TTCCCAAAAA TTTAAAAAAA AAAAAAAAAA AAAAA | |
| TOX4 | NM_001303523.1 | AGCAGAGAGA ACACACGTCC TTGCGGAAGT GACGGCAGTT CCGAGTCCAG TGGGGGCGGT GGGAGCGATG AGGGTCTGAG ACGGTGGGAG CGGTTGTGTG AAGATGGAGA CATTCCATAC ACCAAGCTTG GGTGATGAGG AATTTGAAAT CCCACCTATC TCCTTGGATT CTGATCCCTC ATTGGCTGTC TCAGATGTGG TTGGCCACTT TGATGACCTG GCAGACCCTT CCTCTTCACA GGATGGCAGT TTTTCAGCCC AGTATGGGGT CCAGACATTG GACATGCCTG TGGGCATGAC CCATGGCTTG ATGGAGCAGG GCGGGGGGCT CCTGAGTGGG GGCTTGACCA TGGACTTGGA CCACTCTATA GGAACTCAGT ATAGTGCCAA CCCACCTGTT ACAATTGATG TACCAATGAC AGACATGACA TCTGGCTTGA TGGGGCATAG CCAGTTGACC ACCATTGATC AGTCAGAACT GAGTTCCCAG CTGGGTTTGA GCCTAGGGGG TGGCACCATC CTGCCACCTG CCCAGTCACC TGAAGATCGT CTTTCAACCA CCCCTTCACC TACTAGTTCA CTTCACGAGG ATGGTGTTGA GGATTTCCGG AGGCAACTTC CCAGCCAGAA GACAGTCGTG GTGGAAGCAG GGAAAAAGCA GAAGGCCCCA AAGAAGAGAA AAAAGAAAGA TCCTAATGAA CCTCAGAAAC CAGTTTCAGC ATATGCTTTA TTCTTTCGTG ATACACAGGC TGCCATCAAG GGACAGAATC CTAATGCCAC TTTTGGTGAG GTTTCAAAAA TTGTGGCCTC CATGTGGGAT AGTCTTGGAG AGGAGCAAAA ACAGGTATAT AAGAGGAAAA CTGAGGCTGC CAAGAAAGAG TATCTGAAGG CACTGGCTGC TTACAAAGAC AACCAGGAGT GTCAGGCCAC TGTGGAAACA GTGGAATTGG ATCCAGCACC ACCATCACAA ACTCCTTCTC CACCTCCTAT GGCTACTGTT GACCCAGCAT CTCCAGCACC AGCTTCAATA GAGCCCCCTG CCCTGTCCCC ATCCATTGTT GTTAACTCCA CCCTTTCATC CTATGTGGCA AACCAGGCAT CTTCTGGAGC TGGGGGTCAG CCCAATATCA CCAAGTTGAT TATTACCAAA CAAATGTTGC CCTCTTCTAT TACTATGTCT CAAGGAGGGA TGGTTACTGT TATCCCAGCC ACAGTGGTGA CCTCCCGGGG GCTCCAACTA GGCCAAACCA GTACAGCTAC TATCCAGCCC AGTCAACAAG CCCAGATTGT CACTCGGTCA GTGTTGCAGG CAGCAGCAGC TGCTGCTGCT GCTGCTTCTA TGCAACTGCC TCCACCCCGA CTACAGCCCC CTCCATTACA ACAGATGCCA CAGCCCCCGA CTCAGCAGCA AGTTACCATT CTGCAGCAGC CTCCTCCACT CCAGGCCATG CAACAGCCTC CACCTCAGAA AGTTCGAATC AATTTACAGC AACAGCCTCC TCCTCTGCAG ATCAAGAGTG TGCCTCTACC CACTTTGAAA ATGCAGACTA CCTTAGTCCC ACCAACTGTG GAAAGTAGTC CTGAGCGGCC TATGAACAAC AGCCCTGAGG CCCATACAGT GGAGGCACCT TCTCCTGAGA CTATCTGTGA GATGATCACA GATGTAGTTC CTGAGGTTGA GTCTCCTTCT CAGATGGATG TTGAATTGGT GAGTGGGTCT CCTGTGGCAC TCTCACCCCA GCCTCGATGT GTGAGGTCTG GTTGTGAGAA CCCTCCCATT GTGAGTAAGG ACTGGGACAA TGAATACTGC AGCAATGAGT GTGTGGTGAA GCACTGCAGG GATGTATTCT TGGCCTGGGT AGCCTCTAGA AATTCAAACA | 54 |

TABLE 1-continued

Plasma cell dyscrasia Biomarker/Housekeeper Sequence Information

| Gene Name | RefSeq Accession | Sequence | SEQ ID NO: |
|---|---|---|---|
| | | CAGTGGTGTT TGTGAAATAG TCCTTCCTGT TCTCCAAGCC | |
| | | AGTGAAGAGT TATCTGCTGG GAAAGTGTCC AAGAGCCTGT | |
| | | TTTTGAAACA CAAGCTGGGC TTCTGGTAGT GCCTCATCAC | |
| | | AACCCATGAT GGCTGTTCAT GTTTCACCCC TTTTCTTCCT | |
| | | TCAGCAGAGG CCAGGCTATG GAGCAGGGCC ACTGAATTTG | |
| | | CTGTAATCTG GAGATGCTTT TTACTTTCAA CCATAAGCGG | |
| | | TAATAGCAGA GGAAAGGGTG AAGGGAGTCT GGGCAAGCAA | |
| | | AGCATAGAGA TGGTGGGGTG GTGGTGGGGT TGAAGAAACT | |
| | | TGTTGGTATA ATTGTCATAG GACTTGCCTA AAATATTATT | |
| | | AAAATTACGG GAGTGTACTC AGCTTTGAGC CTAGGAGAAA | |
| | | ATGCCACTGT GTGCATCCAT TTTAAAGGGT TCCCTCATAA | |
| | | AAAAATGTTA TTCCCCATTA TCACATCAGT ACACTGCTTT | |
| | | GAAAACAAAA CTTTTCAACA TGGGCATACT GGGCTACATG | |
| | | GAAAATGACA TCACCCAGGA GTGATTTCTC TTTATATATA | |
| | | TTATTTCTGC AGTTACCATC CTTATCTGAG TTATCACAGT | |
| | | TCATGAATCT AAGAGGCGGA ACTCTACATC ATTAGTAAGA | |
| | | GGTTCCACCA AAGTCTAAAG TTGTATTCAC TTGTGTTTGA | |
| | | TGAACTATCT TTAAAAGACC ATAGGTCTAT CATTATTTCT | |
| | | TAGACATAAT CTAAAGAAAA ACAGACTAGA GAAGCCACCT | |
| | | GGTTGTAACA GAATAAGCAG AAGTTTACAG CATGATAGTC | |
| | | CAAGTGGTGA TAACTTTAAA TAAAACTCAA ATTTTTACTG | |
| | | TTTGTAGACA GGAATGCTGT CCTAGAGAAC CTCCTCCTCA | |
| | | ACCAGCTACG TACATAGTTT TATCCTATGC ATTCCTGTTT | |
| | | TCTGTGTGTT TTTTGTTTTT TTTTTTTTTT TTTTTTTTTG | |
| | | AGACAGAGTC TCGCTCTGTC ACCCAGGCTG GAGTGCAGTG | |
| | | GTGCGACCTC AGCTCACTGA AACCTCTGCC TCCCGGGTTC | |
| | | AAGCGATTCT CCTGCATCAG CCTCCCGAGT AGCTAGGATT | |
| | | ACAGGCGCCC GCCACTACGC CCAGCTAATT TGTGGTATTT | |
| | | TTAGTAGAGA CAGGGTTTCA CCATGTTGGC CAGGCTGGTC | |
| | | TCGAACTCCT GACCTCATGA TCCGCCCGCC TTGACCTCCC | |
| | | AAAGTGCTGG GATTACAGGC ATGAGCCACC GCACCCAGCC | |
| | | TGCATTCCTG TTTTTTTAAT GGTTTTGGAG GGTAGCAGTA | |
| | | GAGATGGGGT CTCACTATGT TGCCCAGTCT AGTCTTGAAC | |
| | | TCCTGGGCTA CAGTTACCCT CCTACCTCGG CTTCCCAAAG | |
| | | TGCTCGGATT ACAGGTGTGA GCCACTGTGC CTAGCCTATA | |
| | | ATGATCATTT TAATGTTTCC CATGCACTCA TTTAGTTTGA | |
| | | ACCTTCACAG CAACCCAATG AGGTAATACT CCCATTTCAC | |
| | | ATATAATACT GAGAGATGAG TTGCACAAGA TTATACACTG | |
| | | TTAAGTAGCA GAGCCAGAAT GGACTTCAGA ATCCCAACTA | |
| | | CAATACAAAT GTTTATTTAA ATAAAGAAGA AAGCTATTGT | |
| | | ACAAATATCA CTCTTCAGGT TTAGCTTACA GAGCCATGGC | |
| | | TATGGATTCT TAGCTCTGTA AGGAAGTGCT TCTATAAATT | |
| | | CTTAGGTTTA GAGATGATAC CATCTGGGTA CCTTTGCTTG | |
| | | AACCGTGCAA CCACATCTGG GTCTAGTAGG TGGATCCCAT | |
| | | CCAGTTGGTT TCCAAGGGTG ATCCTGAAAC AGTGTAAAAG | |
| | | GAGGGGCAAA CCAGAAATCC TGGAATTAGA GGGTTTAATA | |
| | | TTGTTAAAAA ATGCATACCA AATGAAGACT GCCTATCATC | |
| | | ATATCAAATA TGCCAATTCT AAAAAGAGCT TAACATTAGA | |
| | | ATAGTATATG GTAGAATTAC TAGTTCAGAA TTGGCATAGA | |
| | | TTCTGGTGTT AAAATAGACT GGATCTGTAT TATCTGAGGG | |
| | | TTAGTAACTA ATGCTTAGCC AGGCCTGCTT CACAGAGTTG | |
| | | CTACCAGGGA GTATTCTTTG GATAAGCAAA ATGCTAGCAG | |
| | | CATGTGTTTT AAGCTCTGTT AAGGGGTGAA AGATGTAATT | |
| | | ATTGACAGAT TAAATAGATA ACTTCGTAAC CACCAGGGGG | |
| | | CAGATTCAAT ACATCACAGA ATGGCTGAGG AAGATCCTTG | |
| | | GGTTGTGAAG AGAGTAGAAA CCCTAGGGAG CAGTGCTTTT | |
| | | GGGTCCTAGA ACCTGTTGAG TTTCTAATGA ATATTTGTAG | |
| | | AATCTCATAA AACAGTTTAA ATACAAGCTT AAGTGGCTTA | |
| | | TGAATCCTGT GAAGCTCATT TATGGACTAG TGTAAAACAA | |
| | | TGTGAAGCTC TACTAAGTTC TGTCCTTAAT CATAAATAAT | |
| | | AGCCCCTTGA GGACTAGCCT GTTCTCTGGT CACCTTACCA | |
| | | GTTGGGTTGC ACATTGTGTG GTCGTCCAAA TAACTCAATC | |
| | | TTGCGAGTGC CAGGAGATAG TCTTTCAATC ATGCCATAGA | |
| | | TTTCATCTGG TTTATGACTG GTGGAACGAA CCTAGGAAAT | |
| | | AAAAACTAGC TGCTTTTTAA GTTACACAAG AAAAAA | |

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

As used herein, the terms "polynucleotide" and "nucleic acid molecule" are used interchangeably to mean a polymeric form of nucleotides of at least 10 bases or base pairs in length, either ribonucleotides or deoxynucleotides or a modified form of either type of nucleotide, and is meant to include single and double stranded forms of DNA. As used herein, a nucleic acid molecule or nucleic acid sequence that serves as a probe in a microarray analysis preferably comprises a chain of nucleotides, more preferably DNA and/or RNA. In other embodiments, a nucleic acid molecule or nucleic acid sequence comprises other kinds of nucleic acid structures such as for instance a DNA/RNA helix, peptide nucleic acid (PNA), locked nucleic acid (LNA) and/or a ribozyme. Hence, as used herein the term "nucleic acid molecule" also encompasses a chain comprising non-natural nucleotides, modified nucleotides and/or non-nucleotide building blocks which exhibit the same function as natural nucleotides.

As used herein, the terms "hybridize," "hybridizing", "hybridizes," and the like, used in the context of polynucleotides, are meant to refer to conventional hybridization conditions, such as hybridization in 50% formamide/6×SSC/0.1% SDS/100 μg/ml ssDNA, in which temperatures for hybridization are above 37 degrees centigrade and temperatures for washing in 0.1×SSC/0.1% SDS are above 55 degrees C., and preferably to stringent hybridization conditions.

As used herein, the term "normalization" or "normalizer" refers to the expression of a differential value in terms of a standard value to adjust for effects which arise from technical variation due to sample handling, sample preparation, and measurement methods rather than biological variation of biomarker concentration in a sample. For example, when measuring the expression of a differentially expressed protein, the absolute value for the expression of the protein can be expressed in terms of an absolute value for the expression of a standard protein that is substantially constant in expression. In some embodiments, normalizing the expression level of a gene to the expression level of a housekeeping gene means dividing the expression level of the gene by the expression level of the housekeeping gene.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore, the term diagnosis includes: a. prediction (determining if a patient will likely develop aggressive disease (hyperproliferative/invasive)), b. prognosis (predicting whether a patient will likely have a better or worse outcome at a pre-selected time in the future), c. therapy selection, d. therapeutic drug monitoring, and e. relapse monitoring.

The term "providing" as used herein with regard to a biological sample refers to directly or indirectly obtaining the biological sample from a subject. For example, "providing" may refer to the act of directly obtaining the biological sample from a subject (e.g., by a blood draw, tissue biopsy, lavage and the like). Likewise, "providing" may refer to the act of indirectly obtaining the biological sample. For example, providing may refer to the act of a laboratory receiving the sample from the party that directly obtained the sample, or to the act of obtaining the sample from an archive.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

The term "biological sample" as used herein refers to any sample of biological origin potentially containing one or more biomarkers. Examples of biological samples include tissue, organs, or bodily fluids such as whole blood, plasma, serum, tissue, lavage or any other specimen used for detection of disease.

The term "subject" as used herein refers to a mammal, preferably a human.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Biomarker levels may change due to treatment of the disease. The changes in biomarker levels may be measured by the present disclosure. Changes in biomarker levels may be used to monitor the progression of disease or therapy.

"Altered", "changed" or "significantly different" refer to a detectable change or difference from a reasonably comparable state, profile, measurement, or the like. Such changes may be all or none. They may be incremental and need not be linear. They may be by orders of magnitude. A change may be an increase or decrease by 1%, 5%, 10%, 20%, 30%, 40%, 50%, 60%, 70%, 80%, 90%, 95%, 99%, 100%, or more, or any value in between 0% and 100%. Alternatively, the change may be 1-fold, 1.5-fold, 2-fold, 3-fold, 4-fold, 5-fold or more, or any values in between 1-fold and five-fold. The change may be statistically significant with a p value of 0.1, 0.05, 0.001, or 0.0001.

The term "stable disease" refers to a diagnosis for the presence of a plasma cell dyscrasia, however the myeloma has been treated and remains in a stable condition, i.e. one that that is not progressive, as determined by imaging data and/or best clinical judgment.

The term "progressive disease" refers to a diagnosis for the presence of a highly active state of a plasma cell dyscrasia, i.e. one has not been treated and is not stable or has been treated and has not responded to therapy, or has been treated and active disease remains, as determined by imaging data and/or best clinical judgment.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1. Derivation of a 32-Marker Gene Panel

Figure 1A:
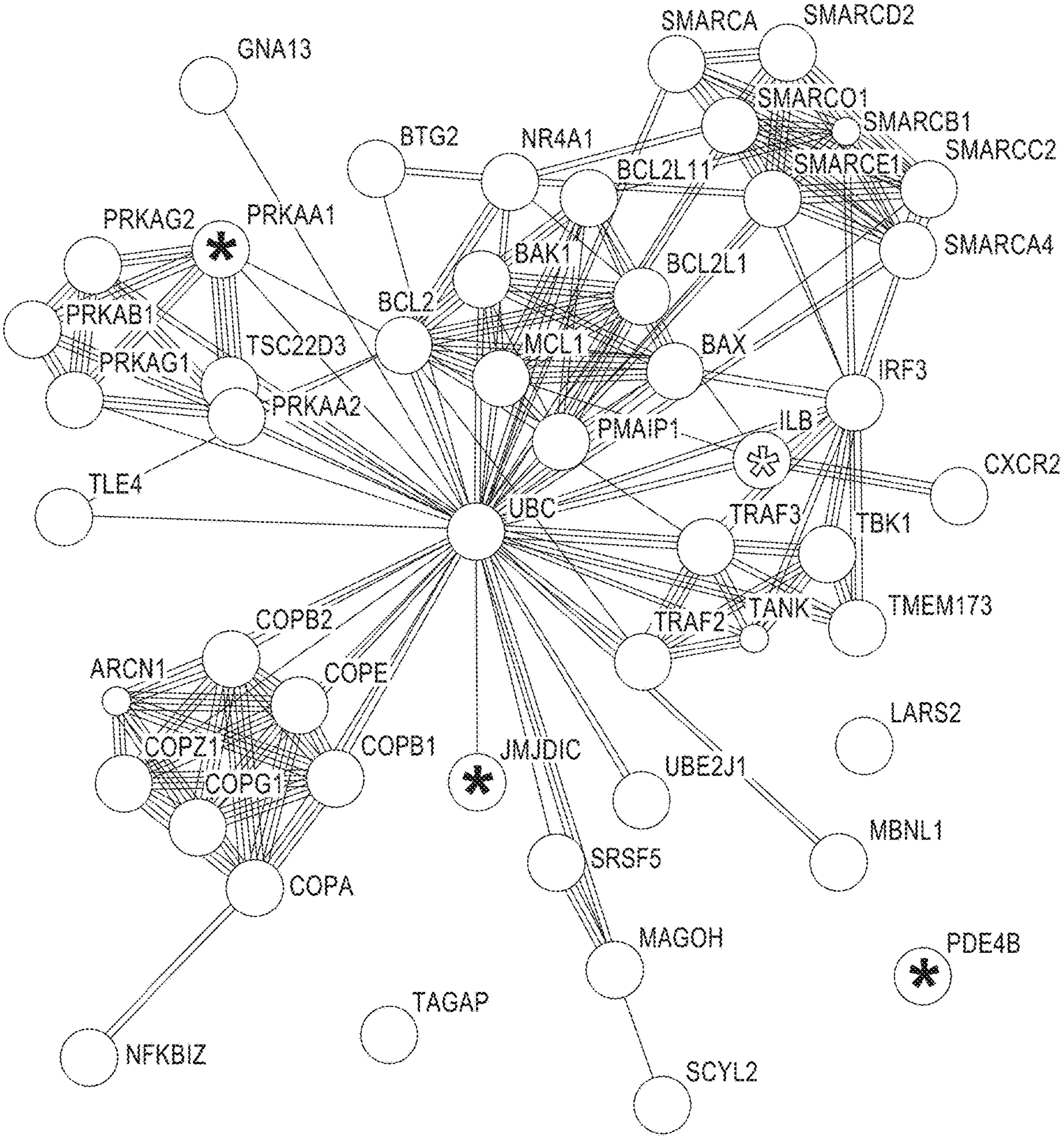
FIG. 1A and FIG. 1B show a graph showing interactive and functional analyses of the normalized 31 target transcripts (26 genes, 5 splice variants) markers of myeloma. Gene transcripts were significantly functionally linked at an interactome level consistent with a common pattern of regulatory activity. Two trancripts, MCL1 and COPA, were linked with Chromosome 1q, an area known to exhibit amplification in myeloma. At a functional level, the markers identified captured a series of biological processes including angiogenesis, apoptosis, immune responsiveness, phenotype definition, protein processing (secretion), proliferation, RNA processing and survival. A number of the transcripts encoded genes that were either potential drug targets or markers for drug target efficacy.
Figure 1B:
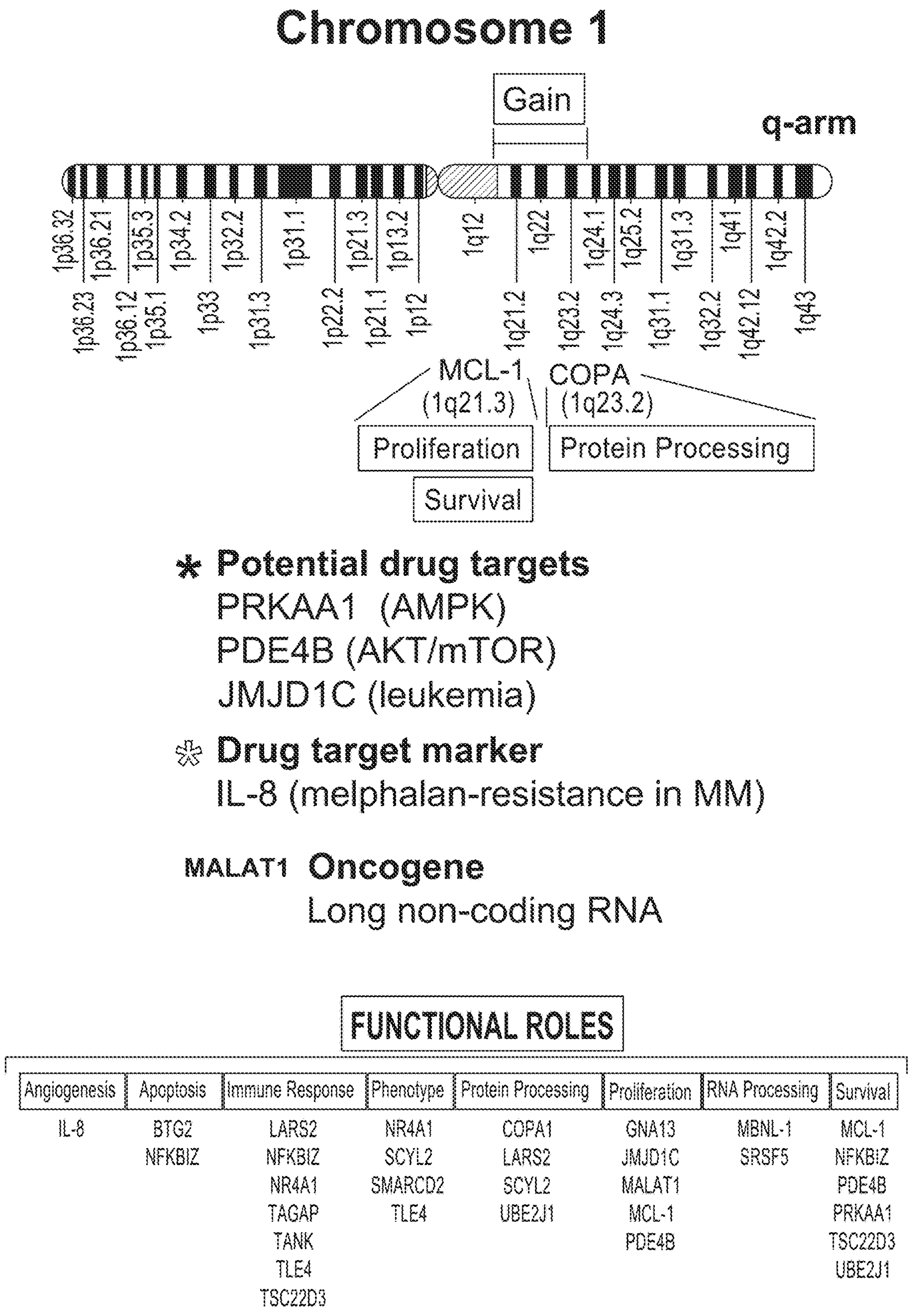

Raw probe intensities (n=1,354,896 features) from n=15 peripheral blood mononuclear cell samples were used to identify genes that best discriminated between controls and multiple myeloma using the transcriptional profile of GSE7116. Following removal of outliers, a total of 31 target transcripts (26 genes, 5 splice variants) and one housekeeping gene was identified in an unbiased manner as potential markers of myeloma (Table 2; FIG. 1A and FIG. 1B). These genes were demonstrated to be expressed in multiple myeloma cell lines, IM-9 (normal diploid karyotype) and MM1R (dexamethasone-resistant), identifying they are produced by transformed B-lymphoblasts.

Then an artificial intelligence model of myeloma disease dynamics was built using normalized gene expression of these 31 markers (normalized to the housekeeping gene, TPT1) in whole blood from Controls (n=45), Responders/Stable (n=24: stable disease), and Newly Diagnosed/Relapsed (n=66: progressive disease) samples. The dataset was randomly split into training and testing partitions for model creation and validation respectively. Twelve algorithms were evaluated (XGB, RF, glmnet, cforest, CART, treebag, knn, nnet, SVM-radial, SVM-linear, NB and mlp) with accuracies ranging from 0.7-0.85). The top performing algorithm (XGB—"gradient boosting") best predicted the training data. In the test set, XGB produced probability scores that predicted the sample. Each probability score reflects the "certainty" of an algorithm that an unknown sample belongs to either "Stable Disease" or "Progressive" class. For example, an unknown sample 51 can have the following probability vector [Control=0.2, Progressive=0.8]. This sample would be considered a myeloma sample that exhibited progressive disease, given a score of 0.8. If the sample came from a patient with MRD or who was under treatment, the score would identify either they are exhibiting progressive disease (will relapse) or are failing the therapy. MyelomX scores >0.2 are considered indicative the sample is from a myeloma patient.

TABLE 2

| Multiple Myeloma Biomarker or Housekeeping Genes | | NCBI Chromosome | UniGene | | Amplicon | Exon | Assay |
|---|---|---|---|---|---|---|---|
| Symbol | Name | location | ID | RefSeq | length | Boundary | Location |
| ASXL1 | additional sex combs like 1, transcriptional regulator | Chr.20: 32358062-32439319 | Hs.374043 | NM_001164603.1 | 95 | 1-2 | 484 |
| BHLHE40 | Basic helix-loop-helix family, member e40 | Chr.3: 4979412-4985181 | Hs.744856 | NM_003670.2 | 66 | 4-5 | 683 |
| BTG2 | BTG anti-proliferation factor 2 | Chr.1: 203305536-203309602 | Hs.519162 | NM_006763.2 | 86 | 1-2 | 215 |
| COPA | coatomer protein complex, subunit alpha | Chr.1: 160288587-160343564 | Hs.162121 | NM_001098398.1 | 82 | 6-7 | 892 |
| FBXW7 | F-box and WD repeat domain containing 7, E3 ubiquitin protein ligase | Chr.4: 152321258-152536095 | Hs.561245 | NM_001013415.1 | 76 | 3-4 | 548 |
| GNA13 | Guanine nucleotide binding protein (G protein), alpha 13 | Chr.17: 65009289-65056802 | Hs.515018 | NM_006572.5 | 70 | 1-2 | 496 |
| IL8 | Interleukin 8 | Chr.4: 74606223-74609433 | Hs.624 | NM_000584.3 | 101 | 1-2 | 222 |
| JMJD1C | Jumonji domain containing 1C | Chr.10: 63167221-63522075 | Hs.413416 | NM_001282948.1 | 115 | 21-22 | 7309 |
| LARS2 | leucyl-tRNA synthetase 2, mitochondrial | Chr.3: 45388561-45548842 | Hs.526975 | NM_015340.3 | 83 | 2-3 | 164 |
| MALAT1 | metastasis associated lung adenocarcinoma transcript 1 (non-protein coding) | Chr.11: 65497679-65504494 | Hs.621695 | NR_002819.2 | 117 | 1-1 | 4952 |
| MBNL1 | muscleblind-like splicing regulator | Chr.3: 152243656-152465780 | Hs.201858 | NM_001314057.1 | 55 | 4-5 | 981 |
| MCL1 | myeloid cell leukemia sequence 1 (BCL2-related) | Chr.1: 150574551-150579738 | Hs.632486 | NM_001197320.1 | 89 | 3-4 | 682 |
| NFKBIZ | nuclear factor of kappa light polypeptide gene enhancer in B-cells inhibitor, zeta | Chr.3: 101827990-101861025 | Hs.319171 | NM_001005474.2 | 62 and 86 | 6-7 and 12-13 | 1322 and 2087 |
| NR4A1 | nuclear receptor subfamily 4, group A, member 1 | Chr.12: 52022832-52059507 | Hs.524430 | NM_001202233.1 | 79 and 87 | 3-4 and 7-8 | 1107 and 1767 |
| PDE4B | phosphodiesterase 4B, cAMP-specific | Chr.1: 65792510-66374579 | Hs.198072 | NM_001037339.2 | 72 | 8-9 | 1429 |
| P1AS2 | protein inhibitor of activated STAT, 2 | Chr:18: 46803224-46920167 | Hs.57769 | NM_001324046.1 | 72 | 12-13 | 1716 |
| PRKAA1 | protein kinase, AMP-activated, alpha 1 catalytic subunit | Chr.5: 40759379-40798195 | Hs.43322 | NM_006251.5 | 93 and 75 | 2-3 and 5-6 | 275 and 606 |
| SCYL2 | SCY1-like 2 (*S. cerevisiae*) | Chr.12: 100267137-100341724 | Hs.506481 | NM_001317784.1 | 151 and 67 | 2-3 and 8-9 | 463 and 1381 |
| SMARCD2 | SWI/SNF related, matrix associated, actin dependent regulator of chromatin, subfamily d, member 2 | Chr.17: 63832081-63842991 | Hs.250581 | NM_001098426.1 | 63 | 4-5 | 885 |
| SP1 | Sp1 transcription factor | Chr.12: 53380195-53416446 | Hs.620754 | NM_001251825.1 | 62 and 72 | 3-4 and 5-6 | 1631 and 2002 |
| SRSF5 | serine/arginine-rich splicing factor 5 | Chr.14: 69767087-69772005 | Hs.632326 | NM_001039465.1 | 102 | 5-6 | 651 |

TABLE 2-continued

| Multiple Myeloma Biomarker or Housekeeping Genes | | NCBI Chromosome | UniGene | | Amplicon | Exon | Assay |
|---|---|---|---|---|---|---|---|
| Symbol | Name | location | ID | RefSeq | length | Boundary | Location |
| TAGAP | T-cell activation RhoGTPase activating protein | Chr.6: 159034468-159045152 | Hs.529984 | NM_001278733.1 | 99 | 3-4 | 552 |
| TANK | TRAF family member-associated NFKB activator | Chr.2: 161136955-161236176 | Hs.132257 | NM_001199135.1 | 89 | 2-3 | 210 |
| TLE4 | transducin-like enhancer of split 4 (E(sp1) homolog, *Drosophila* | Chr.9: 79571773-79726882 | Hs.444213 | NM_001282748.1 | 89 | 2-3 | 1162 |
| TPT1 (housekeeping gene) | tumor protein, translationally-controlled 1 | Chr.13: 45333471-45341284 | Hs.374596 | NM_001286272.1 | 131 | 3-3 | 377 |
| TSC22D3 | TSC22 domain family, member 3 | Chr.X: 107713221-107777329 | Hs.522074 | NM_001015881.1 | 77 | 2-3 | 220 |
| UBE2J1 | Ubiquitin-conjugating enzyme E2, J1 | Chr.6: 89326625-89352917 | Hs.163776 | NM_016021.2 | 61 | 3-4 | 568 |

Example 2. Diagnosis: Identification of Samples as Myeloma

Figure 2A:
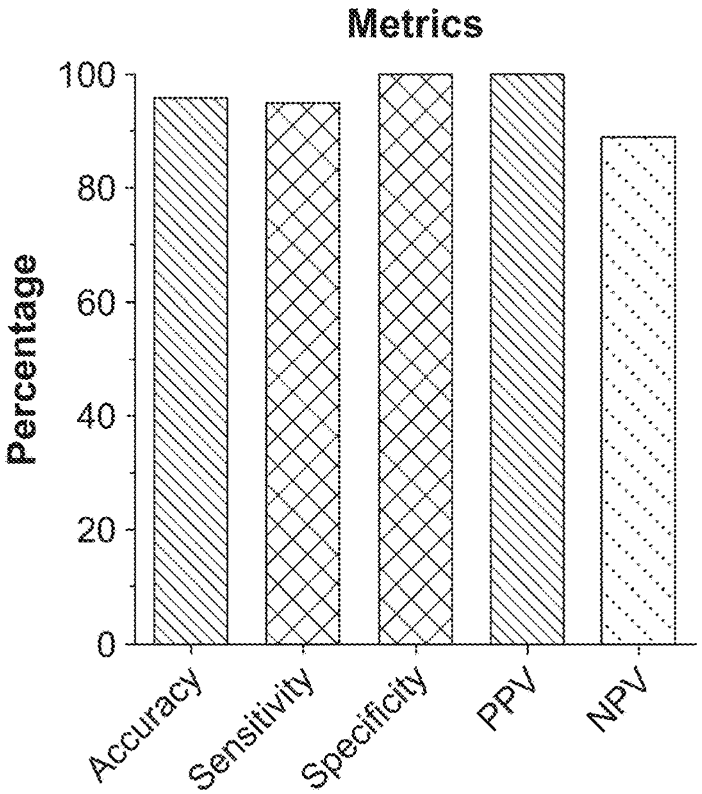
FIG. 2A and FIG. 2B are graphs showing the receiver operator cuver analysis and metrics for MelanomX (normalized expression of the 26 genes and 5 splice variants) in Test Set I.
Figure 2B:
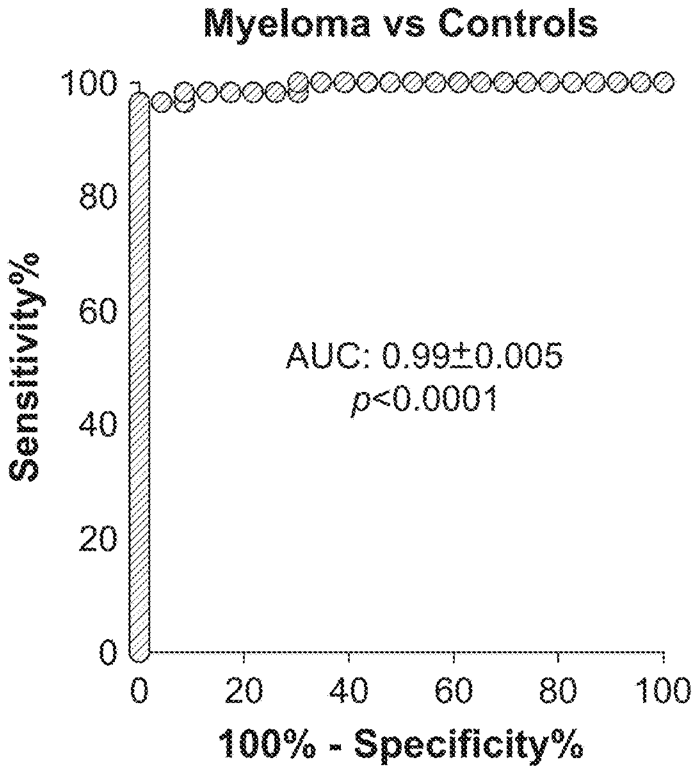

In the test set 1, the data for the utility of the test to differentiate patients with active myeloma disease (n=57) from controls (n=23) are included in Table 3. The receiver operator cuver analysis and metrics are included in FIG. 2B. The score exhibited an area under the curve (AUC) of 0.99. The metrics are: sensitivity >95%, specificity 100%, PPV 100%, NPV 88.5%. The overall accuracy is 96%. The tool can therefore differentiate between controls and aggressive and stable myeloma disease.

Figure 3A:
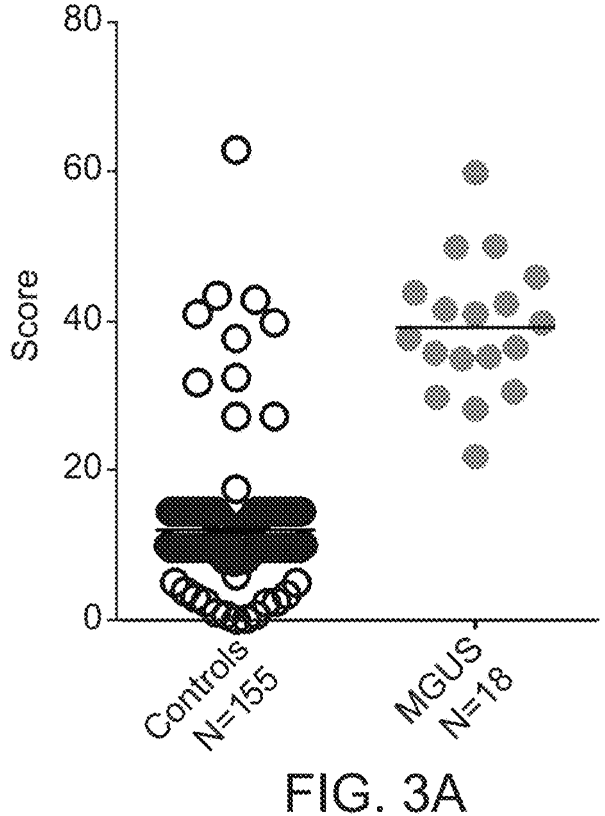
FIG. 3A and FIG. 3B are graphs showing MyelomX scores in MGUS (n=18) versus controls (n=155).
Figure 3B:
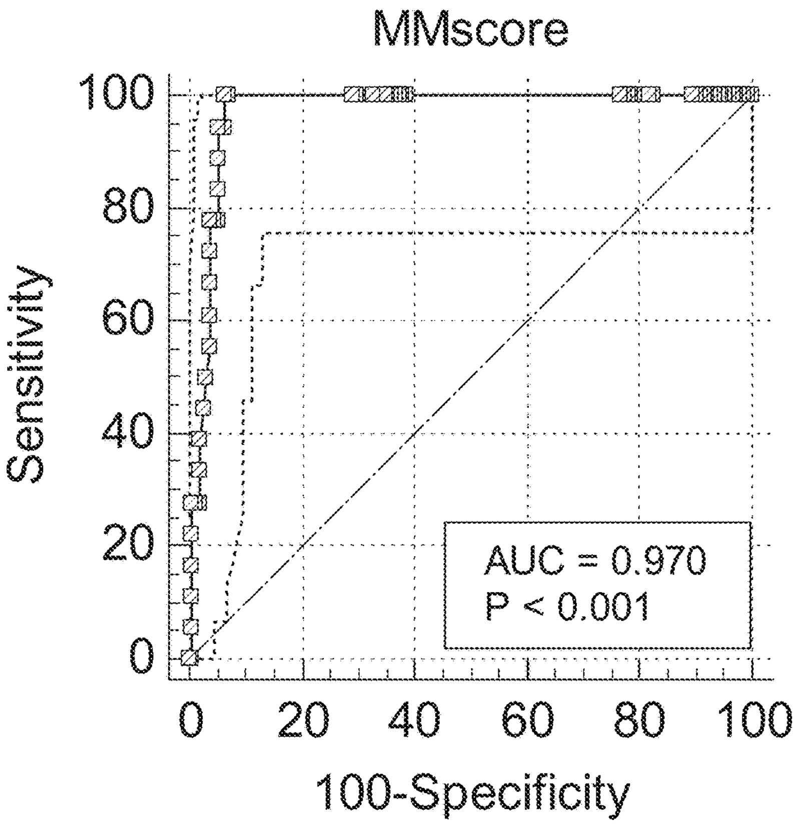

Specific evaluation of the MGUS identified significant differences between this plasma cell dyscrasia (n=18; MyelomX=39±9) and controls (n=155, 12±8, p<0.0001) (FIG. 3A). The AUC for differentiating MGUS from controls 0.97 (FIG. 3B).

Figure 4A:
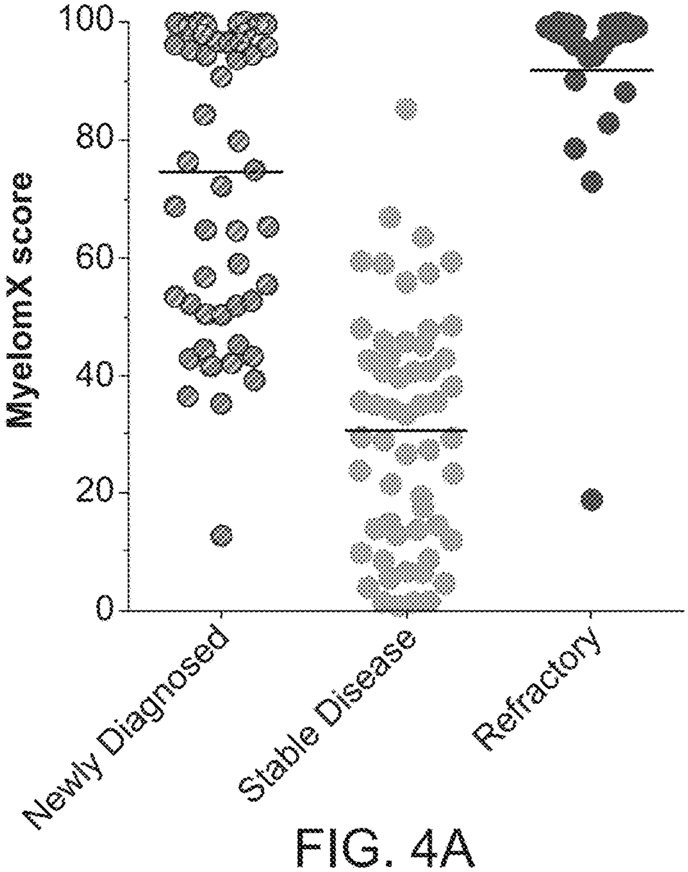
FIG. 4A and FIG. 4B are graphs showing MyelomX scores in different multiple myeloma sub-groups.
Figure 4B:
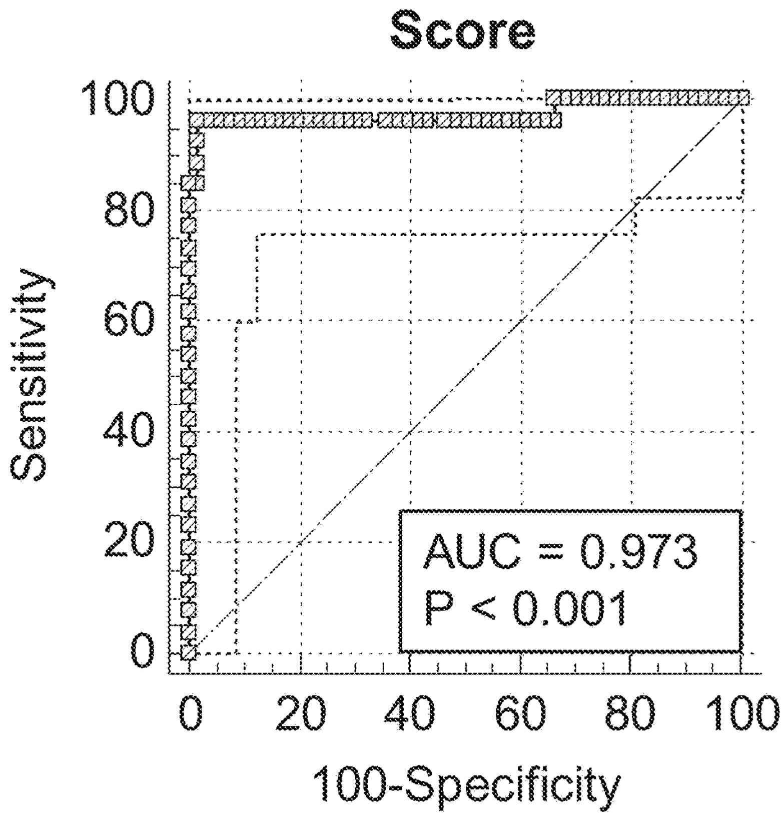

Specific evaluation of the multiple myeloma sub-groups identified significant differences between newly diagnosed patients (n=53; MyelomX=75±25), clinically stable disease (n=56, 31±20, p<0.0001) and refractory disease (n=26, 92±17) (FIG. 4A). The AUC for differentiating stable from refractory disease was 0.97 (FIG. 4B).

Figure 5A:
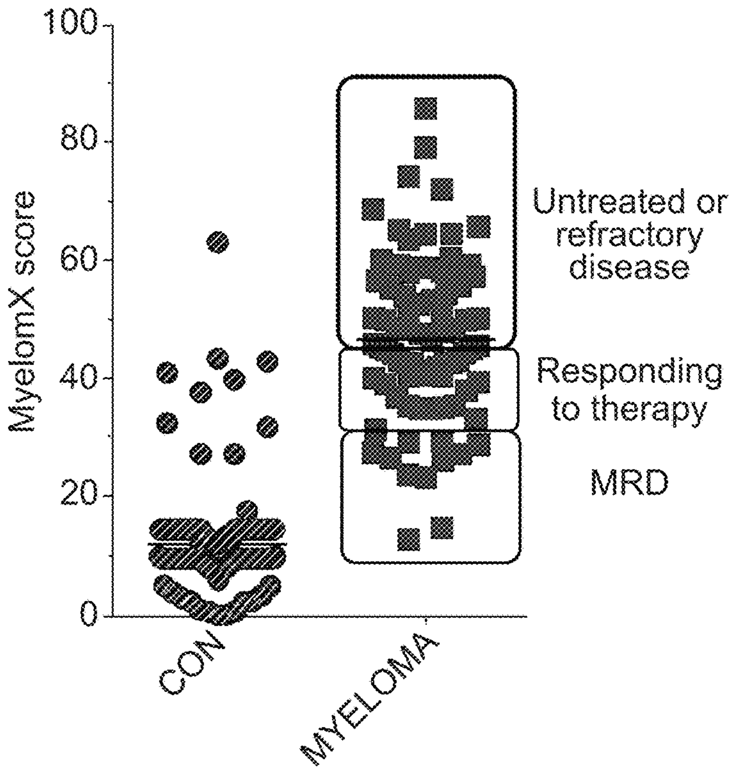
FIG. 5A, FIG. 5B and FIG. 5C are graphs showing MyelomX scores in Test Set II.
Figure 5B:
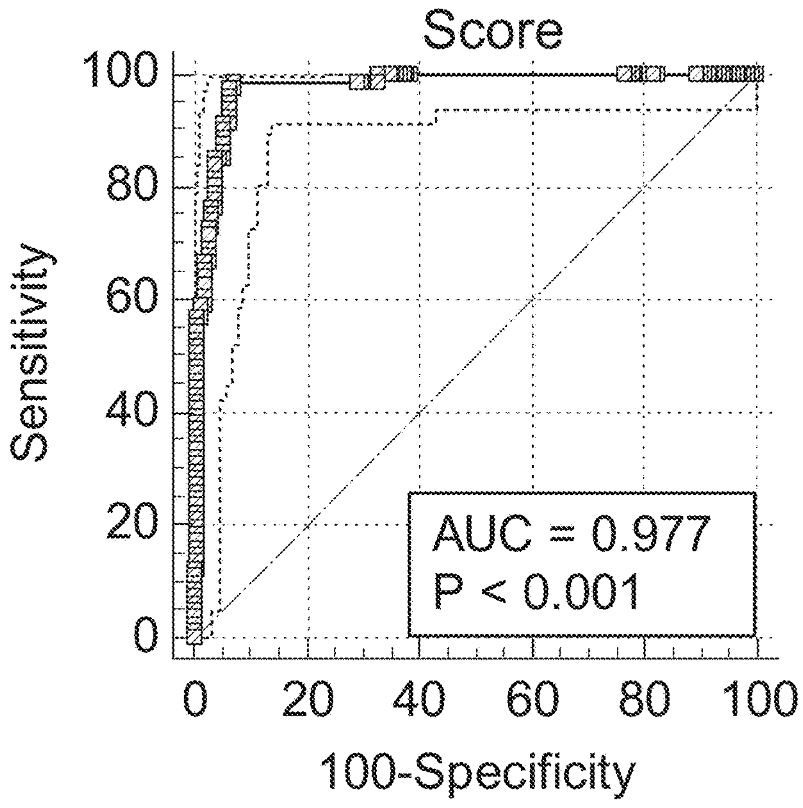
Figure 5C:
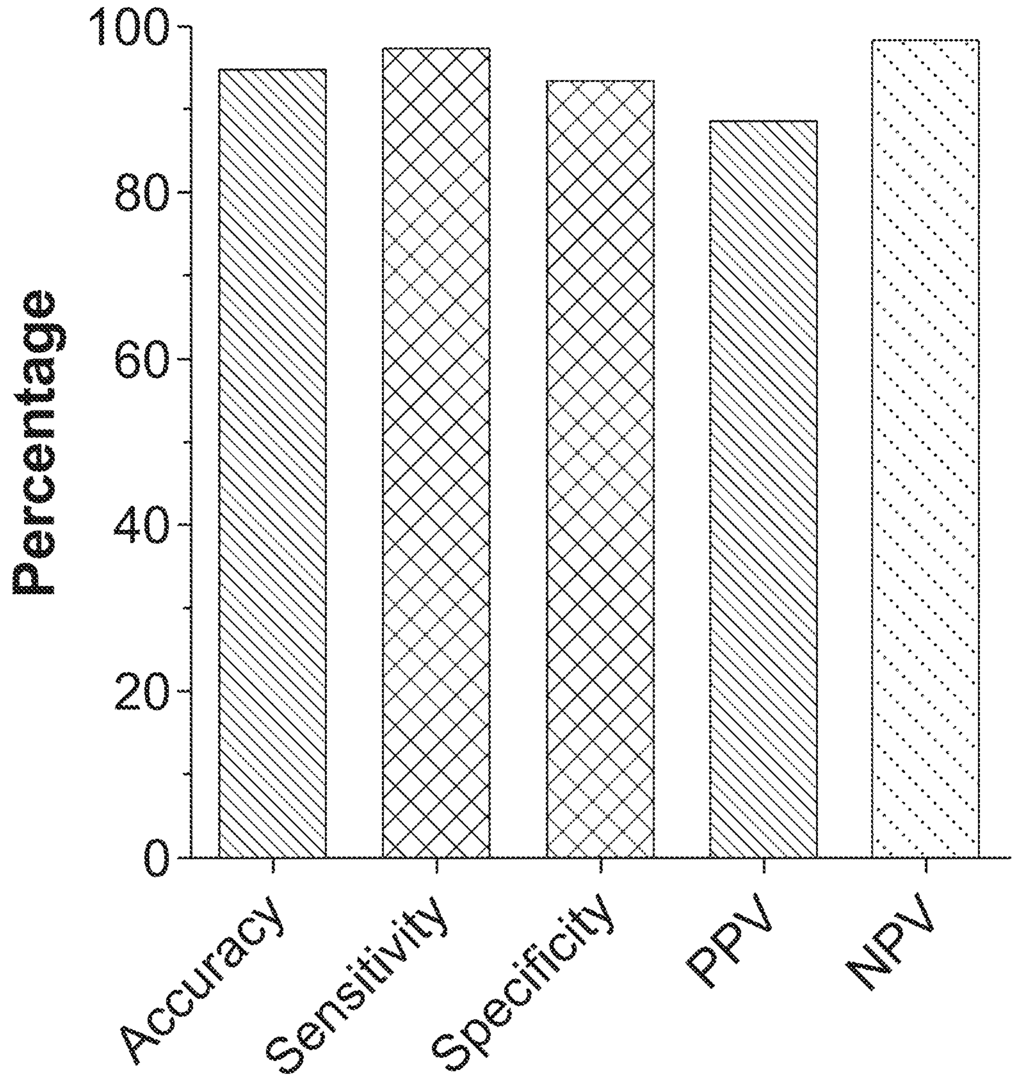

The test was evaluated in a second test set (test set 2) that included 155 healthy controls and 81 myeloma patients, the majority of whom exhibited stable disease including those with MRD. The mean MyelomX score in this myeloma group was 47±14 versus 12±8 in the control group (FIG. 5A). The receiver operator cuver analysis demonstrated the score exhibited an area under the curve (AUC) of 0.97 (FIG. 5B) and the metrics were 89-99% (FIG. 5C).

TABLE 3

Confusion matrix showing classification accuracy of the XGB-algorithm that determines whether a sample is a myeloma or a control in blood samples

| | Reference | |
|---|---|---|
| Predicted | Myeloma | Control |
| Control | 3 | 20 |
| Myeloma | 55 | 2 |
| Sensitivity | 96% | |
| Specificity | 87% | |
| Positive Predictive Value | 95% | |
| Negative Predictive Value | 81% | |
| Accuracy | 94% | |

Example 3. Identification of Minimal Residual Disease

Effective therapy (n=40), decreased the score from 59±14 to 35±12 which was associated with complete remissions (FIG. 6). Evaluation of the MRD group identified ten patients all with high scores (>40) who relapsed at an early time point (within one year). The MyelomX score can therefore biochemically define MRD and identify those who have progressive disease and will relapse at an early time-point.

Example 4. Differentiating Treatment Responders from Refractory Disease

In the therapy series (n=23), treatment with bortemozib (a proteasome inhibitor—PI) for 3 months significantly decreased the MyelomX scores from 64±9 to 23±12 (p<0.0001) in treatment responders but was unchanged in those refractory to PI-treatment (60±9, p=NS) (FIG. 7). This indicates that the MyelomX score can be used to measure the efficacy of proteasome inhibitor therapy in myeloma, that a decrease in score correlates with response to therapeutic intervention and non-responders can accurately be identified.

Example 5. Use of MyelomX Score to Diagnose Myeloma, Demonstrate MRD and Define Therapy Response A confusion matrix identifying the accuracy of the MyelomX score in both data sets is included in Table 4. As a diagnostic, the score is 97% accurate for identifying active disease. For determining MRD it is overall 75% accurate, but is 100% accurate for those who do not recur within one year. For treatment responders, the score is 87% accurate for identifying responders and 97% for those who are failing therapy or are refractory.

TABLE 4

Confusion matrix showing classification accuracy of the XGB-model algorithm and score cut-offs for defining the dynamic state of myeloma disease in blood samples

| Predicted | Reference<br>Control (MMx Score ≤20) | <br>Intermediate MMx Score 21 to 39 | <br>MMx Score ≥40 | <br>Accuracy |
|---|---|---|---|---|
| Control (n = 47) | 45 | 2 | 0 | 96% |
| Multiple myeloma (No MRD) (n = 65) | 2 | 13 | 50 | 97% |
| New Diagnosed (n = 31) | 1 | 1 | 29 | 97% |
| MRD (n = 24) | 2 | 16 | 6 | 75% |
| Treatment Responder (n = 39) | 26 | 8 | 5 | 87% |
| Refractory Disease (n = 34) | 1 | 0 | 33 | 97% |

We confirmed that myeloma was the source for the blood-based gene expression assay by evaluating expression in different myeloma cell lines and in FAC-sorted multiple myeloma tumors form patients.

All 32 genes were highly expressed in all 3 myeloma cell lines. Scores ranged from 86±9 (RPMI-8226) to 76±10 (IM9) to 60±9 (MM-1R) (FIG. 8A).

Spike-in experiments using these 3 cell lines and normal whole blood demonstrated that gene expression scores were detected when as few as 1 cell was spiked into 1 ml of blood. One single myleoma cell was detectable. Scores ranged from 30±7 (RPMI-8226) to 41±7 (IM9) to 21±3 (MM-1R) (FIG. 8B). Scores were significantly elevated compared to control blood (no spike-in; p<0.0001).

We then evaluated gene expression in tumor tissue (FAC sorted CD138+ cells). All 32 genes (and variants) were highly expressed in myeloma and scores were consistent with values from whole blood samples (FIG. 9A). We also compared gene expression in tumor tissue and matched whole blood from the same patient. Gene expression was highly concordant (Pearson r: 0.87-0.95, median: 0.92) identifying gene expression in tumor tissue and blood was concordant (FIG. 9B).

REFERENCES

1. Swerdlow S H, Campo E, Pileri S A, et al. The 2016 revision of the World Health Organization classification of lymphoid neoplasms. Blood. 2016; 127: 2375-2390. doi: 2310.1182/blood-2016-2301-643569. Epub 64216 March 643515.
2. Siegel R L, Miller K D, Jemal A. Cancer Statistics, 2017. C A Cancer J Clin. 2017; 67: 7-30. doi: 10.3322/caac.21387. Epub 2217 January 21385.
3. Michels T C, Petersen K E. Multiple Myeloma: Diagnosis and Treatment. Am Fam Physician. 2017; 95: 373-383.
4. Egan P, Drain S, Conway C, Bjourson A J, Alexander H D. Towards Stratified Medicine in Plasma Cell Myeloma. Int J Mol Sci. 2016; 17(10). E1760.
5. Debes-Marun C S, Dewald G W, Bryant S, et al. Chromosome abnormalities clustering and its implications for pathogenesis and prognosis in myeloma. Leukemia. 2003; 17: 427-436.
6. Kyle R A, Rajkumar S V. Multiple myeloma. Blood. 2008; 111: 2962-2972. doi: 2910.1182/blood-2007-2910-078022.
7. Melchor L, Brioli A, Wardell C P, et al. Single-cell genetic analysis reveals the composition of initiating clones and phylogenetic patterns of branching and parallel evolution in myeloma. Leukemia. 2014; 28: 1705-1715. doi: 1710.1038/leu.2014.1713. Epub 214 January 1713.
8. Fonseca R, Barlogie B, Bataille R, et al. Genetics and cytogenetics of multiple myeloma: a workshop report. Cancer Res. 2004; 64: 1546-1558.
9. Gonzalez D, van der Burg M, Garcia-Sanz R, et al. Immunoglobulin gene rearrangements and the pathogenesis of multiple myeloma. Blood. 2007; 110: 3112-3121. Epub 27 July 3118.
10. Avet-Loiseau H, Gerson F, Magrangeas F, Minvielle S, Harousseau J L, Bataille R. Rearrangements of the c-myc oncogene are present in 15% of primary human multiple myeloma tumors. Blood. 2001; 98: 3082-3086.
11. Walker B A, Wardell C P, Murison A, et al. APOBEC family mutational signatures are associated with poor prognosis translocations in multiple myeloma. Nat Commun. 2015; 6:6997.: 10.1038/ncomms7997.
12. Pawlyn C, Melchor L, Murison A, et al. Coexistent hyperdiploidy does not abrogate poor prognosis in myeloma with adverse cytogenetics and may precede IGH translocations. Blood. 2015; 125: 831-840. doi: 810.1182/blood-2014-1107-584268. Epub 58214 November 584226.
13. Dimopoulos M, Kyle R, Fermand J P, et al. Consensus recommendations for standard investigative workup: report of the International Myeloma Workshop Consensus Panel 3. Blood. 2011; 117: 4701-4705. doi: 4710.1182/blood-2010-4710-299529. Epub 29211 February 299523.
14. Shaughnessy J D, Jr., Zhan F, Burington B E, et al. A validated gene expression model of high-risk multiple myeloma is defined by deregulated expression of genes mapping to chromosome 1. Blood. 2007; 109: 2276-2284. Epub 26 Nov. 2214.
15. Chng W J, Braggio E, Mulligan G, et al. The centrosome index is a powerful prognostic marker in myeloma and identifies a cohort of patients that might benefit from aurora kinase inhibition. Blood. 2008; 111: 1603-1609. Epub 27 Nov. 1615.
16. Decaux O, Lode L, Magrangeas F, et al. Prediction of survival in multiple myeloma based on gene expression profiles reveals cell cycle and chromosomal instability signatures in high-risk patients and hyperdiploid signatures in low-risk patients: a study of the Intergroupe Francophone du Myelome. J Clin Oncol. 2008; 26: 4798-4805. doi: 4710.1200/JCO.2007.4713.8545. Epub 28 June 4730.
17. Dickens N J, Walker B A, Leone P E, et al. Homozygous deletion mapping in myeloma samples identifies genes and an expression signature relevant to pathogenesis and outcome. Clin Cancer Res. 2010; 16: 1856-1864. doi: 1810.1158/1078-0432.CCR-1809-2831. Epub 210 March 1859.
18. Hose D, Reme T, Hielscher T, et al. Proliferation is a central independent prognostic factor and target for personalized and risk-adapted treatment in multiple myeloma. Haematologica. 2011; 96: 87-95. doi: 10.3324/haemato1.2010.030296. Epub 03210 September 030230.
19. Moreaux J, Klein B, Bataille R, et al. A high-risk signature for patients with multiple myeloma established from the molecular classification of human myeloma cell lines. Haematologica. 2011; 96: 574-582. doi: 510.3324/haemato1.2010.033456. Epub 03210 December 033420.
20. Kuiper R, Broyl A, de Knegt Y, et al. A gene expression signature for high-risk multiple myeloma. Leukemia. 2012; 26: 2406-2413. doi: 2410.1038/1eu.2012.2127. Epub 2012 May 2408.
21. Chung T H, Mulligan G, Fonseca R, Chng W J. A novel measure of chromosome instability can account for prognostic difference in multiple myeloma. PLoS One. 2013; 8: e66361. doi: 66310.61371/journal.pone.0066361. Print 0062013.
22. Wu P, Walker B A, Broyl A, et al. A gene expression based predictor for high risk myeloma treated with intensive therapy and autologous stem cell rescue. Leuk Lymphoma. 2015; 56: 594-601. doi: 510.3109/10428194.10422014.10911863. Epub 1042214 August 10428119.
23. Hermansen N E, Borup R, Andersen M K, et al. Gene expression risk signatures maintain prognostic power in multiple myeloma despite microarray probe set translation. Int J Lab Hematol. 2016; 38: 298-307. doi: 210.1111/ijlh.12486. Epub 1216 March 12429.
24. Chng W J, Chung T H, Kumar S, et al. Gene signature combinations improve prognostic stratification of multiple myeloma patients. Leukemia. 2016; 30: 1071-1078. doi: 1010.1038/1eu.2015.1341. Epub 215 December 1016.
25. Kuiper R, van Duin M, van Vliet M H, et al. Prediction of high- and low-risk multiple myeloma based on gene expression and the International Staging System. Blood. 2015; 126: 1996-2004. doi: 1910.1182/blood-2015-1905-644039. Epub 64215 September 644031.
26. Amin S B, Yip W K, Minvielle S, et al. Gene expression profile alone is inadequate in predicting complete response in multiple myeloma. Leukemia. 2014; 28: 2229-2234. doi: 2210.1038/1eu.2014.2140. Epub 214 April 2215.
27. Hanahan D, Weinberg R A. The hallmarks of cancer. Cell. 2000; 100: 57-70.
28. Hanahan D, Weinberg R A. Hallmarks of cancer: the next generation. Cell. 2011; 144: 646-674. doi: 610.1016/j.ce11.2011.1002.1013.
29. Walker B A, Boyle E M, Wardell C P, et al. Mutational Spectrum, Copy Number Changes, and Outcome: Results of a Sequencing Study of Patients With Newly Diagnosed Myeloma. J Clin Oncol. 2015; 33: 3911-3920. doi: 3910.1200/JCO.2014.3959.1503. Epub 215 August 3917.
30. Kidd M, Drozdov I, Modlin I. Blood and tissue neuroendocrine tumor gene cluster analysis correlate, define hallmarks and predict disease status. Endocr Relat Cancer. 2015; 22: 561-575. doi: 510.1530/ERC-1515-0092. Epub 215 June 1532.
31. Li S C, Essaghir A, Martijn C, et al. Global microRNA profiling of well-differentiated small intestinal neuroendocrine tumors. Mod Pathol. 2013; 26: 685-696. doi: 610.1038/modpathol.2012.1216. Epub 213 January 1018.
32. Modlin I, Drozdov I, Kidd M. The Identification of gut neuroendocrine tumor disease by multiple synchronous transcript analysis in blood. Plos One. 2013; e63364.
33. Bodei L, Kidd M, Modlin I M, et al. Measurement of circulating transcripts and gene cluster analysis predicts and defines therapeutic efficacy of peptide receptor radionuclide therapy (PRRT) in neuroendocrine tumors. Eur J Nucl Med Mol Imaging. 2016; 43: 839-851. doi: 810.1007/s00259-00015-03250-z. Epub 0215 November 00223.
34. Munshi N C, Anderson K C. New strategies in the treatment of multiple myeloma. Clin Cancer Res. 2013; 19: 3337-3344. doi: 3310.1158/1078-0432.CCR-3312-1881. Epub 213 March 3320.
35. Raje N, Woo S B, Hande K, et al. Clinical, radiographic, and biochemical characterization of multiple myeloma patients with osteonecrosis of the jaw. Clin Cancer Res. 2008; 14: 2387-2395. doi: 2310.1158/1078-0432.CCR-2307-1430.

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

---

What is claims is:

1. A method of treating a plasma cell dyscrasia in a human subject in need thereof, the method comprising:

a) determining the expression level of 32 biomarkers from a blood sample from the human subject by contacting the blood sample with a plurality of agents specific to detect the expression of the 32 biomarkers, wherein the 32 biomarkers comprise each of:

additional sex combs like 1 transcriptional regulator (ASXL1),

Basic helix-loop-helix family member e40 (BHLHE40),

BTG anti-proliferation factor 2 (BTG2), coatomer protein complex subunit alpha (COPA), F-box and WD repeat domain containing 7 E3 ubiquitin protein ligase (FBXW7), Guanine nucleotide binding protein (G protein) alpha 13 (GNA13), Interleukin 8 (IL8), Jumonji domain containing 1C (JMJDIC), leucyl-tRNA synthetase 2, mitochondrial (LARS2), metastasis associated lung adenocarcinoma transcript 1 (MALAT1), muscleblind-like splicing regulator (MBNL1), myeloid cell leukemia sequence 1 (MCL1), a first splice variant of nuclear factor of kappa light polypeptide gene enhancer in B-cells inhibitor zeta (NFKBIZ) as put forth in Table 2, a second splice variant of NFKBIZ as put forth in Table 2, a first splice variant of nuclear receptor subfamily 4 group A member 1 (NR4A1) as put forth in Table 2, a second splice variant of NR4A1 as put forth in Table 2, phosphodiesterase 4B, cAMP-specific (PDE4B), protein inhibitor of activated STAT 2 (P1AS2), a first splice variant of protein kinase, AMP-activated, alpha 1 catalytic subunit (PRKAA1) as put forth in Table 2, a second splice variant of PRKAA1 as put forth in Table 2, a first splice variant of SCY1-like 2 (SCYL2) as put forth in Table 2, a second splice variant of SCYL2 as put forth in Table 2, SWI/SNF related, matrix associated, actin dependent regulator of chromatin, subfamily d, member 2 (SMARCD2), a first splice variant of Sp1 transcription factor (SP1) as put forth in Table 2, a second splice variant of SP1 as put forth in Table 2, serine/arginine-rich splicing factor 5 (SRSF5), T-cell activation RhoGTPase activating protein (TAGAP), TRAF family member-associated NFKB activator (TANK), transducin-like enhancer of split 4 (TLE4), TSC22 domain family, member 3 (TSC22D3), Ubiquitin-conjugating enzyme E2 J1 (UBE2J1), and at least one housekeeping gene, wherein the at least one housekeeping gene is tumor protein, translationally-controlled 1 (TPT1);

b) normalizing the expression level of each of ASXL1, BHLHE40, BTG2, COPA, FBXW7, GNA13, IL8, JMJDIC, LARS2, MALAT1, MBNL1, MCL1, the first splice variant of NFKBIZ, the second splice variant of NFKBIZ, the first splice variant of NR4A1, the second splice variant of NR4A1, PDE4B, P1AS2, the first splice variant of PRKAA1, the second splice variant of PRKAA1, the first splice variant of SCYL2, the second splice variant of SCYL2, SMARCD2, the first splice variant of SP1, the second splice variant of SP1, SRSF5, TAGAP, TANK, TLE4, TSC22D3, and UBE2J1 to the expression level of the at least one housekeeping gene, thereby obtaining a normalized expression level of each of ASXL1, BHLHE40, BTG2, COPA, FBXW7, GNA13, IL8, JMJDIC, LARS2, MALAT1, MBNL1, MCL1, the first splice variant of NFKBIZ, the second splice variant of NFKBIZ, the first splice variant of NR4A1, the second splice variant of NR4A1, PDE4B, PIAS2, the first splice variant of PRKAA1, the second splice variant of PRKAA1, the first splice variant of SCYL2, the second splice variant of SCYL2, SMARCD2, the first splice variant of SP1, the second splice variant of SP1, SRSF5, TAGAP, TANK, TLE4, TSC22D3, and UBE2J1;

c) inputting each normalized expression level into an algorithm to generate a score;

d) determining that the human subject has a plasma cell dyscrasia by determining that the score is greater than or equal to a first predetermined cutoff value, wherein the first predetermined cutoff value is 20 on a scale of 0 to 100; and d) administering to the subject at least one therapeutically effective amount of at least one of:

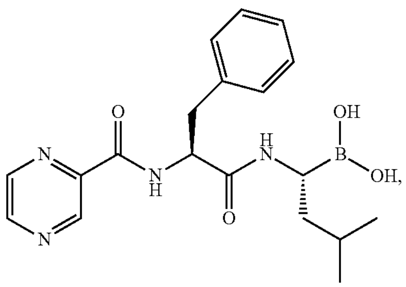 [SMILES: CC(C)C[C@H](NC(=O)[C@H](Cc1ccccc1)NC(=O)c1cnccn1)B(O)O]

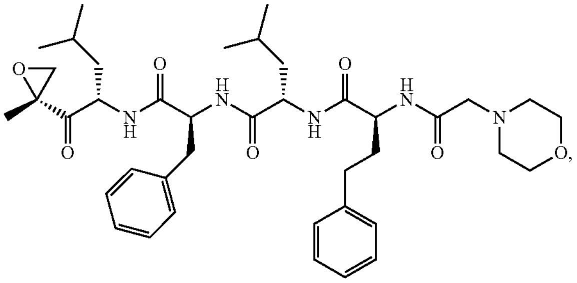 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

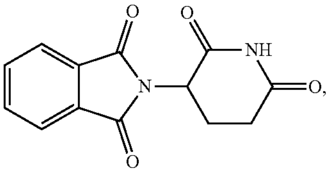 [SMILES: O=C1CCC(N2C(=O)c3ccccc3C2=O)C(=O)N1]

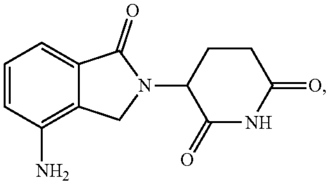 [SMILES: Nc1cccc2c1CN(C1CCC(=O)NC1=O)C2=O]

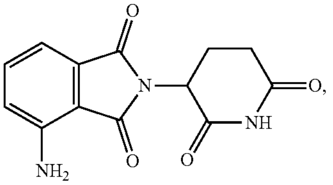

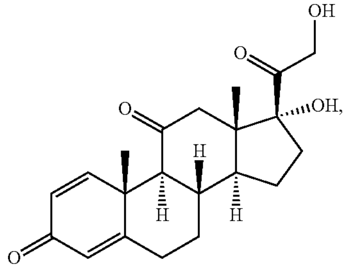

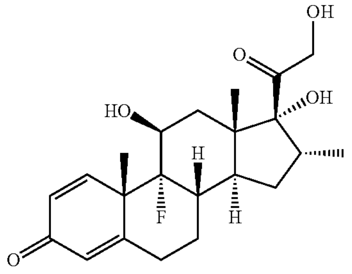

or any combination thereof.

2. The method of claim 1, wherein the method comprises administering at least one therapeutically effective amount of:

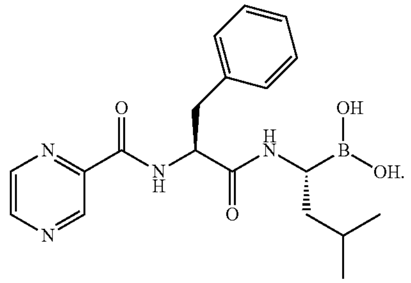

3. The method of claim 1, wherein the method comprises administering at least one therapeutically effective amount of:

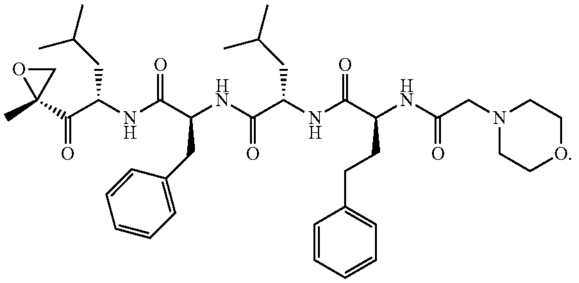

4. The method of claim 1, wherein the method comprises administering at least one therapeutically effective amount of:

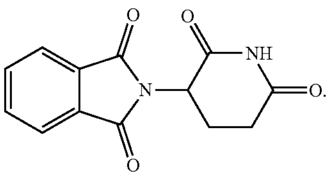

5. The method of claim 1, wherein the method comprises administering at least one therapeutically effective amount of:

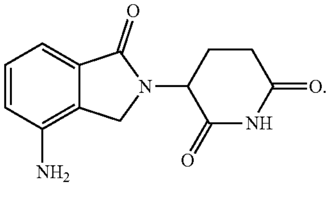

6. The method of claim 1, wherein the method comprises administering at least one therapeutically effective amount of:

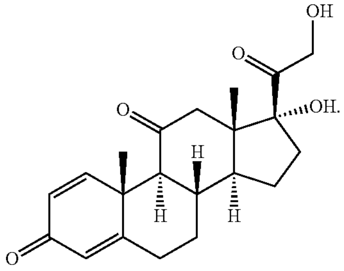

7. The method of claim 1, wherein the method comprises administering at least one therapeutically effective amount of:

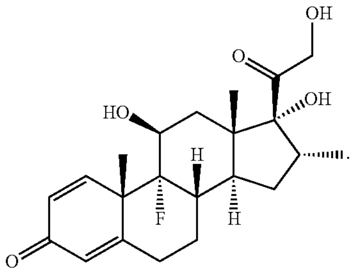

8. The method of claim 1, wherein the plasma cell dyscrasia is monoclonal gammopathy of undetermined significance (MGUS) or myeloma.

9. The method of claim 1, wherein at least one of the 32 biomarkers is RNA, cDNA, or protein.

10. The method of claim 9, wherein when the biomarker is RNA, the RNA is reverse transcribed to produce cDNA, and the produced cDNA expression level is detected.

11. The method of claim 1, wherein the expression level of the biomarker is detected by forming a complex between the biomarker and a labeled probe or primer.

12. The method of claim 9, wherein when the biomarker is protein, the protein is detected by forming a complex between the protein and a labeled antibody.

13. The method of claim 12, wherein the label is a fluorescent label.

14. The method of claim 9, wherein when the biomarker is RNA or cDNA, the RNA or cDNA is detected by forming a complex between the RNA or cDNA and a labeled nucleic acid probe or primer.

15. The method of claim 14, wherein the label is a fluorescent label.

16. The method of claim 14, wherein the complex between the RNA or cDNA and the labeled nucleic acid probe or primer is a hybridization complex.

17. The method of claim 1, wherein the algorithm is XGB, RF, glmnet, cforest, CART, treebag, knn, nnet, SVM-radial, SVM-linear, NB, NNET, mlp, or logistic regression modeling.

18. The method of claim 1, wherein the algorithm comprises a model of myeloma disease dynamics built using the normalized expression levels of ASXL1, BHLHE40, BTG2, COPA, FBXW7, GNA13, IL8, JMJD1C, LARS2, MALAT1, MBNL1, MCL1, the first splice variant of NFKBIZ, the second splice variant of NFKBIZ, the first splice variant of NR4A1, the second splice variant of NR4A1, PDE4B, P1AS2, the first splice variant of PRKAA1, the second splice variant of PRKAA1, the first splice variant of SCYL2, the second splice variant of SCYL2, SMARCD2, the first splice variant of SP1, the second splice variant of SP1, SRSF5, TAGAP, TANK, TLE4, TSC22D3, and UBE2J1 from reference blood samples from at least 135 human subjects.

* * * * *